US011339355B2

(12) United States Patent
Oehlenschlaeger et al.

(10) Patent No.: US 11,339,355 B2
(45) Date of Patent: May 24, 2022

(54) GLYCOSYL HYDROLASES

(71) Applicant: Novozymes A/S, Bagsvaerd (DK)

(72) Inventors: Christian Berg Oehlenschlaeger, Valby (DK); Rebecca Munk Vejborg, Allerod (DK); Dorotea Raventos Segura, Rungsted (DK); Jesper Salomon, Holte (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 16/499,877

(22) PCT Filed: Apr. 4, 2018

(86) PCT No.: PCT/EP2018/058639
§ 371 (c)(1),
(2) Date: Oct. 1, 2019

(87) PCT Pub. No.: WO2018/185181
PCT Pub. Date: Oct. 11, 2018

(65) Prior Publication Data
US 2020/0109353 A1    Apr. 9, 2020

(30) Foreign Application Priority Data

Apr. 4, 2017   (EP) .................... 17164859

(51) Int. Cl.
| | | |
|---|---|---|
| *C11D 3/386* | (2006.01) | |
| *C11D 11/00* | (2006.01) | |
| *C11D 17/00* | (2006.01) | |
| *C12N 9/24* | (2006.01) | |

(52) U.S. Cl.
CPC ...... *C11D 3/38636* (2013.01); *C11D 11/0017* (2013.01); *C11D 17/0039* (2013.01); *C12N 9/2402* (2013.01)

(58) Field of Classification Search
None
See application file for complete search history.

(56) References Cited

U.S. PATENT DOCUMENTS

| | | |
|---|---|---|
| 10,647,947 B2 | 5/2020 | Baltsen |
| 2007/0020624 A1 | 1/2007 | Rubenfeld |
| 2008/0248558 A1 | 10/2008 | Deinhammer |
| 2017/0152462 A1 | 6/2017 | Baltsen |

FOREIGN PATENT DOCUMENTS

| | | |
|---|---|---|
| JP | 2014118533 | 6/2014 |
| WO | 2004/041988 A1 | 5/2004 |
| WO | 2013/087764 A1 | 6/2013 |
| WO | 2014/059541 A1 | 4/2014 |
| WO | 2015/184526 A1 | 12/2015 |

OTHER PUBLICATIONS

Cantarel et al, 2009, Nucleic Acids Res, vol. 37, pp. D233-D238.
Vllo et al, 2015, Uniprot access No. A0A0K1QM56.
Chen et al., GenBank Accession No. AKF83382.1 (2016).
Vilo et al, 2015, Genbank No. AKV06550.1.

*Primary Examiner* — Kagnew H Gebreyesus
(74) *Attorney, Agent, or Firm* — Yoshimi Barron

(57) ABSTRACT

The invention relates to polypeptides having hydrolytic activity and polynucleotides encoding the polypeptides. The invention also relates to nucleic acid constructs, vectors, and host cells comprising the polynucleotides as well as methods of producing and using the polypeptides.

9 Claims, 9 Drawing Sheets

Figure 2:
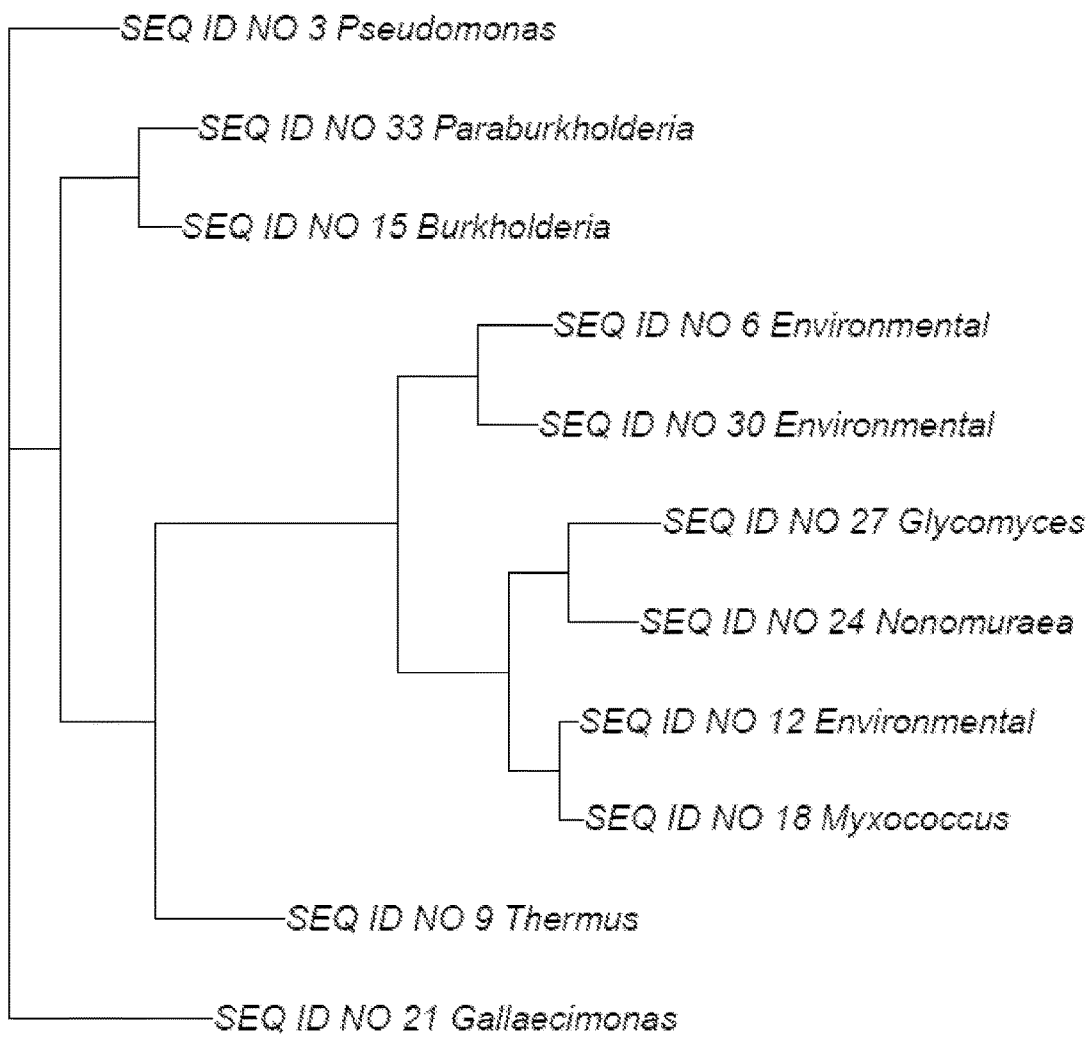

Specification includes a Sequence Listing.

```
SEQ ID NO 3  Pseudomonas sp-62208                        ..........................................
SEQ ID NO 18 Myxococcus macrosporus                      ...................AERSGDAAVLADARTLTCASLQ
SEQ ID NO 12 Environmental bacterial community LE        ...................DDFDTGQDAILPDARTLPCTTLQ
SEQ ID NO 27 Glycomyces rutgersensis                     ..........................................
SEQ ID NO 15 Burkholderia sp-63093                       ..........................................
SEQ ID NO 30 Environmental bacterial community XE        ..........................................
SEQ ID NO 6  Environmental bacterial community A         ..........................................
SEQ ID NO 21 Gallaecimonas pentaromativorans             ..........................................
SEQ ID NO 9  Thermus rehai                               QVDPSHVAQAVRETIQIGGGLEQWSGLPQYPVVLSNTFPA
SEQ ID NO 33 Paraburkholderia phenazinium                ..........................................
SEQ ID NO 24 Nonomuraea coxensis                         ..........................................

SEQ ID NO 3  Pseudomonas sp-62208                        ..........................................
SEQ ID NO 18 Myxococcus macrosporus                      VASGYIGSGQTVQGLNTQTLSGTQDRWAEYVEFSPGTSAT
SEQ ID NO 12 Environmental bacterial community LE        FERGALPSGQSVQGLNTQTLSGTQDRWAEYVEFAPNSSAT
SEQ ID NO 27 Glycomyces rutgersensis                     ..........................................
SEQ ID NO 15 Burkholderia sp-63093                       ..........................................
SEQ ID NO 30 Environmental bacterial community XE        ..........................................
SEQ ID NO 6  Environmental bacterial community A         ..........................................
SEQ ID NO 21 Gallaecimonas pentaromativorans             ..........................................
SEQ ID NO 9  Thermus rehai                               KPVTHGGYFSVAWDDRHLYILGVFEQKAETVKAALPEEHP
SEQ ID NO 33 Paraburkholderia phenazinium                ..........................................
SEQ ID NO 24 Nonomuraea coxensis                         ..........................................

SEQ ID NO 3  Pseudomonas sp-62208                        ..........................................
SEQ ID NO 18 Myxococcus macrosporus                      CTYALPADVGAADVVAAEVGINYRGPHKSQMRWLFEAWDY
SEQ ID NO 12 Environmental bacterial community LE        CTYPLPTGVSADSVVAAEVGVNYRGPTKAQMRWVIEAWDY
SEQ ID NO 27 Glycomyces rutgersensis                     ..........................................
SEQ ID NO 15 Burkholderia sp-63093                       ..........................................
SEQ ID NO 30 Environmental bacterial community XE        ..........................................
SEQ ID NO 6  Environmental bacterial community A         ..........................................
SEQ ID NO 21 Gallaecimonas pentaromativorans             ..........................................
SEQ ID NO 9  Thermus rehai                               EWWNDDTNEVFLKPDPKGVEVIHLAANPKGTRFKAYTFTT
SEQ ID NO 33 Paraburkholderia phenazinium                ..........................................
SEQ ID NO 24 Nonomuraea coxensis                         ..........................................

SEQ ID NO 3  Pseudomonas sp-62208                        ..........................................
SEQ ID NO 18 Myxococcus macrosporus                      EGGAWVLVGDNTFAQSWTWTATSLALTSPQRFVSGGPVKL
SEQ ID NO 12 Environmental bacterial community LE        STNSWALVGDNTPAQSWRWTATSLALPTPARFLSGGPVKL
SEQ ID NO 27 Glycomyces rutgersensis                     ..........................................
SEQ ID NO 15 Burkholderia sp-63093                       ..........................................
SEQ ID NO 30 Environmental bacterial community XE        ..........................................
SEQ ID NO 6  Environmental bacterial community A         ..........................................
SEQ ID NO 21 Gallaecimonas pentaromativorans             ..........................................
SEQ ID NO 9  Thermus rehai                               DYATSGRVEASRWVLEWAIPFASLKTSPPEPGAIWAMKVG
SEQ ID NO 33 Paraburkholderia phenazinium                ..........................................
SEQ ID NO 24 Nonomuraea coxensis                         ..........................................

SEQ ID NO 3  Pseudomonas sp-62208                        RYRTTSTADASLLDLLVVEIQVAASDAGTPGDAGTPGDAG
SEQ ID NO 18 Myxococcus macrosporus                      RYRTDSTADASLLDLLVVEVQVAASDAGTPTDAGTPTDAG
SEQ ID NO 12 Environmental bacterial community LE        ..........................................
SEQ ID NO 27 Glycomyces rutgersensis                     ..........................................
SEQ ID NO 15 Burkholderia sp-63093                       ..........................................
SEQ ID NO 30 Environmental bacterial community XE        ..........................................
SEQ ID NO 6  Environmental bacterial community A         ..........................................
SEQ ID NO 21 Gallaecimonas pentaromativorans             ..........................................
SEQ ID NO 9  Thermus rehai                               REHQAAQEYPLWPNGGDYHAPTNFGYLVFVEKLEDPQALA
SEQ ID NO 33 Paraburkholderia phenazinium                ...................................QTAADAA
SEQ ID NO 24 Nonomuraea coxensis                         ..........................................
```

Figure 1

```
SEQ ID NO  3 Pseudomonas sp-62208                        ......AALTPPS.............TFWYAEEP.PLAE
SEQ ID NO 18 Myxococcus macrosporus                      TPGDAGTETD.GTP.QWEGVNSFT..TN.PQGKL.DTIA
SEQ ID NO 12 Environmental bacterial community LE        TPTDAGTPTD.GT..PWSNVKSFT..TN.PQGKL.DAIA
SEQ ID NO 27 Glycomyces rutgersensis                     DSGETATAAP.DQPA.....NWI.Q.SG.ADGKL.DALV
SEQ ID NO 15 Burkholderia sp-63093                       ...QGAADMP.GPS.............AL..ANP.PVEE
SEQ ID NO 30 Environmental bacterial community XE        .......ASP.LSS.........GSWI.Q.Q...AKP.DVLA
SEQ ID NO  6 Environmental bacterial community A         .........TPGKGKGILSNAKSWV.G.QHI...DL.PTLG
SEQ ID NO 21 Gallaecimonas pentaromativorans             ..........STSDS..............AFFY.QHQ.PLAE
SEQ ID NO  9 Thermus rehai                               QRVQALLGVEPPIRSRLQDIATY....AV..KDPQEAAK
SEQ ID NO 33 Paraburkholderia phenazinium                DNAASATNAS.QPS...........AFFY.GQV.PAAA
SEQ ID NO 24 Nonomuraea coxensis                         ..........PR.PLTEVRSFT.V.QN.P.GRL.DTVA SEQ ID NO  3 Pseudomonas sp-62208                        LAQ..W..E......PGHMT.GDVTT.R....KL.SEP
SEQ ID NO 18 Myxococcus macrosporus                      ASK..L..DLAR..Y.DDWFT.AEIA..K....AQ.KQ.
SEQ ID NO 12 Environmental bacterial community LE        ASK..L..ELVR..S.SGYFT.AEIS..K....AR.KQ.
SEQ ID NO 27 Glycomyces rutgersensis                     AAPHEA..I.LAR..G.EGYFS.DEITS.E....NS.KS
SEQ ID NO 15 Burkholderia sp-63093                       LAT..W..V......PD..AHFDPR.HA....KARPVW
SEQ ID NO 30 Environmental bacterial community XE        ASPY..L.I.YSR..SGGRAYSRADIA..KVKPDGGQRI
SEQ ID NO  6 Environmental bacterial community A         TTTA.LV.I.ASQ..SVEGSFTPADIA..KTKPDGSQRV
SEQ ID NO 21 Gallaecimonas pentaromativorans             MTFYPGV..Q......PDHIS.EELKV.N....ER.IKI
SEQ ID NO  9 Thermus rehai                               LYD..L.VQ......PN.LPKESLAI.K....AN.VR
SEQ ID NO 33 Paraburkholderia phenazinium                LSE..AV..E......PD..SGFDPE.QH....GGHTAV
SEQ ID NO 24 Nonomuraea coxensis                         RAPHQL.I..LSR..TTAGYFS.KEVAKVR....DS.KT SEQ ID NO  3 Pseudomonas sp-62208                        ..I.V..FDGNKA...DITKAGLTA.AVSPVR.DS..NSQ
SEQ ID NO 18 Myxococcus macrosporus                      L..FE.A.DNY....PEWSQV.D.DLK.GPVGG.PNEQ
SEQ ID NO 12 Environmental bacterial community LE        L..FE.A.DEY....PEWSQV.A.DLK.GPVSG.PDEQ
SEQ ID NO 27 Glycomyces rutgersensis                     Y..FTM.I.TY....PEYDAVAATDMI.NQWGD.PDEY
SEQ ID NO 15 Burkholderia sp-63093                       F..V.V..VNPH....AYYSAM.S.AWLP.V.DA..ASH
SEQ ID NO 30 Environmental bacterial community XE        L..LS..G.ADY.FYWGQDWSRT.P.SWL..E.PD.EGNY
SEQ ID NO  6 Environmental bacterial community A         L..FS..G.ADY.FYWDDEWYDQAP.DWLHEE.SD.AGNY
SEQ ID NO 21 Gallaecimonas pentaromativorans             Y..LSV..SDAKD............AKG..KV.AS..QSQ
SEQ ID NO  9 Thermus rehai                               V..LS..G..PE.....DYGQPL.K.EWL.GQ.PN..GSY
SEQ ID NO 33 Paraburkholderia phenazinium                F..V.V..VTPQ....PYYAAM.K.EWLV.H.AA..ESK
SEQ ID NO 24 Nonomuraea coxensis                         ..FE.G.I.RP....TEARTL.A.DLR.NRWLD.PEEH SEQ ID NO  3 Pseudomonas sp-62208                        VHDLTTQA.REYLL....G.AKQLQ.DGYA.LF..L.SF
SEQ ID NO 18 Myxococcus macrosporus                      Y.KY.DER.WPIV....GG.I.QAL...T...L.VVT
SEQ ID NO 12 Environmental bacterial community LE        Y.KY.DER.WPIV....QG.I.RAL...N.C.L.VVT
SEQ ID NO 27 Glycomyces rutgersensis                     H.QY.DQE.WDLVN...QP.L.QAA...D.W.L.VPNA
SEQ ID NO 15 Burkholderia sp-63093                       VIDQTAAE.PAPFV...DKVIAPLWKK.YS.FD..I.S
SEQ ID NO 30 Environmental bacterial community XE        DIRF.DPE.D.QKIILGTPQSYL.RIL...D.V..RV.A
SEQ ID NO  6 Environmental bacterial community A         P.KF.HPD.QAILFGSPDCYL.RII...D.V...A.
SEQ ID NO 21 Gallaecimonas pentaromativorans             IHDQTSTR.KNHL....NT.AKELK.RC.Y.LF..L.S
SEQ ID NO  9 Thermus rehai                               E.DANQKG.QELVL....RLAEGYLK...G.LF....TA
SEQ ID NO 33 Paraburkholderia phenazinium                V.DQDAPG.PAFYL...KQVIAPLWKK.YR.FF..L.S
SEQ ID NO 24 Nonomuraea coxensis                         F.RY.DSR.WDLVL...RP.V.QALR...D.V..L.PLA SEQ ID NO  3 Pseudomonas sp-62208                        QLLP..EASREAQ.KA..GLLRE.HK.QPGLKLFF..G.E
SEQ ID NO 18 Myxococcus macrosporus                      E..P..ANSAGTN.AD..RK.V..IED.SQ.AKAH.PA.K
SEQ ID NO 12 Environmental bacterial community LE        E..P..ANSAGTN.AD..RK.V..IA.INT.AKAR.PD.K
SEQ ID NO 27 Glycomyces rutgersensis                     .D.LALVPGET.ES..VD.VI.AQE.A...GDDLQ
SEQ ID NO 15 Burkholderia sp-63093                       HL.AKTDAARAAQEA..VRVIR.IKK.YPKAKLIF....
SEQ ID NO 30 Environmental bacterial community XE        E.....RNDREMNAPGRRAA.I.FVQDIAR.GRAG.PQ.L
SEQ ID NO  6 Environmental bacterial community A         .I.....DDPALT.PQR.AH.I..VRSLAA.ARARTPS.V
SEQ ID NO 21 Gallaecimonas pentaromativorans             QLLP..QDQQPVQ.QA.LAAVQS.SGQF.QHHLIL..E
SEQ ID NO  9 Thermus rehai                               DLYP......QVAPG.VAIVQ..RE.FPEAILVQ..R
SEQ ID NO 33 Paraburkholderia phenazinium                Q..AKTDADRQRQQAG..VAVIR.IKA.YPRAMLMF..E
SEQ ID NO 24 Nonomuraea coxensis                         E..H.LDRVPGET.AS..RR.NE.IV.ISR.AKKVRF..L
```

Figure 1 continued

Figure 1 continued

```
SEQ ID NO 3  Pseudomonas sp-62208                          DKVLLKRLGLNLMAPAGTQPLTISYQDKALIGAFEAPVQP
SEQ ID NO 18 Myxococcus macrosporus                        ........................................
SEQ ID NO 12 Environmental bacterial community LE          ........................................
SEQ ID NO 27 Glycomyces rutgersensis                       ........................................
SEQ ID NO 15 Burkholderia sp-63093                         ........................................
SEQ ID NO 30 Environmental bacterial community XE          ........................................
SEQ ID NO 6  Environmental bacterial community A           ........................................
SEQ ID NO 21 Gallaecimonas pentaromativorans               SPALLAGLGLNLQSLSPKGPFSQTEMASWLKGETALSLKN
SEQ ID NO 9  Thermus rehai                                 ........................................
SEQ ID NO 33 Paraburkholderia phenazinium                  ........................................
SEQ ID NO 24 Nonomuraea coxensis                           ........................................

SEQ ID NO 3  Pseudomonas sp-62208                          RSRELTAVSLLPQGPKAALLLTGKDGQTFAPVATAKWGGL
SEQ ID NO 18 Myxococcus macrosporus                        ........................................
SEQ ID NO 12 Environmental bacterial community LE          ........................................
SEQ ID NO 27 Glycomyces rutgersensis                       ........................................
SEQ ID NO 15 Burkholderia sp-63093                         ........................................
SEQ ID NO 30 Environmental bacterial community XE          ........................................
SEQ ID NO 6  Environmental bacterial community A           ........................................
SEQ ID NO 21 Gallaecimonas pentaromativorans               LEPYSAT...LAEGAEALISIKAGNGEPVLQQARTDKGAV
SEQ ID NO 9  Thermus rehai                                 ........................................
SEQ ID NO 33 Paraburkholderia phenazinium                  ........................................
SEQ ID NO 24 Nonomuraea coxensis                           ........................................

SEQ ID NO 3  Pseudomonas sp-62208                          ALAPYVLET.NNERSRWILDPFAFLQASLQLPAQPRPDTT
SEQ ID NO 18 Myxococcus macrosporus                        ........................................
SEQ ID NO 12 Environmental bacterial community LE          ........................................
SEQ ID NO 27 Glycomyces rutgersensis                       ........................................
SEQ ID NO 15 Burkholderia sp-63093                         ........................................
SEQ ID NO 30 Environmental bacterial community XE          ........................................
SEQ ID NO 6  Environmental bacterial community A           ........................................
SEQ ID NO 21 Gallaecimonas pentaromativorans               VLSPWLIDALPLEENRWLINPVALLQKGLGLPPIPAPDVT
SEQ ID NO 9  Thermus rehai                                 ........................................
SEQ ID NO 33 Paraburkholderia phenazinium                  ........................................
SEQ ID NO 24 Nonomuraea coxensis                           ........................................

SEQ ID NO 3  Pseudomonas sp-62208                          TENGRRIATVHIDGDGFPSRAEVRGSPYAGKQVLNDFIQP
SEQ ID NO 18 Myxococcus macrosporus                        ........................................
SEQ ID NO 12 Environmental bacterial community LE          ........................................
SEQ ID NO 27 Glycomyces rutgersensis                       ........................................
SEQ ID NO 15 Burkholderia sp-63093                         ........................................
SEQ ID NO 30 Environmental bacterial community XE          ........................................
SEQ ID NO 6  Environmental bacterial community A           ........................................
SEQ ID NO 21 Gallaecimonas pentaromativorans               TESGRRLFTLHIDGDAFPSRARFPGQPFAGEVMEKQIIEH
SEQ ID NO 9  Thermus rehai                                 ........................................
SEQ ID NO 33 Paraburkholderia phenazinium                  ........................................
SEQ ID NO 24 Nonomuraea coxensis                           ........................................

SEQ ID NO 3  Pseudomonas sp-62208                          NPFLTSVSIIEGEISPRGMYPHLARELEPIARELFANPKV
SEQ ID NO 18 Myxococcus macrosporus                        ........................................
SEQ ID NO 12 Environmental bacterial community LE          ........................................
SEQ ID NO 27 Glycomyces rutgersensis                       ........................................
SEQ ID NO 15 Burkholderia sp-63093                         ........................................
SEQ ID NO 30 Environmental bacterial community XE          ........................................
SEQ ID NO 6  Environmental bacterial community A           ........................................
SEQ ID NO 21 Gallaecimonas pentaromativorans               YQLPITVSVIQGEVGPTGMYPKQSPQLEAIARDIFTKPYV
SEQ ID NO 9  Thermus rehai                                 ........................................
SEQ ID NO 33 Paraburkholderia phenazinium                  ........................................
SEQ ID NO 24 Nonomuraea coxensis                           ........................................
```

Figure 1 continued

```
SEQ ID NO 3  Pseudomonas sp-62208                       EVATHTFSHPFY.MQPELAEKDEDFSAEYGLKMAIPGYDK
SEQ ID NO 18 Myxococcus macrosporus                     ........................................
SEQ ID NO 12 Environmental bacterial community LE       ........................................
SEQ ID NO 27 Glycomyces rutgersensis                    ........................................
SEQ ID NO 15 Burkholderia sp-63093                      ........................................
SEQ ID NO 30 Environmental bacterial community XE       ........................................
SEQ ID NO 6  Environmental bacterial community A        ........................................
SEQ ID NO 21 Gallaecimonas pentaromativorans            EIASHTYSHPFFWSQIAGREKLTEQDTEYGFHLNIPGYNK
SEQ ID NO 9  Thermus rehai                              ........................................
SEQ ID NO 33 Paraburkholderia phenazinium               ........................................
SEQ ID NO 24 Nonomuraea coxensis                        ........................................

SEQ ID NO 3  Pseudomonas sp-62208                       IDFKREIFGSRDYINQQLTTPEKPVKMVFWPGDALPSAAT
SEQ ID NO 18 Myxococcus macrosporus                     ........................................
SEQ ID NO 12 Environmental bacterial community LE       ........................................
SEQ ID NO 27 Glycomyces rutgersensis                    ........................................
SEQ ID NO 15 Burkholderia sp-63093                      ........................................
SEQ ID NO 30 Environmental bacterial community XE       ........................................
SEQ ID NO 6  Environmental bacterial community A        ........................................
SEQ ID NO 21 Gallaecimonas pentaromativorans            IDLTKEIDGSIDYINERLAPKDKKVVMMLWSGDAAPGPVA
SEQ ID NO 9  Thermus rehai                              ........................................
SEQ ID NO 33 Paraburkholderia phenazinium               ........................................
SEQ ID NO 24 Nonomuraea coxensis                        ........................................

SEQ ID NO 3  Pseudomonas sp-62208                       IKLAYDAGLKNVNGASTMLTKARPSLTGLNPLLRPTEGGL
SEQ ID NO 18 Myxococcus macrosporus                     ........................................
SEQ ID NO 12 Environmental bacterial community LE       ........................................
SEQ ID NO 27 Glycomyces rutgersensis                    ........................................
SEQ ID NO 15 Burkholderia sp-63093                      ........................................
SEQ ID NO 30 Environmental bacterial community XE       ........................................
SEQ ID NO 6  Environmental bacterial community A        ........................................
SEQ ID NO 21 Gallaecimonas pentaromativorans            LAHARKMGVLNVNGGNTVMTRDNPSLSEIWPIGRPEGGLL
SEQ ID NO 9  Thermus rehai                              ........................................
SEQ ID NO 33 Paraburkholderia phenazinium               ........................................
SEQ ID NO 24 Nonomuraea coxensis                        ........................................

SEQ ID NO 3  Pseudomonas sp-62208                       .QYYAPVINENVYTNLWKGPYYGFRDVIDTYELTDSPRRL
SEQ ID NO 18 Myxococcus macrosporus                     ........................................
SEQ ID NO 12 Environmental bacterial community LE       ........................................
SEQ ID NO 27 Glycomyces rutgersensis                    ........................................
SEQ ID NO 15 Burkholderia sp-63093                      ........................................
SEQ ID NO 30 Environmental bacterial community XE       ........................................
SEQ ID NO 6  Environmental bacterial community A        ........................................
SEQ ID NO 21 Gallaecimonas pentaromativorans            YQVYAPIMNENVYTDLWHGPYFGFRRVRETFDITGHPYRL
SEQ ID NO 9  Thermus rehai                              ........................................
SEQ ID NO 33 Paraburkholderia phenazinium               ........................................
SEQ ID NO 24 Nonomuraea coxensis                        ........................................

SEQ ID NO 3  Pseudomonas sp-62208                       RGIHLYYHPYSATKQASIKAMGEIYGYMREQHPMSLWMSD
SEQ ID NO 18 Myxococcus macrosporus                     ........................................
SEQ ID NO 12 Environmental bacterial community LE       ........................................
SEQ ID NO 27 Glycomyces rutgersensis                    ........................................
SEQ ID NO 15 Burkholderia sp-63093                      ........................................
SEQ ID NO 30 Environmental bacterial community XE       ........................................
SEQ ID NO 6  Environmental bacterial community A        ........................................
SEQ ID NO 21 Gallaecimonas pentaromativorans            KPFGLYFHPYSATNPAGLQALRDDIGYVLGRPNTPAHLSH
SEQ ID NO 9  Thermus rehai                              ........................................
SEQ ID NO 33 Paraburkholderia phenazinium               ........................................
SEQ ID NO 24 Nonomuraea coxensis                        ........................................
```

Figure 1 continued

```
SEQ ID NO 3  Pseudomonas sp-62208                         YLDRLHGLYQASLARTADGAWQIRGMDALRTVRLDPQMGW
SEQ ID NO 18 Myxococcus macrosporus                       ........................................
SEQ ID NO 12 Environmental bacterial community LE         ........................................
SEQ ID NO 27 Glycomyces rutgersensis                      ........................................
SEQ ID NO 15 Burkholderia sp-63093                        ........................................
SEQ ID NO 30 Environmental bacterial community XE         ........................................
SEQ ID NO 6  Environmental bacterial community A          ........................................
SEQ ID NO 21 Gallaecimonas pentaromativorans              YARNAKDFYFSALARDAKGDWLLSS.KYLRTLRLPKALGY
SEQ ID NO 9  Thermus rehai                                ........................................
SEQ ID NO 33 Paraburkholderia phenazinium                 ........................................
SEQ ID NO 24 Nonomuraea coxensis                          ........................................

SEQ ID NO 3  Pseudomonas sp-62208                         PDLLRSQGIAGVRDLPQGRYVHLSSDRALLVLRPDRDDR.
SEQ ID NO 18 Myxococcus macrosporus                       ........................................
SEQ ID NO 12 Environmental bacterial community LE         ........................................
SEQ ID NO 27 Glycomyces rutgersensis                      ........................................
SEQ ID NO 15 Burkholderia sp-63093                        ........................................
SEQ ID NO 30 Environmental bacterial community XE         ........................................
SEQ ID NO 6  Environmental bacterial community A          ........................................
SEQ ID NO 21 Gallaecimonas pentaromativorans              AQLDASQGLAGATE..DGRYLHVVNGDARFALAASASPRK
SEQ ID NO 9  Thermus rehai                                ........................................
SEQ ID NO 33 Paraburkholderia phenazinium                 ........................................
SEQ ID NO 24 Nonomuraea coxensis                          ........................................

SEQ ID NO 3  Pseudomonas sp-62208                         PALEEANVPLTDWRYLDDRRVSFAFAGQFDVTFSVRSASA
SEQ ID NO 18 Myxococcus macrosporus                       ........................................
SEQ ID NO 12 Environmental bacterial community LE         ........................................
SEQ ID NO 27 Glycomyces rutgersensis                      ........................................
SEQ ID NO 15 Burkholderia sp-63093                        ........................................
SEQ ID NO 30 Environmental bacterial community XE         ........................................
SEQ ID NO 6  Environmental bacterial community A          ........................................
SEQ ID NO 21 Gallaecimonas pentaromativorans              PYLVSANVLLKSWQLPGK....VAFKAWQKADLILANAEG
SEQ ID NO 9  Thermus rehai                                ........................................
SEQ ID NO 33 Paraburkholderia phenazinium                 ........................................
SEQ ID NO 24 Nonomuraea coxensis                          ........................................

SEQ ID NO 3  Pseudomonas sp-62208                         CRVEVDGQRFAGKSSAGLWTFQLPMKQVSNGQLLCN...
SEQ ID NO 18 Myxococcus macrosporus                       ........................................
SEQ ID NO 12 Environmental bacterial community LE         ........................................
SEQ ID NO 27 Glycomyces rutgersensis                      ........................................
SEQ ID NO 15 Burkholderia sp-63093                        ........................................
SEQ ID NO 30 Environmental bacterial community XE         ........................................
SEQ ID NO 6  Environmental bacterial community A          ........................................
SEQ ID NO 21 Gallaecimonas pentaromativorans              CRFVSDQGPSYGGQQKGRLTEFSLPEGDFAGHLACGTQQ
SEQ ID NO 9  Thermus rehai                                ........................................
SEQ ID NO 33 Paraburkholderia phenazinium                 ........................................
SEQ ID NO 24 Nonomuraea coxensis                          ........................................
```

Figure 1 continued

GLYCOSYL HYDROLASES

CROSS-REFERENCE TO RELATED APPLICATIONS

This application is a 35 U.S.C. 371 national application of international application no. PCT/EP2018/058639 filed Apr. 4, 2018 which claims priority or the benefit under 35 U.S.C. 119 of European application nos. EP 17164859.5 filed Apr. 4, 2017, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to polypeptides comprising a Glyco_hydro_114 pFam domain (PF03537) having hydrolytic activity and polynucleotides encoding the polypeptides. The invention also relates to nucleic acid constructs, vectors, and host cells comprising the polynucleotides as well as methods of producing and using the polypeptides.

Description of the Related Art

Enzymes have been used in detergents for decades. Usually a cocktail of various enzymes is added to detergent compositions. The enzyme cocktail often comprises various enzymes, wherein each enzyme targets it specific substrate e.g. amylases are active towards starch stains, proteases on protein stains and so forth. Textiles and surfaces such as laundry and dishes become soiled with many different types of soiling. The soiling may compose of proteins, grease, starch etc. Biofilm is an example of soiling and the presence of biofilm provides several disadvantages. Biofilm comprises an extracellular polymeric matrix, composed of e.g. polysaccharides, extracellular DNA (eDNA), and proteins. The extracellular polymeric matrix may be sticky or glueing, which when present on textile, give rise to redeposition or backstaining of soil resulting in a greying of the textile. Another drawback is that malodor may be trapped within the organic structure. Biofilm is therefore not desirable in textiles and surfaces associated with cleaning such as washing machines etc. As biofilm is a complex mixture of polysaccharides, proteins, DNA etc. there is a need for enzymes which effectively prevent, remove or reduce components of such soiling e.g. polysaccharides of components hereof on items such of fabrics. There is a need for enzymes which effectively remove or reduce components of organic soiling such as polysaccharides in e.g. the EPS in cleaning processes such as laundry and hard surface cleaning. The object of the present invention is to provide enzymes, which are compatible with cleaning compositions e.g. detergents and which effectively reduce polysaccharides associated e.g. with EPS.

SUMMARY OF THE INVENTION

The present invention provides polypeptides with hydrolase activity, wherein the polypeptides comprise the Pfam database domain Glyco_hydro_114 (Pfam domain id PF03537, Pfam version 31.0 Finn (2016). Nucleic Acids Research, Database Issue 44:D279-D285). The domain is a functional domain providing hydrolytic activity to the polypeptide. The invention further provides detergent compositions comprising polypeptides comprising the Glyco_hydro_114 domain and the use of such polypeptides for cleaning e.g. deep cleaning in cleaning processes. The polypeptides of the present invention comprising the Glyco_hydro_114 domain have beneficial properties such as cleaning e.g. deep cleaning in cleaning processes. Cleaning processes include laundry and dish wash.

In a first aspect, the present invention relates to a Glyco_hydro_114 glycosyl hydrolase comprising one, two or all three of the motifs GX[FY][LYF]D (SEQ ID NO 34), AYX[SET]XX[EAS] (SEQ ID NO 35) and GXXGX[FY][LYFI]D (SEQ ID NO 97), wherein the Glyco_hydro_114 glycosyl hydrolase has hydrolytic activity, and wherein the Glyco_hydro_114 glycosyl hydrolase comprises or consist of a polypeptide selected from the group consisting of:

(a) a polypeptide having at least 90%, at least 95%, at least 96%, at least 97%, at least 98%, at least 99% or 100% sequence identity to the polypeptide of SEQ ID NO 3;
(b) a polypeptide having at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 6;
(c) a polypeptide having at least 80%, at least 85%, at least 90%, at least 95%, at least 96%, at least 97%, at least 98%, at least 99% or 100% sequence identity to the polypeptide of SEQ ID NO 9;
(d) a polypeptide having at least 99% or 100% sequence identity to the polypeptide of SEQ ID NO 12;
(e) a polypeptide having at least 95%, at least 96%, at least 97%, at least 98%, at least 99% or 100% sequence identity to the polypeptide of SEQ ID NO 15;
(f) a polypeptide having at least 95%, at least 96%, at least 97%, at least 98%, at least 99% or 100% sequence identity to the polypeptide of SEQ ID NO 18;
(g) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 21;
(h) a polypeptide having at least 80%, at least 85%, at least 90%, at least 95%, at least 96%, at least 97%, at least 98%, at least 99% or 100% sequence identity to the polypeptide of SEQ ID NO 24;
(i) a polypeptide having at least 70%, at least 75%, at least 80%, at least 85%, at least 90%, at least 95%, at least 96%, at least 97%, at least 98%, at least 99% or 100% sequence identity to the polypeptide of SEQ ID NO 27;
(j) a polypeptide having at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 30;
(k) a polypeptide having at least 70%, at least 75%, at least 80%, at least 85%, at least 90%, at least 95%, at least 96%, at least 97%, at least 98%, at least 99% or 100% sequence identity to the polypeptide of SEQ ID NO 33;
(l) a polypeptide having 100% sequence identity to the polypeptide of SEQ ID NO 40;
(m) a polypeptide having at least 95%, at least 96%, at least 97%, at least 98%, at least 99% or 100% sequence identity to the polypeptide of SEQ ID NO 43;

(n) a polypeptide having 100% sequence identity to the polypeptide of SEQ ID NO 46;
(o) a polypeptide having at least 95%, at least 96%, at least 97%, at least 98%, at least 99% or 100% sequence identity to the polypeptide of SEQ ID NO 49;
(p) a polypeptide having at least 95%, at least 96%, at least 97%, at least 98%, at least 99% or 100% sequence identity to the polypeptide of SEQ ID NO 52;
(q) a polypeptide having at least 95%, at least 96%, at least 97%, at least 98%, at least 99% or 100% sequence identity to the polypeptide of SEQ ID NO 55;
(r) a polypeptide having at least 75%, at least 80%, at least 85%, at least 90%, at least 95%, at least 96%, at least 97%, at least 98%, at least 99% or 100% sequence identity to the polypeptide of SEQ ID NO 58;
(s) a polypeptide having at least 95%, at least 96%, at least 97%, at least 98%, at least 99% or 100% sequence identity to the polypeptide of SEQ ID NO 61;
(t) a polypeptide having at least 90%, at least 95%, at least 96%, at least 97%, at least 98%, at least 99% or 100% sequence identity to the polypeptide of SEQ ID NO 64;
(u) a polypeptide having at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 67;
(v) a polypeptide having at least 96%, at least 97%, at least 98%, at least 99% or 100% sequence identity to the polypeptide of SEQ ID NO 73;
(w) a polypeptide having at least 96%, at least 97%, at least 98%, at least 99% or 100% sequence identity to the polypeptide of SEQ ID NO 76;
(x) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 79;
(y) a polypeptide having at least 95%, at least 96%, at least 97%, at least 98%, at least 99% or 100% sequence identity to the polypeptide of SEQ ID NO 82;
(z) a polypeptide having at least 50%, at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 85;
(aa) a polypeptide having at least 50%, at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 88;
(bb) a polypeptide having at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 91;
(cc) a polypeptide having at least 80%, at least 85%, at least 90%, at least 95%, at least 96%, at least 97%, at least 98%, at least 99% or 100% sequence identity to the polypeptide of SEQ ID NO 94;
(dd) a polypeptide having at least 70%, at least 75%, at least 80%, at least 85%, at least 90%, at least 95%, at least 96%, at least 97%, at least 98%, at least 99% or 100% sequence identity to the polypeptide of SEQ ID NO 95; and
(ee) a polypeptide having at least 95%, at least 96%, at least 97%, at least 98%, at least 99% or 100% sequence identity to the polypeptide of SEQ ID NO 96.

The present invention also relates to glycosyl hydrolases e.g. polypeptide comprising at least one Glyco_hydro_114 glycosyl hydrolase domain. In particular, the invention relates to polypeptides selected from the group consisting of:
(a) a polypeptide having at least 60%, at least 70%, at least 75%, at least 80%, at least 85%, at least 90%, at least 95%, at least 96%, at least 97%, at least 98%, at least 99% or 100% sequence identity to the polypeptide of SEQ ID NO 3;
(b) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 6;
(c) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 9;
(d) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 12;
(e) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 15;
(f) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 18;
(g) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 21;
(h) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 24;
(i) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 27;
(j) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 30;
(k) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 33;
(l) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 40;
(m) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 43;
(n) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 46;
(o) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 49;
(p) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 52;
(q) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 55;
(r) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 58;
(s) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 61;
(t) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 64;
(u) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 67;
(v) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 70;
(w) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 73;
(x) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 76;
(y) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 79;
(z) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 82;
(aa) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 85;
(bb) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 88;
(cc) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 91;
(dd) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 94;
(ee) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 95;
(ff) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 96;
(gg) a variant of the polypeptide selected from the group consisting of SEQ ID NO 3, SEQ ID NO 6, SEQ ID NO 9, SEQ ID NO 12, SEQ ID NO 15, SEQ ID NO 18, SEQ ID NO 21, SEQ ID NO 24, SEQ ID NO 27, SEQ ID NO 30 and SEQ ID NO 33, SEQ ID NO 40, SEQ ID NO 43, SEQ ID NO 46, SEQ ID NO 49, SEQ ID NO 52, SEQ ID NO 55, SEQ ID NO 58, SEQ ID NO 61, SEQ ID NO 64, SEQ ID NO 67, SEQ ID NO 70, SEQ ID NO 73, SEQ ID NO 76, SEQ ID NO 79, SEQ ID NO 82, SEQ ID NO 85, SEQ ID NO 88, SEQ ID NO 91, SEQ ID NO 94, SEQ ID NO 95 and SEQ ID NO 96, wherein the variant has hydrolytic and/or deacetylase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19 or 20 positions;
(hh) a polypeptide comprising the polypeptide of (a) to (l) and a N-terminal and/or C-terminal His-tag and/or HQ-tag;
(ii) a polypeptide comprising the polypeptide of (a) to (l) and a N-terminal and/or C-terminal extension of between 1 and 10 amino acids; and
(jj) a fragment of the polypeptide of (a) to (l) having hydrolytic and/or deacetylase activity and having at least 90% of the length of the mature polypeptide.

The invention further relates to a cleaning composition e.g. a detergent composition, a ADW composition, a laundry composition, comprising a polypeptide according to the invention. One aspect relates to a cleaning composition comprising:
a) at least 0.001 ppm of at least one Glyco_hydro_114 glycosyl hydrolase according to the invention; and
b) one or more cleaning composition components, preferably selected from surfactants, builders, bleach components, polymers, dispersing agents and additional enzymes.

The invention also relates to a method for laundering an item comprising the steps of:
  a. Exposing an item to a wash liquor comprising a polypeptide according to the invention or a cleaning composition comprising a polypeptide according to the invention;
  b. Completing at least one wash cycle; and
  c. Optionally rinsing the item, wherein the item is a textile.

The invention further relates to a method for laundering an item comprising the steps of:
  a. exposing an item to a wash liquor comprising a Glyco_hydro_114 glycosyl hydrolase according to the invention or a composition according to the invention;
  b. completing at least one wash cycle; and
  c. optionally rinsing the item,
  wherein the item is a textile.

The invention further relates to use of a polypeptide according to the invention for cleaning e.g. deep cleaning of an item, such as textile e.g. fabric. The invention further relates to the use of a polypeptide according to the invention,
  (i) for preventing, reducing or removing stickiness of the item;
  (ii) for pretreating stains on the item;
  (iii) for preventing, reducing or removing redeposition of soil during a wash cycle;
  (iv) for preventing, reducing or removing adherence of soil to the item;
  (v) for maintaining or improving whiteness of the item;
  (vi) for preventing, reducing or removing malodor from the item,
  wherein the item is a textile.

The invention further relates to the use of a Glyco_hydro_114 glycosyl hydrolase in a cleaning process, such as laundry and/or dish wash. The invention also relates to the use of a Glyco_hydro_114 glycosyl hydrolase,
  i. for preventing, reducing or removing stickiness of the item;
  ii. for preventing, reducing or removing biofilm or biofilm components
  iii. for reducing or removing pel stains on the item;
  iv. for preventing, reducing or removing redeposition of soil during a wash cycle;
  v. for preventing, reducing or removing adherence of soil to the item;
  vi. for maintaining or improving whiteness of the item;
  vii. for preventing, reducing or removing malodor from the item,
  wherein the item is a textile.

In one aspect, the invention relates to a granule comprising;
  (a) a core comprising a Glyco_hydro_114 glycosyl hydrolase according to the invention, and
  (b) optionally a coating consisting of one or more layer(s) surrounding the core.

The invention further relates to a polynucleotide encoding the polypeptide of the invention. A nucleic acid construct or expression vector comprising a polynucleotide encoding a polypeptide of the invention, which is operably linked to one or more control sequences that direct the production of the polypeptide in an expression host. The invention further relates to a recombinant host cell comprising a polynucleotide encoding a polypeptide of the invention, which is operably linked to one or more control sequences that direct the production of the polypeptide, wherein the method may further comprise cultivating a cell, which in its wild-type form produces the polypeptide, under conditions conducive for production of the polypeptide and optionally recovering the polypeptide.

Overview of Sequences

SEQ ID NO 1 DNA encoding full length polypeptide from *Pseudomonas* sp-62208
SEQ ID NO 2 polypeptide derived from SEQ ID NO 1
SEQ ID NO 3 mature polypeptide obtained from *Pseudomonas* sp-62208
SEQ ID NO 4 DNA encoding full length polypeptide from Environmental bacterial community A
SEQ ID NO 5 polypeptide derived from SEQ ID NO 4
SEQ ID NO 6 mature polypeptide obtained from Environmental bacterial community A
SEQ ID NO 7 DNA encoding full length polypeptide from *Thermus rehai*
SEQ ID NO 8 polypeptide derived from SEQ ID NO 7
SEQ ID NO 9 mature polypeptide obtained from *Thermus rehai*
SEQ ID NO 10 DNA encoding full length polypeptide from Environmental bacterial community LE
SEQ ID NO 11 polypeptide derived from SEQ ID NO 10
SEQ ID NO 12 mature polypeptide obtained from Environmental bacterial community LE
SEQ ID NO 13 DNA encoding full length polypeptide from *Burkholderia* sp-63093
SEQ ID NO 14 polypeptide derived from SEQ ID NO 13
SEQ ID NO 15 mature polypeptide obtained from *Burkholderia* sp-63093
SEQ ID NO 16 DNA encoding full length polypeptide from *Myxococcus macrosporus*
SEQ ID NO 17 polypeptide derived from SEQ ID NO 16
SEQ ID NO 18 mature polypeptide obtained from *Myxococcus macrosporus*
SEQ ID NO 19 DNA encoding full length polypeptide from *Gallaecimonas pentaromativorans*
SEQ ID NO 20 polypeptide derived from SEQ ID NO 19
SEQ ID NO 21 mature polypeptide obtained from *Gallaecimonas pentaromativorans*
SEQ ID NO 22 DNA encoding full length polypeptide from *Nonomuraea coxensis*
SEQ ID NO 23 polypeptide derived from SEQ ID NO 22
SEQ ID NO 24 mature polypeptide obtained from *Nonomuraea coxensis*
SEQ ID NO 25 DNA encoding full length polypeptide from *Glycomyces rutgersensis*
SEQ ID NO 26 polypeptide derived from SEQ ID NO 25
SEQ ID NO 27 mature polypeptide obtained from *Glycomyces rutgersensis*
SEQ ID NO 28 DNA encoding full length polypeptide from Environmental bact. community XE
SEQ ID NO 29 polypeptide derived from SEQ ID NO 28
SEQ ID NO 30 mature polypeptide obtained from Environmental bact. community XE
SEQ ID NO 31 DNA encoding full length polypeptide from *Paraburkholderia phenazinium*
SEQ ID NO 32 polypeptide derived from SEQ ID NO 31
SEQ ID NO 33 mature polypeptide obtained from *Paraburkholderia phenazinium*
SEQ ID NO 34 motif [G]X[FY][LYF]D
SEQ ID NO 35 motif AYX[SET]XX[EAS]
SEQ ID NO 36 signal peptide MKKPLGKIVASTALLISVAFSSSIASA
SEQ ID NO 37 HHHHHHPR His-tag
SEQ ID NO 38 DNA encoding full length polypeptide from Microbial community
SEQ ID NO 39 polypeptide derived from SEQ ID NO 38

SEQ ID NO 40 mature polypeptide obtained from Microbial community
SEQ ID NO 41 DNA encoding full length polypeptide from *Myxococcus virescens*
SEQ ID NO 42 polypeptide derived from SEQ ID NO 40
SEQ ID NO 43 mature polypeptide obtained from *Myxococcus virescens*
SEQ ID NO 44 DNA encoding full length polypeptide from *Myxococcus fulvus*
SEQ ID NO 45 polypeptide derived from SEQ ID NO 43
SEQ ID NO 46 mature polypeptide obtained from *Myxococcus fulvus*
SEQ ID NO 47 DNA encoding full length polypeptide from *Myxococcus macrosporus*
SEQ ID NO 48 polypeptide derived from SEQ ID NO 47
SEQ ID NO 49 mature polypeptide obtained from *Myxococcus macrosporus*
SEQ ID NO 50 DNA encoding full length polypeptide from *Myxococcus stipitatus*
SEQ ID NO 51 polypeptide derived from SEQ ID NO 50
SEQ ID NO 52 mature polypeptide obtained from *Myxococcus stipitatus*
SEQ ID NO 53 DNA encoding full length polypeptide from *Myxococcus macrosporus*
SEQ ID NO 54 polypeptide derived from SEQ ID NO 53
SEQ ID NO 55 mature polypeptide obtained from *Myxococcus macrosporus*
SEQ ID NO 56 DNA encoding full length polypeptide from *Pseudomonas seleniipraecipitans*
SEQ ID NO 57 polypeptide derived from SEQ ID NO 56
SEQ ID NO 58 mature polypeptide obtained from *Pseudomonas seleniipraecipitans*
SEQ ID NO 59 DNA encoding full length polypeptide from *Pseudomonas migulae*
SEQ ID NO 60 polypeptide derived from SEQ ID NO 59
SEQ ID NO 61 mature polypeptide obtained from *Pseudomonas migulae*
SEQ ID NO 62 DNA encoding full length polypeptide from *Pseudomonas corrugata*
SEQ ID NO 63 polypeptide derived from SEQ ID NO 62
SEQ ID NO 64 mature polypeptide obtained from *Pseudomonas corrugata*
SEQ ID NO 65 DNA encoding full length polypeptide from *Pseudomonas pelagia*
SEQ ID NO 66 polypeptide derived from SEQ ID NO 65
SEQ ID NO 67 mature polypeptide obtained from *Pseudomonas pelagia*
SEQ ID NO 68 DNA encoding full length polypeptide from *Pseudomonas aeruginosa* PAO1
SEQ ID NO 69 polypeptide derived from SEQ ID NO 68
SEQ ID NO 70 mature polypeptide obtained from *Pseudomonas aeruginosa* PAO1
SEQ ID NO 71 DNA encoding full length polypeptide from *Streptomyces griseofuscus*
SEQ ID NO 72 polypeptide derived from SEQ ID NO 71
SEQ ID NO 73 mature polypeptide obtained from *Streptomyces griseofuscus*
SEQ ID NO 74 DNA encoding full length polypeptide from *Lysinibacillus xylanilyticus*
SEQ ID NO 75 polypeptide derived from SEQ ID NO 74
SEQ ID NO 76 mature polypeptide obtained from *Lysinibacillus xylanilyticus*
SEQ ID NO 77 DNA encoding full length polypeptide from *Tumebacillus ginsengisoli*
SEQ ID NO 78 polypeptide derived from SEQ ID NO 77
SEQ ID NO 79 mature polypeptide obtained from *Tumebacillus ginsengisoli*
SEQ ID NO 80 DNA encoding full length polypeptide from *Lysinibacillus boronitolerans*
SEQ ID NO 81 polypeptide derived from SEQ ID NO 80
SEQ ID NO 82 mature polypeptide obtained from *Lysinibacillus boronitolerans*
SEQ ID NO 83 DNA encoding full length polypeptide from *Microbulbifer hydrolyticus*
SEQ ID NO 84 polypeptide derived from SEQ ID NO 83
SEQ ID NO 85 mature polypeptide obtained from *Microbulbifer hydrolyticus*
SEQ ID NO 86 DNA encoding full length polypeptide from *Carnobacterium inhibens* subsp. *gilichinskyi*
SEQ ID NO 87 polypeptide derived from SEQ ID NO 86
SEQ ID NO 88 mature polypeptide obtained from *Carnobacterium inhibens* subsp. *gilichinskyi*
SEQ ID NO 89 DNA encoding full length polypeptide from environmental bacterial community
SEQ ID NO 90 polypeptide derived from SEQ ID NO 89
SEQ ID NO 91 mature polypeptide obtained from environmental bacterial community
SEQ ID NO 92 DNA encoding full length polypeptide from *Pseudomonas composti*
SEQ ID NO 93 polypeptide derived from SEQ ID NO 92
SEQ ID NO 94 mature polypeptide obtained from *Pseudomonas composti*
SEQ ID NO 95 mature polypeptide obtained from *Paraburkholderia phenazinium*
SEQ ID NO 96 mature polypeptide obtained from *Burkholderia* sp-63093
SEQ ID NO 97: motif GXXGX[FY][LYFI]
SEQ ID NO 98: motif [ILFQV]N[RW]G[FL]
SEQ ID NO 99: motif DTLDS[YF]
SEQ ID NO 100: motif G[VL]FLDTLDSF[QTH]L[LMQ]
SEQ ID NO 101: motif DT[VIMA][GD][DNW][VIL][DEN]
SEQ ID NO 102: motif [SETC]IG[EQA][ALI]EXY
SEQ ID NO 103: motif [QL]N[AS]PEL
SEQ ID NO 104: motif [KLYMQ]XX[PV]QN[SA]PE Definitions Activity: The present inventions relates to glycosyl hydrolases (EC 3.2.1.-), which are a widespread group of enzymes that hydrolyse the glyosidic bond between two or more carbohydrates or between a carbohydrate and a non-carbohydrate moiety. A classification of glycoside hydrolases in families based on amino acid sequence similarities has been proposed. The polypeptides of the invention comprise at least one glycosyl hydrolase domain and are in the present context defined as glycosyl hydrolases. Thus, polypeptides of the invention hydrolyse glyosidic bonds and the polypeptide of the invention have hydrolytic activity. The glycosyl hydrolase domain comprised in the polypeptide of the invention may be classified as a Glyco_hydro_114 (Pfam domain id PF03537, Pfam version 31.0 Finn (2016). Nucleic Acids Research, Database Issue 44:D279-D285). The polypeptides of the invention may further comprise a polysaccharide deacetylase domain (CE4) and in a preferred embodiment the polypeptides of the invention have hydrolytic and/or deacetylase activity. Polypeptides according to the invention having hydrolytic and/or deacetylase activity includes Glyco_hydro_114 glycosyl hydrolases. A Glyco_hydro_114 glycosyl hydrolase is in the context of the present invention a glycosyl hydrolase comprising glycosyl hydrolase domain (DUF297), which here is termed Glyco_hydro_114 (Pfam domain id PF03537, Pfam version 31.0 Finn (2016). The Glyco_hydro_114 glycosyl hydrolase domain is located at position 9 to 218 in SEQ ID NO 3, at position 14 to 247 in SEQ ID NO 6, at position 222 to 420 in SEQ ID NO 9, at position 18 to 229 in SEQ ID NO 76, at position 31 to 241 in SEQ ID NO 79, at position 14 to 226 in SEQ ID NO 82, at position 56 to 199 in SEQ ID NO 73, at position 12 to 221 in SEQ ID NO 15, at position 205 to 427 in SEQ ID NO 18, at position 206 to 428 in SEQ ID NO 12, at position 6 to 204 in SEQ ID NO 21, at position 11 to 237 in SEQ ID NO 24, at position 16 to 240 in SEQ ID NO 27, at position 10 to 243 in SEQ ID NO 30, at position 22 to 231 in SEQ ID NO 33, at position 9 to 218 in SEQ ID NO 40, at position 205 to 427 in SEQ ID NO 43, at position 202 to 424 in SEQ ID NO 46, at position 213 to 435 in SEQ ID NO 49, at position 207 to 429 in SEQ ID NO 52, at position 213 to 435 in SEQ ID NO 55, at position 60 to 269 in SEQ ID NO 58, at position 9 to 218 in SEQ ID NO 61, at position 9 to 218 in SEQ ID NO 64, at position 10 to 219 in SEQ ID NO 67, at position 6 to 215 in SEQ ID NO 70, at position 181 to 310 in SEQ ID NO 85, at position 27 to 226 in SEQ ID NO 88, at position 173 to 292 in SEQ ID NO 91, at position 5 to 210 in SEQ ID NO 94, at position 22 to 231 in SEQ ID NO 95, at position 12 to 221 in SEQ ID NO 96. The polypeptides of the invention are glycosyl hydrolases preferably Glyco_hydro_114 glycosyl hydrolases. In one preferred embodiment, the polypeptides of the invention are endo-alpha-1,4-polygalactosaminidases. The polypeptides of the invention have at least hydrolytic activity to glyosidic bond and may also have deacetylase activity. In the context of the present invention the Glyco_hydro_114 glycosyl hydrolase is a PelA enzyme, which is active towards the polysaccharide pel, present in many biofilms. The pellicle (PEL) polysaccharide is synthesized e.g. by *Pseudomonas aeruginosa* and is an important biofilm constituent critical for bacterial virulence and persistence. Pel is a cationic polymer composed of partially acetylated 1→4 glycosidic linkages of N-acetylgalactosamine and N-acetylglucosamine that promotes cell-cell interactions within the biofilm matrix through electrostatic interactions with extracellular DNA (Jennings et al. PNAS September 2015, vol. 112, no 36, 11353-11358; Marmont et. al. J Biol Chem. 2017 Nov. 24; 292(47):19411-19422. 2017).

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Biofilm: A biofilm is organic matter produced by any group of microorganisms in which cells stick to each other or stick to a surface, such as a textile, dishware or hard surface or another kind of surface. These adherent cells are frequently embedded within a self-produced matrix of extracellular polymeric substance (EPS). Biofilm EPS is a polymeric conglomeration generally composed of extracellular DNA, proteins, and polysaccharides. Biofilms may form on living or non-living surfaces. The microbial cells growing in a biofilm are physiologically distinct from planktonic cells of the same organism, which, by contrast, are single-cells that may float or swim in a liquid medium. Bacteria living in a biofilm usually have significantly different properties from planktonic bacteria of the same species, as the dense and protected environment of the film allows them to cooperate and interact in various ways. One benefit of this environment for the microorganisms is increased resistance to detergents and antibiotics, as the dense extracellular matrix and the outer layer of cells protect the interior of the community. On laundry biofilm or EPS producing bacteria can be found among the following species: *Acinetobacter* sp., *Aeromicrobium* sp., *Brevundimonas* sp., *Microbacterium* sp., *Micrococcus luteus*, *Pseudomonas* sp., *Staphylococcus epidermidis*, and *Stenotrophomonas* sp. In one aspect, the biofilm producing strain is *Pseudomonas*. In one aspect, the EPS producing strain is *Pseudomonas aeruginosa*, *Pseudomonas alcaliphila* or *Pseudomonas fluorescens*. In one embodiment, the biofilm is caused by microorganisms or group of microorganisms which produce Pel. In another embodiment, the biofilm produce a polysaccharide that is degradable by the Glyco_hydro_114 glycosyl hydrolases of the invention. The biofilm that may be formed on the surface e.g. such as textiles may be caused by any microorganism or group of microorganisms that forms PelA-dependent biofilm including but not limited to; *Acinetobacter* sp., *Aeromicrobium* sp., *Brevundimonas* sp., *Microbacterium* sp., *Micrococcus luteus*, *Staphylococcus epidermidis*, *Staphylococcus aureus*, *Pseudomonas* sp., *Pseudomonas aeruginosa*, *Pseudomonas alcaliphila*, *Pseudomonas fluorescens*, *Stenotrophomonas* sp., *Paraburkholderia*, *Burkolderia* sp., *Candida* sp., *Bordetella pertussis Yersinia pestis*, *Escherichia coli* and *Aspergillus* sp.

Catalytic domain: The term "catalytic domain" means the region of an enzyme containing the catalytic machinery of the enzyme.

Clade: A clade is a group of polypeptides clustered together on the basis of homologous features traced to a common ancestor. Polypeptide clades can be visualized as phylogenetic trees and a clade is a group of polypeptides that consists of a common ancestor and all its lineal descendants. Example 5 describes generation of phylogenetic trees.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Deep cleaning: The term "deep cleaning" means disruption, reduction or removal of organic components such as polysaccharides e.g. Pel, proteins, DNA, soil or other components present in organic matter such as biofilm.

Cleaning component: The cleaning component e.g. a detergent adjunct ingredient is different to the polypeptides of this invention. The precise nature of these additional cleaning or adjunct components, and levels of incorporation thereof, will depend on the physical form of the composition and the nature of the operation for which it is to be used. Suitable cleaning components include, but are not limited to the components described below such as surfactants, builders, flocculating aid, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric agents, clay soil removal/anti-redeposition agents, brighteners, suds suppressors, dyes, perfumes, structure elasticizing agents, fabric softeners, carriers, hydrotropes, builders and co-builders, fabric huing agents, anti-foaming agents, dispersants, processing aids, and/or pigments.

Cleaning Composition: The term cleaning composition includes "detergent composition" and refers to compositions that find use in the removal of undesired compounds from items to be cleaned, such as textiles. The detergent composition may be used to e.g. clean textiles for both household cleaning and industrial cleaning. The terms encompass any materials/compounds selected for the particular type of cleaning composition desired and the form of the product (e.g., liquid, gel, powder, granulate, paste, or spray compositions) and includes, but is not limited to, detergent compositions (e.g., liquid and/or solid laundry detergents and fine fabric detergents; fabric fresheners; fabric softeners; and textile and laundry pre-spotters/pretreatment). In addition to containing the enzyme of the invention, the detergent formulation may contain one or more additional enzymes (such as proteases, amylases, lipases, cutinases, cellulases, endoglucanases, xyloglucanases, pectinases, pectin lyases, xanthanases, peroxidases, haloperoxygenases, catalases and mannanases, or any mixture thereof), and/or detergent adjunct ingredients such as surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, and solubilizers.

Enzyme Detergency benefit: The term "enzyme detergency benefit" is defined herein as the advantageous effect an enzyme may add to a detergent compared to the same detergent without the enzyme. Important detergency benefits which can be provided by enzymes are stain removal with no or very little visible soils after washing and/or cleaning, prevention or reduction of redeposition of soils released in the washing process (an effect that also is termed anti-redeposition), restoring fully or partly the whiteness of textiles which originally were white but after repeated use and wash have obtained a greyish or yellowish appearance (an effect that also is termed whitening). Textile care benefits, which are not directly related to catalytic stain removal or prevention of redeposition of soils, are also important for enzyme detergency benefits. Examples of such textile care benefits are prevention or reduction of dye transfer from one fabric to another fabric or another part of the same fabric (an effect that is also termed dye transfer inhibition or anti-backstaining), removal of protruding or broken fibers from a fabric surface to decrease pilling tendencies or remove already existing pills or fuzz (an effect that also is termed anti-pilling), improvement of the fabric-softness, colour clarification of the fabric and removal of particulate soils which are trapped in the fibers of the fabric or garment. Enzymatic bleaching is a further enzyme detergency benefit where the catalytic activity generally is used to catalyze the formation of bleaching components such as hydrogen peroxide or other peroxides.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide or a catalytic domain having one or more (e.g., several) amino acids absent from the amino and/or carboxyl terminus of a mature polypeptide or domain; wherein the fragment has activity.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance). An isolated substance may be present in a fermentation broth sample; e.g. a host cell may be genetically modified to express the polypeptide of the invention. The fermentation broth from that host cell will comprise the isolated polypeptide.

Improved wash performance: The term "improved wash performance" is defined herein as an enzyme displaying an increased wash performance in a detergent composition relative to the wash performance of same detergent composition without the enzyme e.g. by increased stain removal or less re-deposition. The term "improved wash performance" includes wash performance in laundry.

Laundering: The term "laundering" relates to both household laundering and industrial laundering and means the process of treating textiles with a solution containing a cleaning or detergent composition of the present invention. The laundering process can for example be carried out using e.g. a household or an industrial washing machine or can be carried out by hand.

Malodor: By the term "malodor" is meant an odor which is not desired on clean items. The cleaned item should smell fresh and clean without malodors adhered to the item. One example of malodor is compounds with an unpleasant smell, which may be produced by microorganisms. Another example is unpleasant smells can be sweat or body odor adhered to an item which has been in contact with human or animal. Another example of malodor can be the odor from spices, which sticks to items for example curry or other exotic spices which smells strongly.

Mature polypeptide: The term "mature polypeptide" means a polypeptide in its final form following translation and any post-translational modifications, such as N-terminal processing, C-terminal truncation, glycosylation, phosphorylation, etc. In some aspects, the mature polypeptide is amino acids 1 to 904 of SEQ ID NO 2 and amino acids −32 to −1 of SEQ ID NO 2 is a signal peptide. In some aspects, the mature polypeptide is the amino acid sequence shown in SEQ ID NO 3. In some aspects, the mature polypeptide is amino acids 1 to 281 of SEQ ID NO 5 and amino acids −21 to −1 of SEQ ID NO 5 is a signal peptide. In some aspects, the mature polypeptide is the amino acid sequence shown in SEQ ID NO 6. In some aspects, the mature polypeptide is amino acids 1 to 458 of SEQ ID NO 8 and amino acids −18 to −1 of SEQ ID NO 8 is a signal peptide. In some aspects, the mature polypeptide is the amino acid sequence having SEQ ID NO 9. In some aspects, the mature polypeptide is amino acids 1 to 468 of SEQ ID NO 11 and amino acids −26 to −1 of SEQ ID NO 11 is a signal peptide. In some aspects, the mature polypeptide is the amino acid sequence having SEQ ID NO 12. In some aspects, the mature polypeptide is amino acids 1 to 266 of SEQ ID NO 14 and amino acids −45 to −1 of SEQ ID NO 14 is a signal peptide. In some aspects, the mature polypeptide is the amino acid sequence having SEQ ID NO 15. In some aspects, the mature polypeptide is amino acids 1 to 467 of SEQ ID NO 17 and amino acids −28 to −1 of SEQ ID NO 17 is a signal peptide. In some aspects, the mature polypeptide is the amino acid sequence having SEQ ID NO 18. In some aspects, the mature polypeptide is amino acids 1 to 882 of SEQ ID NO 20 and amino acids −16 to −1 of SEQ ID NO 20 is a signal peptide. In some aspects, the mature polypeptide is the amino acid sequence having SEQ ID NO 21. In some aspects, the mature polypeptide is amino acids 1 to 279 of SEQ ID NO 23 and amino acids −21 to −1 of SEQ ID NO 23 is a signal peptide. In some aspects, the mature polypeptide is the amino acid sequence having SEQ ID NO 24. In some aspects, the mature polypeptide is amino acids 1 to 276 of SEQ ID NO 26 and amino acids −22 to −1 of SEQ ID NO 26 is a signal peptide. In some aspects, the mature polypeptide is the amino acid sequence having SEQ ID NO 27. In some aspects, the mature polypeptide is amino acids 1 to 277 of SEQ ID NO 29 and amino acids −26 to −1 of SEQ ID NO 29 is a signal peptide. In some aspects, the mature polypeptide is the amino acid sequence having SEQ ID NO 30. In some aspects, the mature polypeptide is amino acids 1 to 271 of SEQ ID NO 32 and amino acids −29 to −1 of SEQ ID NO 32 is a signal peptide. In some aspects, the mature polypeptide is the amino acid sequence having SEQ ID NO 33. In some aspects, the mature polypeptide is amino acids 1 to 905 of SEQ ID NO 39 and amino acids −32 to −1 of SEQ ID NO 39 is a signal peptide. In some aspects, the mature polypeptide is the amino acid sequence having SEQ ID NO 40. In some aspects, the mature polypeptide is amino acids 1 to 467 of SEQ ID NO 42 and amino acids −28 to −1 of SEQ ID NO 42 is a signal peptide. In some aspects, the mature polypeptide is the amino acid sequence having SEQ ID NO 43. In some aspects, the mature polypeptide is amino acids 1 to 464 of SEQ ID NO 45 and amino acids −18 to −1 of SEQ ID NO 45 is a signal peptide. In some aspects, the mature polypeptide is the amino acid sequence having SEQ ID NO 46. In some aspects, the mature polypeptide is amino acids 1 to 475 of SEQ ID NO 48 and amino acids −24 to −1 of SEQ ID NO 48 is a signal peptide. In some aspects, the mature polypeptide is the amino acid sequence having SEQ ID NO 49. In some aspects, the mature polypeptide is amino acids 1 to 469 of SEQ ID NO 51 and amino acids −24 to −1 of SEQ ID NO 51 is a signal peptide. In some aspects, the mature polypeptide is the amino acid sequence having SEQ ID NO 52. In some aspects, the mature polypeptide is amino acids 1 to 475 of SEQ ID NO 54 and amino acids −24 to −1 of SEQ ID NO 54 is a signal peptide. In some aspects, the mature polypeptide is the amino acid sequence having SEQ ID NO 55. In some aspects, the mature polypeptide is amino acids 1 to 906 of SEQ ID NO 57 and amino acids −49 to −1 of SEQ ID NO 57 is a signal peptide. In some aspects, the mature polypeptide is the amino acid sequence having SEQ ID NO 58. In some aspects, the mature polypeptide is amino acids 1 to 905 of SEQ ID NO 60 and amino acids −32 to −1 of SEQ ID NO 60 is a signal peptide. In some aspects, the mature polypeptide is the amino acid sequence having SEQ ID NO 61. In some aspects, the mature polypeptide is amino acids 1 to 905 of SEQ ID NO 63 and amino acids −32 to −1 of SEQ ID NO 63 is a signal peptide. In some aspects, the mature polypeptide is the amino acid sequence having SEQ ID NO 64. In some aspects, the mature polypeptide is amino acids 1 to 906 of SEQ ID NO 66 and amino acids −31 to −1 of SEQ ID NO 66 is a signal peptide. In some aspects, the mature polypeptide is the amino acid sequence having SEQ ID NO 67. In some aspects, the mature polypeptide is amino acids 1 to 257 of SEQ ID NO 69 and in some aspects, the mature polypeptide is the amino acid sequence having SEQ ID NO 70. In some aspects, the mature polypeptide is amino acids 1 to 269 of SEQ ID NO 72 and amino acids −43 to −1 of SEQ ID NO 72 is a signal peptide. In some aspects, the mature polypeptide is the amino acid sequence having SEQ ID NO 73. In some aspects, the mature polypeptide is amino acids 1 to 260 of SEQ ID NO 75 and amino acids −26 to −1 of SEQ ID NO 75 is a signal peptide. In some aspects, the mature polypeptide is the amino acid sequence having SEQ ID NO 76. In some aspects, the mature polypeptide is amino acids 1 to 275 of SEQ ID NO 78 and amino acids −30 to −1 of SEQ ID NO 78 is a signal peptide. In some aspects, the mature polypeptide is the amino acid sequence having SEQ ID NO 79. In some aspects, the mature polypeptide is amino acids 1 to 268 of SEQ ID NO 81 and amino acids −28 to −1 of SEQ ID NO 81 is a signal peptide. In some aspects, the mature polypeptide is the amino acid sequence having SEQ ID NO 82. In some aspects, the mature polypeptide is amino acids 1 to 313 of SEQ ID NO 84 and amino acids −16 to −1 of SEQ ID NO 84 is a signal peptide. In some aspects, the mature polypeptide is the amino acid sequence having SEQ ID NO 85. In some aspects, the mature polypeptide is amino acids 1 to 257 of SEQ ID NO 87 and amino acids −24 to −1 of SEQ ID NO 87 is a signal peptide. In some aspects, the mature polypeptide is the amino acid sequence having SEQ ID NO 88. In some aspects, the mature polypeptide is amino acids 1 to 296 of SEQ ID NO 90 and amino acids −24 to −1 of SEQ ID NO 90 is a signal peptide. In some aspects, the mature polypeptide is the amino acid sequence having SEQ ID NO 91. In some aspects, the mature polypeptide is amino acids 1 to 897 of SEQ ID NO 93 and amino acids −26 to −1 of SEQ ID NO 93 is a signal peptide. In some aspects, the mature polypeptide is the amino acid sequence having SEQ ID NO 94. In some aspects, the mature polypeptide is amino acids 1 to 271 of SEQ ID NO 95. In some aspects, the mature polypeptide is the amino acid sequence having SEQ ID NO 95. In some aspects, the mature polypeptide is amino acids 1 to 271 of SEQ ID NO 96. In some aspects, the mature polypeptide is the amino acid sequence having SEQ ID NO 96.

It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide having activity. In one aspect, the mature polypeptide coding sequence is nucleotides 97 to 2808 of SEQ ID NO 1 and nucleotides 1 to 96 of SEQ ID NO 1 encodes a signal peptide. In one aspect, the mature polypeptide coding sequence is nucleotides 64 to 906 of SEQ ID NO 4 and nucleotides 1 to 63 of SEQ ID NO 4 encodes a signal peptide. In one aspect, the mature polypeptide coding sequence is nucleotides 55 to 1428 of SEQ ID NO 7 and nucleotides 1 to 54 of SEQ ID NO 7 encodes a signal peptide. In one aspect, the mature polypeptide coding sequence is nucleotides 79 to 1482 of SEQ ID NO 10 and nucleotides 1 to 78 of SEQ ID NO 10 encodes a signal peptide. In one aspect, the mature polypeptide coding sequence is nucleotides 136 to 933 of SEQ ID NO 13 and nucleotides 1 to 135 of SEQ ID NO 13 encodes a signal peptide. In one aspect, the mature polypeptide coding sequence is nucleotides 85 to 1485 of SEQ ID NO 16 and nucleotides 1 to 84 of SEQ ID NO 16 encodes a signal peptide. In one aspect, the mature polypeptide coding sequence is nucleotides 49 to 2694 of SEQ ID NO 19 and nucleotides 1 to 48 of SEQ ID NO 19 encodes a signal peptide. In one aspect, the mature polypeptide coding sequence is nucleotides 64 to 900 of SEQ ID NO 22 and nucleotides 1 to 63 of SEQ ID NO 22 encodes a signal peptide. In one aspect, the mature polypeptide coding sequence is nucleotides 67 to 894 of SEQ ID NO 25 and nucleotides 1 to 66 of SEQ ID NO 25 encodes a signal peptide. In one aspect, the mature polypeptide coding sequence is nucleotides 79 to 909 of SEQ ID NO 28 and nucleotides 1 to 78 of SEQ ID NO 28 encodes a signal peptide. In one aspect, the mature polypeptide coding sequence is nucleotides 88 to 900 of SEQ ID NO 31 and nucleotides 1 to 87 of SEQ ID NO 31 encodes a signal peptide.

In one aspect, the mature polypeptide coding sequence is nucleotides 97 to 2811 of SEQ ID NO 38 and nucleotides 1 to 96 of SEQ ID NO 38 encodes a signal peptide. In one aspect, the mature polypeptide coding sequence is nucleotides 85 to 1485 of SEQ ID NO 41 and nucleotides 1 to 84 of SEQ ID NO 41 encodes a signal peptide. In one aspect, the mature polypeptide coding sequence is nucleotides 55 to 1446 of SEQ ID NO 44 and nucleotides 1 to 54 of SEQ ID NO 44 encodes a signal peptide. In one aspect, the mature polypeptide coding sequence is nucleotides 73 to 1497 of SEQ ID NO 47 and nucleotides 1 to 72 of SEQ ID NO 47 encodes a signal peptide. In one aspect, the mature polypeptide coding sequence is nucleotides 73 to 1479 of SEQ ID NO 50 and nucleotides 1 to 72 of SEQ ID NO 50 encodes a signal peptide. In one aspect, the mature polypeptide coding sequence is nucleotides 73 to 1497 of SEQ ID NO 53 and nucleotides 1 to 72 of SEQ ID NO 53 encodes a signal peptide. In one aspect, the mature polypeptide coding sequence is nucleotides 148 to 2865 of SEQ ID NO 56 and nucleotides 1 to 147 of SEQ ID NO 56 encodes a signal peptide. In one aspect, the mature polypeptide coding sequence is nucleotides 97 to 2811 of SEQ ID NO 59 and nucleotides 1 to 96 of SEQ ID NO 59 encodes a signal peptide. In one aspect, the mature polypeptide coding sequence is nucleotides 97 to 2811 of SEQ ID NO 62 and nucleotides 1 to 96 of SEQ ID NO 62 encodes a signal peptide. In one aspect, the mature polypeptide coding sequence is nucleotides 94 to 2811 of SEQ ID NO 65 and nucleotides 1 to 93 of SEQ ID NO 65 encodes a signal peptide. In one aspect, the mature polypeptide coding sequence is nucleotides 1 to 771 of SEQ ID NO 68. In one aspect, the mature polypeptide coding sequence is nucleotides 130 to 936 of SEQ ID NO 71 and nucleotides 1 to 129 of SEQ ID NO 71 encodes a signal peptide. In one aspect, the mature polypeptide coding sequence is nucleotides 79 to 858 of SEQ ID NO 74 and nucleotides 1 to 78 of SEQ ID NO 74 encodes a signal peptide. In one aspect, the mature polypeptide coding sequence is nucleotides 91 to 915 of SEQ ID NO 77 and nucleotides 1 to 90 of SEQ ID NO 77 encodes a signal peptide. In one aspect, the mature polypeptide coding sequence is nucleotides 85 to 888 of SEQ ID NO 80 and nucleotides 1 to 84 of SEQ ID NO 80 encodes a signal peptide. In one aspect, the mature polypeptide coding sequence is nucleotides 49 to 987 of SEQ ID NO 83 and nucleotides 1 to 48 of SEQ ID NO 83 encodes a signal peptide. In one aspect, the mature polypeptide coding sequence is nucleotides 73 to 843 of SEQ ID NO 86 and nucleotides 1 to 72 of SEQ ID NO 86 encodes a signal peptide. In one aspect, the mature polypeptide coding sequence is nucleotides 73 to 960 of SEQ ID NO 89 and nucleotides 1 to 72 of SEQ ID NO 89 encodes a signal peptide. In one aspect, the mature polypeptide coding sequence is nucleotides 79 to 2769 of SEQ ID NO 92 and nucleotides 1 to 78 of SEQ ID NO 92 encodes a signal peptide.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Nomenclature: For purposes of the present invention, the nomenclature [E/Q] means that the amino acid at this position may be a glutamic acid (Glu, E) or a glutamine (Gln, Q). Likewise, the nomenclature [V/G/A/I] means that the amino acid at this position may be a valine (Val, V), glycine (Gly, G), alanine (Ala, A) or isoleucine (Ile, I), and so forth for other combinations as described herein. Unless otherwise limited further, the amino acid X is defined such that it may be any of the 20 natural amino acids.

Operably linked: The term "operably linked" means a configuration in which a control sequence is placed at an appropriate position relative to the coding sequence of a polynucleotide such that the control sequence directs expression of the coding sequence.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment–
Total Number of Gaps in Alignment)

Variant: The term "variant" means a polypeptide having hydrolase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

DETAILED DESCRIPTION OF THE INVENTION

Various enzymes are applied in cleaning processes each targeting specific types of soiling such as protein, starch and grease soiling. Enzymes are now standard ingredients in detergents for laundry and dish wash. The effectiveness of these commercial enzymes provides detergents which removes much of the soiling. However, organic matters such as EPS (extracellular polymeric substance) comprised in much biofilm constitute a challenging type of soiling due to the complex nature of such organic matters. None of the commercially available detergents effectively remove or reduce EPS related soiling. Biofilm is produced by a group of microorganisms in which cells stick to each other or stick to a surface, such as a textile, dishware or hard surface or another kind of surface. These adherent cells are frequently embedded within a self-produced matrix of extracellular polymeric substance (EPS), which constitute 50% to 90% of the biofilm's total organic matter. EPS is mostly composed of polysaccharides (exopolysaccharides) and proteins, but include other macro-molecules such as DNA, lipids and human substances. EPS is the construction material of bacterial settlements and either remain attached to the cell's outer surface, or is secreted into its growth medium. EPS is required for the development and integrity of biofilms produced by a wide variety of bacteria. The inventors have shown that the Glyco_hydro_114 polypeptides comprising the Glyco_hydro_114 glycosyl hydrolase domain and/or the deacetylase CE4 domain have hydrolytic activity to the exopolysaccharide Pel and thus having the potential to reduce or remove components of EPS and thus reduce or remove EPS related soiling of e.g. textiles. It is well known that polypeptides deriving from organisms may share common structural elements, which can be identified by comparing the primary structures e.g. amino acid sequences and grouping the polypeptides according to sequence homology. However, common structural elements may also be identified by comparing the three-dimensional (3D) structure of various polypeptides. Both approaches have been applied in the present invention.

These approaches identified polypeptides, which derive from organisms from divergent taxonomic groups but share structural elements common for the identified group.

The polypeptides of the invention comprise a domain termed here as CE4_PelA_like domain, which are represented by a protein PelA that is encoded by a gene in the pelA-G gene cluster for pellicle production and biofilm formation in *Pseudomonas aeruginosa*. PelA and most of the family members contain a domain of unknown function, DUF297 (PF03537), in the N-terminus and a C-terminal domain that shows high sequence similarity to the catalytic domain of the six-stranded barrel rhizobial NodB-like proteins, which remove N-linked or O-linked acetyl groups from cell wall polysaccharides and belong to the larger carbohydrate esterase 4 (CE4) superfamily. The polypeptides of the present invention comprise the Glyco_hydro_114 domain and several motifs. One example is GX[FY][LYF]D (SEQ ID NO 34) situated in positions corresponding to positions 113 to 117 in *Pseudomonas* sp-62208 (SEQ ID NO 3). Another motif which may be comprised by the polypeptides of the invention is AYX[SET]XX[EAS] (SEQ ID NO 35) situated in positions corresponding to positions 53 to 58 in *Pseudomonas* sp-62208 (SEQ ID NO 3). The polypeptides in Glyco_hydro_114 can be separated into distinct sub-clusters, where we denoted one sub-cluster comprising the motif GX[FY][LYF]D (SEQ ID NO 34) or the motif GXXGX[FY][LYFI]D (SEQ ID NO 97) as family FLD. Another motif characteristic of this domain is AYX[SET]XX[EAS] (SEQ ID NO 35).

One embodiment of the invention relates a glycosyl hydrolase, preferably a Glyco_hydro_114 glycosyl hydrolase polypeptide comprising the DUF297 domain and preferably comprising one, two or all three of the motifs GX[FY][LYF]D (SEQ ID NO 34), AYX[SET]XX[EAS] (SEQ ID NO 35) or GXXGX[FY][LYFI]D (SEQ ID NO 97), wherein the polypeptide has hydrolytic activity, and wherein the polypeptide is selected from the group consisting of:

(a) a polypeptide having at least 60%, at least 70%, at least 75%, at least 80%, at least 85%, at least 90%, at least 95%, at least 96%, at least 97%, at least 98%, at least 99% or 100% sequence identity to the polypeptide of SEQ ID NO 3;

(b) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 6;

(c) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 9;

(d) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 12;

(e) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 15;

(f) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 18;

(g) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 21;

(h) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 24;

(i) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 27;

(j) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 30;

(k) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 33;

(l) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 40;

(m) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 43;

(n) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 46;

(o) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 49;

(p) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 52;

(q) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 55;

(r) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 58;

(s) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 61;

(t) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 64;

(u) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 67;

(v) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 70;

(w) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 73;

(x) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 76;

(y) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 79;

(z) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 82;

(aa) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 85;

(bb) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 88;

(cc) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 91;

(dd) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 94;

(ee) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 95; and (ff) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 96.

The polypeptides of the invention preferably belong to the cluster FLD, which comprises the a glycosyl hydrolytic domain Glyco_hydro_114 and have hydrolytic activity. In some embodiment, the polypeptides additionally comprise a CE4 domain and have deacetylase activity.

The polypeptides of the FLD clade, which includes all PelA Glyco_hydro_114 glycosyl hydrolases comprising the amino acids sequence shown in SEQ ID NO 3, SEQ ID NO 6, SEQ ID NO 9, SEQ ID NO 12, SEQ ID NO 15, SEQ ID NO 18, SEQ ID NO 21, SEQ ID NO 24, SEQ ID NO 27, SEQ ID NO 30, SEQ ID NO 33, SEQ ID NO 40, SEQ ID NO 43, SEQ ID NO 46, SEQ ID NO 49, SEQ ID NO 52, SEQ ID NO 55, SEQ ID NO 58, SEQ ID NO 61, SEQ ID NO 64, SEQ ID NO 67, SEQ ID NO 70, SEQ ID NO 73, SEQ ID NO 76, SEQ ID NO 79, SEQ ID NO 82, SEQ ID NO 85, SEQ ID NO 88, SEQ ID NO 91, SEQ ID NO 94, SEQ ID NO 95 and SEQ ID NO 96. The FLD-clade (or polypeptides of the FLD-domain) may be divided in two further clades or sub-clades (see FIG. 3), which again may be divided into further sub-clades, see below. These sub-clades are termed NRG and IGEAE clades and comprises polypeptides of bacterial origin having hydrolase activity, wherein the polypeptides comprise a Glyco_hydro_114 domain and belong to the FLD clade.

The polypeptides of the NRG clade comprise the motif example [ILFQV]N[RW]G[FL] (SEQ ID NO 98), corresponding to amino acids FNRGF at positions 155 to 159 of SEQ ID NO 3 where N and G (corresponding to position 156 and 158 of SEQ ID NO 3) is fully conserved in NRG clade. Examples of polypeptides of the NRG clade includes SEQ ID NO 3, SEQ ID NO 9, SEQ ID NO 15, SEQ ID NO 21, SEQ ID NO 33, SEQ ID NO 40, SEQ ID NO 58, SEQ ID NO 61, SEQ ID NO 64, SEQ ID NO 67, SEQ ID NO 70, SEQ ID NO 76, SEQ ID NO 79, SEQ ID NO 82, SEQ ID NO 94, SEQ ID NO 95, and SEQ ID NO 96.

One embodiment of the invention relates a glycosyl hydrolase preferably a Glyco_hydro_114 glycosyl hydrolase comprising the motif [ILFQV]N[RW]G[FL] (SEQ ID NO 98), wherein the glycosyl hydrolase is selected from the group consisting of:

(a) a polypeptide having at least 60%, at least 70%, at least 75%, at least 80%, at least 85%, at least 90%, at least 95%, at least 96%, at least 97%, at least 98%, at least 99% or 100% sequence identity to the polypeptide of SEQ ID NO 3;

(b) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 9;

(c) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 15;

(d) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 21;

(e) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 33;

(f) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 40;

(g) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 58;

(h) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 61;

(i) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 64;

(j) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 67;

(k) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 70;

(l) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 76;

(m) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 79;

(n) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 82;

(o) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 94;

(p) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 95; and (q) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 96.

One preferred embodiment relates to a Glyco_hydro_114 glycosyl hydrolase comprising the motif [ILFQV]N[RW]G [FL] (SEQ ID NO 98), wherein the Glyco_hydro_114 glycosyl hydrolase is selected from the group consisting of:

(a) a polypeptide having at least 90%, at least 95%, at least 96%, at least 97%, at least 98%, at least 99% or 100% sequence identity to the polypeptide of SEQ ID NO 3;

(b) a polypeptide having at least 80%, at least 85%, at least 90%, at least 95%, at least 96%, at least 97%, at least 98%, at least 99% or 100% sequence identity to the polypeptide of SEQ ID NO 9;

(c) a polypeptide having at least 95%, at least 96%, at least 97%, at least 98%, at least 99% or 100% sequence identity to the polypeptide of SEQ ID NO 15;

(d) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 21;
(e) a polypeptide having at least 70%, at least 75%, at least 80%, at least 85%, at least 90%, at least 95%, at least 96%, at least 97%, at least 98%, at least 99% or 100% sequence identity to the polypeptide of SEQ ID NO 33;
(f) a polypeptide having 100% sequence identity to the polypeptide of SEQ ID NO 40;
(g) a polypeptide having at least 75%, at least 80%, at least 85%, at least 90%, at least 95%, at least 96%, at least 97%, at least 98%, at least 99% or 100% sequence identity to the polypeptide of SEQ ID NO 58;
(h) a polypeptide having at least 95%, at least 96%, at least 97%, at least 98%, at least 99% or 100% sequence identity to the polypeptide of SEQ ID NO 61;
(i) a polypeptide having at least 90%, at least 95%, at least 96%, at least 97%, at least 98%, at least 99% or 100% sequence identity to the polypeptide of SEQ ID NO 64;
(j) a polypeptide having at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 67;
(k) a polypeptide having at least 96%, at least 97%, at least 98%, at least 99% or 100% sequence identity to the polypeptide of SEQ ID NO 76;
(l) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 79;
(m) a polypeptide having at least 95%, at least 96%, at least 97%, at least 98%, at least 99% or 100% sequence identity to the polypeptide of SEQ ID NO 82;
(n) a polypeptide having at least 80%, at least 85%, at least 90%, at least 95%, at least 96%, at least 97%, at least 98%, at least 99% or 100% sequence identity to the polypeptide of SEQ ID NO 94;
(o) a polypeptide having at least 70%, at least 75%, at least 80%, at least 85%, at least 90%, at least 95%, at least 96%, at least 97%, at least 98%, at least 99% or 100% sequence identity to the polypeptide of SEQ ID NO 95; and
(p) a polypeptide having at least 95%, at least 96%, at least 97%, at least 98%, at least 99% or 100% sequence identity to the polypeptide of SEQ ID NO 96.

Figure 3:
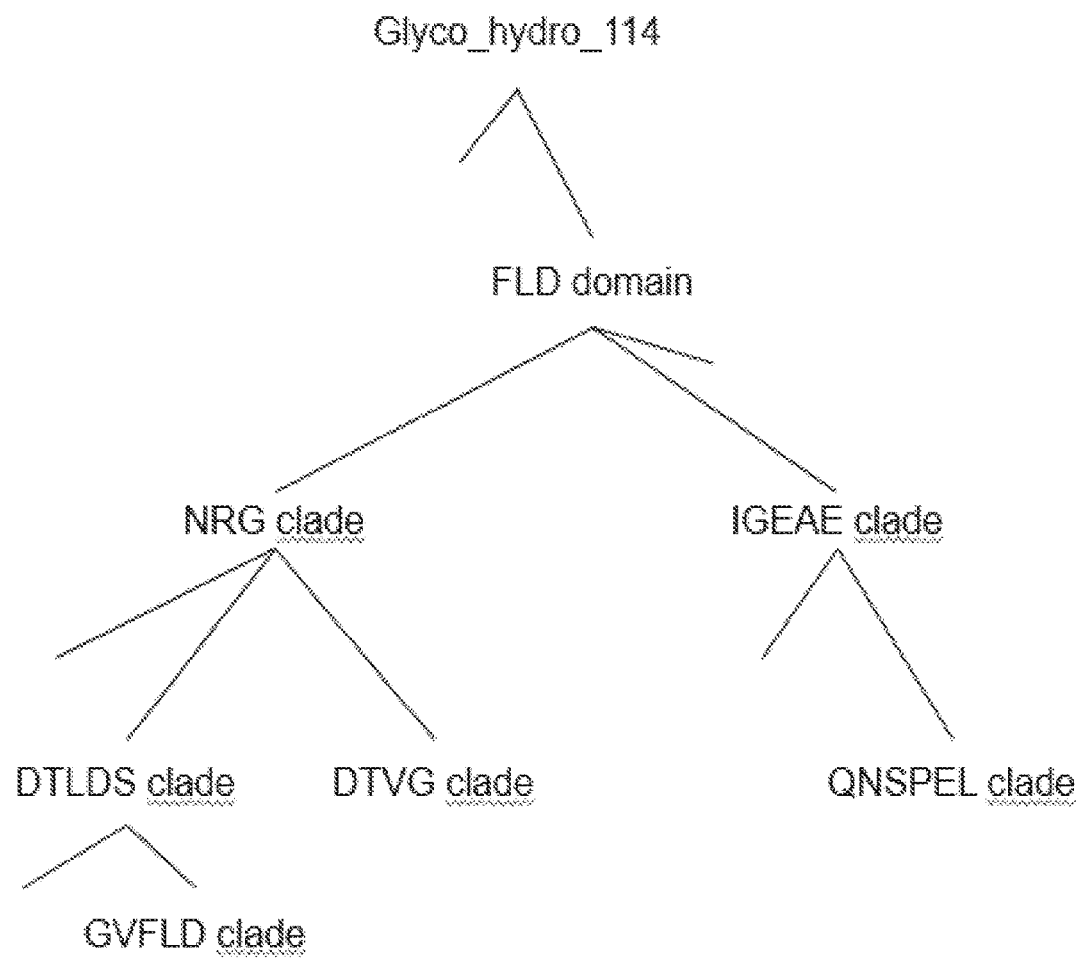

The NRG sub-clade may be further be divided into yet another subgroup, which here is termed DTLDS clade (se FIG. 3). The DTLDS clade comprises polypeptides of bacterial origin having hydrolase activity, wherein the polypeptides comprise a Glyco_hydro_114 domain and belong to the NRG clade (and the FLD-clade). The polypeptides of the clade comprise the motif example DTLDS[YF] (SEQ ID NO 99), corresponding to amino acids DTLDSF positions 117 to 122 of SEQ ID NO 3 where DTLDS (corresponding to positions 117 and 121 of SEQ ID NO 3) is fully conserved in DTLDS clade, and D at position 117 is part of the substrate binding pocket and one of the two putative catalytic site residues. Examples of polypeptides of the DTLDS clade includes SEQ ID NO 3, SEQ ID NO 15, SEQ ID NO 21, SEQ ID NO 33, SEQ ID NO 40, SEQ ID NO 58, SEQ ID NO 61, SEQ ID NO 64, SEQ ID NO 67, SEQ ID NO 70, SEQ ID NO 94, SEQ ID NO 95, and SEQ ID NO 96.

One embodiment of the invention relates a glycosyl hydrolase, preferably a Glyco_hydro_114 glycosyl hydrolase comprising the motif [ILFQV]N[RW]G[FL] (SEQ ID NO 98) and/or the motif DTLDS[YF] (SEQ ID NO 99), wherein the glycosyl hydrolase is selected from the group consisting of:
(a) a polypeptide having at least 60%, at least 70%, at least 75%, at least 80%, at least 85%, at least 90%, at least 95%, at least 96%, at least 97%, at least 98%, at least 99% or 100% sequence identity to the polypeptide of SEQ ID NO 3;
(b) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 15;
(c) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 21;
(d) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 33;
(e) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 40;
(f) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 58;
(g) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 61;
(h) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 64;
(i) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 67;
(j) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 70;
(k) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 94;
(l) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 95; and
(m) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 96.

One preferred embodiment relates to a Glyco_hydro_114 glycosyl hydrolase comprising the motif [ILFQV]N[RW]G[FL] (SEQ ID NO 98) and/or the motif DTLDS[YF] (SEQ ID NO 99), wherein the Glyco_hydro_114 glycosyl hydrolase is selected from the group consisting of:
(a) a polypeptide having at least 90%, at least 95%, at least 96%, at least 97%, at least 98%, at least 99% or 100% sequence identity to the polypeptide of SEQ ID NO 3;
(b) a polypeptide having at least 95%, at least 96%, at least 97%, at least 98%, at least 99% or 100% sequence identity to the polypeptide of SEQ ID NO 15;
(c) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 21;
(d) a polypeptide having at least 70%, at least 75%, at least 80%, at least 85%, at least 90%, at least 95%, at least 96%, at least 97%, at least 98%, at least 99% or 100% sequence identity to the polypeptide of SEQ ID NO 33;
(e) a polypeptide having 100% sequence identity to the polypeptide of SEQ ID NO 40;
(f) a polypeptide having at least 75%, at least 80%, at least 85%, at least 90%, at least 95%, at least 96%, at least 97%, at least 98%, at least 99% or 100% sequence identity to the polypeptide of SEQ ID NO 58;
(g) a polypeptide having at least 95%, at least 96%, at least 97%, at least 98%, at least 99% or 100% sequence identity to the polypeptide of SEQ ID NO 61;
(h) a polypeptide having at least 90%, at least 95%, at least 96%, at least 97%, at least 98%, at least 99% or 100% sequence identity to the polypeptide of SEQ ID NO 64;
(i) a polypeptide having at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 67;
(j) a polypeptide having at least 80%, at least 85%, at least 90%, at least 95%, at least 96%, at least 97%, at least 98%, at least 99% or 100% sequence identity to the polypeptide of SEQ ID NO 94;
(k) a polypeptide having at least 70%, at least 75%, at least 80%, at least 85%, at least 90%, at least 95%, at least 96%, at least 97%, at least 98%, at least 99% or 100% sequence identity to the polypeptide of SEQ ID NO 95; and
(l) a polypeptide having at least 95%, at least 96%, at least 97%, at least 98%, at least 99% or 100% sequence identity to the polypeptide of SEQ ID NO 96.

The DTLDS sub-clade may be further be divided into yet another subgroup, which here is termed GVFLD clade (se FIG. 3). The GVFLD clade comprises polypeptides of bacterial origin having hydrolase activity, wherein the polypeptides comprise a Glyco_hydro_114 domain and belong to the DTLDS clade (and the NRG and FLD-clade). The GVFLD clade comprises polypeptides of bacterial origin having hydrolase activity, wherein the polypeptides comprise a Glyco_hydro_114 domain and belonging to the DTLDS clade (and the NRG and FLD-clade). The polypeptides of the GVFLD clade comprise the motif G[VL]FLDTLDSF[QTH]L[LMQ] (SEQ ID NO 100), corresponding to amino acids GLFLDTLDSFQLL positions 113 to 125 of SEQ ID NO 3 where D (corresponding to position 117 of SEQ ID NO 3) is fully conserved in GVFLD clade, part of the substrate binding pocket, and one of the two putative catalytic site residues. Examples of polypeptides of the GVFLD clade includes SEQ ID NO 3, SEQ ID NO 40, SEQ ID NO 58, SEQ ID NO 61, SEQ ID NO 64, SEQ ID NO 67, SEQ ID NO 70, and SEQ ID NO 94.

One embodiment of the invention relates a glycosyl hydrolase, preferably a Glyco_hydro_114 glycosyl hydrolase comprising the motifs [ILFQV]N[RW]G[FL] (SEQ ID NO 98), DTLDS[YF] (SEQ ID NO 99) and/or G[VL]FLDTLDSF[QTH]L[LMQ] (SEQ ID NO 100), wherein the glycosyl hydrolase is selected from the group consisting of:
(a) a polypeptide having at least 60%, at least 70%, at least 75%, at least 80%, at least 85%, at least 90%, at least 95%, at least 96%, at least 97%, at least 98%, at least 99% or 100% sequence identity to the polypeptide of SEQ ID NO 3;
(b) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 40;
(c) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 58;
(d) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 61;
(e) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 64;
(f) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 67;
(g) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 70; and
(h) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 94.

One preferred embodiment relates to a Glyco_hydro_114 glycosyl hydrolase comprising the motifs [ILFQV]N[RW]G[FL] (SEQ ID NO 98), DTLDS[YF] (SEQ ID NO 99) and/or G[VL]FLDTLDSF[QTH]L[LMQ] (SEQ ID NO 100), wherein the Glyco_hydro_114 glycosyl hydrolase is selected from the group consisting of:
(a) a polypeptide having at least 90%, at least 95%, at least 96%, at least 97%, at least 98%, at least 99% or 100% sequence identity to the polypeptide of SEQ ID NO 3;
(b) a polypeptide having 100% sequence identity to the polypeptide of SEQ ID NO 40;
(c) a polypeptide having at least 75%, at least 80%, at least 85%, at least 90%, at least 95%, at least 96%, at least 97%, at least 98%, at least 99% or 100% sequence identity to the polypeptide of SEQ ID NO 58;

(d) a polypeptide having at least 95%, at least 96%, at least 97%, at least 98%, at least 99% or 100% sequence identity to the polypeptide of SEQ ID NO 61;

(e) a polypeptide having at least 90%, at least 95%, at least 96%, at least 97%, at least 98%, at least 99% or 100% sequence identity to the polypeptide of SEQ ID NO 64;

(f) a polypeptide having at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 67; and (g) a polypeptide having at least 80%, at least 85%, at least 90%, at least 95%, at least 96%, at least 97%, at least 98%, at least 99% or 100% sequence identity to the polypeptide of SEQ ID NO 94.

The NRG sub-clade may be further be divided into another subgroup, which here is termed DTVG clade (se FIG. 3). The DTVG clade comprises polypeptides of bacterial origin having hydrolase activity, wherein the polypeptides comprise a Glyco_hydro_114 domain and belong to the NRG clade (and the FLD clade). The polypeptides of the clade comprise the motif example DT[VIMA][GD][DNW][VIL][DEN] (SEQ ID NO 101), corresponding to amino acids DTVGNIN in SEQ ID NO 76 at positions 134 to 140 of SEQ ID NO 76, where D and T (corresponding to position 134 and 135 of SEQ ID NO 76) is fully conserved in the DTVG clade. Examples of polypeptides of the DTVG clade is SEQ ID NO 76 and SEQ ID NO 82.

One embodiment of the invention relates a glycosyl hydrolase, preferably a Glyco_hydro_114 glycosyl hydrolase comprising the motif [ILFQV]N[RW]G[FL] (SEQ ID NO 98) and/or the motif DT[VIMA][GD][DNW][VIL][DEN] (SEQ ID NO 101), wherein the glycosyl hydrolase is selected from the group consisting of:

(a) a polypeptide having at least 60%, at least 70%, at least 75%, at least 80%, at least 85%, at least 90%, at least 95%, at least 96%, at least 97%, at least 98%, at least 99% or 100% sequence identity to the polypeptide of SEQ ID NO 76; and (b) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 82.

One preferred embodiment relates to a Glyco_hydro_114 glycosyl hydrolase, comprising the motif [ILFQV]N[RW]G[FL] (SEQ ID NO 98) and/or the motif DT[VIMA][GD][DNW][VIL][DEN] (SEQ ID NO 101), wherein the Glyco_hydro_114 glycosyl hydrolase is selected from the group consisting of:

(a) a polypeptide having at least 96%, at least 97%, at least 98%, at least 99% or 100% sequence identity to the polypeptide of SEQ ID NO 76;

(b) a polypeptide having at least 95%, at least 96%, at least 97%, at least 98%, at least 99% or 100% sequence identity to the polypeptide of SEQ ID NO 82.

The glycosyl hydrolases of the FLD clade, may as mentioned above be divided into two clades the clades termed NRG and the IGEAE (see FIG. 3). The IGEAE comprises polypeptides of bacterial origin having hydrolase activity, wherein the polypeptides comprise a Glyco_hydro_114 domain and belong to the FLD clade. The polypeptides of the clade comprise the motif [SETC]IG[EQA][ALI]EXY (SEQ ID NO 102), corresponding to amino acids EIGAIEEY at positions 262 to 269 of SEQ ID NO 12 where G and E (corresponding to position 264 and 267 of SEQ ID NO 12) are fully conserved in IGEAE clade. Residue A at position 265 is part of the substrate binding pocket. Examples of polypeptides of the IGEAE clade is SEQ ID NO 6, SEQ ID NO 12, SEQ ID NO 18, SEQ ID NO 30, SEQ ID NO 43, SEQ ID NO 46, SEQ ID NO 49, SEQ ID NO 52 and SEQ ID NO 55.

One embodiment of the invention relates a glycosyl hydrolase, preferably a Glyco_hydro_114 glycosyl hydrolase comprising the motif [SETC]IG[EQA][ALI]EXY (SEQ ID NO 102), wherein the glycosyl hydrolase is selected from the group consisting of:

(a) a polypeptide having at least 60%, at least 70%, at least 75%, at least 80%, at least 85%, at least 90%, at least 95%, at least 96%, at least 97%, at least 98%, at least 99% or 100% sequence identity to the polypeptide of SEQ ID NO 6;

(b) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 12;

(c) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 18;

(d) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 30;

(e) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 43;

(f) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 46;

(g) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 49;

(h) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 52; and (i) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 55.

One preferred embodiment relates to a Glyco_hydro_114 glycosyl hydrolase, comprising the motif [SETC]IG[EQA][ALI]EXY (SEQ ID NO 102), wherein the Glyco_hydro_114 glycosyl hydrolase is selected from the group consisting of:

(a) a polypeptide having at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 6;
(b) a polypeptide having at least 99% or 100% sequence identity to the polypeptide of SEQ ID NO 12;
(c) a polypeptide having at least 95%, at least 96%, at least 97%, at least 98%, at least 99% or 100% sequence identity to the polypeptide of SEQ ID NO 18;
(d) a polypeptide having at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 30;
(e) a polypeptide having at least 95%, at least 96%, at least 97%, at least 98%, at least 99% or 100% sequence identity to the polypeptide of SEQ ID NO 43;
(f) a polypeptide having 100% sequence identity to the polypeptide of SEQ ID NO 46;
(g) a polypeptide having at least 95%, at least 96%, at least 97%, at least 98%, at least 99% or 100% sequence identity to the polypeptide of SEQ ID NO 49;
(h) a polypeptide having at least 95%, at least 96%, at least 97%, at least 98%, at least 99% or 100% sequence identity to the polypeptide of SEQ ID NO 52; and
(i) a polypeptide having at least 95%, at least 96%, at least 97%, at least 98%, at least 99% or 100% sequence identity to the polypeptide of SEQ ID NO 55.

The IGEAE sub-clade may be further be divided into another subgroup, which here is termed QNSPEL clade (se FIG. 3). The QNSPEL clade comprises polypeptides of bacterial origin having hydrolase activity, comprising a Glyco_hydro_114 domain and belonging to the IGEAE clade. The polypeptides of the clade comprise the motif example [QL]N[AS]PEL (SEQ ID NO 103), corresponding to amino acids QNSPEL at positions 370 to 375 of SEQ ID NO 12 where P, E and L (corresponding to position 373 to 375 of SEQ ID NO 12) are fully conserved in QNSPEL clade. Another conserved motif of this clade is [KLYMQ]XX[PV]QN[SA]PE (SEQ ID NO 104), located at positions 366 to 374 in SEQ ID NO 12, and corresponding to peptide KVVPQNSPE in SEQ ID NO 12. Examples of polypeptides of the QNSPEL clade is SEQ ID NO 12, SEQ ID NO 18, SEQ ID NO 30, SEQ ID NO 43, SEQ ID NO 46, SEQ ID NO 49, SEQ ID NO 52 and SEQ ID NO 55.

One embodiment of the invention relates a glycosyl hydrolase, preferably a Glyco_hydro_114 glycosyl hydrolase comprising the motif [SETC]IG[EQA][ALI]EXY (SEQ ID NO 102) and/or one or both motifs [QL]N[AS]PEL (SEQ ID NO 103), [KLYMQ]XX[PV]QN[SA]PE (SEQ ID NO 104), wherein the glycosyl hydrolase is selected from the group consisting of:
(a) a polypeptide having at least 60%, at least 70%, at least 75%, at least 80%, at least 85%, at least 90%, at least 95%, at least 96%, at least 97%, at least 98%, at least 99% or 100% sequence identity to the polypeptide of SEQ ID NO 12;
(b) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 18;
(c) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 30;
(d) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 43;
(e) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 46;
(f) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 49;
(g) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 52; and
(h) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 55.

One preferred embodiment relates to a Glyco_hydro_114 glycosyl hydrolase comprising the motif [SETC]IG[EQA][ALI]EXY (SEQ ID NO 102) and/or one or both motifs [QL]N[AS]PEL (SEQ ID NO 103), [KLYMQ]XX[PV]QN[SA]PE (SEQ ID NO 104), wherein the Glyco_hydro_114 glycosyl hydrolase is selected from the group consisting of:
(a) a polypeptide having at least 99% or 100% sequence identity to the polypeptide of SEQ ID NO 12;
(b) a polypeptide having at least 95%, at least 96%, at least 97%, at least 98%, at least 99% or 100% sequence identity to the polypeptide of SEQ ID NO 18;
(c) a polypeptide having at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 30;
(d) a polypeptide having at least 95%, at least 96%, at least 97%, at least 98%, at least 99% or 100% sequence identity to the polypeptide of SEQ ID NO 43;
(e) a polypeptide having 100% sequence identity to the polypeptide of SEQ ID NO 46;
(f) a polypeptide having at least 95%, at least 96%, at least 97%, at least 98%, at least 99% or 100% sequence identity to the polypeptide of SEQ ID NO 49;
(g) a polypeptide having at least 95%, at least 96%, at least 97%, at least 98%, at least 99% or 100% sequence identity to the polypeptide of SEQ ID NO 52; and
(h) a polypeptide having at least 95%, at least 96%, at least 97%, at least 98%, at least 99% or 100% sequence identity to the polypeptide of SEQ ID NO 55.

Thus, in one embodiment the Glyco_hydro_114 glycosyl hydrolase comprises one, two or all three of the motifs; GX[FY][LYF]D (SEQ ID NO 34), AYX[SET]XX[EAS] (SEQ ID NO 35), GXXGX[FY][LYFI]D (SEQ ID NO 97) and comprises the motif ([ILFQV]N[RW]G[FL] (SEQ ID NO 98), wherein the Glyco_hydro_114 glycosyl hydrolase is selected from the group consisting of:
(a) a polypeptide having at least 60%, at least 70%, at least 75%, at least 80%, at least 85%, at least 90%, at least 95%, at least 96%, at least 97%, at least 98%, at least 99% or 100% sequence identity to the polypeptide of SEQ ID NO 3;

(b) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 9;

(c) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 15;

(d) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 21;

(e) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 33;

(f) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 40;

(g) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 58;

(h) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 61;

(i) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 64;

(j) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 67;

(k) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 70;

(l) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 76;

(m) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 79;

(n) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 82;

(o) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 94;

(p) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 95; and (q) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 96.

In another embodiment the Glyco_hydro_114 glycosyl hydrolase comprises one, two or all three of the motifs; GX[FY][LYF]D (SEQ ID NO 34), AYX[SET]XX[EAS] (SEQ ID NO 35), GXXGX[FY][LYFI]D (SEQ ID NO 97) and comprises the motif [SETC]IG[EQA][ALI]EXY (SEQ ID NO 102), wherein the Glyco_hydro_114 glycosyl hydrolase is selected from the group consisting of:

(a) a polypeptide having at least 60%, at least 70%, at least 75%, at least 80%, at least 85%, at least 90%, at least 95%, at least 96%, at least 97%, at least 98%, at least 99% or 100% sequence identity to the polypeptide of SEQ ID NO 6;

(b) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 12;

(c) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 18;

(d) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 30;

(e) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 43;

(f) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 46;

(g) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 49;

(h) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 52; and (i) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 55.

The polypeptides of the invention have activity to the exopolysaccharide Pel, which is a component of some biofilm matrix. One embodiment of the invention relates to the use of a polypeptide according to the invention for reduction or removal of Pel, wherein in the Pel is comprised in a biofilm. In particular, the polypeptides of the invention have activity in detergents and is useful in cleaning processes such as laundry and/or dish wash e.g. for deep cleaning of surfaces such as textiles and hard surfaces. The present disclosure also provides a method for preventing, reduction or removal of Pel containing organic soiling on an item comprising applying at least one polypeptide of the invention to an item and optionally rinse the item. The item is preferably a textile or a hard surface, such as dish ware.

Organic matters such as EPS or components hereof may have glue-like properties and the presence of biofilm on e.g. textiles may result in items or areas on items which are "sticky". Soil will in general adhere to the sticky areas and such soil has shown difficult to remove by commercially available detergent compositions. Further, when dirty laundry items are washed together with less dirty laundry items the dirt present in the wash liquor tend to stick to the organic matter and e.g. EPS. As a result, the laundry item is more "soiled" after wash than before wash. This effect may also be termed re-deposition. The Glyco_hydro_114 glycosyl hydrolase polypeptides comprising one or more of the motif(s) GX[FY][LYF]D (SEQ ID NO 34), AYX[SET]XX[EAS] (SEQ ID NO 35), GXXGX[FY][LYFI]D (SEQ ID NO 97), ([ILFQV]N[RW]G[FL] (SEQ ID NO 98), DTLDS[YF] (SEQ ID NO 99), G[VL]FLDTLDSF[QTH]L[LMQ] (SEQ ID NO 100) or DT[VIMA][GD][DNW][VIL][DEN] (SEQ ID NO 101) or one or more of the motifs GX[FY][LYF]D (SEQ ID NO 34), AYX[SET]XX[EAS] (SEQ ID NO 35), GXXGX[FY][LYFI]D (SEQ ID NO 97), ([SETC]IG[EQA][ALI]EXY (SEQ ID NO 102), [QL]N[AS]PEL (SEQ ID NO 103) or [KLYMQ]XX[PV]QN[SA]PE (SEQ ID NO 104) as defined above are useful in reducing or removing re-deposition.

The Glyco_hydro_114 glycosyl hydrolase polypeptides comprising one or more of the motif(s) GX[FY][LYF]D (SEQ ID NO 34), AYX[SET]XX[EAS] (SEQ ID NO 35), GXXGX[FY][LYFI]D (SEQ ID NO 97), ([ILFQV]N[RW]G[FL] (SEQ ID NO 98), DTLDS[YF] (SEQ ID NO 99), G[VL]FLDTLDSF[QTH]L[LMQ] (SEQ ID NO 100) or DT[VIMA][GD][DNW][VIL][DEN] (SEQ ID NO 101) or one or more of the motifs GX[FY][LYF]D (SEQ ID NO 34), AYX[SET]XX[EAS] (SEQ ID NO 35), GXXGX[FY][LYFI]D (SEQ ID NO 97), ([SETC]IG[EQA][ALI]EXY (SEQ ID NO 102), [QL]N[AS]PEL (SEQ ID NO 103) or [KLYMQ]XX[PV]QN[SA]PE (SEQ ID NO 104) as defined above are useful in reducing or removing malodor of items being washed. The inventors have surprisingly found that the polypeptides comprising one or more of the motif(s) GX[FY][LYF]D (SEQ ID NO 34), AYX[SET]XX[EAS] (SEQ ID NO 35), GXXGX[FY][LYFI]D (SEQ ID NO 97), ([ILFQV]N[RW]G[FL] (SEQ ID NO 98), DTLDS[YF] (SEQ ID NO 99), G[VL]FLDTLDSF[QTH]L[LMQ] (SEQ ID NO 100) or DT[VIMA][GD][DNW][VIL][DEN] (SEQ ID NO 101) or one or more of the motifs GX[FY][LYF]D (SEQ ID NO 34), AYX[SET]XX[EAS] (SEQ ID NO 35), GXXGX[FY][LYFI]D (SEQ ID NO 97), ([SETC]IG[EQA][ALI]EXY (SEQ ID NO 102), [QL]N[AS]PEL (SEQ ID NO 103) or [KLYMQ]XX[PV]QN[SA]PE (SEQ ID NO 104) as defined above are useful in reducing or removing laundry associated Pel.

The polypeptides of the present invention are useful in cleaning compositions and are effective in deep cleaning of surfaces such as fabrics. The polypeptides of the present invention are effective in reducing or removing polysaccharide soiling from e.g. organic matter. One example of organic matter is biofilm, which is produced by various microorganisms. The extracellular polymeric matrix of biofilm, EPS is composed of polysaccharides, extracellular DNA and proteins. Biofilm EPS may be sticky or glueing, which when present on textile, may give rise to re-deposition or backstaining of soil resulting in a greying of the textile. Another drawback of organic matter e.g. biofilm is the malodor as various malodor related molecules are often associated with organic matter e.g. biofilm. One aspect of the invention relates to a laundering method for laundering an item comprising the steps of:

a. exposing an item to a wash liquor comprising a polypeptide or a cleaning composition comprising a polypeptide selected from the group consisting of SEQ ID NO 40, SEQ ID NO 43, SEQ ID NO 46, SEQ ID NO 49, SEQ ID NO 52, SEQ ID NO 55, SEQ ID NO 58, SEQ ID NO 61, SEQ ID NO 64, SEQ ID NO 67, SEQ ID NO 70, SEQ ID NO 73, SEQ ID NO 76, SEQ ID NO 79, SEQ ID NO 82, SEQ ID NO 85, SEQ ID NO 88, SEQ ID NO 91, SEQ ID NO 94, SEQ ID NO 95 and SEQ ID NO 96 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto, wherein the polypeptide has hydrolytic and/or deacetylase activity;

b. completing at least one wash cycle; and c. optionally rinsing the item, wherein the item is a textile.

The polypeptides of the invention are therefore useful for prevention, reduction or removal of malodor and for prevention, reduction of re-deposition and improving whiteness.

One embodiment of the invention relates to the use of polypeptide selected from the group consisting of SEQ ID NO 3, SEQ ID NO 6, SEQ ID NO 9, SEQ ID NO 12, SEQ ID NO 15, SEQ ID NO 18, SEQ ID NO 21, SEQ ID NO 24, SEQ ID NO 27, SEQ ID NO 30, SEQ ID NO 33, SEQ ID NO 40, SEQ ID NO 43, SEQ ID NO 46, SEQ ID NO 49, SEQ ID NO 52, SEQ ID NO 55, SEQ ID NO 58, SEQ ID NO 61, SEQ ID NO 64, SEQ ID NO 67, SEQ ID NO 70, SEQ ID NO 73, SEQ ID NO 76, SEQ ID NO 79, SEQ ID NO 82, SEQ ID NO 85, SEQ ID NO 88, SEQ ID NO 91, SEQ ID NO 94, SEQ ID NO 95, SEQ ID NO 96 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto for deep cleaning of an item, wherein the item is a textile. One embodiment of the invention relates to the use of polypeptide selected from the group consisting of SEQ ID NO 3, SEQ ID NO 6, SEQ ID NO 9, SEQ ID NO 12, SEQ ID NO 15, SEQ ID NO 18, SEQ ID NO 21, SEQ ID NO 24, SEQ ID NO 27, SEQ ID NO 30, SEQ ID NO 33, SEQ ID NO 40, SEQ ID NO 43, SEQ ID NO 46, SEQ ID NO 49, SEQ ID NO 52, SEQ ID NO 55, SEQ ID NO 58, SEQ ID NO 61, SEQ ID NO 64, SEQ ID NO 67, SEQ ID NO 70, SEQ ID NO 73, SEQ ID NO 76, SEQ ID NO 79, SEQ ID NO 82, SEQ ID NO 85, SEQ ID NO 88, SEQ ID NO 91, SEQ ID NO 94, SEQ ID NO 95 and SEQ ID NO 96 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto;

(i) for preventing, reducing or removing stickiness of the item;

(ii) for pretreating stains on the item;

(iii) for preventing, reducing or removing redeposition of soil during a wash cycle;
(iv) for preventing, reducing or removing adherence of soil to the item;
(v) for maintaining or improving whiteness of the item;
(vi) for preventing, reducing or removal malodor from the item,
   wherein the item is a textile. The textile may e.g. be cotton or polyester or a mixture hereof.

Further methods and uses are described in the "use" section below.

One embodiment of the invention relates to a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO 3, SEQ ID NO 6, SEQ ID NO 9, SEQ ID NO 12, SEQ ID NO 15, SEQ ID NO 18, SEQ ID NO 21, SEQ ID NO 24, SEQ ID NO 27, SEQ ID NO 30, SEQ ID NO 33, SEQ ID NO 40, SEQ ID NO 43, SEQ ID NO 46, SEQ ID NO 49, SEQ ID NO 52, SEQ ID NO 55, SEQ ID NO 58, SEQ ID NO 61, SEQ ID NO 64, SEQ ID NO 67, SEQ ID NO 70, SEQ ID NO 73, SEQ ID NO 76, SEQ ID NO 79, SEQ ID NO 82, SEQ ID NO 85, SEQ ID NO 88, SEQ ID NO 91, SEQ ID NO 94, SEQ ID NO 95 or SEQ ID NO 96.

One embodiment of the invention relates a Glyco_hydro_114 glycosyl hydrolase polypeptide, wherein the polypeptide has hydrolytic activity, and wherein the polypeptide is selected from the group consisting of:

(a) a polypeptide having at least 60%, at least 70%, at least 75%, at least 80%, at least 85%, at least 90%, at least 95%, at least 96%, at least 97%, at least 98%, at least 99% or 100% sequence identity to the polypeptide of SEQ ID NO 3;

(b) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 6;

(c) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 9;

(d) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 12;

(e) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 15;

(f) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 18;

(g) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 21;

(h) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 24;

(i) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 27;

(j) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 30;

(k) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 33;

(l) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 40;

(m) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 43;

(n) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 46;

(o) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 49;

(p) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 52;

(q) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 55;

(r) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 58;

(s) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 61;

(t) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 64;

(u) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 67;
(v) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 70;
(w) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 73;
(x) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 76;
(y) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 79;
(z) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 82;
(aa) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 85;
(bb) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 88;
(cc) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 91;
(dd) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 94;
(ee) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 95;
(ff) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 96.

One preferred embodiment relates to a Glyco_hydro_114 glycosyl hydrolase polypeptide, wherein the polypeptide has hydrolytic activity, and wherein the polypeptide is selected from the group consisting of:
(a) a polypeptide having at least 90%, at least 95%, at least 96%, at least 97%, at least 98%, at least 99% or 100% sequence identity to the polypeptide of SEQ ID NO 3;
(b) a polypeptide having at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 6;
(c) a polypeptide having at least 80%, at least 85%, at least 90%, at least 95%, at least 96%, at least 97%, at least 98%, at least 99% or 100% sequence identity to the polypeptide of SEQ ID NO 9;
(d) a polypeptide having at least 99% or 100% sequence identity to the polypeptide of SEQ ID NO 12;
(e) a polypeptide having at least 95%, at least 96%, at least 97%, at least 98%, at least 99% or 100% sequence identity to the polypeptide of SEQ ID NO 15;
(f) a polypeptide having at least 95%, at least 96%, at least 97%, at least 98%, at least 99% or 100% sequence identity to the polypeptide of SEQ ID NO 18;
(g) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 21;
(h) a polypeptide having at least 80%, at least 85%, at least 90%, at least 95%, at least 96%, at least 97%, at least 98%, at least 99% or 100% sequence identity to the polypeptide of SEQ ID NO 24;
(i) a polypeptide having at least 70%, at least 75%, at least 80%, at least 85%, at least 90%, at least 95%, at least 96%, at least 97%, at least 98%, at least 99% or 100% sequence identity to the polypeptide of SEQ ID NO 27;
(j) a polypeptide having at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 30;
(k) a polypeptide having at least 70%, at least 75%, at least 80%, at least 85%, at least 90%, at least 95%, at least 96%, at least 97%, at least 98%, at least 99% or 100% sequence identity to the polypeptide of SEQ ID NO 33;
(l) a polypeptide having 100% sequence identity to the polypeptide of SEQ ID NO 40;
(m) a polypeptide having at least 95%, at least 96%, at least 97%, at least 98%, at least 99% or 100% sequence identity to the polypeptide of SEQ ID NO 43;
(n) a polypeptide having 100% sequence identity to the polypeptide of SEQ ID NO 46;
(o) a polypeptide having at least 95%, at least 96%, at least 97%, at least 98%, at least 99% or 100% sequence identity to the polypeptide of SEQ ID NO 49;
(p) a polypeptide having at least 95%, at least 96%, at least 97%, at least 98%, at least 99% or 100% sequence identity to the polypeptide of SEQ ID NO 52;
(q) a polypeptide having at least 95%, at least 96%, at least 97%, at least 98%, at least 99% or 100% sequence identity to the polypeptide of SEQ ID NO 55;
(r) a polypeptide having at least 75%, at least 80%, at least 85%, at least 90%, at least 95%, at least 96%, at least 97%, at least 98%, at least 99% or 100% sequence identity to the polypeptide of SEQ ID NO 58;
(s) a polypeptide having at least 95%, at least 96%, at least 97%, at least 98%, at least 99% or 100% sequence identity to the polypeptide of SEQ ID NO 61;
(t) a polypeptide having at least 90%, at least 95%, at least 96%, at least 97%, at least 98%, at least 99% or 100% sequence identity to the polypeptide of SEQ ID NO 64;
(u) a polypeptide having at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 67;
(v) a polypeptide having at least 96%, at least 97%, at least 98%, at least 99% or 100% sequence identity to the polypeptide of SEQ ID NO 73;
(w) a polypeptide having at least 96%, at least 97%, at least 98%, at least 99% or 100% sequence identity to the polypeptide of SEQ ID NO 76;
(x) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 79;
(y) a polypeptide having at least 95%, at least 96%, at least 97%, at least 98%, at least 99% or 100% sequence identity to the polypeptide of SEQ ID NO 82;
(z) a polypeptide having at least 50%, at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 85;
(aa) a polypeptide having at least 50%, at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 88;
(bb) a polypeptide having at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 91;
(cc) a polypeptide having at least 80%, at least 85%, at least 90%, at least 95%, at least 96%, at least 97%, at least 98%, at least 99% or 100% sequence identity to the polypeptide of SEQ ID NO 94;
(dd) a polypeptide having at least 70%, at least 75%, at least 80%, at least 85%, at least 90%, at least 95%, at least 96%, at least 97%, at least 98%, at least 99% or 100% sequence identity to the polypeptide of SEQ ID NO 95; and
(ee) a polypeptide having at least 95%, at least 96%, at least 97%, at least 98%, at least 99% or 100% sequence identity to the polypeptide of SEQ ID NO 96.

Another preferred embodiment of the invention relates a Glyco_hydro_114 glycosyl hydrolase polypeptide comprising one, two or all three of the motifs GX[FY][LYF]D (SEQ ID NO 34), AYX[SET]XX[EAS] (SEQ ID NO 35) or GXXGX[FY][LYFI]D (SEQ ID NO 97), wherein the polypeptide has hydrolytic activity, and wherein the polypeptide is selected from the group consisting of:
(a) a polypeptide having at least 90%, at least 95%, at least 96%, at least 97%, at least 98%, at least 99% or 100% sequence identity to the polypeptide of SEQ ID NO 3;
(b) a polypeptide having at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 6;
(c) a polypeptide having at least 80%, at least 85%, at least 90%, at least 95%, at least 96%, at least 97%, at least 98%, at least 99% or 100% sequence identity to the polypeptide of SEQ ID NO 9;
(d) a polypeptide having at least 99% or 100% sequence identity to the polypeptide of SEQ ID NO 12;
(e) a polypeptide having at least 95%, at least 96%, at least 97%, at least 98%, at least 99% or 100% sequence identity to the polypeptide of SEQ ID NO 15;
(f) a polypeptide having at least 95%, at least 96%, at least 97%, at least 98%, at least 99% or 100% sequence identity to the polypeptide of SEQ ID NO 18;
(g) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 21;
(h) a polypeptide having at least 80%, at least 85%, at least 90%, at least 95%, at least 96%, at least 97%, at least 98%, at least 99% or 100% sequence identity to the polypeptide of SEQ ID NO 24;
(i) a polypeptide having at least 70%, at least 75%, at least 80%, at least 85%, at least 90%, at least 95%, at least 96%, at least 97%, at least 98%, at least 99% or 100% sequence identity to the polypeptide of SEQ ID NO 27;
(j) a polypeptide having at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 30;
(k) a polypeptide having at least 70%, at least 75%, at least 80%, at least 85%, at least 90%, at least 95%, at least 96%, at least 97%, at least 98%, at least 99% or 100% sequence identity to the polypeptide of SEQ ID NO 33;
(l) a polypeptide having 100% sequence identity to the polypeptide of SEQ ID NO 40;
(m) a polypeptide having at least 95%, at least 96%, at least 97%, at least 98%, at least 99% or 100% sequence identity to the polypeptide of SEQ ID NO 43;
(n) a polypeptide having 100% sequence identity to the polypeptide of SEQ ID NO 46;
(o) a polypeptide having at least 95%, at least 96%, at least 97%, at least 98%, at least 99% or 100% sequence identity to the polypeptide of SEQ ID NO 49;
(p) a polypeptide having at least 95%, at least 96%, at least 97%, at least 98%, at least 99% or 100% sequence identity to the polypeptide of SEQ ID NO 52;
(q) a polypeptide having at least 95%, at least 96%, at least 97%, at least 98%, at least 99% or 100% sequence identity to the polypeptide of SEQ ID NO 55;
(r) a polypeptide having at least 75%, at least 80%, at least 85%, at least 90%, at least 95%, at least 96%, at least 97%, at least 98%, at least 99% or 100% sequence identity to the polypeptide of SEQ ID NO 58;
(s) a polypeptide having at least 95%, at least 96%, at least 97%, at least 98%, at least 99% or 100% sequence identity to the polypeptide of SEQ ID NO 61;
(t) a polypeptide having at least 90%, at least 95%, at least 96%, at least 97%, at least 98%, at least 99% or 100% sequence identity to the polypeptide of SEQ ID NO 64;
(u) a polypeptide having at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 67;
(v) a polypeptide having at least 96%, at least 97%, at least 98%, at least 99% or 100% sequence identity to the polypeptide of SEQ ID NO 73;
(w) a polypeptide having at least 96%, at least 97%, at least 98%, at least 99% or 100% sequence identity to the polypeptide of SEQ ID NO 76;

(x) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 79;
(y) a polypeptide having at least 95%, at least 96%, at least 97%, at least 98%, at least 99% or 100% sequence identity to the polypeptide of SEQ ID NO 82;
(z) a polypeptide having at least 50%, at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 85;
(aa) a polypeptide having at least 50%, at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 88;
(bb) a polypeptide having at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 91;
(cc) a polypeptide having at least 80%, at least 85%, at least 90%, at least 95%, at least 96%, at least 97%, at least 98%, at least 99% or 100% sequence identity to the polypeptide of SEQ ID NO 94;
(dd) a polypeptide having at least 70%, at least 75%, at least 80%, at least 85%, at least 90%, at least 95%, at least 96%, at least 97%, at least 98%, at least 99% or 100% sequence identity to the polypeptide of SEQ ID NO 95; and
(ee) a polypeptide having at least 95%, at least 96%, at least 97%, at least 98%, at least 99% or 100% sequence identity to the polypeptide of SEQ ID NO 96.

In one embodiment, the present invention relates to polypeptides having a sequence identity to the mature polypeptide of SEQ ID NO 2 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic and/or deacetylase activity of the mature polypeptide of SEQ ID NO 2.

In a particular embodiment, the invention relates to polypeptides having a sequence identity to the mature polypeptide of SEQ ID NO 5 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic and/or deacetylase activity of the mature polypeptide of SEQ ID NO 5.

In a particular embodiment, the invention relates to polypeptides having a sequence identity to the mature polypeptide of SEQ ID NO 8 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic and/or deacetylase activity of the mature polypeptide of SEQ ID NO 8.

In a particular embodiment, the invention relates to polypeptides having a sequence identity to the mature polypeptide of SEQ ID NO 11 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic and/or deacetylase activity of the mature polypeptide of SEQ ID NO 11.

In a particular embodiment, the invention relates to polypeptides having a sequence identity to the mature polypeptide of SEQ ID NO 14 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic and/or deacetylase activity of the mature polypeptide of SEQ ID NO 14.

In some embodiment, the present invention relates to polypeptides having a sequence identity to the mature polypeptide of SEQ ID NO 17 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic and/or deacetylase activity of the mature polypeptide of SEQ ID NO 7.

In a particular embodiment, the invention relates to polypeptides having a sequence identity to the mature polypeptide of SEQ ID NO 20 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic and/or deacetylase activity of the mature polypeptide of SEQ ID NO 20.

In a particular embodiment, the invention relates to polypeptides having a sequence identity to the mature polypeptide of SEQ ID NO 23 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic and/or deacetylase activity of the mature polypeptide of SEQ ID NO 23.

In a particular embodiment, the invention relates to polypeptides having a sequence identity to the mature polypeptide of SEQ ID NO 26 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic and/or deacetylase activity of the mature polypeptide of SEQ ID NO 26.

In a particular embodiment, the invention relates to polypeptides having a sequence identity to the mature polypeptide of SEQ ID NO 29 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic and/or deacetylase activity of the mature polypeptide of SEQ ID NO 29.

In a particular embodiment, the invention relates to polypeptides having a sequence identity to the mature polypeptide of SEQ ID NO 32 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic and/or deacetylase activity of the mature polypeptide of SEQ ID NO 32.

In a particular embodiment, the invention relates to polypeptides having a sequence identity to the mature polypeptide of SEQ ID NO 39 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic and/or deacetylase activity of the mature polypeptide of SEQ ID NO 39.

In a particular embodiment, the invention relates to polypeptides having a sequence identity to the mature polypeptide of SEQ ID NO 42 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic and/or deacetylase activity of the mature polypeptide of SEQ ID NO 42.

In a particular embodiment, the invention relates to polypeptides having a sequence identity to the mature polypeptide of SEQ ID NO 45 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic and/or deacetylase activity of the mature polypeptide of SEQ ID NO 45.

In a particular embodiment, the invention relates to polypeptides having a sequence identity to the mature polypeptide of SEQ ID NO 48 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic and/or deacetylase activity of the mature polypeptide of SEQ ID NO 48.

v In a particular embodiment, the invention relates to polypeptides having a sequence identity to the mature polypeptide of SEQ ID NO 51 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic and/or deacetylase activity of the mature polypeptide of SEQ ID NO 51.

In a particular embodiment, the invention relates to polypeptides having a sequence identity to the mature polypeptide of SEQ ID NO 54 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic and/or deacetylase activity of the mature polypeptide of SEQ ID NO 54.

In a particular embodiment, the invention relates to polypeptides having a sequence identity to the mature polypeptide of SEQ ID NO 57 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic and/or deacetylase activity of the mature polypeptide of SEQ ID NO 57.

In a particular embodiment, the invention relates to polypeptides having a sequence identity to the mature polypeptide of SEQ ID NO 60 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic and/or deacetylase activity of the mature polypeptide of SEQ ID NO 60.

In a particular embodiment, the invention relates to polypeptides having a sequence identity to the mature polypeptide of SEQ ID NO 63 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic and/or deacetylase activity of the mature polypeptide of SEQ ID NO 63.

In a particular embodiment, the invention relates to polypeptides having a sequence identity to the mature polypeptide of SEQ ID NO 66 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic and/or deacetylase activity of the mature polypeptide of SEQ ID NO 66.

In a particular embodiment, the invention relates to polypeptides having a sequence identity to the mature polypeptide of SEQ ID NO 69 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic and/or deacetylase activity of the mature polypeptide of SEQ ID NO 69.

In a particular embodiment, the invention relates to polypeptides having a sequence identity to the mature polypeptide of SEQ ID NO 72 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic and/or deacetylase activity of the mature polypeptide of SEQ ID NO 72.

In a particular embodiment, the invention relates to polypeptides having a sequence identity to the mature polypeptide of SEQ ID NO 75 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic and/or deacetylase activity of the mature polypeptide of SEQ ID NO 75.

In a particular embodiment, the invention relates to polypeptides having a sequence identity to the mature polypeptide of SEQ ID NO 78 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic and/or deacetylase activity of the mature polypeptide of SEQ ID NO 78.

In a particular embodiment, the invention relates to polypeptides having a sequence identity to the mature polypeptide of SEQ ID NO 81 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic and/or deacetylase activity of the mature polypeptide of SEQ ID NO 81.

In a particular embodiment, the invention relates to polypeptides having a sequence identity to the mature polypeptide of SEQ ID NO 84 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic and/or deacetylase activity of the mature polypeptide of SEQ ID NO 84.

In a particular embodiment, the invention relates to polypeptides having a sequence identity to the mature polypeptide of SEQ ID NO 87 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic and/or deacetylase activity of the mature polypeptide of SEQ ID NO 87.

In a particular embodiment, the invention relates to polypeptides having a sequence identity to the mature polypeptide of SEQ ID NO 90 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic and/or deacetylase activity of the mature polypeptide of SEQ ID NO 90.

In a particular embodiment, the invention relates to polypeptides having a sequence identity to the mature polypeptide of SEQ ID NO 93 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic and/or deacetylase activity of the mature polypeptide of SEQ ID NO 93.

In a particular embodiment, the invention relates to polypeptides having a sequence identity to the mature polypeptide of SEQ ID NO 95 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic and/or deacetylase activity of the mature polypeptide of SEQ ID NO 95.

In a particular embodiment, the invention relates to polypeptides having a sequence identity to the mature polypeptide of SEQ ID NO 96 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the hydrolytic and/or deacetylase activity of the mature polypeptide of SEQ ID NO 96.

In some embodiment, the polypeptide has been isolated. A polypeptide of the present invention preferably comprises or consists of the amino acid sequence shown in SEQ ID NO 3 or an allelic variant thereof; or is a fragment thereof having hydrolytic and/or deacetylase activity. In another aspect, the polypeptide comprises or consists of the mature polypeptide of SEQ ID NO 2. In another aspect, the polypeptide comprises or consists of amino acids 1 to 904 of SEQ ID NO 2.

In one embodiment, the polypeptide preferably comprises or consists of the amino acid sequence shown in SEQ ID NO 3; comprises the amino acid sequence shown in SEQ ID NO 3 and a N-terminal and/or C-terminal His-tag and/or HQ-tag; comprises the amino acid sequence of SEQ ID NO 3 and a N-terminal and/or C-terminal extension of between 1 and 10 amino acids; or is a fragment thereof having hydrolytic and/or deacetylase activity and having at least 50% such as at least 60%, at least 70%, at least 75%, at least 80%, at least 85%, at least 90%, at least 95%, at least 96%, at least 97%, at least 98% or at least 99% of the length of SEQ ID NO 3.

In some embodiment, the polypeptide has been isolated. A polypeptide of the present invention preferably comprises or consists of the amino acid sequence shown in SEQ ID NO 6 or an allelic variant thereof; or is a fragment thereof having hydrolytic and/or deacetylase activity. In another aspect, the polypeptide comprises or consists of the mature polypeptide of SEQ ID NO 5. In another aspect, the polypeptide comprises or consists of amino acids 1 to 281 of SEQ ID NO 5.

In one embodiment, the polypeptide preferably comprises or consists of the amino acid sequence shown in SEQ ID NO 6; comprises the amino acid sequence shown in SEQ ID NO 6 and a N-terminal and/or C-terminal His-tag and/or HQ-tag; comprises the amino acid sequence of SEQ ID NO 6 and a N-terminal and/or C-terminal extension of between 1 and 10 amino acids; or is a fragment thereof having hydrolytic and/or deacetylase activity and having at least 50% such as at least 60%, at least 70%, at least 75%, at least 80%, at least 85%, at least 90%, at least 95%, at least 96%, at least 97%, at least 98% or at least 99% of the length of SEQ ID NO 6.

In some embodiment, the polypeptide has been isolated. A polypeptide of the present invention preferably comprises or consists of the amino acid sequence shown in SEQ ID NO 9 or an allelic variant thereof; or is a fragment thereof having hydrolytic and/or deacetylase activity. In another aspect, the polypeptide comprises or consists of the mature polypeptide of SEQ ID NO 8. In another aspect, the polypeptide comprises or consists of amino acids 1 to 458 of SEQ ID NO 8.

In one embodiment, the polypeptide preferably comprises or consists of the amino acid sequence shown in SEQ ID NO 9; comprises the amino acid sequence shown in SEQ ID NO 9 and a N-terminal and/or C-terminal His-tag and/or HQ-tag; comprises the amino acid sequence of SEQ ID NO 9 and a N-terminal and/or C-terminal extension of between 1 and 10 amino acids; or is a fragment thereof having hydrolytic and/or deacetylase activity and having at least 50% such as at least 60%, at least 70%, at least 75%, at least 80%, at least 85%, at least 90%, at least 95%, at least 96%, at least 97%, at least 98% or at least 99% of the length of SEQ ID NO 9.

In some embodiment, the polypeptide has been isolated. A polypeptide of the present invention preferably comprises or consists of the amino acid sequence shown in SEQ ID NO 12 or an allelic variant thereof; or is a fragment thereof having hydrolytic and/or deacetylase activity. In another aspect, the polypeptide comprises or consists of the mature polypeptide of SEQ ID NO 11. In another aspect, the polypeptide comprises or consists of amino acids 1 to 468 of SEQ ID NO 11.

In one embodiment, the polypeptide preferably comprises or consists of the amino acid sequence shown in SEQ ID NO 12; comprises the amino acid sequence shown in SEQ ID NO 12 and a N-terminal and/or C-terminal His-tag and/or HQ-tag; comprises the amino acid sequence of SEQ ID NO 12 and a N-terminal and/or C-terminal extension of between 1 and 10 amino acids; or is a fragment thereof having hydrolytic and/or deacetylase activity and having at least 50% such as at least 60%, at least 70%, at least 75%, at least 80%, at least 85%, at least 90%, at least 95%, at least 96%, at least 97%, at least 98% or at least 99% of the length of SEQ ID NO 12.

In some embodiment, the polypeptide has been isolated. A polypeptide of the present invention preferably comprises or consists of the amino acid sequence shown in SEQ ID NO 15 or an allelic variant thereof; or is a fragment thereof having hydrolytic and/or deacetylase activity. In another aspect, the polypeptide comprises or consists of the mature polypeptide of SEQ ID NO 14. In another aspect, the polypeptide comprises or consists of amino acids 1 to 266 of SEQ ID NO 14.

In one embodiment, the polypeptide preferably comprises or consists of the amino acid sequence shown in SEQ ID NO 15; comprises the amino acid sequence shown in SEQ ID NO 15 and a N-terminal and/or C-terminal His-tag and/or HQ-tag; comprises the amino acid sequence of SEQ ID NO 15 and a N-terminal and/or C-terminal extension of between 1 and 10 amino acids; or is a fragment thereof having hydrolytic and/or deacetylase activity and having at least 50% such as at least 60%, at least 70%, at least 75%, at least 80%, at least 85%, at least 90%, at least 95%, at least 96%, at least 97%, at least 98% or at least 99% of the length of SEQ ID NO 15.

In some embodiment, the polypeptide has been isolated. A polypeptide of the present invention preferably comprises or consists of the amino acid sequence shown in SEQ ID NO 18 or an allelic variant thereof; or is a fragment thereof having hydrolytic and/or deacetylase activity. In another aspect, the polypeptide comprises or consists of the mature polypeptide of SEQ ID NO 17. In another aspect, the polypeptide comprises or consists of amino acids 1 to 467 of SEQ ID NO 17.

In one embodiment, the polypeptide preferably comprises or consists of the amino acid sequence shown in SEQ ID NO 18; comprises the amino acid sequence shown in SEQ ID NO 18 and a N-terminal and/or C-terminal His-tag and/or HQ-tag; comprises the amino acid sequence of SEQ ID NO 18 and a N-terminal and/or C-terminal extension of between 1 and 10 amino acids; or is a fragment thereof having hydrolytic and/or deacetylase activity and having at least 50% such as at least 60%, at least 70%, at least 75%, at least 80%, at least 85%, at least 90%, at least 95%, at least 96%, at least 97%, at least 98% or at least 99% of the length of SEQ ID NO 18.

In some embodiment, the polypeptide has been isolated. A polypeptide of the present invention preferably comprises or consists of the amino acid sequence shown in SEQ ID NO 21 or an allelic variant thereof; or is a fragment thereof having hydrolytic and/or deacetylase activity. In another aspect, the polypeptide comprises or consists of the mature polypeptide of SEQ ID NO 20. In another aspect, the polypeptide comprises or consists of amino acids 1 to 882 of SEQ ID NO 20.

In one embodiment, the polypeptide preferably comprises or consists of the amino acid sequence shown in SEQ ID NO 21; comprises the amino acid sequence shown in SEQ ID NO 21 and a N-terminal and/or C-terminal His-tag and/or HQ-tag; comprises the amino acid sequence of SEQ ID NO 21 and a N-terminal and/or C-terminal extension of between 1 and 10 amino acids; or is a fragment thereof having hydrolytic and/or deacetylase activity and having at least 50% such as at least 60%, at least 70%, at least 75%, at least 80%, at least 85%, at least 90%, at least 95%, at least 96%, at least 97%, at least 98% or at least 99% of the length of SEQ ID NO 21.

In some embodiment, the polypeptide has been isolated. A polypeptide of the present invention preferably comprises or consists of the amino acid sequence shown in SEQ ID NO 24 or an allelic variant thereof; or is a fragment thereof having hydrolytic and/or deacetylase activity. In another aspect, the polypeptide comprises or consists of the mature polypeptide of SEQ ID NO 23. In another aspect, the polypeptide comprises or consists of amino acids 1 to 279 of SEQ ID NO 23.

In one embodiment, the polypeptide preferably comprises or consists of the amino acid sequence shown in SEQ ID NO 24; comprises the amino acid sequence shown in SEQ ID NO 24 and a N-terminal and/or C-terminal His-tag and/or HQ-tag; comprises the amino acid sequence of SEQ ID NO 24 and a N-terminal and/or C-terminal extension of between 1 and 10 amino acids; or is a fragment thereof having hydrolytic and/or deacetylase activity and having at least 50% such as at least 60%, at least 70%, at least 75%, at least 80%, at least 85%, at least 90%, at least 95%, at least 96%, at least 97%, at least 98% or at least 99% of the length of SEQ ID NO 24.

In some embodiment, the polypeptide has been isolated. A polypeptide of the present invention preferably comprises or consists of the amino acid sequence shown in SEQ ID NO 27 or an allelic variant thereof; or is a fragment thereof having hydrolytic and/or deacetylase activity. In another aspect, the polypeptide comprises or consists of the mature polypeptide of SEQ ID NO 26. In another aspect, the polypeptide comprises or consists of amino acids 1 to 276 of SEQ ID NO 26.

In one embodiment, the polypeptide preferably comprises or consists of the amino acid sequence shown in SEQ ID NO 27; comprises the amino acid sequence shown in SEQ ID NO 27 and a N-terminal and/or C-terminal His-tag and/or HQ-tag; comprises the amino acid sequence of SEQ ID NO 27 and a N-terminal and/or C-terminal extension of between 1 and 10 amino acids; or is a fragment thereof having hydrolytic and/or deacetylase activity and having at least 50% such as at least 60%, at least 70%, at least 75%, at least 80%, at least 85%, at least 90%, at least 95%, at least 96%, at least 97%, at least 98% or at least 99% of the length of SEQ ID NO 27.

In some embodiment, the polypeptide has been isolated. A polypeptide of the present invention preferably comprises or consists of the amino acid sequence shown in SEQ ID NO 30 or an allelic variant thereof; or is a fragment thereof having hydrolytic and/or deacetylase activity. In another aspect, the polypeptide comprises or consists of the mature polypeptide of SEQ ID NO 29. In another aspect, the polypeptide comprises or consists of amino acids 1 to 277 of SEQ ID NO 29.

In one embodiment, the polypeptide preferably comprises or consists of the amino acid sequence shown in SEQ ID NO 30; comprises the amino acid sequence shown in SEQ ID NO 30 and a N-terminal and/or C-terminal His-tag and/or HQ-tag; comprises the amino acid sequence of SEQ ID NO 30 and a N-terminal and/or C-terminal extension of between 1 and 10 amino acids; or is a fragment thereof having hydrolytic and/or deacetylase activity and having at least 50% such as at least 60%, at least 70%, at least 75%, at least 80%, at least 85%, at least 90%, at least 95%, at least 96%, at least 97%, at least 98% or at least 99% of the length of SEQ ID NO 30.

In some embodiment, the polypeptide has been isolated. A polypeptide of the present invention preferably comprises or consists of the amino acid sequence shown in SEQ ID NO 33 or an allelic variant thereof; or is a fragment thereof having hydrolytic and/or deacetylase activity. In another aspect, the polypeptide comprises or consists of the mature polypeptide of SEQ ID NO 32. In another aspect, the polypeptide comprises or consists of amino acids 1 to 271 of SEQ ID NO 32.

In one embodiment, the polypeptide preferably comprises or consists of the amino acid sequence shown in SEQ ID NO 33; comprises the amino acid sequence shown in SEQ ID NO 33 and a N-terminal and/or C-terminal His-tag and/or HQ-tag; comprises the amino acid sequence of SEQ ID NO 33 and a N-terminal and/or C-terminal extension of between 1 and 10 amino acids; or is a fragment thereof having hydrolytic and/or deacetylase activity and having at least 50% such as at least 60%, at least 70%, at least 75%, at least 80%, at least 85%, at least 90%, at least 95%, at least 96%, at least 97%, at least 98% or at least 99% of the length of SEQ ID NO 33.

In some embodiment, the polypeptide has been isolated. A polypeptide of the present invention preferably comprises or consists of the amino acid sequence shown in SEQ ID NO 40 or an allelic variant thereof; or is a fragment thereof having hydrolytic and/or deacetylase activity. In another aspect, the polypeptide comprises or consists of the mature polypeptide of SEQ ID NO 39. In another aspect, the polypeptide comprises or consists of amino acids 1 to 905 of SEQ ID NO 39.

In one embodiment, the polypeptide preferably comprises or consists of the amino acid sequence shown in SEQ ID NO 40; comprises the amino acid sequence shown in SEQ ID NO 40 and a N-terminal and/or C-terminal His-tag and/or HQ-tag; comprises the amino acid sequence of SEQ ID NO 40 and a N-terminal and/or C-terminal extension of between 1 and 10 amino acids; or is a fragment thereof having hydrolytic and/or deacetylase activity and having at least 50% such as at least 60%, at least 70%, at least 75%, at least 80%, at least 85%, at least 90%, at least 95%, at least 96%, at least 97%, at least 98% or at least 99% of the length of SEQ ID NO 40.

In some embodiment, the polypeptide has been isolated. A polypeptide of the present invention preferably comprises or consists of the amino acid sequence shown in SEQ ID NO 43 or an allelic variant thereof; or is a fragment thereof having hydrolytic and/or deacetylase activity. In another aspect, the polypeptide comprises or consists of the mature polypeptide of SEQ ID NO 42. In another aspect, the polypeptide comprises or consists of amino acids 1 to 467 of SEQ ID NO 42.

In one embodiment, the polypeptide preferably comprises or consists of the amino acid sequence shown in SEQ ID NO 43; comprises the amino acid sequence shown in SEQ ID NO 43 and a N-terminal and/or C-terminal His-tag and/or HQ-tag; comprises the amino acid sequence of SEQ ID NO 43 and a N-terminal and/or C-terminal extension of between 1 and 10 amino acids; or is a fragment thereof having hydrolytic and/or deacetylase activity and having at least 50% such as at least 60%, at least 70%, at least 75%, at least 80%, at least 85%, at least 90%, at least 95%, at least 96%, at least 97%, at least 98% or at least 99% of the length of SEQ ID NO 43.

In some embodiment, the polypeptide has been isolated. A polypeptide of the present invention preferably comprises or consists of the amino acid sequence shown in SEQ ID NO 46 or an allelic variant thereof; or is a fragment thereof having hydrolytic and/or deacetylase activity. In another aspect, the polypeptide comprises or consists of the mature polypeptide of SEQ ID NO 45. In another aspect, the polypeptide comprises or consists of amino acids 1 to 464 of SEQ ID NO 45.

In one embodiment, the polypeptide preferably comprises or consists of the amino acid sequence shown in SEQ ID NO 46; comprises the amino acid sequence shown in SEQ ID NO 46 and a N-terminal and/or C-terminal His-tag and/or HQ-tag; comprises the amino acid sequence of SEQ ID NO 46 and a N-terminal and/or C-terminal extension of between 1 and 10 amino acids; or is a fragment thereof having hydrolytic and/or deacetylase activity and having at least 50% such as at least 60%, at least 70%, at least 75%, at least 80%, at least 85%, at least 90%, at least 95%, at least 96%, at least 97%, at least 98% or at least 99% of the length of SEQ ID NO 46.

In some embodiment, the polypeptide has been isolated. A polypeptide of the present invention preferably comprises or consists of the amino acid sequence shown in SEQ ID NO 49 or an allelic variant thereof; or is a fragment thereof having hydrolytic and/or deacetylase activity. In another aspect, the polypeptide comprises or consists of the mature polypeptide of SEQ ID NO 48. In another aspect, the polypeptide comprises or consists of amino acids 1 to 475 of SEQ ID NO 48.

In one embodiment, the polypeptide preferably comprises or consists of the amino acid sequence shown in SEQ ID NO 49; comprises the amino acid sequence shown in SEQ ID NO 49 and a N-terminal and/or C-terminal His-tag and/or HQ-tag; comprises the amino acid sequence of SEQ ID NO 49 and a N-terminal and/or C-terminal extension of between 1 and 10 amino acids; or is a fragment thereof having hydrolytic and/or deacetylase activity and having at least 50% such as at least 60%, at least 70%, at least 75%, at least 80%, at least 85%, at least 90%, at least 95%, at least 96%, at least 97%, at least 98% or at least 99% of the length of SEQ ID NO 49.

In some embodiment, the polypeptide has been isolated. A polypeptide of the present invention preferably comprises or consists of the amino acid sequence shown in SEQ ID NO 52 or an allelic variant thereof; or is a fragment thereof having hydrolytic and/or deacetylase activity. In another aspect, the polypeptide comprises or consists of the mature polypeptide of SEQ ID NO 51. In another aspect, the polypeptide comprises or consists of amino acids 1 to 469 of SEQ ID NO 51.

In one embodiment, the polypeptide preferably comprises or consists of the amino acid sequence shown in SEQ ID NO 52; comprises the amino acid sequence shown in SEQ ID NO 52 and a N-terminal and/or C-terminal His-tag and/or HQ-tag; comprises the amino acid sequence of SEQ ID NO 52 and a N-terminal and/or C-terminal extension of between 1 and 10 amino acids; or is a fragment thereof having hydrolytic and/or deacetylase activity and having at least 50% such as at least 60%, at least 70%, at least 75%, at least 80%, at least 85%, at least 90%, at least 95%, at least 96%, at least 97%, at least 98% or at least 99% of the length of SEQ ID NO 52.

In some embodiment, the polypeptide has been isolated. A polypeptide of the present invention preferably comprises or consists of the amino acid sequence shown in SEQ ID NO 55 or an allelic variant thereof; or is a fragment thereof having hydrolytic and/or deacetylase activity. In another aspect, the polypeptide comprises or consists of the mature polypeptide of SEQ ID NO 54. In another aspect, the polypeptide comprises or consists of amino acids 1 to 475 of SEQ ID NO 54.

In one embodiment, the polypeptide preferably comprises or consists of the amino acid sequence shown in SEQ ID NO 55; comprises the amino acid sequence shown in SEQ ID NO 55 and a N-terminal and/or C-terminal His-tag and/or HQ-tag; comprises the amino acid sequence of SEQ ID NO 55 and a N-terminal and/or C-terminal extension of between 1 and 10 amino acids; or is a fragment thereof having hydrolytic and/or deacetylase activity and having at least 50% such as at least 60%, at least 70%, at least 75%, at least 80%, at least 85%, at least 90%, at least 95%, at least 96%, at least 97%, at least 98% or at least 99% of the length of SEQ ID NO 55.

In some embodiment, the polypeptide has been isolated. A polypeptide of the present invention preferably comprises or consists of the amino acid sequence shown in SEQ ID NO 58 or an allelic variant thereof; or is a fragment thereof having hydrolytic and/or deacetylase activity. In another aspect, the polypeptide comprises or consists of the mature polypeptide of SEQ ID NO 57. In another aspect, the polypeptide comprises or consists of amino acids 1 to 906 of SEQ ID NO 57.

In one embodiment, the polypeptide preferably comprises or consists of the amino acid sequence shown in SEQ ID NO 58; comprises the amino acid sequence shown in SEQ ID NO 58 and a N-terminal and/or C-terminal His-tag and/or HQ-tag; comprises the amino acid sequence of SEQ ID NO 58 and a N-terminal and/or C-terminal extension of between 1 and 10 amino acids; or is a fragment thereof having hydrolytic and/or deacetylase activity and having at least 50% such as at least 60%, at least 70%, at least 75%, at least 80%, at least 85%, at least 90%, at least 95%, at least 96%, at least 97%, at least 98% or at least 99% of the length of SEQ ID NO 58.

In some embodiment, the polypeptide has been isolated. A polypeptide of the present invention preferably comprises or consists of the amino acid sequence shown in SEQ ID NO 61 or an allelic variant thereof; or is a fragment thereof having hydrolytic and/or deacetylase activity. In another aspect, the polypeptide comprises or consists of the mature polypeptide of SEQ ID NO 60. In another aspect, the polypeptide comprises or consists of amino acids 1 to 905 of SEQ ID NO 60.

In one embodiment, the polypeptide preferably comprises or consists of the amino acid sequence shown in SEQ ID NO 61; comprises the amino acid sequence shown in SEQ ID NO 61 and a N-terminal and/or C-terminal His-tag and/or HQ-tag; comprises the amino acid sequence of SEQ ID NO 61 and a N-terminal and/or C-terminal extension of between 1 and 10 amino acids; or is a fragment thereof having hydrolytic and/or deacetylase activity and having at least 50% such as at least 60%, at least 70%, at least 75%, at least 80%, at least 85%, at least 90%, at least 95%, at least 96%, at least 97%, at least 98% or at least 99% of the length of SEQ ID NO 61.

In some embodiment, the polypeptide has been isolated. A polypeptide of the present invention preferably comprises or consists of the amino acid sequence shown in SEQ ID NO 64 or an allelic variant thereof; or is a fragment thereof having hydrolytic and/or deacetylase activity. In another aspect, the polypeptide comprises or consists of the mature polypeptide of SEQ ID NO 63. In another aspect, the polypeptide comprises or consists of amino acids 1 to 905 of SEQ ID NO 63.

In one embodiment, the polypeptide preferably comprises or consists of the amino acid sequence shown in SEQ ID NO 64; comprises the amino acid sequence shown in SEQ ID NO 64 and a N-terminal and/or C-terminal His-tag and/or HQ-tag; comprises the amino acid sequence of SEQ ID NO 64 and a N-terminal and/or C-terminal extension of between 1 and 10 amino acids; or is a fragment thereof having hydrolytic and/or deacetylase activity and having at least 50% such as at least 60%, at least 70%, at least 75%, at least 80%, at least 85%, at least 90%, at least 95%, at least 96%, at least 97%, at least 98% or at least 99% of the length of SEQ ID NO 64.

In some embodiment, the polypeptide has been isolated. A polypeptide of the present invention preferably comprises or consists of the amino acid sequence shown in SEQ ID NO 67 or an allelic variant thereof; or is a fragment thereof having hydrolytic and/or deacetylase activity. In another aspect, the polypeptide comprises or consists of the mature polypeptide of SEQ ID NO 66. In another aspect, the polypeptide comprises or consists of amino acids 1 to 906 of SEQ ID NO 66.

In one embodiment, the polypeptide preferably comprises or consists of the amino acid sequence shown in SEQ ID NO 67; comprises the amino acid sequence shown in SEQ ID NO 67 and a N-terminal and/or C-terminal His-tag and/or HQ-tag; comprises the amino acid sequence of SEQ ID NO 67 and a N-terminal and/or C-terminal extension of between 1 and 10 amino acids; or is a fragment thereof having hydrolytic and/or deacetylase activity and having at least 50% such as at least 60%, at least 70%, at least 75%, at least 80%, at least 85%, at least 90%, at least 95%, at least 96%, at least 97%, at least 98% or at least 99% of the length of SEQ ID NO 67.

In some embodiment, the polypeptide has been isolated. A polypeptide of the present invention preferably comprises or consists of the amino acid sequence shown in SEQ ID NO 70 or an allelic variant thereof; or is a fragment thereof having hydrolytic and/or deacetylase activity. In another aspect, the polypeptide comprises or consists of the mature polypeptide of SEQ ID NO 69. In another aspect, the polypeptide comprises or consists of amino acids 1 to 257 of SEQ ID NO 69.

In one embodiment, the polypeptide preferably comprises or consists of the amino acid sequence shown in SEQ ID NO 70; comprises the amino acid sequence shown in SEQ ID NO 70 and a N-terminal and/or C-terminal His-tag and/or HQ-tag; comprises the amino acid sequence of SEQ ID NO 70 and a N-terminal and/or C-terminal extension of between 1 and 10 amino acids; or is a fragment thereof having hydrolytic and/or deacetylase activity and having at least 50% such as at least 60%, at least 70%, at least 75%, at least 80%, at least 85%, at least 90%, at least 95%, at least 96%, at least 97%, at least 98% or at least 99% of the length of SEQ ID NO 70.

In some embodiment, the polypeptide has been isolated. A polypeptide of the present invention preferably comprises or consists of the amino acid sequence shown in SEQ ID NO 73 or an allelic variant thereof; or is a fragment thereof having hydrolytic and/or deacetylase activity. In another aspect, the polypeptide comprises or consists of the mature polypeptide of SEQ ID NO 72. In another aspect, the polypeptide comprises or consists of amino acids 1 to 269 of SEQ ID NO 72.

In one embodiment, the polypeptide preferably comprises or consists of the amino acid sequence shown in SEQ ID NO 73; comprises the amino acid sequence shown in SEQ ID NO 73 and a N-terminal and/or C-terminal His-tag and/or HQ-tag; comprises the amino acid sequence of SEQ ID NO 73 and a N-terminal and/or C-terminal extension of between 1 and 10 amino acids; or is a fragment thereof having hydrolytic and/or deacetylase activity and having at least 50% such as at least 60%, at least 70%, at least 75%, at least 80%, at least 85%, at least 90%, at least 95%, at least 96%, at least 97%, at least 98% or at least 99% of the length of SEQ ID NO 73.

In some embodiment, the polypeptide has been isolated. A polypeptide of the present invention preferably comprises or consists of the amino acid sequence shown in SEQ ID NO 76 or an allelic variant thereof; or is a fragment thereof having hydrolytic and/or deacetylase activity. In another aspect, the polypeptide comprises or consists of the mature polypeptide of SEQ ID NO 75. In another aspect, the polypeptide comprises or consists of amino acids 1 to 260 of SEQ ID NO 75.

In one embodiment, the polypeptide preferably comprises or consists of the amino acid sequence shown in SEQ ID NO 76; comprises the amino acid sequence shown in SEQ ID NO 76 and a N-terminal and/or C-terminal His-tag and/or HQ-tag; comprises the amino acid sequence of SEQ ID NO 76 and a N-terminal and/or C-terminal extension of between 1 and 10 amino acids; or is a fragment thereof having hydrolytic and/or deacetylase activity and having at least 50% such as at least 60%, at least 70%, at least 75%, at least 80%, at least 85%, at least 90%, at least 95%, at least 96%, at least 97%, at least 98% or at least 99% of the length of SEQ ID NO 76.

In some embodiment, the polypeptide has been isolated. A polypeptide of the present invention preferably comprises or consists of the amino acid sequence shown in SEQ ID NO 79 or an allelic variant thereof; or is a fragment thereof having hydrolytic and/or deacetylase activity. In another aspect, the polypeptide comprises or consists of the mature polypeptide of SEQ ID NO 78. In another aspect, the polypeptide comprises or consists of amino acids 1 to 275 of SEQ ID NO 78.

In one embodiment, the polypeptide preferably comprises or consists of the amino acid sequence shown in SEQ ID NO 79; comprises the amino acid sequence shown in SEQ ID NO 79 and a N-terminal and/or C-terminal His-tag and/or HQ-tag; comprises the amino acid sequence of SEQ ID NO 79 and a N-terminal and/or C-terminal extension of between 1 and 10 amino acids; or is a fragment thereof having hydrolytic and/or deacetylase activity and having at least 50% such as at least 60%, at least 70%, at least 75%, at least 80%, at least 85%, at least 90%, at least 95%, at least 96%, at least 97%, at least 98% or at least 99% of the length of SEQ ID NO 79.

In some embodiment, the polypeptide has been isolated. A polypeptide of the present invention preferably comprises or consists of the amino acid sequence shown in SEQ ID NO 82 or an allelic variant thereof; or is a fragment thereof having hydrolytic and/or deacetylase activity. In another aspect, the polypeptide comprises or consists of the mature polypeptide of SEQ ID NO 81. In another aspect, the polypeptide comprises or consists of amino acids 1 to 268 of SEQ ID NO 81.

In one embodiment, the polypeptide preferably comprises or consists of the amino acid sequence shown in SEQ ID NO 82; comprises the amino acid sequence shown in SEQ ID NO 82 and a N-terminal and/or C-terminal His-tag and/or HQ-tag; comprises the amino acid sequence of SEQ ID NO 82 and a N-terminal and/or C-terminal extension of between 1 and 10 amino acids; or is a fragment thereof having hydrolytic and/or deacetylase activity and having at least 50% such as at least 60%, at least 70%, at least 75%, at least 80%, at least 85%, at least 90%, at least 95%, at least 96%, at least 97%, at least 98% or at least 99% of the length of SEQ ID NO 82.

In some embodiment, the polypeptide has been isolated. A polypeptide of the present invention preferably comprises or consists of the amino acid sequence shown in SEQ ID NO 85 or an allelic variant thereof; or is a fragment thereof having hydrolytic and/or deacetylase activity. In another aspect, the polypeptide comprises or consists of the mature polypeptide of SEQ ID NO 84. In another aspect, the polypeptide comprises or consists of amino acids 1 to 313 of SEQ ID NO 84.

In one embodiment, the polypeptide preferably comprises or consists of the amino acid sequence shown in SEQ ID NO 85; comprises the amino acid sequence shown in SEQ ID NO 85 and a N-terminal and/or C-terminal His-tag and/or HQ-tag; comprises the amino acid sequence of SEQ ID NO 85 and a N-terminal and/or C-terminal extension of between 1 and 10 amino acids; or is a fragment thereof having hydrolytic and/or deacetylase activity and having at least 50% such as at least 60%, at least 70%, at least 75%, at least 80%, at least 85%, at least 90%, at least 95%, at least 96%, at least 97%, at least 98% or at least 99% of the length of SEQ ID NO 85.

In some embodiment, the polypeptide has been isolated. A polypeptide of the present invention preferably comprises or consists of the amino acid sequence shown in SEQ ID NO 88 or an allelic variant thereof; or is a fragment thereof having hydrolytic and/or deacetylase activity. In another aspect, the polypeptide comprises or consists of the mature polypeptide of SEQ ID NO 87. In another aspect, the polypeptide comprises or consists of amino acids 1 to 257 of SEQ ID NO 87.

In one embodiment, the polypeptide preferably comprises or consists of the amino acid sequence shown in SEQ ID NO 88; comprises the amino acid sequence shown in SEQ ID NO 88 and a N-terminal and/or C-terminal His-tag and/or HQ-tag; comprises the amino acid sequence of SEQ ID NO 88 and a N-terminal and/or C-terminal extension of between 1 and 10 amino acids; or is a fragment thereof having hydrolytic and/or deacetylase activity and having at least 50% such as at least 60%, at least 70%, at least 75%, at least 80%, at least 85%, at least 90%, at least 95%, at least 96%, at least 97%, at least 98% or at least 99% of the length of SEQ ID NO 88.

In some embodiment, the polypeptide has been isolated. A polypeptide of the present invention preferably comprises or consists of the amino acid sequence shown in SEQ ID NO 91 or an allelic variant thereof; or is a fragment thereof having hydrolytic and/or deacetylase activity. In another aspect, the polypeptide comprises or consists of the mature polypeptide of SEQ ID NO 90. In another aspect, the polypeptide comprises or consists of amino acids 1 to 296 of SEQ ID NO 90.

In one embodiment, the polypeptide preferably comprises or consists of the amino acid sequence shown in SEQ ID NO 91; comprises the amino acid sequence shown in SEQ ID NO 91 and a N-terminal and/or C-terminal His-tag and/or HQ-tag; comprises the amino acid sequence of SEQ ID NO 91 and a N-terminal and/or C-terminal extension of between 1 and 10 amino acids; or is a fragment thereof having hydrolytic and/or deacetylase activity and having at least 50% such as at least 60%, at least 70%, at least 75%, at least 80%, at least 85%, at least 90%, at least 95%, at least 96%, at least 97%, at least 98% or at least 99% of the length of SEQ ID NO 91.

In some embodiment, the polypeptide has been isolated. A polypeptide of the present invention preferably comprises or consists of the amino acid sequence shown in SEQ ID NO 94 or an allelic variant thereof; or is a fragment thereof having hydrolytic and/or deacetylase activity. In another aspect, the polypeptide comprises or consists of the mature polypeptide of SEQ ID NO 93. In another aspect, the polypeptide comprises or consists of amino acids 1 to 897 of SEQ ID NO 93.

In one embodiment, the polypeptide preferably comprises or consists of the amino acid sequence shown in SEQ ID NO 94; comprises the amino acid sequence shown in SEQ ID NO 94 and a N-terminal and/or C-terminal His-tag and/or HQ-tag; comprises the amino acid sequence of SEQ ID NO 94 and a N-terminal and/or C-terminal extension of between 1 and 10 amino acids; or is a fragment thereof having hydrolytic and/or deacetylase activity and having at least 50% such as at least 60%, at least 70%, at least 75%, at least 80%, at least 85%, at least 90%, at least 95%, at least 96%, at least 97%, at least 98% or at least 99% of the length of SEQ ID NO 94.

In one embodiment, the polypeptide preferably comprises or consists of the amino acid sequence shown in SEQ ID NO 95; comprises the amino acid sequence shown in SEQ ID NO 95 and a N-terminal and/or C-terminal His-tag and/or HQ-tag; comprises the amino acid sequence of SEQ ID NO 95 and a N-terminal and/or C-terminal extension of between 1 and 10 amino acids; or is a fragment thereof having hydrolytic and/or deacetylase activity and having at least 50% such as at least 60%, at least 70%, at least 75%, at least 80%, at least 85%, at least 90%, at least 95%, at least 96%, at least 97%, at least 98% or at least 99% of the length of SEQ ID NO 95. In some embodiment, the polypeptide has been isolated. A polypeptide of the present invention preferably comprises or consists of the amino acid sequence shown in SEQ ID NO 95 or an allelic variant thereof; or is a fragment thereof having hydrolytic and/or deacetylase activity.

In one embodiment, the polypeptide preferably comprises or consists of the amino acid sequence shown in SEQ ID NO 96; comprises the amino acid sequence shown in SEQ ID NO 96 and a N-terminal and/or C-terminal His-tag and/or HQ-tag; comprises the amino acid sequence of SEQ ID NO 96 and a N-terminal and/or C-terminal extension of between 1 and 10 amino acids; or is a fragment thereof having hydrolytic and/or deacetylase activity and having at least 50% such as at least 60%, at least 70%, at least 75%, at least 80%, at least 85%, at least 90%, at least 95%, at least 96%, at least 97%, at least 98% or at least 99% of the length of SEQ ID NO 96. In some embodiment, the polypeptide has been isolated. A polypeptide of the present invention preferably comprises or consists of the amino acid sequence shown in SEQ ID NO 96 or an allelic variant thereof; or is a fragment thereof having hydrolytic and/or deacetylase activity.

In some aspect, the invention relates to a polypeptide which comprises or consists of the amino acid sequence shown in SEQ ID NO 3.

In some aspect, the invention relates to a polypeptide which comprises or consists of the amino acid sequence shown in SEQ ID NO 6.

In some aspect, the invention relates to a polypeptide which comprises or consists of the amino acid sequence shown in SEQ ID NO 9.

In some aspect, the invention relates to a polypeptide which comprises or consists of the amino acid sequence shown in SEQ ID NO 12.

In some aspect, the invention relates to a polypeptide which comprises or consists of the amino acid sequence shown in SEQ ID NO 15.

In some aspect, the invention relates to a polypeptide which comprises or consists of the amino acid sequence shown in SEQ ID NO 18.

In some aspect, the invention relates to a polypeptide which comprises or consists of the amino acid sequence shown in SEQ ID NO 21.

In some aspect, the invention relates to a polypeptide which comprises or consists of the amino acid sequence shown in SEQ ID NO 24.

In some aspect, the invention relates to a polypeptide which comprises or consists of the amino acid sequence shown in SEQ ID NO 27.

In some aspect, the invention relates to a polypeptide which comprises or consists of the amino acid sequence shown in SEQ ID NO 30.

In some aspect, the invention relates to a polypeptide which comprises or consists of the amino acid sequence shown in SEQ ID NO 33.

In some aspect, the invention relates to a polypeptide which comprises or consists of the amino acid sequence shown in SEQ ID NO 40.

In some aspect, the invention relates to a polypeptide which comprises or consists of the amino acid sequence shown in SEQ ID NO 43.

In some aspect, the invention relates to a polypeptide which comprises or consists of the amino acid sequence shown in SEQ ID NO 46.

In some aspect, the invention relates to a polypeptide which comprises or consists of the amino acid sequence shown in SEQ ID NO 49.

In some aspect, the invention relates to a polypeptide which comprises or consists of the amino acid sequence shown in SEQ ID NO 52.

In some aspect, the invention relates to a polypeptide which comprises or consists of the amino acid sequence shown in SEQ ID NO 55.

In some aspect, the invention relates to a polypeptide which comprises or consists of the amino acid sequence shown in SEQ ID NO 58.

In some aspect, the invention relates to a polypeptide which comprises or consists of the amino acid sequence shown in SEQ ID NO 61.

In some aspect, the invention relates to a polypeptide which comprises or consists of the amino acid sequence shown in SEQ ID NO 64.

In some aspect, the invention relates to a polypeptide which comprises or consists of the amino acid sequence shown in SEQ ID NO 67.

In some aspect, the invention relates to a polypeptide which comprises or consists of the amino acid sequence shown in SEQ ID NO 70.

In some aspect, the invention relates to a polypeptide which comprises or consists of the amino acid sequence shown in SEQ ID NO 73.

In some aspect, the invention relates to a polypeptide which comprises or consists of the amino acid sequence shown in SEQ ID NO 76.

In some aspect, the invention relates to a polypeptide which comprises or consists of the amino acid sequence shown in SEQ ID NO 79.

In some aspect, the invention relates to a polypeptide which comprises or consists of the amino acid sequence shown in SEQ ID NO 82.

In some aspect, the invention relates to a polypeptide which comprises or consists of the amino acid sequence shown in SEQ ID NO 85.

In some aspect, the invention relates to a polypeptide which comprises or consists of the amino acid sequence shown in SEQ ID NO 88.

In some aspect, the invention relates to a polypeptide which comprises or consists of the amino acid sequence shown in SEQ ID NO 91.

In some aspect, the invention relates to a polypeptide which comprises or consists of the amino acid sequence shown in SEQ ID NO 94.

In some aspect, the invention relates to a polypeptide which comprises or consists of the amino acid sequence shown in SEQ ID NO 95.

In some aspect, the invention relates to a polypeptide which comprises or consists of the amino acid sequence shown in SEQ ID NO 96.

In some embodiment, the present invention relates to variants of the mature polypeptide shown in SEQ ID NO 3 comprising a substitution, deletion, and/or insertion at one or more (e.g., several) positions. In some embodiment, the number of amino acid substitutions, deletions and/or insertions introduced into the mature polypeptide shown in SEQ ID NO 3 is up to 10, e.g., 1, 2, 3, 4, 5, 6, 7, 8, 9, or 10.

In some embodiment, the present invention relates to variants of the mature polypeptide shown in SEQ ID NO 6 comprising a substitution, deletion, and/or insertion at one or more (e.g., several) positions. In some embodiment, the number of amino acid substitutions, deletions and/or insertions introduced into the mature polypeptide shown in SEQ ID NO 6 is up to 10, e.g., 1, 2, 3, 4, 5, 6, 7, 8, 9, or 10.

In some embodiment, the present invention relates to variants of the mature polypeptide shown in SEQ ID NO 9 comprising a substitution, deletion, and/or insertion at one or more (e.g., several) positions. In some embodiment, the number of amino acid substitutions, deletions and/or insertions introduced into the mature polypeptide shown in SEQ ID NO 9 is up to 10, e.g., 1, 2, 3, 4, 5, 6, 7, 8, 9, or 10.

In some embodiment, the present invention relates to variants of the mature polypeptide shown in SEQ ID NO 12 comprising a substitution, deletion, and/or insertion at one or more (e.g., several) positions. In some embodiment, the number of amino acid substitutions, deletions and/or insertions introduced into the mature polypeptide shown in SEQ ID NO 12 is up to 10, e.g., 1, 2, 3, 4, 5, 6, 7, 8, 9, or 10.

In some embodiment, the present invention relates to variants of the mature polypeptide shown in SEQ ID NO 15 comprising a substitution, deletion, and/or insertion at one or more (e.g., several) positions. In some embodiment, the number of amino acid substitutions, deletions and/or insertions introduced into the mature polypeptide shown in SEQ ID NO 15 is up to 10, e.g., 1, 2, 3, 4, 5, 6, 7, 8, 9, or 10.

In some embodiment, the present invention relates to variants of the mature polypeptide shown in SEQ ID NO 18 comprising a substitution, deletion, and/or insertion at one or more (e.g., several) positions. In some embodiment, the number of amino acid substitutions, deletions and/or insertions introduced into the mature polypeptide shown in SEQ ID NO 18 is up to 10, e.g., 1, 2, 3, 4, 5, 6, 7, 8, 9, or 10.

In some embodiment, the present invention relates to variants of the mature polypeptide shown in SEQ ID NO 21 comprising a substitution, deletion, and/or insertion at one or more (e.g., several) positions. In some embodiment, the number of amino acid substitutions, deletions and/or insertions introduced into the mature polypeptide shown in SEQ ID NO 21 is up to 10, e.g., 1, 2, 3, 4, 5, 6, 7, 8, 9, or 10.

In some embodiment, the present invention relates to variants of the mature polypeptide shown in SEQ ID NO 24 comprising a substitution, deletion, and/or insertion at one or more (e.g., several) positions. In some embodiment, the number of amino acid substitutions, deletions and/or insertions introduced into the mature polypeptide shown in SEQ ID NO 24 is up to 10, e.g., 1, 2, 3, 4, 5, 6, 7, 8, 9, or 10.

In some embodiment, the present invention relates to variants of the mature polypeptide shown in SEQ ID NO 27 comprising a substitution, deletion, and/or insertion at one or more (e.g., several) positions. In some embodiment, the number of amino acid substitutions, deletions and/or insertions introduced into the mature polypeptide shown in SEQ ID NO 27 is up to 10, e.g., 1, 2, 3, 4, 5, 6, 7, 8, 9, or 10.

In some embodiment, the present invention relates to variants of the mature polypeptide shown in SEQ ID NO 30 comprising a substitution, deletion, and/or insertion at one or more (e.g., several) positions. In some embodiment, the number of amino acid substitutions, deletions and/or insertions introduced into the mature polypeptide shown in SEQ ID NO 30 is up to 10, e.g., 1, 2, 3, 4, 5, 6, 7, 8, 9, or 10.

In some embodiment, the present invention relates to variants of the mature polypeptide shown in SEQ ID NO 33 comprising a substitution, deletion, and/or insertion at one or more (e.g., several) positions. In some embodiment, the number of amino acid substitutions, deletions and/or insertions introduced into the mature polypeptide shown in SEQ ID NO 33 is up to 10, e.g., 1, 2, 3, 4, 5, 6, 7, 8, 9, or 10.

In some embodiment, the present invention relates to variants of the mature polypeptide shown in SEQ ID NO 40 comprising a substitution, deletion, and/or insertion at one or more (e.g., several) positions. In some embodiment, the number of amino acid substitutions, deletions and/or insertions introduced into the mature polypeptide shown in SEQ ID NO 40 is up to 10, e.g., 1, 2, 3, 4, 5, 6, 7, 8, 9, or 10.

In some embodiment, the present invention relates to variants of the mature polypeptide shown in SEQ ID NO 43 comprising a substitution, deletion, and/or insertion at one or more (e.g., several) positions. In some embodiment, the number of amino acid substitutions, deletions and/or insertions introduced into the mature polypeptide shown in SEQ ID NO 43 is up to 10, e.g., 1, 2, 3, 4, 5, 6, 7, 8, 9, or 10.

In some embodiment, the present invention relates to variants of the mature polypeptide shown in SEQ ID NO 46 comprising a substitution, deletion, and/or insertion at one or more (e.g., several) positions. In some embodiment, the number of amino acid substitutions, deletions and/or insertions introduced into the mature polypeptide shown in SEQ ID NO 46 is up to 10, e.g., 1, 2, 3, 4, 5, 6, 7, 8, 9, or 10.

In some embodiment, the present invention relates to variants of the mature polypeptide shown in SEQ ID NO 49 comprising a substitution, deletion, and/or insertion at one or more (e.g., several) positions. In some embodiment, the number of amino acid substitutions, deletions and/or insertions introduced into the mature polypeptide shown in SEQ ID NO 49 is up to 10, e.g., 1, 2, 3, 4, 5, 6, 7, 8, 9, or 10.

In some embodiment, the present invention relates to variants of the mature polypeptide shown in SEQ ID NO 52 comprising a substitution, deletion, and/or insertion at one or more (e.g., several) positions. In some embodiment, the number of amino acid substitutions, deletions and/or insertions introduced into the mature polypeptide shown in SEQ ID NO 52 is up to 10, e.g., 1, 2, 3, 4, 5, 6, 7, 8, 9, or 10.

In some embodiment, the present invention relates to variants of the mature polypeptide shown in SEQ ID NO 55 comprising a substitution, deletion, and/or insertion at one or more (e.g., several) positions. In some embodiment, the number of amino acid substitutions, deletions and/or insertions introduced into the mature polypeptide shown in SEQ ID NO 55 is up to 10, e.g., 1, 2, 3, 4, 5, 6, 7, 8, 9, or 10.

In some embodiment, the present invention relates to variants of the mature polypeptide shown in SEQ ID NO 58 comprising a substitution, deletion, and/or insertion at one or more (e.g., several) positions. In some embodiment, the number of amino acid substitutions, deletions and/or insertions introduced into the mature polypeptide shown in SEQ ID NO 58 is up to 10, e.g., 1, 2, 3, 4, 5, 6, 7, 8, 9, or 10.

In some embodiment, the present invention relates to variants of the mature polypeptide shown in SEQ ID NO 61 comprising a substitution, deletion, and/or insertion at one or more (e.g., several) positions. In some embodiment, the number of amino acid substitutions, deletions and/or insertions introduced into the mature polypeptide shown in SEQ ID NO 61 is up to 10, e.g., 1, 2, 3, 4, 5, 6, 7, 8, 9, or 10.

In some embodiment, the present invention relates to variants of the mature polypeptide shown in SEQ ID NO 64 comprising a substitution, deletion, and/or insertion at one or more (e.g., several) positions. In some embodiment, the number of amino acid substitutions, deletions and/or insertions introduced into the mature polypeptide shown in SEQ ID NO 64 is up to 10, e.g., 1, 2, 3, 4, 5, 6, 7, 8, 9, or 10.

In some embodiment, the present invention relates to variants of the mature polypeptide shown in SEQ ID NO 67 comprising a substitution, deletion, and/or insertion at one or more (e.g., several) positions. In some embodiment, the number of amino acid substitutions, deletions and/or insertions introduced into the mature polypeptide shown in SEQ ID NO 67 is up to 10, e.g., 1, 2, 3, 4, 5, 6, 7, 8, 9, or 10.

In some embodiment, the present invention relates to variants of the mature polypeptide shown in SEQ ID NO 70 comprising a substitution, deletion, and/or insertion at one or more (e.g., several) positions. In some embodiment, the number of amino acid substitutions, deletions and/or insertions introduced into the mature polypeptide shown in SEQ ID NO 70 is up to 10, e.g., 1, 2, 3, 4, 5, 6, 7, 8, 9, or 10.

In some embodiment, the present invention relates to variants of the mature polypeptide shown in SEQ ID NO 73 comprising a substitution, deletion, and/or insertion at one or more (e.g., several) positions. In some embodiment, the number of amino acid substitutions, deletions and/or insertions introduced into the mature polypeptide shown in SEQ ID NO 73 is up to 10, e.g., 1, 2, 3, 4, 5, 6, 7, 8, 9, or 10.

In some embodiment, the present invention relates to variants of the mature polypeptide shown in SEQ ID NO 76 comprising a substitution, deletion, and/or insertion at one or more (e.g., several) positions. In some embodiment, the number of amino acid substitutions, deletions and/or insertions introduced into the mature polypeptide shown in SEQ ID NO 76 is up to 10, e.g., 1, 2, 3, 4, 5, 6, 7, 8, 9, or 10.

In some embodiment, the present invention relates to variants of the mature polypeptide shown in SEQ ID NO 79 comprising a substitution, deletion, and/or insertion at one or more (e.g., several) positions. In some embodiment, the number of amino acid substitutions, deletions and/or insertions introduced into the mature polypeptide shown in SEQ ID NO 79 is up to 10, e.g., 1, 2, 3, 4, 5, 6, 7, 8, 9, or 10.

In some embodiment, the present invention relates to variants of the mature polypeptide shown in SEQ ID NO 82 comprising a substitution, deletion, and/or insertion at one or more (e.g., several) positions. In some embodiment, the number of amino acid substitutions, deletions and/or insertions introduced into the mature polypeptide shown in SEQ ID NO 82 is up to 10, e.g., 1, 2, 3, 4, 5, 6, 7, 8, 9, or 10.

In some embodiment, the present invention relates to variants of the mature polypeptide shown in SEQ ID NO 85 comprising a substitution, deletion, and/or insertion at one or more (e.g., several) positions. In some embodiment, the number of amino acid substitutions, deletions and/or insertions introduced into the mature polypeptide shown in SEQ ID NO 85 is up to 10, e.g., 1, 2, 3, 4, 5, 6, 7, 8, 9, or 10.

In some embodiment, the present invention relates to variants of the mature polypeptide shown in SEQ ID NO 88 comprising a substitution, deletion, and/or insertion at one or more (e.g., several) positions. In some embodiment, the number of amino acid substitutions, deletions and/or insertions introduced into the mature polypeptide shown in SEQ ID NO 88 is up to 10, e.g., 1, 2, 3, 4, 5, 6, 7, 8, 9, or 10.

In some embodiment, the present invention relates to variants of the mature polypeptide shown in SEQ ID NO 91 comprising a substitution, deletion, and/or insertion at one or more (e.g., several) positions. In some embodiment, the number of amino acid substitutions, deletions and/or insertions introduced into the mature polypeptide shown in SEQ ID NO 91 is up to 10, e.g., 1, 2, 3, 4, 5, 6, 7, 8, 9, or 10.

In some embodiment, the present invention relates to variants of the mature polypeptide shown in SEQ ID NO 94 comprising a substitution, deletion, and/or insertion at one or more (e.g., several) positions. In some embodiment, the number of amino acid substitutions, deletions and/or insertions introduced into the mature polypeptide shown in SEQ ID NO 94 is up to 10, e.g., 1, 2, 3, 4, 5, 6, 7, 8, 9, or 10.

In some embodiment, the present invention relates to variants of the mature polypeptide shown in SEQ ID NO 95 comprising a substitution, deletion, and/or insertion at one or more (e.g., several) positions. In some embodiment, the number of amino acid substitutions, deletions and/or insertions introduced into the mature polypeptide shown in SEQ ID NO 95 is up to 10, e.g., 1, 2, 3, 4, 5, 6, 7, 8, 9, or 10.

In some embodiment, the present invention relates to variants of the mature polypeptide shown in SEQ ID NO 96 comprising a substitution, deletion, and/or insertion at one or more (e.g., several) positions. In some embodiment, the number of amino acid substitutions, deletions and/or insertions introduced into the mature polypeptide shown in SEQ ID NO 96 is up to 10, e.g., 1, 2, 3, 4, 5, 6, 7, 8, 9, or 10.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant molecules are tested for hydrolytic and/or deacetylase activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochemistry 30: 10832-10837; U.S. Pat. No. 5,223,409; WO 92/06204), and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, EMBO J. 12: 2575-2583; Dawson et al., 1994, Science 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, J. Ind. Microbiol. Biotechnol. 3: 568-576; Svetina et al., 2000, J. Biotechnol. 76: 245-251; Rasmussen-Wilson et al., 1997, Appl. Environ. Microbiol. 63: 3488-3493; Ward et al., 1995, Biotechnology 13: 498-503; and Contreras et al., 1991, Biotechnology 9: 378-381; Eaton et al., 1986, Biochemistry 25: 505-512; Collins-Racie et al., 1995, Biotechnology 13: 982-987; Carter et al., 1989, Proteins: Structure, Function, and Genetics 6: 240-248; and Stevens, 2003, Drug Discovery World 4: 35-48.

Sources of Polypeptides Having Polypeptide Activity

A polypeptide having hydrolytic and/or deacetylase activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly. In one aspect, the polypeptide is a *Pseudomonas* polypeptide, e.g., a polypeptide obtained from *Pseudomonas* sp-62208, *Pseudomonas seleniipraecipitans, Pseudomonas migulae, Pseudomonas corrugate, Pseudomonas pelagia, Pseudomonas aeruginosa* or *Pseudomonas composti*. In one aspect, the polypeptide is a Bacterial polypeptide, e.g., a polypeptide obtained from Environmental bacterial community A, Environmental bacterial community LE or Environmental bacterial community XE. In one aspect, the polypeptide is a *Thermus* polypeptide, e.g., a polypeptide obtained from *Thermus rehai*. In one aspect, the polypeptide is a *Burkholderia* polypeptide, e.g., a polypeptide obtained from *Burkholderia* sp-63093. In one aspect, the polypeptide is a *Myxococcus* polypeptide, e.g., a polypeptide obtained from *Myxococcus macrosporus, Myxococcus virescens, Myxococcus fulvus* or *Myxococcus stipitatus*. In one aspect, the polypeptide is a *Gallaecimonas* polypeptide, e.g., a polypeptide obtained from *Gallaecimonas pentaromativorans*. In one aspect, the polypeptide is a *Nonomuraea* polypeptide, e.g., a polypeptide obtained from *Nonomuraea coxensis*. In one aspect, the polypeptide is a *Paraburkholderia* polypeptide, e.g., a polypeptide obtained from *Paraburkholderia phenazinium*. In one aspect, the polypeptide is a *Microbulbifer* polypeptide, e.g., a polypeptide obtained from *Microbulbifer hydrolyticus*. In one aspect, the polypeptide is a *Carnobacterium* polypeptide, e.g., a polypeptide obtained from *Carnobacterium inhibens* subsp. *gilichinskyi*.

In one embodiment, the Glyco_hydro_114 glycosyl hydrolase i.e. a polypeptide comprising the Glyco_hydro_114 domain is bacterial. In one embodiment, the Glyco_hydro_114 glycosyl hydrolase i.e. a polypeptide comprising the Glyco_hydro_114 domain is derived from *Pseudomonas* e.g. *Pseudomonas* sp-62208, *Pseudomonas seleniipraecipitans, Pseudomonas migulae, Pseudomonas corrugate, Pseudomonas pelagia, Pseudomonas aeruginosa* or *Pseudomonas composti*. In one embodiment, the Glyco_hydro_114 glycosyl hydrolase is obtained from *Pseudomonas*, preferably *Pseudomonas* sp-62208, *Pseudomonas seleniipraecipitans, Pseudomonas migulae, Pseudomonas corrugate, Pseudomonas pelagia, Pseudomonas aeruginosa* or *Pseudomonas composti*, wherein the Glyco_hydro_114 glycosyl hydrolase comprising one or more, or even all of the motif(s) GX[FY][LYF]D (SEQ ID NO 34), AYX[SET]XX[EAS] (SEQ ID NO 35), GXXGX[FY][LYFI]D (SEQ ID NO 97), [ILFQV]N[RW]G[FL] (SEQ ID NO 98), DTLDS[YF] (SEQ ID NO 99), G[VL]FLDTLDSF[QTH]L[LMQ] (SEQ ID NO 100).

In one embodiment, the Glyco_hydro_114 glycosyl hydrolase is obtained from *Pseudomonas*, preferably *Pseudomonas* sp-62208, *Pseudomonas seleniipraecipitans, Pseudomonas migulae, Pseudomonas corrugate, Pseudomonas pelagia, Pseudomonas aeruginosa* or *Pseudomonas composti*, wherein the Glyco_hydro_114 glycosyl hydrolase is selected from the group consisting of:

(a) a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO 3;

(b) a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO 58;

(c) a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO 61;

(d) a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO 64;

(e) a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO 67; and (f) a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO 94.

One preferred embodiment relates to a Glyco_hydro_114 glycosyl hydrolase, wherein the Glyco_hydro_114 glycosyl hydrolase is obtained from *Pseudomonas*, preferably *Pseudomonas* sp-62208, *Pseudomonas seleniipraecipitans, Pseudomonas migulae, Pseudomonas corrugate, Pseudomonas pelagia, Pseudomonas aeruginosa* or *Pseudomonas composti*, and wherein the Glyco_hydro_114 glycosyl hydrolase is selected from the group consisting of:
  (a) a polypeptide having at least 90%, at least 95%, at least 96%, at least 97%, at least 98%, at least 99% or 100% sequence identity to the polypeptide of SEQ ID NO 3;
  (b) a polypeptide having at least 75%, at least 80%, at least 85%, at least 90%, at least 95%, at least 96%, at least 97%, at least 98%, at least 99% or 100% sequence identity to the polypeptide of SEQ ID NO 58;
  (c) a polypeptide having at least 95%, at least 96%, at least 97%, at least 98%, at least 99% or 100% sequence identity to the polypeptide of SEQ ID NO 61;
  (d) a polypeptide having at least 90%, at least 95%, at least 96%, at least 97%, at least 98%, at least 99% or 100% sequence identity to the polypeptide of SEQ ID NO 64;
  (e) a polypeptide having at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 67; and
  (f) a polypeptide having at least 80%, at least 85%, at least 90%, at least 95%, at least 96%, at least 97%, at least 98%, at least 99% or 100% sequence identity to the polypeptide of SEQ ID NO 94.

One preferred embodiment relates to a Glyco_hydro_114 glycosyl hydrolase, wherein the Glyco_hydro_114 glycosyl hydrolase is obtained from *Pseudomonas*, preferably *Pseudomonas* sp-62208, *Pseudomonas seleniipraecipitans, Pseudomonas migulae, Pseudomonas corrugate, Pseudomonas pelagia, Pseudomonas aeruginosa* or *Pseudomonas composti*, wherein the Glyco_hydro_114 glycosyl comprises four, five or six of the motifs selected from the group consisting of: GX[FY][LYF]D (SEQ ID NO 34), AYX[SET]XX[EAS] (SEQ ID NO 35), GXXGX[FY][LYFI]D (SEQ ID NO 97), [ILFQV]N[RW]G[FL] (SEQ ID NO 98), DTLDS[YF] (SEQ ID NO 99) and G[VL]FLDTLDSF[QTH]L[LMQ] (SEQ ID NO 100) and wherein the Glyco_hydro_114 glycosyl hydrolase is selected from the group consisting of:
  (a) a polypeptide having at least 90%, at least 95%, at least 96%, at least 97%, at least 98%, at least 99% or 100% sequence identity to the polypeptide of SEQ ID NO 3;
  (b) a polypeptide having at least 75%, at least 80%, at least 85%, at least 90%, at least 95%, at least 96%, at least 97%, at least 98%, at least 99% or 100% sequence identity to the polypeptide of SEQ ID NO 58;
  (c) a polypeptide having at least 95%, at least 96%, at least 97%, at least 98%, at least 99% or 100% sequence identity to the polypeptide of SEQ ID NO 61;
  (d) a polypeptide having at least 90%, at least 95%, at least 96%, at least 97%, at least 98%, at least 99% or 100% sequence identity to the polypeptide of SEQ ID NO 64;
  (e) a polypeptide having at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 67; and
  (f) a polypeptide having at least 80%, at least 85%, at least 90%, at least 95%, at least 96%, at least 97%, at least 98%, at least 99% or 100% sequence identity to the polypeptide of SEQ ID NO 94.

In one embodiment, the Glyco_hydro_114 glycosyl hydrolase i.e. a polypeptide comprising the Glyco_hydro_114 domain is bacterial. In one embodiment, the Glyco_hydro_114 glycosyl hydrolase is obtained from *Myxococcus*, preferably *Myxococcus macrosporus, Myxococcus virescens, Myxococcus fulvus* or *Myxococcus stipitatus*, wherein the Glyco_hydro_114 glycosyl hydrolase comprising one or more, or even all of the motif(s) GX[FY][LYF]D (SEQ ID NO 34), AYX[SET]XX[EAS] (SEQ ID NO 35), GXXGX[FY][LYFI]D (SEQ ID NO 97), [SETC]IG[EQA][ALI]EXY(SEQ ID NO 102), [QL]N[AS]PEL (SEQ ID NO 103), [KLYMQ]XX[PV]QN[SA]PE (SEQ ID NO 104).

In one embodiment, the Glyco_hydro_114 glycosyl hydrolase is obtained from *Myxococcus*, preferably *Myxococcus macrosporus, Myxococcus virescens, Myxococcus fulvus* or *Myxococcus stipitatus*, wherein the Glyco_hydro_114 glycosyl hydrolase is selected from the group consisting of:
  (a) a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO 18;
  (b) a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO 43;
  (c) a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO 46;
  (d) a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO 49;
  (e) a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO 52; and
  (f) a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO 55.

One preferred embodiment relates to A Glyco_hydro_114 glycosyl hydrolase, wherein the Glyco_hydro_114 glycosyl hydrolase is obtained from *Myxococcus*, preferably *Myxococcus macrosporus, Myxococcus virescens, Myxococcus fulvus* or *Myxococcus stipitatus*, wherein the Glyco_hydro_114 glycosyl hydrolase is selected from the group consisting of:

(a) a polypeptide having at least 95%, at least 96%, at least 97%, at least 98%, at least 99% or 100% sequence identity to the polypeptide of SEQ ID NO 18;
(b) a polypeptide having at least 95%, at least 96%, at least 97%, at least 98%, at least 99% or 100% sequence identity to the polypeptide of SEQ ID NO 43;
(c) a polypeptide having 100% sequence identity to the polypeptide of SEQ ID NO 46;
(d) a polypeptide having at least 95%, at least 96%, at least 97%, at least 98%, at least 99% or 100% sequence identity to the polypeptide of SEQ ID NO 49;
(e) a polypeptide having at least 95%, at least 96%, at least 97%, at least 98%, at least 99% or 100% sequence identity to the polypeptide of SEQ ID NO 52; and
(f) a polypeptide having at least 95%, at least 96%, at least 97%, at least 98%, at least 99% or 100% sequence identity to the polypeptide of SEQ ID NO 55.

One preferred embodiment relates to A Glyco_hydro_114 glycosyl hydrolase, wherein the Glyco_hydro_114 glycosyl hydrolase is obtained from *Myxococcus*, preferably *Myxococcus macrosporus, Myxococcus virescens, Myxococcus fulvus* or *Myxococcus stipitatus*, wherein the Glyco_hydro_114 glycosyl comprises four, five or six of the motifs selected from the group consisting of: GX[FY][LYF]D (SEQ ID NO 34), AYX[SET]XX[EAS] (SEQ ID NO 35), GXXGX[FY][LYFI]D (SEQ ID NO 97), [SETC]IG[EQA][ALI]EXY(SEQ ID NO 102), [QL]N[AS]PEL (SEQ ID NO 103), [KLYMQ]XX[PV]QN[SA]PE (SEQ ID NO 104) and wherein the Glyco_hydro_114 glycosyl hydrolase is selected from the group consisting of:
(a) a polypeptide having at least 95%, at least 96%, at least 97%, at least 98%, at least 99% or 100% sequence identity to the polypeptide of SEQ ID NO 18;
(b) a polypeptide having at least 95%, at least 96%, at least 97%, at least 98%, at least 99% or 100% sequence identity to the polypeptide of SEQ ID NO 43;
(c) a polypeptide having 100% sequence identity to the polypeptide of SEQ ID NO 46;
(d) a polypeptide having at least 95%, at least 96%, at least 97%, at least 98%, at least 99% or 100% sequence identity to the polypeptide of SEQ ID NO 49;
(e) a polypeptide having at least 95%, at least 96%, at least 97%, at least 98%, at least 99% or 100% sequence identity to the polypeptide of SEQ ID NO 52; and
(f) a polypeptide having at least 95%, at least 96%, at least 97%, at least 98%, at least 99% or 100% sequence identity to the polypeptide of SEQ ID NO 55.

In one embodiment, the Glyco_hydro_114 glycosyl hydrolase is obtained from *Thermus*, preferably *Thermus rehai*, wherein the Glyco_hydro_114 glycosyl hydrolase comprises one or more, or even all of the motif(s)GX[FY][LYF]D (SEQ ID NO 34), AYX[SET]XX[EAS] (SEQ ID NO 35), GXXGX[FY][LYFI]D (SEQ ID NO 97), [ILFQV]N[RW]G[FL] (SEQ ID NO 98). In one embodiment, the Glyco_hydro_114 glycosyl hydrolase is obtained from *Thermus*, preferably *Thermus rehai*, wherein the Glyco_hydro_114 glycosyl hydrolase is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO 9.

In one embodiment, the Glyco_hydro_114 glycosyl hydrolase is obtained from *Burkholderia*, preferably *Burkholderia sp-63093*, wherein the Glyco_hydro_114 glycosyl hydrolase comprises one or more, or even all of the motif(s)GX[FY][LYF]D (SEQ ID NO 34), AYX[SET]XX[EAS] (SEQ ID NO 35), GXXGX[FY][LYFI]D (SEQ ID NO 97), [ILFQV]N[RW]G[FL] (SEQ ID NO 98), DTLDS[YF] (SEQ ID NO 99), In one embodiment, the Glyco_hydro_114 glycosyl hydrolase is obtained from *Burkholderia*, preferably *Burkholderia sp-63093* wherein the Glyco_hydro_114 glycosyl hydrolase is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO 15 or a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO 96.

In one embodiment, the Glyco_hydro_114 glycosyl hydrolase is obtained from *Gallaecimonas*, preferably *Gallaecimonas pentaromativorans*, wherein the Glyco_hydro_114 glycosyl hydrolase comprises one or more, or even all of the motif(s)GX[FY][LYF]D (SEQ ID NO 34), AYX[SET]XX[EAS] (SEQ ID NO 35), GXXGX[FY][LYFI]D (SEQ ID NO 97), [ILFQV]N[RW]G[FL] (SEQ ID NO 98), DTLDS[YF] (SEQ ID NO 99). In one embodiment, the Glyco_hydro_114 glycosyl hydrolase is obtained from *Gallaecimonas*, preferably *Gallaecimonas pentaromativorans*, wherein the Glyco_hydro_114 glycosyl hydrolase is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO 21.

In one embodiment, the Glyco_hydro_114 glycosyl hydrolase is obtained from *Nonomuraea*, preferably *Nonomuraea coxensis*, wherein the Glyco_hydro_114 glycosyl hydrolase comprises one or more, or even all of the motif(s)GX[FY][LYF]D (SEQ ID NO 34), AYX[SET]XX[EAS] (SEQ ID NO 35), GXXGX[FY][LYFI]D (SEQ ID NO 97). In one embodiment, the Glyco_hydro_114 glycosyl hydrolase is obtained from *Nonomuraea*, preferably *Nonomuraea coxensis*, wherein the Glyco_hydro_114 glycosyl hydrolase is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO 24.

In one embodiment, the Glyco_hydro_114 glycosyl hydrolase is obtained from *Glycomyces*, preferably *Glycomyces rutgersensis*, wherein the Glyco_hydro_114 glycosyl hydrolase comprises one or more, or even all of the motif(s)GX[FY][LYF]D (SEQ ID NO 34), AYX[SET]XX[EAS] (SEQ ID NO 35), GXXGX[FY][LYFI]D (SEQ ID NO 97). In one embodiment, the Glyco_hydro_114 glycosyl hydrolase is obtained from *Glycomyces*, preferably *Glycomyces rutgersensis*, wherein the Glyco_hydro_114 glycosyl hydrolase is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO 27.

In one embodiment, the Glyco_hydro_114 glycosyl hydrolase is obtained from *Paraburkholderia*, preferably *Paraburkholderia phenazinium*, wherein the Glyco_hydro_114 glycosyl hydrolase comprises one or more, or even all of the motif(s)GX[FY][LYF]D (SEQ ID NO 34), AYX[SET]XX[EAS] (SEQ ID NO 35), GXXGX[FY][LYFI]D (SEQ ID NO 97), [ILFQV]N[RW]G[FL] (SEQ ID NO 98), DTLDS[YF] (SEQ ID NO 99). In one embodiment, the Glyco_hydro_114 glycosyl hydrolase is obtained from *Paraburkholderia*, preferably *Paraburkholderia phenazinium*, wherein the Glyco_hydro_114 glycosyl hydrolase is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO 33 or a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO 95.

In one embodiment, the Glyco_hydro_114 glycosyl hydrolase is obtained from *Streptomyces*, preferably *Streptomyces griseofuscus*, wherein the Glyco_hydro_114 glycosyl hydrolase comprises one or more, or even all of the motif(s)GX[FY][LYF]D (SEQ ID NO 34), AYX[SET]XX [EAS] (SEQ ID NO 35), GXXGX[FY][LYFI]D (SEQ ID NO 97). In one embodiment, the Glyco_hydro_114 glycosyl hydrolase is obtained from *Streptomyces*, preferably *Streptomyces griseofuscus*, wherein the Glyco_hydro_114 glycosyl hydrolase is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO 73.

In one embodiment, the Glyco_hydro_114 glycosyl hydrolase is obtained from *Lysinibacillus*, preferably *Lysinibacillus xylanilyticus*, wherein the Glyco_hydro_114 glycosyl hydrolase comprises one or more, or even all of the motif(s)GX[FY][LYF]D (SEQ ID NO 34), AYX[SET]XX [EAS] (SEQ ID NO 35), GXXGX[FY][LYFI]D (SEQ ID NO 97), [ILFQV]N[RW]G[FL] (SEQ ID NO 98), DT[VI-MA][GD][DNW][VIL][DEN](SEQ ID NO 101). In one embodiment, the Glyco_hydro_114 glycosyl hydrolase is obtained from *Lysinibacillus*, preferably *Lysinibacillus xylanilyticus*, wherein the Glyco_hydro_114 glycosyl hydrolase is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO 76 or a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO 82.

In one embodiment, the Glyco_hydro_114 glycosyl hydrolase is obtained from *Tumebacillus*, preferably *Tumebacillus ginsengisoli*, wherein the Glyco_hydro_114 glycosyl hydrolase comprises one or more, or even all of the motif(s)GX[FY][LYF]D (SEQ ID NO 34), AYX[SET]XX [EAS] (SEQ ID NO 35), GXXGX[FY][LYFI]D (SEQ ID NO 97), [ILFQV]N[RW]G[FL] (SEQ ID NO 98). In one embodiment, the Glyco_hydro_114 glycosyl hydrolase is obtained from *Tumebacillus*, preferably *Tumebacillus ginsengisoli*, wherein the Glyco_hydro_114 glycosyl hydrolase is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO 79.

In one embodiment, the Glyco_hydro_114 glycosyl hydrolase is obtained from *Microbulbifer*, preferably *Microbulbifer hydrolyticus*, wherein the Glyco_hydro_114 glycosyl hydrolase comprises one or more, or even all of the motif(s)GX[FY][LYF]D (SEQ ID NO 34), AYX[SET]XX [EAS] (SEQ ID NO 35), GXXGX[FY][LYFI]D (SEQ ID NO 97). In one embodiment, the Glyco_hydro_114 glycosyl hydrolase is obtained from *Microbulbifer*, preferably *Microbulbifer hydrolyticus*, wherein the Glyco_hydro_114 glycosyl hydrolase is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO 85.

In one embodiment, the Glyco_hydro_114 glycosyl hydrolase is obtained from *Carnobacterium*, preferably *Carnobacterium inhibens* subsp. *gilichinskyi*, wherein the Glyco_hydro_114 glycosyl hydrolase comprises one or more, or even all of the motif(s)GX[FY][LYF]D (SEQ ID NO 34), AYX[SET]XX[EAS] (SEQ ID NO 35), GXXGX[FY][LYFI]D (SEQ ID NO 97). In one embodiment, the Glyco_hydro_114 glycosyl hydrolase is obtained from *Carnobacterium*, preferably *Carnobacterium inhibens* subsp. *gilichinskyi*, wherein the Glyco_hydro_114 glycosyl hydrolase is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO 88.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polynucleotides

The present invention also relates to polynucleotides encoding a polypeptide of the present invention, as described herein. In some embodiment, the polynucleotide encoding the polypeptide of the present invention has been isolated.

In some embodiment, the present invention relates to a polynucleotide encoding a polypeptide having hydrolytic and/or deacetylase activity, wherein the polynucleotide having a sequence identity to the mature polypeptide coding sequence of SEQ ID NO 1 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic and/or deacetylase activity, wherein the polynucleotide having a sequence identity to the mature polypeptide coding sequence of SEQ ID NO 4 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic and/or deacetylase activity, wherein the polynucleotide having a sequence identity to the mature polypeptide coding sequence of SEQ ID NO 7 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic and/or deacetylase activity, wherein the polynucleotide having a sequence identity to the mature polypeptide coding sequence of SEQ ID NO 10 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic and/or deacetylase activity, wherein the polynucleotide having a sequence identity to the mature polypeptide coding sequence of SEQ ID NO 13 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic and/or deacetylase activity, wherein the polynucleotide having a sequence identity to the mature polypeptide coding sequence of SEQ ID NO 16 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic and/or deacetylase activity, wherein the polynucleotide having a sequence identity to the mature polypeptide coding sequence of SEQ ID NO 19 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic and/or deacetylase activity, wherein the polynucleotide having a sequence identity to the mature polypeptide coding sequence of SEQ ID NO 22 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic and/or deacetylase activity, wherein the polynucleotide having a sequence identity to the mature polypeptide coding sequence of SEQ ID NO 25 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic and/or deacetylase activity, wherein the polynucleotide having a sequence identity to the mature polypeptide coding sequence of SEQ ID NO 28 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic and/or deacetylase activity, wherein the polynucleotide having a sequence identity to the mature polypeptide coding sequence of SEQ ID NO 31 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic and/or deacetylase activity, wherein the polynucleotide having a sequence identity to the mature polypeptide coding sequence of SEQ ID NO 38 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic and/or deacetylase activity, wherein the polynucleotide having a sequence identity to the mature polypeptide coding sequence of SEQ ID NO 41 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic and/or deacetylase activity, wherein the polynucleotide having a sequence identity to the mature polypeptide coding sequence of SEQ ID NO 44 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic and/or deacetylase activity, wherein the polynucleotide having a sequence identity to the mature polypeptide coding sequence of SEQ ID NO 47 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic and/or deacetylase activity, wherein the polynucleotide having a sequence identity to the mature polypeptide coding sequence of SEQ ID NO 50 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic and/or deacetylase activity, wherein the polynucleotide having a sequence identity to the mature polypeptide coding sequence of SEQ ID NO 53 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic and/or deacetylase activity, wherein the polynucleotide having a sequence identity to the mature polypeptide coding sequence of SEQ ID NO 56 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic and/or deacetylase activity, wherein the polynucleotide having a sequence identity to the mature polypeptide coding sequence of SEQ ID NO 59 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic and/or deacetylase activity, wherein the polynucleotide having a sequence identity to the mature polypeptide coding sequence of SEQ ID NO 62 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic and/or deacetylase activity, wherein the polynucleotide having a sequence identity to the mature polypeptide coding sequence of SEQ ID NO 65 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic and/or deacetylase activity, wherein the polynucleotide having a sequence identity to the mature polypeptide coding sequence of SEQ ID NO 68 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic and/or deacetylase activity, wherein the polynucleotide having a sequence identity to the mature polypeptide coding sequence of SEQ ID NO 71 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic and/or deacetylase activity, wherein the polynucleotide having a sequence identity to the mature polypeptide coding sequence of SEQ ID NO 74 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic and/or deacetylase activity, wherein the polynucleotide having a sequence identity to the mature polypeptide coding sequence of SEQ ID NO 77 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic and/or deacetylase activity, wherein the polynucleotide having a sequence identity to the mature polypeptide coding sequence of SEQ ID NO 80 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic and/or deacetylase activity, wherein the polynucleotide having a sequence identity to the mature polypeptide coding sequence of SEQ ID NO 83 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic and/or deacetylase activity, wherein the polynucleotide having a sequence identity to the mature polypeptide coding sequence of SEQ ID NO 86 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic and/or deacetylase activity, wherein the polynucleotide having a sequence identity to the mature polypeptide coding sequence of SEQ ID NO 89 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic and/or deacetylase activity, wherein the polynucleotide having a sequence identity to the mature polypeptide coding sequence of SEQ ID NO 92 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic and/or deacetylase activity, wherein the polynucleotide having a sequence identity to the mature polypeptide coding sequence of SEQ ID NO 95 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In some embodiment, the present invention relates to a polynucleotide encoding a polypeptide having hydrolytic and/or deacetylase activity, wherein the polynucleotide having a sequence identity to the mature polypeptide coding sequence of SEQ ID NO 98 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

The techniques used to isolate or clone a polynucleotide are known in the art and include isolation from genomic DNA or cDNA, or a combination thereof. The cloning of the polynucleotides from genomic DNA can be effected, e.g., by using the well-known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including variant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and variant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative *bacterium*. Gram-positive bacteria include, but are not limited to, *Bacillus*, *Clostridium*, *Enterococcus*, *Geobacillus*, *Lactobacillus*, *Lactococcus*, *Oceanobacillus*, *Staphylococcus*, *Streptococcus*, and *Streptomyces*. Gram-negative bacteria include, but are not limited to, *Campylobacter*, *E. coli*, *Flavobacterium*, *Fusobacterium*, *Helicobacter*, *Ilyobacter*, *Neisseria*, *Pseudomonas*, *Salmonella*, and *Ureaplasma*.

The bacterial host cell may be any *Bacillus* cell including, but not limited to, *Bacillus alkalophilus*, *Bacillus altitudinis*, *Bacillus amyloliquefaciens*, *B. amyloliquefaciens* subsp. *plantarum*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus methylotrophicus*, *Bacillus pumilus*, *Bacillus safensis*, *Bacillus stearothermophilus*, *Bacillus subtilis*, and *Bacillus thuringiensis* cells.

The bacterial host cell may also be any *Streptococcus* cell including, but not limited to, *Streptococcus equisimilis*, *Streptococcus pyogenes*, *Streptococcus uberis*, and *Streptococcus equi* subsp. *Zooepidemicus* cells.

The bacterial host cell may also be any *Streptomyces* cell including, but not limited to, *Streptomyces achromogenes*, *Streptomyces avermitilis*, *Streptomyces coelicolor*, *Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (*Endomycetales*), basidiosporogenous yeast, and yeast belonging to the *Fungi Imperfecti* (*Blastomycetes*). Since the classification of yeast may change in the future, for the purposes of this invention, yeast shall be defined as described in *Biology and Activities of Yeast* (Skinner, Passmore, and Davenport, editors, Soc. App. Bacteriol. Symposium Series No. 9, 1980).

The yeast host cell may be a *Candida*, *Hansenula*, *Kluyveromyces*, *Pichia*, *Saccharomyces*, *Schizosaccharomyces*, or *Yarrowia* cell, such as a *Kluyveromyces lactis*, *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, *Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenaturn, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology,* Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and optionally, (b) recovering the polypeptide.

The present invention also relates to methods of producing a polypeptide of the present invention, comprising (a) cultivating a recombinant host cell of the present invention under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides having hydrolytic and/or deacetylase activity. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification,* Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In some embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Enzyme Compositions

The invention relates to compositions comprising a Polypeptide of the present invention in combination with one or more additional component(s). The choice of additional components is within the skill of the artisan and includes conventional ingredients, including the exemplary non-limiting components set forth below.

Some embodiments of the invention relate to a composition comprising:
  a) at least 0.001 ppm of at least one polypeptide having hydrolytic and/or deacetylase activity, wherein the polypeptide is selected for the group consisting of: SEQ ID NO 3, SEQ ID NO 6, SEQ ID NO 9, SEQ ID NO 12, SEQ ID NO 15, SEQ ID NO 18, SEQ ID NO 21, SEQ ID NO 24, SEQ ID NO 27, SEQ ID NO 30, SEQ ID NO 33, SEQ ID NO 40, SEQ ID NO 43, SEQ ID NO 46, SEQ ID NO 49, SEQ ID NO 52, SEQ ID NO 55, SEQ ID NO 58, SEQ ID NO 61, SEQ ID NO 64, SEQ ID NO 67, SEQ ID NO 70, SEQ ID NO 73, SEQ ID NO 76, SEQ ID NO 79, SEQ ID NO 82, SEQ ID NO 85, SEQ ID NO 88, SEQ ID NO 91, SEQ ID NO 94, SEQ ID NO 95, SEQ ID NO 96 and polypeptides having at least 60%, at least 65%, at least 70%, at least 75%, at least 80%, at least 85%, at least 90%, at least 95%, at least 96%, at least 97%, at least 98%, at least 99% or 100% sequence identity hereto;
  b) one or more adjunct ingredient.

Some embodiments of the invention relate to a cleaning composition comprising:
  a) at least 0.001 ppm of at least one polypeptide having hydrolytic and/or deacetylase activity, wherein the polypeptide is selected for the group consisting of: SEQ ID NO 3, SEQ ID NO 6, SEQ ID NO 9, SEQ ID NO 12, SEQ ID NO 15, SEQ ID NO 18, SEQ ID NO 21, SEQ ID NO 24, SEQ ID NO 27, SEQ ID NO 30, SEQ ID NO 33, SEQ ID NO 40, SEQ ID NO 43, SEQ ID NO 46, SEQ ID NO 49, SEQ ID NO 52, SEQ ID NO 55, SEQ ID NO 58, SEQ ID NO 61, SEQ ID NO 64, SEQ ID NO 67, SEQ ID NO 70, SEQ ID NO 73, SEQ ID NO 76, SEQ ID NO 79, SEQ ID NO 82, SEQ ID NO 85, SEQ ID NO 88, SEQ ID NO 91, SEQ ID NO 94, SEQ ID NO 95, SEQ ID NO 96 and polypeptides having at least 60%, at least 65%, at least 70%, at least 75%, at least 80%, at least 85%, at least 90%, at least 95%, at least 96%, at least 97%, at least 98%, at least 99% or 100% sequence identity hereto;
  b) one or more cleaning composition component, preferably selected from surfactants, builders, bleach components, polymers, dispersing agents and additional enzymes.

Some embodiments of the invention relate to a cleaning composition comprising:
  a) at least 0.001 ppm of at least one polypeptide having hydrolytic and/or deacetylase activity, wherein the polypeptide comprises one or more motif selected from the group consisting of: GX[FY][LYF]D (SEQ ID NO 34), AYX[SET]XX[EAS] (SEQ ID NO 35), GXXGX[FY][LYFI]D (SEQ ID NO 97), [ILFQV]N[RW]G[FL] (SEQ ID NO 98), DTLDS[YF] (SEQ ID NO 99) and G[VL]FLDTLDSF[QTH]L[LMQ] (SEQ ID NO 100), DT[VIMA][GD][DNW][VIL][DEN] (SEQ ID NO 101), [SETC]IG[EQA][ALI]EXY(SEQ ID NO 102), [QL]N[AS]PEL (SEQ ID NO 103), and [KLYMQ]XX[PV]QN[SA]PE (SEQ ID NO 104); and
  b) one or more cleaning composition component, preferably selected from surfactants, builders, bleach components, polymers, dispersing agents and additional enzymes.

One embodiment relates to a cleaning composition comprising:
  a) at least 0.001 ppm of at least one polypeptide having hydrolytic and/or deacetylase activity e.g. a Glyco_hydro_114 glycosyl hydrolase, wherein the polypeptide is selected from the group consisting of:
    i) a polypeptide having at least 60%, at least 70%, at least 75%, at least 80%, at least 85%, at least 90%, at least 95%, at least 96%, at least 97%, at least 98%, at least 99% or 100% sequence identity to the polypeptide of SEQ ID NO 3;
    ii) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 6;

iii) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 9;
iv) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 12;
v) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 15;
vi) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 18;
vii) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 21;
viii) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 24;
ix) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 27;
x) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 30;
xi) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 33;
xii) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 40;
xiii) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 43;
xiv) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 46;
xv) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 49;
xvi) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 52;
xvii) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 55;
xviii) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 58;
xix) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 61;
xx) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 64;
xxi) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 67;
xxii) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 70;
xxiii) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 73;
xxiv) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 76;
xxv) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 79;
xxvi) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 82;
xxvii) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 85;
xxviii) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 88;
xxix) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 91;

xxx) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 94;

xxxi) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 95;

xxxii) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 96; and b) one or more cleaning composition component, preferably selected from surfactants, builders, bleach components, polymers, dispersing agents and additional enzymes.

The choice of cleaning components may include, for textile care, the consideration of the type of textile to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan.

Surfactants

The detergent composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to 60% by weight, such as about 1% to about 40%, or about 3% to about 20%, or about 3% to about 10%. The surfactant(s) is chosen based on the desired cleaning application, and may include any conventional surfactant(s) known in the art.

When included therein the detergent will usually contain from about 1% to about 40% by weight of an anionic surfactant, such as from about 5% to about 30%, including from about 5% to about 15%, or from about 15% to about 20%, or from about 20% to about 25% of an anionic surfactant. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

When included therein the detergent will usually contain from about 1% to about 40% by weigh of a cationic surfactant, for example from about 0.5% to about 30%, in particular from about 1% to about 20%, from about 3% to about 10%, such as from about 3% to about 5%, from about 8% to about 12% or from about 10% to about 12%. Non-limiting examples of cationic surfactants include alkyldimethylethanolamine quat (ADMEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, ester quats, and combinations thereof.

When included therein the detergent will usually contain from about 0.2% to about 40% by weight of a nonionic surfactant, for example from about 0.5% to about 30%, in particular from about 1% to about 20%, from about 3% to about 10%, such as from about 3% to about 5%, from about 8% to about 12%, or from about 10% to about 12%. Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof.

When included therein the detergent will usually contain from about 0.1% to about 10% by weight of a semipolar surfactant. Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, and combinations thereof.

When included therein the detergent will usually contain from about 0.1% to about 10% by weight of a zwitterionic surfactant. Non-limiting examples of zwitterionic surfactants include betaines such as alkyldimethylbetaines, sulfobetaines, and combinations thereof.

Builders and Co-Builders

The detergent composition may contain about 0-65% by weight, such as about 5% to about 50% of a detergent builder or co-builder, or a mixture thereof. In a dish wash detergent, the level of builder is typically 40-65%, particularly 50-65%. The builder and/or co-builder may particularly be a chelating agent that forms water-soluble complexes with Ca and Mg. Any builder and/or co-builder known in the art for use in cleaning detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), diethanolamine (DEA, also known as 2,2'-iminodiethan-1-ol), triethanolamine (TEA, also known as 2,2',2"-nitrilotriethan-1-ol), and (carboxymethyl)inulin (CMI), and combinations thereof.

The detergent composition may also contain 0-50% by weight, such as about 5% to about 30%, of a detergent co-builder. The detergent composition may include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diphosphonic acid (HEDP), ethylenediaminetetra(methylenephosphonic acid) (EDTMPA), diethylenetriaminepentakis(methylenephosphonic acid) (DTMPA or DTPMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl)-aspartic acid (SMAS), N-(2-sulfoethyl)-aspartic acid (SEAS), N-(2-sulfomethyl)-glutamic acid (SMGL), N-(2-sulfoethyl)-glutamic acid (SEGL), N-methyliminodiacetic acid (MIDA), α-alanine-N,N-diacetic acid (α-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA), N-(2-hydroxyethyl)ethylenediamine-N,N',N"-triacetic acid (HEDTA), diethanolglycine (DEG), diethylenetriamine penta(methylenephosphonic acid) (DTPMP), aminotris(methylenephosphonic acid) (ATMP), and combinations and salts thereof. Further exemplary builders and/or co-builders are described in, e.g., WO 09/102854, U.S. Pat. No. 5,977,053.

Bleaching Systems

The detergent may contain 0-30% by weight, such as about 1% to about 20%, of a bleaching system. Any bleaching system comprising components known in the art for use in cleaning detergents may be utilized. Suitable bleaching system components include sources of hydrogen peroxide; sources of peracids; and bleach catalysts or boosters.

Sources of Hydrogen Peroxide:

Suitable sources of hydrogen peroxide are inorganic persalts, including alkali metal salts such as sodium percarbonate and sodium perborates (usually mono- or tetrahydrate), and hydrogen peroxide-urea (1/1).

Sources of Peracids:

Peracids may be (a) incorporated directly as preformed peracids or (b) formed in situ in the wash liquor from hydrogen peroxide and a bleach activator (perhydrolysis) or (c) formed in situ in the wash liquor from hydrogen peroxide and a perhydrolase and a suitable substrate for the latter, e.g., an ester.

a) Suitable preformed peracids include, but are not limited to, peroxycarboxylic acids such as peroxybenzoic acid and its ring-substituted derivatives, peroxy-α-naphthoic acid, peroxyphthalic acid, peroxylauric acid, peroxystearic acid, ε-phthalimidoperoxycaproic acid [phthalimidoperoxyhexanoic acid (PAP)], and o-carboxybenzamidoperoxycaproic acid; aliphatic and aromatic diperoxydicarboxylic acids such as diperoxydodecanedioic acid, diperoxyazelaic acid, diperoxysebacic acid, diperoxybrassylic acid, 2-decyldiperoxybutanedioic acid, and diperoxyphthalic, -isophthalic and -terephthalic acids; perimidic acids; peroxymonosulfuric acid; peroxydisulfuric acid; peroxyphosphoric acid; peroxysilicic acid; and mixtures of said compounds. It is understood that the peracids mentioned may in some cases be best added as suitable salts, such as alkali metal salts (e.g., Oxone®) or alkaline earth-metal salts.

b) Suitable bleach activators include those belonging to the class of esters, amides, imides, nitriles or anhydrides and, where applicable, salts thereof. Suitable examples are tetraacetylethylenediamine (TAED), sodium 4-[(3,5,5-trimethylhexanoyl)oxy]benzene-1-sulfonate (ISONOBS), sodium 4-(dodecanoyloxy)benzene-1-sulfonate (LOBS), sodium 4-(decanoyloxy)benzene-1-sulfonate, 4-(decanoyloxy)benzoic acid (DOBA), sodium 4-(nonanoyloxy)benzene-1-sulfonate (NOBS), and/or those disclosed in WO98/17767. A particular family of bleach activators of interest was disclosed in EP624154 and particularly preferred in that family is acetyl triethyl citrate (ATC). ATC or a short chain triglyceride like triacetin has the advantage that they are environmentally friendly. Furthermore, acetyl triethyl citrate and triacetin have good hydrolytical stability in the product upon storage and are efficient bleach activators. Finally, ATC is multifunctional, as the citrate released in the perhydrolysis reaction may function as a builder.

Bleach Catalysts and Boosters

The bleaching system may also include a bleach catalyst or booster.

Some non-limiting examples of bleach catalysts that may be used in the compositions of the present invention include manganese oxalate, manganese acetate, manganese-collagen, cobalt-amine catalysts and manganese triazacyclononane (MnTACN) catalysts; particularly preferred are complexes of manganese with 1,4,7-trimethyl-1,4,7-triazacyclononane (Me3-TACN) or 1,2,4,7-tetramethyl-1,4,7-triazacyclononane (Me4-TACN), in particular Me3-TACN, such as the dinuclear manganese complex [(Me3-TACN)Mn(O)3Mn(Me3-TACN)](PF6)2, and [2,2',2"-nitrilotris(ethane-1,2-diylazanylylidene-κN-methanylylidene)triphenolato-κ3O]manganese(III). The bleach catalysts may also be other metal compounds; such as iron or cobalt complexes.

In some embodiments, where a source of a peracid is included, an organic bleach catalyst or bleach booster may be used having one of the following formulae:

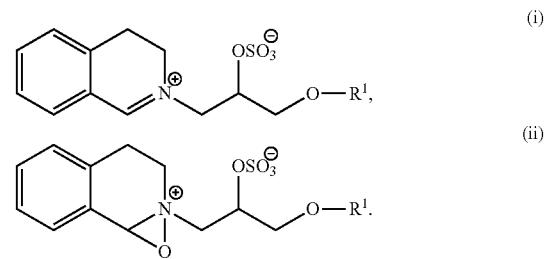

(iii) and mixtures thereof; wherein each R1 is independently a branched alkyl group containing from 9 to 24 carbons or linear alkyl group containing from 11 to 24 carbons, preferably each R1 is independently a branched alkyl group containing from 9 to 18 carbons or linear alkyl group containing from 11 to 18 carbons, more preferably each R1 is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl.

Other exemplary bleaching systems are described, e.g. in WO2007/087258, WO2007/087244, WO2007/087259, EP1867708 (Vitamin K) and WO2007/087242. Suitable photobleaches may for example be sulfonated zinc or aluminium phthalocyanines.

Metal Care Agents

Metal care agents may prevent or reduce the tarnishing, corrosion or oxidation of metals, including aluminium, stainless steel and non-ferrous metals, such as silver and copper. Suitable examples include one or more of the following:

(a) benzatriazoles, including benzotriazole or bis-benzotriazole and substituted derivatives thereof. Benzotriazole derivatives are those compounds in which the available substitution sites on the aromatic ring are partially or completely substituted. Suitable substituents include linear or branch-chain Ci-C20-alkyl groups (e.g., C1-C20-alkyl groups) and hydroxyl, thio, phenyl or halogen such as fluorine, chlorine, bromine and iodine.

(b) metal salts and complexes chosen from the group consisting of zinc, manganese, titanium, zirconium, hafnium, vanadium, cobalt, gallium and cerium salts and/or complexes, the metals being in one of the oxidation states II, III, IV, V or VI. In one aspect, suitable metal salts and/or metal complexes may be chosen from the group consisting of Mn(II) sulphate, Mn(II) citrate, Mn(II) stearate, Mn(II) acetylacetonate, K^TiF6 (e.g., K2TiF6), K^ZrF6 (e.g., K2ZrF6), CoSO4, Co(NOs)2 and Ce(NOs)3, zinc salts, for example zinc sulphate, hydrozincite or zinc acetate;

(c) silicates, including sodium or potassium silicate, sodium disilicate, sodium metasilicate, crystalline phyllosilicate and mixtures thereof.

Further suitable organic and inorganic redox-active substances that act as silver/copper corrosion inhibitors are disclosed in WO 94/26860 and WO 94/26859. Preferably the composition of the invention comprises from 0.1 to 5% by weight of the composition of a metal care agent, preferably the metal care agent is a zinc salt.

Hydrotropes

The detergent may contain 0-10% by weight, for example 0-5% by weight, such as about 0.5 to about 5%, or about 3% to about 5%, of a hydrotrope. Any hydrotrope known in the art for use in detergents may be utilized. Non-limiting examples of hydrotropes include sodium benzenesulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Polymers

The detergent may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or antifoaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly (ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly (oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Suitable examples include PVP-K15, PVP-K30, ChromaBond S-400, ChromaBond S-403E and Chromabond S-100 from Ashland Aqualon, and Sokalan® HP 165, Sokalan® HP 50 (Dispersing agent), Sokalan® HP 53 (Dispersing agent), Sokalan® HP 59 (Dispersing agent), Sokalan® HP 56 (dye transfer inhibitor), Sokalan® HP 66 K (dye transfer inhibitor) from BASF. Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated. Particularly preferred polymer is ethoxylated homopolymer Sokalan® HP 20 from BASF, which helps to prevent redeposition of soil in the wash liquor.

Fabric Hueing Agents

The detergent compositions of the present invention may also include fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/03276 and EP1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g. WO 2007/087257 and WO2007/087243.

Enzymes

The detergent additive as well as the detergent composition may comprise one or more additional enzymes such as one or more lipase, cutinase, an amylase, carbohydrase, cellulase, pectinase, mannanase, arabinase, galactanase, xylanase, oxidase, e.g., a laccase, and/or peroxidase.

In general, the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 0 495 257, EP 0 531

372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and WO99/001544.

Other cellulases are endo-beta-1,4-glucanase enzyme having a sequence of at least 97% identity to the amino acid sequence of position 1 to position 773 of SEQ ID NO2 of WO 2002/099091 or a family 44 xyloglucanase, which a xyloglucanase enzyme having a sequence of at least 60% identity to positions 40-559 of SEQ ID NO 2 of WO 2001/062903.

Commercially available cellulases include Celluzyme™, and Carezyme™ (Novozymes A/S) Carezyme Premium™ (Novozymes A/S), Celluclean™ (Novozymes A/S), Celluclean Classic™ (Novozymes A/S), Cellusoft™ (Novozymes A/S), Whitezyme™ (Novozymes A/S), Clazinase™, and Puradax HA™ (Genencor International Inc.), and KAC-500(B)™ (Kao Corporation).

Mannanases

Suitable mannanases include those of bacterial or fungal origin. Chemically or genetically modified mutants are included. The mannanase may be an alkaline mannanase of Family 5 or 26. It may be a wild-type from Bacillus or Humicola, particularly B. agaradhaerens, B. licheniformis, B. halodurans, B. clausii, or H. insolens. Suitable mannanases are described in WO 1999/064619. A commercially available mannanase is Mannaway (Novozymes A/S).

Peroxidases/Oxidases

Suitable peroxidases/oxidases include those of plant, bacterial or fungal origin. Chemically modified or protein engineered mutants are included. Examples of useful peroxidases include peroxidases from Coprinus, e.g., from C. cinereus, and variants thereof as those described in WO 93/24618, WO 95/10602, and WO 98/15257. Commercially available peroxidases include Guardzyme™ (Novozymes A/S).

Lipases and Cutinases:

Suitable lipases and cutinases include those of bacterial or fungal origin. Chemically modified or protein engineered mutant enzymes are included. Examples include lipase from Thermomyces, e.g. from T. lanuginosus (previously named Humicola lanuginosa) as described in EP258068 and EP305216, cutinase from Humicola, e.g. H. insolens (WO96/13580), lipase from strains of Pseudomonas (some of these now renamed to Burkholderia), e.g. P. alcaligenes or P. pseudoalcaligenes (EP218272), P. cepacia (EP331376), P. sp. strain SD705 (WO95/06720 & WO96/27002), P. wisconsinensis (WO96/12012), GDSL-type Streptomyces lipases (WO10/065455), cutinase from Magnaporthe grisea (WO10/107560), cutinase from Pseudomonas mendocina (U.S. Pat. No. 5,389,536), lipase from Thermobifida fusca (WO11/084412), Geobacillus stearothermophilus lipase (WO11/084417), lipase from Bacillus subtilis (WO11/084599), and lipase from Streptomyces griseus (WO11/150157) and S. pristinaespiralis (WO12/137147).

Other examples are lipase variants such as those described in EP407225, WO92/05249, WO94/01541, WO94/25578, WO95/14783, WO95/30744, WO95/35381, WO95/22615, WO96/00292, WO97/04079, WO97/07202, WO00/34450, WO00/60063, WO01/92502, WO07/87508 and WO09/109500.

Preferred commercial lipase products include Lipolase™, Lipex™; Lipolex™ and Lipoclean™ (Novozymes A/S), Lumafast (originally from Genencor) and Lipomax (originally from Gist-Brocades).

Still other examples are lipases sometimes referred to as acyltransferases or perhydrolases, e.g. acyltransferases with homology to Candida antarctica lipase A (WO10/111143), acyltransferase from Mycobacterium smegmatis (WO05/56782), perhydrolases from the CE 7 family (WO09/67279), and variants of the M. smegmatis perhydrolase in particular the S54V variant used in the commercial product Gentle Power Bleach from Huntsman Textile Effects Pte Ltd (WO10/100028).

Amylases:

Suitable amylases include alpha-amylases and/or a glucoamylases and may be of bacterial or fungal origin. Chemically modified or protein engineered mutants are included. Amylases include, for example, alpha-amylases obtained from Bacillus, e.g., a special strain of Bacillus licheniformis, described in more detail in GB 1,296,839.

Suitable amylases include amylases having SEQ ID NO 2 in WO 95/10603 or variants having 90% sequence identity to SEQ ID NO 3 thereof. Preferred variants are described in WO 94/02597, WO 94/18314, WO 97/43424 and SEQ ID NO 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO 6 in WO 02/010355 or variants thereof having 90% sequence identity to SEQ ID NO 6. Preferred variants of SEQ ID NO 6 are those having a deletion in positions 181 and 182 and a substitution in position 193.

Other amylases which are suitable are hybrid alpha-amylase comprising residues 1-33 of the alpha-amylase derived from B. amyloliquefaciens shown in SEQ ID NO 6 of WO 2006/066594 and residues 36-483 of the B. licheniformis alpha-amylase shown in SEQ ID NO 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, I201, A209 and Q264. Most preferred variants of the hybrid alpha-amylase comprising residues 1-33 of the alpha-amylase derived from B. amyloliquefaciens shown in SEQ ID NO 6 of WO 2006/066594 and residues 36-483 of SEQ ID NO 4 are those having the substitutions:

M197T;

H156Y+A181T+N190F+A209V+Q264S; or

G48A+T49I+G107A+H156Y+A181T+N190F+I201F+A209V+Q264S.

Further amylases which are suitable are amylases having SEQ ID NO 6 in WO 99/019467 or variants thereof having 90% sequence identity to SEQ ID NO 6. Preferred variants of SEQ ID NO 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184.

Additional amylases which can be used are those having SEQ ID NO 1, SEQ ID NO 3, SEQ ID NO 2 or SEQ ID NO 7 of WO 96/023873 or variants thereof having 90% sequence identity to SEQ ID NO 1, SEQ ID NO 2, SEQ ID NO 3 or SEQ ID NO 7. Preferred variants of SEQ ID NO 1, SEQ ID NO 2, SEQ ID NO 3 or SEQ ID NO 7 are those having a substitution, a deletion or an insertion in one or more of the following positions: 140, 181, 182, 183, 184, 195, 206, 212, 243, 260, 269, 304 and 476, using SEQ ID 2 of WO 96/023873 for numbering. More preferred variants are those having a deletion in two positions selected from 181, 182, 183 and 184, such as 181 and 182, 182 and 183, or positions 183 and 184. Most preferred amylase variants of SEQ ID NO 1, SEQ ID NO 2 or SEQ ID NO 7 are those having a deletion in positions 183 and 184 and a substitution in one or more of positions 140, 195, 206, 243, 260, 304 and 476.

Other amylases which can be used are amylases having SEQ ID NO 2 of WO 08/153815, SEQ ID NO 10 in WO 01/66712 or variants thereof having 90% sequence identity to SEQ ID NO 2 of WO 08/153815 or 90% sequence identity to SEQ ID NO 10 in WO 01/66712. Preferred variants of SEQ ID NO 10 in WO 01/66712 are those having a substitution, a deletion or an insertion in one of more of the following positions: 176, 177, 178, 179, 190, 201, 207, 211 and 264.

Further suitable amylases are amylases having SEQ ID NO 2 of WO 09/061380 or variants having 90% sequence identity to SEQ ID NO 2 thereof. Preferred variants of SEQ ID NO 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO 2 are those having the substitution in one of more of the following positions: Q87E,R, Q98R, S125A, N128C, T131I, T165I, K178L, T182G, M201L, F202Y, N225E,R, N272E, R, S243Q,A,E,D, Y305R, R309A, Q320R, Q359E, K444E and G475K and/or deletion in position R180 and/or S181 or of T182 and/or G183. Most preferred amylase variants of SEQ ID NO 2 are those having the substitutions:

N128C+K178L+T182G+Y305R+G475K;
N128C+K178L+T182G+F202Y+Y305R+D319T+G475K;
S125A+N128C+K178L+T182G+Y305R+G475K; or
S125A+N128C+T131I+T165I+K178L+T182G+Y305R+G475K wherein the variants are C-terminally truncated and optionally further comprises a substitution at position 243 and/or a deletion at position 180 and/or position 181.

Further suitable amylases are amylases having SEQ ID NO 1 of WO13184577 or variants having 90% sequence identity to SEQ ID NO 1 thereof. Preferred variants of SEQ ID NO 1 are those having a substitution, a deletion or an insertion in one of more of the following positions: K176, R178, G179, T180, G181, E187, N192, M199, I203, S241, R458, T459, D460, G476 and G477. More preferred variants of SEQ ID NO 1 are those having the substitution in one of more of the following positions: K176L, E187P, N192FYH, M199L, I203YF, S241QADN, R458N, T459S, D460T, G476K and G477K and/or deletion in position R178 and/or S179 or of T180 and/or G181. Most preferred amylase variants of SEQ ID NO 1 are those having the substitutions:

E187P+I203Y+G476K
E187P+I203Y+R458N+T459S+D460T+G476K wherein the variants optionally further comprise a substitution at position 241 and/or a deletion at position 178 and/or position 179.

Further suitable amylases are amylases having SEQ ID NO 1 of WO10104675 or variants having 90% sequence identity to SEQ ID NO 1 thereof. Preferred variants of SEQ ID NO 1 are those having a substitution, a deletion or an insertion in one of more of the following positions: N21, D97, V128 K177, R179, S180, I181, G182, M200, L204, E242, G477 and G478. More preferred variants of SEQ ID NO 1 are those having the substitution in one of more of the following positions: N21D, D97N, V128I K177L, M200L, L204YF, E242QA, G477K and G478K and/or deletion in position R179 and/or S180 or of I181 and/or G182. Most preferred amylase variants of SEQ ID NO 1 are those having the substitutions:

N21D+D97N+V128I wherein the variants optionally further comprise a substitution at position 200 and/or a deletion at position 180 and/or position 181.

Other suitable amylases are the alpha-amylase having SEQ ID NO 12 in WO01/66712 or a variant having at least 90% sequence identity to SEQ ID NO 12. Preferred amylase variants are those having a substitution, a deletion or an insertion in one of more of the following positions of SEQ ID NO 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase variants such as those described in WO2011/098531, WO2013/001078 and WO2013/001087.

Commercially available amylases are Duramyl™, Termamyl™, Fungamyl™, Stainzyme™, Stainzyme Plus™, Natalase™, Liquozyme X and BAN™ (from Novozymes A/S), and Rapidase™, Purastar™/Effectenz™, Powerase, Preferenz S1000, Preferenz S100 and Preferenz S110 (from Genencor International Inc./DuPont).

Proteases:

Suitable proteases include those of bacterial, fungal, plant, viral or animal origin e.g. vegetable or microbial origin. Microbial origin is preferred. Chemically modified or protein engineered mutants are included. It may be an alkaline protease, such as a serine protease or a metalloprotease. A serine protease may for example be of the S1 family, such as trypsin, or the S8 family such as subtilisin. A metalloproteases protease may for example be a thermolysin from e.g. family M4 or other metalloproteases such as those from M5, M7 or M8 families.

The term "subtilases" refers to a sub-group of serine protease according to Siezen et al., Protein Engng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family.

Examples of subtilases are those derived from *Bacillus* such as *Bacillus lentus, Bacillus alkalophilus, Bacillus subtilis, Bacillus amyloliquefaciens, Bacillus pumilus* and *Bacillus gibsonii* described in; U.S. Pat. No. 7,262,042 and WO09/021867, and Subtilisin lentus, Subtilisin Novo, subtilisin Carlsberg, *Bacillus licheniformis*, subtilisin BPN', subtilisin 309, subtilisin 147 and subtilisin 168 and e.g. protease PD138 described in (WO93/18140). Other useful proteases may be those described in WO01/016285 and WO02/016547. Examples of trypsin-like proteases are trypsin (e.g. of porcine or bovine origin) and the *Fusarium* protease described in WO94/25583 and WO05/040372, and the chymotrypsin proteases derived from *Cellumonas* described in WO05/052161 and WO05/052146. A further preferred protease is the alkaline protease from *Bacillus lentus* DSM 5483, as described for example in WO95/23221, and variants thereof which are described in WO92/21760, WO95/23221, EP1921147 and EP1921148.

Examples of metalloproteases are the neutral metalloprotease as described in WO07/044993 (Proctor & Gamble/Genencor Int.) such as those derived from *Bacillus amyloliquefaciens*.

Examples of useful proteases are the variants described in: WO89/06279 WO92/19729, WO96/034946, WO98/20115, WO98/20116, WO99/011768, WO01/44452, WO03/006602, WO04/03186, WO04/041979, WO07/006305, WO11/036263, WO11/036264, especially the variants with substitutions in one or more of the following positions: 3, 4, 9, 15, 24, 27, 42, 55, 59, 60, 66, 74, 85, 96, 97, 98, 99, 100, 101, 102, 104, 116, 118, 121, 126, 127, 128, 154, 156, 157, 158, 161, 164, 176, 179, 182, 185, 188, 189, 193, 198, 199, 200, 203, 206, 211, 212, 216, 218, 226, 229, 230, 239, 246, 255, 256, 268 and 269 wherein the positions correspond to the positions of the *Bacillus lentus* protease shown in SEQ ID NO 1 of WO 2016/001449. More preferred the protease variants may comprise one or more of the mutations selected from the group consisting of: S3T, V4I, S9R, S9E, A15T, S24G, S24R, K27R, N42R, S55P, G59E, G59D, N60D, N60E, V66A, N74D, S85R, A96S, S97G, S97D, S97A, S97SD, S99E, S99D, S99G, S99M, S99N, S99R, S99H, S101A, V102I, V102Y, V102N, S104A, G116V, G116R, H118D, H118N, A120S, S126L, P127Q, S128A, S154D, A156E, G157D, G157P, S158E, Y161A, R164S, Q176E, N179E, S182E, Q185N, A188P, G189E, V193M, N198D, V199I, Y203W, S206G, L211Q, L211D, N212D, N212S, M216S, A226V, K229L, Q230H, Q239R, N246K, N255W, N255D, N255E, L256E, L256D T268A and R269H. The protease variants are preferably variants of the *Bacillus lentus* protease (Savinase®) shown in SEQ ID NO 1 of WO2016/001449, the *Bacillus amylolichenifaciens* protease (BPN') shown in SEQ ID NO 2 of WO2016/001449. The protease variants preferably have at least 80% sequence identity to SEQ ID NO 1 or SEQ ID NO 2 of WO 2016/001449.

A protease variant comprising a substitution at one or more positions corresponding to positions 171, 173, 175, 179, or 180 of SEQ ID NO 1 of WO2004/067737, wherein said protease variant has a sequence identity of at least 75% but less than 100% to SEQ ID NO 1 of WO2004/067737.

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Blaze®, Blaze Evity® 100T, Blaze Evity® 125T, Blaze Evity® 150T, Neutrase®, Everlase® and Esperase® (Novozymes A/S), those sold under the tradename Maxatase®, Maxacal®, Maxapem®, Purafect Ox®, Purafect OxP®, Puramax®, FN2®, FN3®, FN4®, Excellase®, Excellenz P1000™, Excellenz P1250™, Eraser®, Preferenz P100™, Purafect Prime®, Preferenz P110™, Effectenz P1000™, Purafect®™, Effectenz P1050™, Purafect Ox®™, Effectenz P2000™, Purafast®, Properase®, Opticlean® and Optimase® (Danisco/DuPont), Axapem™ (Gist-Brocases N.V.), BLAP (sequence shown in FIG. 29 of U.S. Pat. No. 5,352,604) and variants hereof (Henkel AG) and KAP (*Bacillus alkalophilus* subtilisin) from Kao.

Peroxidases/Oxidases

A peroxidase according to the invention is a peroxidase enzyme comprised by the enzyme classification EC 1.11.1.7, as set out by the Nomenclature Committee of the International Union of Biochemistry and Molecular Biology (IUBMB), or any fragment derived therefrom, exhibiting peroxidase activity.

Suitable peroxidases include those of plant, bacterial or fungal origin. Chemically modified or protein engineered mutants are included. Examples of useful peroxidases include peroxidases from *Coprinopsis*, e.g., from *C. cinerea* (EP 179,486), and variants thereof as those described in WO 93/24618, WO 95/10602, and WO 98/15257.

A suitable peroxidase includes a haloperoxidase enzyme, such as chloroperoxidase, bromoperoxidase and compounds exhibiting chloroperoxidase or bromoperoxidase activity. Haloperoxidases are classified according to their specificity for halide ions. Chloroperoxidases (E.C. 1.11.1.10) catalyze formation of hypochlorite from chloride ions. Preferably, the haloperoxidase is a vanadium haloperoxidase, i.e., a vanadate-containing haloperoxidase. Haloperoxidases have been isolated from many different fungi, in particular from the fungus group dematiaceous hyphomycetes, such as *Caldariomyces*, e.g., *C. fumago*, *Alternaria*, *Curvularia*, e.g., *C. verruculosa* and *C. inaequalis*, *Drechslera*, *Ulocladium* and *Botrytis*.

Haloperoxidases have also been isolated from bacteria such as *Pseudomonas*, e.g., *P. pyrrocinia* and *Streptomyces*, e.g., *S. aureofaciens*.

A suitable oxidase includes in particular, any laccase enzyme comprised by the enzyme classification EC 1.10.3.2, or any fragment derived therefrom exhibiting laccase activity, or a compound exhibiting a similar activity, such as a catechol oxidase (EC 1.10.3.1), an o-aminophenol oxidase (EC 1.10.3.4), or a bilirubin oxidase (EC 1.3.3.5). Preferred laccase enzymes are enzymes of microbial origin. The enzymes may be derived from plants, bacteria or fungi (including filamentous fungi and yeasts). Suitable examples from fungi include a laccase derivable from a strain of *Aspergillus*, *Neurospora*, e.g., *N. crassa*, *Podospora*, *Botrytis*, *Collybia*, *Fomes*, *Lentinus*, *Pleurotus*, *Trametes*, e.g., *T. villosa* and *T. versicolor*, *Rhizoctonia*, e.g., *R. solani*, *Coprinopsis*, e.g., *C. cinerea*, *C. comatus*, *C. friesii*, and *C. plicatilis*, *Psathyrella*, e.g., *P. condelleana*, *Panaeolus*, e.g., *P. papilionaceus*, *Myceliophthora*, e.g., *M. thermophila*, *Schytalidium*, e.g., *S. thermophilum*, *Polyporus*, e.g., *P. pinsitus*, *Phlebia*, e.g., *P. radiata* (WO 92/01046), or *Coriolus*, e.g., *C. hirsutus* (JP 2238885). Suitable examples from bacteria include a laccase derivable from a strain of *Bacillus*. A laccase derived from *Coprinopsis* or *Myceliophthora* is preferred; in particular, a laccase derived from *Coprinopsis cinerea*, as disclosed in WO 97/08325; or from *Myceliophthora thermophila*, as disclosed in WO 95/33836.

Dispersants

The detergent compositions of the present invention can also contain dispersants. In particular, powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents

The detergent compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent Whitening Agent

The detergent compositions of the present invention will preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulfonic acid derivatives, diarylpyrazoline derivatives and bisphenyl-distyryl derivatives. Examples of the diaminostilbene-sulfonic acid derivative type of fluorescent whitening agents include the sodium salts of: 4,4'-bis-(2-diethanolamino-4-anilino-s-triazin-6-ylamino) stilbene-2,2'-disulfonate, 4,4'-bis-(2,4-dianilino-s-triazin-6-ylamino) stilbene-2.2'-disulfonate, 4,4'-bis-(2-anilino-4-(N-methyl-N-2-hydroxy-ethylamino)-s-triazin-6-ylamino) stilbene-2,2'-disulfonate, 4,4'-bis-(4-phenyl-1,2,3-triazol-2-yl)stilbene-2,2'-disulfonate and sodium 5-(2H-naphtho[1,2-d][1,2,3]triazol-2-yl)-2-[(E)-2-phenylvinyl]benzenesulfonate.

Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4-anilino-s-triazin-6-ylamino) stilbene-2,2'-disulfonate. Tinopal CBS is the disodium salt of 2,2'-bis-(phenyl-styryl)-disulfonate. Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins. Suitable fluorescent brightener levels include lower levels of from about 0.01, from 0.05, from about 0.1 or even from about 0.2 wt % to upper levels of 0.5 or even 0.75 wt %.

Soil Release Polymers

The detergent compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers is amphiphilic alkoxylated grease cleaning polymers comprising a core structure and a plurality of alkoxylate groups attached to that core structure. The core structure may comprise a polyalkylenimine structure or a polyalkanolamine structure as described in detail in WO2009/087523 (hereby incorporated by reference). Furthermore, random graft co-polymers are suitable soil release polymers. Suitable graft co-polymers are described in more detail in WO2007/138054, WO2006/108856 and WO2006/113314 (hereby incorporated by reference). Suitable polyethylene glycol polymers include random graft co-polymers comprising: (i) hydrophilic backbone comprising polyethylene glycol; and (ii) side chain(s) selected from the group consisting of: C4-C25 alkyl group, polypropylene, polybutylene, vinyl ester of a saturated C1-C6 mono-carboxylic acid, Cl-C 6 alkyl ester of acrylic or methacrylic acid, and mixtures thereof. Suitable polyethylene glycol polymers have a polyethylene glycol backbone with random grafted polyvinyl acetate side chains. The average molecular weight of the polyethylene glycol backbone can be in the range of from 2,000 Da to 20,000 Da, or from 4,000 Da to 8,000 Da. The molecular weight ratio of the polyethylene glycol backbone to the polyvinyl acetate side chains can be in the range of from 1:1 to 1:5, or from 1:1.2 to 1:2. The average number of graft sites per ethylene oxide units can be less than 1, or less than 0.8, the average number of graft sites per ethylene oxide units can be in the range of from 0.5 to 0.9, or the average number of graft sites per ethylene oxide units can be in the range of from 0.1 to 0.5, or from 0.2 to 0.4. A suitable polyethylene glycol polymer is Sokalan HP22. Other soil release polymers are substituted polysaccharide structures especially substituted cellulosic structures such as modified cellulose derivatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-Redeposition Agents

The detergent compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Rheology Modifiers

The detergent compositions of the present invention may also include one or more rheology modifiers, structurants or thickeners, as distinct from viscosity reducing agents. The rheology modifiers are selected from the group consisting of non-polymeric crystalline, hydroxy-functional materials, polymeric rheology modifiers which impart shear thinning characteristics to the aqueous liquid matrix of a liquid detergent composition. The rheology and viscosity of the detergent can be modified and adjusted by methods known in the art, for example as shown in EP 2169040. Other suitable cleaning composition components include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Formulation of Detergent Products

The detergent composition of the invention may be in any convenient form, e.g., a bar, a homogenous tablet, a tablet having two or more layers, a pouch having one or more compartments, a regular or compact powder, a granule, a paste, a gel, or a regular, compact or concentrated liquid.

Pouches can be configured as single or multicompartments. It can be of any form, shape and material which is suitable for hold the composition, e.g. without allowing the release of the composition to release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be of blended compositions comprising hydrolytically degradable and water soluble polymer blends such as polylactide and polyvinyl alcohol (known under the Trade reference M8630 as sold by Mono-Sol LLC, Indiana, USA) plus plasticisers like glycerol, ethylene glycerol, propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids: US2009/0011970 A1.

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent. A liquid or gel detergent may be non-aqueous.

Granular Detergent Formulations

Non-dusting granulates may be produced, e.g. as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The glycosyl hydrolase e.g. Glyco_hydro_114 glycosyl hydrolase may be formulated as a granule for example as a co-granule that combines one or more enzymes. Each enzyme will then be present in more granules securing a more uniform distribution of enzymes in the detergent. This also reduces the physical segregation of different enzymes due to different particle sizes. Methods for producing multi-enzyme co-granulate for the detergent industry is disclosed in the IP.com disclosure IPCOM000200739D.

Another example of formulation of enzymes by the use of co-granulates are disclosed in WO 2013/188331, which relates to a detergent composition comprising (a) a multi-enzyme co-granule; (b) less than 10 wt zeolite (anhydrous basis); and (c) less than 10 wt phosphate salt (anhydrous basis), wherein said enzyme co-granule comprises from 10 to 98 wt % moisture sink component and the composition additionally comprises from 20 to 80 wt % detergent moisture sink component. The multi-enzyme co-granule may comprise an enzyme of the invention and one or more enzymes selected from the group consisting of proteases, lipases, cellulases, xyloglucanases, perhydrolases, peroxidases, lipoxygenases, laccases, hemicellulases, proteases, cellulases, cellobiose dehydrogenases, xylanases, phospho lipases, esterases, cutinases, pectinases, mannanases, pectate lyases, keratinases, reductases, oxidases, phenoloxidases, ligninases, pullulanases, tannases, pentosanases, lichenases glucanases, arabinosidases, hyaluronidase, chondroitinase, amylases, and mixtures thereof. WO 2013/188331 also relates to a method of treating and/or cleaning a surface, preferably a fabric surface comprising the steps of (i) contacting said surface with the detergent composition as claimed and described herein in aqueous wash liquor, (ii) rinsing and/or drying the surface.

An embodiment of the invention relates to an enzyme granule/particle comprising the glycosyl hydrolase e.g Glyco_hydro_114 glycosyl hydrolase. The granule is composed of a core, and optionally one or more coatings (outer layers) surrounding the core. Typically, the granule/particle size, measured as equivalent spherical diameter (volume based average particle size), of the granule is 20-2000 µm, particularly 50-1500 µm, 100-1500 µm or 250-1200 µm. The core may include additional materials such as fillers, fibre materials (cellulose or synthetic fibres), stabilizing agents, solubilising agents, suspension agents, viscosity regulating agents, light spheres, plasticizers, salts, lubricants and fragrances. The core may include binders, such as synthetic polymer, wax, fat, or carbohydrate. The core may comprise a salt of a multivalent cation, a reducing agent, an antioxidant, a peroxide decomposing catalyst and/or an acidic buffer component, typically as a homogenous blend. The core may consist of an inert particle with the enzyme absorbed into it, or applied onto the surface, e.g., by fluid bed coating. The core may have a diameter of 20-2000 µm, particularly 50-1500 µm, 100-1500 µm or 250-1200 µm. The core can be prepared by granulating a blend of the ingredients, e.g., by a method comprising granulation techniques such as crystallization, precipitation, pan-coating, fluid bed coating, fluid bed agglomeration, rotary atomization, extrusion, prilling, spheronization, size reduction methods, drum granulation, and/or high shear granulation.

Methods for preparing the core can be found in Handbook of Powder Technology; Particle size enlargement by C. E. Capes; Volume 1; 1980; Elsevier.

The core of the enzyme granule/particle may be surrounded by at least one coating, e.g., to improve the storage stability, to reduce dust formation during handling, or for coloring the granule. The optional coating(s) may include a salt coating, or other suitable coating materials, such as polyethylene glycol (PEG), methyl hydroxy-propyl cellulose (MHPC) and polyvinyl alcohol (PVA). Examples of enzyme granules with multiple coatings are shown in WO 93/07263 and WO 97/23606. The coating may be applied in an amount of at least 0.1% by weight of the core, e.g., at least 0.5%, 1% or 5%. The amount may be at most 100%, 70%, 50%, 40% or 30%. The coating is preferably at least 0.1 μm thick, particularly at least 0.5 μm, at least 1 μm or at least 5 μm. In a one embodiment, the thickness of the coating is below 100 μm. In another embodiment, the thickness of the coating is below 60 μm. In an even more particular embodiment the total thickness of the coating is below 40 μm. The coating should encapsulate the core unit by forming a substantially continuous layer. A substantially continuous layer is to be understood as a coating having few or no holes, so that the core unit it is encapsulating/enclosing has few or none uncoated areas. The layer or coating should be homogeneous in thickness. The coating can further contain other materials as known in the art, e.g., fillers, antisticking agents, pigments, dyes, plasticizers and/or binders, such as titanium dioxide, kaolin, calcium carbonate or talc. A salt coating may comprise at least 60% by weight w/w of a salt, e.g., at least 65%, at least 70%, at least 75%, at least 80%, at least 85%, at least 90%, at least 95% or at least 99% by weight w/w. The salt may be added from a salt solution where the salt is completely dissolved or from a salt suspension wherein the fine particles is less than 50 μm, such as less than 10 μm or less than 5 μm. The salt coating may comprise a single salt or a mixture of two or more salts. The salt may be water soluble, and may have a solubility at least 0.1 grams in 100 g of water at 20° C., preferably at least 0.5 g per 100 g water, e.g., at least 1 g per 100 g water, e.g., at least 5 g per 100 g water. The salt may be an inorganic salt, e.g., salts of sulfate, sulfite, phosphate, phosphonate, nitrate, chloride or carbonate or salts of simple organic acids (less than 10 carbon atoms, e.g., 6 or less carbon atoms) such as citrate, malonate or acetate. Examples of cations in these salts are alkali or earth alkali metal ions, the ammonium ion or metal ions of the first transition series, such as sodium, potassium, magnesium, calcium, zinc or aluminium. Examples of anions include chloride, bromide, iodide, sulfate, sulfite, bisulfite, thiosulfate, phosphate, monobasic phosphate, dibasic phosphate, hypophosphite, dihydrogen pyrophosphate, tetraborate, borate, carbonate, bicarbonate, metasilicate, citrate, malate, maleate, malonate, succinate, lactate, formate, acetate, butyrate, propionate, benzoate, tartrate, ascorbate or gluconate. In particular alkali- or earth alkali metal salts of sulfate, sulfite, phosphate, phosphonate, nitrate, chloride or carbonate or salts of simple organic acids such as citrate, malonate or acetate may be used. The salt in the coating may have a constant humidity at 20° C. above 60%, particularly above 70%, above 80% or above 85%, or it may be another hydrate form of such a salt (e.g., anhydrate). The salt coating may be as described in WO 00/01793 or WO 2006/034710. Specific examples of suitable salts are NaCl ($CH_{20°\ C.}$=76%), $Na_2CO_3$ ($CH_{20°\ C.}$=92%), $NaNO_3$ ($CH_{20°\ C.}$=73%), $Na_2HPO_4$ ($CH_{20°\ C.}$=95%), $Na_3PO_4$ ($CH_{25°\ C.}$=92%), $NH_4Cl$ ($CH_{20°\ C.}$=79.5%), $(NH_4)_2HPO_4$ ($CH_{20°\ C.}$=93.0%), $NH_4H_2PO_4$ ($CH_{20°\ C.}$=93.1%), $(NH_4)_2SO_4$ ($CH_{20°\ C.}$=81.1%), KCl ($CH_{20°\ C.}$=85%), $K_2HPO_4$ ($CH_{20°\ C.}$=92%), $KH_2PO_4$ ($CH_{20°\ C.}$=96.5%), $KNO_3$ ($CH_{20°\ C.}$=93.5%), $Na_2SO_4$ ($CH_{20°\ C.}$=93%), $K_2SO_4$ ($CH_{20°\ C.}$=98%), $KHSO_4$ ($CH_{20°\ C.}$=86%), $MgSO_4$ ($CH_{20°\ C.}$=90%), $ZnSO_4$ ($CH_{20°\ C.}$=90%) and sodium citrate ($CH_{25°\ C.}$=86%). Other examples include $NaH_2PO_4$, $(NH_4)H_2PO_4$, $CuSO_4$, $Mg(NO_3)_2$ and magnesium acetate. The salt may be in anhydrous form, or it may be a hydrated salt, i.e. a crystalline salt hydrate with bound water(s) of crystallization, such as described in WO 99/32595. Specific examples include anhydrous sodium sulfate ($Na_2SO_4$), anhydrous magnesium sulfate ($MgSO_4$), magnesium sulfate heptahydrate ($MgSO_4.7H_2O$), zinc sulfate heptahydrate ($ZnSO_4.7H_2O$), sodium phosphate dibasic heptahydrate ($Na_2HPO_4.7H_2O$), magnesium nitrate hexahydrate ($Mg(NO_3)_2(6H_2O)$), sodium citrate dihydrate and magnesium acetate tetrahydrate. Preferably the salt is applied as a solution of the salt, e.g., using a fluid bed. One embodiment of the present invention provides a granule, which comprises:

(a) a core comprising a Glyco_hydro_114 glycosyl hydrolase according to the invention, and (b) optionally a coating consisting of one or more layer(s) surrounding the core.

One embodiment of the invention relates to a granule, which comprises:

(a) a core comprising a Glyco_hydro_114 glycosyl hydrolase having at least 60%, at least 65%, at least 70%, at least 75%, at least 80%, at least 85%, at least 90%, at least 95%, at least 98% or 100% sequence identity to the amino acid sequence shown in SEQ ID NO 3, SEQ ID NO 6, SEQ ID NO 9, SEQ ID NO 12, SEQ ID NO 15, SEQ ID NO 18, SEQ ID NO 21, SEQ ID NO 24, SEQ ID NO 27, SEQ ID NO 30, SEQ ID NO 33, SEQ ID NO 40, SEQ ID NO 43, SEQ ID NO 46, SEQ ID NO 49, SEQ ID NO 52, SEQ ID NO 55, SEQ ID NO 58, SEQ ID NO 61, SEQ ID NO 64, SEQ ID NO 67, SEQ ID NO 70, SEQ ID NO 73, SEQ ID NO 76, SEQ ID NO 79, SEQ ID NO 82, SEQ ID NO 85, SEQ ID NO 88, SEQ ID NO 91, SEQ ID NO 94, SEQ ID NO 95 or SEQ ID NO 96, and (b) optionally a coating consisting of one or more layer(s) surrounding the core.

Medical Cleaning

The present invention further relates to methods of cleaning a medical device and to the use of a composition comprising a glycosyl hydrolase, preferably a Glyco_hydro_114 glycosyl hydrolase and at least one adjunct ingredient for cleaning of a medical device. The invention further relates to a method of preventing biofilm formation on a medical device e.g. an indwelling medical device or implant comprising coating the device with at least one Glyco_hydro_114 glycosyl hydrolase.

One embodiment of the invention relates to a method of preventing biofilm formation on a medical device e.g. an indwelling medical device or implant comprising coating the device with at least one Glyco_hydro_114 glycosyl hydrolase.

The polypeptides suitable for use in medical cleaning and in compositions for medical cleaning are described above and include polypeptides which comprises one or more motif(s) GX[FY][LYF]D (SEQ ID NO 34), AYX[SET]XX[EAS] (SEQ ID NO 35) or GXXGX[FY][LYFI]D (SEQ ID NO 97) and/or polypeptide selected from the group consisting of polypeptides having the amino acid sequence of SEQ ID NO 3, SEQ ID NO 6, SEQ ID NO 9, SEQ ID NO 12, SEQ ID NO 15, SEQ ID NO 18, SEQ ID NO 21, SEQ ID NO 24, SEQ ID NO 27, SEQ ID NO 30, SEQ ID NO 33, SEQ ID NO 40, SEQ ID NO 43, SEQ ID NO 46, SEQ ID NO 49, SEQ ID NO 52, SEQ ID NO 55, SEQ ID NO 58, SEQ ID NO 61, SEQ ID NO 64, SEQ ID NO 67, SEQ ID NO 70, SEQ ID NO 73, SEQ ID NO 76, SEQ ID NO 79, SEQ ID NO 82, SEQ ID NO 85, SEQ ID NO 88, SEQ ID NO 91, SEQ ID NO 94, SEQ ID NO 95 or SEQ ID NO 96 and polypeptides having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity hereto.

One aspect of the invention relates to a method of cleaning a medical device, wherein the method comprises a) contacting the medical device with the composition comprising a glycosyl hydrolase, preferably a Glyco_hydro_114 glycosyl hydrolase, for a period effective to clean the medical device;
b) cleaning, the medical device; and
c) optionally disinfect the medical device.

One aspect of the invention relates to a method of cleaning a medical device, wherein the method comprises
a) contacting the medical device with the composition comprising a Glyco_hydro_114 glycosyl hydrolase, which comprises one or more motif(s) GX[FY][LYF]D (SEQ ID NO 34), AYX[SET]XX[EAS] (SEQ ID NO 35) or GXXGX[FY][LYFI]D (SEQ ID NO 97) and/or is selected from the group consisting of Glyco_hydro_114 glycosyl hydrolases having the amino acid sequence of SEQ ID NO 3, SEQ ID NO 6, SEQ ID NO 9, SEQ ID NO 12, SEQ ID NO 15, SEQ ID NO 18, SEQ ID NO 21, SEQ ID NO 24, SEQ ID NO 27, SEQ ID NO 30, SEQ ID NO 33, SEQ ID NO 40, SEQ ID NO 43, SEQ ID NO 46, SEQ ID NO 49, SEQ ID NO 52, SEQ ID NO 55, SEQ ID NO 58, SEQ ID NO 61, SEQ ID NO 64, SEQ ID NO 67, SEQ ID NO 70, SEQ ID NO 73, SEQ ID NO 76, SEQ ID NO 79, SEQ ID NO 82, SEQ ID NO 85, SEQ ID NO 88, SEQ ID NO 91, SEQ ID NO 94, SEQ ID NO 95 or SEQ ID NO 96 and polypeptides having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity hereto, for a period effective to clean the medical device;
b) cleaning, the medical device; and
c) optionally disinfect the medical device.

One embodiment relates to a composition comprising a glycosyl hydrolase, preferably a Glyco_hydro_114 glycosyl hydrolase, which comprises one or more motif(s) GX[FY][LYF]D (SEQ ID NO 34), AYX[SET]XX[EAS] (SEQ ID NO 35) or GXXGX[FY][LYFI]D (SEQ ID NO 97) and/or is selected from the group consisting of glycosyl hydrolases having the amino acid sequence of SEQ ID NO 3, SEQ ID NO 6, SEQ ID NO 9, SEQ ID NO 12, SEQ ID NO 15, SEQ ID NO 18, SEQ ID NO 21, SEQ ID NO 24, SEQ ID NO 27, SEQ ID NO 30, SEQ ID NO 33, SEQ ID NO 40, SEQ ID NO 43, SEQ ID NO 46, SEQ ID NO 49, SEQ ID NO 52, SEQ ID NO 55, SEQ ID NO 58, SEQ ID NO 61, SEQ ID NO 64, SEQ ID NO 67, SEQ ID NO 70, SEQ ID NO 73, SEQ ID NO 76, SEQ ID NO 79, SEQ ID NO 82, SEQ ID NO 85, SEQ ID NO 88, SEQ ID NO 91, SEQ ID NO 94, SEQ ID NO 95, SEQ ID NO 96 and polypeptides having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity hereto and preferably an adjunct ingredient. The composition may be an anti-biofouling composition and the composition may be a cleaning or pharmaceutical composition. The adjunct ingredient may be any excipient suitable for e.g. cleaning or pharmaceutical compositions. The adjuncts/excipients are within the choice of the skilled artisan. The adjunct ingredient may be selected from the group consisting of surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, and solubilizers. The compositions may be used for detaching biofilm or preventing biofilm formation on surfaces such as medical devices.

One embodiment of the invention relates to the use of a composition comprising a glycosyl hydrolase, preferably a Glyco_hydro_114 glycosyl hydrolase, which comprises one or more motif(s) GX[FY][LYF]D (SEQ ID NO 34), AYX[SET]XX[EAS] (SEQ ID NO 35) or GXXGX[FY][LYFI]D (SEQ ID NO 97) and/or is selected from the group consisting glycosyl hydrolases having the amino acid sequence of SEQ ID NO 3, SEQ ID NO 6, SEQ ID NO 9, SEQ ID NO 12, SEQ ID NO 15, SEQ ID NO 18, SEQ ID NO 21, SEQ ID NO 24, SEQ ID NO 27, SEQ ID NO 30, SEQ ID NO 33, SEQ ID NO 40, SEQ ID NO 43, SEQ ID NO 46, SEQ ID NO 49, SEQ ID NO 52, SEQ ID NO 55, SEQ ID NO 58, SEQ ID NO 61, SEQ ID NO 64, SEQ ID NO 67, SEQ ID NO 70, SEQ ID NO 73, SEQ ID NO 76, SEQ ID NO 79, SEQ ID NO 82, SEQ ID NO 85, SEQ ID NO 88, SEQ ID NO 91, SEQ ID NO 94, SEQ ID NO 95, SEQ ID NO 96 and polypeptides having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity hereto and preferably an adjunct ingredient for cleaning a medical device or an implant.

The medical device may be characterized in that at least a portion of a patient-contactable surface of said device is coated with composition comprising a Glyco_hydro_114 glycosyl hydrolase of the invention. The medical device or implant may be any device or implant that is susceptible to biofilm formation. The medical device may be selected from the group consisting of a catheter such as a central venous catheter, intravascular catheter, urinary catheter, Hickman catheter, peritoneal dialysis catheter, endrotracheal catheter, or wherein the device is a mechanical heart valve, a cardiac pacemaker, an arteriovenous shunt, a scleral buckle, a prosthetic joint, a tympanostomy tube, a tracheostomy tube, a voice prosthetic, a penile prosthetic, an artificial urinary sphincter, a synthetic pubovaginal sling, a surgical suture, a bone anchor, a bone screw, an intraocular lens, a contact lens, an intrauterine device, an aortofemoral graft, a vascular graft, a needle, a Luer-Lok connector, a needleless connector and a surgical instrument.

Uses

The polypeptides of the invention having hydrolytic activity may be used for cleaning e.g. deep cleaning of an item, such as a textile. One embodiment of the invention relates to the use of a glycosyl hydrolase, preferably a Glyco_hydro_114 glycosyl hydrolase in a cleaning process, such as laundry and/or dish wash.

In a preferred embodiment, the Glyco_hydro_114 glycosyl hydrolase polypeptides of the invention comprise one or more of the motif(s) GX[FY][LYF]D (SEQ ID NO 34), AYX[SET]XX[EAS] (SEQ ID NO 35) or GXXGX[FY][LYFI]D (SEQ ID NO 97). In a preferred embodiment the Glyco_hydro_114 glycosyl hydrolase comprising one or more of the motif(s) selected from the group consisting of: GX[FY][LYF]D (SEQ ID NO 34), AYX[SET]XX[EAS] (SEQ ID NO 35), GXXGX[FY][LYFI]D (SEQ ID NO 97), [ILFQV]N[RW]G[FL] (SEQ ID NO 98), DTLDS[YF] (SEQ ID NO 99), G[VL]FLDTLDSF[QTH]L[LMQ] (SEQ ID NO 100), DT[VIMA][GD][DNW][VIL][DEN] (SEQ ID NO 101), [SETC]IG[EQA][ALI]EXY(SEQ ID NO 102), [QL]N[AS]PEL(SEQ ID NO 103) and [KLYMQ]XX[PV]QN[SA]PE (SEQ ID NO 104).

In some embodiments of the invention relate to the use of glycosyl hydrolase, preferably a Glyco_hydro_114 glycosyl hydrolase according to the invention for prevention reduction or removal of malodor. Some embodiment of the invention relates to the use of a polypeptide of the invention for prevention or reduction of anti-redeposition and improvement of whiteness of a textile subjected to multiple washes. One embodiment of the invention relates to the use of a glycosyl hydrolase, preferably a Glyco_hydro_114 glycosyl hydrolase according to the invention for deep cleaning of an item, wherein item is a textile. One embodiment of the invention relates to the use of a glycosyl hydrolase, preferably a Glyco_hydro_114 glycosyl hydrolase polypeptide according to the invention (i) for preventing, reducing or removing stickiness of the item;
(ii) for pretreating stains on the item;
(iii) for preventing, reducing or removing redeposition of soil during a wash cycle;
(iv) for preventing, reducing or removing adherence of soil to the item;
(v) for maintaining or improving whiteness of the item;
(vi) for preventing, reducing or removal malodor from the item,
wherein the item is a textile.

One embodiment of the invention relates to the use of a glycosyl hydrolase, preferably a Glyco_hydro_114 glycosyl hydrolase polypeptide according to the invention for deep cleaning of an item, wherein item is a textile. One embodiment of the invention relates to the use of a glycosyl hydrolase, preferably a Glyco_hydro_114 glycosyl hydrolase polypeptide, (i) for preventing, reducing or removing stickiness of the item;
(ii) for pretreating stains on the item;
(iii) for preventing, reducing or removing redeposition of soil during a wash cycle;
(iv) for preventing, reducing or removing adherence of soil to the item;
(v) for maintaining or improving whiteness of the item;
(vi) for preventing, reducing or removal malodor from the item, optionally wherein the item is a textile, wherein the glycosyl hydrolase polypeptide is selected from the group consisting of:
(a) a polypeptide having at least 60%, at least 70%, at least 75%, at least 80%, at least 85%, at least 90%, at least 95%, at least 96%, at least 97%, at least 98%, at least 99% or 100% sequence identity to the polypeptide of SEQ ID NO 3;
(b) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 6;
(c) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 9;
(d) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 12;
(e) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 15;
(f) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 18;
(g) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 21;
(h) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 24;
(i) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 27;
(j) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 30;
(k) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 33;
(l) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 40;
(m) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 43;
(n) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 46;
(o) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 49;
(p) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 52;
(q) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 55;
(r) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 58;

(s) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 61;
(t) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 64;
(u) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 67;
(v) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 70;
(w) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 73;
(x) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 76;
(y) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 79;
(z) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 82;
(aa) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 85;
(bb) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 88;
(cc) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 91;
(dd) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 94;
(ee) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 95;
(ff) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 96.

One preferred embodiment relates to the use of a Glyco_hydro_114 glycosyl hydrolase,
  i. for preventing, reducing or removing stickiness of the item;
  ii. for preventing, reducing or removing biofilm or biofilm components
  iii. for reducing or removing pel stains on the item;
  iv. for preventing, reducing or removing redeposition of soil during a wash cycle;
  v. for preventing, reducing or removing adherence of soil to the item;
  vi. for maintaining or improving whiteness of the item;
  vii. for preventing, reducing or removal malodor from the item, wherein the item is a textile.

One preferred embodiment relates to the use of a Glyco_hydro_114 glycosyl hydrolase,
  i. for preventing, reducing or removing stickiness of the item;
  ii. for preventing, reducing or removing biofilm or biofilm components
  iii. for reducing or removing pel stains on the item;
  iv. for preventing, reducing or removing redeposition of soil during a wash cycle;
  v. for preventing, reducing or removing adherence of soil to the item;
  vi. for maintaining or improving whiteness of the item;
  vii. for preventing, reducing or removal malodor from the item,
  wherein the item is a textile and wherein the polypeptide is selected from the group consisting of:
  (a) a polypeptide having at least 60%, at least 70%, at least 75%, at least 80%, at least 85%, at least 90%, at least 95%, at least 96%, at least 97%, at least 98%, at least 99% or 100% sequence identity to the polypeptide of SEQ ID NO 3;
  (b) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 6;
  (c) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 9;
  (d) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 12;
  (e) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 15;
  (f) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 18;
  (g) a polypeptide having at least 60%, at least 65%, at least 70%, at least 75%, at least 80%, at least 85%, at least 90%, at least 95%, at least 96%, at least 97%, at the polypeptide of SEQ ID NO 21;
(h) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 24;
(i) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 27;
(j) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 30;
(k) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 33;
(l) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 40;
(m) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 43;
(n) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 46;
(o) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 49;
(p) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 52;
(q) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 55;
(r) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 58;
(s) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 61;
(t) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 64;
(u) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 67;
(v) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 70;
(w) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 73;
(x) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 76;
(y) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 79;
(z) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 82;
(aa) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 85;
(bb) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 88;
(cc) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 91;
(dd) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 94;
(ee) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 95;
(ff) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 96.

One preferred embodiment relates to the use of a Glyco_hydro_114 glycosyl hydrolase,
  i. for preventing, reducing or removing stickiness of the item;
  ii. for preventing, reducing or removing biofilm or biofilm components
  iii. for reducing or removing pel stains on the item;

iv. for preventing, reducing or removing redeposition of soil during a wash cycle;
v. for preventing, reducing or removing adherence of soil to the item;
vi. for maintaining or improving whiteness of the item;
vii. for preventing, reducing or removal malodor from the item,
wherein the item is a textile and wherein the polypeptide is selected from the group consisting of:
(a) a polypeptide having at least 90%, at least 95%, at least 96%, at least 97%, at least 98%, at least 99% or 100% sequence identity to the polypeptide of SEQ ID NO 3;
(b) a polypeptide having at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 6;
(c) a polypeptide having at least 80%, at least 85%, at least 90%, at least 95%, at least 96%, at least 97%, at least 98%, at least 99% or 100% sequence identity to the polypeptide of SEQ ID NO 9;
(d) a polypeptide having at least 99% or 100% sequence identity to the polypeptide of SEQ ID NO 12;
(e) a polypeptide having at least 95%, at least 96%, at least 97%, at least 98%, at least 99% or 100% sequence identity to the polypeptide of SEQ ID NO 15;
(f) a polypeptide having at least 95%, at least 96%, at least 97%, at least 98%, at least 99% or 100% sequence identity to the polypeptide of SEQ ID NO 18;
(g) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 21;
(h) a polypeptide having at least 80%, at least 85%, at least 90%, at least 95%, at least 96%, at least 97%, at least 98%, at least 99% or 100% sequence identity to the polypeptide of SEQ ID NO 24;
(i) a polypeptide having at least 70%, at least 75%, at least 80%, at least 85%, at least 90%, at least 95%, at least 96%, at least 97%, at least 98%, at least 99% or 100% sequence identity to the polypeptide of SEQ ID NO 27;
(j) a polypeptide having at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 30;
(k) a polypeptide having at least 70%, at least 75%, at least 80%, at least 85%, at least 90%, at least 95%, at least 96%, at least 97%, at least 98%, at least 99% or 100% sequence identity to the polypeptide of SEQ ID NO 33;
(l) a polypeptide having 100% sequence identity to the polypeptide of SEQ ID NO 40;
(m) a polypeptide having at least 95%, at least 96%, at least 97%, at least 98%, at least 99% or 100% sequence identity to the polypeptide of SEQ ID NO 43;
(n) a polypeptide having 100% sequence identity to the polypeptide of SEQ ID NO 46;
(o) a polypeptide having at least 95%, at least 96%, at least 97%, at least 98%, at least 99% or 100% sequence identity to the polypeptide of SEQ ID NO 49;
(p) a polypeptide having at least 95%, at least 96%, at least 97%, at least 98%, at least 99% or 100% sequence identity to the polypeptide of SEQ ID NO 52;
(q) a polypeptide having at least 95%, at least 96%, at least 97%, at least 98%, at least 99% or 100% sequence identity to the polypeptide of SEQ ID NO 55;
(r) a polypeptide having at least 75%, at least 80%, at least 85%, at least 90%, at least 95%, at least 96%, at least 97%, at least 98%, at least 99% or 100% sequence identity to the polypeptide of SEQ ID NO 58;
(s) a polypeptide having at least 95%, at least 96%, at least 97%, at least 98%, at least 99% or 100% sequence identity to the polypeptide of SEQ ID NO 61;
(t) a polypeptide having at least 90%, at least 95%, at least 96%, at least 97%, at least 98%, at least 99% or 100% sequence identity to the polypeptide of SEQ ID NO 64;
(u) a polypeptide having at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 67;
(v) a polypeptide having at least 96%, at least 97%, at least 98%, at least 99% or 100% sequence identity to the polypeptide of SEQ ID NO 73;
(w) a polypeptide having at least 96%, at least 97%, at least 98%, at least 99% or 100% sequence identity to the polypeptide of SEQ ID NO 76;
(x) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 79;
(y) a polypeptide having at least 95%, at least 96%, at least 97%, at least 98%, at least 99% or 100% sequence identity to the polypeptide of SEQ ID NO 82;
(z) a polypeptide having at least 50%, at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 85;
(aa) a polypeptide having at least 50%, at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 88;
(bb) a polypeptide having at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 91;
(cc) a polypeptide having at least 80%, at least 85%, at least 90%, at least 95%, at least 96%, at least 97%, at least 98%, at least 99% or 100% sequence identity to the polypeptide of SEQ ID NO 94;
(dd) a polypeptide having at least 70%, at least 75%, at least 80%, at least 85%, at least 90%, at least 95%, at least 96%, at least 97%, at least 98%, at least 99% or 100% sequence identity to the polypeptide of SEQ ID NO 95; and
(ee) a polypeptide having at least 95%, at least 96%, at least 97%, at least 98%, at least 99% or 100% sequence identity to the polypeptide of SEQ ID NO 96.

The polypeptides of the invention are particularly useful in cleaning processes such as laundry, where the polypeptide effectively reduces biofilm components such as Pel comprising biofilm as shown in the examples below. One embodiment of the invention relates to a method for laundering an item comprising the steps of:

a. exposing an item to a wash liquor comprising the Glyco_hydro_114 glycosyl hydrolase or a composition comprising a Glyco_hydro_114 glycosyl hydrolase;
b. completing at least one wash cycle; and
c. optionally rinsing the item,
wherein the item is a textile.

One preferred embodiment of the invention relates to a method for laundering an item comprising the steps of:
d. exposing an item to a wash liquor comprising a glycosyl hydrolase, preferably a Glyco_hydro_114 glycosyl hydrolase or a composition comprising a glycosyl hydrolase; wherein glycosyl hydrolase is selected from the group consisting of;
  (a) a polypeptide having at least 60%, at least 70%, at least 75%, at least 80%, at least 85%, at least 90%, at least 95%, at least 96%, at least 97%, at least 98%, at least 99% or 100% sequence identity to the polypeptide of SEQ ID NO 3;
  (b) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 6;
  (c) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 9;
  (d) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 12;
  (e) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 15;
  (f) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 18;
  (g) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 21,
  (h) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 24;
  (i) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 27;
  (j) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 30;
  (k) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 33;
  (l) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 40;
  (m) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 43;
  (n) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 46;
  (o) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 49;
  (p) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 52;
  (q) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 55;
  (r) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 58;
  (s) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 61,
  (t) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 64;
  (u) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 67;
  (v) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 70;
  (w) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 73;
  (x) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 76;

(y) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 79;
(z) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 82;
(aa) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 85;
(bb) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 88;
(cc) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 91,
(dd) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 94;
(ee) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 95;
(ff) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 96.
e. completing at least one wash cycle; and
f. optionally rinsing the item,
wherein the item is a textile.
A preferred embodiment relates to a method for laundering an item comprising the steps of:
  a. exposing an item to a wash liquor comprising the Glyco_hydro_114 glycosyl hydrolase or a composition comprising a Glyco_hydro_114 glycosyl hydrolase, wherein the Glyco_hydro_114 glycosyl hydrolase is selected from the group consisting of:
  (a) a polypeptide having at least 90%, at least 95%, at least 96%, at least 97%, at least 98%, at least 99% or 100% sequence identity to the polypeptide of SEQ ID NO 3;
  (b) a polypeptide having at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 6;
  (c) a polypeptide having at least 80%, at least 85%, at least 90%, at least 95%, at least 96%, at least 97%, at least 98%, at least 99% or 100% sequence identity to the polypeptide of SEQ ID NO 9;
  (d) a polypeptide having at least 99% or 100% sequence identity to the polypeptide of SEQ ID NO 12;
  (e) a polypeptide having at least 95%, at least 96%, at least 97%, at least 98%, at least 99% or 100% sequence identity to the polypeptide of SEQ ID NO 15;
  (f) a polypeptide having at least 95%, at least 96%, at least 97%, at least 98%, at least 99% or 100% sequence identity to the polypeptide of SEQ ID NO 18;
  (g) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 21;
  (h) a polypeptide having at least 80%, at least 85%, at least 90%, at least 95%, at least 96%, at least 97%, at least 98%, at least 99% or 100% sequence identity to the polypeptide of SEQ ID NO 24;
  (i) a polypeptide having at least 70%, at least 75%, at least 80%, at least 85%, at least 90%, at least 95%, at least 96%, at least 97%, at least 98%, at least 99% or 100% sequence identity to the polypeptide of SEQ ID NO 27;
  (j) a polypeptide having at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 30;
  (k) a polypeptide having at least 70%, at least 75%, at least 80%, at least 85%, at least 90%, at least 95%, at least 96%, at least 97%, at least 98%, at least 99% or 100% sequence identity to the polypeptide of SEQ ID NO 33;
  (l) a polypeptide having 100% sequence identity to the polypeptide of SEQ ID NO 40;
  (m) a polypeptide having at least 95%, at least 96%, at least 97%, at least 98%, at least 99% or 100% sequence identity to the polypeptide of SEQ ID NO 43;
  (n) a polypeptide having 100% sequence identity to the polypeptide of SEQ ID NO 46;
  (o) a polypeptide having at least 95%, at least 96%, at least 97%, at least 98%, at least 99% or 100% sequence identity to the polypeptide of SEQ ID NO 49;
  (p) a polypeptide having at least 95%, at least 96%, at least 97%, at least 98%, at least 99% or 100% sequence identity to the polypeptide of SEQ ID NO 52;
  (q) a polypeptide having at least 95%, at least 96%, at least 97%, at least 98%, at least 99% or 100% sequence identity to the polypeptide of SEQ ID NO 55;
  (r) a polypeptide having at least 75%, at least 80%, at least 85%, at least 90%, at least 95%, at least 96%, at least 97%, at least 98%, at least 99% or 100% sequence identity to the polypeptide of SEQ ID NO 58;
  (s) a polypeptide having at least 95%, at least 96%, at least 97%, at least 98%, at least 99% or 100% sequence identity to the polypeptide of SEQ ID NO 61;
  (t) a polypeptide having at least 90%, at least 95%, at least 96%, at least 97%, at least 98%, at least 99% or 100% sequence identity to the polypeptide of SEQ ID NO 64;
  (u) a polypeptide having at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 67;
  (v) a polypeptide having at least 96%, at least 97%, at least 98%, at least 99% or 100% sequence identity to the polypeptide of SEQ ID NO 73;
  (w) a polypeptide having at least 96%, at least 97%, at least 98%, at least 99% or 100% sequence identity to the polypeptide of SEQ ID NO 76;

(x) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 79;
(y) a polypeptide having at least 95%, at least 96%, at least 97%, at least 98%, at least 99% or 100% sequence identity to the polypeptide of SEQ ID NO 82;
(z) a polypeptide having at least 50%, at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 85;
(aa) a polypeptide having at least 50%, at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 88;
(bb) a polypeptide having at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO 91;
(cc) a polypeptide having at least 80%, at least 85%, at least 90%, at least 95%, at least 96%, at least 97%, at least 98%, at least 99% or 100% sequence identity to the polypeptide of SEQ ID NO 94;
(dd) a polypeptide having at least 70%, at least 75%, at least 80%, at least 85%, at least 90%, at least 95%, at least 96%, at least 97%, at least 98%, at least 99% or 100% sequence identity to the polypeptide of SEQ ID NO 95; and a polypeptide having at least 95%, at least 96%, at least 97%, at least 98%, at least 99% or 100% sequence identity to the polypeptide of SEQ ID NO 96
b. completing at least one wash cycle; and
c. optionally rinsing the item,
wherein the item is a textile.

The invention is further summarized in the following paragraphs:
1. Use of a polypeptide comprising one or more of the motif(s) GX[FY][LYF]D (SEQ ID NO 34), AYX[SET]XX[EAS] (SEQ ID NO 35), GXXGX[FY][LYFI]D (SEQ ID NO 97), ([ILFQV]N[RW]G[FL] (SEQ ID NO 98), DTLDS[YF] (SEQ ID NO 99), G[VL]FLDTLDSF[QTH]L[LMQ] (SEQ ID NO 100) or DT[VIMA][GD][DNW][VIL][DEN] (SEQ ID NO 101) or one or more of the motifs GX[FY][LYF]D (SEQ ID NO 34), AYX[SET]XX[EAS] (SEQ ID NO 35), GXXGX[FY][LYFI]D (SEQ ID NO 97), ([SETC]IG[EQA][ALI]EXY (SEQ ID NO 102) or [KLYMQ]XX[PV]QN[SA]PE (SEQ ID NO 104) for deep cleaning of an item, wherein the item is a textile.
2. Use according to paragraph 1 for preventing, reducing or removing stickiness of the item.
3. Use according to any of paragraphs 1 or 2 for pre-treating stains on the item.
4. Use according to any of paragraphs 1-3 for preventing, reducing or removing re-deposition of soil during a wash cycle.
5. Use according to any of paragraphs 1-4 for preventing, reducing or removing adherence of soil to the item.
6. Use according to any of the preceding paragraphs for maintaining or improving the whiteness of the item.
7. Use according to any of the preceding paragraphs, wherein a malodor is reduced or removed from the item.
8. Use according to any of the preceding composition paragraphs, wherein the surface is a textile surface.
9. Use according to any of the preceding composition paragraphs, wherein the textile is made of cotton, Cotton/Polyester, Polyester, Polyamide, Polyacryl and/or silk.
10. Use according to any of the preceding paragraphs, wherein the polypeptide is a polypeptide of paragraphs 68-108.
11. A composition comprising a polypeptide comprising one or more of the motif(s) GX[FY][LYF]D (SEQ ID NO 34), AYX[SET]XX[EAS] (SEQ ID NO 35), GXXGX[FY][LYFI]D (SEQ ID NO 97), ([ILFQV]N[RW]G[FL] (SEQ ID NO 98), DTLDS[YF] (SEQ ID NO 99), G[VL]FLDTLDSF[QTH]L[LMQ] (SEQ ID NO 100) or DT[VIMA][GD][DNW][VIL][DEN] (SEQ ID NO 101) or one or more of the motifs GX[FY][LYF]D (SEQ ID NO 34), AYX[SET]XX[EAS] (SEQ ID NO 35), GXXGX[FY][LYFI]D (SEQ ID NO 97), ([SETC]IG[EQA][ALI]EXY (SEQ ID NO 102) or [KLYMQ]XX[PV]QN[SA]PE (SEQ ID NO 104) and a cleaning or an adjunct ingredient.
12. Composition according to paragraph 11, wherein the polypeptide is the polypeptide of paragraphs 68-108.
13. Composition according to any of the preceding composition paragraphs, wherein the detergent adjunct ingredient is selected from the group consisting of surfactants, builders, flocculating aid, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, builders and co-builders, fabric huing agents, anti-foaming agents, dispersants, processing aids, and/or pigments.
14. Composition according to any of the preceding composition paragraphs wherein the composition comprises from about 5 wt % to about 50 wt %, from about 5 wt % to about 40 wt %, from about 5 wt % to about 30 wt %, from about 5 wt % to about 20 wt %, from about 5 wt % to about 10 wt % anionic surfactant, preferably selected from linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.
15. Composition according to any of the preceding composition paragraphs wherein the composition comprises from about 10 wt % to about 50 wt % of at least one builder, preferably selected from citric acid, methylglycine-N,N-diacetic acid (MGDA) and/or glutamic acid-N,N-diacetic acid (GLDA) and mixtures thereof.
16. Composition according to any of the proceeding paragraphs comprising from about 5 wt % to about 40 wt % nonionic surfactants, and from about 0 wt % to about 5 wt % anionic surfactants.
17. Composition according to paragraph 16, wherein the nonionic surfactant is selected from alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA) and combinations thereof.

18. Composition according to any of the preceding composition paragraphs, wherein the composition further comprises one or more enzymes selected from the group consisting of proteases, lipases, cutinases, amylases, carbohydrases, cellulases, pectinases, mannanases, arabinases, galactanases, xylanases and oxidases.

19. Composition according to any of the preceding composition paragraphs, wherein the composition is a bar, a homogenous tablet, a tablet having two or more layers, a pouch having one or more compartments, a regular or compact powder, a granule, a paste, a gel, or a regular, compact or concentrated liquid.

20. Composition according to any of the preceding composition paragraphs, wherein the composition is a cleaning composition selected from liquid detergent, powder detergent and granule detergent compositions.

21. Composition according to any of the preceding composition paragraphs wherein the polypeptide comprises one or more motif(s) GX[FY][LYF]D (SEQ ID NO 34), AYX[SET]XX[EAS] (SEQ ID NO 35), GXXGX[FY][LYFI]D (SEQ ID NO 97), ([ILFQV]N[RW]G[FL] (SEQ ID NO 98), DTLDS[YF] (SEQ ID NO 99), G[VL]FLDTLDSF[QTH]L[LMQ] (SEQ ID NO 100) or DT[VIMA][GD][DNW][VIL][DEN] (SEQ ID NO 101) or one or more of the motifs GX[FY][LYF]D (SEQ ID NO 34), AYX[SET]XX[EAS] (SEQ ID NO 35), GXXGX[FY][LYFI]D (SEQ ID NO 97), ([SETC]IG[EQA][ALI]EXY (SEQ ID NO 102) or [KLYMQ]XX[PV]QN[SA]PE (SEQ ID NO 104) and wherein the polypeptide is selected from the group consisting of polypeptides having the amino acid sequence of SEQ ID NO 3, SEQ ID NO 6, SEQ ID NO 9, SEQ ID NO 12, SEQ ID NO 15, SEQ ID NO 18, SEQ ID NO 21, SEQ ID NO 24, SEQ ID NO 27, SEQ ID NO 30, SEQ ID NO 33, SEQ ID NO 40, SEQ ID NO 43, SEQ ID NO 46, SEQ ID NO 49, SEQ ID NO 52, SEQ ID NO 55, SEQ ID NO 58, SEQ ID NO 61, SEQ ID NO 64, SEQ ID NO 67, SEQ ID NO 70, SEQ ID NO 73, SEQ ID NO 76, SEQ ID NO 79, SEQ ID NO 82, SEQ ID NO 85, SEQ ID NO 88, SEQ ID NO 91, SEQ ID NO 94, SEQ ID NO 95, SEQ ID NO 96 and polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

22. Composition according to any of the preceding composition paragraphs wherein the polypeptide comprising one or more motif(s) GX[FY][LYF]D (SEQ ID NO 34), AYX[SET]XX[EAS] (SEQ ID NO 35) or GXXGX[FY][LYFI]D (SEQ ID NO 97) and comprises the amino acid sequence shown SEQ ID NO 3 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

23. Composition according to any of the preceding composition paragraphs wherein the polypeptide comprising one or more motif(s) GX[FY][LYF]D (SEQ ID NO 34), AYX[SET]XX[EAS] (SEQ ID NO 35) or GXXGX[FY][LYFI]D (SEQ ID NO 97) and comprises the amino acid sequence shown SEQ ID NO 6 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

24. Composition according to any of the preceding composition paragraphs wherein the polypeptide comprising one or more motif(s) GX[FY][LYF]D (SEQ ID NO 34), AYX[SET]XX[EAS] (SEQ ID NO 35) or GXXGX[FY][LYFI]D (SEQ ID NO 97) and comprises the amino acid sequence shown SEQ ID NO 9 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

25. Composition according to any of the preceding composition paragraphs wherein the polypeptide comprising one or more motif(s) GX[FY][LYF]D (SEQ ID NO 34), AYX[SET]XX[EAS] (SEQ ID NO 35) or GXXGX[FY][LYFI]D (SEQ ID NO 97) and comprises the amino acid sequence shown SEQ ID NO 12 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

26. Composition according to any of the preceding composition paragraphs wherein the polypeptide comprising one or more motif(s) GX[FY][LYF]D (SEQ ID NO 34), AYX[SET]XX[EAS] (SEQ ID NO 35) or GXXGX[FY][LYFI]D (SEQ ID NO 97) and comprises the amino acid sequence shown SEQ ID NO 15 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

27. Composition according to any of the preceding composition paragraphs wherein the polypeptide comprising one or more motif(s) GX[FY][LYF]D (SEQ ID NO 34), AYX[SET]XX[EAS] (SEQ ID NO 35) or GXXGX[FY][LYFI]D (SEQ ID NO 97) and comprises the amino acid sequence shown SEQ ID NO 18 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

28. Composition according to any of the preceding composition paragraphs wherein the polypeptide comprising one or more motif(s) GX[FY][LYF]D (SEQ ID NO 34), AYX[SET]XX[EAS] (SEQ ID NO 35) or GXXGX[FY][LYFI]D (SEQ ID NO 97) and comprises the amino acid sequence shown SEQ ID NO 21 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

29. Composition according to any of the preceding composition paragraphs wherein the polypeptide comprising one or more motif(s) GX[FY][LYF]D (SEQ ID NO 34), AYX[SET]XX[EAS] (SEQ ID NO 35) or GXXGX[FY][LYFI]D (SEQ ID NO 97) and comprises the amino acid sequence shown SEQ ID NO 24 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

30. Composition according to any of the preceding composition paragraphs wherein the polypeptide comprising one or more motif(s) GX[FY][LYF]D (SEQ ID NO 34), AYX[SET]XX[EAS] (SEQ ID NO 35) or GXXGX[FY][LYFI]D (SEQ ID NO 97) and comprises the amino acid sequence shown SEQ ID NO 27 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

31. Composition according to any of the preceding composition paragraphs wherein the polypeptide comprising one or more motif(s) GX[FY][LYF]D (SEQ ID NO 34), AYX[SET]XX[EAS] (SEQ ID NO 35) or GXXGX[FY][LYFI]D (SEQ ID NO 97) and comprises the amino acid sequence shown SEQ ID NO 30 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

32. Composition according to any of the preceding composition paragraphs wherein the polypeptide comprising one or more motif(s) GX[FY][LYF]D (SEQ ID NO 34), AYX[SET]XX[EAS] (SEQ ID NO 35) or GXXGX[FY][LYFI]D (SEQ ID NO 97) and comprises the amino acid sequence shown SEQ ID NO 33 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

33. Composition according to any of the preceding composition paragraphs wherein the polypeptide comprising one or more motif(s) GX[FY][LYF]D (SEQ ID NO 34), AYX[SET]XX[EAS] (SEQ ID NO 35) or GXXGX[FY][LYFI]D (SEQ ID NO 97) and comprises the amino acid sequence shown SEQ ID NO 40 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

34. Composition according to any of the preceding composition paragraphs wherein the polypeptide comprising one or more motif(s) GX[FY][LYF]D (SEQ ID NO 34), AYX[SET]XX[EAS] (SEQ ID NO 35) or GXXGX[FY][LYFI]D (SEQ ID NO 97) and comprises the amino acid sequence shown SEQ ID NO 43 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

35. Composition according to any of the preceding composition paragraphs wherein the polypeptide comprising one or more motif(s) GX[FY][LYF]D (SEQ ID NO 34), AYX[SET]XX[EAS] (SEQ ID NO 35) or GXXGX[FY][LYFI]D (SEQ ID NO 97) and comprises the amino acid sequence shown SEQ ID NO 46 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

36. Composition according to any of the preceding composition paragraphs wherein the polypeptide comprising one or more motif(s) GX[FY][LYF]D (SEQ ID NO 34), AYX[SET]XX[EAS] (SEQ ID NO 35) or GXXGX[FY][LYFI]D (SEQ ID NO 97) and comprises the amino acid sequence shown SEQ ID NO 49 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

37. Composition according to any of the preceding composition paragraphs wherein the polypeptide comprising one or more motif(s) GX[FY][LYF]D (SEQ ID NO 34), AYX[SET]XX[EAS] (SEQ ID NO 35) or GXXGX[FY][LYFI]D (SEQ ID NO 97) and comprises the amino acid sequence shown SEQ ID NO 52 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

38. Composition according to any of the preceding composition paragraphs wherein the polypeptide comprising one or more motif(s) GX[FY][LYF]D (SEQ ID NO 34), AYX[SET]XX[EAS] (SEQ ID NO 35) or GXXGX[FY][LYFI]D (SEQ ID NO 97) and comprises the amino acid sequence shown SEQ ID NO 55 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

39. Composition according to any of the preceding composition paragraphs wherein the polypeptide comprising one or more motif(s) GX[FY][LYF]D (SEQ ID NO 34), AYX[SET]XX[EAS] (SEQ ID NO 35) or GXXGX[FY][LYFI]D (SEQ ID NO 97) and comprises the amino acid sequence shown SEQ ID NO 58 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

40. Composition according to any of the preceding composition paragraphs wherein the polypeptide comprising one or more motif(s) GX[FY][LYF]D (SEQ ID NO 34), AYX[SET]XX[EAS] (SEQ ID NO 35) or GXXGX[FY][LYFI]D (SEQ ID NO 97) and comprises the amino acid sequence shown SEQ ID NO 61 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

41. Composition according to any of the preceding composition paragraphs wherein the polypeptide comprising one or more motif(s) GX[FY][LYF]D (SEQ ID NO 34), AYX[SET]XX[EAS] (SEQ ID NO 35) or GXXGX[FY][LYFI]D (SEQ ID NO 97) and comprises the amino acid sequence shown SEQ ID NO 64 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

42. Composition according to any of the preceding composition paragraphs wherein the polypeptide comprising one or more motif(s) GX[FY][LYF]D (SEQ ID NO 34), AYX[SET]XX[EAS] (SEQ ID NO 35) or GXXGX[FY][LYFI]D (SEQ ID NO 97) and comprises the amino acid sequence shown SEQ ID NO 67 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

43. Composition according to any of the preceding composition paragraphs wherein the polypeptide comprising one or more motif(s) GX[FY][LYF]D (SEQ ID NO 34), AYX[SET]XX[EAS] (SEQ ID NO 35) or GXXGX[FY][LYFI]D (SEQ ID NO 97) and comprises the amino acid sequence shown SEQ ID NO 70 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

44. Composition according to any of the preceding composition paragraphs wherein the polypeptide comprising one or more motif(s) GX[FY][LYF]D (SEQ ID NO 34), AYX[SET]XX[EAS] (SEQ ID NO 35) or GXXGX[FY][LYFI]D (SEQ ID NO 97) and comprises the amino acid sequence shown SEQ ID NO 73 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

45. Composition according to any of the preceding composition paragraphs wherein the polypeptide comprising one or more motif(s) GX[FY][LYF]D (SEQ ID NO 34), AYX[SET]XX[EAS] (SEQ ID NO 35) or GXXGX[FY][LYFI]D (SEQ ID NO 97) and comprises the amino acid sequence shown SEQ ID NO 76 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

46. Composition according to any of the preceding composition paragraphs wherein the polypeptide comprising one or more motif(s) GX[FY][LYF]D (SEQ ID NO 34), AYX[SET]XX[EAS] (SEQ ID NO 35) or GXXGX[FY][LYFI]D (SEQ ID NO 97) and comprises the amino acid sequence shown SEQ ID NO 79 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

47. Composition according to any of the preceding composition paragraphs wherein the polypeptide comprising one or more motif(s) GX[FY][LYF]D (SEQ ID NO 34), AYX[SET]XX[EAS] (SEQ ID NO 35) or GXXGX[FY][LYFI]D (SEQ ID NO 97) and comprises the amino acid sequence shown SEQ ID NO 82 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

48. Composition according to any of the preceding composition paragraphs wherein the polypeptide comprising one or more motif(s) GX[FY][LYF]D (SEQ ID NO 34), AYX[SET]XX[EAS] (SEQ ID NO 35) or GXXGX[FY][LYFI]D (SEQ ID NO 97) and comprises the amino acid sequence shown SEQ ID NO 85 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

49. Composition according to any of the preceding composition paragraphs wherein the polypeptide comprising one or more motif(s) GX[FY][LYF]D (SEQ ID NO 34), AYX[SET]XX[EAS] (SEQ ID NO 35) or GXXGX[FY][LYFI]D (SEQ ID NO 97) and comprises the amino acid sequence shown SEQ ID NO 88 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

50. Composition according to any of the preceding composition paragraphs wherein the polypeptide comprising one or more motif(s) GX[FY][LYF]D (SEQ ID NO 34), AYX[SET]XX[EAS] (SEQ ID NO 35) or GXXGX[FY][LYFI]D (SEQ ID NO 97) and comprises the amino acid sequence shown SEQ ID NO 91 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

51. Composition according to any of the preceding composition paragraphs wherein the polypeptide comprising one or more motif(s) GX[FY][LYF]D (SEQ ID NO 34), AYX[SET]XX[EAS] (SEQ ID NO 35) or GXXGX[FY][LYFI]D (SEQ ID NO 97) and comprises the amino acid sequence shown SEQ ID NO 94 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

52. Composition according to any of the preceding composition paragraphs wherein the polypeptide comprising one or more motif(s) GX[FY][LYF]D (SEQ ID NO 34), AYX[SET]XX[EAS] (SEQ ID NO 35) or GXXGX[FY][LYFI]D (SEQ ID NO 97) and comprises the amino acid sequence shown SEQ ID NO 95 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

53. Composition according to any of the preceding composition paragraphs wherein the polypeptide comprising one or more motif(s) GX[FY][LYF]D (SEQ ID NO 34), AYX[SET]XX[EAS] (SEQ ID NO 35) or GXXGX[FY][LYFI]D (SEQ ID NO 97) and comprises the amino acid sequence shown SEQ ID NO 96 or polypeptides having at least 60%, at least 65%, at least 70%, at least 75%, at least 80%, at least 85%, at least 90%, at least 95%, at least 96%, at least 97%, at least 98%, at least 99% or 100% sequence identity hereto.

54. A laundering method for laundering an item comprising the steps of:
   a. Exposing an item to a wash liquor comprising a polypeptide of paragraphs 68-108 or a composition according to any of paragraphs 11-53;
   b. Completing at least one wash cycle; and
   c. Optionally rinsing the item,
   wherein the item is a textile.

55. A method of treating an item, wherein the item is preferably a textile, said method comprising the steps of:
   a. Exposing an item to a polypeptide selected from the group consisting of a polypeptide having at least 60%, at least 65%, at least 70%, at least 75%, at least 80%, at least 85%, at least 90%, at least 95%, at least 96%, at least 97%, at least 98%, at least 99% or 100% sequence identity to the mature polypeptide of SEQ ID NO 2, SEQ ID N05, SEQ ID NO 8, SEQ ID NO 11, SEQ ID NO 14, SEQ ID NO 17, SEQ ID NO 20, SEQ ID NO 23, SEQ ID NO 26, SEQ ID NO 29, SEQ ID NO 32, SEQ ID NO 39, SEQ ID NO 42, SEQ ID NO 45, SEQ ID NO 48, SEQ ID NO 51, SEQ ID NO 54, SEQ ID NO 57, SEQ ID NO 60, SEQ ID NO 63, SEQ ID NO 66, SEQ ID NO 69, SEQ ID NO 72, SEQ ID NO 75, SEQ ID NO 78, SEQ ID NO 81, SEQ ID NO 84, SEQ ID NO 87, SEQ ID NO 90, SEQ ID NO 93, SEQ ID NO 95 and SEQ ID NO 96; a wash liquor comprising said polypeptide or a composition according to any proceeding paragraphs.

56. Method according to any proceeding paragraphs, wherein the pH of the wash liquor is in the range of 1 to 11.
57. Method according to any of the preceding method paragraphs, wherein the pH of the wash liquor is in the range 5.5 to 11, such as in the range of 7 to 9, in the range of 7 to 8 or in the range of 7 to 8.5.
58. Method according to any of the preceding method paragraphs, wherein the temperature of the wash liquor is in the range of 5° C. to 95° C., or in the range of 10° C. to 80° C., in the range of 10° C. to 70° C., in the range of 10° C. to 60° C., in the range of 10° C. to 50° C., in the range of 15° C. to 40° C., in the range of 20° C. to 40° C., in the range of 15° C. to 30° C. or in the range of 20° C. to 30° C.
59. Method according to any of the preceding method paragraphs, wherein the temperature of the wash liquor is from about 20° C. to about 40° C.
60. Method according to any of the preceding method paragraphs, wherein the temperature of the wash liquor is from about 15° C. to about 30° C.
61. Method according to any of the preceding method paragraphs, wherein stains present on the item is pretreated with a polypeptide of paragraphs 68-108 or a detergent composition according to any of paragraphs 11-53.
62. Method according to any of the preceding method paragraphs, wherein stickiness of the item is reduced.
63. Method according to any of the preceding method paragraphs, wherein redeposition of soil is reduced.
64. Method according to any of the preceding method paragraphs, wherein adherence of soil to the item is reduced or removed.
65. Method according to any of the preceding method paragraphs, wherein whiteness of the item is maintained or improved.
66. Method according to any of the preceding method paragraphs, wherein malodor is reduced or removed from the item.
67. Method according to any of the preceding method paragraphs, wherein the concentration of the polypeptide having hydrolytic and/or deacetylase activity in the wash liquor is in the range 0.002 mg/L to 2 mg/L, such as 0.02 mg/L to 2 mg/L, such as 0.2 mg/L to 2 mg/L or in the range of 0.0001 mg/L to 10 mg/L or in the range of in the range of 0.001 mg/L to 10 mg/L, or in the range of 0.01 mg/L to 10 mg/L, or in in the range of 0.1 mg/L to 10 mg/L per liter of wash liquor, optionally the concentration of the polypeptide of the invention is 0.0001% to 2 wt %, such as 0.001 to 0.1 wt %, such as 0.005 to 0.1 wt %, such as 0.01 to 0.1 wt %, such as 0.01 to 0.5 wt % or most preferred 0.002 to 0.09 wt % in the total detergent concentration.
68. A polypeptide having hydrolytic and/or deacetylase activity, selected from the group consisting of:
    a. a polypeptide having at least 60%, at least 65%, at least 70%, at least 75%, at least 80%, at least 85%, at least 90%, at least 95%, at least 96%, at least 97%, at least 98%, at least 99% or 100% sequence identity to the mature polypeptide of SEQ ID NO 2, SEQ ID N05, SEQ ID NO 8, SEQ ID NO 11, SEQ ID NO 14, SEQ ID NO 17, SEQ ID NO 20, SEQ ID NO 23, SEQ ID NO 26, SEQ ID NO 29, SEQ ID NO 32, SEQ ID NO 39, SEQ ID NO 42, SEQ ID NO 45, SEQ ID NO 48, SEQ ID NO 51, SEQ ID NO 54, SEQ ID NO 57, SEQ ID NO 60, SEQ ID NO 63, SEQ ID NO 66, SEQ ID NO 69, SEQ ID NO 72, SEQ ID NO 75, SEQ ID NO 78, SEQ ID NO 81, SEQ ID NO 84, SEQ ID NO 87, SEQ ID NO 90, SEQ ID NO 93 or a polypeptide having at least 60%, at least 65%, at least 70%, at least 75%, at least 80%, at least 85%, at least 90%, at least 95%, at least 96%, at least 97%, at least 98%, at least 99% or 100% sequence identity to the mature polypeptide shown in SEQ ID NO 3, SEQ ID NO 6, SEQ ID NO 9, SEQ ID NO 12, SEQ ID NO 15, SEQ ID NO 18, SEQ ID NO 21, SEQ ID NO 24, SEQ ID NO 27, SEQ ID NO 30, SEQ ID NO 33 SEQ ID NO 40, SEQ ID NO 43, SEQ ID NO 46, SEQ ID NO 49, SEQ ID NO 52, SEQ ID NO 55, SEQ ID NO 58, SEQ ID NO 61, SEQ ID NO 64, SEQ ID NO 67, SEQ ID NO 70, SEQ ID NO 73, SEQ ID NO 76, SEQ ID NO 79, SEQ ID NO 82, SEQ ID NO 85, SEQ ID NO 88, SEQ ID NO 91, SEQ ID NO 94, SEQ ID NO 95 or SEQ ID NO 96;
    b. a polypeptide encoded by a polynucleotide that hybridizes under low stringency conditions with
        i. the mature polypeptide coding sequence of SEQ ID NO 1, SEQ ID NO 4, SEQ ID NO 7, SEQ ID NO 10, SEQ ID NO 13, SEQ ID NO 16, SEQ ID NO 19, SEQ ID NO 22, SEQ ID NO 25, SEQ ID NO 28, SEQ ID NO 31, SEQ ID NO 38, SEQ ID NO 41, SEQ ID NO 44, SEQ ID NO 47, SEQ ID NO 50, SEQ ID NO 53, SEQ ID NO 56, SEQ ID NO 59, SEQ ID NO 62, SEQ ID NO 65, SEQ ID NO 68, SEQ ID NO 71, SEQ ID NO 74, SEQ ID NO 77, SEQ ID NO 80, SEQ ID NO 83, SEQ ID NO 86, SEQ ID NO 89, SEQ ID NO 92;
        ii. the cDNA sequence thereof, or
        iii. the full-length complement of (i) or (ii);
    c. a polypeptide encoded by a polynucleotide having at least 60% sequence identity to the mature polypeptide coding sequence of SEQ ID NO 1, SEQ ID NO 4, SEQ ID NO 7, SEQ ID NO 10, SEQ ID NO 13, SEQ ID NO 16, SEQ ID NO 19, SEQ ID NO 22, SEQ ID NO 25, SEQ ID NO 28, SEQ ID NO 31, SEQ ID NO 38, SEQ ID NO 41, SEQ ID NO 44, SEQ ID NO 47, SEQ ID NO 50, SEQ ID NO 53, SEQ ID NO 56, SEQ ID NO 59, SEQ ID NO 62, SEQ ID NO 65, SEQ ID NO 68, SEQ ID NO 71, SEQ ID NO 74, SEQ ID NO 77, SEQ ID NO 80, SEQ ID NO 83, SEQ ID NO 86, SEQ ID NO 89, SEQ ID NO 92 or the cDNA sequence thereof;
    d. a variant of the mature polypeptide shown in SEQ ID NO 3, SEQ ID NO 6, SEQ ID NO 9, SEQ ID NO 12, SEQ ID NO 15, SEQ ID NO 18, SEQ ID NO 21, SEQ ID NO 24, SEQ ID NO 27, SEQ ID NO 30, SEQ ID NO 33, SEQ ID NO 40, SEQ ID NO 43, SEQ ID NO 46, SEQ ID NO 49, SEQ ID NO 52, SEQ ID NO 55, SEQ ID NO 58, SEQ ID NO 61, SEQ ID NO 64, SEQ ID NO 67, SEQ ID NO 70, SEQ ID NO 73, SEQ ID NO 76, SEQ ID NO 79, SEQ ID NO 82, SEQ ID NO 85, SEQ ID NO 88, SEQ ID NO 91, SEQ ID NO 94, SEQ ID NO 95 and SEQ ID NO 96 comprising a substitution, deletion, and/or insertion at one or more positions; and
    e. a fragment of the polypeptide of (a), (b), (c), or (d) that comprises one or more motif(s) GX[FY][LYF]D (SEQ ID NO 34), AYX[SET]XX[EAS] (SEQ ID NO 35), GXXGX[FY][LYFI]D (SEQ ID NO 97), ([ILFQV]N[RW]G[FL] (SEQ ID NO 98), DTLDS[YF] (SEQ ID NO 99), G[VL]FLDTLDSF[QTH]L[LMQ] (SEQ ID NO 100) or DT[VIMA][GD][DNW][VIL][DEN]

(SEQ ID NO 101) or one or more of the motifs GX[FY][LYF]D (SEQ ID NO 34), AYX[SET]XX[EAS] (SEQ ID NO 35), GXXGX[FY][LYFI]D (SEQ ID NO 97), ([SETC]IG[EQA][ALI]EXY (SEQ ID NO 102) or [KLYMQ]XX[PV]QN[SA]PE (SEQ ID NO 104).

69. The polypeptide of paragraph 68, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 2, SEQ ID N05, SEQ ID NO 8, SEQ ID NO 11, SEQ ID NO 14, SEQ ID NO 17, SEQ ID NO 20, SEQ ID NO 23, SEQ ID NO 26, SEQ ID NO 29, SEQ ID NO 32, SEQ ID NO 39, SEQ ID NO 42, SEQ ID NO 45, SEQ ID NO 48, SEQ ID NO 51, SEQ ID NO 54, SEQ ID NO 57, SEQ ID NO 60, SEQ ID NO 63, SEQ ID NO 66, SEQ ID NO 69, SEQ ID NO 72, SEQ ID NO 75, SEQ ID NO 78, SEQ ID NO 81, SEQ ID NO 84, SEQ ID NO 87, SEQ ID NO 90, SEQ ID NO 93 or to the mature polypeptide shown in SEQ ID NO 3, SEQ ID NO 6, SEQ ID NO 9, SEQ ID NO 12, SEQ ID NO 15, SEQ ID NO 18, SEQ ID NO 21, SEQ ID NO 24, SEQ ID NO 27, SEQ ID NO 30, SEQ ID NO 33, SEQ ID NO 40, SEQ ID NO 43, SEQ ID NO 46, SEQ ID NO 49, SEQ ID NO 52, SEQ ID NO 55, SEQ ID NO 58, SEQ ID NO 61, SEQ ID NO 64, SEQ ID NO 67, SEQ ID NO 70, SEQ ID NO 73, SEQ ID NO 76, SEQ ID NO 79, SEQ ID NO 82, SEQ ID NO 85, SEQ ID NO 88, SEQ ID NO 91, SEQ ID NO 94, SEQ ID NO 95 and SEQ ID NO 96.

70. The polypeptide of paragraph 68 or 69, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 2 or to the mature polypeptide shown in SEQ ID NO 3.

71. The polypeptide of paragraph 68 or 69, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 5 or to the mature polypeptide shown in SEQ ID NO 6.

72. The polypeptide of paragraph 68 or 69, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 8 or to the mature polypeptide shown in SEQ ID NO 9.

73. The polypeptide of paragraph 68 or 69, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 11 or to the mature polypeptide shown in SEQ ID NO 12.

74. The polypeptide of paragraph 68 or 69, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 14 or to the mature polypeptide shown in SEQ ID NO 15.

75. The polypeptide of paragraph 68 or 69, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 17 or to the mature polypeptide shown in SEQ ID NO 18.

76. The polypeptide of paragraph 68 or 69, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 20 or to the mature polypeptide shown in SEQ ID NO 21.

77. The polypeptide of paragraph 68 or 69, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 23 or to the mature polypeptide shown in SEQ ID NO 24.

78. The polypeptide of paragraph 68 or 69, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 26 or to the mature polypeptide shown in SEQ ID NO 27.

79. The polypeptide of paragraph 68 or 69, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 29 or to the mature polypeptide shown in SEQ ID NO 30.

80. The polypeptide of paragraph 68 or 69, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 32 or to the mature polypeptide shown in SEQ ID NO 33.

81. The polypeptide of paragraph 68 or 69, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 39 or to the mature polypeptide shown in SEQ ID NO 40.

82. The polypeptide of paragraph 68 or 69, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 42 or to the mature polypeptide shown in SEQ ID NO 43.

83. The polypeptide of paragraph 68 or 69, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 45 or to the mature polypeptide shown in SEQ ID NO 46.

84. The polypeptide of paragraph 68 or 69, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 48 or to the mature polypeptide shown in SEQ ID NO 49.

85. The polypeptide of paragraph 68 or 69, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 51 or to the mature polypeptide shown in SEQ ID NO 52.

86. The polypeptide of paragraph 68 or 69, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 54 or to the mature polypeptide shown in SEQ ID NO 55.

87. The polypeptide of paragraph 68 or 69, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 57 or to the mature polypeptide shown in SEQ ID NO 58.

88. The polypeptide of paragraph 68 or 69, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 60 or to the mature polypeptide shown in SEQ ID NO 61.

89. The polypeptide of paragraph 68 or 69, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 63 or to the mature polypeptide shown in SEQ ID NO 64.

90. v The polypeptide of paragraph 68 or 69, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 66 or to the mature polypeptide shown in SEQ ID NO 67.

91. The polypeptide of paragraph 68 or 69, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 69 or to the mature polypeptide shown in SEQ ID NO 70.

92. The polypeptide of paragraph 68 or 69, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 72 or to the mature polypeptide shown in SEQ ID NO 73.

93. The polypeptide of paragraph 68 or 69, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 75 or to the mature polypeptide shown in SEQ ID NO 76.

94. The polypeptide of paragraph 68 or 69, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 78 or to the mature polypeptide shown in SEQ ID NO 79.

95. The polypeptide of paragraph 68 or 69, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 81 or to the mature polypeptide shown in SEQ ID NO 82.

96. The polypeptide of paragraph 68 or 69, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 84 or to the mature polypeptide shown in SEQ ID NO 85.

97. The polypeptide of paragraph 68 or 69, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 87 or to the mature polypeptide shown in SEQ ID NO 88.

98. The polypeptide of paragraph 68 or 69, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 90 or to the mature polypeptide shown in SEQ ID NO 91.

99. The polypeptide of paragraph 68 or 69, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 93 or to the mature polypeptide shown in SEQ ID NO 94.

100. The polypeptide of paragraph 68 or 69, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide shown in SEQ ID NO 95.

101. The polypeptide of paragraph 68 or 69, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide shown in SEQ ID NO 96.

102. The polypeptide according to any of paragraphs 68 to 101, which is encoded by a polynucleotide that hybridizes under low stringency conditions, low-medium stringency conditions, medium stringency conditions, medium-high stringency conditions, high stringency conditions, or very high stringency conditions with
   i. the mature polypeptide coding sequence of SEQ ID NO 1, SEQ ID NO 4, SEQ ID NO 7, SEQ ID NO 10, SEQ ID NO 13, SEQ ID NO 16, SEQ ID NO 19, SEQ ID NO 22, SEQ ID NO 25, SEQ ID NO 28, SEQ ID NO 31 SEQ ID NO 38, SEQ ID NO 41, SEQ ID NO 44, SEQ ID NO 47, SEQ ID NO 50, SEQ ID NO 53, SEQ ID NO 56, SEQ ID NO 59, SEQ ID NO 62, SEQ ID NO 65, SEQ ID NO 68, SEQ ID NO 71, SEQ ID NO 74, SEQ ID NO 77, SEQ ID NO 80, SEQ ID NO 83, SEQ ID NO 86, SEQ ID NO 89, SEQ ID NO 92;
   ii. the cDNA sequence thereof, or
   iii. the full-length complement of (i) or (ii).

103. The polypeptide according to any of paragraphs 68 to 102, which is encoded by a polynucleotide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide coding sequence of SEQ ID NO 1, SEQ ID NO 4, SEQ ID NO 7, SEQ ID NO 10, SEQ ID NO 13, SEQ ID NO 16, SEQ ID NO 19, SEQ ID NO 22, SEQ ID NO 25, SEQ ID NO 28, SEQ ID NO 31, SEQ ID NO 38, SEQ ID NO 41, SEQ ID NO 44, SEQ ID NO 47, SEQ ID NO 50, SEQ ID NO 53, SEQ ID NO 56, SEQ ID NO 59, SEQ ID NO 62, SEQ ID NO 65, SEQ ID NO 68, SEQ ID NO 71, SEQ ID NO 74, SEQ ID NO 77, SEQ ID NO 80, SEQ ID NO 83, SEQ ID NO 86, SEQ ID NO 89, SEQ ID NO 92 or the cDNA sequence thereof.

104. The polypeptide according to any of paragraphs 68 to 103, comprising or consisting of SEQ ID NO 3, SEQ ID NO 6, SEQ ID NO 9, SEQ ID NO 12, SEQ ID NO 15, SEQ ID NO 18, SEQ ID NO 21, SEQ ID NO 24, SEQ ID NO 27, SEQ ID NO 30, SEQ ID NO 33, SEQ ID NO 40, SEQ ID NO 43, SEQ ID NO 46, SEQ ID NO 49, SEQ ID NO 52, SEQ ID NO 55, SEQ ID NO 58, SEQ ID NO 61, SEQ ID NO 64, SEQ ID NO 67, SEQ ID NO 70, SEQ ID NO 73, SEQ ID NO 76, SEQ ID NO 79, SEQ ID NO 82, SEQ ID NO 85, SEQ ID NO 88, SEQ ID NO 91, SEQ ID NO 94, SEQ ID NO 95, SEQ ID NO 96 or the mature polypeptide of SEQ ID NO 2, SEQ ID NO 5, SEQ ID NO 8, SEQ ID NO 11, SEQ ID NO 14, SEQ ID NO 17, SEQ ID NO 20, SEQ ID NO 23, SEQ ID NO 26, SEQ ID NO 29, SEQ ID NO 32, SEQ ID NO 39, SEQ ID NO 42, SEQ ID NO 45, SEQ ID NO 48, SEQ ID NO 51, SEQ ID NO 54, SEQ ID NO 57, SEQ ID NO 60, SEQ ID NO 63, SEQ ID NO 66, SEQ ID NO 69, SEQ ID NO 72, SEQ ID NO 75, SEQ ID NO 78, SEQ ID NO 81, SEQ ID NO 84, SEQ ID NO 87, SEQ ID NO 90, SEQ ID NO 93.

105. The polypeptide according to any of paragraphs 68 to 104, which is a variant of the any of the polypeptides with SEQ ID NO 3, SEQ ID NO 6, SEQ ID NO 9, SEQ ID NO 12, SEQ ID NO 15, SEQ ID NO 18, SEQ ID NO 21, SEQ ID NO 24, SEQ ID NO 27, SEQ ID NO 30, SEQ ID NO 33, SEQ ID NO 40, SEQ ID NO 43, SEQ ID NO 46, SEQ ID NO 49, SEQ ID NO 52, SEQ ID NO 55, SEQ ID NO 58, SEQ ID NO 61, SEQ ID NO 64, SEQ ID NO 67, SEQ ID NO 70, SEQ ID NO 73, SEQ ID NO 76, SEQ ID NO 79, SEQ ID NO 82, SEQ ID NO 85, SEQ ID NO 88, SEQ ID NO 91, SEQ ID NO 94, SEQ ID NO 95, SEQ ID NO 96, comprising a substitution, deletion, and/or insertion at one or more positions.

106. The polypeptide according to any of paragraphs 68 to 105 for use as a medicament.

107. The polypeptide according to any of paragraphs 68 to 106 for use in treatment or prevention of a bacterial infection, preferably said bacterial infection is an infection caused by Gram-positive or Gram-negative bacteria, further preferably said bacterial infection is selected from a group consisting of: *Staphylococcus* spp. (e.g., *Staphylococcus epidermidis, S. aureus*), *Enterococcus* spp. (e.g., *Enterococcus faecalis*), *Escherichia* spp. (e.g., *Escherichia coli*), *Listeria* spp. (e.g., *Listeria monocytogenes*), *Pseudomonas* spp. (e.g., *Pseudomonas aeruginosa*), *Bacillus* spp., *Salmonella* spp., Coagulase-negative *Staphylococci, Klebsiella* spp. (e.g., *Klebsiella pneumoniae*) infections.

108. The polypeptide according to any of paragraphs 68 to 107 for use in treatment or prevention of a disease selected from the group consisting of: Cystic fibrosis pneumonia (e.g., caused by *Pseudomonas aeruginosa* and/or *Burkholderia cepacia*), Meloidosis (e.g., caused by *Pseudomonas pseudomallei*), Necrotizing fasciitis (e.g., caused by Group A streptococci), Musculoskeletal infections (e.g., caused by Staphylococci and other Gram-positive cocci), Otitis media (e.g., caused by *Haemophilus influenzae*), Biliary tract infection (e.g., caused by *E. coli* and other enteric bacteria), Urinary catheter cystitis (e.g., caused by *E. coli* and other Gram-negative rods), Bacterial prostatitis (e.g., *E. coli* and other Gram-negative bacteria), Periodontitis (e.g., caused by Gram negative anaerobic oral bacteria), Dental caries (e.g., caused by *Streptococcus* spp. and other acidogenic Gram positive cocci).

109. A polynucleotide encoding the polypeptide according to any of paragraphs 68-108.

110. A nucleic acid construct or expression vector comprising the polynucleotide of paragraph 109 operably linked to one or more control sequences that direct the production of the polypeptide in an expression host.

111. A recombinant host cell comprising the polynucleotide of paragraph 109 operably linked to one or more control sequences that direct the production of the polypeptide.

112. A method of producing the polypeptide of any of paragraphs 68-108, comprising cultivating a cell, which in its wild-type form produces the polypeptide, under conditions conducive for production of the polypeptide.

113. The method of paragraph 112, further comprising recovering the polypeptide.

114. A method of producing a polypeptide according to any of paragraphs 68-108, comprising cultivating the host cell of paragraph 111 under conditions conducive for production of the polypeptide.

115. The method of paragraph 114, further comprising recovering the polypeptide.

116. A nucleic acid construct or expression vector comprising a gene encoding a protein operably linked to the polynucleotide of paragraph 109, wherein the gene is foreign to the polynucleotide encoding the signal peptide.

117. A recombinant host cell comprising a gene encoding a protein operably linked to the polynucleotide of paragraph 109, wherein the gene is foreign to the polynucleotide encoding the signal peptide.

118. A method of producing a protein, comprising cultivating a recombinant host cell comprising a gene encoding a protein operably linked to the polynucleotide of paragraph 109, wherein the gene is foreign to the polynucleotide encoding the signal peptide, under conditions conducive for production of the protein.

119. The method of paragraph 118, further comprising recovering the protein.

120. Item laundered according to the method of any of paragraphs 54-67.

The invention is further described in the following paragraphs

Paragraph 1 A composition comprising at least 0.01 mg of active polypeptide per gram of composition, wherein the polypeptide comprises a Glyco_hydro_114 domain and at least one adjunct ingredient.

Paragraph 2 The composition according to paragraph 1, wherein the polypeptide further comprises a CE4 domain.

Paragraph 3 The composition according to any of the proceeding paragraphs, wherein the polypeptide is of the FLD sub family and comprising one or more of the motif(s) [GX[FY][LYF]D (SEQ ID NO 34), AYX[SET]XX[EAS] (SEQ ID NO 35) or GXXGX[FY][LYFI]D (SEQ ID NO 97).

Paragraph 4 The composition of paragraph 1 or 2, wherein the polypeptide has at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide shown in SEQ ID NO 3, SEQ ID NO 6, SEQ ID NO 9, SEQ ID NO 12, SEQ ID NO 15, 1 SEQ ID NO 18, SEQ ID NO 21, SEQ ID NO 24, SEQ ID NO 27, SEQ ID NO 30 or SEQ ID NO 33.

Paragraph 5 The composition of any of paragraphs 1 or 3,
(a) comprising or consisting of SEQ ID NO 3 or the mature polypeptide of SEQ ID NO 2;
(b) comprising or consisting of SEQ ID NO 6 or the mature polypeptide of SEQ ID NO 5;
(c) comprising or consisting of SEQ ID NO 9 or the mature polypeptide of SEQ ID NO 8;
(d) comprising or consisting of SEQ ID NO 12 or the mature polypeptide of SEQ ID NO 11;
(e) comprising or consisting of SEQ ID NO 15 or the mature polypeptide of SEQ ID NO 14;
(f) comprising or consisting of SEQ ID NO 18 or the mature polypeptide of SEQ ID NO 17;
(g) comprising or consisting of SEQ ID NO 21 or the mature polypeptide of SEQ ID NO 20;
(h) comprising or consisting of SEQ ID NO 24 or the mature polypeptide of SEQ ID NO 23;
(i) comprising or consisting of SEQ ID NO 27 or the mature polypeptide of SEQ ID NO 26;
(j) comprising or consisting of SEQ ID NO 30 or the mature polypeptide of SEQ ID NO 29; or
(k) comprising or consisting of SEQ ID NO 33 or the mature polypeptide of SEQ ID NO 32;

Paragraph 6 The composition according to any of paragraphs 1 to 5, wherein the composition is a cleaning composition such as a laundry or dish wash composition Paragraph 7 The composition according to paragraph 6, wherein the adjunct ingredient is selected from the group consisting of,
a) at least one builder,
b) at least one surfactant, and
c) at least one bleach component.

Paragraph 8 A polypeptide having hydrolytic and/or deacetyl activity, wherein the polypeptide is of the FLD sub family, comprising one or more of the motif(s) [GX[FY][LYF]D (SEQ ID NO 34), AYX[SET]XX[EAS] (SEQ ID NO 35) or GXXGX[FY][LYFI]D (SEQ ID NO 97), wherein the polypeptide is selected from the group consisting of:
(a) a polypeptide having at least 80%, at least 85%, at least 90%, at least 95%, at least 96%, at least 97%, at least 98%, at least 99% or 100% sequence identity to the polypeptide of SEQ ID NO 3;
(b) a polypeptide having at least 80%, at least 85%, at least 90%, at least 95%, at least 96%, at least 97%, at least 98%, at least 99% or 100% sequence identity to the polypeptide of SEQ ID NO 6;
(c) a polypeptide having at least 80%, at least 85%, at least 90%, at least 95%, at least 96%, at least 97%, at least 98%, at least 99% or 100% sequence identity to the polypeptide of SEQ ID NO 9;
(d) a polypeptide having at least 80%, at least 85%, at least 90%, at least 95%, at least 96%, at least 97%, at least 98%, at least 99% or 100% sequence identity to the polypeptide of SEQ ID NO 12;
(e) a polypeptide having at least 80%, at least 85%, at least 90%, at least 95%, at least 96%, at least 97%, at least 98%, at least 99% or 100% sequence identity to the polypeptide of SEQ ID NO 15;
(f) a polypeptide having at least 80%, at least 85%, at least 90%, at least 95%, at least 96%, at least 97%, at least 98%, at least 99% or 100% sequence identity to the polypeptide of SEQ ID NO 18;
(g) a polypeptide having at least 80%, at least 85%, at least 90%, at least 95%, at least 96%, at least 97%, at least 98%, at least 99% or 100% sequence identity to the polypeptide of SEQ ID NO 21;
(h) a polypeptide having at least 80%, at least 85%, at least 90%, at least 95%, at least 96%, at least 97%, at least 98%, at least 99% or 100% sequence identity to the polypeptide of SEQ ID NO 24;
(i) a polypeptide having at least 80%, at least 85%, at least 90%, at least 95%, at least 96%, at least 97%, at least 98%, at least 99% or 100% sequence identity to the polypeptide of SEQ ID NO 27;
(j) a polypeptide having at least 80%, at least 85%, at least 90%, at least 95%, at least 96%, at least 97%, at least 98%, at least 99% or 100% sequence identity to the polypeptide of SEQ ID NO 30;
(k) a polypeptide having at least 80%, at least 85%, at least 90%, at least 95%, at least 96%, at least 97%, at least 98%, at least 99% or 100% sequence identity to the polypeptide of SEQ ID NO 33;
(l) a variant of the polypeptide selected from the group consisting of SEQ ID NO 3, SEQ ID NO 6, SEQ ID NO 9, SEQ ID NO 12, SEQ ID NO 15, SEQ ID NO 18, SEQ ID NO 21, SEQ ID NO 24, SEQ ID NO 27, SEQ ID NO 30, SEQ ID NO 33, wherein the variant has hydrolytic and/or deacetylase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19 or 20 positions;

(m) a polypeptide comprising the polypeptide of (a) to (l) and a N-terminal and/or C-terminal His-tag and/or HQ-tag;

(n) a polypeptide comprising the polypeptide of (a) to (l) and a N-terminal and/or C-terminal extension of between 1 and 10 amino acids; and (o) a fragment of the polypeptide of (a) to (l) having hydrolytic and/or deacetylase activity and having at least 90% of the length of the mature polypeptide.

Paragraph 9 The polypeptide of paragraph 8, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO 3, SEQ ID NO 6, SEQ ID NO 9, SEQ ID NO 12, SEQ ID NO 15, SEQ ID NO 18, SEQ ID NO 21, SEQ ID NO 24, SEQ ID NO 27, SEQ ID NO 30, or SEQ ID NO 33.

Paragraph 10 The polypeptide of any of paragraphs 8 to 9, which is encoded by a polynucleotide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide coding sequence of SEQ ID NO 1, SEQ ID NO 4, SEQ ID NO 7, SEQ ID NO 10, SEQ ID NO 13, SEQ ID NO 16, SEQ ID NO 19, SEQ ID NO 22, SEQ ID NO 25, SEQ ID NO 28 or SEQ ID NO 31.

Paragraph 11 The polypeptide of any of paragraphs 8 to 10 selected from the group consisting of polypeptides:

(a) comprising or consisting of SEQ ID NO 3 or the mature polypeptide of SEQ ID NO 2;

(b) comprising or consisting of SEQ ID NO 6 or the mature polypeptide of SEQ ID NO 5;

(c) comprising or consisting of SEQ ID NO 9 or the mature polypeptide of SEQ ID NO 8;

(d) comprising or consisting of SEQ ID NO 12 or the mature polypeptide of SEQ ID NO 11;

(e) comprising or consisting of SEQ ID NO 15 or the mature polypeptide of SEQ ID NO 14.

(f) comprising or consisting of SEQ ID NO 18 or the mature polypeptide of SEQ ID NO 17;

(g) comprising or consisting of SEQ ID NO 21 or the mature polypeptide of SEQ ID NO 20;

(h) comprising or consisting of SEQ ID NO 24 or the mature polypeptide of SEQ ID NO 23;

(i) comprising or consisting of SEQ ID NO 27 or the mature polypeptide of SEQ ID NO 26;

(j) comprising or consisting of SEQ ID NO 30 or the mature polypeptide of SEQ ID NO 29; and (k) comprising or consisting of SEQ ID NO 33 or the mature polypeptide of SEQ ID NO 32.

Paragraph 12 A method for laundering an item comprising the steps of:

a. exposing an item to a wash liquor comprising the polypeptide according to any of paragraphs 8 to 11 or the composition according to any of paragraphs 1 to 7;

b. completing at least one wash cycle; and c. optionally rinsing the item, wherein the item is a textile.

Paragraph 13 Use of a polypeptide comprising a Glyco_hydro_114 domain, preferably a polypeptide comprising a Glyco_hydro_114 domain and a CE4 domain in a cleaning process, such as laundry and/or dish wash.

Paragraph 14 Use of a polypeptide comprising a Glyco_hydro_114 domain, preferably a polypeptide comprising a Glyco_hydro_114 domain and a CE4 domain i. for preventing, reducing or removing stickiness of the item;

ii. for pretreating stains on the item;

iii. for preventing, reducing or removing redeposition of soil during a wash cycle;

iv. for preventing, reducing or removing adherence of soil to the item;

v. for maintaining or improving whiteness of the item;

vi. for preventing, reducing or removal malodor from the item, wherein the item is a textile.

Paragraph 15 Use according to any of the preceding paragraphs, wherein the polypeptide is selected from the group consisting of polypeptides having at least 60% sequence identity to the polypeptide shown in SEQ ID NO 3, SEQ ID NO 6, SEQ ID NO 9, SEQ ID NO 12, SEQ ID NO 15, SEQ ID NO 18, SEQ ID NO 21, SEQ ID NO 24, SEQ ID NO 27, SEQ ID NO 30 or SEQ ID NO 33.

Paragraph 16 Use according to paragraph 14, wherein the polypeptide has at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO 3, SEQ ID NO 6, SEQ ID NO 9, SEQ ID NO 12, SEQ ID NO 15, SEQ ID NO 18, SEQ ID NO 21, SEQ ID NO 24, SEQ ID NO 27, SEQ ID NO 30 or SEQ ID NO 33.

Paragraph 17 Use of a polypeptide according to any of paragraphs 8 to 11 for deep cleaning of an item, wherein item is a textile.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

EXAMPLES

Model Detergents

Model detergent A wash liquor (100%) was prepared by dissolving 3.33 g/I of model detergent A containing 12% LAS, 1.1% AEO Biosoft N25-7 (NI), 7% AEOS (SLES), 6% MPG, 3% ethanol, 3% TEA (triethanolamine), 2.75% cocoa soap, 2.75% soya soap, 2% glycerol, 2% sodium hydroxide, 2% sodium citrate, 1% sodium formiate, 0.2% DTMPA and 0.2% PCA (all percentages are w/w (weight volume) in water with hardness 15 dH.

Triple-20 Nonionic Model Detergent (60% surfactant) was prepared by dissolving 3.33 g/I non-ionic detergent containing NaOH 0.87%, MPG (Monopropylenglycol) 6%, Glycerol 2%, Soap-soy 2.75%, Soap-coco 2.75%, PCA (Sokalon CP-5) 0.2%, AEO Biosoft N25-7(NI) 16%, Sodium formiate 1%, Sodium Citrate 2%, DTMPA 0.2%, Ethanol (96%) 3%, adjustment of pH with NaOH or Citric acid as water to 100% (all percentages are w/w (weight volume) in water with hardness 15 dH.

Model Detergent MC: A medical cleaning model detergent (model detergent MC) was prepared containing 5% MPG (propylene glycol), 5% Pluronic PE 4300 (PO/EO block polymer; 70%/30%, approx. 1750 g/mol), 2% Plurafac LF 305 (fatty alcohol alkoxylate; C6-10+EO/PO), 1% MGDA (methyl glycine diacetic acid, 1% TEA (triethanolamine) (all percentages are w/w). The pH was adjusted to 8.7 with phosphoric acid.

Assays

The activity of the Glyco_hydro_114 glycosyl hydrolases of the invention may be measured in a pNP-acetate assay as described in Marmont et. al. (2017) "PelA and PelB proteins form a modification and secretion complex essential for Pel polysaccharide-dependent biofilm formation in *Pseudomonas aeruginosa*", J. Biol. Chem. 292, 19411-19422 or as described by Colvin, K. M., et. al (2013) "PelA deacetylase activity is required for Pel polysaccharide synthesis in *Pseudomonas aeruginosa*". J. Bacteriol. 195, 2329-2339.

Wash Assay

Mini Launder-O-Meter (MiniLOM) Model Wash System

MiniLOM is a modified mini wash system of the Launder-O-Meter (LOM), which is a medium scale model wash system that can be applied to test up to 20 different wash conditions simultaneously. A LOM is basically a large temperature controlled water bath with 20 closed metal beakers rotating inside it. Each beaker constitutes one small washing machine and during an experiment, each will contain a solution of a specific detergent/enzyme system to be tested along with the soiled and unsoiled fabrics it is tested on. Mechanical stress is achieved by the beakers being rotated in the water bath and by including metal balls in the beaker.

The LOM model wash system is mainly used in medium scale testing of detergents and enzymes at European wash conditions. In a LOM experiment, factors such as the ballast to soil ratio and the fabric to wash liquor ratio can be varied. Therefore, the LOM provides the link between small scale experiments, such as AMSA and mini-wash, and the more time consuming full scale experiments in front loader washing machines. In miniLOM, washes are performed in 50 ml test tubes placed in Stuart rotator.

Example 1 Cloning and Expression of Polypeptides

The DNA encoding the gene of SEQ ID NO 1, SEQ ID NO 4, SEQ ID NO 7, SEQ ID NO 10, SEQ ID NO 13, SEQ ID NO 16, SEQ ID NO 19, SEQ ID NO 22, SEQ ID NO 25, SEQ ID NO 28, SEQ ID NO 31, SEQ ID NO 3, SEQ ID NO 6, SEQ ID NO 9, SEQ ID NO 12, SEQ ID NO 15, SEQ ID NO 18, SEQ ID NO 21, SEQ ID NO 24, SEQ ID NO 27, SEQ ID NO 30, SEQ ID NO 33, SEQ ID NO 40, SEQ ID NO 43, SEQ ID NO 46, SEQ ID NO 49, SEQ ID NO 52, SEQ ID NO 55, SEQ ID NO 58, SEQ ID NO 61, SEQ ID NO 64, SEQ ID NO 67, SEQ ID NO 70, SEQ ID NO 73, SEQ ID NO 76, SEQ ID NO 79, SEQ ID NO 82, SEQ ID NO 85, SEQ ID NO 88, SEQ ID NO 91 and SEQ ID NO 94, were isolated from bacterial strains and environmental bacterial communities isolated from soil samples collected in different countries (see table 1).Chromosomal DNA from the different strains and bacterial communities was subjected to full genome sequencing using Illumina technology. The genome sequence was analyzed for protein sequences that that had glycosyl hydrolase domains (according to the CAZY definition). 11 sequences containing a Glyco_hydro_114 domain, as defined in PFAM (PF03537, Pfam version 31.0 Finn (2016). Nucleic Acids Research, Database Issue 44:D279-D285) were identified in the genomes.

TABLE 1

| enzyme | Donor | country of origin |
|---|---|---|
| SEQ ID NO 3 | *Pseudomonas* sp-62208 | United States |
| SEQ ID NO 6 | Enviromental bacterial community A | United States |
| SEQ ID NO 9 | *Thermus rehai* | China |
| SEQ ID NO 15 | *Burkholderia* sp-63093 | Denmark |
| SEQ ID NO 18 | *Myxococcus macrosporus* | Denmark |
| SEQ ID NO 12 | Enviromental bacterial community E | Denmark |
| SEQ ID NO 21 | *Gallaecimonas pentaromativorans* | Denmark |
| SEQ ID NO 24 | *Nonomuraea coxensis* | Philippines |
| SEQ ID NO 27 | *Glycomyces rutgersensis* | China |
| SEQ ID NO 30 | Enviromental bacterial community E | Denmark |
| SEQ ID NO 33 | *Paraburkholderia phenazinium* | Denmark |
| SEQ ID NO 40 | Environmental bacterial community LA | Denmark |
| SEQ ID NO 43 | *Myxococcus virescens* | Germany |
| SEQ ID NO 46 | *Myxococcus fulvus* | Denmark |
| SEQ ID NO 49 | *Myxococcus macrosporus* | Denmark |
| SEQ ID NO 52 | *Myxococcus stipitatus* | Denmark |
| SEQ ID NO 55 | *Myxococcus macrosporus* | Denmark |
| SEQ ID NO 58 | *Pseudomonas seleniipraecipitans* | United States |
| SEQ ID NO 61 | *Pseudomonas migulae* | United States |
| SEQ ID NO 64 | *Pseudomonas corrugate* | United States |
| SEQ ID NO 67 | *Pseudomonas pelagia* | United States |
| SEQ ID NO 70 | *Pseudomonas aeruginosa* | United States |
| SEQ ID NO 73 | *Streptomyces griseofuscus* | Spain |
| SEQ ID NO 76 | *Lysinibacillus xylanilyticus* | Denmark |
| SEQ ID NO 79 | *Tumebacillus ginsengisoli* | Denmark |
| SEQ ID NO 82 | *Lysinibacillus boronitolerans* | United States |
| SEQ ID NO 85 | *Microbulbifer hydrolyticus* | United States |
| SEQ ID NO 88 | *Carnobacterium inhibens* subsp. *gilichinskyi* | Denmark |
| SEQ ID NO 91 | Environmental bacterial community PA | Denmark |
| SEQ ID NO 94 | *Pseudomonas composti* | Denmark |
| SEQ ID NO 95 | *Paraburkholderia phenazinium* | Denmark |
| SEQ ID NO 96 | *Burkholderia* sp-63093 | Denmark |

Example 2 Cloning and Expression of Polypeptides of the Invention

The DNA encoding the mature peptide of Glyco_hydro_114 genes SEQ ID NO 1, SEQ ID NO 4, SEQ ID NO 7, SEQ ID NO 10, SEQ ID NO 13, SEQ ID NO 16, SEQ ID NO 19, SEQ ID NO 22, SEQ ID NO 25, SEQ ID NO 28, SEQ ID NO 31, SEQ ID NO 38, SEQ ID NO 41, SEQ ID NO 44, SEQ ID NO 47, SEQ ID NO 50, SEQ ID NO 53, SEQ ID NO 56, SEQ ID NO 59, SEQ ID NO 62, SEQ ID NO 65, SEQ ID NO 68, SEQ ID NO 71, SEQ ID NO 74, SEQ ID NO 77, SEQ ID NO 80, SEQ ID NO 83, SEQ ID NO 86, SEQ ID NO 89, SEQ ID NO 92, were amplified from the genomic DNA of the corresponding bacterial strains by standard PCR techniques using specific primers containing an overhang to cloning vector. The amplified PCR fragments were inserted into a *Bacillus* expression vector as described in WO12/025577. Briefly, the DNA encoding the mature peptide of the gene was cloned in frame to a *Bacillus clausii* secretion signal (BcSP; with the following amino acid sequence: MKKPLGKIVASTAL-LISVAFSSSIASA (SEQ ID NO36). BcSP replaced the native secretion signal in the gene. Downstream of the BcSP sequence, an affinity tag sequence was introduced to ease the purification process (His-tag; with the following amino acid sequence: HHHHHHPR (SEQ ID NO 37) The gene that was expressed therefore comprised the BcSP sequence followed by the His-tag sequence followed by the mature wild type Glyco_hydro_114 gene sequence. The final expression plasmid (BcSP-His-tag-Glyco_hydro_114) was transformed into a *Bacillus subtilis* expression host. The Glyco_hydro_114 BcSP-fusion gene was integrated by homologous recombination into the *Bacillus subtilis* host cell genome upon transformation. The gene construct was expressed under the control of a triple promoter system (as described in WO 99/43835). The gene coding for chloramphenicol acetyltransferase was used as maker (as described in (Diderichsen et al., 1993, *Plasmid* 30: 312-315)). Transformants were selected on LB media agar supplemented with 6 microgram of chloramphenicol per ml. One recombinant *Bacillus subtilis* clone containing the Glyco_ hydro_114 expression construct was selected and was cultivated on a rotary shaking table in 500 ml baffled Erlenmeyer flasks each containing 100 ml yeast extract-based media. After 3-5 days' cultivation time at 30° C. to 37° C., the enzyme containing supernatant was harvested by centrifugation and the enzymes was purified by His-tag purification.

Example 3 His Tag Purification Method

The His-tagged Glyco_hydro_114 enzymes were purified by immobilized metal chromatography (IMAC) using $Ni^{2+}$ as the metal ion on 5 mL HisTrap Excel columns (GE Healthcare Life Sciences). The purification took place at pH 7 and the bound protein was eluted with imidazole. The purity of the purified enzymes was checked by SDS-PAGE and the concentration of the enzyme determined by Absorbance 280 nm after a buffer exchange in 50 mM HEPES, 100 mM NaCl pH7.0

Example 4 MiniLOM Deep-Cleaning in Liquid Model Detergent on Pel Swatches

A crude extract of the biofilm extracellular polymer Pel was prepared from *Pseudomonas aeruginosa* (DSM 19882) as follows; The strain was restreaked on LB Agar (pH 7.3) and incubated for 3 days at ambient temperature. 500 mL of T-broth (10 g/L Bacto™ Tryptone (211705, BD), 5 g/L sodium chloride (31434, Sigma-Aldrich)) was then inoculated and incubated statically for 6 days at ambient temperature. The biofilm pellicle was carefully removed from the flask, and pelleted by centrifugation (10 min, 16000 g, 25° C.). The pellet was then resuspended in 3M NaCl, vortexed vigorously and incubated for 15 min at ambient temperature to extract the surface-associated polymer. The cells were then re-pelleted (10 min, 16000 g, 25° C.) and the Pel-containing supernatant was retrieved. The supernatant was then diluted three times with sterile MilliQ water. The extract was stored at −20° C. until further use (termed Pel extract). Wash performance was determined as follows; 50 ul aliquots of the crude Pel extract were spotted on sterile textile swatches (WFK20A, 65% polyester/35% cotton) and incubated for 15 min at ambient temperature. The swatches (sterile or with the extract) were placed in 50 mL test tubes and 10 mL of wash liquor (15° dH water with 0.2 g/L iron(III) oxide nano-powder (544884; Sigma-Aldrich) with 3.33 g/L liquid model A or non-ionic model detergent) and the 5 μg/ml enzyme(s) (when appropriate) was added to each tube. Washes without enzyme were included as controls. The test tubes were placed in a Stuart rotator and incubated for 1 hour at 30° C. and 20 rpm. The wash liquor was then removed, and the swatches were rinsed twice with 15° dH water and dried on filter paper over night.

The color difference (L) values were measured using a Handheld Minolta CR-300, and are displayed in table 2. Delta values ($L_{(swatch\ washed\ with\ enzyme)} - L_{(swatch\ washed\ without\ enzyme)}$) are also indicated.

TABLE 2

Deep-cleaning effects of the PelA homologues in non-ionic model detergent and in model A detergent

| Enzyme | Enzyme concentration (ppm) | L values, non-ionic model detergent | ΔL non-ionic model detergent | L values, model A detergent | ΔL model A detergent |
| --- | --- | --- | --- | --- | --- |
| No enzyme | 0.0 | 67.1 | | 64.7 | |
| SEQ ID NO 3 | 5.0 | 87.8 | 20.7 | 85.6 | 20.9 |
| SEQ ID NO 6 | 5.0 | 75.4 | 8.3 | 69.2 | 4.6 |
| SEQ ID NO 9 | 5.0 | 69.9 | 2.8 | 67.5 | 2.9 |
| SEQ ID NO 12 | 5.0 | 79.8 | 12.7 | 84.1 | 19.4 |
| SEQ ID NO 15 | 5.0 | 73.6 | 6.5 | 78.1 | 13.4 |
| SEQ ID NO 18 | 5.0 | 80.0 | 12.9 | 85.2 | 20.6 |
| SEQ ID NO 21 | 5.0 | 70.5 | 3.4 | 68.9 | 4.3 |
| SEQ ID NO 24 | 5.0 | 76.5 | 9.4 | 67.3 | 2.6 |
| SEQ ID NO 27 | 5.0 | 78.0 | 10.9 | 78.9 | 14.2 |
| SEQ ID NO 30 | 5.0 | 79.5 | 12.5 | 73.0 | 8.3 |
| SEQ ID NO 33 | 5.0 | 75.0 | 8.0 | 67.4 | 2.8 |

Example 5 Construction of Clades and Phylogenetic Trees

The polypeptides of the invention having hydrolase activity and comprises the Glyco_hydro_114 domain as well as clusters such as the clades. A phylogenetic tree was constructed, of polypeptide sequences containing a Glyco_hydro_114 domain, as defined in PFAM (PF03537, Pfam version 31.0 Finn (2016). Nucleic Acids Research, Database Issue 44: D279-D285). The phylogenetic tree was constructed from a multiple alignment of mature polypeptide sequences containing at least one Glyco_hydro_114 domain. The sequences were aligned using the MUSCLE algorithm version 3.8.31 (Edgar, 2004. *Nucleic Acids Research* 32(5): 1792-1797), and the trees were constructed using FastTree version 2.1.8 (Price et al., 2010, *PloS one* 5(3)) and visualized using iTOL (Letunic & Bork, 2007. *Bioinformatics* 23(1): 127-128). The polypeptide comprises of the Glyco_hydro_114 domain comprises several motifs. One example is GX[FY][LYF]D (SEQ ID NO 34) situated in positions corresponding to positions 113 to 117 in *Pseudomonas* sp-62208 (SEQ ID NO 3), where D at position 117 is part of the substrate binding pocket, and one of the two putative catalytic site residues. Another motif which may be comprised by the polypeptides of the invention is AYX[SET]XX[EAS] (SEQ ID NO 35) situated in positions corresponding to positions 53 to 58 in *Pseudomonas* sp-62208 (SEQ ID NO 3). The polypeptides containing a Glyco_hydro_114 domain can be separated into distinct sub-clusters. The sub-clusters are defined by one or more short sequence motifs, as well as containing a Glyco_hydro_114 domain as defined in PFAM (PF03537, Pfam version 31.0). We denoted one sub-cluster comprising the motif GXXGX[FY][LYFI]D (SEQ ID NO 97) as the FLD clade. All polypeptide sequences containing a Glyco_hydro_114 domain as well as the motif will be denoted as belonging to the FLD clade.

The polypeptides in the FLD clade can be further separated into multiple distinct sub-clusters, or clades, where we denoted the clades listed below. The distinct motifs for each clade are described in detail below.

Generation of FLD Clade

A phylogenetic tree was constructed, of polypeptide sequences containing a Glyco_hydro_114 domain, as defined above. The phylogenetic tree was constructed from a multiple alignment of mature polypeptide sequences containing at least one Glyco_hydro_114 domain. The sequences were aligned using the MUSCLE algorithm version 3.8.31 (Edgar, 2004. *Nucleic Acids Research* 32(5): 1792-1797), and the tree was constructed using FastTree version 2.1.8 (Price et al., 2010, *PloS one* 5(3)) and visualized using iTOL (Letunic & Bork, 2007. *Bioinformatics* 23(1): 127-128). Using the phylogenetic tree, the polypeptides in Glyco_hydro_114 can be separated into distinct sub-clusters, one which we denoted FLD.

A characteristic motif for this sub-cluster is the motif GXXGX[FY][LYFI]D (SEQ ID NO 97), corresponding to amino acids GYAGLFLD at positions 110 to 117 in SEQ ID NO 3, where D at position 117 is part of the substrate binding pocket and one of the two putative catalytic site residues of the PelA. The other catalytic site residue is located at position 175 in SEQ ID NO 3. An additional motif of the FLD clade is GX[FY][LYF]D (SEQ ID NO 34), corresponding to amino acid 113 to 117 in the reference polypeptide (SEQ ID NO 3).

Generation of NRG Clade

The NRG clade comprises polypeptides of bacterial origin, containing a Glyco_hydro_114 domain and belonging to the FLD clade, having hydrolase activity. The polypeptides of the clade comprise the motif example [ILFQV]N[RW]G[FL] (SEQ ID NO 98), corresponding to amino acids FNRGF at positions 155 to 159 of SEQ ID NO 3 where N and G (corresponding to position 156 and 158 of SEQ ID NO 3) is fully conserved in NRG clade.

Examples of polypeptides of the NRG clade includes SEQ ID NO 3, SEQ ID NO 9, SEQ ID NO 15, SEQ ID NO 21, SEQ ID NO 33, SEQ ID NO 40, SEQ ID NO 58, SEQ ID NO 61, SEQ ID NO 64, SEQ ID NO 67, SEQ ID NO 70, SEQ ID NO 76, SEQ ID NO 79, SEQ ID NO 82, SEQ ID NO 94, SEQ ID NO 95, and SEQ ID NO 96.

Generation of DTLDS Clade

The DTLDS clade comprises polypeptides of bacterial origin, containing a Glyco_hydro_114 domain and belonging to the NRG clade, having hydrolase activity. The polypeptides of the clade comprise the motif example DTLDS[YF] (SEQ ID NO 99), corresponding to amino acids DTLDSF positions 117 to 122 of SEQ ID NO 3 where DTLDS (corresponding to positions 117 and 121 of SEQ ID NO 3) is fully conserved in DTLDS clade, and D at position 117 is part of the substrate binding pocket and one of the two putative catalytic site residues.

Examples of polypeptides of the DTLDS clade includes SEQ ID NO 3, SEQ ID NO 15, SEQ ID NO 21, SEQ ID NO 33, SEQ ID NO 40, SEQ ID NO 58, SEQ ID NO 61, SEQ ID NO 64, SEQ ID NO 67, SEQ ID NO 70, SEQ ID NO 94, SEQ ID NO 95, and SEQ ID NO 96.

Generation of GVFLD Clade

The GVFLD clade comprises polypeptides of bacterial origin, containing a Glyco_hydro_114 domain and belonging to the DTLDS clade, having hydrolase activity. The polypeptides of the clade comprise the motif example G[VL]FLDTLDSF[QTH]L[LMQ] (SEQ ID NO 100), corresponding to amino acids GLFLDTLDSFQLL positions 113 to 125 of SEQ ID NO 3 where D (corresponding to position 117 of SEQ ID NO 3) is fully conserved in GVFLD clade, part of the substrate binding pocket, and one of the two putative catalytic site residues.

Examples of polypeptides of the GVFLD clade includes SEQ ID NO 3, SEQ ID NO 40, SEQ ID NO 58, SEQ ID NO 61, SEQ ID NO 64, SEQ ID NO 67, SEQ ID NO 70, and SEQ ID NO 94.

Generation of DTVG Clade

The DTVG clade comprises polypeptides of bacterial origin, containing a Glyco_hydro_114 domain and belonging to the NRG clade, having hydrolase activity. The polypeptides of the clade comprise the motif example DT[VIMA][GD][DNW][VIL][DEN] (SEQ ID NO 101), corresponding to amino acids DTVGNIN in SEQ ID NO 76 at positions 134 to 140 of SEQ ID NO 76, where D and T (corresponding to position 134 and 135 of SEQ ID NO 76) is fully conserved in the DTVG clade.

Examples of polypeptides of the DTVG clade is SEQ ID NO 76 and SEQ ID NO 82.

Generation of IGEAE Clade

The IGEAE clade comprises polypeptides of bacterial origin, containing a Glyco_hydro_114 domain and belonging to the FLD clade, having hydrolase activity. The polypeptides of the clade comprise the motif example [SETC]IG[EQA][ALI]EXY (SEQ ID NO 102), corresponding to amino acids EIGAIEEY at positions 262 to 269 of SEQ ID NO 12 where G and E (corresponding to position 264 and 267 of SEQ ID NO 12) are fully conserved in IGEAE clade. Residue A at position 265 is part of the substrate binding pocket.

Examples of polypeptides of the IGEAE clade is SEQ ID NO 6, SEQ ID NO 12, SEQ ID NO 18, SEQ ID NO 30, SEQ ID NO 43, SEQ ID NO 46, SEQ ID NO 49, SEQ ID NO 52 and SEQ ID NO 55.

Generation of QNSPEL Clade

The QNSPEL clade comprises polypeptides of bacterial origin, containing a Glyco_hydro_114 domain and belonging to the IGEAE clade, having hydrolase activity. The polypeptides of the clade comprise the motif example [QL]N[AS]PEL (SEQ ID NO 103), corresponding to amino acids QNSPEL at positions 370 to 375 of SEQ ID NO 12 where P, E and L (corresponding to position 373 to 375 of SEQ ID NO 12) are fully conserved in QNSPEL clade. Another conserved motif of this clade is [KLYMQ]XX[PV]QN[SA]PE (SEQ ID NO 104), located at positions 366 to 374 in SEQ ID NO 12, and corresponding to peptide KVVPQNSPE in SEQ ID NO 12. Examples of polypeptides of the QNSPEL clade is SEQ ID NO 12, SEQ ID NO 18, SEQ ID NO 30, SEQ ID NO 43, SEQ ID NO 46, SEQ ID NO 49, SEQ ID NO 52 and SEQ ID NO 55.

An alignment of some of the polypeptides of the invention comprised in the clade is shown in FIG. 1.

Figure 4:
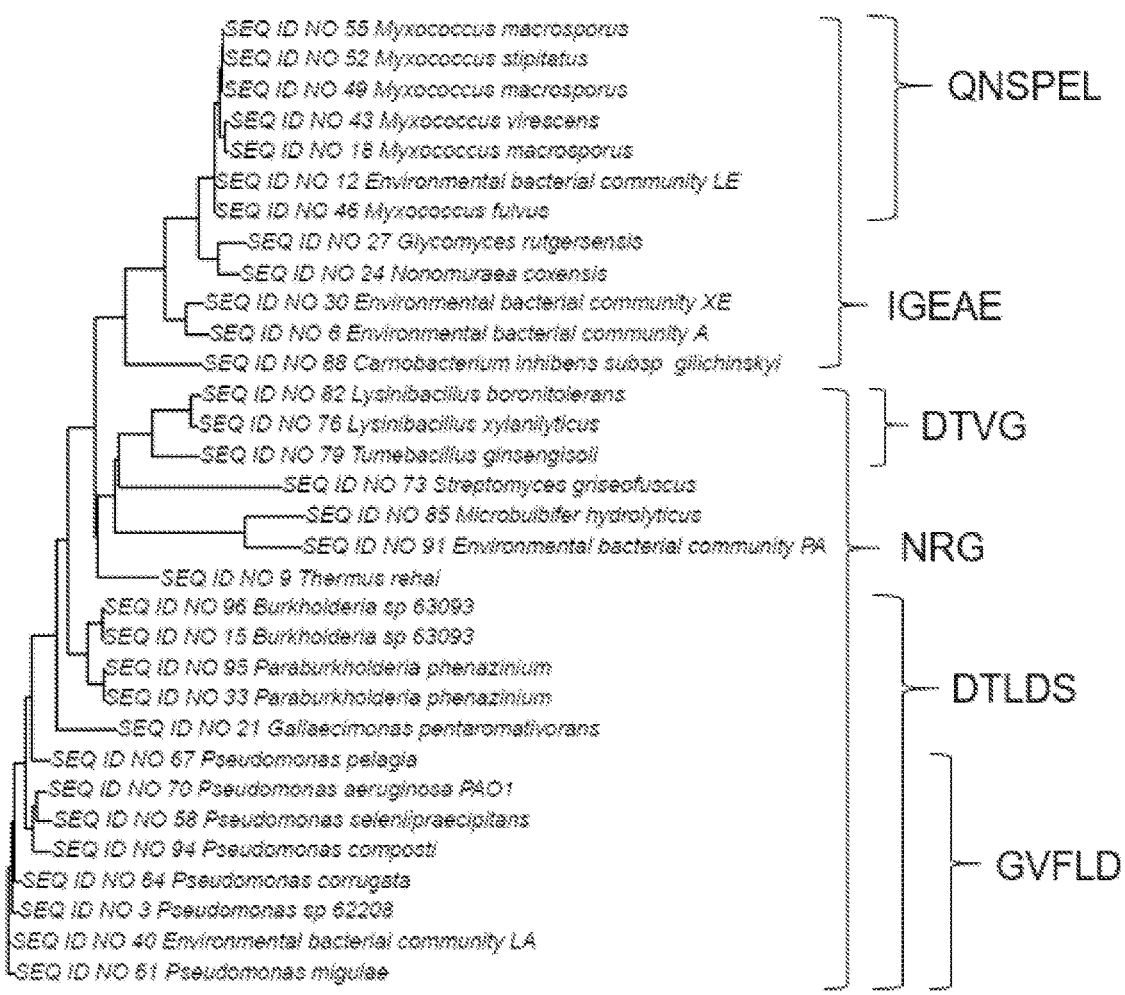

A phylogenetic tree of the polypeptides in the clades is shown in FIG. 2, FIG. 3 and FIG. 4.

Example 6 Biofilm Removal Activity

The Pel-producing *Pseudomonas aeruginosa* strain DSM19882 was used as a model microorganism in the present example. The strain was restreaked on LB agar and incubated at 30° C. An overnight culture was inoculated in 10 mL LB and the culture was incubated for 16 hours at 37° C. under shaking conditions. The culture was subsequently diluted (1:100) in LBNS, added to 96-well microtiter plates (150 µL per well, Thermo Scientific, cat #167008) and Peg lids were inserted (NUNC-TSP, Thermo Scientific, cat #445497). The microtiter plates were incubated for 24 hours at 26° C. under static conditions. After incubation, the peg lids were rinsed in MTP plates with 5° dH water hardness, and transferred to treatments plate with LBNS containing no enzyme (control) or 20 µg/mL enzyme for 1 hour at 26° C. The lids were subsequently rinsed in water hardness and stained with 0.095% crystal violet (Sigma-Aldrich, cat #V5265) for 15 min. Following the staining, the peg lids were rinsed twice, moved to clean microtiter plates and the remaining dye was dissolved with 30% acetic acid. The absorbance was measured at 595 nm. The results are displayed in table 3

TABLE 3

Biofilm reducing properties of Glyco_hydro_114 glycosyl hydrolases

| Enzyme | Conc | % remaining biofilm |
|---|---|---|
| no enzyme | 0 | 100.0 |
| SEQ ID NO 3 | 20 | 2.9 |
| SEQ ID NO 6 | 20 | 31.4 |
| SEQ ID NO 15 | 20 | 37.8 |
| SEQ ID NO 18 | 20 | 35.0 |
| SEQ ID NO 12 | 20 | 7.2 |
| SEQ ID NO 24 | 20 | 54.9 |
| SEQ ID NO 27 | 20 | 39.9 |
| SEQ ID NO 30 | 20 | 25.7 |
| SEQ ID NO 33 | 20 | 52.6 |
| SEQ ID NO 40 | 20 | 54.6 |
| SEQ ID NO 43 | 20 | 15.8 |
| SEQ ID NO 46 | 20 | 8.3 |
| SEQ ID NO 49 | 20 | 13.4 |
| SEQ ID NO 52 | 20 | 10.2 |
| SEQ ID NO 55 | 20 | 16.3 |
| SEQ ID NO 61 | 20 | 41.4 |
| SEQ ID NO 64 | 20 | 2.6 |
| SEQ ID NO 70 | 20 | 3.5 |
| SEQ ID NO 76 | 20 | 2.3 |
| SEQ ID NO 79 | 20 | 49.0 |
| SEQ ID NO 82 | 20 | 1.8 |
| SEQ ID NO 91 | 20 | 1.9 |

All tested Glyco_hydro_114 glycosyl hydrolases showed biofilm reducing properties on the Pel-producing *Pseudomonas aeruginosa* strain DSM19882.

Example 7 Deep-Cleaning in Liquid Model Detergent A on Pel Swatches

A crude extract of the biofilm extracellular polymer Pel was prepared from *Pseudomonas aeruginosa* PA14 (DSM 19882) as described above. The wash performance was determined as follows; 50 ul aliquots of the crude Pel extract were spotted on sterile textile swatches (WFK20A) and incubated for 15 min at ambient temperature. Control swatches were spotted with 3M NaCl. The swatches (sterile or with the extract) were placed in 50 mL test tubes and 10 mL of wash liquor (15° dH water with 0.2 g/L iron(III) oxide nano-powder (544884; Sigma-Aldrich) with 3.33 g/L liquid model A detergent) and the 2 µg/ml enzyme was added to each tube. Washes without enzyme were included as controls. The test tubes were placed in a Stuart rotator and incubated for 1 hour at 30° C. and 20 rpm. The wash liquor was then removed, and the swatches were rinsed twice with 15° dH water and dried on filter paper over night. The color difference (L) values were measured using a Handheld Minolta CR-300, and are displayed in table 4. Wash performance (WP) values ($L_{(swatch\ washed\ with\ enzyme)} - L_{(swatch\ washed\ without\ enzyme)}$) are also indicated.

TABLE 4

Cleaning effects of the PelA homologues (Glyco_hydro_114 glycosyl hydrolases) in model A detergent

| Swatch/Enzyme | Enzyme conc. (µg/ml) | Average L values | WP (ΔL) |
|---|---|---|---|
| wfk20A, no EPS | 0.0 | 88.1 | |
| Wfk20A, EPS, no enzyme | 2 | 82.2 | |
| Wfk20A, EPS, SEQ ID NO 43 | 2 | 91.1 | 8.9 |
| Wfk20A, EPS, SEQ ID NO 46 | 2 | 90.3 | 8.1 |
| Wfk20A, EPS, SEQ ID NO 49 | 2 | 91.4 | 9.2 |
| Wfk20A, EPS, SEQ ID NO 52 | 2 | 90.5 | 8.3 |
| Wfk20A, EPS, SEQ ID NO 55 | 2 | 90.6 | 8.4 |
| Wfk20A, EPS, SEQ ID NO 58 | 2 | 87.8 | 5.6 |
| Wfk20A, EPS, SEQ ID NO 64 | 2 | 86.8 | 4.6 |

All tested Glyco_hydro_114 glycosyl hydrolases showed Wash performance and capability to remove pel stains from textile.

Example 8 Cleaning in Liquid Model Detergent NI on Pel Swatches

A crude extract of the biofilm extracellular polymer Pel was prepared from *Pseudomonas aeruginosa* PA14 (DSM 19882) as mentioned above. Wash performance was determined as follows; 50 ul aliquots of the crude Pel extract were spotted on sterile textile swatches (WFK20A) and incubated for 15 min at ambient temperature. Control swatches without EPS were used as controls. The swatches (sterile or with the extract) were placed in 50 mL test tubes and 10 mL of wash liquor (15° dH water with 0.2 g/L iron(III) oxide nano-powder (544884; Sigma-Aldrich) with 3.33 g/L liquid model NI detergent) and the 10 µg/ml enzyme was added to each tube. Washes without enzyme were included as controls. The test tubes were placed in a Stuart rotator and incubated for 1 hour at 30° C. and 20 rpm. The wash liquor was then removed, and the swatches were rinsed twice with 15° dH water and dried on filter paper over night. The tristimulus light intensity (Y) values were measured using a Handheld Minolta CR-300, and are displayed in table 5. Wash performance, WP ($\Delta Y = Y_{(swatches\ washed\ with\ enzyme)} - Y_{(swatches\ washed\ without\ enzyme)}$) are also indicated.

TABLE 5

Cleaning effects of the PelA homologues (Glyco_hydro_114 glycosyl hydrolases) in model NI detergent

| Swatch | Enzyme | Enzyme concentration (µg/ml) | Average Y values | WP (ΔY) |
|---|---|---|---|---|
| Wfk20A, no EPS | No enzyme | 0 | 74.9 | |
| Wfk20A, Pel EPS swatch | No enzyme | 0 | 64.1 | |
| Wfk20A, Pel EPS swatch | SEQ ID NO 40 | 10 | 70.0 | 5.9 |
| Wfk20A, Pel EPS swatch | SEQ ID NO 61 | 10 | 72.2 | 8.1 |
| Wfk20A, Pel EPS swatch | SEQ ID NO 73 | 10 | 68.5 | 4.4 |
| Wfk20A, Pel EPS swatch | SEQ ID NO 76 | 10 | 73.3 | 9.2 |
| Wfk20A, Pel EPS swatch | SEQ ID NO 79 | 10 | 68.6 | 4.5 |
| Wfk20A, Pel EPS swatch | SEQ ID NO 82 | 10 | 76.1 | 12.0 |
| Wfk20A, Pel EPS swatch | SEQ ID NO 91 | 10 | 77.4 | 13.3 |
| Wfk20A, Pel EPS swatch | SEQ ID NO 67 | 10 | 72.4 | 8.2 |
| Wfk20A, Pel EPS swatch | SEQ ID NO 85 | 10 | 71.3 | 7.2 |
| Wfk20A, Pel EPS swatch | SEQ ID NO 94 | 10 | 66.9 | 2.8 |
| Wfk20A, Pel EPS swatch | SEQ ID NO 88 | 10 | 67.7 | 3.6 |
| Wfk20A, Pel EPS swatch | SEQ ID NO 70 | 10 | 75.1 | 11.0 |

Example 9 Effect of PelA Homologues (Glyco_hydro_114 Glycosyl Hydrolases) on *P. aeruginosa* Biofilm Two different clinical isolates of *P. aeruginosa* were for formation of medical biofilms in the example. One biofilm was produced by *P. aeruginosa* PA14 (DSM19882) and another one by *P. aeruginosa* PA01 (DSM22644). The bacteria were re-streaked on TSA plates and incubated for three days at 30° C. After three days of incubation, 8 mL of Tryptic Soy Broth (TSB) was inoculated with one colony of *P. aeruginosa* PA14 (DSM19882), and 8 mL of TSB was inoculated with *P. aeruginosa* PA01 (DSM22644). The inoculated TSB tubes were incubated overnight at 30° C., 200 rpm, and diluted in TSB to a specific optical density (OD). 150 µl of diluted overnight culture was added to each well in Thermo Scientific™ Nunc™ MicroWell™ 96-Well Microplates (sterile, non-treated). Two plates with *P. aeruginosa* PA14 (DSM19882) were prepared. One plate with *P. aeruginosa* PA01 (DSM22644) was prepared. The plates were incubated at 30° C. for 24 hours. After 24 hours of incubation, the microtiter plates containing biofilm were removed from the incubator and emptied for media using Vacusafe™ Vacuum Aspiration System (INTEGRA Biosciences). Each well was rinsed twice with 200 µl 0.9% NaCl solution. To each well, 200 µl of model detergent liquor with 20 µg/ml enzyme was added. Treatment without enzyme was included as controls. Each treatment was tested in quadruplicates. After addition of detergent liquor+/−enzyme, the microtiter plates were incubated static for 60 minutes at 30° C. After 60 minutes of incubation, the treatment liquor was removed using the vacuum system. Each well was rinsed twice with 200 µl 0.9% NaCl solution, and 200 µl of 0.095% crystal violet solution was added to each well. The plates were incubated for 15 minutes at ambient temperature. The crystal violet solution was removed using the vacuum system, and each well was rinsed twice with 200 µl 0.9% NaCl solution. 150 µl of 30% acetic acid was added to each well. The plates were incubated for 10 minutes at ambient temperature, where after the absorbance at 595 nm was measured using a spectrophotometer (SpectraMax M3, Molecular Devices). The plates were shaken for 10 seconds before absorbance measurements were performed.

The % remaining biofilm after enzymatic treatment was calculated as $$ABS_{595(biofilm\ treated\ with\ model\ detergent+enzyme)} / ABS_{595(biofilm\ treated\ with\ model\ detergent)} \times 100\%.$$

For *P. aeruginosa* PA14 (DSM19882) and average of two plates was calculated. The results are displayed in Table 6.

TABLE 6

% remaining biofilm after treatment with PelA homologues in model detergent

| | | % remaining biofilm | |
|---|---|---|---|
| Enzyme | Concentration (µg/mL) | PA14 (DSM19882) | PA01 (DSM22644) |
| No enzyme | 0 | 100.0 | 100.0 |
| SEQ ID NO 64 | 20 | 50.3 | 57.7 |
| SEQ ID NO 3 | 20 | 39.6 | 52.9 |
| SEQ ID NO 12 | 20 | 45.3 | 61.5 |
| SEQ ID NO 52 | 20 | 55.5 | 54.5 |
| SEQ ID NO 43 | 20 | 49.0 | 46.0 |

Example 10 Endoscope Cleaning in Liquid Model Detergent

Endoscope biofilms were established using *P. aeruginosa* PA14 (DSM19882): The strain was inoculated into 10 mL LB and incubated at 37° C. for 16 hours with shaking (200 rpm). After propagation, the culture was diluted (1:100) in LBNS and the bacterial suspension was added to 96-well microtiter plates (Thermo Scientific, cat #167008) containing sterile pieces (1 cm) of endoscope tubing (4.7 mm diameter, FluoroelastomerNiton®, USP Class VI, Endoscopy Development Company, LLC). Sterile medium was added to control wells. After 24 h at 26° C. (static incubation), the endoscope tubes were treated with a model cleaning solution (5 g/L Model detergent MC in 5° dH water hardness) containing no enzyme (control) or 20 µg/mL enzyme for 1 hour at 26° C. The endoscope pieces were subsequently rinsed with 5° dH water and stained with 0.095% crystal violet (SIGMA V5265) for 15 min. After additional rinses, the endoscope pieces were blotted on absorbent paper and the remaining dye was dissolved using 30% acetic acid. 200 µl aliquots of the suspensions were transferred to a 96-well microtiter plate and the absorbance was measured at 595 nm. The results are displayed in table 7 as percentages of remaining biofilm after enzymatic treatment as compared to the control (endoscope biofilm treated without enzyme).

TABLE 7

Endoscope cleaning properties in medical cleaning model detergent MC

| Enzyme | Enzyme dosage (μg/ml) | Remaining biofilm (% of untreated control) |
|---|---|---|
| No enzyme | 0 | 100.0 |
| SEQ ID NO 12 | 20 | 23.3 |
| SEQ ID NO 3 | 20 | 47.1 |
| SEQ ID NO 70 | 20 | 66.7 |

The results show that the polypeptides of the invention have endoscope cleaning properties i.e. disrupt and/or remove the biofilm or components of the biofilm tested when compared to samples comprising no enzyme.

---

The invention claimed is:

1. A cleaning composition comprising:
   (a) at least 0.001 ppm of a Glyco_hydro_114 glycosyl hydrolase having at least 95% sequence identity to the polypeptide of SEQ ID NO: 12 or SEQ ID NO: 46, which comprises the motif GX[FY][LYF]D (SEQ ID NO 34); and
   (b) a surfactant.

2. The cleaning composition of claim 1, further comprising one or more components selected from the group consisting of builders, bleach components, polymers, dispersing agents and additional enzymes.

3. The cleaning composition of claim 1, which is in the form of a bar, a homogenous tablet, a tablet having two or more layers, a pouch having one or more compartments, a regular or compact powder, a granule, a paste, a gel, or a regular, compact or concentrated liquid.

4. A method for laundering a textile, comprising:
   a) exposing the textile to a wash liquor comprising the cleaning composition of claim 1; and
   (b) completing at least one wash cycle.

5. The method of claim 4, further comprising rinsing the textile.

6. The cleaning composition of claim 1, wherein the Glyco_hydro_114 glycosyl hydrolase has at least 97% sequence identity to the polypeptide of SEQ ID NO: 12 or SEQ ID NO: 46.

7. The cleaning composition of claim 1, wherein the Glyco_hydro_114 glycosyl hydrolase has at least 99% sequence identity to the polypeptide of SEQ ID NO: 12 or SEQ ID NO: 46.

8. The cleaning composition of claim 1, wherein the Glyco_hydro_114 glycosyl hydrolase is the polypeptide of SEQ ID NO: 12 or SEQ ID NO: 46.

9. The cleaning composition of claim 1, wherein the Glyco_hydro_114 glycosyl hydrolase is the polypeptide of SEQ ID NO: 12.

* * * * *

SEQUENCE LISTING

<160> NUMBER OF SEQ ID NOS: 104

<210> SEQ ID NO 1
<211> LENGTH: 2811
<212> TYPE: DNA
<213> ORGANISM: Pseudomonas sp-62208
<220> FEATURE:
<221> NAME/KEY: CDS
<222> LOCATION: (1)..(2808)
<220> FEATURE:
<221> NAME/KEY: sig_peptide
<222> LOCATION: (1)..(96)
<220> FEATURE:
<221> NAME/KEY: mat_peptide
<222> LOCATION: (97)..(2808)

<400> SEQUENCE: 1

```
atg gaa atc gtt ttt cgc agg acg cgt gtc cgc tcg gtc gcc aag cga      48
Met Glu Ile Val Phe Arg Arg Thr Arg Val Arg Ser Val Ala Lys Arg
        -30                 -25                 -20 ctg tta gcc gct ctg gca ctg tgc gtg agc ggg ccc gcc gta caa gcc      96
Leu Leu Ala Ala Leu Ala Leu Cys Val Ser Gly Pro Ala Val Gln Ala
    -15                 -10                  -5                  -1 gct gca ctg act ccc ccc tcc agc gtg acc ttc tgg tat gcc gaa gag     144
Ala Ala Leu Thr Pro Pro Ser Ser Val Thr Phe Trp Tyr Ala Glu Glu
1                   5                  10                  15 ccg cca ctg gcc gaa ctg gct cag ttc gac tgg gcg gtg gta gag cct     192
Pro Pro Leu Ala Glu Leu Ala Gln Phe Asp Trp Ala Val Val Glu Pro
                20                  25                  30 ggg cac atg acc gcg ggc gat gtc acg acg ctt cgc aag ttg ggc agc     240
Gly His Met Thr Ala Gly Asp Val Thr Thr Leu Arg Lys Leu Gly Ser
            35                  40                  45 gag ccc ttc gcg tac ctg tcg gtg ggt gag ttc gac ggc aac aag gcg     288
Glu Pro Phe Ala Tyr Leu Ser Val Gly Glu Phe Asp Gly Asn Lys Ala
        50                  55                  60 gac atc acc aag gcc ggt ctc acc gcc gcg gtt tcc ccg gtg cgc aat     336
Asp Ile Thr Lys Ala Gly Leu Thr Ala Ala Val Ser Pro Val Arg Asn
65                  70                  75                  80 gac tcg tgg aac agc cag gtc atg gac ctc acc act cag gcc tgg cgt     384
Asp Ser Trp Asn Ser Gln Val Met Asp Leu Thr Thr Gln Ala Trp Arg
                85                  90                  95 gaa tac ttg ctt ggc cgt gcc aag cag ctg cag gcc cag ggt tat gcc     432
Glu Tyr Leu Leu Gly Arg Ala Lys Gln Leu Gln Ala Gln Gly Tyr Ala
            100                 105                 110 ggc ctg ttc ctc gac acc ctc gac agt ttt caa ctg ttg ccg gaa gcc     480
Gly Leu Phe Leu Asp Thr Leu Asp Ser Phe Gln Leu Leu Pro Glu Ala
        115                 120                 125
```

-continued

| | | |
|---|---|---|
| tct cgg gaa gcg caa cgc aag gcg ctc gcc agt ttg ctg cgt gaa ctg<br>Ser Arg Glu Ala Gln Arg Lys Ala Leu Ala Ser Leu Leu Arg Glu Leu<br>130                        135                        140 | | 528 |
| cac aag cgt cag cca ggc ttg aaa ctg ttc ttc aac cgc ggt ttt gaa<br>His Lys Arg Gln Pro Gly Leu Lys Leu Phe Phe Asn Arg Gly Phe Glu<br>145                        150                        155                        160 | | 576 |
| gtg ctg ccc gaa ctt gat ggc gtg gca tca gcc gtc gcg ttc gag tcg<br>Val Leu Pro Glu Leu Asp Gly Val Ala Ser Ala Val Ala Phe Glu Ser<br>                        165                        170                        175 | | 624 |
| ctg tac gcc ggt tgg gat gca gcc gcc aag cgc tat cgc ccg gtg ccg<br>Leu Tyr Ala Gly Trp Asp Ala Ala Ala Lys Arg Tyr Arg Pro Val Pro<br>                    180                        185                        190 | | 672 |
| gaa gcg gat cgc cag tgg ctg ttg ggc gaa ctt gca ccc ttg cgt gcc<br>Glu Ala Asp Arg Gln Trp Leu Leu Gly Glu Leu Ala Pro Leu Arg Ala<br>              195                        200                        205 | | 720 |
| aag ggc att ccg ttg gtg gca atc gac tat ttg cca ccg gag cgt cgt<br>Lys Gly Ile Pro Leu Val Ala Ile Asp Tyr Leu Pro Pro Glu Arg Arg<br>210                        215                        220 | | 768 |
| gaa gaa gct cgc aag ctg gcc aag cgt ctg cgc gat gaa ggc tac att<br>Glu Glu Ala Arg Lys Leu Ala Lys Arg Leu Arg Asp Glu Gly Tyr Ile<br>225                        230                        235                        240 | | 816 |
| ccg ttc atc agc acc cct gag ttg aac tcg atg ggc atc agc aac gtc<br>Pro Phe Ile Ser Thr Pro Glu Leu Asn Ser Met Gly Ile Ser Asn Val<br>                        245                        250                        255 | | 864 |
| gag gtc cag cca cgc cgc gtc gct ttg gtc tac gac cct cgg gaa ggt<br>Glu Val Gln Pro Arg Arg Val Ala Leu Val Tyr Asp Pro Arg Glu Gly<br>                    260                        265                        270 | | 912 |
| gac ctg acg gtg aac gcc ggc cat acc atg ttg ggt ggc ctg ctc gaa<br>Asp Leu Thr Val Asn Ala Gly His Thr Met Leu Gly Gly Leu Leu Glu<br>              275                        280                        285 | | 960 |
| tac ctc ggt tac cgg gtc gat tac ctg gct gtc gac agc ctg ccg gaa<br>Tyr Leu Gly Tyr Arg Val Asp Tyr Leu Ala Val Asp Ser Leu Pro Glu<br>290                        295                        300 | | 1008 |
| cat cgt ttc agc ggc ttg tac gcc ggc atc att acc tgg atg gcc agc<br>His Arg Phe Ser Gly Leu Tyr Ala Gly Ile Ile Thr Trp Met Ala Ser<br>305                        310                        315                        320 | | 1056 |
| ggc ccg ccg cag gac ggt gcc acg ttc aac cgt tgg ctc ggc aag cgt<br>Gly Pro Pro Gln Asp Gly Ala Thr Phe Asn Arg Trp Leu Gly Lys Arg<br>                    325                        330                        335 | | 1104 |
| ctc gac gag caa gtg ccg gtg gtg ttt ttc gcc ggc ctg ccc act gag<br>Leu Asp Glu Gln Val Pro Val Val Phe Phe Ala Gly Leu Pro Thr Glu<br>                    340                        345                        350 | | 1152 |
| gac aag gtg ttg ctc aaa cgc ctg gga ctc aat ctc atg gcg ccc gcc<br>Asp Lys Val Leu Leu Lys Arg Leu Gly Leu Asn Leu Met Ala Pro Ala<br>              355                        360                        365 | | 1200 |
| ggt acc cag cca ctg acc atc agc tat cag gac aag gct ctg atc ggt<br>Gly Thr Gln Pro Leu Thr Ile Ser Tyr Gln Asp Lys Ala Leu Ile Gly<br>370                        375                        380 | | 1248 |
| gca ttc gaa gca ccg gtg cag ccg cgg tcc cgc gaa ctc acc gct gta<br>Ala Phe Glu Ala Pro Val Gln Pro Arg Ser Arg Glu Leu Thr Ala Val<br>385                        390                        395                        400 | | 1296 |
| tcc ttg ctt ccc caa ggg cct aaa gcc gct ttg ctg ttg acc ggc aag<br>Ser Leu Leu Pro Gln Gly Pro Lys Ala Ala Leu Leu Leu Thr Gly Lys<br>                    405                        410                        415 | | 1344 |
| gac ggc cag acc ttc gcc ccg gta gcc act gcc aag tgg ggt ggg ctg<br>Asp Gly Gln Thr Phe Ala Pro Val Ala Thr Ala Lys Trp Gly Gly Leu<br>              420                        425                        430 | | 1392 |
| gca ctg gca ccc tat gtt ctt gaa acc aac aat gag cgc agc cgc tgg<br>Ala Leu Ala Pro Tyr Val Leu Glu Thr Asn Asn Glu Arg Ser Arg Trp<br>              435                        440                        445 | | 1440 |

-continued

| | |
|---|---|
| atc ctc gac ccg ttc gct ttc ctg cag gcc agc ctg caa ttg cca gcg<br>Ile Leu Asp Pro Phe Ala Phe Leu Gln Ala Ser Leu Gln Leu Pro Ala<br>450                             455                     460 | 1488 |
| cag cca cga ccg gac acc acc acg gaa aac ggc cgc cgg atc gcc acg<br>Gln Pro Arg Pro Asp Thr Thr Thr Glu Asn Gly Arg Arg Ile Ala Thr<br>465                      470                      475                    480 | 1536 |
| gtg cac atc gac ggc gac ggt ttt cca tcc cgc gcc gaa gtg cgc ggt<br>Val His Ile Asp Gly Asp Gly Phe Pro Ser Arg Ala Glu Val Arg Gly<br>                        485                           490                      495 | 1584 |
| tcg cct tat gcc ggc aag caa gtg ctg aat gac ttc att cag ccc aac<br>Ser Pro Tyr Ala Gly Lys Gln Val Leu Asn Asp Phe Ile Gln Pro Asn<br>                 500                           505                      510 | 1632 |
| ccg ttc ctg act tcc gtg tcg atc atc gag ggt gag att tct ccc cgc<br>Pro Phe Leu Thr Ser Val Ser Ile Ile Glu Gly Glu Ile Ser Pro Arg<br>               515                         520                       525 | 1680 |
| ggg atg tac ccg cat ctg gcg cgc gaa ctg gag ccg att gct cgc gag<br>Gly Met Tyr Pro His Leu Ala Arg Glu Leu Glu Pro Ile Ala Arg Glu<br>530                             535                     540 | 1728 |
| ttg ttt gcc aac ccc aag gtc gaa gtc gcc acc cac acc ttc agc cat<br>Leu Phe Ala Asn Pro Lys Val Glu Val Ala Thr His Thr Phe Ser His<br>545                           550                      555                    560 | 1776 |
| ccg ttc tac atg cag ccg gaa ctg gca gag aaa gac gaa gat ttc agt<br>Pro Phe Tyr Met Gln Pro Glu Leu Ala Glu Lys Asp Glu Asp Phe Ser<br>               565                         570                      575 | 1824 |
| gcc gaa tac ggt ttg aaa atg gcc atc ccg ggc tac gac aaa atc gat<br>Ala Glu Tyr Gly Leu Lys Met Ala Ile Pro Gly Tyr Asp Lys Ile Asp<br>                 580                         585                     590 | 1872 |
| ttc aag cgt gaa atc ttt ggt tca cgc gac tac atc aac cag caa ctg<br>Phe Lys Arg Glu Ile Phe Gly Ser Arg Asp Tyr Ile Asn Gln Gln Leu<br>           595                      600                      605 | 1920 |
| acc acc ccg gaa aaa ccg gtc aag atg gtc ttc tgg cca ggg gat gcg<br>Thr Thr Pro Glu Lys Pro Val Lys Met Val Phe Trp Pro Gly Asp Ala<br>610                           615                      620 | 1968 |
| ctg ccg tcg gcc gcg acc atc aag ctg gct tac gac gcg ggc ctg aaa<br>Leu Pro Ser Ala Ala Thr Ile Lys Leu Ala Tyr Asp Ala Gly Leu Lys<br>625                           630                      635                    640 | 2016 |
| aac gtc aac ggt gcc tcc acc atg ctc acc aag gcc cgg cca tca ctg<br>Asn Val Asn Gly Ala Ser Thr Met Leu Thr Lys Ala Arg Pro Ser Leu<br>                 645                         650                      655 | 2064 |
| acc ggc ctc aat ccg ctg ctg cgg ccc acc gaa ggc ggc ctg caa tac<br>Thr Gly Leu Asn Pro Leu Leu Arg Pro Thr Glu Gly Gly Leu Gln Tyr<br>                     660                         665                      670 | 2112 |
| tac gcc ccg gtc atc aac gag aac gtg tac acc aat ctg tgg aaa gga<br>Tyr Ala Pro Val Ile Asn Glu Asn Val Tyr Thr Asn Leu Trp Lys Gly<br>             675                       680                      685 | 2160 |
| ccg tac tac ggc ttt cgc gat gtc atc gat acc tat gag ctg act gac<br>Pro Tyr Tyr Gly Phe Arg Asp Val Ile Asp Thr Tyr Glu Leu Thr Asp<br>690                             695                       700 | 2208 |
| agc cca cgt cgt ctg cgc ggc atc cac ctc tac tac cac ttc tat tcg<br>Ser Pro Arg Arg Leu Arg Gly Ile His Leu Tyr Tyr His Phe Tyr Ser<br>705                           710                      715                    720 | 2256 |
| gcg acc aag cag gcc tcc atc aag gcc atg ggc gag atc tac ggg tac<br>Ala Thr Lys Gln Ala Ser Ile Lys Ala Met Gly Glu Ile Tyr Gly Tyr<br>                 725                         730                     735 | 2304 |
| atg cgc gag cag cat cct atg tcg ctg tgg atg agc gat tac ctg gat<br>Met Arg Glu Gln His Pro Met Ser Leu Trp Met Ser Asp Tyr Leu Asp<br>           740                      745                      750 | 2352 |
| cgc ctg cat ggc ctg tat cag gcc agc ctg gca cgt acc gct gac ggc<br>Arg Leu His Gly Leu Tyr Gln Ala Ser Leu Ala Arg Thr Ala Asp Gly | 2400 |

-continued

```
                755                 760                 765
gcc tgg cag atc cgc ggc atg gac gcg ctg cgc acc gtg cgc ctg gac    2448
Ala Trp Gln Ile Arg Gly Met Asp Ala Leu Arg Thr Val Arg Leu Asp
770                 775                 780 ccg caa atg ggc tgg ccg gat ctg ttg cgt tcc caa ggc atc gcc ggc    2496
Pro Gln Met Gly Trp Pro Asp Leu Leu Arg Ser Gln Gly Ile Ala Gly
785                 790                 795                 800 gtt cgt gac ctg ccg caa ggg cgt tac gtg cac ctg agc agc gat cgc    2544
Val Arg Asp Leu Pro Gln Gly Arg Tyr Val His Leu Ser Ser Asp Arg
                805                 810                 815 gca ttg ctg gtg ctg cgt ccc gat cgg gat gac aga ccg gcg ctg gag    2592
Ala Leu Leu Val Leu Arg Pro Asp Arg Asp Asp Arg Pro Ala Leu Glu
            820                 825                 830 gaa gcc aac gtg ccg ttg acg gac tgg cgt tat ctg gat gat cga cgc    2640
Glu Ala Asn Val Pro Leu Thr Asp Trp Arg Tyr Leu Asp Asp Arg Arg
        835                 840                 845 gtg agt ttc gcc ttc gcc ggg cag ttc gac gtg acc ttc tcg gtc cgc    2688
Val Ser Phe Ala Phe Ala Gly Gln Phe Asp Val Thr Phe Ser Val Arg
    850                 855                 860 tcg gcg agt gcc tgc cgg gtc gaa gtg gat gga cag cgt ttt gca ggc    2736
Ser Ala Ser Ala Cys Arg Val Glu Val Asp Gly Gln Arg Phe Ala Gly
865                 870                 875                 880 aag tcg tct gcg ggc ctt tgg act ttt caa tta cca atg aag cag gtg    2784
Lys Ser Ser Ala Gly Leu Trp Thr Phe Gln Leu Pro Met Lys Gln Val
                885                 890                 895 agt aat ggt cag ctc ctc tgc aac taa                                2811
Ser Asn Gly Gln Leu Leu Cys Asn
            900
```

<210> SEQ ID NO 2
<211> LENGTH: 936
<212> TYPE: PRT
<213> ORGANISM: Pseudomonas sp-62208

<400> SEQUENCE: 2

```
Met Glu Ile Val Phe Arg Arg Thr Arg Val Arg Ser Val Ala Lys Arg
            -30                 -25                 -20

Leu Leu Ala Ala Leu Ala Leu Cys Val Ser Gly Pro Ala Val Gln Ala
    -15                 -10                 -5                  -1

Ala Ala Leu Thr Pro Pro Ser Ser Val Thr Phe Trp Tyr Ala Glu Glu
1               5                   10                  15

Pro Pro Leu Ala Glu Leu Ala Gln Phe Asp Trp Ala Val Val Glu Pro
                20                  25                  30

Gly His Met Thr Ala Gly Asp Val Thr Thr Leu Arg Lys Leu Gly Ser
            35                  40                  45

Glu Pro Phe Ala Tyr Leu Ser Val Gly Glu Phe Asp Gly Asn Lys Ala
        50                  55                  60

Asp Ile Thr Lys Ala Gly Leu Thr Ala Ala Val Ser Pro Val Arg Asn
65                  70                  75                  80

Asp Ser Trp Asn Ser Gln Val Met Asp Leu Thr Thr Gln Ala Trp Arg
                85                  90                  95

Glu Tyr Leu Leu Gly Arg Ala Lys Gln Leu Gln Ala Gln Gly Tyr Ala
            100                 105                 110

Gly Leu Phe Leu Asp Thr Leu Asp Ser Phe Gln Leu Leu Pro Glu Ala
        115                 120                 125

Ser Arg Glu Ala Gln Arg Lys Ala Leu Ala Ser Leu Leu Arg Glu Leu
    130                 135                 140
```

```
His Lys Arg Gln Pro Gly Leu Lys Leu Phe Phe Asn Arg Gly Phe Glu
145                 150                 155                 160

Val Leu Pro Glu Leu Asp Gly Val Ala Ser Ala Val Ala Phe Glu Ser
            165                 170                 175

Leu Tyr Ala Gly Trp Asp Ala Ala Lys Arg Tyr Arg Pro Val Pro
        180                 185                 190

Glu Ala Asp Arg Gln Trp Leu Leu Gly Glu Leu Ala Pro Leu Arg Ala
    195                 200                 205

Lys Gly Ile Pro Leu Val Ala Ile Asp Tyr Leu Pro Pro Glu Arg Arg
210                 215                 220

Glu Glu Ala Arg Lys Leu Ala Lys Arg Leu Arg Asp Glu Gly Tyr Ile
225                 230                 235                 240

Pro Phe Ile Ser Thr Pro Glu Leu Asn Ser Met Gly Ile Ser Asn Val
            245                 250                 255

Glu Val Gln Pro Arg Arg Val Ala Leu Val Tyr Asp Pro Arg Glu Gly
            260                 265                 270

Asp Leu Thr Val Asn Ala Gly His Thr Met Leu Gly Gly Leu Leu Glu
        275                 280                 285

Tyr Leu Gly Tyr Arg Val Asp Tyr Leu Ala Val Asp Ser Leu Pro Glu
290                 295                 300

His Arg Phe Ser Gly Leu Tyr Ala Gly Ile Ile Thr Trp Met Ala Ser
305                 310                 315                 320

Gly Pro Pro Gln Asp Gly Ala Thr Phe Asn Arg Trp Leu Gly Lys Arg
            325                 330                 335

Leu Asp Glu Gln Val Pro Val Val Phe Phe Ala Gly Leu Pro Thr Glu
            340                 345                 350

Asp Lys Val Leu Leu Lys Arg Leu Gly Leu Asn Leu Met Ala Pro Ala
        355                 360                 365

Gly Thr Gln Pro Leu Thr Ile Ser Tyr Gln Asp Lys Ala Leu Ile Gly
        370                 375                 380

Ala Phe Glu Ala Pro Val Gln Pro Arg Ser Arg Glu Leu Thr Ala Val
385                 390                 395                 400

Ser Leu Leu Pro Gln Gly Pro Lys Ala Ala Leu Leu Leu Thr Gly Lys
            405                 410                 415

Asp Gly Gln Thr Phe Ala Pro Val Ala Thr Ala Lys Trp Gly Gly Leu
            420                 425                 430

Ala Leu Ala Pro Tyr Val Leu Glu Thr Asn Asn Glu Arg Ser Arg Trp
        435                 440                 445

Ile Leu Asp Pro Phe Ala Phe Leu Gln Ala Ser Leu Gln Leu Pro Ala
        450                 455                 460

Gln Pro Arg Pro Asp Thr Thr Thr Glu Asn Gly Arg Arg Ile Ala Thr
465                 470                 475                 480

Val His Ile Asp Gly Asp Gly Phe Pro Ser Arg Ala Glu Val Arg Gly
            485                 490                 495

Ser Pro Tyr Ala Gly Lys Gln Val Leu Asn Asp Phe Ile Gln Pro Asn
            500                 505                 510

Pro Phe Leu Thr Ser Val Ser Ile Ile Glu Gly Glu Ile Ser Pro Arg
        515                 520                 525

Gly Met Tyr Pro His Leu Ala Arg Glu Leu Glu Pro Ile Ala Arg Glu
        530                 535                 540

Leu Phe Ala Asn Pro Lys Val Glu Val Ala Thr His Thr Phe Ser His
545                 550                 555                 560

Pro Phe Tyr Met Gln Pro Glu Leu Ala Glu Lys Asp Glu Asp Phe Ser
```

```
                565                 570                 575
Ala Glu Tyr Gly Leu Lys Met Ala Ile Pro Gly Tyr Asp Lys Ile Asp
            580                 585                 590

Phe Lys Arg Glu Ile Phe Gly Ser Arg Asp Tyr Ile Asn Gln Gln Leu
            595                 600                 605

Thr Thr Pro Glu Lys Pro Val Lys Met Val Phe Trp Pro Gly Asp Ala
610                 615                 620

Leu Pro Ser Ala Ala Thr Ile Lys Leu Ala Tyr Asp Ala Gly Leu Lys
625                 630                 635                 640

Asn Val Asn Gly Ala Ser Thr Met Leu Thr Lys Ala Arg Pro Ser Leu
            645                 650                 655

Thr Gly Leu Asn Pro Leu Leu Arg Pro Thr Glu Gly Gly Leu Gln Tyr
            660                 665                 670

Tyr Ala Pro Val Ile Asn Glu Asn Val Tyr Thr Asn Leu Trp Lys Gly
            675                 680                 685

Pro Tyr Tyr Gly Phe Arg Asp Val Ile Asp Thr Tyr Glu Leu Thr Asp
            690                 695                 700

Ser Pro Arg Arg Leu Arg Gly Ile His Leu Tyr Tyr His Phe Tyr Ser
705                 710                 715                 720

Ala Thr Lys Gln Ala Ser Ile Lys Ala Met Gly Glu Ile Tyr Gly Tyr
            725                 730                 735

Met Arg Glu Gln His Pro Met Ser Leu Trp Met Ser Asp Tyr Leu Asp
            740                 745                 750

Arg Leu His Gly Leu Tyr Gln Ala Ser Leu Ala Arg Thr Ala Asp Gly
            755                 760                 765

Ala Trp Gln Ile Arg Gly Met Asp Ala Leu Arg Thr Val Arg Leu Asp
770                 775                 780

Pro Gln Met Gly Trp Pro Asp Leu Leu Arg Ser Gln Gly Ile Ala Gly
785                 790                 795                 800

Val Arg Asp Leu Pro Gln Gly Arg Tyr Val His Leu Ser Ser Asp Arg
            805                 810                 815

Ala Leu Leu Val Leu Arg Pro Asp Arg Asp Arg Pro Ala Leu Glu
            820                 825                 830

Glu Ala Asn Val Pro Leu Thr Asp Trp Arg Tyr Leu Asp Asp Arg Arg
            835                 840                 845

Val Ser Phe Ala Phe Ala Gly Gln Phe Asp Val Thr Phe Ser Val Arg
850                 855                 860

Ser Ala Ser Ala Cys Arg Val Glu Val Asp Gly Gln Arg Phe Ala Gly
865                 870                 875                 880

Lys Ser Ser Ala Gly Leu Trp Thr Phe Gln Leu Pro Met Lys Gln Val
            885                 890                 895

Ser Asn Gly Gln Leu Leu Cys Asn
            900

<210> SEQ ID NO 3
<211> LENGTH: 904
<212> TYPE: PRT
<213> ORGANISM: Pseudomonas sp-62208

<400> SEQUENCE: 3

Ala Ala Leu Thr Pro Pro Ser Ser Val Thr Phe Trp Tyr Ala Glu Glu
1               5                   10                  15

Pro Pro Leu Ala Glu Leu Ala Gln Phe Asp Trp Ala Val Val Glu Pro
            20                  25                  30
```

-continued

Gly His Met Thr Ala Gly Asp Val Thr Thr Leu Arg Lys Leu Gly Ser
         35                  40                  45

Glu Pro Phe Ala Tyr Leu Ser Val Gly Glu Phe Asp Gly Asn Lys Ala
 50                  55                  60

Asp Ile Thr Lys Ala Gly Leu Thr Ala Ala Val Ser Pro Val Arg Asn
 65                  70                  75                  80

Asp Ser Trp Asn Ser Gln Val Met Asp Leu Thr Thr Gln Ala Trp Arg
                 85                  90                  95

Glu Tyr Leu Leu Gly Arg Ala Lys Gln Leu Gln Ala Gln Gly Tyr Ala
                100                 105                 110

Gly Leu Phe Leu Asp Thr Leu Asp Ser Phe Gln Leu Leu Pro Glu Ala
            115                 120                 125

Ser Arg Glu Ala Gln Arg Lys Ala Leu Ala Ser Leu Leu Arg Glu Leu
130                 135                 140

His Lys Arg Gln Pro Gly Leu Lys Leu Phe Phe Asn Arg Gly Phe Glu
145                 150                 155                 160

Val Leu Pro Glu Leu Asp Gly Val Ala Ser Ala Val Ala Phe Glu Ser
                165                 170                 175

Leu Tyr Ala Gly Trp Asp Ala Ala Ala Lys Arg Tyr Arg Pro Val Pro
            180                 185                 190

Glu Ala Asp Arg Gln Trp Leu Leu Gly Glu Leu Ala Pro Leu Arg Ala
        195                 200                 205

Lys Gly Ile Pro Leu Val Ala Ile Asp Tyr Leu Pro Pro Glu Arg Arg
210                 215                 220

Glu Glu Ala Arg Lys Leu Ala Lys Arg Leu Arg Asp Glu Gly Tyr Ile
225                 230                 235                 240

Pro Phe Ile Ser Thr Pro Glu Leu Asn Ser Met Gly Ile Ser Asn Val
                245                 250                 255

Glu Val Gln Pro Arg Arg Val Ala Leu Val Tyr Asp Pro Arg Glu Gly
            260                 265                 270

Asp Leu Thr Val Asn Ala Gly His Thr Met Leu Gly Gly Leu Leu Glu
        275                 280                 285

Tyr Leu Gly Tyr Arg Val Asp Tyr Leu Ala Val Asp Ser Leu Pro Glu
290                 295                 300

His Arg Phe Ser Gly Leu Tyr Ala Gly Ile Ile Thr Trp Met Ala Ser
305                 310                 315                 320

Gly Pro Pro Gln Asp Gly Ala Thr Phe Asn Arg Trp Leu Gly Lys Arg
                325                 330                 335

Leu Asp Glu Gln Val Pro Val Phe Phe Ala Gly Leu Pro Thr Glu
            340                 345                 350

Asp Lys Val Leu Leu Lys Arg Leu Gly Leu Asn Leu Met Ala Pro Ala
        355                 360                 365

Gly Thr Gln Pro Leu Thr Ile Ser Tyr Gln Asp Lys Ala Leu Ile Gly
370                 375                 380

Ala Phe Glu Ala Pro Val Gln Pro Arg Ser Arg Glu Leu Thr Ala Val
385                 390                 395                 400

Ser Leu Leu Pro Gln Gly Pro Lys Ala Ala Leu Leu Thr Gly Lys
                405                 410                 415

Asp Gly Gln Thr Phe Ala Pro Val Ala Thr Ala Lys Trp Gly Gly Leu
            420                 425                 430

Ala Leu Ala Pro Tyr Val Leu Glu Thr Asn Asn Glu Arg Ser Arg Trp
        435                 440                 445

Ile Leu Asp Pro Phe Ala Phe Leu Gln Ala Ser Leu Gln Leu Pro Ala

```
            450                 455                 460
Gln Pro Arg Pro Asp Thr Thr Thr Glu Asn Gly Arg Arg Ile Ala Thr
465                 470                 475                 480

Val His Ile Asp Gly Asp Gly Phe Pro Ser Arg Ala Glu Val Arg Gly
                485                 490                 495

Ser Pro Tyr Ala Gly Lys Gln Val Leu Asn Asp Phe Ile Gln Pro Asn
                500                 505                 510

Pro Phe Leu Thr Ser Val Ser Ile Ile Glu Gly Glu Ile Ser Pro Arg
                515                 520                 525

Gly Met Tyr Pro His Leu Ala Arg Glu Leu Glu Pro Ile Ala Arg Glu
                530                 535                 540

Leu Phe Ala Asn Pro Lys Val Glu Val Ala Thr His Thr Phe Ser His
545                 550                 555                 560

Pro Phe Tyr Met Gln Pro Glu Leu Ala Glu Lys Asp Glu Asp Phe Ser
                565                 570                 575

Ala Glu Tyr Gly Leu Lys Met Ala Ile Pro Gly Tyr Asp Lys Ile Asp
                580                 585                 590

Phe Lys Arg Glu Ile Phe Gly Ser Arg Asp Tyr Ile Asn Gln Gln Leu
                595                 600                 605

Thr Thr Pro Glu Lys Pro Val Lys Met Val Phe Trp Pro Gly Asp Ala
                610                 615                 620

Leu Pro Ser Ala Ala Thr Ile Lys Leu Ala Tyr Asp Ala Gly Leu Lys
625                 630                 635                 640

Asn Val Asn Gly Ala Ser Thr Met Leu Thr Lys Ala Arg Pro Ser Leu
                645                 650                 655

Thr Gly Leu Asn Pro Leu Leu Arg Pro Thr Glu Gly Gly Leu Gln Tyr
                660                 665                 670

Tyr Ala Pro Val Ile Asn Glu Asn Val Tyr Thr Asn Leu Trp Lys Gly
                675                 680                 685

Pro Tyr Tyr Gly Phe Arg Asp Val Ile Asp Thr Tyr Glu Leu Thr Asp
                690                 695                 700

Ser Pro Arg Arg Leu Arg Gly Ile His Leu Tyr Tyr His Phe Tyr Ser
705                 710                 715                 720

Ala Thr Lys Gln Ala Ser Ile Lys Ala Met Gly Glu Ile Tyr Gly Tyr
                725                 730                 735

Met Arg Glu Gln His Pro Met Ser Leu Trp Met Ser Tyr Leu Asp
                740                 745                 750

Arg Leu His Gly Leu Tyr Gln Ala Ser Leu Ala Arg Thr Ala Asp Gly
                755                 760                 765

Ala Trp Gln Ile Arg Gly Met Asp Ala Leu Arg Thr Val Arg Leu Asp
770                 775                 780

Pro Gln Met Gly Trp Pro Asp Leu Leu Arg Ser Gln Gly Ile Ala Gly
785                 790                 795                 800

Val Arg Asp Leu Pro Gln Gly Arg Tyr Val His Leu Ser Ser Asp Arg
                805                 810                 815

Ala Leu Leu Val Leu Arg Pro Asp Arg Asp Arg Pro Ala Leu Glu
                820                 825                 830

Glu Ala Asn Val Pro Leu Thr Asp Trp Arg Tyr Leu Asp Asp Arg Arg
                835                 840                 845

Val Ser Phe Ala Phe Ala Gly Gln Phe Asp Val Thr Phe Ser Val Arg
                850                 855                 860

Ser Ala Ser Ala Cys Arg Val Glu Val Asp Gly Gln Arg Phe Ala Gly
865                 870                 875                 880
```

-continued

```
Lys Ser Ser Ala Gly Leu Trp Thr Phe Gln Leu Pro Met Lys Gln Val
                885                 890                 895
Ser Asn Gly Gln Leu Leu Cys Asn
            900

<210> SEQ ID NO 4
<211> LENGTH: 909
<212> TYPE: DNA
<213> ORGANISM: Environmental bacterial community A
<220> FEATURE:
<221> NAME/KEY: CDS
<222> LOCATION: (1)..(906)
<220> FEATURE:
<221> NAME/KEY: sig_peptide
<222> LOCATION: (1)..(63)
<220> FEATURE:
<221> NAME/KEY: mat_peptide
<222> LOCATION: (64)..(906)

<400> SEQUENCE: 4 atg cgc act cat ctc atc ggt ctt gcc gcg atc atg gca gct ttt ccg        48
Met Arg Thr His Leu Ile Gly Leu Ala Ala Ile Met Ala Ala Phe Pro
    -20                 -15                 -10 gtc tgg acc caa gcg acg cca ggc atg ggc aag ggc atc ttg tcc aat        96
Val Trp Thr Gln Ala Thr Pro Gly Met Gly Lys Gly Ile Leu Ser Asn
 -5              -1  1               5                  10 gca aag tcc tgg gtc tat cag ctc cag cac atc gac ctg ccg acc ttg       144
Ala Lys Ser Trp Val Tyr Gln Leu Gln His Ile Asp Leu Pro Thr Leu
                15                  20                  25 ggg acc acc act gcg gac ctg gtt gta atc gac gcg tct caa gac ggc       192
Gly Thr Thr Thr Ala Asp Leu Val Val Ile Asp Ala Ser Gln Asp Gly
             30                  35                  40 tcg gtc gaa ggc tca ttt acg ccg gct gat att gcg gcg ctc aag acc       240
Ser Val Glu Gly Ser Phe Thr Pro Ala Asp Ile Ala Ala Leu Lys Thr
         45                  50                  55 aag ccc gat ggg tcg cag cga gtc gtt ctg gct tat ttt tcc atc ggt       288
Lys Pro Asp Gly Ser Gln Arg Val Val Leu Ala Tyr Phe Ser Ile Gly
 60                  65                  70                  75 gaa gct gag gac tat cgg ttc tat tgg gac gac gaa tgg tac gat cag       336
Glu Ala Glu Asp Tyr Arg Phe Tyr Trp Asp Asp Glu Trp Tyr Asp Gln
                 80                  85                  90 gcg ccc gat tgg ctt cat gag gaa aac agt gac tgg gcc ggc aac tac       384
Ala Pro Asp Trp Leu His Glu Glu Asn Ser Asp Trp Ala Gly Asn Tyr
             95                 100                 105 ccg gtc aag ttc tgg cac cct gac tgg cag gca att ctg ttc gga tca       432
Pro Val Lys Phe Trp His Pro Asp Trp Gln Ala Ile Leu Phe Gly Ser
        110                 115                 120 ccc gat tgc tat ctc gac cgg atc atc gcc gct gga ttt gac gga gtc       480
Pro Asp Cys Tyr Leu Asp Arg Ile Ile Ala Ala Gly Phe Asp Gly Val
    125                 130                 135 tat ctc gat cgt gtc gac gct ttc gaa att gat gat ccg gct ctg aca       528
Tyr Leu Asp Arg Val Asp Ala Phe Glu Ile Asp Asp Pro Ala Leu Thr
140                 145                 150                 155 cga ccg cag cgc gcg gcg cac atg atc gcg ctg gtt cgc tcg ctt gca       576
Arg Pro Gln Arg Ala Ala His Met Ile Ala Leu Val Arg Ser Leu Ala
                160                 165                 170 gct tac gcc cgg gca cgg acg cct agt ttt gtc gtc gtc gct cag aat       624
Ala Tyr Ala Arg Ala Arg Thr Pro Ser Phe Val Val Val Ala Gln Asn
            175                 180                 185 ggg gaa gaa ctg ctg gcc gat ggg tcc tac cgg cac acc gtt gat gga       672
Gly Glu Glu Leu Leu Ala Asp Gly Ser Tyr Arg His Thr Val Asp Gly
        190                 195                 200
```

```
gta ggc aag gag gat ctc ctc tat ggc ctc gag tcc gac ggc aag cgc    720
Val Gly Lys Glu Asp Leu Leu Tyr Gly Leu Glu Ser Asp Gly Lys Arg
    205             210             215 aat gcc aac ggc gat att cgc gtc agt ctg gac tac ctc agg cgc cta    768
Asn Ala Asn Gly Asp Ile Arg Val Ser Leu Asp Tyr Leu Arg Arg Leu
220             225             230             235 gct gaa gca gga aaa ccg gtc ttt ctc gtc gaa tac ctg act gag cca    816
Ala Glu Ala Gly Lys Pro Val Phe Leu Val Glu Tyr Leu Thr Glu Pro
                240             245             250 cag aca atc gcc cag gcc cat gcg gat gca gaa acc ctc gga atg ccg    864
Gln Thr Ile Ala Gln Ala His Ala Asp Ala Glu Thr Leu Gly Met Pro
            255             260             265 att ttc ata acc gat cga gat ctc gac aat gct tac tct cgc tga        909
Ile Phe Ile Thr Asp Arg Asp Leu Asp Asn Ala Tyr Ser Arg
        270             275             280
```

<210> SEQ ID NO 5
<211> LENGTH: 302
<212> TYPE: PRT
<213> ORGANISM: Environmental bacterial community A

<400> SEQUENCE: 5

```
Met Arg Thr His Leu Ile Gly Leu Ala Ala Ile Met Ala Ala Phe Pro
    -20             -15             -10

Val Trp Thr Gln Ala Thr Pro Gly Met Gly Lys Gly Ile Leu Ser Asn
-5           -1  1             5                      10

Ala Lys Ser Trp Val Tyr Gln Leu Gln His Ile Asp Leu Pro Thr Leu
            15              20              25

Gly Thr Thr Thr Ala Asp Leu Val Val Ile Asp Ala Ser Gln Asp Gly
            30              35              40

Ser Val Glu Gly Ser Phe Thr Pro Ala Asp Ile Ala Ala Leu Lys Thr
    45              50              55

Lys Pro Asp Gly Ser Gln Arg Val Val Leu Ala Tyr Phe Ser Ile Gly
60              65              70              75

Glu Ala Glu Asp Tyr Arg Phe Tyr Trp Asp Asp Glu Trp Tyr Asp Gln
                80              85              90

Ala Pro Asp Trp Leu His Glu Glu Asn Ser Asp Trp Ala Gly Asn Tyr
            95              100             105

Pro Val Lys Phe Trp His Pro Asp Trp Gln Ala Ile Leu Phe Gly Ser
            110             115             120

Pro Asp Cys Tyr Leu Asp Arg Ile Ile Ala Ala Gly Phe Asp Gly Val
        125             130             135

Tyr Leu Asp Arg Val Asp Ala Phe Glu Ile Asp Pro Ala Leu Thr
140             145             150             155

Arg Pro Gln Arg Ala Ala His Met Ile Ala Leu Val Arg Ser Leu Ala
                160             165             170

Ala Tyr Ala Arg Ala Arg Thr Pro Ser Phe Val Val Ala Gln Asn
            175             180             185

Gly Glu Glu Leu Leu Ala Asp Gly Ser Tyr Arg His Thr Val Asp Gly
            190             195             200

Val Gly Lys Glu Asp Leu Leu Tyr Gly Leu Glu Ser Asp Gly Lys Arg
    205             210             215

Asn Ala Asn Gly Asp Ile Arg Val Ser Leu Asp Tyr Leu Arg Arg Leu
220             225             230             235

Ala Glu Ala Gly Lys Pro Val Phe Leu Val Glu Tyr Leu Thr Glu Pro
                240             245             250
```

```
Gln Thr Ile Ala Gln Ala His Ala Asp Ala Glu Thr Leu Gly Met Pro
            255                 260                 265

Ile Phe Ile Thr Asp Arg Asp Leu Asp Asn Ala Tyr Ser Arg
        270                 275                 280

<210> SEQ ID NO 6
<211> LENGTH: 281
<212> TYPE: PRT
<213> ORGANISM: Environmental bacterial community A

<400> SEQUENCE: 6

Thr Pro Gly Met Gly Lys Gly Ile Leu Ser Asn Ala Lys Ser Trp Val
1               5                   10                  15

Tyr Gln Leu Gln His Ile Asp Leu Pro Thr Leu Gly Thr Thr Thr Ala
            20                  25                  30

Asp Leu Val Val Ile Asp Ala Ser Gln Asp Gly Ser Val Glu Gly Ser
        35                  40                  45

Phe Thr Pro Ala Asp Ile Ala Ala Leu Lys Thr Lys Pro Asp Gly Ser
    50                  55                  60

Gln Arg Val Val Leu Ala Tyr Phe Ser Ile Gly Glu Ala Glu Asp Tyr
65                  70                  75                  80

Arg Phe Tyr Trp Asp Asp Glu Trp Tyr Asp Gln Ala Pro Asp Trp Leu
                85                  90                  95

His Glu Glu Asn Ser Asp Trp Ala Gly Asn Tyr Pro Val Lys Phe Trp
            100                 105                 110

His Pro Asp Trp Gln Ala Ile Leu Phe Gly Ser Pro Asp Cys Tyr Leu
        115                 120                 125

Asp Arg Ile Ile Ala Ala Gly Phe Asp Gly Val Tyr Leu Asp Arg Val
    130                 135                 140

Asp Ala Phe Glu Ile Asp Asp Pro Ala Leu Thr Arg Pro Gln Arg Ala
145                 150                 155                 160

Ala His Met Ile Ala Leu Val Arg Ser Leu Ala Ala Tyr Ala Arg Ala
                165                 170                 175

Arg Thr Pro Ser Phe Val Val Ala Gln Asn Gly Glu Glu Leu Leu
            180                 185                 190

Ala Asp Gly Ser Tyr Arg His Thr Val Asp Gly Val Gly Lys Glu Asp
        195                 200                 205

Leu Leu Tyr Gly Leu Glu Ser Asp Gly Lys Arg Asn Ala Asn Gly Asp
    210                 215                 220

Ile Arg Val Ser Leu Asp Tyr Leu Arg Arg Leu Ala Glu Ala Gly Lys
225                 230                 235                 240

Pro Val Phe Leu Val Glu Tyr Leu Thr Glu Pro Gln Thr Ile Ala Gln
                245                 250                 255

Ala His Ala Asp Ala Glu Thr Leu Gly Met Pro Ile Phe Ile Thr Asp
            260                 265                 270

Arg Asp Leu Asp Asn Ala Tyr Ser Arg
        275                 280

<210> SEQ ID NO 7
<211> LENGTH: 1431
<212> TYPE: DNA
<213> ORGANISM: Thermus rehai
<220> FEATURE:
<221> NAME/KEY: CDS
<222> LOCATION: (1)..(1428)
<220> FEATURE:
<221> NAME/KEY: sig_peptide
```

```
<222> LOCATION: (1)..(54)
<220> FEATURE:
<221> NAME/KEY: mat_peptide
<222> LOCATION: (55)..(1428)

<400> SEQUENCE: 7 atg aga aga acc ctt tgg tcc atc gct ctg ctg gcc ctg ggc ctt ggt        48
Met Arg Arg Thr Leu Trp Ser Ile Ala Leu Leu Ala Leu Gly Leu Gly
        -15                 -10                  -5 tgg gcg cag gtg gac ccc agc cac gtg gcc cag gcg gtg cgg cgc acc        96
Trp Ala Gln Val Asp Pro Ser His Val Ala Gln Ala Val Arg Arg Thr
 -1   1                   5                  10 atc cag atc ggc ggg ggg ctg gag cag tgg agc ggc ctg ccc caa tac       144
Ile Gln Ile Gly Gly Gly Leu Glu Gln Trp Ser Gly Leu Pro Gln Tyr
 15                  20                  25                  30 ccc gtg gtc ctc tcc aac acc ttc ccg gcc aaa ccg gtg acc cac ggg       192
Pro Val Val Leu Ser Asn Thr Phe Pro Ala Lys Pro Val Thr His Gly
                     35                  40                  45 ggc tac ttc agc gtg gcc tgg gat gac cgc cac ctc tac atc ctg ggc       240
Gly Tyr Phe Ser Val Ala Trp Asp Asp Arg His Leu Tyr Ile Leu Gly
             50                  55                  60 gtc ttt gag cag aag gcc gaa acc gtc aag gcc gcc ctc ccc gag gag       288
Val Phe Glu Gln Lys Ala Glu Thr Val Lys Ala Ala Leu Pro Glu Glu
         65                  70                  75 cac ccg gag tgg tgg aac gac gac acc atg gag gtg ttc ctg aag cca       336
His Pro Glu Trp Trp Asn Asp Asp Thr Met Glu Val Phe Leu Lys Pro
 80                  85                  90 gac ccg aag ggc gtg gag gtc atc cac ctg gcc gct aac ccc aag ggc       384
Asp Pro Lys Gly Val Glu Val Ile His Leu Ala Ala Asn Pro Lys Gly
 95                 100                 105                 110 acc cgc ttc aag gcc tac acc ttc acc acg gac tac gcc acc tcc ggg       432
Thr Arg Phe Lys Ala Tyr Thr Phe Thr Thr Asp Tyr Ala Thr Ser Gly
                 115                 120                 125 cgg gtg gag gcc agc cgc tgg gtg ttg gaa tgg gcc atc ccc ttc gcc       480
Arg Val Glu Ala Ser Arg Trp Val Leu Glu Trp Ala Ile Pro Phe Ala
             130                 135                 140 tcc ttg aaa acc tcc ccg cct gag ccc ggg gcc atc tgg gcc atg aag       528
Ser Leu Lys Thr Ser Pro Pro Glu Pro Gly Ala Ile Trp Ala Met Lys
         145                 150                 155 gtg ggc cgc gaa cac caa gcc gcc cag gaa tac ccc ctt tgg ccc atg       576
Val Gly Arg Glu His Gln Ala Ala Gln Glu Tyr Pro Leu Trp Pro Met
 160                 165                 170 ggc ggc gac tac cac gcc ccc acc aac ttc ggc tac ctg gtc ttc gtg       624
Gly Gly Asp Tyr His Ala Pro Thr Asn Phe Gly Tyr Leu Val Phe Val
 175                 180                 185                 190 gag aag ctg gag gat ccc cag gcc ctg gcc cag cgg gtc cag gcg ctt       672
Glu Lys Leu Glu Asp Pro Gln Ala Leu Ala Gln Arg Val Gln Ala Leu
                 195                 200                 205 ctg ggg gtg gag ccc ccc atc cga agc cgg ctt cag gac atc gcc acc       720
Leu Gly Val Glu Pro Pro Ile Arg Ser Arg Leu Gln Asp Ile Ala Thr
             210                 215                 220 tac gcg gtg tac tac ggc aag gac ccc cag gag gcg gcc aag ctg gtg       768
Tyr Ala Val Tyr Tyr Gly Lys Asp Pro Gln Glu Ala Ala Lys Leu Val
         225                 230                 235 gac ttt gac ctg gcc atc gtg cag ccc aac ctg ccc aag gag agc ctg       816
Asp Phe Asp Leu Ala Ile Val Gln Pro Asn Leu Pro Lys Glu Ser Leu
 240                 245                 250 gct ctc ctg aag gcc aac ggg gtg cgg gtg gtg gcg tac ctg tcc atc       864
Ala Leu Leu Lys Ala Asn Gly Val Arg Val Val Ala Tyr Leu Ser Ile
 255                 260                 265                 270
```

```
ggg gag gcc gaa ccc gag cgg gac tac ggg caa ccc ctg ccc aag gag      912
Gly Glu Ala Glu Pro Glu Arg Asp Tyr Gly Gln Pro Leu Pro Lys Glu
            275                 280                 285 tgg ctc ctg ggc cag aac ccc aac tgg ggg agc tac ttc gtg gac gcc      960
Trp Leu Leu Gly Gln Asn Pro Asn Trp Gly Ser Tyr Phe Val Asp Ala
        290                 295                 300 aac cag aag ggg tgg caa gag ctg gtg ctc cgg ctg gca gaa ggc tac     1008
Asn Gln Lys Gly Trp Gln Glu Leu Val Leu Arg Leu Ala Glu Gly Tyr
    305                 310                 315 ctg aag gcg ggg ttt gac ggc ctc ttc ctg gac acc ctg gac acc gcg     1056
Leu Lys Ala Gly Phe Asp Gly Leu Phe Leu Asp Thr Leu Asp Thr Ala
320                 325                 330 gac ctc tac ccc cag gtg gcc ccc gga ctg gtg gcc atc gtg caa gcc     1104
Asp Leu Tyr Pro Gln Val Ala Pro Gly Leu Val Ala Ile Val Gln Ala
335                 340                 345                 350 ctc agg gag cgt ttt cct gaa gcc atc ctg gtg cag aac cgc ggc ttc     1152
Leu Arg Glu Arg Phe Pro Glu Ala Ile Leu Val Gln Asn Arg Gly Phe
            355                 360                 365 cgc ctc ctc cct aag acg gcg gag ctg gtg gat gcg gtc atg tac gag     1200
Arg Leu Leu Pro Lys Thr Ala Glu Leu Val Asp Ala Val Met Tyr Glu
        370                 375                 380 aac ctc tcg gcc atg tac aac ttc caa gag aaa cgg tat gtg gcc gtg     1248
Asn Leu Ser Ala Met Tyr Asn Phe Gln Glu Lys Arg Tyr Val Ala Val
    385                 390                 395 gac ggc gac ccc acc ccc gtc ctc ccc tac gcc aag cgg gga ctg gtg     1296
Asp Gly Asp Pro Thr Pro Val Leu Pro Tyr Ala Lys Arg Gly Leu Val
400                 405                 410 gtc ctg gcc ttg gac tac gcc ctc ccc gag gac gta gac ctg gtc cgc     1344
Val Leu Ala Leu Asp Tyr Ala Leu Pro Glu Asp Val Asp Leu Val Arg
415                 420                 425                 430 cgg gcc tac gtg cgg gcg cgg gag ctg ggc ttt gtg ccc tat gta tcc     1392
Arg Ala Tyr Val Arg Ala Arg Glu Leu Gly Phe Val Pro Tyr Val Ser
            435                 440                 445 gtg atc cgc ctg gat agg gtc ttc ctg cac aac cca tag                 1431
Val Ile Arg Leu Asp Arg Val Phe Leu His Asn Pro
        450                 455

<210> SEQ ID NO 8
<211> LENGTH: 476
<212> TYPE: PRT
<213> ORGANISM: Thermus rehai

<400> SEQUENCE: 8

Met Arg Arg Thr Leu Trp Ser Ile Ala Leu Leu Ala Leu Gly Leu Gly
            -15                 -10                  -5

Trp Ala Gln Val Asp Pro Ser His Val Ala Gln Ala Val Arg Arg Thr
 -1   1                   5                  10

Ile Gln Ile Gly Gly Gly Leu Glu Gln Trp Ser Gly Leu Pro Gln Tyr
 15                  20                  25                  30

Pro Val Val Leu Ser Asn Thr Phe Pro Ala Lys Pro Val Thr His Gly
                 35                  40                  45

Gly Tyr Phe Ser Val Ala Trp Asp Asp Arg His Leu Tyr Ile Leu Gly
             50                  55                  60

Val Phe Glu Gln Lys Ala Glu Thr Val Lys Ala Leu Pro Glu Glu
 65                  70                  75

His Pro Glu Trp Trp Asn Asp Asp Thr Met Glu Val Phe Leu Lys Pro
             80                  85                  90

Asp Pro Lys Gly Val Glu Val Ile His Leu Ala Ala Asn Pro Lys Gly
 95                 100                 105                 110
```

```
Thr Arg Phe Lys Ala Tyr Thr Phe Thr Thr Asp Tyr Ala Thr Ser Gly
            115                 120                 125

Arg Val Glu Ala Ser Arg Trp Val Leu Glu Trp Ala Ile Pro Phe Ala
            130                 135                 140

Ser Leu Lys Thr Ser Pro Pro Glu Pro Gly Ala Ile Trp Ala Met Lys
            145                 150                 155

Val Gly Arg Glu His Gln Ala Ala Gln Glu Tyr Pro Leu Trp Pro Met
160                 165                 170

Gly Gly Asp Tyr His Ala Pro Thr Asn Phe Gly Tyr Leu Val Phe Val
175                 180                 185                 190

Glu Lys Leu Glu Asp Pro Gln Ala Leu Ala Gln Arg Val Gln Ala Leu
                195                 200                 205

Leu Gly Val Glu Pro Pro Ile Arg Ser Arg Leu Gln Asp Ile Ala Thr
            210                 215                 220

Tyr Ala Val Tyr Tyr Gly Lys Asp Pro Gln Glu Ala Ala Lys Leu Val
            225                 230                 235

Asp Phe Asp Leu Ala Ile Val Gln Pro Asn Leu Pro Lys Glu Ser Leu
            240                 245                 250

Ala Leu Leu Lys Ala Asn Gly Val Arg Val Val Ala Tyr Leu Ser Ile
255                 260                 265                 270

Gly Glu Ala Glu Pro Glu Arg Asp Tyr Gly Gln Pro Leu Pro Lys Glu
                275                 280                 285

Trp Leu Leu Gly Gln Asn Pro Asn Trp Gly Ser Tyr Phe Val Asp Ala
            290                 295                 300

Asn Gln Lys Gly Trp Gln Glu Leu Val Leu Arg Leu Ala Glu Gly Tyr
            305                 310                 315

Leu Lys Ala Gly Phe Asp Gly Leu Phe Leu Asp Thr Leu Asp Thr Ala
            320                 325                 330

Asp Leu Tyr Pro Gln Val Ala Pro Gly Leu Val Ala Ile Val Gln Ala
335                 340                 345                 350

Leu Arg Glu Arg Phe Pro Glu Ala Ile Leu Val Gln Asn Arg Gly Phe
                355                 360                 365

Arg Leu Leu Pro Lys Thr Ala Glu Leu Val Asp Ala Val Met Tyr Glu
            370                 375                 380

Asn Leu Ser Ala Met Tyr Asn Phe Gln Glu Lys Arg Tyr Val Ala Val
            385                 390                 395

Asp Gly Asp Pro Thr Pro Val Leu Pro Tyr Ala Lys Arg Gly Leu Val
400                 405                 410

Val Leu Ala Leu Asp Tyr Ala Leu Pro Glu Asp Val Asp Leu Val Arg
415                 420                 425                 430

Arg Ala Tyr Val Arg Ala Arg Glu Leu Gly Phe Val Pro Tyr Val Ser
                435                 440                 445

Val Ile Arg Leu Asp Arg Val Phe Leu His Asn Pro
            450                 455

<210> SEQ ID NO 9
<211> LENGTH: 458
<212> TYPE: PRT
<213> ORGANISM: Thermus rehai

<400> SEQUENCE: 9

Gln Val Asp Pro Ser His Val Ala Gln Ala Val Arg Arg Thr Ile Gln
1               5                   10                  15

Ile Gly Gly Gly Leu Glu Gln Trp Ser Gly Leu Pro Gln Tyr Pro Val
```

```
                20                  25                  30
Val Leu Ser Asn Thr Phe Pro Ala Lys Pro Val Thr His Gly Gly Tyr
             35                  40                  45
Phe Ser Val Ala Trp Asp Asp Arg His Leu Tyr Ile Leu Gly Val Phe
         50                  55                  60
Glu Gln Lys Ala Glu Thr Val Lys Ala Ala Leu Pro Glu Glu His Pro
 65                  70                  75                  80
Glu Trp Trp Asn Asp Asp Thr Met Glu Val Phe Leu Lys Pro Asp Pro
                 85                  90                  95
Lys Gly Val Glu Val Ile His Leu Ala Ala Asn Pro Lys Gly Thr Arg
                100                 105                 110
Phe Lys Ala Tyr Thr Phe Thr Thr Asp Tyr Ala Thr Ser Gly Arg Val
                115                 120                 125
Glu Ala Ser Arg Trp Val Leu Glu Trp Ala Ile Pro Phe Ala Ser Leu
            130                 135                 140
Lys Thr Ser Pro Pro Glu Pro Gly Ala Ile Trp Ala Met Lys Val Gly
145                 150                 155                 160
Arg Glu His Gln Ala Ala Gln Glu Tyr Pro Leu Trp Pro Met Gly Gly
                165                 170                 175
Asp Tyr His Ala Pro Thr Asn Phe Gly Tyr Leu Val Phe Val Glu Lys
            180                 185                 190
Leu Glu Asp Pro Gln Ala Leu Ala Gln Arg Val Gln Ala Leu Leu Gly
            195                 200                 205
Val Glu Pro Pro Ile Arg Ser Arg Leu Gln Asp Ile Ala Thr Tyr Ala
            210                 215                 220
Val Tyr Tyr Gly Lys Asp Pro Gln Glu Ala Ala Lys Leu Val Asp Phe
225                 230                 235                 240
Asp Leu Ala Ile Val Gln Pro Asn Leu Pro Lys Glu Ser Leu Ala Leu
                245                 250                 255
Leu Lys Ala Asn Gly Val Arg Val Val Ala Tyr Leu Ser Ile Gly Glu
            260                 265                 270
Ala Glu Pro Glu Arg Asp Tyr Gly Gln Pro Leu Pro Lys Glu Trp Leu
            275                 280                 285
Leu Gly Gln Asn Pro Asn Trp Gly Ser Tyr Phe Val Asp Ala Asn Gln
            290                 295                 300
Lys Gly Trp Gln Glu Leu Val Leu Arg Leu Ala Glu Gly Tyr Leu Lys
305                 310                 315                 320
Ala Gly Phe Asp Gly Leu Phe Leu Asp Thr Leu Asp Thr Ala Asp Leu
                325                 330                 335
Tyr Pro Gln Val Ala Pro Gly Leu Val Ala Ile Val Gln Ala Leu Arg
                340                 345                 350
Glu Arg Phe Pro Glu Ala Ile Leu Val Gln Asn Arg Gly Phe Arg Leu
            355                 360                 365
Leu Pro Lys Thr Ala Glu Leu Val Asp Ala Val Met Tyr Glu Asn Leu
            370                 375                 380
Ser Ala Met Tyr Asn Phe Gln Glu Lys Arg Tyr Val Ala Val Asp Gly
385                 390                 395                 400
Asp Pro Thr Pro Val Leu Pro Tyr Ala Lys Arg Gly Leu Val Val Leu
                405                 410                 415
Ala Leu Asp Tyr Ala Leu Pro Glu Asp Val Asp Leu Val Arg Arg Ala
            420                 425                 430
Tyr Val Arg Ala Arg Glu Leu Gly Phe Val Pro Tyr Val Ser Val Ile
            435                 440                 445
```

```
Arg Leu Asp Arg Val Phe Leu His Asn Pro
    450             455

<210> SEQ ID NO 10
<211> LENGTH: 1485
<212> TYPE: DNA
<213> ORGANISM: Environmental bacterial community LE
<220> FEATURE:
<221> NAME/KEY: CDS
<222> LOCATION: (1)..(1482)
<220> FEATURE:
<221> NAME/KEY: sig_peptide
<222> LOCATION: (1)..(78)
<220> FEATURE:
<221> NAME/KEY: mat_peptide
<222> LOCATION: (79)..(1482)

<400> SEQUENCE: 10 atg cga gtc gcg atg aag tgg ttg ttg gcc tgg acc tgg ctg gcc ctg      48
Met Arg Val Ala Met Lys Trp Leu Leu Ala Trp Thr Trp Leu Ala Leu
    -25             -20                 -15 gtg gcc gcg tgt ggc gac aag gcc acg cac gat gat ttc gac acc gga      96
Val Ala Ala Cys Gly Asp Lys Ala Thr His Asp Asp Phe Asp Thr Gly
-10              -5                  -1  1               5 cag gac gcc atc ctg ccc gac gcg cgg acc ctg ccc tgc acc acg ctc     144
Gln Asp Ala Ile Leu Pro Asp Ala Arg Thr Leu Pro Cys Thr Thr Leu
            10                  15                  20 cag ttc gag cgc ggc gcc ctc ccc tcg gga cag agc gtc cag ggc ctc     192
Gln Phe Glu Arg Gly Ala Leu Pro Ser Gly Gln Ser Val Gln Gly Leu
        25                  30                  35 aac acg cag acg ttg tcc gga acg cag gac cgc tgg gcc gag tac gtc     240
Asn Thr Gln Thr Leu Ser Gly Thr Gln Asp Arg Trp Ala Glu Tyr Val
    40                  45                  50 gag ttc gcg ccg aac agc tcc gcc acg tgc acc tat ccg ctg ccc acc     288
Glu Phe Ala Pro Asn Ser Ser Ala Thr Cys Thr Tyr Pro Leu Pro Thr
55                  60                  65                  70 ggc gtg agc gcg gac agc gtc gtc gcg gcc gag gtc ggc gtg aac tac     336
Gly Val Ser Ala Asp Ser Val Val Ala Ala Glu Val Gly Val Asn Tyr
                75                  80                  85 cga ggc ccc acg aag gcg cag atg cgc tgg gtc atc gag gcg tgg gac     384
Arg Gly Pro Thr Lys Ala Gln Met Arg Trp Val Ile Glu Ala Trp Asp
        90                  95                  100 tac tcg acg aac agc tgg gcc ctg gtg gga gac aac acc ttc gcg cag     432
Tyr Ser Thr Asn Ser Trp Ala Leu Val Gly Asp Asn Thr Phe Ala Gln
            105                 110                 115 tcg tgg cgc tgg acg gcc acg tca ctg gcc ctg ccc acg ccc gcg cgc     480
Ser Trp Arg Trp Thr Ala Thr Ser Leu Ala Leu Pro Thr Pro Ala Arg
        120                 125                 130 ttc ctg tcc ggc ggc ccg gtg aag ctg cgc tac cgc acg gac tcc acc     528
Phe Leu Ser Gly Gly Pro Val Lys Leu Arg Tyr Arg Thr Asp Ser Thr
135                 140                 145                 150 gcg gat gcg tcg ctg ctg gac ctg ctc gtc gtg cgc gta cag gtg gcg     576
Ala Asp Ala Ser Leu Leu Asp Leu Leu Val Val Arg Val Gln Val Ala
                155                 160                 165 gcg agc gac gcg ggc act ccc acc gac gcg ggg act ccg acg gac gcg     624
Ala Ser Asp Ala Gly Thr Pro Thr Asp Ala Gly Thr Pro Thr Asp Ala
        170                 175                 180 ggc act ccc acc gac gcg ggg act ccg acg gac gcg ggc acg cag gtg     672
Gly Thr Pro Thr Asp Ala Gly Thr Pro Thr Asp Ala Gly Thr Gln Val
            185                 190                 195 ccc tgg tcg aac gtg aag agc ttc acg tac cag ctc acc aac tat cca     720
Pro Trp Ser Asn Val Lys Ser Phe Thr Tyr Gln Leu Thr Asn Tyr Pro
```

```
cag ggc aag ctc gat gcg att gcc gca tcg aag ttc gac ctc gcc atc    768
Gln Gly Lys Leu Asp Ala Ile Ala Ala Ser Lys Phe Asp Leu Ala Ile
215                 220                 225                 230 gtc gag ctc gtg cgc gac ggc tcc agc ggc tac ttc acc gcc gcg gag    816
Val Glu Leu Val Arg Asp Gly Ser Ser Gly Tyr Phe Thr Ala Ala Glu
                235                 240                 245 att tcg gcg ctc aag gcc cgg ggc aag cag gtg ctc gcc tac ttc gag    864
Ile Ser Ala Leu Lys Ala Arg Gly Lys Gln Val Leu Ala Tyr Phe Glu
            250                 255                 260 att ggc gcc atc gag gag tac cgc ccc gag tgg agc cag gtg ccc gcg    912
Ile Gly Ala Ile Glu Glu Tyr Arg Pro Glu Trp Ser Gln Val Pro Ala
        265                 270                 275 gac ctg aag ctc ggc ccc gtg tcc ggc tgg ccc gac gag cag tac gtg    960
Asp Leu Lys Leu Gly Pro Val Ser Gly Trp Pro Asp Glu Gln Tyr Val
280                 285                 290 aag tac tgg gac gag cgc tgg tgg ccc atc gtc cag ggc cgc atc gac   1008
Lys Tyr Trp Asp Glu Arg Trp Trp Pro Ile Val Gln Gly Arg Ile Asp
295                 300                 305                 310 cgc gcg ctc gcc gcc ggg ttc aac ggc tgc tac ctc gac atg gtt gtc   1056
Arg Ala Leu Ala Ala Gly Phe Asn Gly Cys Tyr Leu Asp Met Val Val
                315                 320                 325 acg tac gag gag att ccc gcc aac tcc gcc ggc acc aac cgc gcc gac   1104
Thr Tyr Glu Glu Ile Pro Ala Asn Ser Ala Gly Thr Asn Arg Ala Asp
            330                 335                 340 ctc gcg cgg aag atg gtg gcc ctc atc gcg cgc atc aac acg tac gcg   1152
Leu Ala Arg Lys Met Val Ala Leu Ile Ala Arg Ile Asn Thr Tyr Ala
        345                 350                 355 aag gcg cgc aac ccg gac ttc aag gtg gtg ccg cag aac tca ccg gag   1200
Lys Ala Arg Asn Pro Asp Phe Lys Val Val Pro Gln Asn Ser Pro Glu
    360                 365                 370 ctg gtc gat gac ccg gcc tac ctg ccc gcc atc gac ggg ctg ggc atg   1248
Leu Val Asp Asp Pro Ala Tyr Leu Pro Ala Ile Asp Gly Leu Gly Met
375                 380                 385                 390 gag gac atg tac tgg tcc gac gac gtg gcc tgc gac gag ggc tgg tgc   1296
Glu Asp Met Tyr Trp Ser Asp Asp Val Ala Cys Asp Glu Gly Trp Cys
                395                 400                 405 gag gag aac cgc acc aac gcc gct cgc gtg cgc gcc gcg ggc aag ctg   1344
Glu Glu Asn Arg Thr Asn Ala Ala Arg Val Arg Ala Ala Gly Lys Leu
            410                 415                 420 gtg ctg tcc act gac tac gcc acg cag tcc gcc cac gtc gcg gat gcg   1392
Val Leu Ser Thr Asp Tyr Ala Thr Gln Ser Ala His Val Ala Asp Ala
        425                 430                 435 tac acc cgc tcg cgt gcc gcc ggc ttc gtg ccc tac gtc acc gtg cgc   1440
Tyr Thr Arg Ser Arg Ala Ala Gly Phe Val Pro Tyr Val Thr Val Arg
    440                 445                 450 gcg ctg gac cgc gtg acg gtg aac gcg gga tgg gac ccg cag tag       1485
Ala Leu Asp Arg Val Thr Val Asn Ala Gly Trp Asp Pro Gln
455                 460                 465

<210> SEQ ID NO 11
<211> LENGTH: 494
<212> TYPE: PRT
<213> ORGANISM: Environmental bacterial community LE

<400> SEQUENCE: 11

Met Arg Val Ala Met Lys Trp Leu Leu Ala Trp Thr Trp Leu Ala Leu
    -25                 -20                 -15

Val Ala Ala Cys Gly Asp Lys Ala Thr His Asp Asp Phe Asp Thr Gly
-10                  -5                  -1   1               5
```

```
Gln Asp Ala Ile Leu Pro Asp Ala Arg Thr Leu Pro Cys Thr Thr Leu
                 10                  15                  20
Gln Phe Glu Arg Gly Ala Leu Pro Ser Gly Gln Ser Val Gln Gly Leu
             25                  30                  35
Asn Thr Gln Thr Leu Ser Gly Thr Gln Asp Arg Trp Ala Glu Tyr Val
         40                  45                  50
Glu Phe Ala Pro Asn Ser Ser Ala Thr Cys Thr Tyr Pro Leu Pro Thr
55                  60                  65                  70
Gly Val Ser Ala Asp Ser Val Val Ala Glu Val Gly Val Asn Tyr
                     75                  80                  85
Arg Gly Pro Thr Lys Ala Gln Met Arg Trp Val Ile Glu Ala Trp Asp
                 90                  95                 100
Tyr Ser Thr Asn Ser Trp Ala Leu Val Gly Asp Asn Thr Phe Ala Gln
                105                 110                 115
Ser Trp Arg Trp Thr Ala Thr Ser Leu Ala Leu Pro Thr Pro Ala Arg
120                 125                 130
Phe Leu Ser Gly Gly Pro Val Lys Leu Arg Tyr Arg Thr Asp Ser Thr
135                 140                 145                 150
Ala Asp Ala Ser Leu Leu Asp Leu Leu Val Val Arg Val Gln Val Ala
                155                 160                 165
Ala Ser Asp Ala Gly Thr Pro Thr Asp Ala Gly Thr Pro Thr Asp Ala
                170                 175                 180
Gly Thr Pro Thr Asp Ala Gly Thr Pro Thr Asp Ala Gly Thr Gln Val
                185                 190                 195
Pro Trp Ser Asn Val Lys Ser Phe Thr Tyr Gln Leu Thr Asn Tyr Pro
                200                 205                 210
Gln Gly Lys Leu Asp Ala Ile Ala Ala Ser Lys Phe Asp Leu Ala Ile
215                 220                 225                 230
Val Glu Leu Val Arg Asp Gly Ser Ser Gly Tyr Phe Thr Ala Ala Glu
                235                 240                 245
Ile Ser Ala Leu Lys Ala Arg Gly Lys Gln Val Leu Ala Tyr Phe Glu
                250                 255                 260
Ile Gly Ala Ile Glu Glu Tyr Arg Pro Glu Trp Ser Gln Val Pro Ala
                265                 270                 275
Asp Leu Lys Leu Gly Pro Val Ser Gly Trp Pro Asp Glu Gln Tyr Val
                280                 285                 290
Lys Tyr Trp Asp Glu Arg Trp Trp Pro Ile Val Gln Gly Arg Ile Asp
295                 300                 305                 310
Arg Ala Leu Ala Ala Gly Phe Asn Gly Cys Tyr Leu Asp Met Val Val
                315                 320                 325
Thr Tyr Glu Glu Ile Pro Ala Asn Ser Ala Gly Thr Asn Arg Ala Asp
                330                 335                 340
Leu Ala Arg Lys Met Val Ala Leu Ile Ala Arg Ile Asn Thr Tyr Ala
                345                 350                 355
Lys Ala Arg Asn Pro Asp Phe Lys Val Val Pro Gln Asn Ser Pro Glu
                360                 365                 370
Leu Val Asp Asp Pro Ala Tyr Leu Pro Ala Ile Asp Gly Leu Gly Met
375                 380                 385                 390
Glu Asp Met Tyr Trp Ser Asp Val Ala Cys Asp Glu Gly Trp Cys
                    395                 400                 405
Glu Glu Asn Arg Thr Asn Ala Ala Arg Val Arg Ala Ala Gly Lys Leu
                410                 415                 420
```

```
Val Leu Ser Thr Asp Tyr Ala Thr Gln Ser Ala His Val Ala Asp Ala
            425                 430                 435

Tyr Thr Arg Ser Arg Ala Ala Gly Phe Val Pro Tyr Val Thr Val Arg
    440                 445                 450

Ala Leu Asp Arg Val Thr Val Asn Ala Gly Trp Asp Pro Gln
455                 460                 465

<210> SEQ ID NO 12
<211> LENGTH: 468
<212> TYPE: PRT
<213> ORGANISM: Environmental bacterial community LE

<400> SEQUENCE: 12

Asp Asp Phe Asp Thr Gly Gln Asp Ala Ile Leu Pro Asp Ala Arg Thr
1               5                   10                  15

Leu Pro Cys Thr Thr Leu Gln Phe Glu Arg Gly Ala Leu Pro Ser Gly
            20                  25                  30

Gln Ser Val Gln Gly Leu Asn Thr Gln Thr Leu Ser Gly Thr Gln Asp
        35                  40                  45

Arg Trp Ala Glu Tyr Val Glu Phe Ala Pro Asn Ser Ser Ala Thr Cys
    50                  55                  60

Thr Tyr Pro Leu Pro Thr Gly Val Ser Ala Asp Ser Val Val Ala Ala
65                  70                  75                  80

Glu Val Gly Val Asn Tyr Arg Gly Pro Thr Lys Ala Gln Met Arg Trp
                85                  90                  95

Val Ile Glu Ala Trp Asp Tyr Ser Thr Asn Ser Trp Ala Leu Val Gly
            100                 105                 110

Asp Asn Thr Phe Ala Gln Ser Trp Arg Trp Thr Ala Thr Ser Leu Ala
        115                 120                 125

Leu Pro Thr Pro Ala Arg Phe Leu Ser Gly Gly Pro Val Lys Leu Arg
    130                 135                 140

Tyr Arg Thr Asp Ser Thr Ala Asp Ala Ser Leu Leu Asp Leu Leu Val
145                 150                 155                 160

Val Arg Val Gln Val Ala Ala Ser Asp Ala Gly Thr Pro Thr Asp Ala
                165                 170                 175

Gly Thr Pro Thr Asp Ala Gly Thr Pro Thr Asp Ala Gly Thr Pro Thr
            180                 185                 190

Asp Ala Gly Thr Gln Val Pro Trp Ser Asn Val Lys Ser Phe Thr Tyr
        195                 200                 205

Gln Leu Thr Asn Tyr Pro Gln Gly Lys Leu Asp Ala Ile Ala Ala Ser
    210                 215                 220

Lys Phe Asp Leu Ala Ile Val Glu Leu Val Arg Asp Gly Ser Ser Gly
225                 230                 235                 240

Tyr Phe Thr Ala Ala Glu Ile Ser Ala Leu Lys Ala Arg Gly Lys Gln
                245                 250                 255

Val Leu Ala Tyr Phe Glu Ile Gly Ala Ile Glu Glu Tyr Arg Pro Glu
            260                 265                 270

Trp Ser Gln Val Pro Ala Asp Leu Lys Leu Gly Pro Val Ser Gly Trp
        275                 280                 285

Pro Asp Glu Gln Tyr Val Lys Tyr Trp Asp Glu Arg Trp Trp Pro Ile
    290                 295                 300

Val Gln Gly Arg Ile Asp Arg Ala Leu Ala Ala Gly Phe Asn Gly Cys
305                 310                 315                 320

Tyr Leu Asp Met Val Val Thr Tyr Glu Glu Ile Pro Ala Asn Ser Ala
                325                 330                 335
```

-continued

```
Gly Thr Asn Arg Ala Asp Leu Ala Arg Lys Met Val Ala Leu Ile Ala
            340                 345                 350
Arg Ile Asn Thr Tyr Ala Lys Ala Arg Asn Pro Asp Phe Lys Val Val
        355                 360                 365
Pro Gln Asn Ser Pro Glu Leu Val Asp Pro Ala Tyr Leu Pro Ala
    370                 375                 380
Ile Asp Gly Leu Gly Met Glu Asp Met Tyr Trp Ser Asp Val Ala
385                 390                 395                 400
Cys Asp Glu Gly Trp Cys Glu Glu Asn Arg Thr Asn Ala Ala Arg Val
                405                 410                 415
Arg Ala Ala Gly Lys Leu Val Leu Ser Thr Asp Tyr Ala Thr Gln Ser
            420                 425                 430
Ala His Val Ala Asp Ala Tyr Thr Arg Ser Arg Ala Ala Gly Phe Val
        435                 440                 445
Pro Tyr Val Thr Val Arg Ala Leu Asp Arg Val Thr Val Asn Ala Gly
    450                 455                 460
Trp Asp Pro Gln
465

<210> SEQ ID NO 13
<211> LENGTH: 936
<212> TYPE: DNA
<213> ORGANISM: Burkholderia sp-63093
<220> FEATURE:
<221> NAME/KEY: CDS
<222> LOCATION: (1)..(933)
<220> FEATURE:
<221> NAME/KEY: sig_peptide
<222> LOCATION: (1)..(135)
<220> FEATURE:
<221> NAME/KEY: mat_peptide
<222> LOCATION: (136)..(933)

<400> SEQUENCE: 13 atg aaa gag gaa ccg gct ttg tcc gag cac gat cac gat cac gac cga    48
Met Lys Glu Glu Pro Ala Leu Ser Glu His Asp His Asp His Asp Arg
-45                 -40                 -35                 -30 cgt ttc acc ttg cgc gcg ctg ttg cgt cgt gtc agc cgg ttc gcg cgc    96
Arg Phe Thr Leu Arg Ala Leu Leu Arg Arg Val Ser Arg Phe Ala Arg
                -25                 -20                 -15 atg gcc gcg ctc ggc gcg ctg gct tcg gtg gcg cac gcg cag ggc gcg   144
Met Ala Ala Leu Gly Ala Leu Ala Ser Val Ala His Ala Gln Gly Ala
            -10                  -5                  -1  1 gcg gac atg ccg gcg gga ccg tcg gtg gcg ctg tac tac ggc gcg aat   192
Ala Asp Met Pro Ala Gly Pro Ser Val Ala Leu Tyr Tyr Gly Ala Asn
        5                   10                  15 ccg ccc gtc gaa gaa ctg gcc aca ttc gat gtc gtc gtg gtc gat ccc   240
Pro Pro Val Glu Glu Leu Ala Thr Phe Asp Val Val Val Val Asp Pro
20                  25                  30                  35 gac gcg cac ttc gat ccg cgc gct cac gcg aag gcg cat ccg gtg tgg   288
Asp Ala His Phe Asp Pro Arg Ala His Ala Lys Ala His Pro Val Trp
                40                  45                  50 ttc gct tat gtg agc gtc ggc gag gtg aac ccg cat cgc gcg tat tac   336
Phe Ala Tyr Val Ser Val Gly Glu Val Asn Pro His Arg Ala Tyr Tyr
            55                  60                  65 agc gcc atg cct tcc gcg tgg ctg ccg ggc gtg aac gac gcg tgg gcc   384
Ser Ala Met Pro Ser Ala Trp Leu Pro Gly Val Asn Asp Ala Trp Ala
        70                  75                  80 tcg cac gtg atc gat cag acg gcc gct gaa tgg ccg gcg ttt ttc gtc   432
Ser His Val Ile Asp Gln Thr Ala Ala Glu Trp Pro Ala Phe Phe Val
```

```
gac aag gtg atc gcg ccg ttg tgg aaa aaa ggc tat cgg ggc ttt ttc      480
Asp Lys Val Ile Ala Pro Leu Trp Lys Lys Gly Tyr Arg Gly Phe Phe
100                 105                 110                 115 ctc gac acg ctc gac tcc tac cat ctg atc gcc aaa acc gac gcc gcg      528
Leu Asp Thr Leu Asp Ser Tyr His Leu Ile Ala Lys Thr Asp Ala Ala
                120                 125                 130 cga gcc gcg cag gaa gct gga ctg gtc cgc gtc atc cgc gcg atc aag      576
Arg Ala Ala Gln Glu Ala Gly Leu Val Arg Val Ile Arg Ala Ile Lys
            135                 140                 145 aag cgt tat ccg aag gcg aag ctg atc ttc aac cgc ggg ttc gag gta      624
Lys Arg Tyr Pro Lys Ala Lys Leu Ile Phe Asn Arg Gly Phe Glu Val
        150                 155                 160 ttg ccg cag atc cat gat ctc gcc tac atg gtg gcg ttc gaa tcg ctg      672
Leu Pro Gln Ile His Asp Leu Ala Tyr Met Val Ala Phe Glu Ser Leu
165                 170                 175 tac cgc ggt tgg gat gcc ggc aag cag cgt tat acc gaa gtg ccg cag      720
Tyr Arg Gly Trp Asp Ala Gly Lys Gln Arg Tyr Thr Glu Val Pro Gln
180                 185                 190                 195 gcc gat cgc gac tgg ctg ctg atg cag gcg gcg acc atc cgc gat caa      768
Ala Asp Arg Asp Trp Leu Leu Met Gln Ala Ala Thr Ile Arg Asp Gln
                200                 205                 210 tac aag ctg ccg gtg ctg tcc atc gac tat tgc ccg ccc gcc gac gac      816
Tyr Lys Leu Pro Val Leu Ser Ile Asp Tyr Cys Pro Pro Ala Asp Asp
            215                 220                 225 acg tgc gca gcc gcc acc gcg gca cgg att acg caa gcc ggc ttc gtg      864
Thr Cys Ala Ala Ala Thr Ala Ala Arg Ile Thr Gln Ala Gly Phe Val
        230                 235                 240 ccc tac gtc acc gac ggc gga ctc gcg acc gtc ggc gtc ggc gcg gcc      912
Pro Tyr Val Thr Asp Gly Gly Leu Ala Thr Val Gly Val Gly Ala Ala
245                 250                 255 ggg acc ggc aat gag cgg ccg tga                                       936
Gly Thr Gly Asn Glu Arg Pro
260                 265

<210> SEQ ID NO 14
<211> LENGTH: 311
<212> TYPE: PRT
<213> ORGANISM: Burkholderia sp-63093

<400> SEQUENCE: 14

Met Lys Glu Glu Pro Ala Leu Ser Glu His Asp His Asp His Asp Arg
-45                 -40                 -35                 -30

Arg Phe Thr Leu Arg Ala Leu Leu Arg Arg Val Ser Arg Phe Ala Arg
                -25                 -20                 -15

Met Ala Ala Leu Gly Ala Leu Ala Ser Val Ala His Ala Gln G

```
            85                  90                  95
Asp Lys Val Ile Ala Pro Leu Trp Lys Lys Gly Tyr Arg Gly Phe Phe
100                 105                 110                 115

Leu Asp Thr Leu Asp Ser Tyr His Leu Ile Ala Lys Thr Asp Ala Ala
                120                 125                 130

Arg Ala Ala Gln Glu Ala Gly Leu Val Arg Val Ile Arg Ala Ile Lys
                135                 140                 145

Lys Arg Tyr Pro Lys Ala Lys Leu Ile Phe Asn Arg Gly Phe Glu Val
                150                 155                 160

Leu Pro Gln Ile His Asp Leu Ala Tyr Met Val Ala Phe Glu Ser Leu
                165                 170                 175

Tyr Arg Gly Trp Asp Ala Gly Lys Gln Arg Tyr Thr Glu Val Pro Gln
180                 185                 190                 195

Ala Asp Arg Asp Trp Leu Leu Met Gln Ala Ala Thr Ile Arg Asp Gln
                200                 205                 210

Tyr Lys Leu Pro Val Leu Ser Ile Asp Tyr Cys Pro Pro Ala Asp Asp
                215                 220                 225

Thr Cys Ala Ala Ala Thr Ala Ala Arg Ile Thr Gln Ala Gly Phe Val
                230                 235                 240

Pro Tyr Val Thr Asp Gly Gly Leu Ala Thr Val Gly Val Gly Ala Ala
                245                 250                 255

Gly Thr Gly Asn Glu Arg Pro
260                 265

<210> SEQ ID NO 15
<211> LENGTH: 266
<212> TYPE: PRT
<213> ORGANISM: Burkholderia sp-63093

<400> SEQUENCE: 15

Gln Gly Ala Ala Asp Met Pro Ala Gly Pro Ser Val Ala Leu Tyr Tyr
1               5                   10                  15

Gly Ala Asn Pro Pro Val Glu Glu Leu Ala Thr Phe Asp Val Val Val
                20                  25                  30

Val Asp Pro Asp Ala His Phe Asp Pro Arg Ala His Ala Lys Ala His
                35                  40                  45

Pro Val Trp Phe Ala Tyr Val Ser Val Gly Glu Val Asn Pro His Arg
                50                  55                  60

Ala Tyr Tyr Ser Ala Met Pro Ser Ala Trp Leu Pro Gly Val Asn Asp
65              70                  75                  80

Ala Trp Ala Ser His Val Ile Asp Gln Thr Ala Ala Glu Trp Pro Ala
                85                  90                  95

Phe Phe Val Asp Lys Val Ile Ala Pro Leu Trp Lys Lys Gly Tyr Arg
                100                 105                 110

Gly Phe Phe Leu Asp Thr Leu Asp Ser Tyr His Leu Ile Ala Lys Thr
                115                 120                 125

Asp Ala Ala Arg Ala Ala Gln Glu Ala Gly Leu Val Arg Val Ile Arg
                130                 135                 140

Ala Ile Lys Lys Arg Tyr Pro Lys Ala Lys Leu Ile Phe Asn Arg Gly
145             150                 155                 160

Phe Glu Val Leu Pro Gln Ile His Asp Leu Ala Tyr Met Val Ala Phe
                165                 170                 175

Glu Ser Leu Tyr Arg Gly Trp Asp Ala Gly Lys Gln Arg Tyr Thr Glu
                180                 185                 190
```

Val Pro Gln Ala Asp Arg Asp Trp Leu Leu Met Gln Ala Thr Ile
            195                 200                 205

Arg Asp Gln Tyr Lys Leu Pro Val Leu Ser Ile Asp Tyr Cys Pro Pro
210                 215                 220

Ala Asp Thr Cys Ala Ala Thr Ala Ala Arg Ile Thr Gln Ala
225                 230                 235                 240

Gly Phe Val Pro Tyr Val Thr Asp Gly Leu Ala Thr Val Gly Val
                245                 250                 255

Gly Ala Ala Gly Thr Gly Asn Glu Arg Pro
            260                 265

<210> SEQ ID NO 16
<211> LENGTH: 1488
<212> TYPE: DNA
<213> ORGANISM: Myxococcus macrosporus
<220> FEATURE:
<221> NAME/KEY: CDS
<222> LOCATION: (1)..(1485)
<220> FEATURE:
<221> NAME/KEY: sig_peptide
<222> LOCATION: (1)..(84)
<220> FEATURE:
<221> NAME/KEY: mat_peptide
<222> LOCATION: (85)..(1485)

<400> SEQUENCE: 16

| | |
|---|---:|
| atg cga gtc gcg gta gta ggg tgg acg agt ttg tgg tgc atc gcg ctg<br>Met Arg Val Ala Val Val Gly Trp Thr Ser Leu Trp Cys Ile Ala Leu<br>               -25                     -20                  -15 | 48 |
| ttc gcc tgt ggt ggt tcc tcc gga agc gcg gac agc gcg gag cgg agc<br>Phe Ala Cys Gly Gly Ser Ser Gly Ser Ala Asp Ser Ala Glu Arg Ser<br>       -10                   -5                      -1 1 | 96 |
| ggg gac gcg gcg gtc ctc gcg gat gct cgg acc ttg acg tgc gcc agt<br>Gly Asp Ala Ala Val Leu Ala Asp Ala Arg Thr Leu Thr Cys Ala Ser<br>5                   10                 15                 20 | 144 |
| ctc cag gtc gcg agc ggc tac att ggc tcg ggg cag acc gtc cag ggg<br>Leu Gln Val Ala Ser Gly Tyr Ile Gly Ser Gly Gln Thr Val Gln Gly<br>                 25                 30                 35 | 192 |
| ctg cac acg cag acg ttg tcg ggc acg cag gac cgc tgg gcg gag tac<br>Leu His Thr Gln Thr Leu Ser Gly Thr Gln Asp Arg Trp Ala Glu Tyr<br>          40                     45                   50 | 240 |
| gtc gag ttc tcg ccc ggc acc tcc gcc acg tgc acg tac gca ctc ccc<br>Val Glu Phe Ser Pro Gly Thr Ser Ala Thr Cys Thr Tyr Ala Leu Pro<br>          55                     60                   65 | 288 |
| gcg gac gtg ggc gcc gcc gac gtt gtc gcc gcc gag gtg ggc atc aac<br>Ala Asp Val Gly Ala Ala Asp Val Val Ala Ala Glu Val Gly Ile Asn<br>70                   75                 80 | 336 |
| tat cga ggg ccc cac aag tcg cag atg cgc tgg ctg ttc gag gcg tgg<br>Tyr Arg Gly Pro His Lys Ser Gln Met Arg Trp Leu Phe Glu Ala Trp<br>85                   90                 95                 100 | 384 |
| gac tac gag ggg ggc gcc tgg gtg ctg gtg ggc gac aac acc ttc gcg<br>Asp Tyr Glu Gly Gly Ala Trp Val Leu Val Gly Asp Asn Thr Phe Ala<br>                 105                 110                 115 | 432 |
| cag tcc tgg acg tgg acc gcc acg tcg ctc gcg ctg acg tct ccc cag<br>Gln Ser Trp Thr Trp Thr Ala Thr Ser Leu Ala Leu Thr Ser Pro Gln<br>                 120                 125                 130 | 480 |
| cgc ttc gtc agc gga ggc ccg gtg aag ctg cgg tac cgc acg acg tcc<br>Arg Phe Val Ser Gly Gly Pro Val Lys Leu Arg Tyr Arg Thr Thr Ser<br>               135                 140                 145 | 528 |
| acg gcg gat gcg tcg ctg ctg gac ctg ctc gtg gtg cgc atc cag gtc<br>Thr Ala Asp Ala Ser Leu Leu Asp Leu Leu Val Val Arg Ile Gln Val<br>          150                     155                 160 | 576 |

```
gcc gcc tcg gac gcg ggc acc cct ggc gac gcg ggc acg ccc ggc gac      624
Ala Ala Ser Asp Ala Gly Thr Pro Gly Asp Ala Gly Thr Pro Gly Asp
165                 170                 175                 180 gcg ggc acc cct ggc gac gcg gga acg gag acc gac gcc ggc acg ccc      672
Ala Gly Thr Pro Gly Asp Ala Gly Thr Glu Thr Asp Ala Gly Thr Pro
                185                 190                 195 gtg cag tgg gag ggc gtc aac agc ttc acc tac caa ctc acg aac tat      720
Val Gln Trp Glu Gly Val Asn Ser Phe Thr Tyr Gln Leu Thr Asn Tyr
            200                 205                 210 ccc cag ggg aag ctc gac acc atc gcc gcc tcg aag ttc gac ctc gcc      768
Pro Gln Gly Lys Leu Asp Thr Ile Ala Ala Ser Lys Phe Asp Leu Ala
        215                 220                 225 atc gtc gac ctg gcg cgc gac ggc tac gat gac tgg ttc acc gct gcc      816
Ile Val Asp Leu Ala Arg Asp Gly Tyr Asp Asp Trp Phe Thr Ala Ala
    230                 235                 240 gaa atc gcc gcg ctc aag gcc cag ggc aag cag gtg ctc gcg tac ttc      864
Glu Ile Ala Ala Leu Lys Ala Gln Gly Lys Gln Val Leu Ala Tyr Phe
245                 250                 255                 260 gag att ggc gcc atc gag aat tac cgc ccc gag tgg tcc cag gtg cct      912
Glu Ile Gly Ala Ile Glu Asn Tyr Arg Pro Glu Trp Ser Gln Val Pro
                265                 270                 275 gac gac ctg aag ctc ggc ccc gtg ggc ggc tgg ccc aac gag cag tac      960
Asp Asp Leu Lys Leu Gly Pro Val Gly Gly Trp Pro Asn Glu Gln Tyr
            280                 285                 290 gtg aag tac tgg gac gag cgc tgg tgg ccc atc gtc cag ggc cgc atc     1008
Val Lys Tyr Trp Asp Glu Arg Trp Trp Pro Ile Val Gln Gly Arg Ile
        295                 300                 305 gac cag gcg ctc gcc gcg ggc ttc acc ggg tgc tac ctg gac atg gtg     1056
Asp Gln Ala Leu Ala Ala Gly Phe Thr Gly Cys Tyr Leu Asp Met Val
    310                 315                 320 gtg acg tac gag gag att ccc gcg aac tcc gcg ggc acc aat cgc gcc     1104
Val Thr Tyr Glu Glu Ile Pro Ala Asn Ser Ala Gly Thr Asn Arg Ala
325                 330                 335                 340 gac ctc gcg cgg aag atg gtg gcc ctc atc gag cgc atc agc cag tac     1152
Asp Leu Ala Arg Lys Met Val Ala Leu Ile Glu Arg Ile Ser Gln Tyr
                345                 350                 355 gcc aag gca cac aac ccg gcc ttc aag gtg atg ccg cag aac tcc ccg     1200
Ala Lys Ala His Asn Pro Ala Phe Lys Val Met Pro Gln Asn Ser Pro
            360                 365                 370 gag ctg gtg gat gac ccc gcc tac ctg ccc gcc atc gac ggg ctg ggc     1248
Glu Leu Val Asp Asp Pro Ala Tyr Leu Pro Ala Ile Asp Gly Leu Gly
        375                 380                 385 atg gag gac atg tac tgg tcc gac gac aac ccc tgc gac gag ggg tgg     1296
Met Glu Asp Met Tyr Trp Ser Asp Asp Asn Pro Cys Asp Glu Gly Trp
    390                 395                 400 tgc gag gag aac cgg acg aac gcc gcc cgg gtc cgc gcg gcc ggc aag     1344
Cys Glu Glu Asn Arg Thr Asn Ala Ala Arg Val Arg Ala Ala Gly Lys
405                 410                 415                 420 ctg gtg ctc tcc acc gac tac gcc acc cag gcc gcg cac gtc gcg gac     1392
Leu Val Leu Ser Thr Asp Tyr Ala Thr Gln Ala Ala His Val Ala Asp
                425                 430                 435 gcc tac acc cgt tcg cgc gcg gcg ggc ttc gtc ccc tac gtc acc gtg     1440
Ala Tyr Thr Arg Ser Arg Ala Ala Gly Phe Val Pro Tyr Val Thr Val
            440                 445                 450 cga gcg ctg gac cag atg acg gtg aac gcg ggg tgg gat ccg cag tag     1488
Arg Ala Leu Asp Gln Met Thr Val Asn Ala Gly Trp Asp Pro Gln
        455                 460                 465
```

<210> SEQ ID NO 17

<211> LENGTH: 495
<212> TYPE: PRT
<213> ORGANISM: Myxococcus macrosporus

<400> SEQUENCE: 17

```
Met Arg Val Ala Val Gly Trp Thr Ser Leu Trp Cys Ile Ala Leu
            -25                 -20                 -15

Phe Ala Cys Gly Gly Ser Ser Gly Ser Ala Asp Ser Ala Glu Arg Ser
            -10                  -5                  -1   1

Gly Asp Ala Ala Val Leu Ala Asp Ala Arg Thr Leu Thr Cys Ala Ser
  5                  10                  15                  20

Leu Gln Val Ala Ser Gly Tyr Ile Gly Ser Gly Gln Thr Val Gln Gly
                 25                  30                  35

Leu His Thr Gln Thr Leu Ser Gly Thr Gln Asp Arg Trp Ala Glu Tyr
                 40                  45                  50

Val Glu Phe Ser Pro Gly Thr Ser Ala Thr Cys Thr Tyr Ala Leu Pro
             55                  60                  65

Ala Asp Val Gly Ala Ala Asp Val Val Ala Ala Glu Val Gly Ile Asn
         70                  75                  80

Tyr Arg Gly Pro His Lys Ser Gln Met Arg Trp Leu Phe Glu Ala Trp
 85                  90                  95                 100

Asp Tyr Glu Gly Gly Ala Trp Val Leu Val Gly Asp Asn Thr Phe Ala
                105                 110                 115

Gln Ser Trp Thr Trp Thr Ala Thr Ser Leu Ala Leu Thr Ser Pro Gln
                120                 125                 130

Arg Phe Val Ser Gly Gly Pro Val Lys Leu Arg Tyr Arg Thr Thr Ser
                135                 140                 145

Thr Ala Asp Ala Ser Leu Leu Asp Leu Leu Val Val Arg Ile Gln Val
    150                 155                 160

Ala Ala Ser Asp Ala Gly Thr Pro Gly Asp Ala Gly Thr Pro Gly Asp
165                 170                 175                 180

Ala Gly Thr Pro Gly Asp Ala Gly Thr Glu Thr Asp Ala Gly Thr Pro
                185                 190                 195

Val Gln Trp Glu Gly Val Asn Ser Phe Thr Tyr Gln Leu Thr Asn Tyr
                200                 205                 210

Pro Gln Gly Lys Leu Asp Thr Ile Ala Ala Ser Lys Phe Asp Leu Ala
                215                 220                 225

Ile Val Asp Leu Ala Arg Asp Gly Tyr Asp Asp Trp Phe Thr Ala Ala
                230                 235                 240

Glu Ile Ala Ala Leu Lys Ala Gln Gly Lys Gln Val Leu Ala Tyr Phe
245                 250                 255                 260

Glu Ile Gly Ala Ile Glu Asn Tyr Arg Pro Glu Trp Ser Gln Val Pro
                265                 270                 275

Asp Asp Leu Lys Leu Gly Pro Val Gly Gly Trp Pro Asn Glu Gln Tyr
                280                 285                 290

Val Lys Tyr Trp Asp Glu Arg Trp Trp Pro Ile Val Gln Gly Arg Ile
                295                 300                 305

Asp Gln Ala Leu Ala Ala Gly Phe Thr Gly Cys Tyr Leu Asp Met Val
    310                 315                 320

Val Thr Tyr Glu Glu Ile Pro Ala Asn Ser Ala Gly Thr Asn Arg Ala
325                 330                 335                 340

Asp Leu Ala Arg Lys Met Val Ala Leu Ile Glu Arg Ile Ser Gln Tyr
                345                 350                 355

Ala Lys Ala His Asn Pro Ala Phe Lys Val Met Pro Gln Asn Ser Pro
```

```
                360             365             370
Glu Leu Val Asp Asp Pro Ala Tyr Leu Pro Ala Ile Asp Gly Leu Gly
            375             380             385

Met Glu Asp Met Tyr Trp Ser Asp Asp Asn Pro Cys Asp Glu Gly Trp
        390             395             400

Cys Glu Glu Asn Arg Thr Asn Ala Ala Arg Val Arg Ala Ala Gly Lys
405             410             415             420

Leu Val Leu Ser Thr Asp Tyr Ala Thr Gln Ala Ala His Val Ala Asp
            425             430             435

Ala Tyr Thr Arg Ser Arg Ala Ala Gly Phe Val Pro Tyr Val Thr Val
            440             445             450

Arg Ala Leu Asp Gln Met Thr Val Asn Ala Gly Trp Asp Pro Gln
            455             460             465

<210> SEQ ID NO 18
<211> LENGTH: 467
<212> TYPE: PRT
<213> ORGANISM: Myxococcus macrosporus

<400> SEQUENCE: 18

Ala Glu Arg Ser Gly Asp Ala Ala Val Leu Ala Asp Ala Arg Thr Leu
1               5                   10                  15

Thr Cys Ala Ser Leu Gln Val Ala Ser Gly Tyr Ile Gly Ser Gly Gln
            20                  25                  30

Thr Val Gln Gly Leu His Thr Gln Thr Leu Ser Gly Thr Gln Asp Arg
        35                  40                  45

Trp Ala Glu Tyr Val Glu Phe Ser Pro Gly Thr Ser Ala Thr Cys Thr
    50                  55                  60

Tyr Ala Leu Pro Ala Asp Val Gly Ala Ala Asp Val Val Ala Ala Glu
65                  70                  75                  80

Val Gly Ile Asn Tyr Arg Gly Pro His Lys Ser Gln Met Arg Trp Leu
                85                  90                  95

Phe Glu Ala Trp Asp Tyr Glu Gly Gly Ala Trp Val Leu Val Gly Asp
            100                 105                 110

Asn Thr Phe Ala Gln Ser Trp Thr Trp Thr Ala Thr Ser Leu Ala Leu
        115                 120                 125

Thr Ser Pro Gln Arg Phe Val Ser Gly Gly Pro Val Lys Leu Arg Tyr
    130                 135                 140

Arg Thr Thr Ser Thr Ala Asp Ala Ser Leu Leu Asp Leu Leu Val Val
145                 150                 155                 160

Arg Ile Gln Val Ala Ala Ser Asp Ala Gly Thr Pro Gly Asp Ala Gly
                165                 170                 175

Thr Pro Gly Asp Ala Gly Thr Pro Gly Asp Ala Gly Thr Glu Thr Asp
            180                 185                 190

Ala Gly Thr Pro Val Gln Trp Glu Gly Val Asn Ser Phe Thr Tyr Gln
        195                 200                 205

Leu Thr Asn Tyr Pro Gln Gly Lys Leu Asp Thr Ile Ala Ala Ser Lys
    210                 215                 220

Phe Asp Leu Ala Ile Val Asp Leu Ala Arg Asp Gly Tyr Asp Asp Trp
225                 230                 235                 240

Phe Thr Ala Ala Glu Ile Ala Ala Leu Lys Ala Gln Gly Lys Gln Val
                245                 250                 255

Leu Ala Tyr Phe Glu Ile Gly Ala Ile Glu Asn Tyr Arg Pro Glu Trp
            260                 265                 270
```

```
Ser Gln Val Pro Asp Asp Leu Lys Leu Gly Pro Val Gly Trp Pro
            275                 280                 285

Asn Glu Gln Tyr Val Lys Tyr Trp Asp Glu Arg Trp Pro Ile Val
        290                 295                 300

Gln Gly Arg Ile Asp Gln Ala Leu Ala Ala Gly Phe Thr Gly Cys Tyr
305                 310                 315                 320

Leu Asp Met Val Val Thr Tyr Glu Glu Ile Pro Ala Asn Ser Ala Gly
                325                 330                 335

Thr Asn Arg Ala Asp Leu Ala Arg Lys Met Val Ala Leu Ile Glu Arg
                340                 345                 350

Ile Ser Gln Tyr Ala Lys Ala His Asn Pro Ala Phe Lys Val Met Pro
            355                 360                 365

Gln Asn Ser Pro Glu Leu Val Asp Asp Pro Ala Tyr Leu Pro Ala Ile
        370                 375                 380

Asp Gly Leu Gly Met Glu Asp Met Tyr Trp Ser Asp Asp Asn Pro Cys
385                 390                 395                 400

Asp Glu Gly Trp Cys Glu Glu Asn Arg Thr Asn Ala Ala Arg Val Arg
                405                 410                 415

Ala Ala Gly Lys Leu Val Leu Ser Thr Asp Tyr Ala Thr Gln Ala Ala
            420                 425                 430

His Val Ala Asp Ala Tyr Thr Arg Ser Arg Ala Ala Gly Phe Val Pro
            435                 440                 445

Tyr Val Thr Val Arg Ala Leu Asp Gln Met Thr Val Asn Ala Gly Trp
        450                 455                 460

Asp Pro Gln
465

<210> SEQ ID NO 19
<211> LENGTH: 2697
<212> TYPE: DNA
<213> ORGANISM: Gallaecimonas pentaromativorans
<220> FEATURE:
<221> NAME/KEY: CDS
<222> LOCATION: (1)..(2694)
<220> FEATURE:
<221> NAME/KEY: sig_peptide
<222> LOCATION: (1)..(48)
<220> FEATURE:
<221> NAME/KEY: mat_peptide
<222> LOCATION: (49)..(2694)

<400> SEQUENCE: 19 atg atg cgt tgg ctt ctt gcc ctt ttt atc agc ttt cat act tgg gct    48
Met Met Arg Trp Leu Leu Ala Leu Phe Ile Ser Phe His Thr Trp Ala
    -15                 -10                 -5                  -1 tcg acc agc gac agc gtt gcc ttt ttc tat ggc caa cac caa ccg cta    96
Ser Thr Ser Asp Ser Val Ala Phe Phe Tyr Gly Gln His Gln Pro Leu
1               5                   10                  15 gcc gag atg acc ttc tat ccc ggc gtg gtg gtc cag ccc gat cat atc    144
Ala Glu Met Thr Phe Tyr Pro Gly Val Val Val Gln Pro Asp His Ile
                20                  25                  30 agt gcc gaa gag ctc aaa tgg ctg aac gaa aga ggc att aaa acc tat    192
Ser Ala Glu Glu Leu Lys Trp Leu Asn Glu Arg Gly Ile Lys Thr Tyr
            35                  40                  45 gcc tat ctg agc gtt ggc gag tcc gat gcc aaa gac gcc aag ggt ctc    240
Ala Tyr Leu Ser Val Gly Glu Ser Asp Ala Lys Asp Ala Lys Gly Leu
        50                  55                  60 aaa gtc aac gcc agt tgg caa agc cag atc atg gac caa acc agc acc    288
Lys Val Asn Ala Ser Trp Gln Ser Gln Ile Met Asp Gln Thr Ser Thr
65                  70                  75                  80
```

| | | | | | | | | | | | | | | | | |
|---|---|---|---|---|---|---|---|---|---|---|---|---|---|---|---|---|
| cgc | tgg | aaa | aac | cac | ctt | aat | acc | cgc | gct | aag | gaa | ctc | aag | gcc | agg | 336 |
| Arg | Trp | Lys | Asn | His | Leu | Asn | Thr | Arg | Ala | Lys | Glu | Leu | Lys | Ala | Arg | |
| | | | | 85 | | | | 90 | | | | | 95 | | | |
| ggc | ttt | tat | ggc | ctg | ttc | ctc | gat | acc | ctc | gac | agt | tac | cag | cta | ctg | 384 |
| Gly | Phe | Tyr | Gly | Leu | Phe | Leu | Asp | Thr | Leu | Asp | Ser | Tyr | Gln | Leu | Leu | |
| | | | 100 | | | | | 105 | | | | | 110 | | | |
| ccc | caa | gac | caa | caa | ccc | gtc | cag | cgc | cag | gca | ctg | ctg | gct | gcc | gtg | 432 |
| Pro | Gln | Asp | Gln | Gln | Pro | Val | Gln | Arg | Gln | Ala | Leu | Leu | Ala | Ala | Val | |
| | | | 115 | | | | | 120 | | | | | 125 | | | |
| cag | tcc | ttg | tcg | ggg | cag | ttt | cag | cac | cac | ctg | att | tta | aac | cgc | ggc | 480 |
| Gln | Ser | Leu | Ser | Gly | Gln | Phe | Gln | His | His | Leu | Ile | Leu | Asn | Arg | Gly | |
| | | 130 | | | | | 135 | | | | | 140 | | | | |
| ttt | gag | ttg | ctg | ccc | tgg | ctc | aag | ggc | cag | gcc | gag | cgg | gtg | gtg | gcc | 528 |
| Phe | Glu | Leu | Leu | Pro | Trp | Leu | Lys | Gly | Gln | Ala | Glu | Arg | Val | Val | Ala | |
| 145 | | | | | 150 | | | | | 155 | | | | | 160 | |
| gaa | ggc | ttg | ttg | agc | cat | ttc | aat | ccc | gaa | gac | aac | agc | tac | aaa | ggc | 576 |
| Glu | Gly | Leu | Leu | Ser | His | Phe | Asn | Pro | Glu | Asp | Asn | Ser | Tyr | Lys | Gly | |
| | | | | 165 | | | | | 170 | | | | | 175 | | |
| acc | agc | cag | gct | gac | cag | caa | tgg | ctg | agc | gcc | cag | cta | aac | acc | gcc | 624 |
| Thr | Ser | Gln | Ala | Asp | Gln | Gln | Trp | Leu | Ser | Ala | Gln | Leu | Asn | Thr | Ala | |
| | | | 180 | | | | | 185 | | | | | 190 | | | |
| aag | gcc | ctg | ggc | ttt | gcg | gtg | caa | gtc | att | gat | tat | gcg | ccc | ttt | gcc | 672 |
| Lys | Ala | Leu | Gly | Phe | Ala | Val | Gln | Val | Ile | Asp | Tyr | Ala | Pro | Phe | Ala | |
| | | | 195 | | | | | 200 | | | | | 205 | | | |
| aaa | aga | gct | gcc | atg | gcc | cag | cag | atc | gcc | aag | gcc | ggc | ttt | gcc | ccc | 720 |
| Lys | Arg | Ala | Ala | Met | Ala | Gln | Gln | Ile | Ala | Lys | Ala | Gly | Phe | Ala | Pro | |
| | | 210 | | | | | 215 | | | | | 220 | | | | |
| tgg | gta | acc | gac | ggc | cac | ctg | ctg | acc | tgg | ggc | agc | tcc | gag | ctg | act | 768 |
| Trp | Val | Thr | Asp | Gly | His | Leu | Leu | Thr | Trp | Gly | Ser | Ser | Glu | Leu | Thr | |
| 225 | | | | | 230 | | | | | 235 | | | | | 240 | |
| ccg | gtg | cca | cgg | cga | gtg | ata | gtg | ccc | ttc | gac | agt | acc | ctc | aag | cca | 816 |
| Pro | Val | Pro | Arg | Arg | Val | Ile | Val | Pro | Phe | Asp | Ser | Thr | Leu | Lys | Pro | |
| | | | 245 | | | | | 250 | | | | | 255 | | | |
| ctc | atc | aac | acc | caa | gtg | cac | cag | cgc | ctg | tcc | acc | ttg | att | gag | tac | 864 |
| Leu | Ile | Asn | Thr | Gln | Val | His | Gln | Arg | Leu | Ser | Thr | Leu | Ile | Glu | Tyr | |
| | | | 260 | | | | | 265 | | | | | 270 | | | |
| ctg | ggt | tac | ctg | ccc | gat | tac | atc | gac | atc | agc | aaa | gag | ccg | ctg | cct | 912 |
| Leu | Gly | Tyr | Leu | Pro | Asp | Tyr | Ile | Asp | Ile | Ser | Lys | Glu | Pro | Leu | Pro | |
| | | | 275 | | | | | 280 | | | | | 285 | | | |
| ccg | gct | gac | aag | gcg | ctc | ttt | gcc | ggc | gtg | gtg | gtg | tgg | gcc | gaa | agc | 960 |
| Pro | Ala | Asp | Lys | Ala | Leu | Phe | Ala | Gly | Val | Val | Val | Trp | Ala | Glu | Ser | |
| | | 290 | | | | | 295 | | | | | 300 | | | | |
| gcc | gct | ttc | tac | cgc | cct | gag | ctg | gtg | agc | tgg | ctg | gaa | aag | gtg | cag | 1008 |
| Ala | Ala | Phe | Tyr | Arg | Pro | Glu | Leu | Val | Ser | Trp | Leu | Glu | Lys | Val | Gln | |
| 305 | | | | | 310 | | | | | 315 | | | | | 320 | |
| ggc | aag | tta | ccg | gaa | ctg | ctg | ctg | ggg | gag | atc | ccg | cag | tcg | ccc | gcg | 1056 |
| Gly | Lys | Leu | Pro | Glu | Leu | Leu | Leu | Gly | Glu | Ile | Pro | Gln | Ser | Pro | Ala | |
| | | | | 325 | | | | | 330 | | | | | 335 | | |
| cta | ttg | gcc | ggc | cta | ggc | ctt | aac | ctg | caa | agc | ctc | tcc | ccc | aaa | ggc | 1104 |
| Leu | Leu | Ala | Gly | Leu | Gly | Leu | Asn | Leu | Gln | Ser | Leu | Ser | Pro | Lys | Gly | |
| | | | 340 | | | | | 345 | | | | | 350 | | | |
| ccc | ttc | agc | cag | acc | gag | atg | gcc | tcc | tgg | ctt | aaa | ggt | gag | acg | gcg | 1152 |
| Pro | Phe | Ser | Gln | Thr | Glu | Met | Ala | Ser | Trp | Leu | Lys | Gly | Glu | Thr | Ala | |
| | | 355 | | | | | 360 | | | | | 365 | | | | |
| ttg | tcg | ctg | aaa | aac | ctc | gaa | cct | tac | tct | gcc | acc | ctc | gcc | gag | ggc | 1200 |
| Leu | Ser | Leu | Lys | Asn | Leu | Glu | Pro | Tyr | Ser | Ala | Thr | Leu | Ala | Glu | Gly | |
| | | 370 | | | | | 375 | | | | | 380 | | | | |
| gcc | gag | gcg | ctg | atc | agc | atc | aag | gcc | ggt | aac | ggc | gag | ccg | gta | ttg | 1248 |
| Ala | Glu | Ala | Leu | Ile | Ser | Ile | Lys | Ala | Gly | Asn | Gly | Glu | Pro | Val | Leu | |

```
              385                 390                 395                 400
caa ggc gcc cgc acc gat aaa ggc gcc gtg gtg ctg tca ccc tgg ctt        1296
Gln Gly Ala Arg Thr Asp Lys Gly Ala Val Val Leu Ser Pro Trp Leu
                405                 410                 415 atc gat gcc ctg cca ctc gaa gaa aac cgc tgg ctg ata aac ccc gtc        1344
Ile Asp Ala Leu Pro Leu Glu Glu Asn Arg Trp Leu Ile Asn Pro Val
                420                 425                 430 gcc ctg ctg caa aaa ggc ctg ggg ctg ccg cct att ccg gcg cct gat        1392
Ala Leu Leu Gln Lys Gly Leu Gly Leu Pro Pro Ile Pro Ala Pro Asp
                435                 440                 445 gtc act acc gaa agc ggc cgg cgc ctc ttt acc ctg cat atc gac ggc        1440
Val Thr Thr Glu Ser Gly Arg Arg Leu Phe Thr Leu His Ile Asp Gly
                450                 455                 460 gac gcc ttc ccc agc cgt gcc cgc ttc ccc ggc cag ccc ttt gcc ggt        1488
Asp Ala Phe Pro Ser Arg Ala Arg Phe Pro Gly Gln Pro Phe Ala Gly
465                 470                 475                 480 gaa gtg atg gaa aaa cag atc atc gag cac tac cag ctg cct att acc        1536
Glu Val Met Glu Lys Gln Ile Ile Glu His Tyr Gln Leu Pro Ile Thr
                485                 490                 495 gtg tcg gtt atc cag ggg gaa gtg ggc cct acc ggc atg tac ccc aaa        1584
Val Ser Val Ile Gln Gly Glu Val Gly Pro Thr Gly Met Tyr Pro Lys
                500                 505                 510 caa agc ccg cag ctt gag gcc atc gcc cga gac atc ttc aca aag ccc        1632
Gln Ser Pro Gln Leu Glu Ala Ile Ala Arg Asp Ile Phe Thr Lys Pro
                515                 520                 525 tat gtg gaa att gcc tcc cac acc tac agc cat ccc ttt ttc tgg tcg        1680
Tyr Val Glu Ile Ala Ser His Thr Tyr Ser His Pro Phe Phe Trp Ser
                530                 535                 540 caa ata gcc ggg cgc gaa aag ctc acc gag caa gac acc gag tac ggc        1728
Gln Ile Ala Gly Arg Glu Lys Leu Thr Glu Gln Asp Thr Glu Tyr Gly
545                 550                 555                 560 ttt cat ctt aat att ccc ggc tac aac aag att gat ctc acc aag gaa        1776
Phe His Leu Asn Ile Pro Gly Tyr Asn Lys Ile Asp Leu Thr Lys Glu
                565                 570                 575 atc gac ggc tcc atc gac tac atc aac gag cgc ctg gcc cct aaa gat        1824
Ile Asp Gly Ser Ile Asp Tyr Ile Asn Glu Arg Leu Ala Pro Lys Asp
                580                 585                 590 aag aaa gtg gtg atg atg ctg tgg agc ggt gac gcc gcc ccc ggc ccg        1872
Lys Lys Val Val Met Met Leu Trp Ser Gly Asp Ala Ala Pro Gly Pro
                595                 600                 605 gtg gcg cta gcc cac gcc cgc aag atg ggg gtg ctc aac gtc aac ggc        1920
Val Ala Leu Ala His Ala Arg Lys Met Gly Val Leu Asn Val Asn Gly
                610                 615                 620 ggc aac acc gtg atg acc cgc gac aac ccc agc ctc tcc gag atc tgg        1968
Gly Asn Thr Val Met Thr Arg Asp Asn Pro Ser Leu Ser Glu Ile Trp
625                 630                 635                 640 ccc atc ggc cgc ccc gag ggc gac ctg ctg tat cag gtg tac gcc ccc        2016
Pro Ile Gly Arg Pro Glu Gly Asp Leu Leu Tyr Gln Val Tyr Ala Pro
                645                 650                 655 atc atg aac gag aac gtc tac acc gat ctc tgg cat ggc ccc tat ttc        2064
Ile Met Asn Glu Asn Val Tyr Thr Asp Leu Trp His Gly Pro Tyr Phe
                660                 665                 670 ggc ttc cgg cgg gtc agg gaa acc ttc gac atc acc ggc cac ccc tac        2112
Gly Phe Arg Arg Val Arg Glu Thr Phe Asp Ile Thr Gly His Pro Tyr
                675                 680                 685 cgg ctc aag ccg ttc ggg ctg tac ttc cac ttt tac tcc gcc acc aac        2160
Arg Leu Lys Pro Phe Gly Leu Tyr Phe His Phe Tyr Ser Ala Thr Asn
                690                 695                 700 ccg gca ggc ctc cag gcc ctt agg gac gac atc ggc tat gtg ctg ggc        2208
Pro Ala Gly Leu Gln Ala Leu Arg Asp Asp Ile Gly Tyr Val Leu Gly
```

```
Pro Ala Gly Leu Gln Ala Leu Arg Asp Asp Ile Gly Tyr Val Leu Gly
705                 710                 715                 720 cgc ccc aat acc ccg gcg cac ttg agc cac tac gcc cgc atg gcc aag     2256
Arg Pro Asn Thr Pro Ala His Leu Ser His Tyr Ala Arg Met Ala Lys
                725                 730                 735 gat ttt tac ttc agc gcc ctg gcc cgc gat gcc aaa ggt gac tgg ctg     2304
Asp Phe Tyr Phe Ser Ala Leu Ala Arg Asp Ala Lys Gly Asp Trp Leu
            740                 745                 750 ctg agc agc aaa tat ctg cgc acc ctg cgc ctg cca aaa gcg ctc ggt     2352
Leu Ser Ser Lys Tyr Leu Arg Thr Leu Arg Leu Pro Lys Ala Leu Gly
        755                 760                 765 tat gcc cag ctc gac gcc agc cag ggc ctg gct ggg gcc acc gaa gat     2400
Tyr Ala Gln Leu Asp Ala Ser Gln Gly Leu Ala Gly Ala Thr Glu Asp
    770                 775                 780 ggc cgc tac ctg cat gtg gta aac ggc gat gcc cgc ttt gcc ctg gca     2448
Gly Arg Tyr Leu His Val Val Asn Gly Asp Ala Arg Phe Ala Leu Ala
785                 790                 795                 800 gcc agc gcc agc ccc cgc aag cct tat ctg gtg tcg gcc aac gtg ctg     2496
Ala Ser Ala Ser Pro Arg Lys Pro Tyr Leu Val Ser Ala Asn Val Leu
                805                 810                 815 ctg aaa agc tgg cag ttg ccg ggc aag gtg gcc ttc aag gcc tgg caa     2544
Leu Lys Ser Trp Gln Leu Pro Gly Lys Val Ala Phe Lys Ala Trp Gln
            820                 825                 830 aaa gcg gac ctc atc ctc gct aac gcc gag ggc tgc cgt ttt gtc agc     2592
Lys Ala Asp Leu Ile Leu Ala Asn Ala Glu Gly Cys Arg Phe Val Ser
        835                 840                 845 gac cag ggc ccc tct tat ggc ggc cag caa aaa ggc cgg ctg acc gag     2640
Asp Gln Gly Pro Ser Tyr Gly Gly Gln Gln Lys Gly Arg Leu Thr Glu
    850                 855                 860 ttt tca ctg cct gaa ggc gac ttt gcc ggg cac ctt gcc tgt ggg acg     2688
Phe Ser Leu Pro Glu Gly Asp Phe Ala Gly His Leu Ala Cys Gly Thr
865                 870                 875                 880 cag cag tga                                                          2697
Gln Gln <210> SEQ ID NO 20
<211> LENGTH: 898
<212> TYPE: PRT
<213> ORGANISM: Gallaecimonas pentaromativorans

<400> SEQUENCE: 20

Met Met Arg Trp Leu Leu Ala Leu Phe Ile Ser Phe His Thr Trp Ala
        -15                 -10                  -5                  -1

Ser Thr Ser Asp Ser Val Ala Phe Phe Tyr Gly Gln His Gln Pro Leu
  1                   5                  10                  15

Ala Glu Met Thr Phe Tyr Pro Gly Val Val Gln Pro Asp His Ile
                 20                  25                  30

Ser Ala Glu Glu Leu Lys Trp Leu Asn Glu Arg Gly Ile Lys Thr Tyr
             35                  40                  45

Ala Tyr Leu Ser Val Gly Glu Ser Asp Ala Lys Asp Ala Lys Gly Leu
         50                  55                  60

Lys Val Asn Ala Ser Trp Gln Ser Gln Ile Met Asp Gln Thr Ser Thr
 65                  70                  75                  80

Arg Trp Lys Asn His Leu Asn Thr Arg Ala Lys Glu Leu Lys Ala Arg
                 85                  90                  95

Gly Phe Tyr Gly Leu Phe Leu Asp Thr Leu Asp Ser Tyr Gln Leu Leu
                100                 105                 110

Pro Gln Asp Gln Gln Pro Val Gln Arg Gln Ala Leu Leu Ala Ala Val
```

-continued

```
            115                 120                 125
Gln Ser Leu Ser Gly Gln Phe Gln His His Leu Ile Leu Asn Arg Gly
        130                 135                 140
Phe Glu Leu Leu Pro Trp Leu Lys Gly Gln Ala Glu Arg Val Val Ala
145                 150                 155                 160
Glu Gly Leu Leu Ser His Phe Asn Pro Glu Asp Asn Ser Tyr Lys Gly
                165                 170                 175
Thr Ser Gln Ala Asp Gln Gln Trp Leu Ser Ala Gln Leu Asn Thr Ala
            180                 185                 190
Lys Ala Leu Gly Phe Ala Val Gln Val Ile Asp Tyr Ala Pro Phe Ala
        195                 200                 205
Lys Arg Ala Ala Met Ala Gln Gln Ile Ala Lys Ala Gly Phe Ala Pro
    210                 215                 220
Trp Val Thr Asp Gly His Leu Leu Thr Trp Gly Ser Ser Glu Leu Thr
225                 230                 235                 240
Pro Val Pro Arg Arg Val Ile Val Pro Phe Asp Ser Thr Leu Lys Pro
                245                 250                 255
Leu Ile Asn Thr Gln Val His Gln Arg Leu Ser Thr Leu Ile Glu Tyr
            260                 265                 270
Leu Gly Tyr Leu Pro Asp Tyr Ile Asp Ile Ser Lys Glu Pro Leu Pro
        275                 280                 285
Pro Ala Asp Lys Ala Leu Phe Ala Gly Val Val Trp Ala Glu Ser
    290                 295                 300
Ala Ala Phe Tyr Arg Pro Glu Leu Val Ser Trp Leu Glu Lys Val Gln
305                 310                 315                 320
Gly Lys Leu Pro Glu Leu Leu Gly Glu Ile Pro Gln Ser Pro Ala
                325                 330                 335
Leu Leu Ala Gly Leu Gly Leu Asn Leu Gln Ser Leu Ser Pro Lys Gly
            340                 345                 350
Pro Phe Ser Gln Thr Glu Met Ala Ser Trp Leu Lys Gly Glu Thr Ala
        355                 360                 365
Leu Ser Leu Lys Asn Leu Glu Pro Tyr Ser Ala Thr Leu Ala Glu Gly
    370                 375                 380
Ala Glu Ala Leu Ile Ser Ile Lys Ala Gly Asn Gly Glu Pro Val Leu
385                 390                 395                 400
Gln Gly Ala Arg Thr Asp Lys Gly Ala Val Val Leu Ser Pro Trp Leu
                405                 410                 415
Ile Asp Ala Leu Pro Leu Glu Glu Asn Arg Trp Leu Ile Asn Pro Val
            420                 425                 430
Ala Leu Leu Gln Lys Gly Leu Gly Leu Pro Pro Ile Pro Ala Pro Asp
        435                 440                 445
Val Thr Thr Glu Ser Gly Arg Arg Leu Phe Thr Leu His Ile Asp Gly
    450                 455                 460
Asp Ala Phe Pro Ser Arg Ala Arg Phe Pro Gly Gln Pro Phe Ala Gly
465                 470                 475                 480
Glu Val Met Glu Lys Gln Ile Ile Glu His Tyr Gln Leu Pro Ile Thr
                485                 490                 495
Val Ser Val Ile Gln Gly Glu Val Gly Pro Thr Gly Met Tyr Pro Lys
            500                 505                 510
Gln Ser Pro Gln Leu Glu Ala Ile Ala Arg Asp Ile Phe Thr Lys Pro
        515                 520                 525
Tyr Val Glu Ile Ala Ser His Thr Tyr Ser His Pro Phe Phe Trp Ser
    530                 535                 540
```

```
Gln Ile Ala Gly Arg Glu Lys Leu Thr Glu Gln Asp Thr Glu Tyr Gly
545                 550                 555                 560

Phe His Leu Asn Ile Pro Gly Tyr Asn Lys Ile Asp Leu Thr Lys Glu
            565                 570                 575

Ile Asp Gly Ser Ile Asp Tyr Ile Asn Glu Arg Leu Ala Pro Lys Asp
        580                 585                 590

Lys Lys Val Val Met Met Leu Trp Ser Gly Asp Ala Ala Pro Gly Pro
    595                 600                 605

Val Ala Leu Ala His Ala Arg Lys Met Gly Val Leu Asn Val Asn Gly
610                 615                 620

Gly Asn Thr Val Met Thr Arg Asp Asn Pro Ser Leu Ser Glu Ile Trp
625                 630                 635                 640

Pro Ile Gly Arg Pro Glu Gly Asp Leu Leu Tyr Gln Val Tyr Ala Pro
                645                 650                 655

Ile Met Asn Glu Asn Val Tyr Thr Asp Leu Trp His Gly Pro Tyr Phe
            660                 665                 670

Gly Phe Arg Arg Val Arg Glu Thr Phe Asp Ile Thr Gly His Pro Tyr
        675                 680                 685

Arg Leu Lys Pro Phe Gly Leu Tyr Phe His Phe Tyr Ser Ala Thr Asn
690                 695                 700

Pro Ala Gly Leu Gln Ala Leu Arg Asp Asp Ile Gly Tyr Val Leu Gly
705                 710                 715                 720

Arg Pro Asn Thr Pro Ala His Leu Ser His Tyr Ala Arg Met Ala Lys
                725                 730                 735

Asp Phe Tyr Phe Ser Ala Leu Ala Arg Asp Ala Lys Gly Asp Trp Leu
            740                 745                 750

Leu Ser Ser Lys Tyr Leu Arg Thr Leu Arg Leu Pro Lys Ala Leu Gly
        755                 760                 765

Tyr Ala Gln Leu Asp Ala Ser Gln Gly Leu Ala Gly Ala Thr Glu Asp
770                 775                 780

Gly Arg Tyr Leu His Val Val Asn Gly Asp Ala Arg Phe Ala Leu Ala
785                 790                 795                 800

Ala Ser Ala Ser Pro Arg Lys Pro Tyr Leu Val Ser Ala Asn Val Leu
                805                 810                 815

Leu Lys Ser Trp Gln Leu Pro Gly Lys Val Ala Phe Lys Ala Trp Gln
            820                 825                 830

Lys Ala Asp Leu Ile Leu Ala Asn Ala Glu Gly Cys Arg Phe Val Ser
        835                 840                 845

Asp Gln Gly Pro Ser Tyr Gly Gln Gln Lys Gly Arg Leu Thr Glu
850                 855                 860

Phe Ser Leu Pro Glu Gly Asp Phe Ala Gly His Leu Ala Cys Gly Thr
865                 870                 875                 880

Gln Gln

<210> SEQ ID NO 21
<211> LENGTH: 882
<212> TYPE: PRT
<213> ORGANISM: Gallaecimonas pentaromativorans

<400> SEQUENCE: 21

Ser Thr Ser Asp Ser Val Ala Phe Phe Tyr Gly Gln His Gln Pro Leu
1               5                   10                  15

Ala Glu Met Thr Phe Tyr Pro Gly Val Val Gln Pro Asp His Ile
            20                  25                  30
```

```
Ser Ala Glu Glu Leu Lys Trp Leu Asn Glu Arg Gly Ile Lys Thr Tyr
     35                  40                  45

Ala Tyr Leu Ser Val Gly Glu Ser Asp Ala Lys Asp Ala Lys Gly Leu
 50                  55                  60

Lys Val Asn Ala Ser Trp Gln Ser Gln Ile Met Asp Gln Thr Ser Thr
 65                  70                  75                  80

Arg Trp Lys Asn His Leu Asn Thr Arg Ala Lys Glu Leu Lys Ala Arg
                 85                  90                  95

Gly Phe Tyr Gly Leu Phe Leu Asp Thr Leu Asp Ser Tyr Gln Leu Leu
                100                 105                 110

Pro Gln Asp Gln Gln Pro Val Gln Arg Gln Ala Leu Leu Ala Ala Val
            115                 120                 125

Gln Ser Leu Ser Gly Gln Phe Gln His His Leu Ile Leu Asn Arg Gly
        130                 135                 140

Phe Glu Leu Leu Pro Trp Leu Lys Gly Gln Ala Glu Arg Val Val Ala
145                 150                 155                 160

Glu Gly Leu Leu Ser His Phe Asn Pro Glu Asp Asn Ser Tyr Lys Gly
                165                 170                 175

Thr Ser Gln Ala Asp Gln Gln Trp Leu Ser Ala Gln Leu Asn Thr Ala
                180                 185                 190

Lys Ala Leu Gly Phe Ala Val Gln Val Ile Asp Tyr Ala Pro Phe Ala
            195                 200                 205

Lys Arg Ala Ala Met Ala Gln Gln Ile Ala Lys Ala Gly Phe Ala Pro
        210                 215                 220

Trp Val Thr Asp Gly His Leu Leu Thr Trp Gly Ser Ser Glu Leu Thr
225                 230                 235                 240

Pro Val Pro Arg Arg Val Ile Val Pro Phe Asp Ser Thr Leu Lys Pro
                245                 250                 255

Leu Ile Asn Thr Gln Val His Gln Arg Leu Ser Thr Leu Ile Glu Tyr
                260                 265                 270

Leu Gly Tyr Leu Pro Asp Tyr Ile Asp Ile Ser Lys Glu Pro Leu Pro
            275                 280                 285

Pro Ala Asp Lys Ala Leu Phe Ala Gly Val Val Trp Ala Glu Ser
        290                 295                 300

Ala Ala Phe Tyr Arg Pro Glu Leu Val Ser Trp Leu Glu Lys Val Gln
305                 310                 315                 320

Gly Lys Leu Pro Glu Leu Leu Gly Glu Ile Pro Gln Ser Pro Ala
                325                 330                 335

Leu Leu Ala Gly Leu Gly Leu Asn Leu Gln Ser Leu Ser Pro Lys Gly
            340                 345                 350

Pro Phe Ser Gln Thr Glu Met Ala Ser Trp Leu Lys Gly Glu Thr Ala
        355                 360                 365

Leu Ser Leu Lys Asn Leu Glu Pro Tyr Ser Ala Thr Leu Ala Glu Gly
370                 375                 380

Ala Glu Ala Leu Ile Ser Ile Lys Ala Gly Asn Gly Glu Pro Val Leu
385                 390                 395                 400

Gln Gly Ala Arg Thr Asp Lys Gly Ala Val Val Leu Ser Pro Trp Leu
                405                 410                 415

Ile Asp Ala Leu Pro Leu Glu Glu Asn Arg Trp Leu Ile Asn Pro Val
                420                 425                 430

Ala Leu Leu Gln Lys Gly Leu Gly Leu Pro Pro Ile Pro Ala Pro Asp
            435                 440                 445
```

```
Val Thr Thr Glu Ser Gly Arg Arg Leu Phe Thr Leu His Ile Asp Gly
    450                 455                 460

Asp Ala Phe Pro Ser Arg Ala Arg Phe Pro Gly Gln Pro Phe Ala Gly
465                 470                 475                 480

Glu Val Met Glu Lys Gln Ile Ile Glu His Tyr Gln Leu Pro Ile Thr
                485                 490                 495

Val Ser Val Ile Gln Gly Glu Val Gly Pro Thr Gly Met Tyr Pro Lys
                500                 505                 510

Gln Ser Pro Gln Leu Glu Ala Ile Ala Arg Asp Ile Phe Thr Lys Pro
            515                 520                 525

Tyr Val Glu Ile Ala Ser His Thr Tyr Ser His Pro Phe Phe Trp Ser
530                 535                 540

Gln Ile Ala Gly Arg Glu Lys Leu Thr Glu Gln Asp Thr Glu Tyr Gly
545                 550                 555                 560

Phe His Leu Asn Ile Pro Gly Tyr Asn Lys Ile Asp Leu Thr Lys Glu
                565                 570                 575

Ile Asp Gly Ser Ile Asp Tyr Ile Asn Glu Arg Leu Ala Pro Lys Asp
                580                 585                 590

Lys Lys Val Val Met Met Leu Trp Ser Gly Asp Ala Ala Pro Gly Pro
            595                 600                 605

Val Ala Leu Ala His Ala Arg Lys Met Gly Val Leu Asn Val Asn Gly
610                 615                 620

Gly Asn Thr Val Met Thr Arg Asp Asn Pro Ser Leu Ser Glu Ile Trp
625                 630                 635                 640

Pro Ile Gly Arg Pro Glu Gly Asp Leu Leu Tyr Gln Val Tyr Ala Pro
                645                 650                 655

Ile Met Asn Glu Asn Val Tyr Thr Asp Leu Trp His Gly Pro Tyr Phe
                660                 665                 670

Gly Phe Arg Arg Val Arg Glu Thr Phe Asp Ile Thr Gly His Pro Tyr
            675                 680                 685

Arg Leu Lys Pro Phe Gly Leu Tyr Phe His Phe Tyr Ser Ala Thr Asn
690                 695                 700

Pro Ala Gly Leu Gln Ala Leu Arg Asp Asp Ile Gly Tyr Val Leu Gly
705                 710                 715                 720

Arg Pro Asn Thr Pro Ala His Leu Ser His Tyr Ala Arg Met Ala Lys
                725                 730                 735

Asp Phe Tyr Phe Ser Ala Leu Ala Arg Asp Ala Lys Gly Asp Trp Leu
                740                 745                 750

Leu Ser Ser Lys Tyr Leu Arg Thr Leu Arg Leu Pro Lys Ala Leu Gly
            755                 760                 765

Tyr Ala Gln Leu Asp Ala Ser Gln Gly Leu Ala Gly Ala Thr Glu Asp
770                 775                 780

Gly Arg Tyr Leu His Val Val Asn Gly Asp Ala Arg Phe Ala Leu Ala
785                 790                 795                 800

Ala Ser Ala Ser Pro Arg Lys Pro Tyr Leu Val Ser Ala Asn Val Leu
                805                 810                 815

Leu Lys Ser Trp Gln Leu Pro Gly Lys Val Ala Phe Lys Ala Trp Gln
                820                 825                 830

Lys Ala Asp Leu Ile Leu Ala Asn Ala Glu Gly Cys Arg Phe Val Ser
            835                 840                 845

Asp Gln Gly Pro Ser Tyr Gly Gly Gln Lys Gly Arg Leu Thr Glu
850                 855                 860

Phe Ser Leu Pro Glu Gly Asp Phe Ala Gly His Leu Ala Cys Gly Thr
```

Gln Gln

```
<210> SEQ ID NO 22
<211> LENGTH: 903
<212> TYPE: DNA
<213> ORGANISM: Nonomuraea coxensis
<220> FEATURE:
<221> NAME/KEY: CDS
<222> LOCATION: (1)..(900)
<220> FEATURE:
<221> NAME/KEY: sig_peptide
<222> LOCATION: (1)..(63)
<220> FEATURE:
<221> NAME/KEY: mat_peptide
<222> LOCATION: (64)..(900)

<400> SEQUENCE: 22
```

| | | | | | | | | | | | | | | | | |
|---|---|---|---|---|---|---|---|---|---|---|---|---|---|---|---|---|
| gtg | agg | agg | ctc | tgg | acg | gcc | gtg | atg | ctg | gcc | ggc | ctg | ccg | gcc | gcg | 48 |
| Val | Arg | Arg | Leu | Trp | Thr | Ala | Val | Met | Leu | Ala | Gly | Leu | Pro | Ala | Ala | |
| | -20 | | | | -15 | | | | -10 | | | | | | | |
| ctc | acg | tcc | tgc | gcg | ccc | cgc | gtc | ccg | ctg | acc | gag | gtg | cgt | tcc | ttc | 96 |
| Leu | Thr | Ser | Cys | Ala | Pro | Arg | Val | Pro | Leu | Thr | Glu | Val | Arg | Ser | Phe | |
| -5 | | | | -1 | 1 | | | | 5 | | | | | 10 | | |
| acc | tac | gtc | ctg | cag | aac | tac | ccc | ggc | ggc | cgg | ctc | gac | acg | gtc | gcc | 144 |
| Thr | Tyr | Val | Leu | Gln | Asn | Tyr | Pro | Gly | Gly | Arg | Leu | Asp | Thr | Val | Ala | |
| | | | | 15 | | | | | 20 | | | | | 25 | | |
| cgc | gcg | ccg | cac | cag | ctc | gcc | atc | gtg | gac | ctg | tcc | cgc | gac | ggc | acc | 192 |
| Arg | Ala | Pro | His | Gln | Leu | Ala | Ile | Val | Asp | Leu | Ser | Arg | Asp | Gly | Thr | |
| | | 30 | | | | | 35 | | | | | 40 | | | | |
| acg | gcc | ggc | tac | ttc | tcc | gcg | aag | gag | gtc | gcc | aag | gtc | cgg | gac | tcc | 240 |
| Thr | Ala | Gly | Tyr | Phe | Ser | Ala | Lys | Glu | Val | Ala | Lys | Val | Arg | Asp | Ser | |
| | 45 | | | | | 50 | | | | | 55 | | | | | |
| ggc | aag | acc | gtc | ctc | gcc | tac | ttc | gag | atc | ggc | agc | atc | gag | cgc | ttc | 288 |
| Gly | Lys | Thr | Val | Leu | Ala | Tyr | Phe | Glu | Ile | Gly | Ser | Ile | Glu | Arg | Phe | |
| 60 | | | | | 65 | | | | | 70 | | | | | 75 | |
| cgc | acc | gag | gcc | cgc | acc | ctg | ccc | gcc | gac | ctg | cgg | ctc | aac | cgc | tgg | 336 |
| Arg | Thr | Glu | Ala | Arg | Thr | Leu | Pro | Ala | Asp | Leu | Arg | Leu | Asn | Arg | Trp | |
| | | | | 80 | | | | | 85 | | | | | 90 | | |
| ctc | gac | tgg | ccg | gag | gag | cac | ttc | gtc | cgc | tac | tgg | gac | tcc | cgc | tgg | 384 |
| Leu | Asp | Trp | Pro | Glu | Glu | His | Phe | Val | Arg | Tyr | Trp | Asp | Ser | Arg | Trp | |
| | | | 95 | | | | | 100 | | | | | 105 | | | |
| tgg | gac | ctc | gtg | ctg | cgg | ccg | cgc | gtc | gac | cag | gcg | ctg | cgg | gcc | ggg | 432 |
| Trp | Asp | Leu | Val | Leu | Arg | Pro | Arg | Val | Asp | Gln | Ala | Leu | Arg | Ala | Gly | |
| | | 110 | | | | | 115 | | | | | 120 | | | | |
| ttc | gac | ggg | gtc | tac | ctc | gac | acg | ccg | ctc | gcg | tac | gag | gag | atc | cac | 480 |
| Phe | Asp | Gly | Val | Tyr | Leu | Asp | Thr | Pro | Leu | Ala | Tyr | Glu | Glu | Ile | His | |
| | 125 | | | | | 130 | | | | | 135 | | | | | |
| ctc | gac | cgc | gtg | ccc | ggc | gag | acc | cgc | gcg | agc | ctc | gcc | cgc | cgg | atg | 528 |
| Leu | Asp | Arg | Val | Pro | Gly | Glu | Thr | Arg | Ala | Ser | Leu | Ala | Arg | Arg | Met | |
| 140 | | | | | 145 | | | | | 150 | | | | | 155 | |
| aac | gag | ctg | atc | gtc | cgg | atc | agc | agg | tat | gcc | aag | aag | gtg | cgc | ccc | 576 |
| Asn | Glu | Leu | Ile | Val | Arg | Ile | Ser | Arg | Tyr | Ala | Lys | Lys | Val | Arg | Pro | |
| | | | | 160 | | | | | 165 | | | | | 170 | | |
| ggc | ttc | ctc | atc | gtc | ccg | cag | aac | tcg | ccc | gag | ctg | cgc | ctc | cag | ccc | 624 |
| Gly | Phe | Leu | Ile | Val | Pro | Gln | Asn | Ser | Pro | Glu | Leu | Arg | Leu | Gln | Pro | |
| | | | 175 | | | | | 180 | | | | | 185 | | | |
| ggc | tac | gtc | gag | gcg | atc | gac | ggc | atc | ggc | atg | gag | gag | ctg | ttc | ttc | 672 |
| Gly | Tyr | Val | Glu | Ala | Ile | Asp | Gly | Ile | Gly | Met | Glu | Glu | Leu | Phe | Phe | |
| | | 190 | | | | | 195 | | | | | 200 | | | | |
| cgc | gcc | acc | ggc | cgg | ccg | tgc | acc | acc | ggc | tgg | tgc | gcg | gag | aac | ctg | 720 |
| Arg | Ala | Thr | Gly | Arg | Pro | Cys | Thr | Thr | Gly | Trp | Cys | Ala | Glu | Asn | Leu | |

```
                        205                     210                     215
gcg cac gcg ctc gcc ctg cgc aaa ctc ggc aag gcc gtg ctc gcc acc       768
Ala His Ala Leu Ala Leu Arg Lys Leu Gly Lys Ala Val Leu Ala Thr
220                     225                     230                 235 gac tac gcc acc cgc ccg gcc gac gtg gcc gcg gcc tgc gcc cgc tat       816
Asp Tyr Ala Thr Arg Pro Ala Asp Val Ala Ala Ala Cys Ala Arg Tyr
                240                     245                     250 cgc cgc cac ggc atc gcg ggc aac gtc acc gtg gtc gac ctc gac cgc       864
Arg Arg His Gly Ile Ala Gly Asn Val Thr Val Val Asp Leu Asp Arg
                    255                     260                     265 gtc agt cca ctc tgc acc gtt gcg aaa gaa gga gct tga                   903
Val Ser Pro Leu Cys Thr Val Ala Lys Glu Gly Ala
            270                     275

<210> SEQ ID NO 23
<211> LENGTH: 300
<212> TYPE: PRT
<213> ORGANISM: Nonomuraea coxensis

<400> SEQUENCE: 23

Val Arg Arg Leu Trp Thr Ala Val Met Leu Ala Gly Leu Pro Ala Ala
    -20                 -15                 -10

Leu Thr Ser Cys Ala Pro Arg Val Pro Leu Thr Glu Val Arg Ser Phe
 -5              -1  1               5                      10

Thr Tyr Val Leu Gln Asn Tyr Pro Gly Gly Arg Leu Asp Thr Val Ala
                15                  20                  25

Arg Ala Pro His Gln Leu Ala Ile Val Asp Leu Ser Arg Asp Gly Thr
                30                  35                  40

Thr Ala Gly Tyr Phe Ser Ala Lys Glu Val Ala Lys Val Arg Asp Ser
 45                  50                  55

Gly Lys Thr Val Leu Ala Tyr Phe Glu Ile Gly Ser Ile Glu Arg Phe
 60                  65                  70                  75

Arg Thr Glu Ala Arg Thr Leu Pro Ala Asp Leu Arg Leu Asn Arg Trp
                 80                  85                  90

Leu Asp Trp Pro Glu Glu His Phe Val Arg Tyr Trp Asp Ser Arg Trp
                 95                 100                 105

Trp Asp Leu Val Leu Arg Pro Arg Val Asp Gln Ala Leu Arg Ala Gly
                110                 115                 120

Phe Asp Gly Val Tyr Leu Asp Thr Pro Leu Ala Tyr Glu Glu Ile His
    125                 130                 135

Leu Asp Arg Val Pro Gly Glu Thr Arg Ala Ser Leu Ala Arg Arg Met
140                 145                 150                 155

Asn Glu Leu Ile Val Arg Ile Ser Arg Tyr Ala Lys Lys Val Arg Pro
                160                 165                 170

Gly Phe Leu Ile Val Pro Gln Asn Ser Pro Glu Leu Arg Leu Gln Pro
                175                 180                 185

Gly Tyr Val Glu Ala Ile Asp Gly Ile Gly Met Glu Glu Leu Phe Phe
                190                 195                 200

Arg Ala Thr Gly Arg Pro Cys Thr Thr Gly Trp Cys Ala Glu Asn Leu
    205                 210                 215

Ala His Ala Leu Ala Leu Arg Lys Leu Gly Lys Ala Val Leu Ala Thr
220                 225                 230                 235

Asp Tyr Ala Thr Arg Pro Ala Asp Val Ala Ala Ala Cys Ala Arg Tyr
                240                 245                 250

Arg Arg His Gly Ile Ala Gly Asn Val Thr Val Val Asp Leu Asp Arg
                255                 260                 265
```

```
Val Ser Pro Leu Cys Thr Val Ala Lys Glu Gly Ala
        270                 275

<210> SEQ ID NO 24
<211> LENGTH: 279
<212> TYPE: PRT
<213> ORGANISM: Nonomuraea coxensis

<400> SEQUENCE: 24

Pro Arg Val Pro Leu Thr Glu Val Arg Ser Phe Thr Tyr Val Leu Gln
1               5                   10                  15

Asn Tyr Pro Gly Gly Arg Leu Asp Thr Val Ala Arg Ala Pro His Gln
            20                  25                  30

Leu Ala Ile Val Asp Leu Ser Arg Asp Gly Thr Thr Ala Gly Tyr Phe
        35                  40                  45

Ser Ala Lys Glu Val Ala Lys Val Arg Asp Ser Gly Lys Thr Val Leu
    50                  55                  60

Ala Tyr Phe Glu Ile Gly Ser Ile Glu Arg Phe Arg Thr Glu Ala Arg
65                  70                  75                  80

Thr Leu Pro Ala Asp Leu Arg Leu Asn Arg Trp Leu Asp Trp Pro Glu
                85                  90                  95

Glu His Phe Val Arg Tyr Trp Asp Ser Arg Trp Asp Leu Val Leu
            100                 105                 110

Arg Pro Arg Val Asp Gln Ala Leu Arg Ala Gly Phe Asp Gly Val Tyr
        115                 120                 125

Leu Asp Thr Pro Leu Ala Tyr Glu Glu Ile His Leu Asp Arg Val Pro
    130                 135                 140

Gly Glu Thr Arg Ala Ser Leu Ala Arg Arg Met Asn Glu Leu Ile Val
145                 150                 155                 160

Arg Ile Ser Arg Tyr Ala Lys Lys Val Arg Pro Gly Phe Leu Ile Val
                165                 170                 175

Pro Gln Asn Ser Pro Glu Leu Arg Leu Gln Pro Gly Tyr Val Glu Ala
            180                 185                 190

Ile Asp Gly Ile Gly Met Glu Glu Leu Phe Phe Arg Ala Thr Gly Arg
        195                 200                 205

Pro Cys Thr Thr Gly Trp Cys Ala Glu Asn Leu Ala His Ala Leu Ala
    210                 215                 220

Leu Arg Lys Leu Gly Lys Ala Val Leu Ala Thr Asp Tyr Ala Thr Arg
225                 230                 235                 240

Pro Ala Asp Val Ala Ala Cys Ala Arg Tyr Arg Arg His Gly Ile
                245                 250                 255

Ala Gly Asn Val Thr Val Val Asp Leu Asp Arg Val Ser Pro Leu Cys
            260                 265                 270

Thr Val Ala Lys Glu Gly Ala
        275

<210> SEQ ID NO 25
<211> LENGTH: 897
<212> TYPE: DNA
<213> ORGANISM: Glycomyces rutgersensis
<220> FEATURE:
<221> NAME/KEY: CDS
<222> LOCATION: (1)..(894)
<220> FEATURE:
<221> NAME/KEY: sig_peptide
<222> LOCATION: (1)..(66)
<220> FEATURE:
<221> NAME/KEY: mat_peptide
```

<222> LOCATION: (67)..(894)

<400> SEQUENCE: 25

| | | | | | | | | | | | | | | | | |
|---|---|---|---|---|---|---|---|---|---|---|---|---|---|---|---|---|
| gtg | ctg | ctc | gtg | ctg | ccc | ctg | ctg | ctc | gcc | ggg | tgc | gtg | cag | gag | gcc | 48 |
| Val | Leu | Leu | Val | Leu | Pro | Leu | Leu | Leu | Ala | Gly | Cys | Val | Gln | Glu | Ala | |
| | | -20 | | | | -15 | | | | | -10 | | | | | |
| ggg | tcg | gac | acc | gac | gcg | gat | tcg | ggc | gag | acc | gcg | acc | gcc | gct | ccc | 96 |
| Gly | Ser | Asp | Thr | Asp | Ala | Asp | Ser | Gly | Glu | Thr | Ala | Thr | Ala | Ala | Pro | |
| | -5 | | | | | -1 | 1 | | | 5 | | | | | 10 | |
| gcc | gac | cag | ccc | gcg | aac | tgg | atc | tac | cag | ctc | tcc | ggg | tac | gcc | gac | 144 |
| Ala | Asp | Gln | Pro | Ala | Asn | Trp | Ile | Tyr | Gln | Leu | Ser | Gly | Tyr | Ala | Asp | |
| | | | | 15 | | | | | 20 | | | | | 25 | | |
| ggc | aaa | ctc | gac | gcg | ctc | gtc | gcg | gcc | ccc | cac | gag | gcg | gcc | gtg | atc | 192 |
| Gly | Lys | Leu | Asp | Ala | Leu | Val | Ala | Ala | Pro | His | Glu | Ala | Ala | Val | Ile | |
| | | | 30 | | | | | 35 | | | | | 40 | | | |
| gac | ctc | gcg | cgc | gac | ggc | ggc | gaa | ggc | tac | ttc | agc | gcc | gac | gag | atc | 240 |
| Asp | Leu | Ala | Arg | Asp | Gly | Gly | Glu | Gly | Tyr | Phe | Ser | Ala | Asp | Glu | Ile | |
| | | 45 | | | | | 50 | | | | | 55 | | | | |
| acc | tcc | ctc | gag | aac | tcc | ggc | aag | agc | gtc | tac | gcc | tac | ttc | acc | atg | 288 |
| Thr | Ser | Leu | Glu | Asn | Ser | Gly | Lys | Ser | Val | Tyr | Ala | Tyr | Phe | Thr | Met | |
| | 60 | | | | | 65 | | | | | 70 | | | | | |
| ggc | tcc | atc | gag | acc | tac | cgg | ccc | gaa | tac | gac | gcc | gtc | gcc | gcc | acc | 336 |
| Gly | Ser | Ile | Glu | Thr | Tyr | Arg | Pro | Glu | Tyr | Asp | Ala | Val | Ala | Ala | Thr | |
| 75 | | | | | 80 | | | | | 85 | | | | | 90 | |
| gac | atg | atc | ctc | aac | cag | tgg | ggc | gac | tgg | ccc | gac | gag | tac | ttc | gtc | 384 |
| Asp | Met | Ile | Leu | Asn | Gln | Trp | Gly | Asp | Trp | Pro | Asp | Glu | Tyr | Phe | Val | |
| | | | | 95 | | | | | 100 | | | | | 105 | | |
| cag | tac | tgg | gac | cag | gaa | tgg | tgg | gac | ctc | gtc | atg | cag | ccc | cgc | ctc | 432 |
| Gln | Tyr | Trp | Asp | Gln | Glu | Trp | Trp | Asp | Leu | Val | Met | Gln | Pro | Arg | Leu | |
| | | | 110 | | | | | 115 | | | | | 120 | | | |
| gac | cag | gcc | gcc | gcc | gcc | ggg | ttc | gac | ggc | gtc | tac | ctc | gac | gtg | ccc | 480 |
| Asp | Gln | Ala | Ala | Ala | Ala | Gly | Phe | Asp | Gly | Val | Tyr | Leu | Asp | Val | Pro | |
| | | 125 | | | | | 130 | | | | | 135 | | | | |
| aac | gcc | tac | gag | gag | atc | gac | ctc | gcg | ctc | gtc | ccc | ggg | gag | acc | cgg | 528 |
| Asn | Ala | Tyr | Glu | Glu | Ile | Asp | Leu | Ala | Leu | Val | Pro | Gly | Glu | Thr | Arg | |
| | 140 | | | | | 145 | | | | | 150 | | | | | |
| gaa | tca | ctg | gcg | cag | aag | atg | gtc | gac | ctc | gtg | atc | cgc | gcg | caa | gag | 576 |
| Glu | Ser | Leu | Ala | Gln | Lys | Met | Val | Asp | Leu | Val | Ile | Arg | Ala | Gln | Glu | |
| 155 | | | | | 160 | | | | | 165 | | | | | 170 | |
| tac | gcc | ggg | gac | gac | ctc | cag | atc | ctc | gtc | cag | aac | tcc | ccc | gag | ctc | 624 |
| Tyr | Ala | Gly | Asp | Asp | Leu | Gln | Ile | Leu | Val | Gln | Asn | Ser | Pro | Glu | Leu | |
| | | | 175 | | | | | 180 | | | | | 185 | | | |
| cgc | gaa | tac | ccc | ggc | tac | ctc | gac | gcg | atc | gac | ggg | atc | ggc | atc | gag | 672 |
| Arg | Glu | Tyr | Pro | Gly | Tyr | Leu | Asp | Ala | Ile | Asp | Gly | Ile | Gly | Ile | Glu | |
| | | 190 | | | | | 195 | | | | | 200 | | | | |
| gag | ctg | ttc | ttc | ctc | aac | gcc | gac | gag | ccc | tgc | acc | gag | gac | tgg | tgc | 720 |
| Glu | Leu | Phe | Phe | Leu | Asn | Ala | Asp | Glu | Pro | Cys | Thr | Glu | Asp | Trp | Cys | |
| | | 205 | | | | | 210 | | | | | 215 | | | | |
| gcc | gag | aac | ctc | gac | aac | acc | cgc | gcg | atc | cgc | gac | gcc | ggg | aaa | ctc | 768 |
| Ala | Glu | Asn | Leu | Asp | Asn | Thr | Arg | Ala | Ile | Arg | Asp | Ala | Gly | Lys | Leu | |
| | 220 | | | | | 225 | | | | | 230 | | | | | |
| gtc | ctc | gcc | gtc | gac | tac | gcc | tcc | gaa | ccg | gcc | aac | acc | gcc | gcc | gcc | 816 |
| Val | Leu | Ala | Val | Asp | Tyr | Ala | Ser | Glu | Pro | Ala | Asn | Thr | Ala | Ala | Ala | |
| 235 | | | | | 240 | | | | | 245 | | | | | 250 | |
| tgc | gag | cac | tac | gcc | gag | gag | gga | ttc | gcg | gga | gcc | gtc | gcc | gga | gtc | 864 |
| Cys | Glu | His | Tyr | Ala | Glu | Glu | Gly | Phe | Ala | Gly | Ala | Val | Ala | Gly | Val | |
| | | | | 255 | | | | | 260 | | | | | 265 | | |
| gac | ctc | gac | gcg | atc | tac | gag | ccc | tgc | ccc | tga | | | | | | 897 |
| Asp | Leu | Asp | Ala | Ile | Tyr | Glu | Pro | Cys | Pro | | | | | | | |
| | | | 270 | | | | | 275 | | | | | | | | |

<210> SEQ ID NO 26
<211> LENGTH: 298
<212> TYPE: PRT
<213> ORGANISM: Glycomyces rutgersensis

<400> SEQUENCE: 26

Val Leu Leu Val Leu Pro Leu Leu Ala Gly Cys Val Gln Glu Ala
            -20             -15             -10

Gly Ser Asp Thr Asp Ala Asp Ser Gly Glu Thr Ala Thr Ala Ala Pro
    -5              -1  1               5                   10

Ala Asp Gln Pro Ala Asn Trp Ile Tyr Gln Leu Ser Gly Tyr Ala Asp
                15                  20                  25

Gly Lys Leu Asp Ala Leu Val Ala Ala Pro His Glu Ala Ala Val Ile
                30                  35                  40

Asp Leu Ala Arg Asp Gly Gly Glu Gly Tyr Phe Ser Ala Asp Glu Ile
            45                  50                  55

Thr Ser Leu Glu Asn Ser Gly Lys Ser Val Tyr Ala Tyr Phe Thr Met
    60                  65                  70

Gly Ser Ile Glu Thr Tyr Arg Pro Glu Tyr Asp Ala Val Ala Ala Thr
75                  80                  85                  90

Asp Met Ile Leu Asn Gln Trp Gly Asp Trp Pro Asp Glu Tyr Phe Val
                95                  100                 105

Gln Tyr Trp Asp Gln Glu Trp Trp Asp Leu Val Met Gln Pro Arg Leu
                110                 115                 120

Asp Gln Ala Ala Ala Gly Phe Asp Gly Val Tyr Leu Asp Val Pro
            125                 130                 135

Asn Ala Tyr Glu Glu Ile Asp Leu Ala Leu Val Pro Gly Glu Thr Arg
    140                 145                 150

Glu Ser Leu Ala Gln Lys Met Val Asp Leu Val Ile Arg Ala Gln Glu
155                 160                 165                 170

Tyr Ala Gly Asp Asp Leu Gln Ile Leu Val Gln Asn Ser Pro Glu Leu
                175                 180                 185

Arg Glu Tyr Pro Gly Tyr Leu Asp Ala Ile Asp Gly Ile Gly Ile Glu
                190                 195                 200

Glu Leu Phe Phe Leu Asn Ala Asp Glu Pro Cys Thr Glu Asp Trp Cys
                205                 210                 215

Ala Glu Asn Leu Asp Asn Thr Arg Ala Ile Arg Asp Ala Gly Lys Leu
            220                 225                 230

Val Leu Ala Val Asp Tyr Ala Ser Glu Pro Ala Asn Thr Ala Ala Ala
235                 240                 245                 250

Cys Glu His Tyr Ala Glu Glu Gly Phe Ala Gly Ala Val Ala Gly Val
                255                 260                 265

Asp Leu Asp Ala Ile Tyr Glu Pro Cys Pro
                270                 275

<210> SEQ ID NO 27
<211> LENGTH: 276
<212> TYPE: PRT
<213> ORGANISM: Glycomyces rutgersensis

<400> SEQUENCE: 27

Asp Ser Gly Glu Thr Ala Thr Ala Ala Pro Ala Asp Gln Pro Ala Asn
1               5                   10                  15

Trp Ile Tyr Gln Leu Ser Gly Tyr Ala Asp Gly Lys Leu Asp Ala Leu
            20                  25                  30

```
Val Ala Ala Pro His Glu Ala Ala Val Ile Asp Leu Ala Arg Asp Gly
         35                  40                  45

Gly Glu Gly Tyr Phe Ser Ala Asp Glu Ile Thr Ser Leu Glu Asn Ser
     50                  55                  60

Gly Lys Ser Val Tyr Ala Tyr Phe Thr Met Gly Ser Ile Glu Thr Tyr
 65                  70                  75                  80

Arg Pro Glu Tyr Asp Ala Val Ala Ala Thr Asp Met Ile Leu Asn Gln
                 85                  90                  95

Trp Gly Asp Trp Pro Asp Glu Tyr Phe Val Gln Tyr Trp Asp Gln Glu
            100                 105                 110

Trp Trp Asp Leu Val Met Gln Pro Arg Leu Asp Gln Ala Ala Ala Ala
        115                 120                 125

Gly Phe Asp Gly Val Tyr Leu Asp Val Pro Asn Ala Tyr Glu Ile
    130                 135                 140

Asp Leu Ala Leu Val Pro Gly Glu Thr Arg Glu Ser Leu Ala Gln Lys
145                 150                 155                 160

Met Val Asp Leu Val Ile Arg Ala Gln Glu Tyr Ala Gly Asp Asp Leu
                165                 170                 175

Gln Ile Leu Val Gln Asn Ser Pro Glu Leu Arg Glu Tyr Pro Gly Tyr
            180                 185                 190

Leu Asp Ala Ile Asp Gly Ile Gly Ile Glu Glu Leu Phe Phe Leu Asn
        195                 200                 205

Ala Asp Glu Pro Cys Thr Glu Asp Trp Cys Ala Glu Asn Leu Asp Asn
    210                 215                 220

Thr Arg Ala Ile Arg Asp Ala Gly Lys Leu Val Leu Ala Val Asp Tyr
225                 230                 235                 240

Ala Ser Glu Pro Ala Asn Thr Ala Ala Cys Glu His Tyr Ala Glu
                245                 250                 255

Glu Gly Phe Ala Gly Ala Val Ala Gly Val Asp Leu Asp Ala Ile Tyr
            260                 265                 270

Glu Pro Cys Pro
        275

<210> SEQ ID NO 28
<211> LENGTH: 912
<212> TYPE: DNA
<213> ORGANISM: Environmental bacterial community XE
<220> FEATURE:
<221> NAME/KEY: CDS
<222> LOCATION: (1)..(909)
<220> FEATURE:
<221> NAME/KEY: sig_peptide
<222> LOCATION: (1)..(78)
<220> FEATURE:
<221> NAME/KEY: mat_peptide
<222> LOCATION: (79)..(909)

<400> SEQUENCE: 28 atg gct aca cca aag gcc agt ctt gct gcg gtt ctt acg agc ctg cca    48
Met Ala Thr Pro Lys Ala Ser Leu Ala Ala Val Leu Thr Ser Leu Pro
    -25                 -20                 -15 ctg gca ttg ggt tcc atg tcg gca cca gct gcc agc ccg gcg ctt tcc    96
Leu Ala Leu Gly Ser Met Ser Ala Pro Ala Ala Ser Pro Ala Leu Ser
-10                  -5                  -1   1                5 agc gta ggg agc tgg att tac cag ctt cag ggc gca aag ccc gat gtc   144
Ser Val Gly Ser Trp Ile Tyr Gln Leu Gln Gly Ala Lys Pro Asp Val
                10                  15                  20 ctg gcg gcg tct ccc tat gac atg gcg gtc atc gac tat tca cgc gac   192
```

```
            Leu Ala Ala Ser Pro Tyr Asp Met Ala Val Ile Asp Tyr Ser Arg Asp
                         25                  30                  35 ggc tcc ggc ggg cgc gct tat tca cgt gcg gat atc gca gcg ctc aag            240
Gly Ser Gly Gly Arg Ala Tyr Ser Arg Ala Asp Ile Ala Ala Leu Lys
 40                  45                  50 gtc aaa ccc gac ggc ggt cag cga atc gtt ttg gcc tac ctc tcg atc            288
Val Lys Pro Asp Gly Gly Gln Arg Ile Val Leu Ala Tyr Leu Ser Ile
 55                  60                  65                  70 ggg gaa gcc gag gac tat cgg ttt tac tgg ggg caa gac tgg tcc aga            336
Gly Glu Ala Glu Asp Tyr Arg Phe Tyr Trp Gly Gln Asp Trp Ser Arg
                 75                  80                  85 acc ccg ccc tcc tgg ttg ctt ggc gaa aat ccc gac tgg gaa ggc aat            384
Thr Pro Pro Ser Trp Leu Leu Gly Glu Asn Pro Asp Trp Glu Gly Asn
             90                  95                 100 tac gac atc cgc ttt tgg gac ccc gag tgg caa aag atc att ttg ggc            432
Tyr Asp Ile Arg Phe Trp Asp Pro Glu Trp Gln Lys Ile Ile Leu Gly
            105                 110                 115 acg cca caa agc tat ctc gac agg ata ctg gcc gcc gga ttt gac ggg            480
Thr Pro Gln Ser Tyr Leu Asp Arg Ile Leu Ala Ala Gly Phe Asp Gly
120                 125                 130 gtc tat ctc gat cgg gtc gat gcc tat gag cgc aac gac cgc gaa atg            528
Val Tyr Leu Asp Arg Val Asp Ala Tyr Glu Arg Asn Asp Arg Glu Met
135                 140                 145                 150 aat gca ccg ggt cgc cgc gct gcg atg atc gcg ttc gtg caa gac atc            576
Asn Ala Pro Gly Arg Arg Ala Ala Met Ile Ala Phe Val Gln Asp Ile
                155                 160                 165 gcg cgc tat ggc cgc gcc cag aac ccc caa ttc ctc gtg gtc ccc cag            624
Ala Arg Tyr Gly Arg Ala Gln Asn Pro Gln Phe Leu Val Val Pro Gln
            170                 175                 180 aac ggg gaa gag ctg ctc agc gat gcc ggt tat cgg cag gtg gtc agc            672
Asn Gly Glu Glu Leu Leu Ser Asp Ala Gly Tyr Arg Gln Val Val Ser
            185                 190                 195 ggg ttg gcc aag gaa gat ctg ctg tat ggg ctg gac gga gac gaa tcg            720
Gly Leu Ala Lys Glu Asp Leu Leu Tyr Gly Leu Asp Gly Asp Glu Ser
200                 205                 210 cgc aat cgc aac ggg gaa atc cgg gca agc ctt tcg ttt ctc aac cgg            768
Arg Asn Arg Asn Gly Glu Ile Arg Ala Ser Leu Ser Phe Leu Asn Arg
215                 220                 225                 230 ctg gtt gcc gag gga aag ccc gtc ttt ctc gca gaa tat ctc tct tca            816
Leu Val Ala Glu Gly Lys Pro Val Phe Leu Ala Glu Tyr Leu Ser Ser
                235                 240                 245 cca gaa ttg atc gat acc gca cac gcc gaa gcg tcc gag ctg gag atg            864
Pro Glu Leu Ile Asp Thr Ala His Ala Glu Ala Ser Glu Leu Glu Met
            250                 255                 260 gtg ctg ttt atc gga gac cgg gag ctc gac aat gcg aac tca aag taa            912
Val Leu Phe Ile Gly Asp Arg Glu Leu Asp Asn Ala Asn Ser Lys
            265                 270                 275

<210> SEQ ID NO 29
<211> LENGTH: 303
<212> TYPE: PRT
<213> ORGANISM: Environmental bacterial community XE

<400> SEQUENCE: 29

Met Ala Thr Pro Lys Ala Ser Leu Ala Ala Val Leu Thr Ser Leu Pro
    -25                 -20                 -15

Leu Ala Leu Gly Ser Met Ser Ala Pro Ala Ala Ser Pro Ala Leu Ser
-10                  -5                  -1  1                   5

Ser Val Gly Ser Trp Ile Tyr Gln Leu Gln Gly Ala Lys Pro Asp Val
                 10                  15                  20
```

Leu Ala Ala Ser Pro Tyr Asp Met Ala Val Ile Asp Tyr Ser Arg Asp
                25                  30                  35

Gly Ser Gly Gly Arg Ala Tyr Ser Arg Ala Asp Ile Ala Ala Leu Lys
        40                  45                  50

Val Lys Pro Asp Gly Gln Arg Ile Val Leu Ala Tyr Leu Ser Ile
55                  60                  65                  70

Gly Glu Ala Glu Asp Tyr Arg Phe Tyr Trp Gly Gln Asp Trp Ser Arg
                75                  80                  85

Thr Pro Pro Ser Trp Leu Leu Gly Glu Asn Pro Asp Trp Glu Gly Asn
            90                  95                 100

Tyr Asp Ile Arg Phe Trp Asp Pro Glu Trp Gln Lys Ile Ile Leu Gly
               105                 110                 115

Thr Pro Gln Ser Tyr Leu Asp Arg Ile Leu Ala Ala Gly Phe Asp Gly
           120                 125                 130

Val Tyr Leu Asp Arg Val Asp Ala Tyr Glu Arg Asn Asp Arg Glu Met
135                 140                 145                 150

Asn Ala Pro Gly Arg Arg Ala Ala Met Ile Ala Phe Val Gln Asp Ile
               155                 160                 165

Ala Arg Tyr Gly Arg Ala Gln Asn Pro Gln Phe Leu Val Val Pro Gln
           170                 175                 180

Asn Gly Glu Glu Leu Leu Ser Asp Ala Gly Tyr Arg Gln Val Val Ser
           185                 190                 195

Gly Leu Ala Lys Glu Asp Leu Leu Tyr Gly Leu Asp Gly Asp Glu Ser
           200                 205                 210

Arg Asn Arg Asn Gly Glu Ile Arg Ala Ser Leu Ser Phe Leu Asn Arg
215                 220                 225                 230

Leu Val Ala Glu Gly Lys Pro Val Phe Leu Ala Glu Tyr Leu Ser Ser
               235                 240                 245

Pro Glu Leu Ile Asp Thr Ala His Ala Glu Ala Ser Glu Leu Glu Met
           250                 255                 260

Val Leu Phe Ile Gly Asp Arg Glu Leu Asp Asn Ala Asn Ser Lys
           265                 270                 275

<210> SEQ ID NO 30
<211> LENGTH: 277
<212> TYPE: PRT
<213> ORGANISM: Environmental bacterial community XE

<400> SEQUENCE: 30

Ala Ser Pro Ala Leu Ser Ser Val Gly Ser Trp Ile Tyr Gln Leu Gln
1               5                  10                  15

Gly Ala Lys Pro Asp Val Leu Ala Ala Ser Pro Tyr Asp Met Ala Val
               20                  25                  30

Ile Asp Tyr Ser Arg Asp Gly Ser Gly Gly Arg Ala Tyr Ser Arg Ala
           35                  40                  45

Asp Ile Ala Ala Leu Lys Val Lys Pro Asp Gly Gln Arg Ile Val
       50                  55                  60

Leu Ala Tyr Leu Ser Ile Gly Glu Ala Glu Asp Tyr Arg Phe Tyr Trp
65                  70                  75                  80

Gly Gln Asp Trp Ser Arg Thr Pro Pro Ser Trp Leu Leu Gly Glu Asn
                85                  90                  95

Pro Asp Trp Glu Gly Asn Tyr Asp Ile Arg Phe Trp Asp Pro Glu Trp
               100                 105                 110

Gln Lys Ile Ile Leu Gly Thr Pro Gln Ser Tyr Leu Asp Arg Ile Leu

```
                115                 120                 125
Ala Ala Gly Phe Asp Gly Val Tyr Leu Asp Arg Val Asp Ala Tyr Glu
    130                 135                 140

Arg Asn Asp Arg Glu Met Asn Ala Pro Gly Arg Arg Ala Ala Met Ile
145                 150                 155                 160

Ala Phe Val Gln Asp Ile Ala Arg Tyr Gly Arg Ala Gln Asn Pro Gln
                165                 170                 175

Phe Leu Val Val Pro Gln Asn Gly Glu Glu Leu Leu Ser Asp Ala Gly
            180                 185                 190

Tyr Arg Gln Val Val Ser Gly Leu Ala Lys Glu Asp Leu Leu Tyr Gly
        195                 200                 205

Leu Asp Gly Asp Glu Ser Arg Asn Arg Asn Gly Glu Ile Arg Ala Ser
    210                 215                 220

Leu Ser Phe Leu Asn Arg Leu Val Ala Glu Gly Lys Pro Val Phe Leu
225                 230                 235                 240

Ala Glu Tyr Leu Ser Ser Pro Glu Leu Ile Asp Thr Ala His Ala Glu
                245                 250                 255

Ala Ser Glu Leu Glu Met Val Leu Phe Ile Gly Asp Arg Glu Leu Asp
            260                 265                 270

Asn Ala Asn Ser Lys
        275

<210> SEQ ID NO 31
<211> LENGTH: 903
<212> TYPE: DNA
<213> ORGANISM: Paraburkholderia phenazinium
<220> FEATURE:
<221> NAME/KEY: CDS
<222> LOCATION: (1)..(900)
<220> FEATURE:
<221> NAME/KEY: sig_peptide
<222> LOCATION: (1)..(87)
<220> FEATURE:
<221> NAME/KEY: mat_peptide
<222> LOCATION: (88)..(900)

<400> SEQUENCE: 31 atg ttc atg gtg cgc gcg ctg tgc cgc ttt gcc gcc tgg gtg gcc tgc    48
Met Phe Met Val Arg Ala Leu Cys Arg Phe Ala Ala Trp Val Ala Cys
            -25                 -20                 -15 ttc ggc acg gct gcc ggg atg gcg ccg ctc gcg cag gcc cag acg gcg    96
Phe Gly Thr Ala Ala Gly Met Ala Pro Leu Ala Gln Ala Gln Thr Ala
        -10                 -5              -1   1 gcc gat gcg gcg gac aat gcc gcc agt gca acg aat gct tcc gcg cag   144
Ala Asp Ala Ala Asp Asn Ala Ala Ser Ala Thr Asn Ala Ser Ala Gln
    5                   10                  15 cct tcc gtg gcg ttc ttc tat ggc ggg cag gtg ccg gct gcg gcc ttg   192
Pro Ser Val Ala Phe Phe Tyr Gly Gly Gln Val Pro Ala Ala Ala Leu
20                  25                  30                  35 tcc gag ttc gat gcg gta gtg gtc gaa ccg gat agc ggc ttc gac cca   240
Ser Glu Phe Asp Ala Val Val Val Glu Pro Asp Ser Gly Phe Asp Pro
                40                  45                  50 gag gct caa cac ggc ggc cac acc gcc tgg ttc gcg tat gtc agc gtc   288
Glu Ala Gln His Gly Gly His Thr Ala Trp Phe Ala Tyr Val Ser Val
            55                  60                  65 ggc gaa gtg acg ccg caa cgc ccg tat tac gcg gcg atg ccg aag gag   336
Gly Glu Val Thr Pro Gln Arg Pro Tyr Tyr Ala Ala Met Pro Lys Glu
        70                  75                  80 tgg ctc gtc gga cac aac gct gcg tgg gag tcg aag gtc gtc gat cag   384
Trp Leu Val Gly His Asn Ala Ala Trp Glu Ser Lys Val Val Asp Gln
```

```
gac gct ccc ggc tgg ccg gcg ttt tac ttg aag cag gtg att gcc ccg      432
Asp Ala Pro Gly Trp Pro Ala Phe Tyr Leu Lys Gln Val Ile Ala Pro
100             105                 110                 115 ctg tgg cgc aaa ggc tat cgc ggc ttc ttt ctc gac acg ctc gat tcg      480
Leu Trp Arg Lys Gly Tyr Arg Gly Phe Phe Leu Asp Thr Leu Asp Ser
            120                 125                 130 tat cag ttg atc gcc aaa acc gac gcg gac cgc cag cgc cag cag gcg      528
Tyr Gln Leu Ile Ala Lys Thr Asp Ala Asp Arg Gln Arg Gln Gln Ala
        135                 140                 145 gga ctg gtg gcg gtg att cgc gcg atc aag gcg cgc tat ccg cgc gcg      576
Gly Leu Val Ala Val Ile Arg Ala Ile Lys Ala Arg Tyr Pro Arg Ala
    150                 155                 160 atg ctc atg ttc aac cgg ggc ttc gag atc ctg ccg cag gtg cac gaa      624
Met Leu Met Phe Asn Arg Gly Phe Glu Ile Leu Pro Gln Val His Glu
165                 170                 175 ctg gtg tac gcg gtg gcg ttc gaa tcg ctc tat agc ggc tgg gac cag      672
Leu Val Tyr Ala Val Ala Phe Glu Ser Leu Tyr Ser Gly Trp Asp Gln
180                 185                 190                 195 acg aag caa agc tat aca cag gtg ccg ctg gcg gat cgc gac tgg ctg      720
Thr Lys Gln Ser Tyr Thr Gln Val Pro Leu Ala Asp Arg Asp Trp Leu
            200                 205                 210 ctc ggg caa gcc aga atc atc cgt gaa cag tac cgc ttg ccg gtg atc      768
Leu Gly Gln Ala Arg Ile Ile Arg Glu Gln Tyr Arg Leu Pro Val Ile
        215                 220                 225 tcg atc gac tac tgt gcg ccg ggc gat gag cag tgc gcg cgc gat acg      816
Ser Ile Asp Tyr Cys Ala Pro Gly Asp Glu Gln Cys Ala Arg Asp Thr
    230                 235                 240 gtg cag aag atc tgc aag gat ggg ctg gtg ccg tac gtg acg gac ggc      864
Val Gln Lys Ile Cys Lys Asp Gly Leu Val Pro Tyr Val Thr Asp Gly
245                 250                 255 gcg ttg caa acc gtt ggg gta ggg cgc gca ggg aga tga                  903
Ala Leu Gln Thr Val Gly Val Gly Arg Ala Gly Arg
260                 265                 270
```

<210> SEQ ID NO 32
<211> LENGTH: 300
<212> TYPE: PRT
<213> ORGANISM: Paraburkholderia phenazinium

<400> SEQUENCE: 32

```
Met Phe Met Val Arg Ala Leu Cys Arg Phe Ala Ala Trp Val Ala Cys
                -25                 -20                 -15

Phe Gly Thr Ala Ala Gly Met Ala Pro Leu Ala Gln Ala Gln Thr Ala
            -10                  -5                  -1   1

Ala Asp Ala Ala Asp Asn Ala Ala Ser Ala Thr Asn Ala Ser Ala Gln
  5                  10                  15

Pro Ser Val Ala Phe Phe Tyr Gly Gly Gln Val Pro Ala Ala Leu
20                  25                  30                  35

Ser Glu Phe Asp Ala Val Val Glu Pro Asp Ser Gly Phe Asp Pro
            40                  45                  50

Glu Ala Gln His Gly Gly His Thr Ala Trp Phe Ala Tyr Val Ser Val
        55                  60                  65

Gly Glu Val Thr Pro Gln Arg Pro Tyr Tyr Ala Ala Met Pro Lys Glu
    70                  75                  80

Trp Leu Val Gly His Asn Ala Ala Trp Glu Ser Lys Val Val Asp Gln
85                  90                  95

Asp Ala Pro Gly Trp Pro Ala Phe Tyr Leu Lys Gln Val Ile Ala Pro
```

```
            100                 105                 110                 115
Leu Trp Arg Lys Gly Tyr Arg Gly Phe Phe Leu Asp Thr Leu Asp Ser
            120                 125                 130

Tyr Gln Leu Ile Ala Lys Thr Asp Ala Asp Arg Gln Arg Gln Gln Ala
            135                 140                 145

Gly Leu Val Ala Val Ile Arg Ala Ile Lys Ala Arg Tyr Pro Arg Ala
            150                 155                 160

Met Leu Met Phe Asn Arg Gly Phe Glu Ile Leu Pro Gln Val His Glu
            165                 170                 175

Leu Val Tyr Ala Val Ala Phe Glu Ser Leu Tyr Ser Gly Trp Asp Gln
180                 185                 190                 195

Thr Lys Gln Ser Tyr Thr Gln Val Pro Leu Ala Asp Arg Asp Trp Leu
                200                 205                 210

Leu Gly Gln Ala Arg Ile Ile Arg Glu Gln Tyr Arg Leu Pro Val Ile
            215                 220                 225

Ser Ile Asp Tyr Cys Ala Pro Gly Asp Glu Gln Cys Ala Arg Asp Thr
            230                 235                 240

Val Gln Lys Ile Cys Lys Asp Gly Leu Val Pro Tyr Val Thr Asp Gly
            245                 250                 255

Ala Leu Gln Thr Val Gly Val Gly Arg Ala Gly Arg
260                 265                 270

<210> SEQ ID NO 33
<211> LENGTH: 271
<212> TYPE: PRT
<213> ORGANISM: Paraburkholderia phenazinium

<400> SEQUENCE: 33

Gln Thr Ala Ala Asp Ala Ala Asp Asn Ala Ala Ser Ala Thr Asn Ala
1               5                   10                  15

Ser Ala Gln Pro Ser Val Ala Phe Phe Tyr Gly Gly Gln Val Pro Ala
                20                  25                  30

Ala Ala Leu Ser Glu Phe Asp Ala Val Val Val Glu Pro Asp Ser Gly
            35                  40                  45

Phe Asp Pro Glu Ala Gln His Gly Gly His Thr Ala Trp Phe Ala Tyr
    50                  55                  60

Val Ser Val Gly Glu Val Thr Pro Gln Arg Pro Tyr Tyr Ala Ala Met
65                  70                  75                  80

Pro Lys Glu Trp Leu Val Gly His Asn Ala Ala Trp Glu Ser Lys Val
                85                  90                  95

Val Asp Gln Asp Ala Pro Gly Trp Pro Ala Phe Tyr Leu Lys Gln Val
            100                 105                 110

Ile Ala Pro Leu Trp Arg Lys Gly Tyr Arg Gly Phe Phe Leu Asp Thr
        115                 120                 125

Leu Asp Ser Tyr Gln Leu Ile Ala Lys Thr Asp Ala Asp Arg Gln Arg
    130                 135                 140

Gln Gln Ala Gly Leu Val Ala Val Ile Arg Ala Ile Lys Ala Arg Tyr
145                 150                 155                 160

Pro Arg Ala Met Leu Met Phe Asn Arg Gly Phe Glu Ile Leu Pro Gln
                165                 170                 175

Val His Glu Leu Val Tyr Ala Val Ala Phe Glu Ser Leu Tyr Ser Gly
            180                 185                 190

Trp Asp Gln Thr Lys Gln Ser Tyr Thr Gln Val Pro Leu Ala Asp Arg
        195                 200                 205
```

```
Asp Trp Leu Leu Gly Gln Ala Arg Ile Ile Arg Glu Gln Tyr Arg Leu
    210                 215                 220

Pro Val Ile Ser Ile Asp Tyr Cys Ala Pro Gly Asp Glu Gln Cys Ala
225                 230                 235                 240

Arg Asp Thr Val Gln Lys Ile Cys Lys Asp Gly Leu Val Pro Tyr Val
                245                 250                 255

Thr Asp Gly Ala Leu Gln Thr Val Gly Val Gly Arg Ala Gly Arg
            260                 265                 270

<210> SEQ ID NO 34
<211> LENGTH: 5
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (2)..(2)
<223> OTHER INFORMATION: Xaa = any amino acid
<220> FEATURE:
<221> NAME/KEY: MISC_FEATURE
<222> LOCATION: (3)..(3)
<223> OTHER INFORMATION: Xaa = F (Phe) or Y (Tyr)
<220> FEATURE:
<221> NAME/KEY: MISC_FEATURE
<222> LOCATION: (4)..(4)
<223> OTHER INFORMATION: Xaa = L (Leu) or Y (Tyr) or F (Phe)

<400> SEQUENCE: 34

Gly Xaa Xaa Xaa Asp
1               5

<210> SEQ ID NO 35
<211> LENGTH: 7
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (3)..(3)
<223> OTHER INFORMATION: Xaa = any amino acids
<220> FEATURE:
<221> NAME/KEY: MISC_FEATURE
<222> LOCATION: (4)..(4)
<223> OTHER INFORMATION: Xaa = S (Ser) or E (Glu) or T (Tyr)
<220> FEATURE:
<221> NAME/KEY: MISC_FEATURE
<222> LOCATION: (5)..(5)
<223> OTHER INFORMATION: Xaa = any amino acids
<220> FEATURE:
<221> NAME/KEY: MISC_FEATURE
<222> LOCATION: (6)..(6)
<223> OTHER INFORMATION: Xaa = any amino acids
<220> FEATURE:
<221> NAME/KEY: MISC_FEATURE
<222> LOCATION: (7)..(7)
<223> OTHER INFORMATION: Xaa = E (Glu) or A (Ala) or S (Ser)
<220> FEATURE:
<221> NAME/KEY: MISC_FEATURE
<222> LOCATION: (7)..(7)
<223> OTHER INFORMATION: Xaa = E (Glu) or A (Ala) or S (Ser)

<400> SEQUENCE: 35

Ala Tyr Xaa Xaa Xaa Xaa Xaa
1               5

<210> SEQ ID NO 36
<211> LENGTH: 27
<212> TYPE: PRT
<213> ORGANISM: Artificial
```

```
<220> FEATURE:
<223> OTHER INFORMATION: Signal peptide

<400> SEQUENCE: 36

Met Lys Lys Pro Leu Gly Lys Ile Val Ala Ser Thr Ala Leu Leu Ile
1               5                   10                  15
Ser Val Ala Phe Ser Ser Ile Ala Ser Ala
            20                  25

<210> SEQ ID NO 37
<211> LENGTH: 8
<212> TYPE: PRT
<213> ORGANISM: Artificial
<220> FEATURE:
<223> OTHER INFORMATION: His tag

<400> SEQUENCE: 37

His His His His His His Pro Arg
1               5

<210> SEQ ID NO 38
<211> LENGTH: 2814
<212> TYPE: DNA
<213> ORGANISM: Microbial community
<220> FEATURE:
<221> NAME/KEY: CDS
<222> LOCATION: (1)..(2811)
<220> FEATURE:
<221> NAME/KEY: sig_peptide
<222> LOCATION: (1)..(96)
<220> FEATURE:
<221> NAME/KEY: mat_peptide
<222> LOCATION: (97)..(2811)

<400> SEQUENCE: 38 atg gaa atc gtt ttt cgc agg acg cgt gtc cgc gcg gcc gct aaa cgg      48
Met Glu Ile Val Phe Arg Arg Thr Arg Val Arg Ala Ala Ala Lys Arg
        -30                 -25                 -20 ctg ctc gcc gct tta gcg ttg ttc gtg agt ggg ccc gct gtt cag gcc      96
Leu Leu Ala Ala Leu Ala Leu Phe Val Ser Gly Pro Ala Val Gln Ala
    -15                 -10                  -5                  -1 gca gca ttg ccg caa ccc gcc agc gtg gtt ttc tgg tac gcc gat caa     144
Ala Ala Leu Pro Gln Pro Ala Ser Val Val Phe Trp Tyr Ala Asp Gln
1               5                   10                  15 cca ccc att tcc gag ttg gct cag ttc gac tgg tca gtg gtc gag ccg     192
Pro Pro Ile Ser Glu Leu Ala Gln Phe Asp Trp Ser Val Val Glu Pro
            20                  25                  30 ggg cat ctg acc gcg ggc gac gtc aaa acc ctg cgc aag ttg ggc agc     240
Gly His Leu Thr Ala Gly Asp Val Lys Thr Leu Arg Lys Leu Gly Ser
        35                  40                  45 cag ccg ttc gcc tac ctg tcg gtg ggc gag ttc cat ggt ggg aag gcc     288
Gln Pro Phe Ala Tyr Leu Ser Val Gly Glu Phe His Gly Gly Lys Ala
    50                  55                  60 gag ctc gaa aag gca tcc ctc acg gga gcg gtc agc ccg gtg cgc aat     336
Glu Leu Glu Lys Ala Ser Leu Thr Gly Ala Val Ser Pro Val Arg Asn
65                  70                  75                  80 ggt gcg tgg gac agc cag gtc atg gac ctc gcg gca cct gcc tgg cgt     384
Gly Ala Trp Asp Ser Gln Val Met Asp Leu Ala Ala Pro Ala Trp Arg
                85                  90                  95 gaa cat ttg ttc ggc cga gcc aag gcg ttg cag gct gaa ggc tac gcc     432
Glu His Leu Phe Gly Arg Ala Lys Ala Leu Gln Ala Glu Gly Tyr Ala
            100                 105                 110 ggg ttg ttc ctc gat acc ctc gac agc ttc cag ttg ctg ccg gag tcg     480
Gly Leu Phe Leu Asp Thr Leu Asp Ser Phe Gln Leu Leu Pro Glu Ser
```

```
            115                 120                 125
gca cga gaa aca cag cgt gtg gca ctc gcc ggt ttc ctg cgg gaa ttg    528
Ala Arg Glu Thr Gln Arg Val Ala Leu Ala Gly Phe Leu Arg Glu Leu
        130                 135                 140 cac cag cgc caa ccg aac ctg aag ctg ttt ttc aac cgt ggc ttc gaa    576
His Gln Arg Gln Pro Asn Leu Lys Leu Phe Phe Asn Arg Gly Phe Glu
145                 150                 155                 160 gtg ctg ccc gac ctc gat ggc gtg gcc gcc gcc gtg gcg atc gaa tcg    624
Val Leu Pro Asp Leu Asp Gly Val Ala Ala Ala Val Ala Ile Glu Ser
                165                 170                 175 att cat gcc ggt tgg gat gct tcc gcc aag cgt tat cgc ccg gta ccg    672
Ile His Ala Gly Trp Asp Ala Ser Ala Lys Arg Tyr Arg Pro Val Pro
            180                 185                 190 gaa gcc gac cgc gaa tgg ctg gaa acc cag atc cag ccg ttg cgc gcc    720
Glu Ala Asp Arg Glu Trp Leu Glu Thr Gln Ile Gln Pro Leu Arg Ala
        195                 200                 205 aaa ggt att ccg ctg gta gcg att gac tat ctg ccg ccg gag cgc cgc    768
Lys Gly Ile Pro Leu Val Ala Ile Asp Tyr Leu Pro Pro Glu Arg Arg
    210                 215                 220 gat gaa gcg cgc aaa ctg gcc aag cgt ctg cgc gat gag ggc ttc att    816
Asp Glu Ala Arg Lys Leu Ala Lys Arg Leu Arg Asp Glu Gly Phe Ile
225                 230                 235                 240 ccc tat atc ggc acg cct gag ctg gac tcg atg ggc atc agc agc atc    864
Pro Tyr Ile Gly Thr Pro Glu Leu Asp Ser Met Gly Ile Ser Ser Ile
                245                 250                 255 gaa atc cag ccg cgc cga atc gcg ctg ctt tac gac ccg cgc gaa ggc    912
Glu Ile Gln Pro Arg Arg Ile Ala Leu Leu Tyr Asp Pro Arg Glu Gly
            260                 265                 270 gat ctg gtg cgc aac gcc ggg cac acc ttg ctc ggc ggt ttg ctt gaa    960
Asp Leu Val Arg Asn Ala Gly His Thr Leu Leu Gly Gly Leu Leu Glu
        275                 280                 285 tac ctc ggc tac cgg gtc gat tac ctg ccg gtc gac ggc tcg ctg ccg   1008
Tyr Leu Gly Tyr Arg Val Asp Tyr Leu Pro Val Asp Gly Ser Leu Pro
    290                 295                 300 gag cac cgt ttc agc ggt ttg tac gcc ggg atc gtg acc tgg atg acc   1056
Glu His Arg Phe Ser Gly Leu Tyr Ala Gly Ile Val Thr Trp Met Thr
305                 310                 315                 320 agc ggc ccg ccg cag gac gca tcg gct ttc aat agc tgg atc ggc aaa   1104
Ser Gly Pro Pro Gln Asp Ala Ser Ala Phe Asn Ser Trp Ile Gly Lys
                325                 330                 335 cgt ctg gac gaa cag gtg cca gtg gtg ttc ttt tcc ggc ctg ccg att   1152
Arg Leu Asp Glu Gln Val Pro Val Val Phe Phe Ser Gly Leu Pro Ile
            340                 345                 350 caa gac ccg ctg ctg ctc aag cgc ctg ggc ctg aac cgc tcg gcg ccg   1200
Gln Asp Pro Leu Leu Leu Lys Arg Leu Gly Leu Asn Arg Ser Ala Pro
        355                 360                 365 atc ggt act cag gcc ttg acc atc agc tat cag gac aag gcg ctg atc   1248
Ile Gly Thr Gln Ala Leu Thr Ile Ser Tyr Gln Asp Lys Ala Leu Ile
    370                 375                 380 ggc gcg ttc gaa gcc ccg gtg cag ccc cgg tcc cgt gac ctg acc gca   1296
Gly Ala Phe Glu Ala Pro Val Gln Pro Arg Ser Arg Asp Leu Thr Ala
385                 390                 395                 400 atc tcc ctg ctg ccc aaa ggc ccg aaa gcc gcg ttg ctg ctg acc gct   1344
Ile Ser Leu Leu Pro Lys Gly Pro Lys Ala Ala Leu Leu Leu Thr Ala
                405                 410                 415 gcc gac ggc cag aca ttt gcc ccg gtg gcg acg gcc gag tgg ggc ggt   1392
Ala Asp Gly Gln Thr Phe Ala Pro Val Ala Thr Ala Glu Trp Gly Gly
            420                 425                 430 gtt gcc ctt gcg ccg tac att ctc gaa acg aat aac gag cgc agc cgc   1440
Val Ala Leu Ala Pro Tyr Ile Leu Glu Thr Asn Asn Glu Arg Ser Arg
```

| | |
|---|---|
| Val Ala Leu Ala Pro Tyr Ile Leu Glu Thr Asn Asn Glu Arg Ser Arg<br>     435        440       445 | |
| tgg att ctc gat ccg ttc gct ttc ctc cag gcc agc ttg cgc ctg ccg<br>Trp Ile Leu Asp Pro Phe Ala Phe Leu Gln Ala Ser Leu Arg Leu Pro<br>450        455       460 | 1488 |
| gtt cag cca cgc ccc gac acc acc acc gaa aac ggc cgc cgc atc gcc<br>Val Gln Pro Arg Pro Asp Thr Thr Thr Glu Asn Gly Arg Arg Ile Ala<br>465        470       475       480 | 1536 |
| acc gtg cac atc gac ggc gat ggt ttc ccg tcg cgc gct gaa gtg cgc<br>Thr Val His Ile Asp Gly Asp Gly Phe Pro Ser Arg Ala Glu Val Arg<br>         485       490       495 | 1584 |
| ggc acg ccg tat gcc ggc aag cag gtg ctc gac gat ttc atc cgg ccc<br>Gly Thr Pro Tyr Ala Gly Lys Gln Val Leu Asp Asp Phe Ile Arg Pro<br>     500       505      510 | 1632 |
| aac ccg ttc ctg act tcg gtg tcg atc gtc gaa ggc gag att tca ccg<br>Asn Pro Phe Leu Thr Ser Val Ser Ile Val Glu Gly Glu Ile Ser Pro<br>     515       520      525 | 1680 |
| cgc ggc atg ttc ccg ttc ctg gcg cgc gaa ctg gaa ccc att gcc cgt<br>Arg Gly Met Phe Pro Phe Leu Ala Arg Glu Leu Glu Pro Ile Ala Arg<br>530        535       540 | 1728 |
| gag ttg ttt gcc aac ccg aaa gtc gaa gtc gcc acc cac acc ttc agc<br>Glu Leu Phe Ala Asn Pro Lys Val Glu Val Ala Thr His Thr Phe Ser<br>545        550       555       560 | 1776 |
| cat ccg ttt ttc atg cag ccg gaa gtg gcg cag aaa cgt gag aac ttc<br>His Pro Phe Phe Met Gln Pro Glu Val Ala Gln Lys Arg Glu Asn Phe<br>         565       570       575 | 1824 |
| aac ccg gaa tac ggc ttg aag atg gcc att ccg ggc tac gac aaa atc<br>Asn Pro Glu Tyr Gly Leu Lys Met Ala Ile Pro Gly Tyr Asp Lys Ile<br>     580       585      590 | 1872 |
| gat ttc cgc cgc gag att ttt ggc tcg cgc gac tac atc aac cag cag<br>Asp Phe Arg Arg Glu Ile Phe Gly Ser Arg Asp Tyr Ile Asn Gln Gln<br>     595       600      605 | 1920 |
| ctc acc acc ccg gaa aaa ccg gtg aag ctg gtc ttc tgg ccg ggc gat<br>Leu Thr Thr Pro Glu Lys Pro Val Lys Leu Val Phe Trp Pro Gly Asp<br>610        615       620 | 1968 |
| gcc ttg ccc tcg gca gcg acc ttg aag ctg gcc tac gac gcg ggc ctg<br>Ala Leu Pro Ser Ala Ala Thr Leu Lys Leu Ala Tyr Asp Ala Gly Leu<br>625        630       635       640 | 2016 |
| aaa aac gtc aac ggc gcc gag acc atg ctg acc aag gcc aac ccg tcg<br>Lys Asn Val Asn Gly Ala Glu Thr Met Leu Thr Lys Ala Asn Pro Ser<br>         645       650       655 | 2064 |
| ctg acc ggc ctc aat cct ttg ctg cgt ccc acc gaa ggc ggc ctg cag<br>Leu Thr Gly Leu Asn Pro Leu Leu Arg Pro Thr Glu Gly Gly Leu Gln<br>     660       665      670 | 2112 |
| tac tac gcg ccg atc atc aac gag aac ctc tac acc aac ctg tgg aag<br>Tyr Tyr Ala Pro Ile Ile Asn Glu Asn Leu Tyr Thr Asn Leu Trp Lys<br>     675       680      685 | 2160 |
| ggg ccg tat tac ggt ttc cgc gat gtg atc gac acc ttc gaa ctc acc<br>Gly Pro Tyr Tyr Gly Phe Arg Asp Val Ile Asp Thr Phe Glu Leu Thr<br>690        695       700 | 2208 |
| gac agc cct cgg cgc ttg cgc ggc ctg cac ctg tat tac cac ttc tat<br>Asp Ser Pro Arg Arg Leu Arg Gly Leu His Leu Tyr Tyr His Phe Tyr<br>705        710       715       720 | 2256 |
| tcg agc acc aag cag gcc tcg atc aag gcg atg aac gag atc tac ggc<br>Ser Ser Thr Lys Gln Ala Ser Ile Lys Ala Met Asn Glu Ile Tyr Gly<br>         725       730       735 | 2304 |
| tac atg aag gac cag caa ccg atg tcg ctg tgg atg agc gat tac ctc<br>Tyr Met Lys Asp Gln Gln Pro Met Ser Leu Trp Met Ser Asp Tyr Leu<br>     740       745      750 | 2352 |

```
gat cgt gtg cac ggt ttg tat cag gcc agt ctg gcg cgc acc gcc gag        2400
Asp Arg Val His Gly Leu Tyr Gln Ala Ser Leu Ala Arg Thr Ala Glu
        755                 760                 765 ggt gac tgg cag gtt cgc ggc atg gac gcg ctg cgc acc ctt cga ctc        2448
Gly Asp Trp Gln Val Arg Gly Met Asp Ala Leu Arg Thr Leu Arg Leu
770                 775                 780 gac ccg caa atg ggc tgg ccg gac ctg ctg cgt tcg aaa ggc gtt gcc        2496
Asp Pro Gln Met Gly Trp Pro Asp Leu Leu Arg Ser Lys Gly Val Ala
785                 790                 795                 800 ggt gtt cgt gac ttg ccg caa ggc cgg tat gtg gcg ttg agc agc gac        2544
Gly Val Arg Asp Leu Pro Gln Gly Arg Tyr Val Ala Leu Ser Ser Asp
                805                 810                 815 cag gcg ttg ctg gtg ttg cgt ccc gac cgg gat gaa cgg ccg gcg ctg        2592
Gln Ala Leu Leu Val Leu Arg Pro Asp Arg Asp Glu Arg Pro Ala Leu
        820                 825                 830 gag gag gcc aac ctg ccg ttg gtg gac tgg aaa tat gtg gat gag aaa        2640
Glu Glu Ala Asn Leu Pro Leu Val Asp Trp Lys Tyr Val Asp Glu Lys
    835                 840                 845 cac gtg agc ttt tcg ttt gcc ggt caa gtg gac ctg agc ttc tcc gtg        2688
His Val Ser Phe Ser Phe Ala Gly Gln Val Asp Leu Ser Phe Ser Val
850                 855                 860 cgc tcg gcg agc agt tgc cgg gtg gaa gtg gac ggg caa act ttt gca        2736
Arg Ser Ala Ser Ser Cys Arg Val Glu Val Asp Gly Gln Thr Phe Ala
865                 870                 875                 880 gcc aag gca tcc gcc ggt ctg tgg act ttt caa tta cca atg aag cag        2784
Ala Lys Ala Ser Ala Gly Leu Trp Thr Phe Gln Leu Pro Met Lys Gln
                885                 890                 895 gtg agt cat ggt cag ctc tac tgc atc taa                                2814
Val Ser His Gly Gln Leu Tyr Cys Ile
        900                 905
```

<210> SEQ ID NO 39
<211> LENGTH: 937
<212> TYPE: PRT
<213> ORGANISM: Microbial community

<400> SEQUENCE: 39

```
Met Glu Ile Val Phe Arg Arg Thr Arg Val Arg Ala Ala Lys Arg
        -30                 -25                 -20

Leu Leu Ala Ala Leu Ala Leu Phe Val Ser Gly Pro Ala Val Gln Ala
    -15                 -10                  -5              -1

Ala Ala Leu Pro Gln Pro Ala Ser Val Val Phe Trp Tyr Ala Asp Gln
1                5                  10                  15

Pro Pro Ile Ser Glu Leu Ala Gln Phe Asp Trp Ser Val Val Glu Pro
                20                  25                  30

Gly His Leu Thr Ala Gly Asp Val Lys Thr Leu Arg Lys Leu Gly Ser
        35                  40                  45

Gln Pro Phe Ala Tyr Leu Ser Val Gly Glu Phe His Gly Gly Lys Ala
    50                  55                  60

Glu Leu Glu Lys Ala Ser Leu Thr Gly Ala Val Ser Pro Val Arg Asn
65                  70                  75                  80

Gly Ala Trp Asp Ser Gln Val Met Asp Leu Ala Ala Pro Ala Trp Arg
                85                  90                  95

Glu His Leu Phe Gly Arg Ala Lys Ala Leu Gln Ala Glu Gly Tyr Ala
            100                 105                 110

Gly Leu Phe Leu Asp Thr Leu Asp Ser Phe Gln Leu Leu Pro Glu Ser
        115                 120                 125

Ala Arg Glu Thr Gln Arg Val Ala Leu Ala Gly Phe Leu Arg Glu Leu
```

```
            130                 135                 140
His Gln Arg Gln Pro Asn Leu Lys Leu Phe Phe Asn Arg Gly Phe Glu
145                 150                 155                 160

Val Leu Pro Asp Leu Asp Gly Val Ala Ala Val Ala Ile Glu Ser
                165                 170                 175

Ile His Ala Gly Trp Asp Ala Ser Ala Lys Arg Tyr Arg Pro Val Pro
                180                 185                 190

Glu Ala Asp Arg Glu Trp Leu Glu Thr Gln Ile Gln Pro Leu Arg Ala
                195                 200                 205

Lys Gly Ile Pro Leu Val Ala Ile Asp Tyr Leu Pro Pro Glu Arg Arg
210                 215                 220

Asp Glu Ala Arg Lys Leu Ala Lys Arg Leu Arg Asp Glu Gly Phe Ile
225                 230                 235                 240

Pro Tyr Ile Gly Thr Pro Glu Leu Asp Ser Met Gly Ile Ser Ser Ile
                245                 250                 255

Glu Ile Gln Pro Arg Arg Ile Ala Leu Leu Tyr Asp Pro Arg Glu Gly
                260                 265                 270

Asp Leu Val Arg Asn Ala Gly His Thr Leu Leu Gly Gly Leu Leu Glu
                275                 280                 285

Tyr Leu Gly Tyr Arg Val Asp Tyr Leu Pro Val Asp Gly Ser Leu Pro
290                 295                 300

Glu His Arg Phe Ser Gly Leu Tyr Ala Gly Ile Val Thr Trp Met Thr
305                 310                 315                 320

Ser Gly Pro Pro Gln Asp Ala Ser Ala Phe Asn Ser Trp Ile Gly Lys
                325                 330                 335

Arg Leu Asp Glu Gln Val Pro Val Val Phe Phe Ser Gly Leu Pro Ile
                340                 345                 350

Gln Asp Pro Leu Leu Leu Lys Arg Leu Gly Leu Asn Arg Ser Ala Pro
                355                 360                 365

Ile Gly Thr Gln Ala Leu Thr Ile Ser Tyr Gln Asp Lys Ala Leu Ile
                370                 375                 380

Gly Ala Phe Glu Ala Pro Val Gln Pro Arg Ser Arg Asp Leu Thr Ala
385                 390                 395                 400

Ile Ser Leu Leu Pro Lys Gly Pro Lys Ala Ala Leu Leu Leu Thr Ala
                405                 410                 415

Ala Asp Gly Gln Thr Phe Ala Pro Val Ala Thr Ala Glu Trp Gly Gly
                420                 425                 430

Val Ala Leu Ala Pro Tyr Ile Leu Glu Thr Asn Asn Glu Arg Ser Arg
                435                 440                 445

Trp Ile Leu Asp Pro Phe Ala Phe Leu Gln Ala Ser Leu Arg Leu Pro
450                 455                 460

Val Gln Pro Arg Pro Asp Thr Thr Thr Glu Asn Gly Arg Arg Ile Ala
465                 470                 475                 480

Thr Val His Ile Asp Gly Asp Gly Phe Pro Ser Arg Ala Glu Val Arg
                485                 490                 495

Gly Thr Pro Tyr Ala Gly Lys Gln Val Leu Asp Asp Phe Ile Arg Pro
                500                 505                 510

Asn Pro Phe Leu Thr Ser Val Ser Ile Val Glu Gly Glu Ile Ser Pro
                515                 520                 525

Arg Gly Met Phe Pro Phe Leu Ala Arg Glu Leu Glu Pro Ile Ala Arg
                530                 535                 540

Glu Leu Phe Ala Asn Pro Lys Val Glu Val Ala Thr His Thr Phe Ser
545                 550                 555                 560
```

His Pro Phe Phe Met Gln Pro Glu Val Ala Gln Lys Arg Glu Asn Phe
            565                 570                 575

Asn Pro Glu Tyr Gly Leu Lys Met Ala Ile Pro Gly Tyr Asp Lys Ile
            580                 585                 590

Asp Phe Arg Arg Glu Ile Phe Gly Ser Arg Asp Tyr Ile Asn Gln Gln
            595                 600                 605

Leu Thr Thr Pro Glu Lys Pro Val Lys Leu Val Phe Trp Pro Gly Asp
            610                 615                 620

Ala Leu Pro Ser Ala Ala Thr Leu Lys Leu Ala Tyr Asp Ala Gly Leu
625                 630                 635                 640

Lys Asn Val Asn Gly Ala Glu Thr Met Leu Thr Lys Ala Asn Pro Ser
            645                 650                 655

Leu Thr Gly Leu Asn Pro Leu Leu Arg Pro Thr Glu Gly Gly Leu Gln
            660                 665                 670

Tyr Tyr Ala Pro Ile Ile Asn Glu Asn Leu Tyr Thr Asn Leu Trp Lys
            675                 680                 685

Gly Pro Tyr Tyr Gly Phe Arg Asp Val Ile Asp Thr Phe Glu Leu Thr
            690                 695                 700

Asp Ser Pro Arg Arg Leu Arg Gly Leu His Leu Tyr Tyr His Phe Tyr
705                 710                 715                 720

Ser Ser Thr Lys Gln Ala Ser Ile Lys Ala Met Asn Glu Ile Tyr Gly
            725                 730                 735

Tyr Met Lys Asp Gln Pro Met Ser Leu Trp Met Ser Asp Tyr Leu
            740                 745                 750

Asp Arg Val His Gly Leu Tyr Gln Ala Ser Leu Ala Arg Thr Ala Glu
            755                 760                 765

Gly Asp Trp Gln Val Arg Gly Met Asp Ala Leu Arg Thr Leu Arg Leu
770                 775                 780

Asp Pro Gln Met Gly Trp Pro Asp Leu Leu Arg Ser Lys Gly Val Ala
785                 790                 795                 800

Gly Val Arg Asp Leu Pro Gln Gly Arg Tyr Val Ala Leu Ser Ser Asp
            805                 810                 815

Gln Ala Leu Leu Val Leu Arg Pro Asp Arg Asp Glu Arg Pro Ala Leu
            820                 825                 830

Glu Glu Ala Asn Leu Pro Leu Val Asp Trp Lys Tyr Val Asp Glu Lys
            835                 840                 845

His Val Ser Phe Ser Phe Ala Gly Gln Val Asp Leu Ser Phe Ser Val
850                 855                 860

Arg Ser Ala Ser Ser Cys Arg Val Glu Val Asp Gly Gln Thr Phe Ala
865                 870                 875                 880

Ala Lys Ala Ser Ala Gly Leu Trp Thr Phe Gln Leu Pro Met Lys Gln
            885                 890                 895

Val Ser His Gly Gln Leu Tyr Cys Ile
            900                 905

<210> SEQ ID NO 40
<211> LENGTH: 905
<212> TYPE: PRT
<213> ORGANISM: Microbial community

<400> SEQUENCE: 40

Ala Ala Leu Pro Gln Pro Ala Ser Val Val Phe Trp Tyr Ala Asp Gln
1               5                   10                  15

Pro Pro Ile Ser Glu Leu Ala Gln Phe Asp Trp Ser Val Val Glu Pro

-continued

```
                 20                  25                  30
Gly His Leu Thr Ala Gly Asp Val Lys Thr Leu Arg Lys Leu Gly Ser
             35                  40                  45
Gln Pro Phe Ala Tyr Leu Ser Val Gly Glu Phe His Gly Gly Lys Ala
         50                  55                  60
Glu Leu Glu Lys Ala Ser Leu Thr Gly Ala Val Ser Pro Val Arg Asn
 65                  70                  75                  80
Gly Ala Trp Asp Ser Gln Val Met Asp Leu Ala Ala Pro Ala Trp Arg
                 85                  90                  95
Glu His Leu Phe Gly Arg Ala Lys Ala Leu Gln Ala Glu Gly Tyr Ala
            100                 105                 110
Gly Leu Phe Leu Asp Thr Leu Asp Ser Phe Gln Leu Leu Pro Glu Ser
        115                 120                 125
Ala Arg Glu Thr Gln Arg Val Ala Leu Ala Gly Phe Leu Arg Glu Leu
    130                 135                 140
His Gln Arg Gln Pro Asn Leu Lys Leu Phe Phe Asn Arg Gly Phe Glu
145                 150                 155                 160
Val Leu Pro Asp Leu Asp Gly Val Ala Ala Val Ala Ile Glu Ser
                165                 170                 175
Ile His Ala Gly Trp Asp Ala Ser Ala Lys Arg Tyr Arg Pro Val Pro
            180                 185                 190
Glu Ala Asp Arg Glu Trp Leu Glu Thr Gln Ile Gln Pro Leu Arg Ala
        195                 200                 205
Lys Gly Ile Pro Leu Val Ala Ile Asp Tyr Leu Pro Pro Glu Arg Arg
    210                 215                 220
Asp Glu Ala Arg Lys Leu Ala Lys Arg Leu Arg Asp Glu Gly Phe Ile
225                 230                 235                 240
Pro Tyr Ile Gly Thr Pro Glu Leu Asp Ser Met Gly Ile Ser Ser Ile
                245                 250                 255
Glu Ile Gln Pro Arg Arg Ile Ala Leu Leu Tyr Asp Pro Arg Glu Gly
            260                 265                 270
Asp Leu Val Arg Asn Ala Gly His Thr Leu Gly Gly Leu Leu Glu
        275                 280                 285
Tyr Leu Gly Tyr Arg Val Asp Tyr Leu Pro Val Asp Gly Ser Leu Pro
    290                 295                 300
Glu His Arg Phe Ser Gly Leu Tyr Ala Gly Ile Val Thr Trp Met Thr
305                 310                 315                 320
Ser Gly Pro Pro Gln Asp Ala Ser Ala Phe Asn Ser Trp Ile Gly Lys
                325                 330                 335
Arg Leu Asp Glu Gln Val Pro Val Val Phe Phe Ser Gly Leu Pro Ile
            340                 345                 350
Gln Asp Pro Leu Leu Lys Arg Leu Gly Leu Asn Arg Ser Ala Pro
        355                 360                 365
Ile Gly Thr Gln Ala Leu Thr Ile Ser Tyr Gln Asp Lys Ala Leu Ile
    370                 375                 380
Gly Ala Phe Glu Ala Pro Val Gln Pro Arg Ser Arg Asp Leu Thr Ala
385                 390                 395                 400
Ile Ser Leu Leu Pro Lys Gly Pro Lys Ala Ala Leu Leu Leu Thr Ala
                405                 410                 415
Ala Asp Gly Gln Thr Phe Ala Pro Val Ala Thr Ala Glu Trp Gly Gly
            420                 425                 430
Val Ala Leu Ala Pro Tyr Ile Leu Glu Thr Asn Asn Glu Arg Ser Arg
        435                 440                 445
```

```
Trp Ile Leu Asp Pro Phe Ala Phe Leu Gln Ala Ser Leu Arg Leu Pro
    450                 455                 460

Val Gln Pro Arg Pro Asp Thr Thr Glu Asn Gly Arg Arg Ile Ala
465                 470                 475                 480

Thr Val His Ile Asp Gly Asp Gly Phe Pro Ser Arg Ala Glu Val Arg
                    485                 490                 495

Gly Thr Pro Tyr Ala Gly Lys Gln Val Leu Asp Asp Phe Ile Arg Pro
                500                 505                 510

Asn Pro Phe Leu Thr Ser Val Ser Ile Val Glu Gly Glu Ile Ser Pro
            515                 520                 525

Arg Gly Met Phe Pro Phe Leu Ala Arg Glu Leu Glu Pro Ile Ala Arg
    530                 535                 540

Glu Leu Phe Ala Asn Pro Lys Val Glu Val Ala Thr His Thr Phe Ser
545                 550                 555                 560

His Pro Phe Phe Met Gln Pro Glu Val Ala Gln Lys Arg Glu Asn Phe
                565                 570                 575

Asn Pro Glu Tyr Gly Leu Lys Met Ala Ile Pro Gly Tyr Asp Lys Ile
            580                 585                 590

Asp Phe Arg Arg Glu Ile Phe Gly Ser Arg Asp Tyr Ile Asn Gln Gln
    595                 600                 605

Leu Thr Thr Pro Glu Lys Pro Val Lys Leu Val Phe Trp Pro Gly Asp
    610                 615                 620

Ala Leu Pro Ser Ala Ala Thr Leu Lys Leu Ala Tyr Asp Ala Gly Leu
625                 630                 635                 640

Lys Asn Val Asn Gly Ala Glu Thr Met Leu Thr Lys Ala Asn Pro Ser
                    645                 650                 655

Leu Thr Gly Leu Asn Pro Leu Leu Arg Pro Thr Glu Gly Gly Leu Gln
                660                 665                 670

Tyr Tyr Ala Pro Ile Ile Asn Glu Asn Leu Tyr Thr Asn Leu Trp Lys
            675                 680                 685

Gly Pro Tyr Tyr Gly Phe Arg Asp Val Ile Asp Thr Phe Glu Leu Thr
    690                 695                 700

Asp Ser Pro Arg Arg Leu Arg Gly Leu His Leu Tyr Tyr His Phe Tyr
705                 710                 715                 720

Ser Ser Thr Lys Gln Ala Ser Ile Lys Ala Met Asn Glu Ile Tyr Gly
                725                 730                 735

Tyr Met Lys Asp Gln Gln Pro Met Ser Leu Trp Met Ser Asp Tyr Leu
            740                 745                 750

Asp Arg Val His Gly Leu Tyr Gln Ala Ser Leu Ala Arg Thr Ala Glu
    755                 760                 765

Gly Asp Trp Gln Val Arg Gly Met Asp Ala Leu Arg Thr Leu Arg Leu
770                 775                 780

Asp Pro Gln Met Gly Trp Pro Asp Leu Leu Arg Ser Lys Gly Val Ala
785                 790                 795                 800

Gly Val Arg Asp Leu Pro Gln Gly Arg Tyr Val Ala Leu Ser Ser Asp
                    805                 810                 815

Gln Ala Leu Leu Val Leu Arg Pro Asp Arg Asp Glu Arg Pro Ala Leu
                820                 825                 830

Glu Glu Ala Asn Leu Pro Leu Val Asp Trp Lys Tyr Val Asp Glu Lys
            835                 840                 845

His Val Ser Phe Ser Phe Ala Gly Gln Val Asp Leu Ser Phe Ser Val
    850                 855                 860
```

```
Arg Ser Ala Ser Ser Cys Arg Val Glu Val Asp Gly Gln Thr Phe Ala
865                 870                 875                 880

Ala Lys Ala Ser Ala Gly Leu Trp Thr Phe Gln Leu Pro Met Lys Gln
                885                 890                 895

Val Ser His Gly Gln Leu Tyr Cys Ile
                900                 905

<210> SEQ ID NO 41
<211> LENGTH: 1488
<212> TYPE: DNA
<213> ORGANISM: myxococcus virescens
<220> FEATURE:
<221> NAME/KEY: CDS
<222> LOCATION: (1)..(1485)
<220> FEATURE:
<221> NAME/KEY: sig_peptide
<222> LOCATION: (1)..(84)
<220> FEATURE:
<221> NAME/KEY: mat_peptide
<222> LOCATION: (85)..(1485)

<400> SEQUENCE: 41
```

| | | |
|---|---|---|
| atg cga gtc gcg gca gta ggg tgg acg agt ctg tgg tgc atc gcg ctg<br>Met Arg Val Ala Ala Val Gly Trp Thr Ser Leu Trp Cys Ile Ala Leu<br>          -25                 -20                -15 | | 48 |
| ttc gcc tgt ggt ggt tcc tcc gga agg gcg gac agc gcg gag cgg agc<br>Phe Ala Cys Gly Gly Ser Ser Gly Arg Ala Asp Ser Ala Glu Arg Ser<br>          -10                  -5                -1 1 | | 96 |
| gag gac acg gcg ggc ctc gcg gat gct cga act ttg acg tgc gca agt<br>Glu Asp Thr Ala Gly Leu Ala Asp Ala Arg Thr Leu Thr Cys Ala Ser<br>5                 10                 15               20 | | 144 |
| ctc cag gtc gcg agc ggc gcc atc ggc tcg ggg cag agc gtc cag ggg<br>Leu Gln Val Ala Ser Gly Ala Ile Gly Ser Gly Gln Ser Val Gln Gly<br>           25                 30                 35 | | 192 |
| ctg cac acg cag aca ttg tcg ggc acg cag gac cgc tgg acg gag tac<br>Leu His Thr Gln Thr Leu Ser Gly Thr Gln Asp Arg Trp Thr Glu Tyr<br>           40                 45                 50 | | 240 |
| gtc gag ttc ttc ccc ggc acc tcc gcc acg tgc acg tac gcg ctc ccc<br>Val Glu Phe Phe Pro Gly Thr Ser Ala Thr Cys Thr Tyr Ala Leu Pro<br>           55                 60                 65 | | 288 |
| gcg gac gtg ggc gcc gcc gac gtc atc gcc gcc gag gtg ggc atc aac<br>Ala Asp Val Gly Ala Ala Asp Val Ile Ala Ala Glu Val Gly Ile Asn<br>70                75                 80 | | 336 |
| tat cgc ggg ccc gcc agg tcg cag atg cgc tgg ctg ttc gag gcg tgg<br>Tyr Arg Gly Pro Ala Arg Ser Gln Met Arg Trp Leu Phe Glu Ala Trp<br>85                90                95              100 | | 384 |
| gac tac gcg gcg ggc gcc tgg gtg ctg gtg ggc gac aac acc ttc gcg<br>Asp Tyr Ala Ala Gly Ala Trp Val Leu Val Gly Asp Asn Thr Phe Ala<br>               105                110              115 | | 432 |
| cag tcc tgg agg tgg acc gcc acg tcg ctc gcg ctg aca tct ccc cag<br>Gln Ser Trp Arg Trp Thr Ala Thr Ser Leu Ala Leu Thr Ser Pro Gln<br>           120                125              130 | | 480 |
| cgc ttc gtc agc gga ggc ccg gtg aag ctg cgc tac cgc acg acg tcc<br>Arg Phe Val Ser Gly Gly Pro Val Lys Leu Arg Tyr Arg Thr Thr Ser<br>               135                140              145 | | 528 |
| acg gcg gat gcg tcg ctg ctg gac ctg ctc gtg gtg cgc atc cag gtc<br>Thr Ala Asp Ala Ser Leu Leu Asp Leu Leu Val Val Arg Ile Gln Val<br>          150                155              160 | | 576 |
| gcc gcc tcg gac gcg ggc acg ccc ggc gat gcg ggg act ccc acg gac<br>Ala Ala Ser Asp Ala Gly Thr Pro Gly Asp Ala Gly Thr Pro Thr Asp<br>165               170                175              180 | | 624 |
| gcg ggc acc cct ggc gac gcg gga acg ggg acc gac gcc ggt acg ccc | | 672 |

-continued

```
                Ala Gly Thr Pro Gly Asp Ala Gly Thr Gly Thr Asp Ala Gly Thr Pro
                            185                 190                 195 gtg tcg tgg gag ggc gtc cac agc ttc acc tac caa ctc acg aac tat         720
Val Ser Trp Glu Gly Val His Ser Phe Thr Tyr Gln Leu Thr Asn Tyr
            200                 205                 210 ccc cag ggg aag ctg gac acc atc gcc aac tcg aag ttc gac ctg gcc         768
Pro Gln Gly Lys Leu Asp Thr Ile Ala Asn Ser Lys Phe Asp Leu Ala
        215                 220                 225 atc gtc gac ctg tcg cgc gac ggc tat gac gac tgg ttc acc gcc gcc         816
Ile Val Asp Leu Ser Arg Asp Gly Tyr Asp Asp Trp Phe Thr Ala Ala
    230                 235                 240 gaa atc acc gcg ctc aag gcc aag ggc aag cag gtg ctc gcg tac ttc         864
Glu Ile Thr Ala Leu Lys Ala Lys Gly Lys Gln Val Leu Ala Tyr Phe
245                 250                 255                 260 gag att ggc gcc atc gag gag tac cgc ccc gag tgg tcc cag gtg ccc         912
Glu Ile Gly Ala Ile Glu Glu Tyr Arg Pro Glu Trp Ser Gln Val Pro
                265                 270                 275 gag gac ctg aag ctc ggc ccc gtg ggc ggc tgg ccc gac gag cag tac         960
Glu Asp Leu Lys Leu Gly Pro Val Gly Gly Trp Pro Asp Glu Gln Tyr
            280                 285                 290 gtg aag tac tgg gac gag cgc tgg tgg ccc atc gtc cag ggc cgc ctc        1008
Val Lys Tyr Trp Asp Glu Arg Trp Trp Pro Ile Val Gln Gly Arg Leu
        295                 300                 305 gac cag gcg ctc gcc gcg ggc ttc acc ggg tgc tac ctg gac atg gtg        1056
Asp Gln Ala Leu Ala Ala Gly Phe Thr Gly Cys Tyr Leu Asp Met Val
    310                 315                 320 gtg acg tat gag gag att ccc gcg aac gcc gcg ggc acc aac cgc gcc        1104
Val Thr Tyr Glu Glu Ile Pro Ala Asn Ala Ala Gly Thr Asn Arg Ala
325                 330                 335                 340 gac ctc gcg cgg aag atg gtg gcc ctc ctg gcg cgc atc aac cag tac        1152
Asp Leu Ala Arg Lys Met Val Ala Leu Leu Ala Arg Ile Asn Gln Tyr
                345                 350                 355 gcg aag gcc cgc gac ccg ggc ttc aag gtg atg ccc cag aac tcc ccg        1200
Ala Lys Ala Arg Asp Pro Gly Phe Lys Val Met Pro Gln Asn Ser Pro
            360                 365                 370 gag ctg gtg gat gac ccc gcc tac ctg ccc gcc atc gac ggg ctg ggc        1248
Glu Leu Val Asp Asp Pro Ala Tyr Leu Pro Ala Ile Asp Gly Leu Gly
        375                 380                 385 atg gag gac ctg tac tgg tcc gac gac aac gcc tgc gac gag ggt tgg        1296
Met Glu Asp Leu Tyr Trp Ser Asp Asp Asn Ala Cys Asp Glu Gly Trp
    390                 395                 400 tgc gag gag aac cgg gcc aac gcg gcc cgg gtc cgc gcg gcc ggc aag        1344
Cys Glu Glu Asn Arg Ala Asn Ala Ala Arg Val Arg Ala Ala Gly Lys
405                 410                 415                 420 ctg gtg ctc tcc acc gac tac gcc gtg cag gcc gcg aac gtc gcg gac        1392
Leu Val Leu Ser Thr Asp Tyr Ala Val Gln Ala Ala Asn Val Ala Asp
                425                 430                 435 gcc tat acc cgc tcg cgc gcg gcg ggc ttc gtc ccc tac gtc tcc gtg        1440
Ala Tyr Thr Arg Ser Arg Ala Ala Gly Phe Val Pro Tyr Val Ser Val
            440                 445                 450 cgc gcg ttg gac cgg atg acg gtg aac gcg ggg tgg gat ccg cag tag        1488
Arg Ala Leu Asp Arg Met Thr Val Asn Ala Gly Trp Asp Pro Gln
        455                 460                 465
```

<210> SEQ ID NO 42
<211> LENGTH: 495
<212> TYPE: PRT
<213> ORGANISM: myxococcus virescens

<400> SEQUENCE: 42

```
Met Arg Val Ala Ala Val Gly Trp Thr Ser Leu Trp Cys Ile Ala Leu
        -25              -20              -15
Phe Ala Cys Gly Gly Ser Ser Gly Arg Ala Asp Ser Ala Glu Arg Ser
        -10              -5                -1   1
Glu Asp Thr Ala Gly Leu Ala Asp Ala Arg Thr Leu Thr Cys Ala Ser
 5                   10                   15                  20
Leu Gln Val Ala Ser Gly Ala Ile Gly Ser Gln Ser Val Gln Gly
                 25              30                   35
Leu His Thr Gln Thr Leu Ser Gly Thr Gln Asp Arg Trp Thr Glu Tyr
                 40                   45                   50
Val Glu Phe Phe Pro Gly Thr Ser Ala Thr Cys Thr Tyr Ala Leu Pro
             55                   60              65
Ala Asp Val Gly Ala Ala Asp Val Ile Ala Ala Glu Val Gly Ile Asn
 70                   75                   80
Tyr Arg Gly Pro Ala Arg Ser Gln Met Arg Trp Leu Phe Glu Ala Trp
 85                   90                   95                 100
Asp Tyr Ala Ala Gly Ala Trp Val Leu Val Gly Asp Asn Thr Phe Ala
                 105                  110                  115
Gln Ser Trp Arg Trp Thr Ala Thr Ser Leu Ala Leu Thr Ser Pro Gln
             120                  125                  130
Arg Phe Val Ser Gly Gly Pro Val Lys Leu Arg Tyr Arg Thr Thr Ser
             135                  140                  145
Thr Ala Asp Ala Ser Leu Leu Asp Leu Leu Val Val Arg Ile Gln Val
             150                  155                  160
Ala Ala Ser Asp Ala Gly Thr Pro Gly Asp Ala Gly Thr Pro Thr Asp
 165                  170                  175                  180
Ala Gly Thr Pro Gly Asp Ala Gly Thr Gly Thr Asp Ala Gly Thr Pro
                 185                  190                  195
Val Ser Trp Glu Gly Val His Ser Phe Thr Tyr Gln Leu Thr Asn Tyr
             200                  205                  210
Pro Gln Gly Lys Leu Asp Thr Ile Ala Asn Ser Lys Phe Asp Leu Ala
             215                  220                  225
Ile Val Asp Leu Ser Arg Asp Gly Tyr Asp Asp Trp Phe Thr Ala Ala
 230                  235                  240
Glu Ile Thr Ala Leu Lys Ala Lys Gly Lys Gln Val Leu Ala Tyr Phe
 245                  250                  255                  260
Glu Ile Gly Ala Ile Glu Glu Tyr Arg Pro Glu Trp Ser Gln Val Pro
                 265                  270                  275
Glu Asp Leu Lys Leu Gly Pro Val Gly Gly Trp Pro Asp Glu Gln Tyr
             280                  285                  290
Val Lys Tyr Trp Asp Glu Arg Trp Pro Ile Val Gln Gly Arg Leu
             295                  300                  305
Asp Gln Ala Leu Ala Ala Gly Phe Thr Gly Cys Tyr Leu Asp Met Val
             310                  315                  320
Val Thr Tyr Glu Glu Ile Pro Ala Asn Ala Ala Gly Thr Asn Arg Ala
 325                  330                  335                  340
Asp Leu Ala Arg Lys Met Val Ala Leu Leu Ala Arg Ile Asn Gln Tyr
                 345                  350                  355
Ala Lys Ala Arg Asp Pro Gly Phe Lys Val Met Pro Gln Asn Ser Pro
                 360                  365                  370
Glu Leu Val Asp Asp Pro Ala Tyr Leu Pro Ala Ile Asp Gly Leu Gly
             375                  380                  385
Met Glu Asp Leu Tyr Trp Ser Asp Asp Asn Ala Cys Asp Glu Gly Trp
```

```
                390                 395                 400
Cys Glu Glu Asn Arg Ala Asn Ala Ala Arg Val Arg Ala Ala Gly Lys
405                 410                 415                 420

Leu Val Leu Ser Thr Asp Tyr Ala Val Gln Ala Ala Asn Val Ala Asp
                425                 430                 435

Ala Tyr Thr Arg Ser Arg Ala Ala Gly Phe Val Pro Tyr Val Ser Val
                440                 445                 450

Arg Ala Leu Asp Arg Met Thr Val Asn Ala Gly Trp Asp Pro Gln
                455                 460                 465

<210> SEQ ID NO 43
<211> LENGTH: 467
<212> TYPE: PRT
<213> ORGANISM: Myxococcus virescens

<400> SEQUENCE: 43

Ala Glu Arg Ser Glu Asp Thr Ala Gly Leu Ala Asp Ala Arg Thr Leu
1               5                   10                  15

Thr Cys Ala Ser Leu Gln Val Ala Ser Gly Ala Ile Gly Ser Gly Gln
                20                  25                  30

Ser Val Gln Gly Leu His Thr Gln Thr Leu Ser Gly Thr Gln Asp Arg
            35                  40                  45

Trp Thr Glu Tyr Val Glu Phe Phe Pro Gly Thr Ser Ala Thr Cys Thr
50                  55                  60

Tyr Ala Leu Pro Ala Asp Val Gly Ala Ala Asp Val Ile Ala Ala Glu
65                  70                  75                  80

Val Gly Ile Asn Tyr Arg Gly Pro Ala Arg Ser Gln Met Arg Trp Leu
                85                  90                  95

Phe Glu Ala Trp Asp Tyr Ala Ala Gly Ala Trp Val Leu Val Gly Asp
            100                 105                 110

Asn Thr Phe Ala Gln Ser Trp Arg Trp Thr Ala Thr Ser Leu Ala Leu
        115                 120                 125

Thr Ser Pro Gln Arg Phe Val Ser Gly Gly Pro Val Lys Leu Arg Tyr
130                 135                 140

Arg Thr Thr Ser Thr Ala Asp Ala Ser Leu Leu Asp Leu Leu Val Val
145                 150                 155                 160

Arg Ile Gln Val Ala Ala Ser Asp Ala Gly Thr Pro Gly Asp Ala Gly
                165                 170                 175

Thr Pro Thr Asp Ala Gly Thr Pro Gly Asp Ala Gly Thr Gly Thr Asp
            180                 185                 190

Ala Gly Thr Pro Val Ser Trp Glu Gly Val His Ser Phe Thr Tyr Gln
        195                 200                 205

Leu Thr Asn Tyr Pro Gln Gly Lys Leu Asp Thr Ile Ala Asn Ser Lys
    210                 215                 220

Phe Asp Leu Ala Ile Val Asp Leu Ser Arg Asp Gly Tyr Asp Trp
225                 230                 235                 240

Phe Thr Ala Ala Glu Ile Thr Ala Leu Lys Ala Lys Gly Lys Gln Val
                245                 250                 255

Leu Ala Tyr Phe Glu Ile Gly Ala Ile Glu Glu Tyr Arg Pro Glu Trp
            260                 265                 270

Ser Gln Val Pro Glu Asp Leu Lys Leu Gly Pro Val Gly Gly Trp Pro
        275                 280                 285

Asp Glu Gln Tyr Val Lys Tyr Trp Asp Glu Arg Trp Trp Pro Ile Val
    290                 295                 300
```

```
Gln Gly Arg Leu Asp Gln Ala Leu Ala Ala Gly Phe Thr Gly Cys Tyr
305                 310                 315                 320

Leu Asp Met Val Val Thr Tyr Glu Glu Ile Pro Ala Asn Ala Ala Gly
                325                 330                 335

Thr Asn Arg Ala Asp Leu Ala Arg Lys Met Val Ala Leu Leu Ala Arg
            340                 345                 350

Ile Asn Gln Tyr Ala Lys Ala Arg Asp Pro Gly Phe Lys Val Met Pro
        355                 360                 365

Gln Asn Ser Pro Glu Leu Val Asp Asp Pro Ala Tyr Leu Pro Ala Ile
    370                 375                 380

Asp Gly Leu Gly Met Glu Asp Leu Tyr Trp Ser Asp Asp Asn Ala Cys
385                 390                 395                 400

Asp Glu Gly Trp Cys Glu Glu Asn Arg Ala Asn Ala Ala Arg Val Arg
                405                 410                 415

Ala Ala Gly Lys Leu Val Leu Ser Thr Asp Tyr Ala Val Gln Ala Ala
            420                 425                 430

Asn Val Ala Asp Ala Tyr Thr Arg Ser Arg Ala Ala Gly Phe Val Pro
        435                 440                 445

Tyr Val Ser Val Arg Ala Leu Asp Arg Met Thr Val Asn Ala Gly Trp
    450                 455                 460

Asp Pro Gln
465

<210> SEQ ID NO 44
<211> LENGTH: 1449
<212> TYPE: DNA
<213> ORGANISM: Myxococcus fulvus
<220> FEATURE:
<221> NAME/KEY: CDS
<222> LOCATION: (1)..(1446)
<220> FEATURE:
<221> NAME/KEY: sig_peptide
<222> LOCATION: (1)..(54)
<220> FEATURE:
<221> NAME/KEY: mat_peptide
<222> LOCATION: (55)..(1446)

<400> SEQUENCE: 44 atg cga gtc gcg atg aag tgg ttg ttg gct tgg acc tgg ctg gcc ctg     48
Met Arg Val Ala Met Lys Trp Leu Leu Ala Trp Thr Trp Leu Ala Leu
            -15                 -10                  -5 ctg gcc gcg tgt ggc gac aag gcc ccg cac gat gat ttc gac acc gga     96
Leu Ala Ala Cys Gly Asp Lys Ala Pro His Asp Asp Phe Asp Thr Gly
         -1   1               5                  10 cag gac gcc atc ctg ccc gac gcg cgg acc ctg ccc tgc acc acg ctc    144
Gln Asp Ala Ile Leu Pro Asp Ala Arg Thr Leu Pro Cys Thr Thr Leu
 15                  20                  25                  30 cag ttc gag cgc ggc gcc ctg ccc tcg ggc cag agc gtc cag gga ctc    192
Gln Phe Glu Arg Gly Ala Leu Pro Ser Gly Gln Ser Val Gln Gly Leu
                 35                  40                  45 aac acc cag acg ttg tcc gga acg cag gac cgc tgg gcc gag tac gtc    240
Asn Thr Gln Thr Leu Ser Gly Thr Gln Asp Arg Trp Ala Glu Tyr Val
             50                  55                  60 gag ttc gcg ccg aac agc tcc gcc acg tgc acc cat ccg ctg ccc acc    288
Glu Phe Ala Pro Asn Ser Ser Ala Thr Cys Thr His Pro Leu Pro Thr
         65                  70                  75 ggc gtg agc gcg gac agc gtc gtc gcg gcc gag gtc ggc gtg aac tac    336
Gly Val Ser Ala Asp Ser Val Val Ala Ala Glu Val Gly Val Asn Tyr
 80                  85                  90 cga ggc ccc acg aag gcg cag atg cgc tgg gtc atc gag gcg tgg gac    384
Arg Gly Pro Thr Lys Ala Gln Met Arg Trp Val Ile Glu Ala Trp Asp
```

```
                Arg Gly Pro Thr Lys Ala Gln Met Arg Trp Val Ile Glu Ala Trp Asp
                 95                 100                 105                 110 tac tcg acg aac agc tgg gcc ctg gtg ggt gac aac acc ttc gcg cag        432
Tyr Ser Thr Asn Ser Trp Ala Leu Val Gly Asp Asn Thr Phe Ala Gln
                115                 120                 125 tcg tgg cgc tgg acg gcc acg tcg ctg gcc ctg ccc acg ccc gcg cgc        480
Ser Trp Arg Trp Thr Ala Thr Ser Leu Ala Leu Pro Thr Pro Ala Arg
            130                 135                 140 ttc ctg tcc ggc ggc ccg gtg aag ctg cgc tac cgc acg gac tcc acc        528
Phe Leu Ser Gly Gly Pro Val Lys Leu Arg Tyr Arg Thr Asp Ser Thr
        145                 150                 155 gcg gac gcg tcg ctg ctg gac ctg ctc gtc gtg cgc gta cag gtc gcg        576
Ala Asp Ala Ser Leu Leu Asp Leu Leu Val Val Arg Val Gln Val Ala
    160                 165                 170 gcg agc gac gcg ggc act ccc acc gac gcg ggg act ccg acg gac gcg        624
Ala Ser Asp Ala Gly Thr Pro Thr Asp Ala Gly Thr Pro Thr Asp Ala
175                 180                 185                 190 ggc acg cag gta ccc tgg tcg aac gtg aag agc ttc acg tac cag ctc        672
Gly Thr Gln Val Pro Trp Ser Asn Val Lys Ser Phe Thr Tyr Gln Leu
                195                 200                 205 acc aac tat ccg cag ggc aag ctc gac gcg att gcc gcg tcg aag ttc        720
Thr Asn Tyr Pro Gln Gly Lys Leu Asp Ala Ile Ala Ala Ser Lys Phe
            210                 215                 220 gac ctg gcc atc gtc gag ctc gtg cgc gac ggc tcc agc ggc tac ttc        768
Asp Leu Ala Ile Val Glu Leu Val Arg Asp Gly Ser Ser Gly Tyr Phe
        225                 230                 235 acc gcg gcg gag att tcg gcg ctc aag gcc cgg ggc aag cag gtg ctc        816
Thr Ala Ala Glu Ile Ser Ala Leu Lys Ala Arg Gly Lys Gln Val Leu
    240                 245                 250 gcg tac ttc gag att ggc gcc atc gag gag tac cgc ccc gag tgg agc        864
Ala Tyr Phe Glu Ile Gly Ala Ile Glu Glu Tyr Arg Pro Glu Trp Ser
255                 260                 265                 270 cag gtg ccc gcg gac ctg aag ctc ggc ccc gtc tcc ggc tgg ccc gac        912
Gln Val Pro Ala Asp Leu Lys Leu Gly Pro Val Ser Gly Trp Pro Asp
                275                 280                 285 gag cag tac gtg aag tac tgg gac gag cgc tgg tgg ccc atc gtc cag        960
Glu Gln Tyr Val Lys Tyr Trp Asp Glu Arg Trp Trp Pro Ile Val Gln
            290                 295                 300 ggc cgc atc gac cgc gcg ctc gcc gcg ggc ttc aac ggc tgc tac ctc       1008
Gly Arg Ile Asp Arg Ala Leu Ala Ala Gly Phe Asn Gly Cys Tyr Leu
        305                 310                 315 gac atg gtc gtc acg tac gag gag att ccc gcc aac tcc gcc ggc acc       1056
Asp Met Val Val Thr Tyr Glu Glu Ile Pro Ala Asn Ser Ala Gly Thr
    320                 325                 330 aac cgc gcc gac ctc gcg cgg aag atg gtg gcc ctc atc gcg cgc atc       1104
Asn Arg Ala Asp Leu Ala Arg Lys Met Val Ala Leu Ile Ala Arg Ile
335                 340                 345                 350 aac acg tac gcg aag gcg cgc aac ccg gac ttc aag gtg gtg ccg cag       1152
Asn Thr Tyr Ala Lys Ala Arg Asn Pro Asp Phe Lys Val Val Pro Gln
                355                 360                 365 aac tcg ccg gag ctg gtc gat gac ccg gcc tac ctg ccc gcc atc gac       1200
Asn Ser Pro Glu Leu Val Asp Asp Pro Ala Tyr Leu Pro Ala Ile Asp
            370                 375                 380 ggg ctg ggc atg gag gac atg tac tgg tcc gac gac gtg gcc tgc gac       1248
Gly Leu Gly Met Glu Asp Met Tyr Trp Ser Asp Asp Val Ala Cys Asp
        385                 390                 395 gag ggc tgg tgc gag gag aac cgc acc aac gcc gct cgc gtg cgc gcc       1296
Glu Gly Trp Cys Glu Glu Asn Arg Thr Asn Ala Ala Arg Val Arg Ala
    400                 405                 410
```

```
gcg ggc aag ctg gtg ctg tcc acc gac tat gcc acg cag tcc gcc cac    1344
Ala Gly Lys Leu Val Leu Ser Thr Asp Tyr Ala Thr Gln Ser Ala His
415                 420                 425                 430 gtc gcg gat gcg tac acc cgc tcg cgc gcc gcg ggc ttc gtg ccc tac    1392
Val Ala Asp Ala Tyr Thr Arg Ser Arg Ala Ala Gly Phe Val Pro Tyr
                435                 440                 445 gtc acc gtg cgc gcg ctg gac cgc gtg acg gtg aac gcg gga tgg gac    1440
Val Thr Val Arg Ala Leu Asp Arg Val Thr Val Asn Ala Gly Trp Asp
            450                 455                 460 ccg cag tag                                                         1449
Pro Gln <210> SEQ ID NO 45
<211> LENGTH: 482
<212> TYPE: PRT
<213> ORGANISM: Myxococcus fulvus

<400> SEQUENCE: 45

Met Arg Val Ala Met Lys Trp Leu Leu Ala Trp Thr Trp Leu Ala Leu
                -15                 -10                 -5

Leu Ala Ala Cys Gly Asp Lys Ala Pro His Asp Asp Phe Asp Thr Gly
    -1  1               5                   10

Gln Asp Ala Ile Leu Pro Asp Ala Arg Thr Leu Pro Cys Thr Thr Leu
15                  20                  25                  30

Gln Phe Glu Arg Gly Ala Leu Pro Ser Gly Gln Ser Val Gln Gly Leu
                35                  40                  45

Asn Thr Gln Thr Leu Ser Gly Thr Gln Asp Arg Trp Ala Glu Tyr Val
            50                  55                  60

Glu Phe Ala Pro Asn Ser Ser Ala Thr Cys Thr His Pro Leu Pro Thr
65                  70                  75

Gly Val Ser Ala Asp Ser Val Val Ala Glu Val Gly Val Asn Tyr
            80                  85                  90

Arg Gly Pro Thr Lys Ala Gln Met Arg Trp Val Ile Glu Ala Trp Asp
95                  100                 105                 110

Tyr Ser Thr Asn Ser Trp Ala Leu Val Gly Asp Asn Thr Phe Ala Gln
                115                 120                 125

Ser Trp Arg Trp Thr Ala Thr Ser Leu Ala Leu Pro Thr Pro Ala Arg
            130                 135                 140

Phe Leu Ser Gly Gly Pro Val Lys Leu Arg Tyr Arg Thr Asp Ser Thr
145                 150                 155

Ala Asp Ala Ser Leu Leu Asp Leu Leu Val Val Arg Val Gln Val Ala
            160                 165                 170

Ala Ser Asp Ala Gly Thr Pro Thr Asp Ala Gly Thr Pro Thr Asp Ala
175                 180                 185                 190

Gly Thr Gln Val Pro Trp Ser Asn Val Lys Ser Phe Thr Tyr Gln Leu
                195                 200                 205

Thr Asn Tyr Pro Gln Gly Lys Leu Asp Ala Ile Ala Ala Ser Lys Phe
            210                 215                 220

Asp Leu Ala Ile Val Glu Leu Val Arg Asp Gly Ser Ser Gly Tyr Phe
225                 230                 235

Thr Ala Ala Glu Ile Ser Ala Leu Lys Ala Arg Gly Lys Gln Val Leu
            240                 245                 250

Ala Tyr Phe Glu Ile Gly Ala Ile Glu Glu Tyr Arg Pro Glu Trp Ser
255                 260                 265                 270

Gln Val Pro Ala Asp Leu Lys Leu Gly Pro Val Ser Gly Trp Pro Asp
                275                 280                 285
```

-continued

Glu Gln Tyr Val Lys Tyr Trp Asp Glu Arg Trp Pro Ile Val Gln
            290                 295                 300

Gly Arg Ile Asp Arg Ala Leu Ala Ala Gly Phe Asn Gly Cys Tyr Leu
            305                 310                 315

Asp Met Val Val Thr Tyr Glu Glu Ile Pro Ala Asn Ser Ala Gly Thr
320                 325                 330

Asn Arg Ala Asp Leu Ala Arg Lys Met Val Ala Leu Ile Ala Arg Ile
335                 340                 345                 350

Asn Thr Tyr Ala Lys Ala Arg Asn Pro Asp Phe Lys Val Val Pro Gln
                355                 360                 365

Asn Ser Pro Glu Leu Val Asp Asp Pro Ala Tyr Leu Pro Ala Ile Asp
            370                 375                 380

Gly Leu Gly Met Glu Asp Met Tyr Trp Ser Asp Asp Val Ala Cys Asp
            385                 390                 395

Glu Gly Trp Cys Glu Glu Asn Arg Thr Asn Ala Ala Arg Val Arg Ala
            400                 405                 410

Ala Gly Lys Leu Val Leu Ser Thr Asp Tyr Ala Thr Gln Ser Ala His
415                 420                 425                 430

Val Ala Asp Ala Tyr Thr Arg Ser Arg Ala Ala Gly Phe Val Pro Tyr
                435                 440                 445

Val Thr Val Arg Ala Leu Asp Arg Val Thr Val Asn Ala Gly Trp Asp
            450                 455                 460

Pro Gln

<210> SEQ ID NO 46
<211> LENGTH: 464
<212> TYPE: PRT
<213> ORGANISM: Myxococcus fulvus

<400> SEQUENCE: 46

Ala Cys Gly Asp Lys Ala Pro His Asp Asp Phe Asp Thr Gly Gln Asp
1               5                   10                  15

Ala Ile Leu Pro Asp Ala Arg Thr Leu Pro Cys Thr Thr Leu Gln Phe
            20                  25                  30

Glu Arg Gly Ala Leu Pro Ser Gly Gln Ser Val Gln Gly Leu Asn Thr
        35                  40                  45

Gln Thr Leu Ser Gly Thr Gln Asp Arg Trp Ala Glu Tyr Val Glu Phe
    50                  55                  60

Ala Pro Asn Ser Ser Ala Thr Cys Thr His Pro Leu Pro Thr Gly Val
65                  70                  75                  80

Ser Ala Asp Ser Val Val Ala Ala Glu Val Gly Val Asn Tyr Arg Gly
                85                  90                  95

Pro Thr Lys Ala Gln Met Arg Trp Val Ile Glu Ala Trp Asp Tyr Ser
            100                 105                 110

Thr Asn Ser Trp Ala Leu Val Gly Asp Asn Thr Phe Ala Gln Ser Trp
        115                 120                 125

Arg Trp Thr Ala Thr Ser Leu Ala Leu Pro Thr Pro Ala Arg Phe Leu
    130                 135                 140

Ser Gly Gly Pro Val Lys Leu Arg Tyr Arg Thr Asp Ser Thr Ala Asp
145                 150                 155                 160

Ala Ser Leu Leu Asp Leu Leu Val Val Arg Val Gln Val Ala Ala Ser
                165                 170                 175

Asp Ala Gly Thr Pro Thr Asp Ala Gly Thr Pro Thr Asp Ala Gly Thr
            180                 185                 190

```
Gln Val Pro Trp Ser Asn Val Lys Ser Phe Thr Tyr Gln Leu Thr Asn
            195                 200                 205

Tyr Pro Gln Gly Lys Leu Asp Ala Ile Ala Ala Ser Lys Phe Asp Leu
    210                 215                 220

Ala Ile Val Glu Leu Val Arg Asp Gly Ser Ser Gly Tyr Phe Thr Ala
225                 230                 235                 240

Ala Glu Ile Ser Ala Leu Lys Ala Arg Gly Lys Gln Val Leu Ala Tyr
                245                 250                 255

Phe Glu Ile Gly Ala Ile Glu Glu Tyr Arg Pro Glu Trp Ser Gln Val
            260                 265                 270

Pro Ala Asp Leu Lys Leu Gly Pro Val Ser Gly Trp Pro Asp Glu Gln
    275                 280                 285

Tyr Val Lys Tyr Trp Asp Glu Arg Trp Pro Ile Val Gln Gly Arg
    290                 295                 300

Ile Asp Arg Ala Leu Ala Ala Gly Phe Asn Gly Cys Tyr Leu Asp Met
305                 310                 315                 320

Val Val Thr Tyr Glu Glu Ile Pro Ala Asn Ser Ala Gly Thr Asn Arg
                325                 330                 335

Ala Asp Leu Ala Arg Lys Met Val Ala Leu Ile Ala Arg Ile Asn Thr
            340                 345                 350

Tyr Ala Lys Ala Arg Asn Pro Asp Phe Lys Val Val Pro Gln Asn Ser
    355                 360                 365

Pro Glu Leu Val Asp Asp Pro Ala Tyr Leu Pro Ala Ile Asp Gly Leu
370                 375                 380

Gly Met Glu Asp Met Tyr Trp Ser Asp Val Ala Cys Asp Glu Gly
385                 390                 395                 400

Trp Cys Glu Glu Asn Arg Thr Asn Ala Ala Arg Val Arg Ala Ala Gly
                405                 410                 415

Lys Leu Val Leu Ser Thr Asp Tyr Ala Thr Gln Ser Ala His Val Ala
            420                 425                 430

Asp Ala Tyr Thr Arg Ser Arg Ala Ala Gly Phe Val Pro Tyr Val Thr
    435                 440                 445

Val Arg Ala Leu Asp Arg Val Thr Val Asn Ala Gly Trp Asp Pro Gln
450                 455                 460

<210> SEQ ID NO 47
<211> LENGTH: 1500
<212> TYPE: DNA
<213> ORGANISM: Myxococcus macrosporus
<220> FEATURE:
<221> NAME/KEY: CDS
<222> LOCATION: (1)..(1497)
<220> FEATURE:
<221> NAME/KEY: sig_peptide
<222> LOCATION: (1)..(72)
<220> FEATURE:
<221> NAME/KEY: mat_peptide
<222> LOCATION: (73)..(1497)

<400> SEQUENCE: 47 atg cga gtc gct gtg aag tgg ttg acg tgg acc tgc ctg gcc ttg ctg      48
Met Arg Val Ala Val Lys Trp Leu Thr Trp Thr Cys Leu Ala Leu Leu
            -20                 -15                 -10 gcc gcc tgt ggt gga agc agt gcg cgt gat tcg ctc gac gac gag cgc      96
Ala Ala Cys Gly Gly Ser Ser Ala Arg Asp Ser Leu Asp Asp Glu Arg
        -5                  -1  1                   5 ggc gcg att ctc ccc gat gcg cag acg ctc acc tgc gcc acc ctc cag     144
Gly Ala Ile Leu Pro Asp Ala Gln Thr Leu Thr Cys Ala Thr Leu Gln
```

-continued

|  |  |  |  |
|---|---|---|---|
| ctc gcg cgg ggc tcc atc ggc tcg ggc cag ggc gtg cag ggc ctg cac<br>Leu Ala Arg Gly Ser Ile Gly Ser Gly Gln Gly Val Gln Gly Leu His<br>25                         30                           35                        40 | 192 |
| acg cag acg ctg tcc gga acg cag gac cgc tgg gcg gag tac gtc gag<br>Thr Gln Thr Leu Ser Gly Thr Gln Asp Arg Trp Ala Glu Tyr Val Glu<br>                        45                         50                        55 | 240 |
| ttc gcc ccg aac agc tcc gcc acg tgc acc tat ccg ctg ccc gcg ggc<br>Phe Ala Pro Asn Ser Ser Ala Thr Cys Thr Tyr Pro Leu Pro Ala Gly<br>              60                        65                        70 | 288 |
| gtg agc gcg gac acc gtc gtc gcg gct gaa atc gga gtg aac ttc cgg<br>Val Ser Ala Asp Thr Val Val Ala Ala Glu Ile Gly Val Asn Phe Arg<br>        75                        80                        85 | 336 |
| ggc ccg acg aag tcg gcg atg cgc tgg ctg ttc gag gcc tgg gac tat<br>Gly Pro Thr Lys Ser Ala Met Arg Trp Leu Phe Glu Ala Trp Asp Tyr<br>90                         95                         100 | 384 |
| tcg acg gga gcc tgg gtc gtc gtc gga gac aac gtc ttc gcg cag tcg<br>Ser Thr Gly Ala Trp Val Val Val Gly Asp Asn Val Phe Ala Gln Ser<br>105                       110                      115                   120 | 432 |
| tgg aag tgg tcc gcc acg tcg ctg gcc ctc acc tcc ccc tcg cgg ttc<br>Trp Lys Trp Ser Ala Thr Ser Leu Ala Leu Thr Ser Pro Ser Arg Phe<br>                        125                       130                   135 | 480 |
| ttc tcc gga ggg ccg gtg aag ctg cgc tac cgc acg gag tcc tcg gcg<br>Phe Ser Gly Gly Pro Val Lys Leu Arg Tyr Arg Thr Glu Ser Ser Ala<br>        140                       145                       150 | 528 |
| gat gcg tcg ctg ctg gac ctg ctg gtg gtg cgc gtg cag gtg gcg gcg<br>Asp Ala Ser Leu Leu Asp Leu Leu Val Val Arg Val Gln Val Ala Ala<br>            155                       160                     165 | 576 |
| acg gac gcg ggg act ccc acg gat gcg ggc acg ccg acg gat gcc gga<br>Thr Asp Ala Gly Thr Pro Thr Asp Ala Gly Thr Pro Thr Asp Ala Gly<br>170                       175                      180 | 624 |
| act ccg acg gac gcc ggg aca ccc acc gat gca ggc acc tcc acc gat<br>Thr Pro Thr Asp Ala Gly Thr Pro Thr Asp Ala Gly Thr Ser Thr Asp<br>185                       190                      195                   200 | 672 |
| gcg ggc acg ccg gtt ccc tgg gag ggc gtc agc agc ttc acg tac cag<br>Ala Gly Thr Pro Val Pro Trp Glu Gly Val Ser Ser Phe Thr Tyr Gln<br>                        205                       210                   215 | 720 |
| ctc acc aac tat ccc cag ggc aag ctc gac gcg att gcc gcc tcg aag<br>Leu Thr Asn Tyr Pro Gln Gly Lys Leu Asp Ala Ile Ala Ala Ser Lys<br>        220                       225                       230 | 768 |
| ttc gac ctc gcc atc gtc gag ctg gtg cga gac ggc tcg agc ggc tac<br>Phe Asp Leu Ala Ile Val Glu Leu Val Arg Asp Gly Ser Ser Gly Tyr<br>            235                     240                       245 | 816 |
| ttc acc gcc gcc gag att tcc gcg ctc aag gcc cgg ggc aag cag gtg<br>Phe Thr Ala Ala Glu Ile Ser Ala Leu Lys Ala Arg Gly Lys Gln Val<br>250                       255                      260 | 864 |
| ctc gcc tac ttc gag att ggc gcg att gaa gag tac cgc ccc gag tgg<br>Leu Ala Tyr Phe Glu Ile Gly Ala Ile Glu Glu Tyr Arg Pro Glu Trp<br>265                       270                      275                   280 | 912 |
| agc cag gtg ccc gcg gac ctg aag ctc ggc ccc gtg gat ggc tgg ccc<br>Ser Gln Val Pro Ala Asp Leu Lys Leu Gly Pro Val Asp Gly Trp Pro<br>                        285                       290                   295 | 960 |
| gat gag cag tac gtg aag tac tgg gac gag cgc tgg tgg ccc atc gtc<br>Asp Glu Gln Tyr Val Lys Tyr Trp Asp Glu Arg Trp Trp Pro Ile Val<br>        300                       305                       310 | 1008 |
| cag ggc cgc atc gac cgc gcg ctc gcc gcg ggc ttc acc ggc tgc tac<br>Gln Gly Arg Ile Asp Arg Ala Leu Ala Ala Gly Phe Thr Gly Cys Tyr<br>            315                     320                      325 | 1056 |
| ctg gac atg gtg gtg acg tac gag gag att ccc gcc aac gct gcg ggc<br>  | 1104 |

```
Leu Asp Met Val Val Thr Tyr Glu Glu Ile Pro Ala Asn Ala Ala Gly
    330                 335                 340 acc aac cgc gcc gac ctc gct cgg aag atg gtg gcg ctc atc gcc cgc    1152
Thr Asn Arg Ala Asp Leu Ala Arg Lys Met Val Ala Leu Ile Ala Arg
345                 350                 355                 360 atc agc cag tac gcg aag gcg cgc aac ccg gcc ttc aag gtg atg ccg    1200
Ile Ser Gln Tyr Ala Lys Ala Arg Asn Pro Ala Phe Lys Val Met Pro
            365                 370                 375 cag aac tcc ccg gag ctc gtc gat gac ccg gcc tac ctg ccc gtc atc    1248
Gln Asn Ser Pro Glu Leu Val Asp Asp Pro Ala Tyr Leu Pro Val Ile
                380                 385                 390 gat ggc ctg ggc atg gag gac atg tac tgg tcc gac gac gtc gcg tgc    1296
Asp Gly Leu Gly Met Glu Asp Met Tyr Trp Ser Asp Asp Val Ala Cys
            395                 400                 405 gac gcg agc tgg tgc gcg gag aac cgc gcc aac gcc gcc cgg gtg cgc    1344
Asp Ala Ser Trp Cys Ala Glu Asn Arg Ala Asn Ala Ala Arg Val Arg
410                 415                 420 gcc gcg ggc aag ctg gtg ctg tcc acc gac tac gcc gtc cag tcc gcc    1392
Ala Ala Gly Lys Leu Val Leu Ser Thr Asp Tyr Ala Val Gln Ser Ala
425                 430                 435                 440 cac gtc gcg gat gcg tac acg cgc tct cgc gcc gcg ggc ttc gtc ccg    1440
His Val Ala Asp Ala Tyr Thr Arg Ser Arg Ala Ala Gly Phe Val Pro
                445                 450                 455 tac gtc acg gtg cgc gcc ttg gac cgg gtg acg gtg aac gcg ggg tgg    1488
Tyr Val Thr Val Arg Ala Leu Asp Arg Val Thr Val Asn Ala Gly Trp
            460                 465                 470 gac ccg cag tag                                                    1500
Asp Pro Gln
    475

<210> SEQ ID NO 48
<211> LENGTH: 499
<212> TYPE: PRT
<213> ORGANISM: Myxococcus macrosporus

<400> SEQUENCE: 48

Met Arg Val Ala Val Lys Trp Leu Thr Trp Thr Cys Leu Ala Leu Leu
                -20                 -15                 -10

Ala Ala Cys Gly Gly Ser Ser Ala Arg Asp Ser Leu Asp Asp Glu Arg
            -5                  -1   1               5

Gly Ala Ile Leu Pro Asp Ala Gln Thr Leu Thr Cys Ala Thr Leu Gln
                10                  15                  20

Leu Ala Arg Gly Ser Ile Gly Ser Gly Gln Gly Val Gln Gly Leu His
25                  30                  35                  40

Thr Gln Thr Leu Ser Gly Thr Gln Asp Arg Trp Ala Glu Tyr Val Glu
                45                  50                  55

Phe Ala Pro Asn Ser Ser Ala Thr Cys Thr Tyr Pro Leu Pro Ala Gly
            60                  65                  70

Val Ser Ala Asp Thr Val Val Ala Ala Glu Ile Gly Val Asn Phe Arg
        75                  80                  85

Gly Pro Thr Lys Ser Ala Met Arg Trp Leu Phe Glu Ala Trp Asp Tyr
    90                  95                  100

Ser Thr Gly Ala Trp Val Val Gly Asp Asn Val Phe Ala Gln Ser
105                 110                 115                 120

Trp Lys Trp Ser Ala Thr Ser Leu Ala Leu Thr Ser Pro Ser Arg Phe
                125                 130                 135

Phe Ser Gly Gly Pro Val Lys Leu Arg Tyr Arg Thr Glu Ser Ser Ala
            140                 145                 150
```

Asp Ala Ser Leu Leu Asp Leu Leu Val Val Arg Val Gln Val Ala Ala
            155                 160                 165

Thr Asp Ala Gly Thr Pro Asp Ala Gly Thr Pro Thr Asp Ala Gly
    170                 175                 180

Thr Pro Thr Asp Ala Gly Thr Pro Thr Asp Ala Gly Thr Ser Thr Asp
185                 190                 195                 200

Ala Gly Thr Pro Val Pro Trp Glu Gly Val Ser Ser Phe Thr Tyr Gln
                205                 210                 215

Leu Thr Asn Tyr Pro Gln Gly Lys Leu Asp Ala Ile Ala Ala Ser Lys
            220                 225                 230

Phe Asp Leu Ala Ile Val Glu Leu Val Arg Asp Gly Ser Ser Gly Tyr
            235                 240                 245

Phe Thr Ala Ala Glu Ile Ser Ala Leu Lys Ala Arg Gly Lys Gln Val
            250                 255                 260

Leu Ala Tyr Phe Glu Ile Gly Ala Ile Glu Glu Tyr Arg Pro Glu Trp
265                 270                 275                 280

Ser Gln Val Pro Ala Asp Leu Lys Leu Gly Pro Val Asp Gly Trp Pro
                285                 290                 295

Asp Glu Gln Tyr Val Lys Tyr Trp Asp Glu Arg Trp Pro Ile Val
            300                 305                 310

Gln Gly Arg Ile Asp Arg Ala Leu Ala Ala Gly Phe Thr Gly Cys Tyr
            315                 320                 325

Leu Asp Met Val Val Thr Tyr Glu Glu Ile Pro Ala Asn Ala Ala Gly
            330                 335                 340

Thr Asn Arg Ala Asp Leu Ala Arg Lys Met Val Ala Leu Ile Ala Arg
345                 350                 355                 360

Ile Ser Gln Tyr Ala Lys Ala Arg Asn Pro Ala Phe Lys Val Met Pro
            365                 370                 375

Gln Asn Ser Pro Glu Leu Val Asp Asp Pro Ala Tyr Leu Pro Val Ile
            380                 385                 390

Asp Gly Leu Gly Met Glu Asp Met Tyr Trp Ser Asp Val Ala Cys
            395                 400                 405

Asp Ala Ser Trp Cys Ala Glu Asn Arg Ala Asn Ala Ala Arg Val Arg
    410                 415                 420

Ala Ala Gly Lys Leu Val Leu Ser Thr Asp Tyr Ala Val Gln Ser Ala
425                 430                 435                 440

His Val Ala Asp Ala Tyr Thr Arg Ser Arg Ala Ala Gly Phe Val Pro
            445                 450                 455

Tyr Val Thr Val Arg Ala Leu Asp Arg Val Thr Val Asn Ala Gly Trp
            460                 465                 470

Asp Pro Gln
        475

<210> SEQ ID NO 49
<211> LENGTH: 475
<212> TYPE: PRT
<213> ORGANISM: Myxococcus macrosporus

<400> SEQUENCE: 49

Arg Asp Ser Leu Asp Asp Glu Arg Gly Ala Ile Leu Pro Asp Ala Gln
1               5                   10                  15

Thr Leu Thr Cys Ala Thr Leu Gln Leu Ala Arg Gly Ser Ile Gly Ser
            20                  25                  30

Gly Gln Gly Val Gln Gly Leu His Thr Gln Thr Leu Ser Gly Thr Gln

-continued

```
                35                  40                  45
Asp Arg Trp Ala Glu Tyr Val Glu Phe Ala Pro Asn Ser Ser Ala Thr
 50                  55                  60
Cys Thr Tyr Pro Leu Pro Ala Gly Val Ser Asp Thr Val Val Ala
 65                  70                  75                  80
Ala Glu Ile Gly Val Asn Phe Arg Gly Pro Thr Lys Ser Ala Met Arg
                     85                  90                  95
Trp Leu Phe Glu Ala Trp Asp Tyr Ser Thr Gly Ala Trp Val Val Val
                100                 105                 110
Gly Asp Asn Val Phe Ala Gln Ser Trp Lys Trp Ser Ala Thr Ser Leu
                115                 120                 125
Ala Leu Thr Ser Pro Ser Arg Phe Phe Ser Gly Pro Val Lys Leu
130                 135                 140
Arg Tyr Arg Thr Glu Ser Ser Ala Asp Ala Ser Leu Leu Asp Leu Leu
145                 150                 155                 160
Val Val Arg Val Gln Val Ala Ala Thr Asp Ala Gly Thr Pro Thr Asp
                165                 170                 175
Ala Gly Thr Pro Thr Asp Ala Gly Thr Pro Thr Asp Ala Gly Thr Pro
                180                 185                 190
Thr Asp Ala Gly Thr Ser Thr Asp Ala Gly Thr Pro Val Pro Trp Glu
                195                 200                 205
Gly Val Ser Ser Phe Thr Tyr Gln Leu Thr Asn Tyr Pro Gln Gly Lys
                210                 215                 220
Leu Asp Ala Ile Ala Ala Ser Lys Phe Asp Leu Ala Ile Val Glu Leu
225                 230                 235                 240
Val Arg Asp Gly Ser Ser Gly Tyr Phe Thr Ala Ala Glu Ile Ser Ala
                245                 250                 255
Leu Lys Ala Arg Gly Lys Gln Val Leu Ala Tyr Phe Glu Ile Gly Ala
                260                 265                 270
Ile Glu Glu Tyr Arg Pro Glu Trp Ser Gln Val Pro Ala Asp Leu Lys
                275                 280                 285
Leu Gly Pro Val Asp Gly Trp Pro Asp Glu Gln Tyr Val Lys Tyr Trp
                290                 295                 300
Asp Glu Arg Trp Trp Pro Ile Val Gln Gly Arg Ile Asp Arg Ala Leu
305                 310                 315                 320
Ala Ala Gly Phe Thr Gly Cys Tyr Leu Asp Met Val Val Thr Tyr Glu
                325                 330                 335
Glu Ile Pro Ala Asn Ala Ala Gly Thr Asn Arg Ala Asp Leu Ala Arg
                340                 345                 350
Lys Met Val Ala Leu Ile Ala Arg Ile Ser Gln Tyr Ala Lys Ala Arg
                355                 360                 365
Asn Pro Ala Phe Lys Val Met Pro Gln Asn Ser Pro Glu Leu Val Asp
                370                 375                 380
Asp Pro Ala Tyr Leu Pro Val Ile Asp Gly Leu Gly Met Glu Asp Met
385                 390                 395                 400
Tyr Trp Ser Asp Asp Val Ala Cys Asp Ala Ser Trp Cys Ala Glu Asn
                405                 410                 415
Arg Ala Asn Ala Ala Arg Val Arg Ala Ala Gly Lys Leu Val Leu Ser
                420                 425                 430
Thr Asp Tyr Ala Val Gln Ser Ala His Val Ala Asp Ala Tyr Thr Arg
                435                 440                 445
Ser Arg Ala Ala Gly Phe Val Pro Tyr Val Thr Val Arg Ala Leu Asp
                450                 455                 460
```

```
Arg Val Thr Val Asn Ala Gly Trp Asp Pro Gln
465                 470                 475

<210> SEQ ID NO 50
<211> LENGTH: 1482
<212> TYPE: DNA
<213> ORGANISM: Myxococcus stipitatus
<220> FEATURE:
<221> NAME/KEY: CDS
<222> LOCATION: (1)..(1479)
<220> FEATURE:
<221> NAME/KEY: sig_peptide
<222> LOCATION: (1)..(72)
<220> FEATURE:
<221> NAME/KEY: mat_peptide
<222> LOCATION: (73)..(1479)

<400> SEQUENCE: 50 atg cga ttc gct gtg aag tgg ttg acc tgg acc tgc ctg gcc ctg ctg        48
Met Arg Phe Ala Val Lys Trp Leu Thr Trp Thr Cys Leu Ala Leu Leu
            -20                 -15                 -10 gcc gcg tgt ggt gga agc ggt gcg cgt gac acg ctc gat gac gag cgc        96
Ala Ala Cys Gly Gly Ser Gly Ala Arg Asp Thr Leu Asp Asp Glu Arg
        -5                  -1  1               5 ggc gcg att ctc ccc gat gca cag acg ctc acc tgc acc acc ctc cag       144
Gly Ala Ile Leu Pro Asp Ala Gln Thr Leu Thr Cys Thr Thr Leu Gln
     10                  15                  20 ctg gcg cgc ggc tcc atc ggc tcg ggc cag ggc gtc cag ggc ctg cac       192
Leu Ala Arg Gly Ser Ile Gly Ser Gly Gln Gly Val Gln Gly Leu His
25                  30                  35                  40 acg cag acg ctg tcc gga acg cag gac cgc tgg gcg gag tac gtg gag       240
Thr Gln Thr Leu Ser Gly Thr Gln Asp Arg Trp Ala Glu Tyr Val Glu
                45                  50                  55 ttc acc gcc aac agc tcc gcc acc tgc acc tat ccg cta ccc gcg ggc       288
Phe Thr Ala Asn Ser Ser Ala Thr Cys Thr Tyr Pro Leu Pro Ala Gly
            60                  65                  70 gtg agc gcg gac acc gtc gtc gcg gct gaa atc ggc gtg aac ttc cgg       336
Val Ser Ala Asp Thr Val Val Ala Ala Glu Ile Gly Val Asn Phe Arg
        75                  80                  85 ggc ccg acg aag tcg gcg atg cgc tgg ctg ttc gag gcc tgg gac tac       384
Gly Pro Thr Lys Ser Ala Met Arg Trp Leu Phe Glu Ala Trp Asp Tyr
     90                  95                 100 tcg acg ggc acc tgg gtc gtc gtg ggt gac aac gcc ttc gcg cag tcg       432
Ser Thr Gly Thr Trp Val Val Val Gly Asp Asn Ala Phe Ala Gln Ser
105                 110                 115                 120 tgg aag tgg tcc gcc acc tcg ctc gcc ctc acc tcc ccc gcg cgg ttc       480
Trp Lys Trp Ser Ala Thr Ser Leu Ala Leu Thr Ser Pro Ala Arg Phe
                125                 130                 135 ttc tcc ggg ggc ccc gtg aag ctg cgc tac cgc acg gag tcc tcg gcg       528
Phe Ser Gly Gly Pro Val Lys Leu Arg Tyr Arg Thr Glu Ser Ser Ala
            140                 145                 150 gat gcg tcg ctg ctg gac ctg ctc gtg gtg cgc gtc cag gtg gcc gcg       576
Asp Ala Ser Leu Leu Asp Leu Leu Val Val Arg Val Gln Val Ala Ala
        155                 160                 165 tcg gat gcg ggg act tcc acc gac gcg ggc act ccg acg gac gcg ggg       624
Ser Asp Ala Gly Thr Ser Thr Asp Ala Gly Thr Pro Thr Asp Ala Gly
    170                 175                 180 act ccc acc gat gcg ggc acg tcc acg gac gcg ggc acg ccg gtt ccc       672
Thr Pro Thr Asp Ala Gly Thr Ser Thr Asp Ala Gly Thr Pro Val Pro
185                 190                 195                 200 tgg gag ggg gtc agc agc ttc acg tac cag ctc acc gac tat ccc cag       720
Trp Glu Gly Val Ser Ser Phe Thr Tyr Gln Leu Thr Asp Tyr Pro Gln
```

-continued

| | | | | 205 | | | | | 210 | | | | | 215 | | |
|---|---|---|---|---|---|---|---|---|---|---|---|---|---|---|---|---|

| ggc | aag | ctc | gac | acg | att | gcc | gcc | tcg | aag | ttc | gac | ctc | gcc | atc | atc | 768 |
| Gly | Lys | Leu | Asp | Thr | Ile | Ala | Ala | Ser | Lys | Phe | Asp | Leu | Ala | Ile | Ile | |
| | | | 220 | | | | | 225 | | | | | 230 | | | |

| gag | ttg | gtg | aga | gac | ggc | tcc | agc | ggc | tac | ttc | acc | gcc | gcc | gag | att | 816 |
| Glu | Leu | Val | Arg | Asp | Gly | Ser | Ser | Gly | Tyr | Phe | Thr | Ala | Ala | Glu | Ile | |
| | | | 235 | | | | | 240 | | | | | 245 | | | |

| tcc | gcg | ctc | aag | gcc | ggg | ggc | aag | cag | gtg | ctc | gcg | tac | ttc | gag | att | 864 |
| Ser | Ala | Leu | Lys | Ala | Gly | Gly | Lys | Gln | Val | Leu | Ala | Tyr | Phe | Glu | Ile | |
| 250 | | | | | 255 | | | | | 260 | | | | | | |

| ggc | gcc | atc | gag | gag | tac | cgg | ccc | gag | tgg | agt | cag | gtg | ccc | tcg | gac | 912 |
| Gly | Ala | Ile | Glu | Glu | Tyr | Arg | Pro | Glu | Trp | Ser | Gln | Val | Pro | Ser | Asp | |
| 265 | | | | 270 | | | | | 275 | | | | | 280 | | |

| atg | aag | ctg | ggc | ccc | gtg | gat | ggc | tgg | ccc | gac | gag | cag | tac | gtg | aag | 960 |
| Met | Lys | Leu | Gly | Pro | Val | Asp | Gly | Trp | Pro | Asp | Glu | Gln | Tyr | Val | Lys | |
| | | | | 285 | | | | | 290 | | | | | 295 | | |

| tac | tgg | gac | gag | cgc | tgg | tgg | ccc | atc | gtc | cag | ggc | cgc | ctg | gac | cgc | 1008 |
| Tyr | Trp | Asp | Glu | Arg | Trp | Trp | Pro | Ile | Val | Gln | Gly | Arg | Leu | Asp | Arg | |
| | | | 300 | | | | | 305 | | | | | 310 | | | |

| gcg | ctc | gcc | gcg | ggc | ttc | acc | ggc | tgc | tac | ctg | gac | atg | gtg | gtg | acg | 1056 |
| Ala | Leu | Ala | Ala | Gly | Phe | Thr | Gly | Cys | Tyr | Leu | Asp | Met | Val | Val | Thr | |
| | | | 315 | | | | | 320 | | | | | 325 | | | |

| tac | gag | gag | att | ccc | gcc | aac | tcc | gcg | ggc | acc | aac | cgc | gcc | gac | ctc | 1104 |
| Tyr | Glu | Glu | Ile | Pro | Ala | Asn | Ser | Ala | Gly | Thr | Asn | Arg | Ala | Asp | Leu | |
| 330 | | | | | 335 | | | | | 340 | | | | | | |

| gcg | cgg | aag | atg | gtg | gcc | ctc | atc | gcc | cgc | atc | agc | cag | tac | gcg | aag | 1152 |
| Ala | Arg | Lys | Met | Val | Ala | Leu | Ile | Ala | Arg | Ile | Ser | Gln | Tyr | Ala | Lys | |
| 345 | | | | 350 | | | | | 355 | | | | | 360 | | |

| gcg | cgc | aac | ccg | gcc | ttc | aag | gtg | atg | ccg | cag | aac | tct | ccg | gag | ctc | 1200 |
| Ala | Arg | Asn | Pro | Ala | Phe | Lys | Val | Met | Pro | Gln | Asn | Ser | Pro | Glu | Leu | |
| | | | | 365 | | | | | 370 | | | | | 375 | | |

| gtc | gat | gac | ccc | atc | tat | ctg | ccc | gcc | atc | gac | ggc | ctg | ggc | atg | gag | 1248 |
| Val | Asp | Asp | Pro | Ile | Tyr | Leu | Pro | Ala | Ile | Asp | Gly | Leu | Gly | Met | Glu | |
| | | | 380 | | | | | 385 | | | | | 390 | | | |

| gac | atg | tac | tgg | tcc | gac | gac | gtc | gca | tgc | gac | gcg | ggc | tgg | tgc | gcg | 1296 |
| Asp | Met | Tyr | Trp | Ser | Asp | Asp | Val | Ala | Cys | Asp | Ala | Gly | Trp | Cys | Ala | |
| | | | 395 | | | | | 400 | | | | | 405 | | | |

| gag | aat | cgc | gcc | aac | gcc | gcc | cgg | gtg | cgc | gcc | gcg | ggc | aag | ctg | gtg | 1344 |
| Glu | Asn | Arg | Ala | Asn | Ala | Ala | Arg | Val | Arg | Ala | Ala | Gly | Lys | Leu | Val | |
| | | 410 | | | | | 415 | | | | | 420 | | | | |

| ctg | tcc | acc | gac | tac | gcc | gtc | cag | tcc | gcc | cac | gtc | gcg | gat | gcg | tac | 1392 |
| Leu | Ser | Thr | Asp | Tyr | Ala | Val | Gln | Ser | Ala | His | Val | Ala | Asp | Ala | Tyr | |
| 425 | | | | 430 | | | | | 435 | | | | | 440 | | |

| acg | cgc | tct | cgc | gcc | gcg | ggc | ttc | atc | ccg | tac | gtc | acg | gtg | cgc | gcg | 1440 |
| Thr | Arg | Ser | Arg | Ala | Ala | Gly | Phe | Ile | Pro | Tyr | Val | Thr | Val | Arg | Ala | |
| | | | | 445 | | | | | 450 | | | | | 455 | | |

| ttg | gac | cgg | gtg | acg | gtg | aac | gcg | gga | tgg | gac | ccg | cag | tag | | | 1482 |
| Leu | Asp | Arg | Val | Thr | Val | Asn | Ala | Gly | Trp | Asp | Pro | Gln | | | | |
| | | | 460 | | | | | 465 | | | | | | | | |

<210> SEQ ID NO 51
<211> LENGTH: 493
<212> TYPE: PRT
<213> ORGANISM: Myxococcus stipitatus

<400> SEQUENCE: 51

| Met | Arg | Phe | Ala | Val | Lys | Trp | Leu | Thr | Trp | Thr | Cys | Leu | Ala | Leu | Leu |
|---|---|---|---|---|---|---|---|---|---|---|---|---|---|---|---|
| | | | | | -20 | | | | -15 | | | | | -10 | |

| Ala | Ala | Cys | Gly | Gly | Ser | Gly | Ala | Arg | Asp | Thr | Leu | Asp | Asp | Glu | Arg |
|---|---|---|---|---|---|---|---|---|---|---|---|---|---|---|---|
| | | | -5 | | | | -1 | 1 | | | | 5 | | | |

```
Gly Ala Ile Leu Pro Asp Ala Gln Thr Leu Thr Cys Thr Thr Leu Gln
         10                  15                  20
Leu Ala Arg Gly Ser Ile Gly Ser Gly Gln Gly Val Gln Gly Leu His
 25                  30                  35                  40
Thr Gln Thr Leu Ser Gly Thr Gln Asp Arg Trp Ala Glu Tyr Val Glu
                 45                  50                  55
Phe Thr Ala Asn Ser Ser Ala Thr Cys Thr Tyr Pro Leu Pro Ala Gly
             60                  65                  70
Val Ser Ala Asp Thr Val Val Ala Glu Ile Gly Val Asn Phe Arg
         75                  80                  85
Gly Pro Thr Lys Ser Ala Met Arg Trp Leu Phe Glu Ala Trp Asp Tyr
     90                  95                 100
Ser Thr Gly Thr Trp Val Val Gly Asp Asn Ala Phe Ala Gln Ser
105                 110                 115                 120
Trp Lys Trp Ser Ala Thr Ser Leu Ala Leu Thr Ser Pro Ala Arg Phe
                125                 130                 135
Phe Ser Gly Gly Pro Val Lys Leu Arg Tyr Arg Thr Glu Ser Ser Ala
                140                 145                 150
Asp Ala Ser Leu Leu Asp Leu Leu Val Arg Val Gln Val Ala Ala
             155                 160                 165
Ser Asp Ala Gly Thr Ser Thr Asp Ala Gly Thr Pro Thr Asp Ala Gly
170                 175                 180
Thr Pro Thr Asp Ala Gly Thr Ser Thr Asp Ala Gly Thr Pro Val Pro
185                 190                 195                 200
Trp Glu Gly Val Ser Ser Phe Thr Tyr Gln Leu Thr Asp Tyr Pro Gln
                205                 210                 215
Gly Lys Leu Asp Thr Ile Ala Ala Ser Lys Phe Asp Leu Ala Ile Ile
                220                 225                 230
Glu Leu Val Arg Asp Gly Ser Ser Gly Tyr Phe Thr Ala Ala Glu Ile
                235                 240                 245
Ser Ala Leu Lys Ala Gly Gly Lys Gln Val Leu Ala Tyr Phe Glu Ile
250                 255                 260
Gly Ala Ile Glu Glu Tyr Arg Pro Glu Trp Ser Gln Val Pro Ser Asp
265                 270                 275                 280
Met Lys Leu Gly Pro Val Asp Gly Trp Pro Asp Glu Gln Tyr Val Lys
                285                 290                 295
Tyr Trp Asp Glu Arg Trp Trp Pro Ile Val Gln Gly Arg Leu Asp Arg
                300                 305                 310
Ala Leu Ala Ala Gly Phe Thr Gly Cys Tyr Leu Asp Met Val Val Thr
             315                 320                 325
Tyr Glu Glu Ile Pro Ala Asn Ser Ala Gly Thr Asn Arg Ala Asp Leu
             330                 335                 340
Ala Arg Lys Met Val Ala Leu Ile Ala Arg Ile Ser Gln Tyr Ala Lys
345                 350                 355                 360
Ala Arg Asn Pro Ala Phe Lys Val Met Pro Gln Asn Ser Pro Glu Leu
                365                 370                 375
Val Asp Asp Pro Ile Tyr Leu Pro Ala Ile Asp Gly Leu Gly Met Glu
                380                 385                 390
Asp Met Tyr Trp Ser Asp Asp Val Ala Cys Asp Ala Gly Trp Cys Ala
             395                 400                 405
Glu Asn Arg Ala Asn Ala Ala Arg Val Arg Ala Ala Gly Lys Leu Val
     410                 415                 420
```

```
Leu Ser Thr Asp Tyr Ala Val Gln Ser Ala His Val Ala Asp Ala Tyr
425                 430                 435                 440

Thr Arg Ser Arg Ala Ala Gly Phe Ile Pro Tyr Val Thr Val Arg Ala
                445                 450                 455

Leu Asp Arg Val Thr Val Asn Ala Gly Trp Asp Pro Gln
                460                 465

<210> SEQ ID NO 52
<211> LENGTH: 469
<212> TYPE: PRT
<213> ORGANISM: Myxococcus stipitatus

<400> SEQUENCE: 52

Arg Asp Thr Leu Asp Asp Glu Arg Gly Ala Ile Leu Pro Asp Ala Gln
1               5                   10                  15

Thr Leu Thr Cys Thr Thr Leu Gln Leu Ala Arg Gly Ser Ile Gly Ser
                20                  25                  30

Gly Gln Gly Val Gln Gly Leu His Thr Gln Thr Leu Ser Gly Thr Gln
            35                  40                  45

Asp Arg Trp Ala Glu Tyr Val Glu Phe Thr Ala Asn Ser Ser Ala Thr
50                  55                  60

Cys Thr Tyr Pro Leu Pro Ala Gly Val Ser Ala Asp Thr Val Val Ala
65                  70                  75                  80

Ala Glu Ile Gly Val Asn Phe Arg Gly Pro Thr Lys Ser Ala Met Arg
                85                  90                  95

Trp Leu Phe Glu Ala Trp Asp Tyr Ser Thr Gly Thr Trp Val Val Val
                100                 105                 110

Gly Asp Asn Ala Phe Ala Gln Ser Trp Lys Trp Ser Ala Thr Ser Leu
            115                 120                 125

Ala Leu Thr Ser Pro Ala Arg Phe Phe Ser Gly Gly Pro Val Lys Leu
    130                 135                 140

Arg Tyr Arg Thr Glu Ser Ser Ala Asp Ala Ser Leu Leu Asp Leu Leu
145                 150                 155                 160

Val Val Arg Val Gln Val Ala Ala Ser Asp Ala Gly Thr Ser Thr Asp
                165                 170                 175

Ala Gly Thr Pro Thr Asp Ala Gly Thr Pro Thr Asp Ala Gly Thr Ser
                180                 185                 190

Thr Asp Ala Gly Thr Pro Val Pro Trp Glu Gly Val Ser Ser Phe Thr
            195                 200                 205

Tyr Gln Leu Thr Asp Tyr Pro Gln Gly Lys Leu Asp Thr Ile Ala Ala
    210                 215                 220

Ser Lys Phe Asp Leu Ala Ile Ile Glu Leu Val Arg Asp Gly Ser Ser
225                 230                 235                 240

Gly Tyr Phe Thr Ala Ala Glu Ile Ser Ala Leu Lys Ala Gly Gly Lys
                245                 250                 255

Gln Val Leu Ala Tyr Phe Glu Ile Gly Ala Ile Glu Glu Tyr Arg Pro
                260                 265                 270

Glu Trp Ser Gln Val Pro Ser Asp Met Lys Leu Gly Pro Val Asp Gly
            275                 280                 285

Trp Pro Asp Glu Gln Tyr Val Lys Tyr Trp Asp Glu Arg Trp Trp Pro
    290                 295                 300

Ile Val Gln Gly Arg Leu Asp Arg Ala Leu Ala Ala Gly Phe Thr Gly
305                 310                 315                 320

Cys Tyr Leu Asp Met Val Val Thr Tyr Glu Glu Ile Pro Ala Asn Ser
                325                 330                 335
```

```
Ala Gly Thr Asn Arg Ala Asp Leu Ala Arg Lys Met Val Ala Leu Ile
                    340                 345                 350

Ala Arg Ile Ser Gln Tyr Ala Lys Ala Arg Asn Pro Ala Phe Lys Val
            355                 360                 365

Met Pro Gln Asn Ser Pro Glu Leu Val Asp Asp Pro Ile Tyr Leu Pro
370                 375                 380

Ala Ile Asp Gly Leu Gly Met Glu Asp Met Tyr Trp Ser Asp Asp Val
385                 390                 395                 400

Ala Cys Asp Ala Gly Trp Cys Ala Glu Asn Arg Ala Asn Ala Ala Arg
                405                 410                 415

Val Arg Ala Ala Gly Lys Leu Val Leu Ser Thr Asp Tyr Ala Val Gln
                420                 425                 430

Ser Ala His Val Ala Asp Ala Tyr Thr Arg Ser Arg Ala Ala Gly Phe
            435                 440                 445

Ile Pro Tyr Val Thr Val Arg Ala Leu Asp Arg Val Thr Val Asn Ala
        450                 455                 460

Gly Trp Asp Pro Gln
465

<210> SEQ ID NO 53
<211> LENGTH: 1500
<212> TYPE: DNA
<213> ORGANISM: Myxococcus macrosporus
<220> FEATURE:
<221> NAME/KEY: CDS
<222> LOCATION: (1)..(1497)
<220> FEATURE:
<221> NAME/KEY: sig_peptide
<222> LOCATION: (1)..(72)
<220> FEATURE:
<221> NAME/KEY: mat_peptide
<222> LOCATION: (73)..(1497)

<400> SEQUENCE: 53 atg cga gtc gct gtg aag tgg ttg acc tgg acc tgc ctg gcc ttg ctg       48
Met Arg Val Ala Val Lys Trp Leu Thr Trp Thr Cys Leu Ala Leu Leu
                -20                 -15                 -10 gcc gcg tgt ggt gga agc agt gcg cgt gac ccg ctc gac gac gag cgc       96
Ala Ala Cys Gly Gly Ser Ser Ala Arg Asp Pro Leu Asp Asp Glu Arg
        -5                  -1   1               5 ggc gcg ata ctc ccc gat gcg cag acg ctc acc tgc gcc acc ctc cag      144
Gly Ala Ile Leu Pro Asp Ala Gln Thr Leu Thr Cys Ala Thr Leu Gln
        10                  15                  20 ctc gcg cgg ggc tcc atc ggc tcg ggc cag ggc gtc cag ggc ctg cac      192
Leu Ala Arg Gly Ser Ile Gly Ser Gly Gln Gly Val Gln Gly Leu His
25                  30                  35                  40 acg cag aca ctg tcc ggg acg cag gac cgc tgg gcg gag tac gtg gag      240
Thr Gln Thr Leu Ser Gly Thr Gln Asp Arg Trp Ala Glu Tyr Val Glu
                45                  50                  55 ttc acc gcc aac agc tcc gcc acg tgc acc tac ccg ctg ccc tcg ggc      288
Phe Thr Ala Asn Ser Ser Ala Thr Cys Thr Tyr Pro Leu Pro Ser Gly
            60                  65                  70 gtg agc gcg gac acc gtc gtc gcg gct gaa atc ggc gtg aac ttc cgg      336
Val Ser Ala Asp Thr Val Val Ala Ala Glu Ile Gly Val Asn Phe Arg
        75                  80                  85 ggc ccg acg aag tcg gcg atg cgc tgg ctg ttc gag gcc tgg gac tac      384
Gly Pro Thr Lys Ser Ala Met Arg Trp Leu Phe Glu Ala Trp Asp Tyr
    90                  95                  100 tcg acg ggc gcc tgg gtc atc gtc ggt gac aac gcc ttc gcg cag tcg      432
Ser Thr Gly Ala Trp Val Ile Val Gly Asp Asn Ala Phe Ala Gln Ser
```

|  |  |
|---|---|
| tgg aag tgg tcc gcg acg tcg ctg gcc ctc acc tcc ccc gcg cgg ttc<br>Trp Lys Trp Ser Ala Thr Ser Leu Ala Leu Thr Ser Pro Ala Arg Phe<br>                    125                          130                          135 | 480 |
| ttc tcc ggt ggc ccc gtg aag ctg cgc tac cgc acg gag tcc tcg gcg<br>Phe Ser Gly Gly Pro Val Lys Leu Arg Tyr Arg Thr Glu Ser Ser Ala<br>                    140                          145                          150 | 528 |
| gat gcg tcg ctg ttg gac ctg ctg gtg gtg cgc gtg cag gtg gcg gcg<br>Asp Ala Ser Leu Leu Asp Leu Leu Val Val Arg Val Gln Val Ala Ala<br>                    155                          160                          165 | 576 |
| tca gac gcg ggg act ctc acg gat gcg ggc acg ccc aac gat gcg ggc<br>Ser Asp Ala Gly Thr Leu Thr Asp Ala Gly Thr Pro Asn Asp Ala Gly<br>170                          175                          180 | 624 |
| act ccg acg gac gct gga act ccc acc gac gcg ggc acg tcc acg gac<br>Thr Pro Thr Asp Ala Gly Thr Pro Thr Asp Ala Gly Thr Ser Thr Asp<br>185                          190                          195                          200 | 672 |
| gcg ggc acg ccg gtg ccg tgg gag ggt gtc agc agc ttc acg tac cag<br>Ala Gly Thr Pro Val Pro Trp Glu Gly Val Ser Ser Phe Thr Tyr Gln<br>                              205                          210                          215 | 720 |
| ctc acc aac tat ccc cag ggc aag ctc gac gcg att gcc gcc tcg aag<br>Leu Thr Asn Tyr Pro Gln Gly Lys Leu Asp Ala Ile Ala Ala Ser Lys<br>                    220                          225                          230 | 768 |
| ttc gac ctc gcc atc gtc gag ctg gtg cga gac ggc tcc agc ggc tac<br>Phe Asp Leu Ala Ile Val Glu Leu Val Arg Asp Gly Ser Ser Gly Tyr<br>                    235                          240                          245 | 816 |
| ttc acc gcc gcc gag att tcc gcg ctc aag acc cgg ggc aag cag gtg<br>Phe Thr Ala Ala Glu Ile Ser Ala Leu Lys Thr Arg Gly Lys Gln Val<br>                    250                          255                          260 | 864 |
| ctc gcc tac ttc gag att ggc gcc atc gag gag tac cgc ccc gag tgg<br>Leu Ala Tyr Phe Glu Ile Gly Ala Ile Glu Glu Tyr Arg Pro Glu Trp<br>265                          270                          275                          280 | 912 |
| aac cag gtg ccc gcg gac ctg aag ctg ggc ccc gtg gat ggc tgg ccc<br>Asn Gln Val Pro Ala Asp Leu Lys Leu Gly Pro Val Asp Gly Trp Pro<br>                    285                          290                          295 | 960 |
| gat gag cag tat gtg aag tac tgg gac gag cgc tgg tgg ccc atc gtc<br>Asp Glu Gln Tyr Val Lys Tyr Trp Asp Glu Arg Trp Trp Pro Ile Val<br>                    300                          305                          310 | 1008 |
| cag ggc cgc atc gac cgc gcg ctc gcc gcg ggc ttc acc ggc tgc tac<br>Gln Gly Arg Ile Asp Arg Ala Leu Ala Ala Gly Phe Thr Gly Cys Tyr<br>                    315                          320                          325 | 1056 |
| ctg gac atg gtg gtg acg tac gag gag att ccc gcc agc tcc gcg ggc<br>Leu Asp Met Val Val Thr Tyr Glu Glu Ile Pro Ala Ser Ser Ala Gly<br>330                          335                          340 | 1104 |
| acc aac cgc gcc gac ctc gcg cgg aag atg gtg gcc ctc atc gcc cgc<br>Thr Asn Arg Ala Asp Leu Ala Arg Lys Met Val Ala Leu Ile Ala Arg<br>345                          350                          355                          360 | 1152 |
| atc agc cag tac gcg aag gcg cgc aac ccg gcc ttc aag gtg gtg ccg<br>Ile Ser Gln Tyr Ala Lys Ala Arg Asn Pro Ala Phe Lys Val Val Pro<br>                    365                          370                          375 | 1200 |
| cag aac tcc ccg gag ctc gtc gat gac ccc atc tat ctg ccc gcc atc<br>Gln Asn Ser Pro Glu Leu Val Asp Asp Pro Ile Tyr Leu Pro Ala Ile<br>                    380                          385                          390 | 1248 |
| gac ggc ctg ggc atg gag gac atg tac tgg tcc gac gac gtc gcg tgc<br>Asp Gly Leu Gly Met Glu Asp Met Tyr Trp Ser Asp Asp Val Ala Cys<br>                    395                          400                          405 | 1296 |
| gac gcg ggc tgg tgc gcg gag aat cgc gcc aac gcc gca cgg gtg cgc<br>Asp Ala Gly Trp Cys Ala Glu Asn Arg Ala Asn Ala Ala Arg Val Arg<br>                    410                          415                          420 | 1344 |
| gcc gcg ggc aag ctg gtg ctg tcc acc gac tac gcc gtc cag tcc gcc | 1392 |

```
Ala Ala Gly Lys Leu Val Leu Ser Thr Asp Tyr Ala Val Gln Ser Ala
425                 430                 435                 440 cac gtc gcg gat gcg tac acg cgc tct cgc gcc gcg ggc ttc gtc ccg    1440
His Val Ala Asp Ala Tyr Thr Arg Ser Arg Ala Ala Gly Phe Val Pro
                445                 450                 455 tac gtc acg gtg cgc gcc ttg gac cgg gtg acg gtg aac gcg ggg tgg    1488
Tyr Val Thr Val Arg Ala Leu Asp Arg Val Thr Val Asn Ala Gly Trp
            460                 465                 470 gac ccg cag tag                                                    1500
Asp Pro Gln
        475

<210> SEQ ID NO 54
<211> LENGTH: 499
<212> TYPE: PRT
<213> ORGANISM: Myxococcus macrosporus

<400> SEQUENCE: 54

Met Arg Val Ala Val Lys Trp Leu Thr Trp Thr Cys Leu Ala Leu Leu
                -20                 -15                 -10

Ala Ala Cys Gly Gly Ser Ser Ala Arg Asp Pro Leu Asp Asp Glu Arg
            -5                  -1   1               5

Gly Ala Ile Leu Pro Asp Ala Gln Thr Leu Thr Cys Ala Thr Leu Gln
        10                  15                  20

Leu Ala Arg Gly Ser Ile Gly Ser Gly Gln Gly Val Gln Gly Leu His
25                  30                  35                  40

Thr Gln Thr Leu Ser Gly Thr Gln Asp Arg Trp Ala Glu Tyr Val Glu
                45                  50                  55

Phe Thr Ala Asn Ser Ser Ala Thr Cys Thr Tyr Pro Leu Pro Ser Gly
                60                  65                  70

Val Ser Ala Asp Thr Val Ala Ala Glu Ile Gly Val Asn Phe Arg
                75                  80                  85

Gly Pro Thr Lys Ser Ala Met Arg Trp Leu Phe Glu Ala Trp Asp Tyr
        90                  95                  100

Ser Thr Gly Ala Trp Val Ile Val Gly Asp Asn Ala Phe Ala Gln Ser
105                 110                 115                 120

Trp Lys Trp Ser Ala Thr Ser Leu Ala Leu Thr Ser Pro Ala Arg Phe
                125                 130                 135

Phe Ser Gly Gly Pro Val Lys Leu Arg Tyr Arg Thr Glu Ser Ser Ala
            140                 145                 150

Asp Ala Ser Leu Leu Asp Leu Leu Val Val Arg Val Gln Val Ala Ala
                155                 160                 165

Ser Asp Ala Gly Thr Leu Thr Asp Ala Gly Thr Pro Asn Asp Ala Gly
        170                 175                 180

Thr Pro Thr Asp Ala Gly Thr Pro Thr Asp Ala Gly Thr Ser Thr Asp
185                 190                 195                 200

Ala Gly Thr Pro Val Pro Trp Glu Gly Val Ser Ser Phe Thr Tyr Gln
                205                 210                 215

Leu Thr Asn Tyr Pro Gln Gly Lys Leu Asp Ala Ile Ala Ala Ser Lys
                220                 225                 230

Phe Asp Leu Ala Ile Val Glu Leu Val Arg Asp Gly Ser Ser Gly Tyr
        235                 240                 245

Phe Thr Ala Ala Glu Ile Ser Ala Leu Lys Thr Arg Gly Lys Gln Val
250                 255                 260

Leu Ala Tyr Phe Glu Ile Gly Ala Ile Glu Glu Tyr Arg Pro Glu Trp
265                 270                 275                 280
```

Asn Gln Val Pro Ala Asp Leu Lys Leu Gly Pro Val Asp Gly Trp Pro
            285                 290                 295

Asp Glu Gln Tyr Val Lys Tyr Trp Asp Glu Arg Trp Trp Pro Ile Val
            300                 305                 310

Gln Gly Arg Ile Asp Arg Ala Leu Ala Ala Gly Phe Thr Gly Cys Tyr
            315                 320                 325

Leu Asp Met Val Val Thr Tyr Glu Glu Ile Pro Ala Ser Ser Ala Gly
            330                 335                 340

Thr Asn Arg Ala Asp Leu Ala Arg Lys Met Val Ala Leu Ile Ala Arg
345                 350                 355                 360

Ile Ser Gln Tyr Ala Lys Ala Arg Asn Pro Ala Phe Lys Val Val Pro
            365                 370                 375

Gln Asn Ser Pro Glu Leu Val Asp Asp Pro Ile Tyr Leu Pro Ala Ile
            380                 385                 390

Asp Gly Leu Gly Met Glu Asp Met Tyr Trp Ser Asp Val Ala Cys
            395                 400                 405

Asp Ala Gly Trp Cys Ala Glu Asn Arg Ala Asn Ala Ala Arg Val Arg
            410                 415                 420

Ala Ala Gly Lys Leu Val Leu Ser Thr Asp Tyr Ala Val Gln Ser Ala
425                 430                 435                 440

His Val Ala Asp Ala Tyr Thr Arg Ser Arg Ala Ala Gly Phe Val Pro
            445                 450                 455

Tyr Val Thr Val Arg Ala Leu Asp Arg Val Thr Val Asn Ala Gly Trp
            460                 465                 470

Asp Pro Gln
            475

<210> SEQ ID NO 55
<211> LENGTH: 475
<212> TYPE: PRT
<213> ORGANISM: Myxococcus macrosporus

<400> SEQUENCE: 55

Arg Asp Pro Leu Asp Asp Glu Arg Gly Ala Ile Leu Pro Asp Ala Gln
1               5                   10                  15

Thr Leu Thr Cys Ala Thr Leu Gln Leu Ala Arg Gly Ser Ile Gly Ser
            20                  25                  30

Gly Gln Gly Val Gln Gly Leu His Thr Gln Thr Leu Ser Gly Thr Gln
            35                  40                  45

Asp Arg Trp Ala Glu Tyr Val Glu Phe Thr Ala Asn Ser Ser Ala Thr
        50                  55                  60

Cys Thr Tyr Pro Leu Pro Ser Gly Val Ser Ala Asp Thr Val Val Ala
65                  70                  75                  80

Ala Glu Ile Gly Val Asn Phe Arg Gly Pro Thr Lys Ser Ala Met Arg
            85                  90                  95

Trp Leu Phe Glu Ala Trp Asp Tyr Ser Thr Gly Ala Trp Val Ile Val
            100                 105                 110

Gly Asp Asn Ala Phe Ala Gln Ser Trp Lys Trp Ser Ala Thr Ser Leu
            115                 120                 125

Ala Leu Thr Ser Pro Ala Arg Phe Phe Ser Gly Gly Pro Val Lys Leu
            130                 135                 140

Arg Tyr Arg Thr Glu Ser Ser Ala Asp Ala Ser Leu Leu Asp Leu Leu
145                 150                 155                 160

Val Val Arg Val Gln Val Ala Ala Ser Asp Ala Gly Thr Leu Thr Asp 165                 170                 175
Ala Gly Thr Pro Asn Asp Ala Gly Thr Pro Thr Asp Ala Gly Thr Pro
            180                 185                 190

Thr Asp Ala Gly Thr Ser Thr Asp Ala Gly Thr Pro Val Pro Trp Glu
            195                 200                 205

Gly Val Ser Ser Phe Thr Tyr Gln Leu Thr Asn Tyr Pro Gln Gly Lys
            210                 215                 220

Leu Asp Ala Ile Ala Ala Ser Lys Phe Asp Leu Ala Ile Val Glu Leu
225                 230                 235                 240

Val Arg Asp Gly Ser Ser Gly Tyr Phe Thr Ala Ala Glu Ile Ser Ala
                245                 250                 255

Leu Lys Thr Arg Gly Lys Gln Val Leu Ala Tyr Phe Glu Ile Gly Ala
                260                 265                 270

Ile Glu Glu Tyr Arg Pro Glu Trp Asn Gln Val Pro Ala Asp Leu Lys
                275                 280                 285

Leu Gly Pro Val Asp Gly Trp Pro Asp Glu Gln Tyr Val Lys Tyr Trp
            290                 295                 300

Asp Glu Arg Trp Trp Pro Ile Val Gln Gly Arg Ile Asp Arg Ala Leu
305                 310                 315                 320

Ala Ala Gly Phe Thr Gly Cys Tyr Leu Asp Met Val Val Thr Tyr Glu
                325                 330                 335

Glu Ile Pro Ala Ser Ser Ala Gly Thr Asn Arg Ala Asp Leu Ala Arg
            340                 345                 350

Lys Met Val Ala Leu Ile Ala Arg Ile Ser Gln Tyr Ala Lys Ala Arg
                355                 360                 365

Asn Pro Ala Phe Lys Val Val Pro Gln Asn Ser Pro Glu Leu Val Asp
            370                 375                 380

Asp Pro Ile Tyr Leu Pro Ala Ile Asp Gly Leu Gly Met Glu Asp Met
385                 390                 395                 400

Tyr Trp Ser Asp Asp Val Ala Cys Asp Ala Gly Trp Cys Ala Glu Asn
                405                 410                 415

Arg Ala Asn Ala Ala Arg Val Arg Ala Ala Gly Lys Leu Val Leu Ser
            420                 425                 430

Thr Asp Tyr Ala Val Gln Ser Ala His Val Ala Asp Ala Tyr Thr Arg
            435                 440                 445

Ser Arg Ala Ala Gly Phe Val Pro Tyr Val Thr Val Arg Ala Leu Asp
            450                 455                 460

Arg Val Thr Val Asn Ala Gly Trp Asp Pro Gln
465                 470                 475

<210> SEQ ID NO 56
<211> LENGTH: 2868
<212> TYPE: DNA
<213> ORGANISM: Pseudomonas seleniipraecipitans
<220> FEATURE:
<221> NAME/KEY: CDS
<222> LOCATION: (1)..(2865)
<220> FEATURE:
<221> NAME/KEY: sig_peptide
<222> LOCATION: (1)..(147)
<220> FEATURE:
<221> NAME/KEY: mat_peptide
<222> LOCATION: (148)..(2865)

<400> SEQUENCE: 56 atg ctc ggt gtt aca gca ttg cgt cat ggg gaa gag cgt gga gtt gtc     48
Met Leu Gly Val Thr Ala Leu Arg His Gly Glu Glu Arg Gly Val Val
            -45                 -40                 -35

```
tcg tct gga ttg aat gtc acc ttc agg aag acg gtc att cgc gcg ttt        96
Ser Ser Gly Leu Asn Val Thr Phe Arg Lys Thr Val Ile Arg Ala Phe
            -30             -25                 -20 acc tgg ctt ttc agt ctg tgt gct gca ctg tcc gcc gtc gct tcg cag       144
Thr Trp Leu Phe Ser Leu Cys Ala Ala Leu Ser Ala Val Ala Ser Gln
        -15                 -10                  -5 gcg gcg ggg ttg agc cct gcc ggc ccg caa agc gtg gcg ttc tgg tac       192
Ala Ala Gly Leu Ser Pro Ala Gly Pro Gln Ser Val Ala Phe Trp Tyr
 -1   1              5                  10                  15 gcc ccc aat cct ccg tac tcc gag ttg gcc cag ttc gac tgg agc gtg       240
Ala Pro Asn Pro Pro Tyr Ser Glu Leu Ala Gln Phe Asp Trp Ser Val
                20                  25                  30 ctg gag ccg tcg cac gtt cag gcc aag gat gtg gcg ttt ctg cgt gcg       288
Leu Glu Pro Ser His Val Gln Ala Lys Asp Val Ala Phe Leu Arg Ala
            35                  40                  45 cag ggc aat cag ccc ttt gcc tac ttg tcg att ggc gag ttc gac ggc       336
Gln Gly Asn Gln Pro Phe Ala Tyr Leu Ser Ile Gly Glu Phe Asp Gly
        50                  55                  60 gac ctg gct gtt gtc acc ggc agt gcg tcc aac agc ggt gca agt gcg       384
Asp Leu Ala Val Val Thr Gly Ser Ala Ser Asn Ser Gly Ala Ser Ala
 65                  70                  75 gta cag aac aag gcc tgg ggc agc cag gtc atg cac ttg tct tcc ccc       432
Val Gln Asn Lys Ala Trp Gly Ser Gln Val Met His Leu Ser Ser Pro
 80                  85                  90                  95 gag tgg cgc gcc tac ttg ttg cgc cgc gcc agc gaa ttg cgc gaa gcc       480
Glu Trp Arg Ala Tyr Leu Leu Arg Arg Ala Ser Glu Leu Arg Glu Ala
                100                 105                 110 ggg tat gcc ggc ctg ttt ctc gat aca ttg gac agt ttc caa ctt ctg       528
Gly Tyr Ala Gly Leu Phe Leu Asp Thr Leu Asp Ser Phe Gln Leu Leu
            115                 120                 125 ccc gct gcg gaa cat gaa act cag cgc gcg gcc ctg cgt gac ttc ctg       576
Pro Ala Ala Glu His Glu Thr Gln Arg Ala Ala Leu Arg Asp Phe Leu
        130                 135                 140 agc gag ctg aaa cgc cag gaa ccc ggt ttg aag ttg ttc ttc aac cgc       624
Ser Glu Leu Lys Arg Gln Glu Pro Gly Leu Lys Leu Phe Phe Asn Arg
145                 150                 155 ggt ttc gag gta ctg ccg gaa ttg cct ggc gtg gcg gcc gcc gtg gcg       672
Gly Phe Glu Val Leu Pro Glu Leu Pro Gly Val Ala Ala Ala Val Ala
160                 165                 170                 175 gtc gag tcg atc cat gcc ggc tgg gac gcc cag cgc cgc acc tac cgg       720
Val Glu Ser Ile His Ala Gly Trp Asp Ala Gln Arg Arg Thr Tyr Arg
                180                 185                 190 atc gtg ccc cag gcg gat cgc gac tgg ctc gac ggt cac ctg cag ccc       768
Ile Val Pro Gln Ala Asp Arg Asp Trp Leu Asp Gly His Leu Gln Pro
            195                 200                 205 ctg cgc gac aaa ggc att ccg ctg gtc gcc atc gag tac ctg ccg ccc       816
Leu Arg Asp Lys Gly Ile Pro Leu Val Ala Ile Glu Tyr Leu Pro Pro
        210                 215                 220 gac cgc cgc aac gag gca ccg gcc ctg gtc gcc cgg ctc gtg agc gaa       864
Asp Arg Arg Asn Glu Ala Pro Ala Leu Val Ala Arg Leu Val Ser Glu
225                 230                 235 ggc ttc gtg ccc tat gtc acc gtg ccc aac ctg gat tac ctg ggc gtc       912
Gly Phe Val Pro Tyr Val Thr Val Pro Asn Leu Asp Tyr Leu Gly Val
240                 245                 250                 255 agc acg gtc gac gtg cag ccg cgc cgc att gcg atg atc ttc gac ccc       960
Ser Thr Val Asp Val Gln Pro Arg Arg Ile Ala Met Ile Phe Asp Pro
                260                 265                 270 cgc gag ggc acg ctg tac cag aac ccc ggg cac atg tat gtc ggc ggg      1008
Arg Glu Gly Thr Leu Tyr Gln Asn Pro Gly His Met Tyr Val Gly Gly
```

-continued

```
                        275                 280                 285
ctg ctg gag tac ctc ggg tac cgc gtc gac tac ttc gag gcg gat caa      1056
Leu Leu Glu Tyr Leu Gly Tyr Arg Val Asp Tyr Phe Glu Ala Asp Gln
        290                 295                 300 ctg ccc aac cgg ccc atg agc ggg ttg tac gcc ggt gtg gtg gtg tgg      1104
Leu Pro Asn Arg Pro Met Ser Gly Leu Tyr Ala Gly Val Val Val Trp
305                 310                 315 atg acc agc ggc ccg ccc gag aat gcc ctg gtg ttc aac cag tgg ctg      1152
Met Thr Ser Gly Pro Pro Glu Asn Ala Leu Val Phe Asn Gln Trp Leu
320                 325                 330                 335 tcg gcc cgg gcc gat gag cat gtg ccc ctg gcg ttc ctt gct ggc ctg      1200
Ser Ala Arg Ala Asp Glu His Val Pro Leu Ala Phe Leu Ala Gly Leu
                340                 345                 350 ccg gtg gag aac gac ggt gtg ctg cgc cgc ttc ggc ctg cgc cgt acc      1248
Pro Val Glu Asn Asp Gly Val Leu Arg Arg Phe Gly Leu Arg Arg Thr
        355                 360                 365 ttc acg ccg ctg acc gcc ccg gcc gaa gtg gcc cag cag gac gac gcg      1296
Phe Thr Pro Leu Thr Ala Pro Ala Glu Val Ala Gln Gln Asp Asp Ala
370                 375                 380 ctg att ggc cat ttc gag gcg ccg gtg gtg gtg cgt acc cgt gac ctg      1344
Leu Ile Gly His Phe Glu Ala Pro Val Val Val Arg Thr Arg Asp Leu
385                 390                 395 ccg tcc ctg acc acc ctg gac ggc ggc ccg acg ccg gtc ctc ggc ctg      1392
Pro Ser Leu Thr Thr Leu Asp Gly Gly Pro Thr Pro Val Leu Gly Leu
400                 405                 410                 415 cgc gac agc cag cag cgc atc ttc acc ccg gtg gcc atc ggc gac tgg      1440
Arg Asp Ser Gln Gln Arg Ile Phe Thr Pro Val Ala Ile Gly Asp Trp
                420                 425                 430 ggc ggt atc gcg ctg tcg ccg tat gtg gtg gag gag ggc gcg gac cag      1488
Gly Gly Ile Ala Leu Ser Pro Tyr Val Val Glu Glu Gly Ala Asp Gln
        435                 440                 445 cgc cgc tgg atc atc gac ccc ttc gcc ttc ctg cag aaa gcc ctg cgc      1536
Arg Arg Trp Ile Ile Asp Pro Phe Ala Phe Leu Gln Lys Ala Leu Arg
450                 455                 460 ctg ccg gcc atg ccg cgc ccg gat acc acc acc gag aac ggt cgg cgg      1584
Leu Pro Ala Met Pro Arg Pro Asp Thr Thr Thr Glu Asn Gly Arg Arg
465                 470                 475 gtg gcg acc gtg cac atc gac ggc gac ggc ttc gtg tcc cgt gcc gag      1632
Val Ala Thr Val His Ile Asp Gly Asp Gly Phe Val Ser Arg Ala Glu
480                 485                 490                 495 gcc gtg ggc acg ccg tat tcc ggc gac ctg gtg ctg cgc gac ttc atc      1680
Ala Val Gly Thr Pro Tyr Ser Gly Asp Leu Val Leu Arg Asp Phe Ile
                500                 505                 510 aag cct tac ccg ttc ctc acg tcg gtc tcg gtg atc gag ggc gaa gtg      1728
Lys Pro Tyr Pro Phe Leu Thr Ser Val Ser Val Ile Glu Gly Glu Val
        515                 520                 525 ggg ccc cgg ggt gcg ttc ccg cac ctg gcc cgc gaa ctg gag ccc atc      1776
Gly Pro Arg Gly Ala Phe Pro His Leu Ala Arg Glu Leu Glu Pro Ile
530                 535                 540 gcc cgc aag atc ttc gcc gag ccc aag gtc gaa gtg gcg acg cac acc      1824
Ala Arg Lys Ile Phe Ala Glu Pro Lys Val Glu Val Ala Thr His Thr
545                 550                 555 ttc agc cac ccg ttc ttc tgg cag ccg gaa gtg gcg gag aag cgc gag      1872
Phe Ser His Pro Phe Phe Trp Gln Pro Glu Val Ala Glu Lys Arg Glu
560                 565                 570                 575 ggc ttc aac ccc gaa tac ggc tac atg atg aag atc ccg ggc tac gac      1920
Gly Phe Asn Pro Glu Tyr Gly Tyr Met Met Lys Ile Pro Gly Tyr Asp
                580                 585                 590 aag ctg gac ttc aac cgc gag atc gcc ggt tcc acg gcc tac atc aac      1968
```

```
                    Lys Leu Asp Phe Asn Arg Glu Ile Ala Gly Ser Thr Ala Tyr Ile Asn
                                    595                 600                 605 cag aac ctg acc acg ccg cag aag ccg gtg aaa atg gtg ttc tgg tcc          2016
Gln Asn Leu Thr Thr Pro Gln Lys Pro Val Lys Met Val Phe Trp Ser
                610                 615                 620 ggt gac gcc atg ccg gac gaa gcc acc atc aaa ctg gcg tat gac aac          2064
Gly Asp Ala Met Pro Asp Glu Ala Thr Ile Lys Leu Ala Tyr Asp Asn
            625                 630                 635 ggg ctg acc aac gtc aac ggc ggc aat acc gcg ctg acc aat gcc tac          2112
Gly Leu Thr Asn Val Asn Gly Gly Asn Thr Ala Leu Thr Asn Ala Tyr
        640                 645                 650                 655 ccg tcg ctc acc ggc ctg tac ccg ctg atc cgc ccg acc tcc ggc ggc          2160
Pro Ser Leu Thr Gly Leu Tyr Pro Leu Ile Arg Pro Thr Ser Gly Gly
                660                 665                 670 atc cac tac tac gca ccg gtg atc aac gag aac gtc tac acc aac ctg          2208
Ile His Tyr Tyr Ala Pro Val Ile Asn Glu Asn Val Tyr Thr Asn Leu
            675                 680                 685 tgg acc ggc ccg tac tac ggc ttc cgt ggc gtg atg gaa acc ttc gcc          2256
Trp Thr Gly Pro Tyr Tyr Gly Phe Arg Gly Val Met Glu Thr Phe Ala
        690                 695                 700 ctg acc gac aaa ccc cgt cgt ctg cgc ggg ctg cac ctt tat tac cac          2304
Leu Thr Asp Lys Pro Arg Arg Leu Arg Gly Leu His Leu Tyr Tyr His
    705                 710                 715 ttc tat tcc ggg acc aag cag gcc tcg atc cgg gtc atg aac gac atc          2352
Phe Tyr Ser Gly Thr Lys Gln Ala Ser Ile Arg Val Met Asn Asp Ile
720                 725                 730                 735 tac aaa tcg atg gcg gcc gag cac ccg att tcc ctg tgg atg agc gac          2400
Tyr Lys Ser Met Ala Ala Glu His Pro Ile Ser Leu Trp Met Ser Asp
                740                 745                 750 tac gtg ccg cgc atg cac ggc ctc tac cag gcc agc ctg gcc cgt cgc          2448
Tyr Val Pro Arg Met His Gly Leu Tyr Gln Ala Ser Leu Ala Arg Arg
            755                 760                 765 gcc gac ggt gcc tgg cag att cgc ggc ctg gac ggg ctg cgc acc gtg          2496
Ala Asp Gly Ala Trp Gln Ile Arg Gly Leu Asp Gly Leu Arg Thr Val
        770                 775                 780 cgc ctc gat gcg gcc atg ggt tgg ccg gac ctc agc cgc tcc agc ggt          2544
Arg Leu Asp Ala Ala Met Gly Trp Pro Asp Leu Ser Arg Ser Ser Gly
    785                 790                 795 gtg gcc ggg gtg cgt gac ctg ccc cag ggg cgc tac gtg cac ctg gcc          2592
Val Ala Gly Val Arg Asp Leu Pro Gln Gly Arg Tyr Val His Leu Ala
800                 805                 810                 815 agt gga cag gcg gtg ctg gcc ctg cgt gac acc cgc gat ccg cgc ccg          2640
Ser Gly Gln Ala Val Leu Ala Leu Arg Asp Thr Arg Asp Pro Arg Pro
                820                 825                 830 gcg ctg gag gag gcc aac ctg ccg ctg ctg gcc tgg acc tac ctg gac          2688
Ala Leu Glu Glu Ala Asn Leu Pro Leu Leu Ala Trp Thr Tyr Leu Asp
            835                 840                 845 gac cac cgg gtg aaa ctc tcg ttc gcc ggc agc atg cca ctg caa ttc          2736
Asp His Arg Val Lys Leu Ser Phe Ala Gly Ser Met Pro Leu Gln Phe
        850                 855                 860 agc gtt cgg gcg cag ggc acc tgc cgc ctc gag gtc gcc ggg aaa tcg          2784
Ser Val Arg Ala Gln Gly Thr Cys Arg Leu Glu Val Ala Gly Lys Ser
    865                 870                 875 tat tcg ggt acc cgc cag cag gat ctg tgg cgg ttc agc ttg cct atg          2832
Tyr Ser Gly Thr Arg Gln Gln Asp Leu Trp Arg Phe Ser Leu Pro Met
880                 885                 890                 895 gag cgg gtg ctc gat gca caa ctc acc tgt cgt taa                          2868
Glu Arg Val Leu Asp Ala Gln Leu Thr Cys Arg
                900                 905
```

<210> SEQ ID NO 57
<211> LENGTH: 955
<212> TYPE: PRT
<213> ORGANISM: Pseudomonas seleniipraecipitans

<400> SEQUENCE: 57

```
Met Leu Gly Val Thr Ala Leu Arg His Gly Glu Glu Arg Gly Val Val
                -45                 -40                 -35

Ser Ser Gly Leu Asn Val Thr Phe Arg Lys Thr Val Ile Arg Ala Phe
            -30                 -25                 -20

Thr Trp Leu Phe Ser Leu Cys Ala Ala Leu Ser Ala Val Ala Ser Gln
        -15                 -10                  -5

Ala Ala Gly Leu Ser Pro Ala Gly Pro Gln Ser Val Ala Phe Trp Tyr
 -1   1              5                  10                  15

Ala Pro Asn Pro Tyr Ser Glu Leu Ala Gln Phe Asp Trp Ser Val
                 20                  25                  30

Leu Glu Pro Ser His Val Gln Ala Lys Asp Val Ala Phe Leu Arg Ala
                 35                  40                  45

Gln Gly Asn Gln Pro Phe Ala Tyr Leu Ser Ile Gly Glu Phe Asp Gly
                 50                  55                  60

Asp Leu Ala Val Val Thr Gly Ser Ala Ser Asn Ser Gly Ala Ser Ala
 65                  70                  75

Val Gln Asn Lys Ala Trp Gly Ser Gln Val Met His Leu Ser Ser Pro
 80                  85                  90                  95

Glu Trp Arg Ala Tyr Leu Leu Arg Arg Ala Ser Glu Leu Arg Glu Ala
                100                 105                 110

Gly Tyr Ala Gly Leu Phe Leu Asp Thr Leu Asp Ser Phe Gln Leu Leu
                115                 120                 125

Pro Ala Ala Glu His Glu Thr Gln Arg Ala Ala Leu Arg Asp Phe Leu
                130                 135                 140

Ser Glu Leu Lys Arg Gln Glu Pro Gly Leu Lys Leu Phe Phe Asn Arg
                145                 150                 155

Gly Phe Glu Val Leu Pro Glu Leu Pro Gly Val Ala Ala Val Ala
160                 165                 170                 175

Val Glu Ser Ile His Ala Gly Trp Asp Ala Gln Arg Arg Thr Tyr Arg
                180                 185                 190

Ile Val Pro Gln Ala Asp Arg Asp Trp Leu Asp Gly His Leu Gln Pro
                195                 200                 205

Leu Arg Asp Lys Gly Ile Pro Leu Val Ala Ile Glu Tyr Leu Pro Pro
                210                 215                 220

Asp Arg Arg Asn Glu Ala Pro Ala Leu Val Ala Arg Leu Val Ser Glu
                225                 230                 235

Gly Phe Val Pro Tyr Val Thr Val Pro Asn Leu Asp Tyr Leu Gly Val
240                 245                 250                 255

Ser Thr Val Asp Val Gln Pro Arg Arg Ile Ala Met Ile Phe Asp Pro
                260                 265                 270

Arg Glu Gly Thr Leu Tyr Gln Asn Pro Gly His Met Tyr Val Gly Gly
                275                 280                 285

Leu Leu Glu Tyr Leu Gly Tyr Arg Val Asp Tyr Phe Glu Ala Asp Gln
                290                 295                 300

Leu Pro Asn Arg Pro Met Ser Gly Leu Tyr Ala Gly Val Val Trp
                305                 310                 315

Met Thr Ser Gly Pro Pro Glu Asn Ala Leu Val Phe Asn Gln Trp Leu
320                 325                 330                 335
```

```
Ser Ala Arg Ala Asp Glu His Val Pro Leu Ala Phe Leu Ala Gly Leu
            340                 345                 350

Pro Val Glu Asn Asp Gly Val Leu Arg Arg Phe Gly Leu Arg Arg Thr
        355                 360                 365

Phe Thr Pro Leu Thr Ala Pro Ala Glu Val Ala Gln Gln Asp Asp Ala
    370                 375                 380

Leu Ile Gly His Phe Glu Ala Pro Val Val Arg Thr Arg Asp Leu
385                 390                 395

Pro Ser Leu Thr Thr Leu Asp Gly Gly Pro Thr Pro Val Leu Gly Leu
400             405                 410                 415

Arg Asp Ser Gln Gln Arg Ile Phe Thr Pro Val Ala Ile Gly Asp Trp
                420                 425                 430

Gly Gly Ile Ala Leu Ser Pro Tyr Val Val Glu Glu Gly Ala Asp Gln
            435                 440                 445

Arg Arg Trp Ile Ile Asp Pro Phe Ala Phe Leu Gln Lys Ala Leu Arg
            450                 455                 460

Leu Pro Ala Met Pro Arg Pro Asp Thr Thr Thr Glu Asn Gly Arg Arg
465                 470                 475

Val Ala Thr Val His Ile Asp Gly Asp Gly Phe Val Ser Arg Ala Glu
480                 485                 490                 495

Ala Val Gly Thr Pro Tyr Ser Gly Asp Leu Val Leu Arg Asp Phe Ile
                500                 505                 510

Lys Pro Tyr Pro Phe Leu Thr Ser Val Ser Val Ile Glu Gly Glu Val
                515                 520                 525

Gly Pro Arg Gly Ala Phe Pro His Leu Ala Arg Glu Leu Glu Pro Ile
            530                 535                 540

Ala Arg Lys Ile Phe Ala Glu Pro Lys Val Glu Val Ala Thr His Thr
            545                 550                 555

Phe Ser His Pro Phe Phe Trp Gln Pro Glu Val Ala Glu Lys Arg Glu
560                 565                 570                 575

Gly Phe Asn Pro Glu Tyr Gly Tyr Met Met Lys Ile Pro Gly Tyr Asp
                580                 585                 590

Lys Leu Asp Phe Asn Arg Glu Ile Ala Gly Ser Thr Ala Tyr Ile Asn
                595                 600                 605

Gln Asn Leu Thr Thr Pro Gln Lys Pro Val Lys Met Val Phe Trp Ser
            610                 615                 620

Gly Asp Ala Met Pro Asp Glu Ala Thr Ile Lys Leu Ala Tyr Asp Asn
625                 630                 635

Gly Leu Thr Asn Val Asn Gly Gly Asn Thr Ala Leu Thr Asn Ala Tyr
640                 645                 650                 655

Pro Ser Leu Thr Gly Leu Tyr Pro Leu Ile Arg Pro Thr Ser Gly Gly
                660                 665                 670

Ile His Tyr Tyr Ala Pro Val Ile Asn Glu Asn Val Tyr Thr Asn Leu
            675                 680                 685

Trp Thr Gly Pro Tyr Tyr Gly Phe Arg Gly Val Met Glu Thr Phe Ala
            690                 695                 700

Leu Thr Asp Lys Pro Arg Arg Leu Arg Gly Leu His Leu Tyr Tyr His
705                 710                 715

Phe Tyr Ser Gly Thr Lys Gln Ala Ser Ile Arg Val Met Asn Asp Ile
720                 725                 730                 735

Tyr Lys Ser Met Ala Ala Glu His Pro Ile Ser Leu Trp Met Ser Asp
                740                 745                 750
```

```
Tyr Val Pro Arg Met His Gly Leu Tyr Gln Ala Ser Leu Ala Arg Arg
                755                 760                 765

Ala Asp Gly Ala Trp Gln Ile Arg Gly Leu Asp Gly Leu Arg Thr Val
        770                 775                 780

Arg Leu Asp Ala Ala Met Gly Trp Pro Asp Leu Ser Arg Ser Ser Gly
785                 790                 795

Val Ala Gly Val Arg Asp Leu Pro Gln Gly Arg Tyr Val His Leu Ala
800                 805                 810                 815

Ser Gly Gln Ala Val Leu Ala Leu Arg Asp Thr Arg Asp Pro Arg Pro
                820                 825                 830

Ala Leu Glu Glu Ala Asn Leu Pro Leu Leu Ala Trp Thr Tyr Leu Asp
        835                 840                 845

Asp His Arg Val Lys Leu Ser Phe Ala Gly Ser Met Pro Leu Gln Phe
        850                 855                 860

Ser Val Arg Ala Gln Gly Thr Cys Arg Leu Glu Val Ala Gly Lys Ser
865                 870                 875

Tyr Ser Gly Thr Arg Gln Gln Asp Leu Trp Arg Phe Ser Leu Pro Met
880                 885                 890                 895

Glu Arg Val Leu Asp Ala Gln Leu Thr Cys Arg
                900                 905

<210> SEQ ID NO 58
<211> LENGTH: 906
<212> TYPE: PRT
<213> ORGANISM: Pseudomonas seleniipraecipitans

<400> SEQUENCE: 58

Ala Gly Leu Ser Pro Ala Gly Pro Gln Ser Val Ala Phe Trp Tyr Ala
1               5                   10                  15

Pro Asn Pro Pro Tyr Ser Glu Leu Ala Gln Phe Asp Trp Ser Val Leu
                20                  25                  30

Glu Pro Ser His Val Gln Ala Lys Asp Val Ala Phe Leu Arg Ala Gln
        35                  40                  45

Gly Asn Gln Pro Phe Ala Tyr Leu Ser Ile Gly Glu Phe Asp Gly Asp
    50                  55                  60

Leu Ala Val Val Thr Gly Ser Ala Ser Asn Ser Gly Ala Ser Ala Val
65                  70                  75                  80

Gln Asn Lys Ala Trp Gly Ser Gln Val Met His Leu Ser Ser Pro Glu
                85                  90                  95

Trp Arg Ala Tyr Leu Leu Arg Arg Ala Ser Glu Leu Arg Glu Ala Gly
                100                 105                 110

Tyr Ala Gly Leu Phe Leu Asp Thr Leu Asp Ser Phe Gln Leu Leu Pro
        115                 120                 125

Ala Ala Glu His Glu Thr Gln Arg Ala Ala Leu Arg Asp Phe Leu Ser
    130                 135                 140

Glu Leu Lys Arg Gln Glu Pro Gly Leu Lys Leu Phe Phe Asn Arg Gly
145                 150                 155                 160

Phe Glu Val Leu Pro Glu Leu Pro Gly Val Ala Ala Ala Val Ala Val
                165                 170                 175

Glu Ser Ile His Ala Gly Trp Asp Ala Gln Arg Arg Thr Tyr Arg Ile
        180                 185                 190

Val Pro Gln Ala Asp Arg Asp Trp Leu Asp Gly His Leu Gln Pro Leu
    195                 200                 205

Arg Asp Lys Gly Ile Pro Leu Val Ala Ile Glu Tyr Leu Pro Pro Asp
210                 215                 220
```

```
Arg Arg Asn Glu Ala Pro Ala Leu Val Ala Arg Leu Val Ser Glu Gly
225                 230                 235                 240

Phe Val Pro Tyr Val Thr Val Pro Asn Leu Asp Tyr Leu Gly Val Ser
            245                 250                 255

Thr Val Asp Val Gln Pro Arg Arg Ile Ala Met Ile Phe Asp Pro Arg
        260                 265                 270

Glu Gly Thr Leu Tyr Gln Asn Pro Gly His Met Tyr Val Gly Gly Leu
    275                 280                 285

Leu Glu Tyr Leu Gly Tyr Arg Val Asp Tyr Phe Glu Ala Asp Gln Leu
290                 295                 300

Pro Asn Arg Pro Met Ser Gly Leu Tyr Ala Gly Val Val Val Trp Met
305                 310                 315                 320

Thr Ser Gly Pro Pro Glu Asn Ala Leu Val Phe Asn Gln Trp Leu Ser
            325                 330                 335

Ala Arg Ala Asp Glu His Val Pro Leu Ala Phe Leu Ala Gly Leu Pro
        340                 345                 350

Val Glu Asn Asp Gly Val Leu Arg Arg Phe Gly Leu Arg Arg Thr Phe
    355                 360                 365

Thr Pro Leu Thr Ala Pro Ala Glu Val Ala Gln Gln Asp Asp Ala Leu
370                 375                 380

Ile Gly His Phe Glu Ala Pro Val Val Arg Thr Arg Asp Leu Pro
385                 390                 395                 400

Ser Leu Thr Thr Leu Asp Gly Gly Pro Thr Pro Val Leu Gly Leu Arg
            405                 410                 415

Asp Ser Gln Gln Arg Ile Phe Thr Pro Val Ala Ile Gly Asp Trp Gly
        420                 425                 430

Gly Ile Ala Leu Ser Pro Tyr Val Val Glu Glu Gly Ala Asp Gln Arg
    435                 440                 445

Arg Trp Ile Ile Asp Pro Phe Ala Phe Leu Gln Lys Ala Leu Arg Leu
450                 455                 460

Pro Ala Met Pro Arg Pro Asp Thr Thr Thr Glu Asn Gly Arg Arg Val
465                 470                 475                 480

Ala Thr Val His Ile Asp Gly Asp Gly Phe Val Ser Arg Ala Glu Ala
            485                 490                 495

Val Gly Thr Pro Tyr Ser Gly Asp Leu Val Leu Arg Asp Phe Ile Lys
        500                 505                 510

Pro Tyr Pro Phe Leu Thr Ser Val Ser Val Ile Glu Gly Glu Val Gly
    515                 520                 525

Pro Arg Gly Ala Phe Pro His Leu Ala Arg Glu Leu Glu Pro Ile Ala
530                 535                 540

Arg Lys Ile Phe Ala Glu Pro Lys Val Glu Val Ala Thr His Thr Phe
545                 550                 555                 560

Ser His Pro Phe Phe Trp Gln Pro Glu Val Ala Glu Lys Arg Glu Gly
            565                 570                 575

Phe Asn Pro Glu Tyr Gly Tyr Met Met Lys Ile Pro Gly Tyr Asp Lys
        580                 585                 590

Leu Asp Phe Asn Arg Glu Ile Ala Gly Ser Thr Ala Tyr Ile Asn Gln
    595                 600                 605

Asn Leu Thr Thr Pro Gln Lys Pro Val Lys Met Val Phe Trp Ser Gly
610                 615                 620

Asp Ala Met Pro Asp Glu Ala Thr Ile Lys Leu Ala Tyr Asp Asn Gly
625                 630                 635                 640
```

```
Leu Thr Asn Val Asn Gly Gly Asn Thr Ala Leu Thr Asn Ala Tyr Pro
            645                 650                 655

Ser Leu Thr Gly Leu Tyr Pro Leu Ile Arg Pro Thr Ser Gly Gly Ile
        660                 665                 670

His Tyr Tyr Ala Pro Val Ile Asn Glu Asn Val Tyr Thr Asn Leu Trp
    675                 680                 685

Thr Gly Pro Tyr Tyr Gly Phe Arg Gly Val Met Glu Thr Phe Ala Leu
690                 695                 700

Thr Asp Lys Pro Arg Arg Leu Arg Gly Leu His Leu Tyr Tyr His Phe
705                 710                 715                 720

Tyr Ser Gly Thr Lys Gln Ala Ser Ile Arg Val Met Asn Asp Ile Tyr
                725                 730                 735

Lys Ser Met Ala Ala Glu His Pro Ile Ser Leu Trp Met Ser Asp Tyr
            740                 745                 750

Val Pro Arg Met His Gly Leu Tyr Gln Ala Ser Leu Ala Arg Arg Ala
        755                 760                 765

Asp Gly Ala Trp Gln Ile Arg Gly Leu Asp Gly Leu Arg Thr Val Arg
    770                 775                 780

Leu Asp Ala Ala Met Gly Trp Pro Asp Leu Ser Arg Ser Ser Gly Val
785                 790                 795                 800

Ala Gly Val Arg Asp Leu Pro Gln Gly Arg Tyr Val His Leu Ala Ser
                805                 810                 815

Gly Gln Ala Val Leu Ala Leu Arg Asp Thr Arg Asp Pro Arg Pro Ala
            820                 825                 830

Leu Glu Glu Ala Asn Leu Pro Leu Leu Ala Trp Thr Tyr Leu Asp Asp
        835                 840                 845

His Arg Val Lys Leu Ser Phe Ala Gly Ser Met Pro Leu Gln Phe Ser
    850                 855                 860

Val Arg Ala Gln Gly Thr Cys Arg Leu Glu Val Ala Gly Lys Ser Tyr
865                 870                 875                 880

Ser Gly Thr Arg Gln Gln Asp Leu Trp Arg Phe Ser Leu Pro Met Glu
                885                 890                 895

Arg Val Leu Asp Ala Gln Leu Thr Cys Arg
            900                 905

<210> SEQ ID NO 59
<211> LENGTH: 2814
<212> TYPE: DNA
<213> ORGANISM: Pseudomonas migulae
<220> FEATURE:
<221> NAME/KEY: CDS
<222> LOCATION: (1)..(2811)
<220> FEATURE:
<221> NAME/KEY: sig_peptide
<222> LOCATION: (1)..(96)
<220> FEATURE:
<221> NAME/KEY: mat_peptide
<222> LOCATION: (97)..(2811)

<400> SEQUENCE: 59 atg gaa atc gtt ttt cgc agg acg cgt gtc cgc tcg gcc gcc aaa cgg      48
Met Glu Ile Val Phe Arg Arg Thr Arg Val Arg Ser Ala Ala Lys Arg
        -30                 -25                 -20 ctg ttg gct gcc atc gcg ctt atc gtg agt ggc ccg gca gcc cag gcc      96
Leu Leu Ala Ala Ile Ala Leu Ile Val Ser Gly Pro Ala Ala Gln Ala
    -15                 -10                 -5                  -1 gca gct ttg cca cag ccc tcc agc gtg acc ttt tgg tac gcc gct cag     144
Ala Ala Leu Pro Gln Pro Ser Ser Val Thr Phe Trp Tyr Ala Ala Gln
1               5                   10                  15
```

```
cct ccg ata ccg gag ctt gca cag ttc gac tgg tcg gtg gtc gag cct    192
Pro Pro Ile Pro Glu Leu Ala Gln Phe Asp Trp Ser Val Val Glu Pro
        20              25                  30 ggg cat ttg acc aag gac gac gtc aaa acc ctg cgt gat ttg ggc agc    240
Gly His Leu Thr Lys Asp Asp Val Lys Thr Leu Arg Asp Leu Gly Ser
            35              40              45 cag ccg ttt gcg tat gta tcc atc ggc gag ttt gcc ggc agc aag gca    288
Gln Pro Phe Ala Tyr Val Ser Ile Gly Glu Phe Ala Gly Ser Lys Ala
    50              55              60 gac att gaa aaa gcc cac ctt tcg gac gcg atc agc ccg gtg cgc aac    336
Asp Ile Glu Lys Ala His Leu Ser Asp Ala Ile Ser Pro Val Arg Asn
65              70              75              80 ggc gcc tgg gac agc cag gtg atg aac ctt tct gca ccg gcc tgg cgt    384
Gly Ala Trp Asp Ser Gln Val Met Asn Leu Ser Ala Pro Ala Trp Arg
                85              90              95 gag cat ttg ttc ggt cgc gcc aag aca tta cag gcc gaa ggt tat gcc    432
Glu His Leu Phe Gly Arg Ala Lys Thr Leu Gln Ala Glu Gly Tyr Ala
            100             105             110 ggg ttg ttc ctc gac acc ctc gac agc ttc cag ttg cag cca gag gct    480
Gly Leu Phe Leu Asp Thr Leu Asp Ser Phe Gln Leu Gln Pro Glu Ala
        115             120             125 gat cga gaa aaa cag cgc ctg gca ctc gcc agc ttc ctg cgc gaa ttg    528
Asp Arg Glu Lys Gln Arg Leu Ala Leu Ala Ser Phe Leu Arg Glu Leu
    130             135             140 cac cag cgt cag ccg aca ttg aaa ctg ttt ttc aac cgt ggc ttt gaa    576
His Gln Arg Gln Pro Thr Leu Lys Leu Phe Phe Asn Arg Gly Phe Glu
145             150             155             160 gtc ctg ccc gaa ctt gat ggt gtg gcg gcc gca gtg gct gtc gag tcg    624
Val Leu Pro Glu Leu Asp Gly Val Ala Ala Ala Val Ala Val Glu Ser
                165             170             175 att cat gcc ggt tgg gat gca acg gcc aag cgt tat cgc ccg gtg cct    672
Ile His Ala Gly Trp Asp Ala Thr Ala Lys Arg Tyr Arg Pro Val Pro
            180             185             190 gag gcc gac cgt gcc tgg ctg gaa acc cag ctc cag cct ttg cgc gcc    720
Glu Ala Asp Arg Ala Trp Leu Glu Thr Gln Leu Gln Pro Leu Arg Ala
        195             200             205 aaa ggc atc ccg ctg gtg gcc atc gac tac ttg ccg ccg gag cgt cgc    768
Lys Gly Ile Pro Leu Val Ala Ile Asp Tyr Leu Pro Pro Glu Arg Arg
210             215             220 gat gaa gcg cgc aag ctg gca aag cgt ctg cgc gag gag ggg ttc att    816
Asp Glu Ala Arg Lys Leu Ala Lys Arg Leu Arg Glu Glu Gly Phe Ile
225             230             235             240 ccg tac atc ggc acc cct gaa ctg gac tcg atg ggc atc agc aat att    864
Pro Tyr Ile Gly Thr Pro Glu Leu Asp Ser Met Gly Ile Ser Asn Ile
                245             250             255 gaa gtt cag ccg cgc cgg gtc gca ctg ctt tac gac ctg cgc gaa gat    912
Glu Val Gln Pro Arg Arg Val Ala Leu Leu Tyr Asp Leu Arg Glu Asp
            260             265             270 gac ctg act caa aat gac gga cac aca ttg ctg ggc ggt ttg ctg gaa    960
Asp Leu Thr Gln Asn Asp Gly His Thr Leu Leu Gly Gly Leu Leu Glu
        275             280             285 tac ctt ggc tac cgc gtg gat tac ctg ccg gtc gac gac acc ctg tcg   1008
Tyr Leu Gly Tyr Arg Val Asp Tyr Leu Pro Val Asp Asp Thr Leu Ser
    290             295             300 gaa cgt cgc ttc agc ggt ctg tac gct ggc gtc atc acc tgg atg acc   1056
Glu Arg Arg Phe Ser Gly Leu Tyr Ala Gly Val Ile Thr Trp Met Thr
305             310             315             320 agc ggc ccg ccg cag aac gct gcg gcg ttc aat acc tgg atc ggc aag   1104
Ser Gly Pro Pro Gln Asn Ala Ala Ala Phe Asn Thr Trp Ile Gly Lys
```

-continued

|  |  |  | 325 |  |  |  | 330 |  |  |  | 335 |  |  |  |  |
|---|---|---|---|---|---|---|---|---|---|---|---|---|---|---|---| cgt ctg gat gag aaa gtg ccg gtg gtg ttt ttt gcc ggg ctg ccg att     1152
Arg Leu Asp Glu Lys Val Pro Val Val Phe Phe Ala Gly Leu Pro Ile
            340                 345                 350 cag gac acc tcg ctg ctc aag cgt ctt ggc ctg aac cgt aca gcg cca     1200
Gln Asp Thr Ser Leu Leu Lys Arg Leu Gly Leu Asn Arg Thr Ala Pro
            355                 360                 365 atc ggc acg caa acg ttg agc atc acc tct cag gac aag gcg ctg atc     1248
Ile Gly Thr Gln Thr Leu Ser Ile Thr Ser Gln Asp Lys Ala Leu Ile
370                 375                 380 gga gcg ttc gaa gca ccg gtg cag ccc cga tcc cgt gac ctg acc gcg     1296
Gly Ala Phe Glu Ala Pro Val Gln Pro Arg Ser Arg Asp Leu Thr Ala
385                 390                 395                 400 att tcc ctg ctg cca aaa ggc ccc aaa gcc gca ttg ctg ttg acc gca     1344
Ile Ser Leu Leu Pro Lys Gly Pro Lys Ala Ala Leu Leu Leu Thr Ala
                405                 410                 415 gca gac ggc cag acc ttt gct ccg gtt gcg gtc gcc gat tgg ggt gga     1392
Ala Asp Gly Gln Thr Phe Ala Pro Val Ala Val Ala Asp Trp Gly Gly
                420                 425                 430 ctg gcc ctt gca cct tac att ctc gaa acg aac aac gaa cgc agt cgc     1440
Leu Ala Leu Ala Pro Tyr Ile Leu Glu Thr Asn Asn Glu Arg Ser Arg
                435                 440                 445 tgg att ctc gac ccc ttc gca ttc ctt cag gcc agc ttg cgt ttg ccg     1488
Trp Ile Leu Asp Pro Phe Ala Phe Leu Gln Ala Ser Leu Arg Leu Pro
            450                 455                 460 gtc cag cca cgc ccg gac acc acc acc gaa aac ggt cgg cgc atc gcc     1536
Val Gln Pro Arg Pro Asp Thr Thr Thr Glu Asn Gly Arg Arg Ile Ala
465                 470                 475                 480 acc gtg cat atc gat ggc gat ggt ttc ccg tcg cgc gcc gag gtg cga     1584
Thr Val His Ile Asp Gly Asp Gly Phe Pro Ser Arg Ala Glu Val Arg
                485                 490                 495 ggc acg ccg tat gcc ggc aga cag gtg tac gac gat ttc att cga ccc     1632
Gly Thr Pro Tyr Ala Gly Arg Gln Val Tyr Asp Asp Phe Ile Arg Pro
                500                 505                 510 aat ccg ttt ctg act tcg gtg tcg gtg atc gaa ggt gaa att tcg ccg     1680
Asn Pro Phe Leu Thr Ser Val Ser Val Ile Glu Gly Glu Ile Ser Pro
            515                 520                 525 cgc ggg atg ttc ccg ttt ctc gcc ggc gaa ctg gaa ccg att gcc cgt     1728
Arg Gly Met Phe Pro Phe Leu Ala Gly Glu Leu Glu Pro Ile Ala Arg
            530                 535                 540 gag atc ttc gcc gac ccg aaa gtc gaa gtc gcc acg cac acc ttc agc     1776
Glu Ile Phe Ala Asp Pro Lys Val Glu Val Ala Thr His Thr Phe Ser
545                 550                 555                 560 cat ccg ttt ttc tgg cag cct gaa ctg gcg aaa aag caa gaa aac ttc     1824
His Pro Phe Phe Trp Gln Pro Glu Leu Ala Lys Lys Gln Glu Asn Phe
                565                 570                 575 agc ccg gaa tac ggc ctg aac atg gcc atc ccg aac tac gac aaa atc     1872
Ser Pro Glu Tyr Gly Leu Asn Met Ala Ile Pro Asn Tyr Asp Lys Ile
                580                 585                 590 gat ttc cgc cga gag att ttt ggc tcg cgc gac tac atc aat cag cag     1920
Asp Phe Arg Arg Glu Ile Phe Gly Ser Arg Asp Tyr Ile Asn Gln Gln
                595                 600                 605 ctc acc acc ccg gaa aaa ccg gtg aag atg gtg ttc tgg ccg ggc gac     1968
Leu Thr Thr Pro Glu Lys Pro Val Lys Met Val Phe Trp Pro Gly Asp
            610                 615                 620 gcg ttg ccg tcg gcc tcc tcc atc aaa ctg gct tac gac gcc ggc ctg     2016
Ala Leu Pro Ser Ala Ser Ser Ile Lys Leu Ala Tyr Asp Ala Gly Leu
625                 630                 635                 640 aaa aac gtc aac ggc gcg gcg acc atg ctg acc aag gcc aac ccg tcg     2064

```
         Lys Asn Val Asn Gly Ala Ala Thr Met Leu Thr Lys Ala Asn Pro Ser
                         645                 650                 655 atg acc ggt ttg cag ccg ttg ctg cga ccc acc gaa ggc ggt ttg cag         2112
Met Thr Gly Leu Gln Pro Leu Leu Arg Pro Thr Glu Gly Gly Leu Gln
            660                 665                 670 tac tac gca ccc att atc aac gag aac ctc tac acc aac ctg tgg aaa         2160
Tyr Tyr Ala Pro Ile Ile Asn Glu Asn Leu Tyr Thr Asn Leu Trp Lys
            675                 680                 685 ggc ccg tat tac ggc ttc cgc gat gtg atc gac acc ttc gag ctt acc         2208
Gly Pro Tyr Tyr Gly Phe Arg Asp Val Ile Asp Thr Phe Glu Leu Thr
690                 695                 700 gac agc cca cgg cgc atg cgc ggt ctg cac ctg tat tac cac ttc tat         2256
Asp Ser Pro Arg Arg Met Arg Gly Leu His Leu Tyr Tyr His Phe Tyr
705                 710                 715                 720 tca agc acc aag cag gcc tcg atc aag gtc atg ggc gag atc tac ggc         2304
Ser Ser Thr Lys Gln Ala Ser Ile Lys Val Met Gly Glu Ile Tyr Gly
                725                 730                 735 tac atg aag acg caa cag ccg atg tca ctg tgg atg agc gat tat ctc         2352
Tyr Met Lys Thr Gln Gln Pro Met Ser Leu Trp Met Ser Asp Tyr Leu
            740                 745                 750 gat cgt ttg cac ggt ttg tat cag gtc agc ctg gcg cgc acc gcc gaa         2400
Asp Arg Leu His Gly Leu Tyr Gln Val Ser Leu Ala Arg Thr Ala Glu
            755                 760                 765 ggt gac tgg cag gtt cgt ggc ctg gac gcg cta cgt acc ctg cgg ctc         2448
Gly Asp Trp Gln Val Arg Gly Leu Asp Ala Leu Arg Thr Leu Arg Leu
770                 775                 780 gac ccg caa atg ggc tgg cca gac ctg atg cgt tcg caa ggt gtc gcc         2496
Asp Pro Gln Met Gly Trp Pro Asp Leu Met Arg Ser Gln Gly Val Ala
785                 790                 795                 800 ggt gtt cgc gac ttg cct caa ggc cgt tac gtg gca ttg agc agc gac         2544
Gly Val Arg Asp Leu Pro Gln Gly Arg Tyr Val Ala Leu Ser Ser Asp
                805                 810                 815 cgt gca ttg ctc gta tta cgt cct gat cgg gac aac cat ccg gca ttg         2592
Arg Ala Leu Leu Val Leu Arg Pro Asp Arg Asp Asn His Pro Ala Leu
            820                 825                 830 gag gag gcc aat ctg cca ctg gtg gat tgg cgt tac gtc aat gag cgt         2640
Glu Glu Ala Asn Leu Pro Leu Val Asp Trp Arg Tyr Val Asn Glu Arg
            835                 840                 845 cag gtg gac ttc tcg ttt gcc ggt cag gtc gac ctg acc ttc tcc gtg         2688
Gln Val Asp Phe Ser Phe Ala Gly Gln Val Asp Leu Thr Phe Ser Val
850                 855                 860 cgg ttg ccc ggc acg tgc cgg gtt gag gtg gac gga caa cat ttt gca         2736
Arg Leu Pro Gly Thr Cys Arg Val Glu Val Asp Gly Gln His Phe Ala
865                 870                 875                 880 ggc aag gca tcc gcc ggt ctg tgg act ttt caa tta ccg atg aag cag         2784
Gly Lys Ala Ser Ala Gly Leu Trp Thr Phe Gln Leu Pro Met Lys Gln
                885                 890                 895 gtg agt cat ggt caa ctc ttc tgc agc taa                                 2814
Val Ser His Gly Gln Leu Phe Cys Ser
            900                 905

<210> SEQ ID NO 60
<211> LENGTH: 937
<212> TYPE: PRT
<213> ORGANISM: Pseudomonas migulae

<400> SEQUENCE: 60

Met Glu Ile Val Phe Arg Arg Thr Arg Val Arg Ser Ala Ala Lys Arg
        -30                 -25                 -20

Leu Leu Ala Ala Ile Ala Leu Ile Val Ser Gly Pro Ala Ala Gln Ala
```

```
              -15            -10              -5              -1
Ala Ala Leu Pro Gln Pro Ser Ser Val Thr Phe Trp Tyr Ala Ala Gln
1               5                   10                  15

Pro Pro Ile Pro Glu Leu Ala Gln Phe Asp Trp Ser Val Val Glu Pro
                20                  25                  30

Gly His Leu Thr Lys Asp Asp Val Lys Thr Leu Arg Asp Leu Gly Ser
                35                  40                  45

Gln Pro Phe Ala Tyr Val Ser Ile Gly Glu Phe Ala Gly Ser Lys Ala
        50                  55                  60

Asp Ile Glu Lys Ala His Leu Ser Asp Ala Ile Ser Pro Val Arg Asn
65                  70                  75                  80

Gly Ala Trp Asp Ser Gln Val Met Asn Leu Ser Ala Pro Ala Trp Arg
                85                  90                  95

Glu His Leu Phe Gly Arg Ala Lys Thr Leu Gln Ala Glu Gly Tyr Ala
                100                 105                 110

Gly Leu Phe Leu Asp Thr Leu Asp Ser Phe Gln Leu Gln Pro Glu Ala
            115                 120                 125

Asp Arg Glu Lys Gln Arg Leu Ala Leu Ala Ser Phe Leu Arg Glu Leu
        130                 135                 140

His Gln Arg Gln Pro Thr Leu Lys Leu Phe Phe Asn Arg Gly Phe Glu
145                 150                 155                 160

Val Leu Pro Glu Leu Asp Gly Val Ala Ala Val Ala Val Glu Ser
                165                 170                 175

Ile His Ala Gly Trp Asp Ala Thr Ala Lys Arg Tyr Arg Pro Val Pro
                180                 185                 190

Glu Ala Asp Arg Ala Trp Leu Glu Thr Gln Leu Gln Pro Leu Arg Ala
            195                 200                 205

Lys Gly Ile Pro Leu Val Ala Ile Asp Tyr Leu Pro Pro Glu Arg Arg
        210                 215                 220

Asp Glu Ala Arg Lys Leu Ala Lys Arg Leu Arg Glu Glu Gly Phe Ile
225                 230                 235                 240

Pro Tyr Ile Gly Thr Pro Glu Leu Asp Ser Met Gly Ile Ser Asn Ile
                245                 250                 255

Glu Val Gln Pro Arg Arg Val Ala Leu Leu Tyr Asp Leu Arg Glu Asp
                260                 265                 270

Asp Leu Thr Gln Asn Asp Gly His Thr Leu Leu Gly Gly Leu Leu Glu
            275                 280                 285

Tyr Leu Gly Tyr Arg Val Asp Tyr Leu Pro Val Asp Asp Thr Leu Ser
        290                 295                 300

Glu Arg Arg Phe Ser Gly Leu Tyr Ala Gly Val Ile Thr Trp Met Thr
305                 310                 315                 320

Ser Gly Pro Pro Gln Asn Ala Ala Ala Phe Asn Thr Trp Ile Gly Lys
                325                 330                 335

Arg Leu Asp Glu Lys Val Pro Val Phe Ala Gly Leu Pro Ile
                340                 345                 350

Gln Asp Thr Ser Leu Leu Lys Arg Leu Gly Leu Asn Arg Thr Ala Pro
            355                 360                 365

Ile Gly Thr Gln Thr Leu Ser Ile Thr Ser Gln Asp Lys Ala Leu Ile
        370                 375                 380

Gly Ala Phe Glu Ala Pro Val Gln Pro Arg Ser Arg Asp Leu Thr Ala
385                 390                 395                 400

Ile Ser Leu Leu Pro Lys Gly Pro Lys Ala Ala Leu Leu Leu Thr Ala
                405                 410                 415
```

```
Ala Asp Gly Gln Thr Phe Ala Pro Val Ala Val Ala Asp Trp Gly Gly
            420                 425                 430

Leu Ala Leu Ala Pro Tyr Ile Leu Glu Thr Asn Asn Glu Arg Ser Arg
            435                 440                 445

Trp Ile Leu Asp Pro Phe Ala Phe Leu Gln Ala Ser Leu Arg Leu Pro
            450                 455                 460

Val Gln Pro Arg Pro Asp Thr Thr Glu Asn Gly Arg Arg Ile Ala
465                 470                 475                 480

Thr Val His Ile Asp Gly Asp Phe Pro Ser Arg Ala Glu Val Arg
            485                 490                 495

Gly Thr Pro Tyr Ala Gly Arg Gln Val Tyr Asp Phe Ile Arg Pro
            500                 505                 510

Asn Pro Phe Leu Thr Ser Val Ser Val Ile Glu Gly Glu Ile Ser Pro
            515                 520                 525

Arg Gly Met Phe Pro Phe Leu Ala Gly Glu Leu Glu Pro Ile Ala Arg
            530                 535                 540

Glu Ile Phe Ala Asp Pro Lys Val Glu Val Ala Thr His Thr Phe Ser
545                 550                 555                 560

His Pro Phe Phe Trp Gln Pro Glu Leu Ala Lys Lys Gln Glu Asn Phe
            565                 570                 575

Ser Pro Glu Tyr Gly Leu Asn Met Ala Ile Pro Asn Tyr Asp Lys Ile
            580                 585                 590

Asp Phe Arg Arg Glu Ile Phe Gly Ser Arg Asp Tyr Ile Asn Gln Gln
            595                 600                 605

Leu Thr Thr Pro Glu Lys Pro Val Lys Met Val Phe Trp Pro Gly Asp
            610                 615                 620

Ala Leu Pro Ser Ala Ser Ser Ile Lys Leu Ala Tyr Asp Ala Gly Leu
625                 630                 635                 640

Lys Asn Val Asn Gly Ala Ala Thr Met Leu Thr Lys Ala Asn Pro Ser
            645                 650                 655

Met Thr Gly Leu Gln Pro Leu Leu Arg Pro Thr Glu Gly Gly Leu Gln
            660                 665                 670

Tyr Tyr Ala Pro Ile Ile Asn Glu Asn Leu Tyr Thr Asn Leu Trp Lys
            675                 680                 685

Gly Pro Tyr Tyr Gly Phe Arg Asp Val Ile Asp Thr Phe Glu Leu Thr
            690                 695                 700

Asp Ser Pro Arg Arg Met Arg Gly Leu His Leu Tyr Tyr His Phe Tyr
705                 710                 715                 720

Ser Ser Thr Lys Gln Ala Ser Ile Lys Val Met Gly Glu Ile Tyr Gly
            725                 730                 735

Tyr Met Lys Thr Gln Gln Pro Met Ser Leu Trp Met Ser Asp Tyr Leu
            740                 745                 750

Asp Arg Leu His Gly Leu Tyr Gln Val Ser Leu Ala Arg Thr Ala Glu
            755                 760                 765

Gly Asp Trp Gln Val Arg Gly Leu Asp Ala Leu Arg Thr Leu Arg Leu
            770                 775                 780

Asp Pro Gln Met Gly Trp Pro Asp Leu Met Arg Ser Gln Gly Val Ala
785                 790                 795                 800

Gly Val Arg Asp Leu Pro Gln Gly Arg Tyr Val Ala Leu Ser Ser Asp
            805                 810                 815

Arg Ala Leu Leu Val Leu Arg Pro Asp Arg Asp Asn His Pro Ala Leu
            820                 825                 830
```

```
Glu Glu Ala Asn Leu Pro Leu Val Asp Trp Arg Tyr Val Asn Glu Arg
            835                 840                 845

Gln Val Asp Phe Ser Phe Ala Gly Gln Val Asp Leu Thr Phe Ser Val
    850                 855                 860

Arg Leu Pro Gly Thr Cys Arg Val Glu Val Asp Gly Gln His Phe Ala
865                 870                 875                 880

Gly Lys Ala Ser Ala Gly Leu Trp Thr Phe Gln Leu Pro Met Lys Gln
                885                 890                 895

Val Ser His Gly Gln Leu Phe Cys Ser
                900                 905

<210> SEQ ID NO 61
<211> LENGTH: 905
<212> TYPE: PRT
<213> ORGANISM: Pseudomonas migulae

<400> SEQUENCE: 61

Ala Ala Leu Pro Gln Pro Ser Ser Val Thr Phe Trp Tyr Ala Ala Gln
1               5                   10                  15

Pro Pro Ile Pro Glu Leu Ala Gln Phe Asp Trp Ser Val Val Glu Pro
            20                  25                  30

Gly His Leu Thr Lys Asp Asp Val Lys Thr Leu Arg Asp Leu Gly Ser
        35                  40                  45

Gln Pro Phe Ala Tyr Val Ser Ile Gly Glu Phe Ala Gly Ser Lys Ala
    50                  55                  60

Asp Ile Glu Lys Ala His Leu Ser Asp Ala Ile Ser Pro Val Arg Asn
65                  70                  75                  80

Gly Ala Trp Asp Ser Gln Val Met Asn Leu Ser Ala Pro Ala Trp Arg
                85                  90                  95

Glu His Leu Phe Gly Arg Ala Lys Thr Leu Gln Ala Glu Gly Tyr Ala
            100                 105                 110

Gly Leu Phe Leu Asp Thr Leu Asp Ser Phe Gln Leu Gln Pro Glu Ala
        115                 120                 125

Asp Arg Glu Lys Gln Arg Leu Ala Leu Ala Ser Phe Leu Arg Glu Leu
    130                 135                 140

His Gln Arg Gln Pro Thr Leu Lys Leu Phe Phe Asn Arg Gly Phe Glu
145                 150                 155                 160

Val Leu Pro Glu Leu Asp Gly Val Ala Ala Val Ala Val Glu Ser
                165                 170                 175

Ile His Ala Gly Trp Asp Ala Thr Ala Lys Arg Tyr Arg Pro Val Pro
            180                 185                 190

Glu Ala Asp Arg Ala Trp Leu Glu Thr Gln Leu Gln Pro Leu Arg Ala
        195                 200                 205

Lys Gly Ile Pro Leu Val Ala Ile Asp Tyr Leu Pro Pro Glu Arg Arg
    210                 215                 220

Asp Glu Ala Arg Lys Leu Ala Lys Arg Leu Arg Glu Glu Gly Phe Ile
225                 230                 235                 240

Pro Tyr Ile Gly Thr Pro Glu Leu Asp Ser Met Gly Ile Ser Asn Ile
                245                 250                 255

Glu Val Gln Pro Arg Arg Val Ala Leu Leu Tyr Asp Leu Arg Glu Asp
            260                 265                 270

Asp Leu Thr Gln Asn Asp Gly His Thr Leu Leu Gly Leu Leu Glu
        275                 280                 285

Tyr Leu Gly Tyr Arg Val Asp Tyr Leu Pro Val Asp Asp Thr Leu Ser
    290                 295                 300
```

```
Glu Arg Arg Phe Ser Gly Leu Tyr Ala Gly Val Ile Thr Trp Met Thr
305                 310                 315                 320

Ser Gly Pro Pro Gln Asn Ala Ala Phe Asn Thr Trp Ile Gly Lys
            325                 330                 335

Arg Leu Asp Glu Lys Val Pro Val Val Phe Ala Gly Leu Pro Ile
            340                 345                 350

Gln Asp Thr Ser Leu Leu Lys Arg Leu Gly Leu Asn Arg Thr Ala Pro
            355                 360                 365

Ile Gly Thr Gln Thr Leu Ser Ile Thr Ser Gln Asp Lys Ala Leu Ile
370                 375                 380

Gly Ala Phe Glu Ala Pro Val Gln Pro Arg Ser Arg Asp Leu Thr Ala
385                 390                 395                 400

Ile Ser Leu Leu Pro Lys Gly Pro Lys Ala Ala Leu Leu Thr Ala
            405                 410                 415

Ala Asp Gly Gln Thr Phe Ala Pro Val Ala Val Ala Asp Trp Gly Gly
            420                 425                 430

Leu Ala Leu Ala Pro Tyr Ile Leu Glu Thr Asn Asn Glu Arg Ser Arg
            435                 440                 445

Trp Ile Leu Asp Pro Phe Ala Phe Leu Gln Ala Ser Leu Arg Leu Pro
    450                 455                 460

Val Gln Pro Arg Pro Asp Thr Thr Thr Glu Asn Gly Arg Arg Ile Ala
465                 470                 475                 480

Thr Val His Ile Asp Gly Asp Gly Phe Pro Ser Arg Ala Glu Val Arg
            485                 490                 495

Gly Thr Pro Tyr Ala Gly Arg Gln Val Tyr Asp Asp Phe Ile Arg Pro
            500                 505                 510

Asn Pro Phe Leu Thr Ser Val Ser Val Ile Glu Gly Glu Ile Ser Pro
            515                 520                 525

Arg Gly Met Phe Pro Phe Leu Ala Gly Glu Leu Glu Pro Ile Ala Arg
    530                 535                 540

Glu Ile Phe Ala Asp Pro Lys Val Glu Val Ala Thr His Thr Phe Ser
545                 550                 555                 560

His Pro Phe Phe Trp Gln Pro Glu Leu Ala Lys Lys Gln Glu Asn Phe
                565                 570                 575

Ser Pro Glu Tyr Gly Leu Asn Met Ala Ile Pro Asn Tyr Asp Lys Ile
            580                 585                 590

Asp Phe Arg Arg Glu Ile Phe Gly Ser Arg Asp Tyr Ile Asn Gln Gln
            595                 600                 605

Leu Thr Thr Pro Glu Lys Pro Val Lys Met Val Phe Trp Pro Gly Asp
            610                 615                 620

Ala Leu Pro Ser Ala Ser Ser Ile Lys Leu Ala Tyr Asp Ala Gly Leu
625                 630                 635                 640

Lys Asn Val Asn Gly Ala Ala Thr Met Leu Thr Lys Ala Asn Pro Ser
                645                 650                 655

Met Thr Gly Leu Gln Pro Leu Leu Arg Pro Thr Glu Gly Gly Leu Gln
            660                 665                 670

Tyr Tyr Ala Pro Ile Ile Asn Glu Asn Leu Tyr Thr Asn Leu Trp Lys
            675                 680                 685

Gly Pro Tyr Tyr Gly Phe Arg Asp Val Ile Asp Thr Phe Glu Leu Thr
            690                 695                 700

Asp Ser Pro Arg Arg Met Arg Gly Leu His Leu Tyr Tyr His Phe Tyr
705                 710                 715                 720
```

```
Ser Ser Thr Lys Gln Ala Ser Ile Lys Val Met Gly Glu Ile Tyr Gly
            725                 730                 735

Tyr Met Lys Thr Gln Gln Pro Met Ser Leu Trp Met Ser Asp Tyr Leu
        740                 745                 750

Asp Arg Leu His Gly Leu Tyr Gln Val Ser Leu Ala Arg Thr Ala Glu
            755                 760                 765

Gly Asp Trp Gln Val Arg Gly Leu Asp Ala Leu Arg Thr Leu Arg Leu
    770                 775                 780

Asp Pro Gln Met Gly Trp Pro Asp Leu Met Arg Ser Gln Gly Val Ala
785                 790                 795                 800

Gly Val Arg Asp Leu Pro Gln Gly Arg Tyr Val Ala Leu Ser Ser Asp
                805                 810                 815

Arg Ala Leu Leu Val Leu Arg Pro Asp Arg Asp Asn His Pro Ala Leu
            820                 825                 830

Glu Glu Ala Asn Leu Pro Leu Val Asp Trp Arg Tyr Val Asn Glu Arg
        835                 840                 845

Gln Val Asp Phe Ser Phe Ala Gly Gln Val Asp Leu Thr Phe Ser Val
    850                 855                 860

Arg Leu Pro Gly Thr Cys Arg Val Glu Val Asp Gly Gln His Phe Ala
865                 870                 875                 880

Gly Lys Ala Ser Ala Gly Leu Trp Thr Phe Gln Leu Pro Met Lys Gln
                885                 890                 895

Val Ser His Gly Gln Leu Phe Cys Ser
            900                 905

<210> SEQ ID NO 62
<211> LENGTH: 2814
<212> TYPE: DNA
<213> ORGANISM: Pseudomonas corrugata
<220> FEATURE:
<221> NAME/KEY: CDS
<222> LOCATION: (1)..(2811)
<220> FEATURE:
<221> NAME/KEY: sig_peptide
<222> LOCATION: (1)..(96)
<220> FEATURE:
<221> NAME/KEY: mat_peptide
<222> LOCATION: (97)..(2811)

<400> SEQUENCE: 62 atg gaa atc gtt tct cgc agg acg cgc gtc cgc gcg gtt gcc aag cgg      48
Met Glu Ile Val Ser Arg Arg Thr Arg Val Arg Ala Val Ala Lys Arg
        -30                 -25                 -20 ctg ttc gcg gcc ctg gcc ctt ttc gcc agc gga ccc tcc gtc cag gct      96
Leu Phe Ala Ala Leu Ala Leu Phe Ala Ser Gly Pro Ser Val Gln Ala
    -15                 -10                 -5                  -1 tca gcc ttg ccg caa ccg gcc agc gtg gcg ttc tgg tac gcc gat caa     144
Ser Ala Leu Pro Gln Pro Ala Ser Val Ala Phe Trp Tyr Ala Asp Gln
1               5                   10                  15 ccg ccg ctg tcc gag ctg gcg cag ttc gaa tgg tcg gtg gtg gag ccg     192
Pro Pro Leu Ser Glu Leu Ala Gln Phe Glu Trp Ser Val Val Glu Pro
            20                  25                  30 ggg cac atg acg ccc ggc gac gtc aaa acc ctg cgc gag ctg ggc agt     240
Gly His Met Thr Pro Gly Asp Val Lys Thr Leu Arg Glu Leu Gly Ser
        35                  40                  45 cat cca ttc gcc tac gtg tcc gtc ggc gag ttc gac ggc aac aag gct     288
His Pro Phe Ala Tyr Val Ser Val Gly Glu Phe Asp Gly Asn Lys Ala
    50                  55                  60 gaa atc gac aag gcg ggc ctg cgc cag gcg gtc agc ccg gtg cgt aat     336
Glu Ile Asp Lys Ala Gly Leu Arg Gln Ala Val Ser Pro Val Arg Asn
```

```
                65                  70                  75                  80
gat tcc tgg aac agc cag gtc atg gac ctg acg gcg ccg gcc tgg cgc      384
Asp Ser Trp Asn Ser Gln Val Met Asp Leu Thr Ala Pro Ala Trp Arg
            85                  90                  95 gaa cac ttg ctc ggt cgc gcc aag gcg ttg cag gcg caa ggt tat gac      432
Glu His Leu Leu Gly Arg Ala Lys Ala Leu Gln Ala Gln Gly Tyr Asp
            100                 105                 110 ggg ctg ttt ctc gac acc ctc gac agt ttc cag ctg ttg ccg gaa ggc      480
Gly Leu Phe Leu Asp Thr Leu Asp Ser Phe Gln Leu Leu Pro Glu Gly
            115                 120                 125 gcc cgg gaa gcg cag cgc gtg gcc ctg gcc agc ctg ctg cgc gaa atg      528
Ala Arg Glu Ala Gln Arg Val Ala Leu Ala Ser Leu Leu Arg Glu Met
130                 135                 140 cac aag cgc cag ccg acc ctg aag ctg ttc ttc aac cgc ggt ttt gaa      576
His Lys Arg Gln Pro Thr Leu Lys Leu Phe Phe Asn Arg Gly Phe Glu
145                 150                 155                 160 gtg ttg cct gag ctg gac ggt gtc gcc gcg gcg gtg gcg ttc gag tcc      624
Val Leu Pro Glu Leu Asp Gly Val Ala Ala Ala Val Ala Phe Glu Ser
                165                 170                 175 ctg tat gcc ggt tgg gat gct gca gcc aag cgc tat cgc ccg gtg ccg      672
Leu Tyr Ala Gly Trp Asp Ala Ala Ala Lys Arg Tyr Arg Pro Val Pro
                180                 185                 190 gaa gcc gac cgg cag tgg ttg ctc ggc gaa ctg cag ccc ctg cgt gcc      720
Glu Ala Asp Arg Gln Trp Leu Leu Gly Glu Leu Gln Pro Leu Arg Ala
                195                 200                 205 aaa ggc atc ccg ctg gtg gcc atc gac tac ctg cca ccg gag cgt cgc      768
Lys Gly Ile Pro Leu Val Ala Ile Asp Tyr Leu Pro Pro Glu Arg Arg
            210                 215                 220 gac gag gcg cgc aag ctg gcc aag cga ttg cgt gac gag ggt ttc att      816
Asp Glu Ala Arg Lys Leu Ala Lys Arg Leu Arg Asp Glu Gly Phe Ile
225                 230                 235                 240 cct ttc atc agt acc ccg gag ctg gat tcg atc ggc ctc agc aac atc      864
Pro Phe Ile Ser Thr Pro Glu Leu Asp Ser Ile Gly Leu Ser Asn Ile
                245                 250                 255 gag gtg cag ccg cgc cgc atc gcc ttc gtt tac gac gag cgc gaa ggg      912
Glu Val Gln Pro Arg Arg Ile Ala Phe Val Tyr Asp Glu Arg Glu Gly
                260                 265                 270 gcg ctg gag gac aac ggc ggt cat acg gtg ctc ggc ggt ctg ctc gaa      960
Ala Leu Glu Asp Asn Gly Gly His Thr Val Leu Gly Gly Leu Leu Glu
                275                 280                 285 tac ctg ggc tat cgc gtc gac tac att ccc gcg agc agc gcc atg ccg     1008
Tyr Leu Gly Tyr Arg Val Asp Tyr Ile Pro Ala Ser Ser Ala Met Pro
            290                 295                 300 ggt tac cgg ttc agt ggc ttg tat gca ggt gtc gtc acc tgg atg acc     1056
Gly Tyr Arg Phe Ser Gly Leu Tyr Ala Gly Val Val Thr Trp Met Thr
305                 310                 315                 320 agt ggt ccg ccg cag gac gcg ccg gcg ttc aac cgc tgg atc acc gcg     1104
Ser Gly Pro Pro Gln Asp Ala Pro Ala Phe Asn Arg Trp Ile Thr Ala
                325                 330                 335 cgt ctg gac gag cag gtg ccc gtg gtg ttc ttc agc ggc ctg ccg gtc     1152
Arg Leu Asp Glu Gln Val Pro Val Val Phe Phe Ser Gly Leu Pro Val
                340                 345                 350 gaa gac aag ttg ctg ctc aaa cgc atg ggg ctc aag cgc gaa gcg ccg     1200
Glu Asp Lys Leu Leu Leu Lys Arg Met Gly Leu Lys Arg Glu Ala Pro
            355                 360                 365 ccg ggc gtg cag cca ctg acc atc acc cac cag gac aag gcc ctg att     1248
Pro Gly Val Gln Pro Leu Thr Ile Thr His Gln Asp Lys Ala Leu Ile
370                 375                 380 ggc gcc ttc gaa gcg ccg gtg cag cca cgt tcc cgt gac ctg acg gcg     1296
Gly Ala Phe Glu Ala Pro Val Gln Pro Arg Ser Arg Asp Leu Thr Ala
```

```
                Gly Ala Phe Glu Ala Pro Val Gln Pro Arg Ser Arg Asp Leu Thr Ala
                385                 390                 395                 400 gta tcg gta ctg ccc aac ggt ccc aag ccg gtg ttg tcg ctg acc aac        1344
Val Ser Val Leu Pro Asn Gly Pro Lys Pro Val Leu Ser Leu Thr Asn
                405                 410                 415 gcc agt ggc gag gtg ttc acg ccg gtc gtg acc gcc aag tgg ggc ggc        1392
Ala Ser Gly Glu Val Phe Thr Pro Val Val Thr Ala Lys Trp Gly Gly
                    420                 425                 430 ctg gcg ctg gca ccc tac ctg ctg gag gcg aac aac gag cgc agc cgc        1440
Leu Ala Leu Ala Pro Tyr Leu Leu Glu Ala Asn Asn Glu Arg Ser Arg
                435                 440                 445 tgg atc atc gat ccg ttc gcg ttc ctg caa acc agc ctg caa ctg ccc        1488
Trp Ile Ile Asp Pro Phe Ala Phe Leu Gln Thr Ser Leu Gln Leu Pro
        450                 455                 460 gag caa ccg cgc ccg gac agc acc acc gaa aac ggt cgg cgg gtc gct        1536
Glu Gln Pro Arg Pro Asp Ser Thr Thr Glu Asn Gly Arg Arg Val Ala
465                 470                 475                 480 acg gtg cac atc gat ggc gac ggt ttc cct tcc cgc gcc gag gtg cgt        1584
Thr Val His Ile Asp Gly Asp Gly Phe Pro Ser Arg Ala Glu Val Arg
                        485                 490                 495 ggc acg cct tac gcc ggt cgc cat acg ctg gac gac tac atc aag cca        1632
Gly Thr Pro Tyr Ala Gly Arg His Thr Leu Asp Asp Tyr Ile Lys Pro
                500                 505                 510 aac ccg ttc ctg acg tcg gtg tcg atc gtc gag ggt gaa att tca ccg        1680
Asn Pro Phe Leu Thr Ser Val Ser Ile Val Glu Gly Glu Ile Ser Pro
            515                 520                 525 cgc ggc atg ttc ccg cac ctg gcc cgc gag ctg gag ccg att gcc cgc        1728
Arg Gly Met Phe Pro His Leu Ala Arg Glu Leu Glu Pro Ile Ala Arg
530                 535                 540 gaa att ttc gcc aac ccg aaa gtc gaa gtg gcc acg cac acc ttc agc        1776
Glu Ile Phe Ala Asn Pro Lys Val Glu Val Ala Thr His Thr Phe Ser
545                 550                 555                 560 cac ccg ttt ttc atg cag ccg gac aaa gcg ctc aag cgc gaa aat ttt        1824
His Pro Phe Phe Met Gln Pro Asp Lys Ala Leu Lys Arg Glu Asn Phe
                565                 570                 575 cat ccg gaa tac ggc atg aac atg gcc att ccg ggc tac ggc aag atc        1872
His Pro Glu Tyr Gly Met Asn Met Ala Ile Pro Gly Tyr Gly Lys Ile
                580                 585                 590 gat ttt cgc cgg gag att ttc ggc tcg cgc gac tac atc aac cag aac        1920
Asp Phe Arg Arg Glu Ile Phe Gly Ser Arg Asp Tyr Ile Asn Gln Asn
            595                 600                 605 ctc acc acc ccg gaa aaa ccg gtg aag atg gtg ttc tgg cca ggt gat        1968
Leu Thr Thr Pro Glu Lys Pro Val Lys Met Val Phe Trp Pro Gly Asp
        610                 615                 620 gcg ctg cct tcg gcc tcg acc ctg aag ctg gcg tat gac gcc ggg ctc        2016
Ala Leu Pro Ser Ala Ser Thr Leu Lys Leu Ala Tyr Asp Ala Gly Leu
625                 630                 635                 640 aag aac gtc aac ggc gca gaa acc atg atg acc aag gcc aac ccg tct        2064
Lys Asn Val Asn Gly Ala Glu Thr Met Met Thr Lys Ala Asn Pro Ser
                645                 650                 655 gtg acg ggc ctg aac ccc ttg ctg cgc ccg acc gaa ggc ggc ctg cag        2112
Val Thr Gly Leu Asn Pro Leu Leu Arg Pro Thr Glu Gly Gly Leu Gln
                660                 665                 670 tat tac gcg ccg gtc atc aac gag aac ctg ttc acc aac ttg tgg aaa        2160
Tyr Tyr Ala Pro Val Ile Asn Glu Asn Leu Phe Thr Asn Leu Trp Lys
                675                 680                 685 ggc ccg tac tac ggc ttc cgc gaa gtg atc gat acc ttc gaa ttg acc        2208
Gly Pro Tyr Tyr Gly Phe Arg Glu Val Ile Asp Thr Phe Glu Leu Thr
    690                 695                 700
```

| | | |
|---|---|---|
| gac agc ccg cgc cgt ctg cgc ggt ctg cac ctg tat tac cac ttt tac<br>Asp Ser Pro Arg Arg Leu Arg Gly Leu His Leu Tyr Tyr His Phe Tyr<br>705                         710                 715                  720 | 2256 |
| tcc agc acc aag caa gcc tcg atc aag gcg atg cat gag atc tac ggt<br>Ser Ser Thr Lys Gln Ala Ser Ile Lys Ala Met His Glu Ile Tyr Gly<br>                 725                     730                 735 | 2304 |
| ttc atg cgc gaa cag cat ccg ctg tcg ctg tgg atg agt gat tac atc<br>Phe Met Arg Glu Gln His Pro Leu Ser Leu Trp Met Ser Asp Tyr Ile<br>                   740                     745                 750 | 2352 |
| gac cgt ctg cat ggc ctg tac cag gcc agc ctg gcg cgg acc tcc gac<br>Asp Arg Leu His Gly Leu Tyr Gln Ala Ser Leu Ala Arg Thr Ser Asp<br>755                         760                 765 | 2400 |
| ggt gcc tgg cag att cgc ggg atg gac gcc ttg cgc acc gtg cgc ctg<br>Gly Ala Trp Gln Ile Arg Gly Met Asp Ala Leu Arg Thr Val Arg Leu<br>    770                     775                     780 | 2448 |
| gat cca ggg atg ggt tgg ccg gac ctg ctg cgc tcg caa ggt atc gcc<br>Asp Pro Gly Met Gly Trp Pro Asp Leu Leu Arg Ser Gln Gly Ile Ala<br>785                       790                 795                 800 | 2496 |
| ggc gtg cgc gac ctg ccg caa ggg cgc tac gtg cac ctg agc agt gat<br>Gly Val Arg Asp Leu Pro Gln Gly Arg Tyr Val His Leu Ser Ser Asp<br>                   805                     810                 815 | 2544 |
| cgg gcg ctg ctg gtg ctg cgt ccc gac cgg gat gat cgc ccg gcg ctg<br>Arg Ala Leu Leu Val Leu Arg Pro Asp Arg Asp Asp Arg Pro Ala Leu<br>             820                     825                 830 | 2592 |
| gag gaa gcc aat ctg ccg ttg gtg gag tgg cgg tac ctg gat gac cgg<br>Glu Glu Ala Asn Leu Pro Leu Val Glu Trp Arg Tyr Leu Asp Asp Arg<br>835                       840                     845 | 2640 |
| cgc gtg agc ttc ggg ttc tcc ggc cag ttc gat ctg acc ttc tcc gtg<br>Arg Val Ser Phe Gly Phe Ser Gly Gln Phe Asp Leu Thr Phe Ser Val<br>    850                     855                     860 | 2688 |
| cgt tcc gcc aat ccg tgc cgg gtc gaa gtg gat ggg cag cgt ttt gct<br>Arg Ser Ala Asn Pro Cys Arg Val Glu Val Asp Gly Gln Arg Phe Ala<br>865                       870                     875                 880 | 2736 |
| ggc aag gcg gcg gcc ggc ctg tgg act ttc caa tta ccc atg aag cag<br>Gly Lys Ala Ala Ala Gly Leu Trp Thr Phe Gln Leu Pro Met Lys Gln<br>                   885                     890                 895 | 2784 |
| gtg agt cat gct caa ctc gtc tgc aac taa<br>Val Ser His Ala Gln Leu Val Cys Asn<br>    900                     905 | 2814 |

```
<210> SEQ ID NO 63
<211> LENGTH: 937
<212> TYPE: PRT
<213> ORGANISM: Pseudomonas corrugata

<400> SEQUENCE: 63
```

Met Glu Ile Val Ser Arg Arg Thr Arg Val Arg Ala Val Ala Lys Arg
        -30                     -25                    -20

Leu Phe Ala Ala Leu Ala Leu Phe Ala Ser Gly Pro Ser Val Gln Ala
    -15                     -10                   -5                  -1

Ser Ala Leu Pro Gln Pro Ala Ser Val Ala Phe Trp Tyr Ala Asp Gln
1                 5                    10                    15

Pro Pro Leu Ser Glu Leu Ala Gln Phe Glu Trp Ser Val Val Glu Pro
         20                    25                  30

Gly His Met Thr Pro Gly Asp Val Lys Thr Leu Arg Glu Leu Gly Ser
            35                    40                  45

His Pro Phe Ala Tyr Val Ser Val Gly Glu Phe Asp Gly Asn Lys Ala
     50                     55                  60

Glu Ile Asp Lys Ala Gly Leu Arg Gln Ala Val Ser Pro Val Arg Asn

-continued

```
                65                  70                  75                  80
            Asp Ser Trp Asn Ser Gln Val Met Asp Leu Thr Ala Pro Ala Trp Arg
                            85                  90                  95

Glu His Leu Leu Gly Arg Ala Lys Ala Leu Gln Ala Gln Gly Tyr Asp
                        100                 105                 110

Gly Leu Phe Leu Asp Thr Leu Asp Ser Phe Gln Leu Leu Pro Glu Gly
                        115                 120                 125

Ala Arg Glu Ala Gln Arg Val Ala Leu Ala Ser Leu Leu Arg Glu Met
                    130                 135                 140

His Lys Arg Gln Pro Thr Leu Lys Leu Phe Phe Asn Arg Gly Phe Glu
            145                 150                 155                 160

Val Leu Pro Glu Leu Asp Gly Val Ala Ala Val Ala Phe Glu Ser
                            165                 170                 175

Leu Tyr Ala Gly Trp Asp Ala Ala Lys Arg Tyr Arg Pro Val Pro
                        180                 185                 190

Glu Ala Asp Arg Gln Trp Leu Leu Gly Glu Leu Gln Pro Leu Arg Ala
                        195                 200                 205

Lys Gly Ile Pro Leu Val Ala Ile Asp Tyr Leu Pro Pro Glu Arg Arg
                    210                 215                 220

Asp Glu Ala Arg Lys Leu Ala Lys Arg Leu Arg Asp Glu Gly Phe Ile
            225                 230                 235                 240

Pro Phe Ile Ser Thr Pro Glu Leu Asp Ser Ile Gly Leu Ser Asn Ile
                            245                 250                 255

Glu Val Gln Pro Arg Arg Ile Ala Phe Val Tyr Asp Glu Arg Glu Gly
                        260                 265                 270

Ala Leu Glu Asp Asn Gly Gly His Thr Val Leu Gly Leu Leu Glu
                        275                 280                 285

Tyr Leu Gly Tyr Arg Val Asp Tyr Ile Pro Ala Ser Ser Ala Met Pro
                    290                 295                 300

Gly Tyr Arg Phe Ser Gly Leu Tyr Ala Gly Val Val Thr Trp Met Thr
            305                 310                 315                 320

Ser Gly Pro Pro Gln Asp Ala Pro Ala Phe Asn Arg Trp Ile Thr Ala
                            325                 330                 335

Arg Leu Asp Glu Gln Val Pro Val Val Phe Phe Ser Gly Leu Pro Val
                        340                 345                 350

Glu Asp Lys Leu Leu Leu Lys Arg Met Gly Leu Lys Arg Glu Ala Pro
                        355                 360                 365

Pro Gly Val Gln Pro Leu Thr Ile Thr His Gln Asp Lys Ala Leu Ile
                    370                 375                 380

Gly Ala Phe Glu Ala Pro Val Gln Pro Arg Ser Arg Asp Leu Thr Ala
            385                 390                 395                 400

Val Ser Val Leu Pro Asn Gly Pro Lys Pro Val Leu Ser Leu Thr Asn
                            405                 410                 415

Ala Ser Gly Glu Val Phe Thr Pro Val Val Thr Ala Lys Trp Gly Gly
                        420                 425                 430

Leu Ala Leu Ala Pro Tyr Leu Leu Glu Ala Asn Asn Glu Arg Ser Arg
                        435                 440                 445

Trp Ile Ile Asp Pro Phe Ala Phe Leu Gln Thr Ser Leu Gln Leu Pro
                    450                 455                 460

Glu Gln Pro Arg Pro Asp Ser Thr Thr Glu Asn Gly Arg Arg Val Ala
            465                 470                 475                 480

Thr Val His Ile Asp Gly Asp Gly Phe Pro Ser Arg Ala Glu Val Arg
                            485                 490                 495
```

```
Gly Thr Pro Tyr Ala Gly Arg His Thr Leu Asp Asp Tyr Ile Lys Pro
            500                 505                 510

Asn Pro Phe Leu Thr Ser Val Ser Ile Val Glu Gly Glu Ile Ser Pro
            515                 520                 525

Arg Gly Met Phe Pro His Leu Ala Arg Glu Leu Glu Pro Ile Ala Arg
530                 535                 540

Glu Ile Phe Ala Asn Pro Lys Val Glu Val Ala Thr His Thr Phe Ser
545                 550                 555                 560

His Pro Phe Phe Met Gln Pro Asp Lys Ala Leu Lys Arg Glu Asn Phe
                565                 570                 575

His Pro Glu Tyr Gly Met Asn Met Ala Ile Pro Gly Tyr Gly Lys Ile
            580                 585                 590

Asp Phe Arg Arg Glu Ile Phe Gly Ser Arg Asp Tyr Ile Asn Gln Asn
            595                 600                 605

Leu Thr Thr Pro Glu Lys Pro Val Lys Met Val Phe Trp Pro Gly Asp
            610                 615                 620

Ala Leu Pro Ser Ala Ser Thr Leu Lys Leu Ala Tyr Asp Ala Gly Leu
625                 630                 635                 640

Lys Asn Val Asn Gly Ala Glu Thr Met Met Thr Lys Ala Asn Pro Ser
                645                 650                 655

Val Thr Gly Leu Asn Pro Leu Leu Arg Pro Thr Glu Gly Gly Leu Gln
            660                 665                 670

Tyr Tyr Ala Pro Val Ile Asn Glu Asn Leu Phe Thr Asn Leu Trp Lys
            675                 680                 685

Gly Pro Tyr Tyr Gly Phe Arg Glu Val Ile Asp Thr Phe Glu Leu Thr
            690                 695                 700

Asp Ser Pro Arg Arg Leu Arg Gly Leu His Leu Tyr Tyr His Phe Tyr
705                 710                 715                 720

Ser Ser Thr Lys Gln Ala Ser Ile Lys Ala Met His Glu Ile Tyr Gly
                725                 730                 735

Phe Met Arg Glu Gln His Pro Leu Ser Leu Trp Met Ser Asp Tyr Ile
            740                 745                 750

Asp Arg Leu His Gly Leu Tyr Gln Ala Ser Leu Ala Arg Thr Ser Asp
            755                 760                 765

Gly Ala Trp Gln Ile Arg Gly Met Asp Ala Leu Arg Thr Val Arg Leu
770                 775                 780

Asp Pro Gly Met Gly Trp Pro Asp Leu Leu Arg Ser Gln Gly Ile Ala
785                 790                 795                 800

Gly Val Arg Asp Leu Pro Gln Gly Arg Tyr Val His Leu Ser Ser Asp
                805                 810                 815

Arg Ala Leu Leu Val Leu Arg Pro Asp Arg Asp Asp Arg Pro Ala Leu
            820                 825                 830

Glu Glu Ala Asn Leu Pro Leu Val Glu Trp Arg Tyr Leu Asp Asp Arg
            835                 840                 845

Arg Val Ser Phe Gly Phe Ser Gly Gln Phe Asp Leu Thr Phe Ser Val
            850                 855                 860

Arg Ser Ala Asn Pro Cys Arg Val Glu Val Asp Gly Gln Arg Phe Ala
865                 870                 875                 880

Gly Lys Ala Ala Ala Gly Leu Trp Thr Phe Gln Leu Pro Met Lys Gln
                885                 890                 895

Val Ser His Ala Gln Leu Val Cys Asn
            900                 905
```

<210> SEQ ID NO 64
<211> LENGTH: 905
<212> TYPE: PRT
<213> ORGANISM: Pseudomonas corrugata

<400> SEQUENCE: 64

Ser Ala Leu Pro Gln Pro Ala Ser Val Ala Phe Trp Tyr Ala Asp Gln
1               5                   10                  15

Pro Pro Leu Ser Glu Leu Ala Gln Phe Glu Trp Ser Val Val Glu Pro
            20                  25                  30

Gly His Met Thr Pro Gly Asp Val Lys Thr Leu Arg Glu Leu Gly Ser
        35                  40                  45

His Pro Phe Ala Tyr Val Ser Val Gly Glu Phe Asp Gly Asn Lys Ala
    50                  55                  60

Glu Ile Asp Lys Ala Gly Leu Arg Gln Ala Val Ser Pro Val Arg Asn
65                  70                  75                  80

Asp Ser Trp Asn Ser Gln Val Met Asp Leu Thr Ala Pro Ala Trp Arg
                85                  90                  95

Glu His Leu Leu Gly Arg Ala Lys Ala Leu Gln Ala Gln Gly Tyr Asp
            100                 105                 110

Gly Leu Phe Leu Asp Thr Leu Asp Ser Phe Gln Leu Leu Pro Glu Gly
        115                 120                 125

Ala Arg Glu Ala Gln Arg Val Ala Leu Ala Ser Leu Leu Arg Glu Met
    130                 135                 140

His Lys Arg Gln Pro Thr Leu Lys Leu Phe Phe Asn Arg Gly Phe Glu
145                 150                 155                 160

Val Leu Pro Glu Leu Asp Gly Val Ala Ala Val Ala Phe Glu Ser
                165                 170                 175

Leu Tyr Ala Gly Trp Asp Ala Ala Lys Arg Tyr Arg Pro Val Pro
            180                 185                 190

Glu Ala Asp Arg Gln Trp Leu Leu Gly Glu Leu Gln Pro Leu Arg Ala
        195                 200                 205

Lys Gly Ile Pro Leu Val Ala Ile Asp Tyr Leu Pro Pro Glu Arg Arg
    210                 215                 220

Asp Glu Ala Arg Lys Leu Ala Lys Arg Leu Arg Asp Glu Gly Phe Ile
225                 230                 235                 240

Pro Phe Ile Ser Thr Pro Glu Leu Asp Ser Ile Gly Leu Ser Asn Ile
                245                 250                 255

Glu Val Gln Pro Arg Arg Ile Ala Phe Val Tyr Asp Glu Arg Glu Gly
            260                 265                 270

Ala Leu Glu Asp Asn Gly Gly His Thr Val Leu Gly Gly Leu Leu Glu
        275                 280                 285

Tyr Leu Gly Tyr Arg Val Asp Tyr Ile Pro Ala Ser Ser Ala Met Pro
    290                 295                 300

Gly Tyr Arg Phe Ser Gly Leu Tyr Ala Gly Val Val Thr Trp Met Thr
305                 310                 315                 320

Ser Gly Pro Pro Gln Asp Ala Pro Ala Phe Asn Arg Trp Ile Thr Ala
                325                 330                 335

Arg Leu Asp Glu Gln Val Pro Val Phe Phe Ser Leu Pro Val
            340                 345                 350

Glu Asp Lys Leu Leu Leu Lys Arg Met Gly Leu Lys Arg Glu Ala Pro
        355                 360                 365

Pro Gly Val Gln Pro Leu Thr Ile Thr His Gln Asp Lys Ala Leu Ile
    370                 375                 380

-continued

```
Gly Ala Phe Glu Ala Pro Val Gln Pro Arg Ser Arg Asp Leu Thr Ala
385                 390                 395                 400
Val Ser Val Leu Pro Asn Gly Pro Lys Pro Val Leu Ser Leu Thr Asn
            405                 410                 415
Ala Ser Gly Glu Val Phe Thr Pro Val Val Thr Ala Lys Trp Gly Gly
        420                 425                 430
Leu Ala Leu Ala Pro Tyr Leu Leu Glu Ala Asn Asn Glu Arg Ser Arg
    435                 440                 445
Trp Ile Ile Asp Pro Phe Ala Phe Leu Gln Thr Ser Leu Gln Leu Pro
450                 455                 460
Glu Gln Pro Arg Pro Asp Ser Thr Thr Glu Asn Gly Arg Arg Val Ala
465                 470                 475                 480
Thr Val His Ile Asp Gly Asp Gly Phe Pro Ser Arg Ala Glu Val Arg
            485                 490                 495
Gly Thr Pro Tyr Ala Gly Arg His Thr Leu Asp Asp Tyr Ile Lys Pro
        500                 505                 510
Asn Pro Phe Leu Thr Ser Val Ser Ile Val Glu Gly Glu Ile Ser Pro
    515                 520                 525
Arg Gly Met Phe Pro His Leu Ala Arg Glu Leu Glu Pro Ile Ala Arg
530                 535                 540
Glu Ile Phe Ala Asn Pro Lys Val Glu Val Ala Thr His Thr Phe Ser
545                 550                 555                 560
His Pro Phe Phe Met Gln Pro Asp Lys Ala Leu Lys Arg Glu Asn Phe
                565                 570                 575
His Pro Glu Tyr Gly Met Asn Met Ala Ile Pro Gly Tyr Gly Lys Ile
            580                 585                 590
Asp Phe Arg Arg Glu Ile Phe Gly Ser Arg Asp Tyr Ile Asn Gln Asn
    595                 600                 605
Leu Thr Thr Pro Glu Lys Pro Val Lys Met Val Phe Trp Pro Gly Asp
610                 615                 620
Ala Leu Pro Ser Ala Ser Thr Leu Lys Leu Ala Tyr Asp Ala Gly Leu
625                 630                 635                 640
Lys Asn Val Asn Gly Ala Glu Thr Met Met Thr Lys Ala Asn Pro Ser
                645                 650                 655
Val Thr Gly Leu Asn Pro Leu Leu Arg Pro Thr Glu Gly Gly Leu Gln
            660                 665                 670
Tyr Tyr Ala Pro Val Ile Asn Glu Asn Leu Phe Thr Asn Leu Trp Lys
    675                 680                 685
Gly Pro Tyr Tyr Gly Phe Arg Glu Val Ile Asp Thr Phe Glu Leu Thr
690                 695                 700
Asp Ser Pro Arg Arg Leu Arg Gly Leu His Leu Tyr Tyr His Phe Tyr
705                 710                 715                 720
Ser Ser Thr Lys Gln Ala Ser Ile Lys Ala Met His Glu Ile Tyr Gly
                725                 730                 735
Phe Met Arg Glu Gln His Pro Leu Ser Leu Trp Met Ser Asp Tyr Ile
            740                 745                 750
Asp Arg Leu His Gly Leu Tyr Gln Ala Ser Leu Ala Arg Thr Ser Asp
    755                 760                 765
Gly Ala Trp Gln Ile Arg Gly Met Asp Ala Leu Arg Thr Val Arg Leu
770                 775                 780
Asp Pro Gly Met Gly Trp Pro Asp Leu Leu Arg Ser Gln Gly Ile Ala
785                 790                 795                 800
```

```
Gly Val Arg Asp Leu Pro Gln Gly Arg Tyr Val His Leu Ser Ser Asp
                805                 810                 815

Arg Ala Leu Leu Val Leu Arg Pro Asp Arg Asp Arg Pro Ala Leu
            820                 825                 830

Glu Glu Ala Asn Leu Pro Leu Val Glu Trp Arg Tyr Leu Asp Asp Arg
        835                 840                 845

Arg Val Ser Phe Gly Phe Ser Gly Gln Phe Asp Leu Thr Phe Ser Val
    850                 855                 860

Arg Ser Ala Asn Pro Cys Arg Val Glu Val Asp Gly Gln Arg Phe Ala
865                 870                 875                 880

Gly Lys Ala Ala Ala Gly Leu Trp Thr Phe Gln Leu Pro Met Lys Gln
                885                 890                 895

Val Ser His Ala Gln Leu Val Cys Asn
            900                 905

<210> SEQ ID NO 65
<211> LENGTH: 2814
<212> TYPE: DNA
<213> ORGANISM: Pseudomonas pelagia
<220> FEATURE:
<221> NAME/KEY: CDS
<222> LOCATION: (1)..(2811)
<220> FEATURE:
<221> NAME/KEY: sig_peptide
<222> LOCATION: (1)..(93)
<220> FEATURE:
<221> NAME/KEY: mat_peptide
<222> LOCATION: (94)..(2811)

<400> SEQUENCE: 65 atg gcc ggg agt aat ttt cgc caa gca cta acc agc acc tta aag ttg      48
Met Ala Gly Ser Asn Phe Arg Gln Ala Leu Thr Ser Thr Leu Lys Leu
 -30                 -25                 -20 ctc ggt atg ctg gct act gtg ctg ctt tcg ctt ggc gcc gtt gcc ggc      96
Leu Gly Met Leu Ala Thr Val Leu Leu Ser Leu Gly Ala Val Ala Gly
 -15                 -10                  -5                  -1  1 ccg gta aaa tcc ggc ccg gcc agt gtc gct ttc tgg tac gcc gag cag     144
Pro Val Lys Ser Gly Pro Ala Ser Val Ala Phe Trp Tyr Ala Glu Gln
              5                  10                  15 ccg ccg ttg ggc gag ctt gcg cag ttc gat tgg gtg gta ttc gaa ccg     192
Pro Pro Leu Gly Glu Leu Ala Gln Phe Asp Trp Val Val Phe Glu Pro
         20                  25                  30 gcg cac ctg acg ccc aag gac gtc agt ttc gtg gtc gcc cag ggg tcg     240
Ala His Leu Thr Pro Lys Asp Val Ser Phe Val Val Ala Gln Gly Ser
     35                  40                  45 ctg cca ttc gcc tat ctg tcc att ggc gag ctg aac gat cac ctc gcg     288
Leu Pro Phe Ala Tyr Leu Ser Ile Gly Glu Leu Asn Asp His Leu Ala
 50                  55                  60                  65 cag tcc agc cca ggc ctt ctg gat aac agc gct gat cag atc cgc aat     336
Gln Ser Ser Pro Gly Leu Leu Asp Asn Ser Ala Asp Gln Ile Arg Asn
                 70                  75                  80 ccc ggt tgg aac agc cat gtg atg gac ctc act agc gct ggc tgg cag     384
Pro Gly Trp Asn Ser His Val Met Asp Leu Thr Ser Ala Gly Trp Gln
             85                  90                  95 gag cat atc ctc ggt cag gtg ggt gag ttc gcc aaa cag ggc tac gcc     432
Glu His Ile Leu Gly Gln Val Gly Glu Phe Ala Lys Gln Gly Tyr Ala
        100                 105                 110 ggt gta ttt ctc gat acc ctt gac agc ttt acc ctg ctc cct gaa gac     480
Gly Val Phe Leu Asp Thr Leu Asp Ser Phe Thr Leu Leu Pro Glu Asp
    115                 120                 125 cag cga ccc gcc cag cgt gat gcg tta gcg gcg ctt ttg cgt gac atg     528
```

```
Gln Arg Pro Ala Gln Arg Asp Ala Leu Ala Ala Leu Leu Arg Asp Met
130                 135                 140                 145 cat aag cgc tat cca gac atg aag ctg ttc ttc aat cgg ggc ttc gag       576
His Lys Arg Tyr Pro Asp Met Lys Leu Phe Phe Asn Arg Gly Phe Glu
                150                 155                 160 gtg ctt gct gac gtt cag cag ggc gtc gcg gcg gtc gca gtc gag tca       624
Val Leu Ala Asp Val Gln Gln Gly Val Ala Ala Val Ala Val Glu Ser
                165                 170                 175 atc tat gcc agt tgg gat gcc gct gcg cag gtg tat cgc ccg gta tcc       672
Ile Tyr Ala Ser Trp Asp Ala Ala Ala Gln Val Tyr Arg Pro Val Ser
                180                 185                 190 gaa aat gat cgc acc tgg ctt gcg ggt cag gtc cag cct ctg cgc gcg       720
Glu Asn Asp Arg Thr Trp Leu Ala Gly Gln Val Gln Pro Leu Arg Ala
                195                 200                 205 cgt aat atc ccg atc gtg gcg atc gat tat ctg ccg gta gaa cgg cgc       768
Arg Asn Ile Pro Ile Val Ala Ile Asp Tyr Leu Pro Val Glu Arg Arg
210                 215                 220                 225 gcc gaa gcc cgt gaa ctg gct gca agg ctg att gaa gaa ggc ttc ctg       816
Ala Glu Ala Arg Glu Leu Ala Ala Arg Leu Ile Glu Glu Gly Phe Leu
                230                 235                 240 cct tat gtt ggt acc ccc gag ctg gat acg ctg ggt gtc agc agc att       864
Pro Tyr Val Gly Thr Pro Glu Leu Asp Thr Leu Gly Val Ser Ser Ile
                245                 250                 255 gaa gtg cag ccc cgg cgc atc gcc gtg atg tat gac ccg cgt gag ggt       912
Glu Val Gln Pro Arg Arg Ile Ala Val Met Tyr Asp Pro Arg Glu Gly
                260                 265                 270 gag ctg acg cgc acc ggt gga ttc cgg tcc ctg ggc ggg ctg ttg gag       960
Glu Leu Thr Arg Thr Gly Gly Phe Arg Ser Leu Gly Gly Leu Leu Glu
275                 280                 285 tac atg ggg tat cgg gtt gat tat ctg ccg gtc gag ggt tcg ctg ccg      1008
Tyr Met Gly Tyr Arg Val Asp Tyr Leu Pro Val Glu Gly Ser Leu Pro
290                 295                 300                 305 agt gct ccc atg acc ggt ctc tat gct ggc gtc atc gtc tgg atg acc      1056
Ser Ala Pro Met Thr Gly Leu Tyr Ala Gly Val Ile Val Trp Met Thr
                310                 315                 320 tct ggc ccg ccg cct gac agc agt gct ttc aac cgc tgg ata ggt cgg      1104
Ser Gly Pro Pro Pro Asp Ser Ser Ala Phe Asn Arg Trp Ile Gly Arg
                325                 330                 335 cgt ctt gat gaa ggc acc ccc ttg gcg ttt ttc cag ggg atg ccg att      1152
Arg Leu Asp Glu Gly Thr Pro Leu Ala Phe Phe Gln Gly Met Pro Ile
                340                 345                 350 gac gat gcg gcg att ttg cgc agg ctg ggt ttg cag cgc act ggc gtt      1200
Asp Asp Ala Ala Ile Leu Arg Arg Leu Gly Leu Gln Arg Thr Gly Val
355                 360                 365 cag ccg gtt tcc ggt ctg caa ttg gtc aat cat gat gcg cag ttg gtc      1248
Gln Pro Val Ser Gly Leu Gln Leu Val Asn His Asp Ala Gln Leu Val
370                 375                 380                 385 ggc tcg ttc gag gcg ccg ctg gtg gtg cgc tcg cgt ggc ctg acc ggg      1296
Gly Ser Phe Glu Ala Pro Leu Val Val Arg Ser Arg Gly Leu Thr Gly
                390                 395                 400 att ggc acg cag tcg cgt tac aac aag gtc gcg ctg gcg ctg gtg gat      1344
Ile Gly Thr Gln Ser Arg Tyr Asn Lys Val Ala Leu Ala Leu Val Asp
                405                 410                 415 gac gcc ggg cgc gag cac acg cca gtg gtc acc ggt gac tgg ggt ggg      1392
Asp Ala Gly Arg Glu His Thr Pro Val Val Thr Gly Asp Trp Gly Gly
                420                 425                 430 gtt gcg ctg gca ccc tat gtg ttc gag ggt gag gac gat acc cgg cgc      1440
Val Ala Leu Ala Pro Tyr Val Phe Glu Gly Glu Asp Asp Thr Arg Arg
435                 440                 445
```

```
tgg atc att gat ccc ttt gcc ttc ctg cag cag gca ttg caa ttg ccc    1488
Trp Ile Ile Asp Pro Phe Ala Phe Leu Gln Gln Ala Leu Gln Leu Pro
450             455                 460                 465 gca cag cct gca cct gat gtc act acc gaa aat ggt cgg cgt atc gct    1536
Ala Gln Pro Ala Pro Asp Val Thr Thr Glu Asn Gly Arg Arg Ile Ala
                470                 475                 480 acc gtg cac att gac ggc gat ggc ttt cct tca cgg gca gaa att ccg    1584
Thr Val His Ile Asp Gly Asp Gly Phe Pro Ser Arg Ala Glu Ile Pro
            485                 490                 495 ggt acg ccc tat tcc ggt agc gcg gta ctc aat cag ttc atc aag cct    1632
Gly Thr Pro Tyr Ser Gly Ser Ala Val Leu Asn Gln Phe Ile Lys Pro
        500                 505                 510 tac cca ctg ctg acc tcg gta tcc ttt atc gag ggc gag gtt ggg ccg    1680
Tyr Pro Leu Leu Thr Ser Val Ser Phe Ile Glu Gly Glu Val Gly Pro
    515                 520                 525 gcg ggc atg tat ccc tat ctt tca cgt gag ctg aaa ccc ctg gct cgg    1728
Ala Gly Met Tyr Pro Tyr Leu Ser Arg Glu Leu Glu Pro Leu Ala Arg
530                 535                 540                 545 cag atc ctc gcc cat gaa cgg gta gag ccc gcg acc cat acc tac agc    1776
Gln Ile Leu Ala His Glu Arg Val Glu Pro Ala Thr His Thr Tyr Ser
                550                 555                 560 cat ccg tat ttc tgg cag gcc gag agg gac agt cag cgg gag ggc ttc    1824
His Pro Tyr Phe Trp Gln Ala Glu Arg Asp Ser Gln Arg Glu Gly Phe
            565                 570                 575 cgt gct gac tac ggc ttg aaa atg ccc att cct ggc tac gac act att    1872
Arg Ala Asp Tyr Gly Leu Lys Met Pro Ile Pro Gly Tyr Asp Thr Ile
        580                 585                 590 gat ttc agg cgc gag gtg ttc ggc tcg cgt gac tat gtc gcc agc cgc    1920
Asp Phe Arg Arg Glu Val Phe Gly Ser Arg Asp Tyr Val Ala Ser Arg
    595                 600                 605 ctg gcg cca gcg gac aag cca gtc aaa atg att ttc tgg agc ggt gac    1968
Leu Ala Pro Ala Asp Lys Pro Val Lys Met Ile Phe Trp Ser Gly Asp
610                 615                 620                 625 gcg ata ccg gat gcg gcg acc atc aag ctc tcc tat gac gca ggc atg    2016
Ala Ile Pro Asp Ala Ala Thr Ile Lys Leu Ser Tyr Asp Ala Gly Met
                630                 635                 640 ctc aac gtc aac ggc ggg gag acg cgc ctg acg cgt gcc gac ccc tca    2064
Leu Asn Val Asn Gly Gly Glu Thr Arg Leu Thr Arg Ala Asp Pro Ser
            645                 650                 655 ctg acc ggg ctc tat ccg ctg ctg cgg cca act gcc ggc ggc ctg cag    2112
Leu Thr Gly Leu Tyr Pro Leu Leu Arg Pro Thr Ala Gly Gly Leu Gln
        660                 665                 670 gtg tac gcg cct atc atc aac gag aac gtc tac acc aat ttg tgg cag    2160
Val Tyr Ala Pro Ile Ile Asn Glu Asn Val Tyr Thr Asn Leu Trp Gln
    675                 680                 685 ggc ccc tat tac ggc ttt cgg gaa gtg gtc gaa act ttc gag ttg acc    2208
Gly Pro Tyr Tyr Gly Phe Arg Glu Val Val Glu Thr Phe Glu Leu Thr
690                 695                 700                 705 gac tcg ccg cgc cgc atg cgc ggt ctg cat ctg tat tac cac ttt tat    2256
Asp Ser Pro Arg Arg Met Arg Gly Leu His Leu Tyr Tyr His Phe Tyr
                710                 715                 720 tcc ggt acc aag cca gcg gcg atc aag gtg atg ggc gat att tac cgc    2304
Ser Gly Thr Lys Pro Ala Ala Ile Lys Val Met Gly Asp Ile Tyr Arg
            725                 730                 735 cat atg ctt gaa cag cag ccg ctg tcc ctg tgg atg agc gat tac ctg    2352
His Met Leu Glu Gln Gln Pro Leu Ser Leu Trp Met Ser Asp Tyr Leu
        740                 745                 750 ctg cgc gct cac ggc ctg cac acc gct tcg ctg gcc cgt acc agc agt    2400
Leu Arg Ala His Gly Leu His Thr Ala Ser Leu Ala Arg Thr Ser Ser
    755                 760                 765
```

| | | | | | | | | | | | | | | | | |
|---|---|---|---|---|---|---|---|---|---|---|---|---|---|---|---|---|
| ggc | gcg | tgg | cag | att | cgc | gcg | ctg | cag | ggg | ttg | cgt | act | gtg | cgc | ttg | 2448 |
| Gly | Ala | Trp | Gln | Ile | Arg | Ala | Leu | Gln | Gly | Leu | Arg | Thr | Val | Arg | Leu | |
| 770 | | | | 775 | | | | | 780 | | | | | 785 | | |
| gac | ccc | tcg | ctg | ggc | tgg | cca | gat | ctg | atg | gca | tcc | gaa | ggt | att | gcc | 2496 |
| Asp | Pro | Ser | Leu | Gly | Trp | Pro | Asp | Leu | Met | Ala | Ser | Glu | Gly | Ile | Ala | |
| | | | | 790 | | | | | 795 | | | | | 800 | | |
| ggt | gtt | ctg | gac | ttg | cct | cag | ggt | cgt | tat | gtt | cat | ctc | agt | gcc | gac | 2544 |
| Gly | Val | Leu | Asp | Leu | Pro | Gln | Gly | Arg | Tyr | Val | His | Leu | Ser | Ala | Asp | |
| | | | | 805 | | | | | 810 | | | | | 815 | | |
| cgc | gct | gtg | ctg | gcg | ttg | cag | gct | aac | cga | gac | aca | acg | cca | gcg | ctg | 2592 |
| Arg | Ala | Val | Leu | Ala | Leu | Gln | Ala | Asn | Arg | Asp | Thr | Thr | Pro | Ala | Leu | |
| | | 820 | | | | | 825 | | | | | 830 | | | | |
| gag | cag | gcc | aat | gtg | cca | ctg | act | gcc | tgg | cgt | tat | ctt | gat | gaa | cgg | 2640 |
| Glu | Gln | Ala | Asn | Val | Pro | Leu | Thr | Ala | Trp | Arg | Tyr | Leu | Asp | Glu | Arg | |
| | | 835 | | | | | 840 | | | | | 845 | | | | |
| cgg | atc | caa | ttg | tct | ttt | gcc | ggt | gaa | ttc | ccc | atc | gcc | ttc | tcc | gtt | 2688 |
| Arg | Ile | Gln | Leu | Ser | Phe | Ala | Gly | Glu | Phe | Pro | Ile | Ala | Phe | Ser | Val | |
| 850 | | | | | 855 | | | | | 860 | | | | | 865 | |
| cgt | tca | gct | tcc | ccc | tgc | cgg | cta | gat | gtg | gct | ggc | cgc | gag | gtc | aag | 2736 |
| Arg | Ser | Ala | Ser | Pro | Cys | Arg | Leu | Asp | Val | Ala | Gly | Arg | Glu | Val | Lys | |
| | | | | 870 | | | | | 875 | | | | | 880 | | |
| gga | cgc | ggg | gcg | aac | ggg | ctc | tgg | cat | ttc | tcc | tta | tcg | act | aaa | cag | 2784 |
| Gly | Arg | Gly | Ala | Asn | Gly | Leu | Trp | His | Phe | Ser | Leu | Ser | Thr | Lys | Gln | |
| | | 885 | | | | | 890 | | | | | 895 | | | | |
| gtg | agt | gat | gcg | caa | ctc | gtc | tgc | gag | taa | | | | | | | 2814 |
| Val | Ser | Asp | Ala | Gln | Leu | Val | Cys | Glu | | | | | | | | |
| | | 900 | | | | | 905 | | | | | | | | | |

<210> SEQ ID NO 66
<211> LENGTH: 937
<212> TYPE: PRT
<213> ORGANISM: Pseudomonas pelagia

<400> SEQUENCE: 66

Met Ala Gly Ser Asn Phe Arg Gln Ala Leu Thr Ser Thr Leu Lys Leu
    -30                  -25                    -20

Leu Gly Met Leu Ala Thr Val Leu Leu Ser Leu Gly Ala Val Ala Gly
-15                 -10                  -5                  -1  1

Pro Val Lys Ser Gly Pro Ala Ser Val Ala Phe Trp Tyr Ala Glu Gln
             5                    10                    15

Pro Pro Leu Gly Glu Leu Ala Gln Phe Asp Trp Val Phe Glu Pro
        20                    25                  30

Ala His Leu Thr Pro Lys Asp Val Ser Phe Val Ala Gln Gly Ser
 35                    40                  45

Leu Pro Phe Ala Tyr Leu Ser Ile Gly Glu Leu Asn Asp His Leu Ala
50                  55                  60                  65

Gln Ser Ser Pro Gly Leu Leu Asp Asn Ser Ala Asp Gln Ile Arg Asn
        70                    75                  80

Pro Gly Trp Asn Ser His Val Met Asp Leu Thr Ser Ala Gly Trp Gln
             85                    90                    95

Glu His Ile Leu Gly Gln Val Gly Glu Phe Ala Lys Gln Gly Tyr Ala
            100                   105                 110

Gly Val Phe Leu Asp Thr Asp Leu Asp Ser Phe Thr Leu Pro Glu Asp
            115                   120                 125

Gln Arg Pro Ala Gln Arg Asp Ala Leu Ala Ala Leu Leu Arg Asp Met
130                  135                  140                  145

His Lys Arg Tyr Pro Asp Met Lys Leu Phe Phe Asn Arg Gly Phe Glu

```
                150                 155                 160
Val Leu Ala Asp Val Gln Gln Gly Val Ala Ala Val Ala Val Glu Ser
            165                 170                 175

Ile Tyr Ala Ser Trp Asp Ala Ala Gln Val Tyr Arg Pro Val Ser
            180                 185                 190

Glu Asn Asp Arg Thr Trp Leu Ala Gly Gln Val Gln Pro Leu Arg Ala
            195                 200                 205

Arg Asn Ile Pro Ile Val Ala Ile Asp Tyr Leu Pro Val Glu Arg Arg
210                 215                 220                 225

Ala Glu Ala Arg Glu Leu Ala Ala Arg Leu Ile Glu Glu Gly Phe Leu
                230                 235                 240

Pro Tyr Val Gly Thr Pro Glu Leu Asp Thr Leu Gly Val Ser Ser Ile
            245                 250                 255

Glu Val Gln Pro Arg Arg Ile Ala Val Met Tyr Asp Pro Arg Glu Gly
            260                 265                 270

Glu Leu Thr Arg Thr Gly Gly Phe Arg Ser Leu Gly Gly Leu Leu Glu
            275                 280                 285

Tyr Met Gly Tyr Arg Val Asp Tyr Leu Pro Val Glu Gly Ser Leu Pro
290                 295                 300                 305

Ser Ala Pro Met Thr Gly Leu Tyr Ala Gly Val Ile Val Trp Met Thr
                310                 315                 320

Ser Gly Pro Pro Asp Ser Ser Ala Phe Asn Arg Trp Ile Gly Arg
            325                 330                 335

Arg Leu Asp Glu Gly Thr Pro Leu Ala Phe Phe Gln Gly Met Pro Ile
            340                 345                 350

Asp Asp Ala Ala Ile Leu Arg Arg Leu Gly Leu Gln Arg Thr Gly Val
            355                 360                 365

Gln Pro Val Ser Gly Leu Gln Leu Val Asn His Asp Ala Gln Leu Val
370                 375                 380                 385

Gly Ser Phe Glu Ala Pro Leu Val Val Arg Ser Arg Gly Leu Thr Gly
                390                 395                 400

Ile Gly Thr Gln Ser Arg Tyr Asn Lys Val Ala Leu Ala Leu Val Asp
            405                 410                 415

Asp Ala Gly Arg Glu His Thr Pro Val Val Thr Gly Asp Trp Gly Gly
            420                 425                 430

Val Ala Leu Ala Pro Tyr Val Phe Glu Gly Glu Asp Asp Thr Arg Arg
            435                 440                 445

Trp Ile Ile Asp Pro Phe Ala Phe Leu Gln Gln Ala Leu Gln Leu Pro
450                 455                 460                 465

Ala Gln Pro Ala Pro Asp Val Thr Thr Glu Asn Gly Arg Arg Ile Ala
                470                 475                 480

Thr Val His Ile Asp Gly Asp Gly Phe Pro Ser Arg Ala Glu Ile Pro
            485                 490                 495

Gly Thr Pro Tyr Ser Gly Ser Ala Val Leu Asn Gln Phe Ile Lys Pro
            500                 505                 510

Tyr Pro Leu Leu Thr Ser Val Ser Phe Ile Glu Gly Glu Val Gly Pro
            515                 520                 525

Ala Gly Met Tyr Pro Tyr Leu Ser Arg Glu Leu Glu Pro Leu Ala Arg
530                 535                 540                 545

Gln Ile Leu Ala His Glu Arg Val Glu Pro Ala Thr His Thr Tyr Ser
                550                 555                 560

His Pro Tyr Phe Trp Gln Ala Glu Arg Asp Ser Gln Arg Glu Gly Phe
            565                 570                 575
```

Arg Ala Asp Tyr Gly Leu Lys Met Pro Ile Pro Gly Tyr Asp Thr Ile
            580                 585                 590

Asp Phe Arg Arg Glu Val Phe Gly Ser Arg Asp Tyr Val Ala Ser Arg
595                 600                 605

Leu Ala Pro Ala Asp Lys Pro Val Lys Met Ile Phe Trp Ser Gly Asp
610                 615                 620                 625

Ala Ile Pro Asp Ala Thr Ile Lys Leu Ser Tyr Asp Ala Gly Met
            630                 635                 640

Leu Asn Val Asn Gly Gly Glu Thr Arg Leu Thr Arg Ala Asp Pro Ser
            645                 650                 655

Leu Thr Gly Leu Tyr Pro Leu Leu Arg Pro Thr Ala Gly Gly Leu Gln
            660                 665                 670

Val Tyr Ala Pro Ile Ile Asn Glu Asn Val Tyr Thr Asn Leu Trp Gln
            675                 680                 685

Gly Pro Tyr Tyr Gly Phe Arg Glu Val Val Glu Thr Phe Glu Leu Thr
690                 695                 700                 705

Asp Ser Pro Arg Arg Met Arg Gly Leu His Leu Tyr Tyr His Phe Tyr
            710                 715                 720

Ser Gly Thr Lys Pro Ala Ala Ile Lys Val Met Gly Asp Ile Tyr Arg
            725                 730                 735

His Met Leu Glu Gln Gln Pro Leu Ser Leu Trp Met Ser Asp Tyr Leu
            740                 745                 750

Leu Arg Ala His Gly Leu His Thr Ala Ser Leu Ala Arg Thr Ser Ser
            755                 760                 765

Gly Ala Trp Gln Ile Arg Ala Leu Gln Gly Leu Arg Thr Val Arg Leu
770                 775                 780                 785

Asp Pro Ser Leu Gly Trp Pro Asp Leu Met Ala Ser Glu Gly Ile Ala
            790                 795                 800

Gly Val Leu Asp Leu Pro Gln Gly Arg Tyr Val His Leu Ser Ala Asp
            805                 810                 815

Arg Ala Val Leu Ala Leu Gln Ala Asn Arg Asp Thr Thr Pro Ala Leu
            820                 825                 830

Glu Gln Ala Asn Val Pro Leu Thr Ala Trp Arg Tyr Leu Asp Glu Arg
            835                 840                 845

Arg Ile Gln Leu Ser Phe Ala Gly Glu Phe Pro Ile Ala Phe Ser Val
850                 855                 860                 865

Arg Ser Ala Ser Pro Cys Arg Leu Asp Val Ala Gly Arg Glu Val Lys
            870                 875                 880

Gly Arg Gly Ala Asn Gly Leu Trp His Phe Ser Leu Ser Thr Lys Gln
            885                 890                 895

Val Ser Asp Ala Gln Leu Val Cys Glu
            900                 905

<210> SEQ ID NO 67
<211> LENGTH: 906
<212> TYPE: PRT
<213> ORGANISM: Pseudomonas pelagia

<400> SEQUENCE: 67

Gly Pro Val Lys Ser Gly Pro Ala Ser Val Ala Phe Trp Tyr Ala Glu
1               5                   10                  15

Gln Pro Pro Leu Gly Glu Leu Ala Gln Phe Asp Trp Val Val Phe Glu
            20                  25                  30

Pro Ala His Leu Thr Pro Lys Asp Val Ser Phe Val Val Ala Gln Gly

```
            35                  40                  45
Ser Leu Pro Phe Ala Tyr Leu Ser Ile Gly Glu Leu Asn Asp His Leu
 50                  55                  60

Ala Gln Ser Ser Pro Gly Leu Leu Asp Asn Ser Ala Asp Gln Ile Arg
 65                  70                  75                  80

Asn Pro Gly Trp Asn Ser His Val Met Asp Leu Thr Ser Ala Gly Trp
                     85                  90                  95

Gln Glu His Ile Leu Gly Gln Val Gly Glu Phe Ala Lys Gln Gly Tyr
                    100                 105                 110

Ala Gly Val Phe Leu Asp Thr Leu Asp Ser Phe Thr Leu Leu Pro Glu
                115                 120                 125

Asp Gln Arg Pro Ala Gln Arg Asp Ala Leu Ala Leu Leu Arg Asp
                130                 135                 140

Met His Lys Arg Tyr Pro Asp Met Lys Leu Phe Phe Asn Arg Gly Phe
145                 150                 155                 160

Glu Val Leu Ala Asp Val Gln Gln Gly Val Ala Ala Val Ala Val Glu
                165                 170                 175

Ser Ile Tyr Ala Ser Trp Asp Ala Ala Ala Gln Val Tyr Arg Pro Val
                180                 185                 190

Ser Glu Asn Asp Arg Thr Trp Leu Ala Gly Gln Val Gln Pro Leu Arg
                195                 200                 205

Ala Arg Asn Ile Pro Ile Val Ala Ile Asp Tyr Leu Pro Val Glu Arg
210                 215                 220

Arg Ala Glu Ala Arg Glu Leu Ala Ala Arg Leu Ile Glu Glu Gly Phe
225                 230                 235                 240

Leu Pro Tyr Val Gly Thr Pro Glu Leu Asp Thr Leu Gly Val Ser Ser
                245                 250                 255

Ile Glu Val Gln Pro Arg Arg Ile Ala Val Met Tyr Asp Pro Arg Glu
                260                 265                 270

Gly Glu Leu Thr Arg Thr Gly Gly Phe Arg Ser Leu Gly Gly Leu Leu
                275                 280                 285

Glu Tyr Met Gly Tyr Arg Val Asp Tyr Leu Pro Val Glu Gly Ser Leu
290                 295                 300

Pro Ser Ala Pro Met Thr Gly Leu Tyr Ala Gly Val Ile Val Trp Met
305                 310                 315                 320

Thr Ser Gly Pro Pro Asp Ser Ser Ala Phe Asn Arg Trp Ile Gly
                325                 330                 335

Arg Arg Leu Asp Glu Gly Thr Pro Leu Ala Phe Phe Gln Gly Met Pro
                340                 345                 350

Ile Asp Asp Ala Ala Ile Leu Arg Arg Leu Gly Leu Gln Arg Thr Gly
                355                 360                 365

Val Gln Pro Val Ser Gly Leu Gln Leu Val Asn His Asp Ala Gln Leu
                370                 375                 380

Val Gly Ser Phe Glu Ala Pro Leu Val Val Arg Ser Arg Gly Leu Thr
385                 390                 395                 400

Gly Ile Gly Thr Gln Ser Arg Tyr Asn Lys Val Ala Leu Ala Leu Val
                405                 410                 415

Asp Asp Ala Gly Arg Glu His Thr Pro Val Val Thr Gly Asp Trp Gly
                420                 425                 430

Gly Val Ala Leu Ala Pro Tyr Val Phe Glu Gly Glu Asp Asp Thr Arg
                435                 440                 445

Arg Trp Ile Ile Asp Pro Phe Ala Phe Leu Gln Gln Ala Leu Gln Leu
450                 455                 460
```

```
Pro Ala Gln Pro Ala Pro Asp Val Thr Thr Glu Asn Gly Arg Arg Ile
465                 470                 475                 480

Ala Thr Val His Ile Asp Gly Asp Gly Phe Pro Ser Arg Ala Glu Ile
                485                 490                 495

Pro Gly Thr Pro Tyr Ser Gly Ser Ala Val Leu Asn Gln Phe Ile Lys
            500                 505                 510

Pro Tyr Pro Leu Leu Thr Ser Val Ser Phe Ile Glu Gly Glu Val Gly
            515                 520                 525

Pro Ala Gly Met Tyr Pro Tyr Leu Ser Arg Glu Leu Glu Pro Leu Ala
            530                 535                 540

Arg Gln Ile Leu Ala His Glu Arg Val Glu Pro Ala Thr His Thr Tyr
545                 550                 555                 560

Ser His Pro Tyr Phe Trp Gln Ala Glu Arg Asp Ser Gln Arg Glu Gly
                565                 570                 575

Phe Arg Ala Asp Tyr Gly Leu Lys Met Pro Ile Pro Gly Tyr Asp Thr
            580                 585                 590

Ile Asp Phe Arg Arg Glu Val Phe Gly Ser Arg Asp Tyr Val Ala Ser
            595                 600                 605

Arg Leu Ala Pro Ala Asp Lys Pro Val Lys Met Ile Phe Trp Ser Gly
            610                 615                 620

Asp Ala Ile Pro Asp Ala Ala Thr Ile Lys Leu Ser Tyr Asp Ala Gly
625                 630                 635                 640

Met Leu Asn Val Asn Gly Gly Glu Thr Arg Leu Thr Arg Ala Asp Pro
                645                 650                 655

Ser Leu Thr Gly Leu Tyr Pro Leu Leu Arg Pro Thr Ala Gly Gly Leu
            660                 665                 670

Gln Val Tyr Ala Pro Ile Ile Asn Glu Asn Val Tyr Thr Asn Leu Trp
            675                 680                 685

Gln Gly Pro Tyr Tyr Gly Phe Arg Glu Val Val Glu Thr Phe Glu Leu
            690                 695                 700

Thr Asp Ser Pro Arg Arg Met Arg Gly Leu His Leu Tyr His Phe
705                 710                 715                 720

Tyr Ser Gly Thr Lys Pro Ala Ala Ile Lys Val Met Gly Asp Ile Tyr
            725                 730                 735

Arg His Met Leu Glu Gln Gln Pro Leu Ser Leu Trp Met Ser Asp Tyr
            740                 745                 750

Leu Leu Arg Ala His Gly Leu His Thr Ala Ser Leu Ala Arg Thr Ser
            755                 760                 765

Ser Gly Ala Trp Gln Ile Arg Ala Leu Gln Gly Leu Arg Thr Val Arg
            770                 775                 780

Leu Asp Pro Ser Leu Gly Trp Pro Asp Leu Met Ala Ser Glu Gly Ile
785                 790                 795                 800

Ala Gly Val Leu Asp Leu Pro Gln Gly Arg Tyr Val His Leu Ser Ala
                805                 810                 815

Asp Arg Ala Val Leu Ala Leu Gln Ala Asn Arg Asp Thr Thr Pro Ala
            820                 825                 830

Leu Glu Gln Ala Asn Val Pro Leu Thr Ala Trp Arg Tyr Leu Asp Glu
            835                 840                 845

Arg Arg Ile Gln Leu Ser Phe Ala Gly Glu Phe Pro Ile Ala Phe Ser
            850                 855                 860

Val Arg Ser Ala Ser Pro Cys Arg Leu Asp Val Ala Gly Arg Glu Val
865                 870                 875                 880
```

Lys Gly Arg Gly Ala Asn Gly Leu Trp His Phe Ser Leu Ser Thr Lys
                885                 890                 895

Gln Val Ser Asp Ala Gln Leu Val Cys Glu
            900                 905

<210> SEQ ID NO 68
<211> LENGTH: 771
<212> TYPE: DNA
<213> ORGANISM: Pseudomonas aeruginosa
<220> FEATURE:
<221> NAME/KEY: CDS
<222> LOCATION: (1)..(771)

<400> SEQUENCE: 68

| | |
|---|---|
| ggt ggt cct agc agc gta gct ttt tgg tac gct gaa cgc cca cct ctt<br>Gly Gly Pro Ser Ser Val Ala Phe Trp Tyr Ala Glu Arg Pro Pro Leu<br>1               5                   10                  15 | 48 |
| gcg gag tta tca caa ttt gac tgg gta gta tta gaa gca gca cac ttg<br>Ala Glu Leu Ser Gln Phe Asp Trp Val Val Leu Glu Ala Ala His Leu<br>            20                  25                  30 | 96 |
| aaa cct gcg gat gtt ggt tat ctt aaa gaa caa gga tct act cct ttt<br>Lys Pro Ala Asp Val Gly Tyr Leu Lys Glu Gln Gly Ser Thr Pro Phe<br>        35                  40                  45 | 144 |
| gct tac tta tct gtt gga gag ttt gac gga gat gcg gct gct atc gct<br>Ala Tyr Leu Ser Val Gly Glu Phe Asp Gly Asp Ala Ala Ala Ile Ala<br>    50                  55                  60 | 192 |
| gac tca gga ctt gct cgt ggt aaa tct gct gta cgt aat caa gcg tgg<br>Asp Ser Gly Leu Ala Arg Gly Lys Ser Ala Val Arg Asn Gln Ala Trp<br>65                  70                  75                  80 | 240 |
| aac agc caa gtt atg gat ctt gct gct cct tct tgg cgt gct cac ctt<br>Asn Ser Gln Val Met Asp Leu Ala Ala Pro Ser Trp Arg Ala His Leu<br>                85                  90                  95 | 288 |
| ctt aaa cgt gct gcg gaa ctt cgt aaa caa ggt tat gct ggc ctt ttc<br>Leu Lys Arg Ala Ala Glu Leu Arg Lys Gln Gly Tyr Ala Gly Leu Phe<br>            100                 105                 110 | 336 |
| tta gac act tta gat tct ttt caa ctt caa gct gaa gag cgt cgc gag<br>Leu Asp Thr Leu Asp Ser Phe Gln Leu Gln Ala Glu Glu Arg Arg Glu<br>        115                 120                 125 | 384 |
| ggt caa cgt cgc gca ctt gct tct ttc ttg gct caa ctt cat cgt caa<br>Gly Gln Arg Arg Ala Leu Ala Ser Phe Leu Ala Gln Leu His Arg Gln<br>    130                 135                 140 | 432 |
| gaa cct gga ctt aaa ctt ttc ttc aat cgt ggt ttt gaa gta tta cca<br>Glu Pro Gly Leu Lys Leu Phe Phe Asn Arg Gly Phe Glu Val Leu Pro<br>145                 150                 155                 160 | 480 |
| gaa ctt cca ggt gtt gct tct gct gta gcg gta gaa tct att cac gct<br>Glu Leu Pro Gly Val Ala Ser Ala Val Ala Val Glu Ser Ile His Ala<br>                165                 170                 175 | 528 |
| gga tgg gat gct gca gct ggt caa tac cgt gag gtt cct caa gat gat<br>Gly Trp Asp Ala Ala Ala Gly Gln Tyr Arg Glu Val Pro Gln Asp Asp<br>            180                 185                 190 | 576 |
| cgc gat tgg ctt aaa ggt cat tta gac gcc ctt cgt gca caa ggt atg<br>Arg Asp Trp Leu Lys Gly His Leu Asp Ala Leu Arg Ala Gln Gly Met<br>        195                 200                 205 | 624 |
| cct atc gta gca atc gac tac ctt cca cca gag cgt cgt gat gaa gct<br>Pro Ile Val Ala Ile Asp Tyr Leu Pro Pro Glu Arg Arg Asp Glu Ala<br>    210                 215                 220 | 672 |
| cgt gct ctt gca gca cgt ctt cgt tct gaa gga tac gta cca ttc gtt<br>Arg Ala Leu Ala Ala Arg Leu Arg Ser Glu Gly Tyr Val Pro Phe Val<br>225                 230                 235                 240 | 720 |
| tct aca cct gct ctt gat tac ctt gga gtt tca gac gtt gaa gtt cag<br>Ser Thr Pro Ala Leu Asp Tyr Leu Gly Val Ser Asp Val Glu Val Gln | 768 |

```
                     245                 250                 255 cca                                                                          771
Pro <210> SEQ ID NO 69
<211> LENGTH: 257
<212> TYPE: PRT
<213> ORGANISM: Pseudomonas aeruginosa

<400> SEQUENCE: 69

Gly Gly Pro Ser Ser Val Ala Phe Trp Tyr Ala Glu Arg Pro Pro Leu
1               5                   10                  15

Ala Glu Leu Ser Gln Phe Asp Trp Val Val Leu Glu Ala Ala His Leu
            20                  25                  30

Lys Pro Ala Asp Val Gly Tyr Leu Lys Glu Gln Gly Ser Thr Pro Phe
        35                  40                  45

Ala Tyr Leu Ser Val Gly Glu Phe Asp Gly Asp Ala Ala Ile Ala
    50                  55                  60

Asp Ser Gly Leu Ala Arg Gly Lys Ser Ala Val Arg Asn Gln Ala Trp
65                  70                  75                  80

Asn Ser Gln Val Met Asp Leu Ala Ala Pro Ser Trp Arg Ala His Leu
                85                  90                  95

Leu Lys Arg Ala Ala Glu Leu Arg Lys Gln Gly Tyr Ala Gly Leu Phe
            100                 105                 110

Leu Asp Thr Leu Asp Ser Phe Gln Leu Gln Ala Glu Glu Arg Arg Glu
        115                 120                 125

Gly Gln Arg Arg Ala Leu Ala Ser Phe Leu Ala Gln Leu His Arg Gln
    130                 135                 140

Glu Pro Gly Leu Lys Leu Phe Phe Asn Arg Gly Phe Glu Val Leu Pro
145                 150                 155                 160

Glu Leu Pro Gly Val Ala Ser Ala Val Ala Val Glu Ser Ile His Ala
                165                 170                 175

Gly Trp Asp Ala Ala Ala Gly Gln Tyr Arg Glu Val Pro Gln Asp Asp
            180                 185                 190

Arg Asp Trp Leu Lys Gly His Leu Asp Ala Leu Arg Ala Gln Gly Met
        195                 200                 205

Pro Ile Val Ala Ile Asp Tyr Leu Pro Pro Glu Arg Arg Asp Glu Ala
    210                 215                 220

Arg Ala Leu Ala Ala Arg Leu Arg Ser Glu Gly Tyr Val Pro Phe Val
225                 230                 235                 240

Ser Thr Pro Ala Leu Asp Tyr Leu Gly Val Ser Asp Val Glu Val Gln
                245                 250                 255

Pro

<210> SEQ ID NO 70
<211> LENGTH: 257
<212> TYPE: PRT
<213> ORGANISM: Pseudomonas aeruginosa

<400> SEQUENCE: 70

Gly Gly Pro Ser Ser Val Ala Phe Trp Tyr Ala Glu Arg Pro Pro Leu
1               5                   10                  15

Ala Glu Leu Ser Gln Phe Asp Trp Val Val Leu Glu Ala Ala His Leu
            20                  25                  30

Lys Pro Ala Asp Val Gly Tyr Leu Lys Glu Gln Gly Ser Thr Pro Phe
        35                  40                  45
```

-continued

```
Ala Tyr Leu Ser Val Gly Glu Phe Asp Gly Asp Ala Ala Ile Ala
 50                  55                  60

Asp Ser Gly Leu Ala Arg Gly Lys Ser Ala Val Arg Asn Gln Ala Trp
 65                  70                  75                  80

Asn Ser Gln Val Met Asp Leu Ala Ala Pro Ser Trp Arg Ala His Leu
                 85                  90                  95

Leu Lys Arg Ala Ala Glu Leu Arg Lys Gln Gly Tyr Ala Gly Leu Phe
             100                 105                 110

Leu Asp Thr Leu Asp Ser Phe Gln Leu Gln Ala Glu Glu Arg Arg Glu
         115                 120                 125

Gly Gln Arg Arg Ala Leu Ala Ser Phe Leu Ala Gln Leu His Arg Gln
 130                 135                 140

Glu Pro Gly Leu Lys Leu Phe Phe Asn Arg Gly Phe Glu Val Leu Pro
145                 150                 155                 160

Glu Leu Pro Gly Val Ala Ser Ala Val Ala Val Glu Ser Ile His Ala
                165                 170                 175

Gly Trp Asp Ala Ala Gly Gln Tyr Arg Glu Val Pro Gln Asp Asp
            180                 185                 190

Arg Asp Trp Leu Lys Gly His Leu Asp Ala Leu Arg Ala Gln Gly Met
        195                 200                 205

Pro Ile Val Ala Ile Asp Tyr Leu Pro Pro Glu Arg Arg Asp Glu Ala
    210                 215                 220

Arg Ala Leu Ala Ala Arg Leu Arg Ser Glu Gly Tyr Val Pro Phe Val
225                 230                 235                 240

Ser Thr Pro Ala Leu Asp Tyr Leu Gly Val Ser Asp Val Glu Val Gln
                245                 250                 255

Pro

<210> SEQ ID NO 71
<211> LENGTH: 939
<212> TYPE: DNA
<213> ORGANISM: Streptomyces griseofuscus
<220> FEATURE:
<221> NAME/KEY: CDS
<222> LOCATION: (1)..(936)
<220> FEATURE:
<221> NAME/KEY: sig_peptide
<222> LOCATION: (1)..(129)
<220> FEATURE:
<221> NAME/KEY: mat_peptide
<222> LOCATION: (130)..(936)

<400> SEQUENCE: 71 atg aga agc agg agt cac ttg gac cgc cgg tcg ggc gcc gca agg agg    48
Met Arg Ser Arg Ser His Leu Asp Arg Arg Ser Gly Ala Ala Arg Arg
                -40                 -35                 -30 cgc cgc ctg tgt gcg gcg gcc gtg agc gcg ggc ctg gcc gcc ggc gcc    96
Arg Arg Leu Cys Ala Ala Ala Val Ser Ala Gly Leu Ala Ala Gly Ala
        -25                 -20                 -15 ctg gtc tcc ctc ccc gtc ggc gac gcg tcc gct gcc gcc ggg atc aag   144
Leu Val Ser Leu Pro Val Gly Asp Ala Ser Ala Ala Gly Ile Lys
    -10                  -5                  -1  1           5 cag cag gtg gcc gta ccg gcg tac ttc tac ccc ggt gac tcg ggt gac   192
Gln Gln Val Ala Val Pro Ala Tyr Phe Tyr Pro Gly Asp Ser Gly Asp
                     10                  15                  20 tcg ggt gcc ggc aat ctg tgg gca cag ctg tcc act ccg gcc ccc ggc   240
Ser Gly Ala Gly Asn Leu Trp Ala Gln Leu Ser Thr Pro Ala Pro Gly
         25                  30                  35
```

| | | | | | | | | | | | | | | | |
|---|---|---|---|---|---|---|---|---|---|---|---|---|---|---|---|
| gcg | ggc | ctg | gcc | gtc | gcc | aac | ccg | gcg | tcc | gga | ccc | ggc | gac | agc | gag | 288
| Ala | Gly | Leu | Ala | Val | Ala | Asn | Pro | Ala | Ser | Gly | Pro | Gly | Asp | Ser | Glu |
| | | 40 | | | | 45 | | | | 50 | | | | | |

```
gac ggc acc tac gcg aac gcc atc cgg acg gcg cac aac gcc ggg acg      336
Asp Gly Thr Tyr Ala Asn Ala Ile Arg Thr Ala His Asn Ala Gly Thr
        55                  60                  65 aag gtg atc gga tac gtc gac tcc gga tat ctc ggc acc aag ggc ggg      384
Lys Val Ile Gly Tyr Val Asp Ser Gly Tyr Leu Gly Thr Lys Gly Gly
 70                  75                  80                  85 gcc gcg ccc gac gga ggc acg tcc atc gac gac tgg gtc gaa ggc gcg      432
Ala Ala Pro Asp Gly Gly Thr Ser Ile Asp Asp Trp Val Glu Gly Ala
                 90                  95                 100 gag cga aac gtc gac aag tgg tac agc tac tac ggc ggt tcg ggc ctg      480
Glu Arg Asn Val Asp Lys Trp Tyr Ser Tyr Tyr Gly Gly Ser Gly Leu
                    105                 110                 115 gac ggg atc ttc ttc gac gac ggc ctc acc gct tgc ggc acc ccg tcc      528
Asp Gly Ile Phe Phe Asp Asp Gly Leu Thr Ala Cys Gly Thr Pro Ser
                    120                 125                 130 gac gcc aac gcc ttc gtc gac gcc tac aag agg ctc cag tcc tat gtg      576
Asp Ala Asn Ala Phe Val Asp Ala Tyr Lys Arg Leu Gln Ser Tyr Val
                    135                 140                 145 aag ggc aag gac gcc gac gcc aag gtc gtc atc aac ccg gga gcc tcg      624
Lys Gly Lys Asp Ala Asp Ala Lys Val Val Ile Asn Pro Gly Ala Ser
150                 155                 160                 165 ccc gag cag tgc tac aca ggg gcc gcc gac aca ctg gtc acc ttc gag      672
Pro Glu Gln Cys Tyr Thr Gly Ala Ala Asp Thr Leu Val Thr Phe Glu
                    170                 175                 180 ggc acc tac gac gac tat gtg aac cac tac ggc gac gac cgc gag tcc      720
Gly Thr Tyr Asp Asp Tyr Val Asn His Tyr Gly Asp Asp Arg Glu Ser
                    185                 190                 195 tgg gag gca tcg gcc gac ccg tcg aag atc tgg cac ctg atc cac acc      768
Trp Glu Ala Ser Ala Asp Pro Ser Lys Ile Trp His Leu Ile His Thr
                200                 205                 210 acg gga agc cag gcg cgg atg cag aac gcc atc gcc ctc tcg aag cag      816
Thr Gly Ser Gln Ala Arg Met Gln Asn Ala Ile Ala Leu Ser Lys Gln
    215                 220                 225 cgc aac gcg ggc tac gtc tac gcc acc gac gac gac aac tcc cgc ccc      864
Arg Asn Ala Gly Tyr Val Tyr Ala Thr Asp Asp Asp Asn Ser Arg Pro
230                 235                 240                 245 tcg ggc cag gac tgg ggc aac ccg tgg gac acc ctc ccg tcg tac tgg      912
Ser Gly Gln Asp Trp Gly Asn Pro Trp Asp Thr Leu Pro Ser Tyr Trp
                250                 255                 260 tcc gcc gag gtg aac acc gtc aac tga                                   939
Ser Ala Glu Val Asn Thr Val Asn
            265

<210> SEQ ID NO 72
<211> LENGTH: 312
<212> TYPE: PRT
<213> ORGANISM: Streptomyces griseofuscus

<400> SEQUENCE: 72

Met Arg Ser Arg Ser His Leu Asp Arg Arg Ser Gly Ala Ala Arg Arg
            -40                 -35                 -30

Arg Arg Leu Cys Ala Ala Ala Val Ser Ala Gly Leu Ala Ala Gly Ala
        -25                 -20                 -15

Leu Val Ser Leu Pro Val Gly Asp Ala Ser Ala Ala Gly Ile Lys
    -10                  -5                  -1   1               5

Gln Gln Val Ala Val Pro Ala Tyr Phe Tyr Pro Gly Asp Ser Gly Asp
                 10                  15                  20
```

```
Ser Gly Ala Gly Asn Leu Trp Ala Gln Leu Ser Thr Pro Ala Pro Gly
            25                  30                  35

Ala Gly Leu Ala Val Ala Asn Pro Ala Ser Gly Pro Gly Asp Ser Glu
        40                  45                  50

Asp Gly Thr Tyr Ala Asn Ala Ile Arg Thr Ala His Asn Ala Gly Thr
    55                  60                  65

Lys Val Ile Gly Tyr Val Asp Ser Gly Tyr Leu Gly Thr Lys Gly Gly
70                  75                  80                  85

Ala Ala Pro Asp Gly Gly Thr Ser Ile Asp Asp Trp Val Glu Gly Ala
                90                  95                  100

Glu Arg Asn Val Asp Lys Trp Tyr Ser Tyr Gly Gly Ser Gly Leu
                105                 110                 115

Asp Gly Ile Phe Phe Asp Asp Gly Leu Thr Ala Cys Gly Thr Pro Ser
            120                 125                 130

Asp Ala Asn Ala Phe Val Asp Ala Tyr Lys Arg Leu Gln Ser Tyr Val
    135                 140                 145

Lys Gly Lys Asp Ala Asp Ala Lys Val Val Ile Asn Pro Gly Ala Ser
150                 155                 160                 165

Pro Glu Gln Cys Tyr Thr Gly Ala Ala Asp Thr Leu Val Thr Phe Glu
                170                 175                 180

Gly Thr Tyr Asp Asp Tyr Val Asn His Tyr Gly Asp Arg Glu Ser
                185                 190                 195

Trp Glu Ala Ser Ala Asp Pro Ser Lys Ile Trp His Leu Ile His Thr
            200                 205                 210

Thr Gly Ser Gln Ala Arg Met Gln Asn Ala Ile Ala Leu Ser Lys Gln
    215                 220                 225

Arg Asn Ala Gly Tyr Val Tyr Ala Thr Asp Asp Asn Ser Arg Pro
230                 235                 240                 245

Ser Gly Gln Asp Trp Gly Asn Pro Trp Asp Thr Leu Pro Ser Tyr Trp
                250                 255                 260

Ser Ala Glu Val Asn Thr Val Asn
                265

<210> SEQ ID NO 73
<211> LENGTH: 269
<212> TYPE: PRT
<213> ORGANISM: Streptomyces griseofuscus

<400> SEQUENCE: 73

Ala Ala Gly Ile Lys Gln Gln Val Ala Val Pro Ala Tyr Phe Tyr Pro
1               5                   10                  15

Gly Asp Ser Gly Asp Ser Gly Ala Gly Asn Leu Trp Ala Gln Leu Ser
                20                  25                  30

Thr Pro Ala Pro Gly Ala Gly Leu Ala Val Ala Asn Pro Ala Ser Gly
            35                  40                  45

Pro Gly Asp Ser Glu Asp Gly Thr Tyr Ala Asn Ala Ile Arg Thr Ala
    50                  55                  60

His Asn Ala Gly Thr Lys Val Ile Gly Tyr Val Asp Ser Gly Tyr Leu
65                  70                  75                  80

Gly Thr Lys Gly Gly Ala Ala Pro Asp Gly Gly Thr Ser Ile Asp Asp
                85                  90                  95

Trp Val Glu Gly Ala Glu Arg Asn Val Asp Lys Trp Tyr Ser Tyr Tyr
                100                 105                 110

Gly Gly Ser Gly Leu Asp Gly Ile Phe Phe Asp Asp Gly Leu Thr Ala
```

|  |  |  | 115 |  |  |  | 120 |  |  |  | 125 |  |  |
|---|---|---|---|---|---|---|---|---|---|---|---|---|---|
| Cys | Gly | Thr | Pro | Ser | Asp | Ala | Asn | Ala | Phe | Val | Asp | Ala | Tyr | Lys | Arg |
|  |  |  | 130 |  |  |  | 135 |  |  |  | 140 |  |  |

Cys Gly Thr Pro Ser Asp Ala Asn Ala Phe Val Asp Ala Tyr Lys Arg
             130             135             140

Leu Gln Ser Tyr Val Lys Gly Lys Asp Ala Asp Ala Lys Val Val Ile
145             150             155             160

Asn Pro Gly Ala Ser Pro Glu Gln Cys Tyr Thr Gly Ala Ala Asp Thr
             165             170             175

Leu Val Thr Phe Glu Gly Thr Tyr Asp Asp Tyr Val Asn His Tyr Gly
             180             185             190

Asp Asp Arg Glu Ser Trp Glu Ala Ser Ala Asp Pro Ser Lys Ile Trp
             195             200             205

His Leu Ile His Thr Thr Gly Ser Gln Ala Arg Met Gln Asn Ala Ile
             210             215             220

Ala Leu Ser Lys Gln Arg Asn Ala Gly Tyr Val Tyr Ala Thr Asp Asp
225             230             235             240

Asp Asn Ser Arg Pro Ser Gly Gln Asp Trp Gly Asn Pro Trp Asp Thr
             245             250             255

Leu Pro Ser Tyr Trp Ser Ala Glu Val Asn Thr Val Asn
             260             265

<210> SEQ ID NO 74
<211> LENGTH: 861
<212> TYPE: DNA
<213> ORGANISM: Lysinibacillus xylanilyticus
<220> FEATURE:
<221> NAME/KEY: CDS
<222> LOCATION: (1)..(858)
<220> FEATURE:
<221> NAME/KEY: sig_peptide
<222> LOCATION: (1)..(78)
<220> FEATURE:
<221> NAME/KEY: mat_peptide
<222> LOCATION: (79)..(858)

<400> SEQUENCE: 74

```
atg cgt aaa tta ctt ttc acc att act act ata att gta ttg cta ggc      48
Met Arg Lys Leu Leu Phe Thr Ile Thr Thr Ile Ile Val Leu Leu Gly
 -25                 -20                 -15 att tgg tta cta att tct tcg aat cag gcc act gaa tct aca aca agc      96
Ile Trp Leu Leu Ile Ser Ser Asn Gln Ala Thr Glu Ser Thr Thr Ser
-10                  -5                  -1   1               5 atc caa gcg aag cta gct gac ata aag gag tac aaa tat tat tta gat     144
Ile Gln Ala Lys Leu Ala Asp Ile Lys Glu Tyr Lys Tyr Tyr Leu Asp
                 10                  15                  20 caa gga aac gat aag att ggc aag gaa atg gct aac atg gat ttg gtc     192
Gln Gly Asn Asp Lys Ile Gly Lys Glu Met Ala Asn Met Asp Leu Val
             25                  30                  35 att gtg gag cca atc gaa atg cag cag aag tat atc gac cat gct caa     240
Ile Val Glu Pro Ile Glu Met Gln Gln Lys Tyr Ile Asp His Ala Gln
         40                  45                  50 aaa aat gga aca cta gta tac ggc tat ata aat gct atg gaa gca gac     288
Lys Asn Gly Thr Leu Val Tyr Gly Tyr Ile Asn Ala Met Glu Ala Asp
 55                  60                  65                  70 aaa tgg aat tca gcg ctt tat agc caa tta aat aaa gca gat ttt tat     336
Lys Trp Asn Ser Ala Leu Tyr Ser Gln Leu Asn Lys Ala Asp Phe Tyr
                 75                  80                  85 aaa gat gcg cat gga gaa aag atg tat ttc act gag tgg gat tcg tat     384
Lys Asp Ala His Gly Glu Lys Met Tyr Phe Thr Glu Trp Asp Ser Tyr
             90                  95                 100 tta atg gat atg acc tct caa cat tat caa aag ctt tta cta gaa gaa     432
Leu Met Asp Met Thr Ser Gln His Tyr Gln Lys Leu Leu Leu Glu Glu
```

```
                                                                        480
att cag aag caa att gtt caa aaa ggg tta gat ggt gtg ttt tta gac
Ile Gln Lys Gln Ile Val Gln Lys Gly Leu Asp Gly Val Phe Leu Asp
    120                 125                 130

528
act gtg ggc aac att aat tct tat tta cct gaa aaa gag cag gaa gca
Thr Val Gly Asn Ile Asn Ser Tyr Leu Pro Glu Lys Glu Gln Glu Ala
135                 140                 145                 150

576
caa aat gaa gca atg tta tcc ttc atc aaa aaa ata aaa cag caa tat
Gln Asn Glu Ala Met Leu Ser Phe Ile Lys Lys Ile Lys Gln Gln Tyr
                155                 160                 165

624
aac ggc ttg tct gtt gcg caa aat tgg ggc ttt caa aca tta gct gat
Asn Gly Leu Ser Val Ala Gln Asn Trp Gly Phe Gln Thr Leu Ala Asp
            170                 175                 180

672
tac aca gcg cca tat atc gac ttt atc atg tgg gaa aac ttc tcg tat
Tyr Thr Ala Pro Tyr Ile Asp Phe Ile Met Trp Glu Asn Phe Ser Tyr
        185                 190                 195

720
gat gta gtt gga gaa gat gac tgg gca ttg gat agg atg aag caa tta
Asp Val Val Gly Glu Asp Asp Trp Ala Leu Asp Arg Met Lys Gln Leu
    200                 205                 210

768
gtt cac ata cga gat aaa ttc ggt act cag gtg atg gcg att gga ttt
Val His Ile Arg Asp Lys Phe Gly Thr Gln Val Met Ala Ile Gly Phe
215                 220                 225                 230

816
gag gat gaa gaa aaa agt cgt gct tta gca gag aaa tat caa ttt aaa
Glu Asp Glu Glu Lys Ser Arg Ala Leu Ala Glu Lys Tyr Gln Phe Lys
                235                 240                 245

861
ttt ttc tat agc ccc gct gga tct cac tac aat act tgg cag taa
Phe Phe Tyr Ser Pro Ala Gly Ser His Tyr Asn Thr Trp Gln
            250                 255                 260

<210> SEQ ID NO 75
<211> LENGTH: 286
<212> TYPE: PRT
<213> ORGANISM: Lysinibacillus xylanilyticus

<400> SEQUENCE: 75

Met Arg Lys Leu Leu Phe Thr Ile Thr Thr Ile Ile Val Leu Leu Gly
    -25                 -20                 -15

Ile Trp Leu Leu Ile Ser Ser Asn Gln Ala Thr Glu Ser Thr Thr Ser
-10                  -5             -1  1                  5

Ile Gln Ala Lys Leu Ala Asp Ile Lys Glu Tyr Lys Tyr Tyr Leu Asp
                10                  15                  20

Gln Gly Asn Asp Lys Ile Gly Lys Glu Met Ala Asn Met Asp Leu Val
            25                  30                  35

Ile Val Glu Pro Ile Glu Met Gln Lys Tyr Ile Asp His Ala Gln
    40                  45                  50

Lys Asn Gly Thr Leu Val Tyr Gly Tyr Ile Asn Ala Met Glu Ala Asp
55                  60                  65                  70

Lys Trp Asn Ser Ala Leu Tyr Ser Gln Leu Asn Lys Ala Asp Phe Tyr
                75                  80                  85

Lys Asp Ala His Gly Glu Lys Met Tyr Phe Thr Glu Trp Asp Ser Tyr
            90                  95                  100

Leu Met Asp Met Thr Ser Gln His Tyr Gln Lys Leu Leu Leu Glu Glu
        105                 110                 115

Ile Gln Lys Gln Ile Val Gln Lys Gly Leu Asp Gly Val Phe Leu Asp
    120                 125                 130

Thr Val Gly Asn Ile Asn Ser Tyr Leu Pro Glu Lys Glu Gln Glu Ala
135                 140                 145                 150
```

Gln Asn Glu Ala Met Leu Ser Phe Ile Lys Lys Ile Lys Gln Gln Tyr
                155                 160                 165

Asn Gly Leu Ser Val Ala Gln Asn Trp Gly Phe Gln Thr Leu Ala Asp
            170                 175                 180

Tyr Thr Ala Pro Tyr Ile Asp Phe Ile Met Trp Glu Asn Phe Ser Tyr
        185                 190                 195

Asp Val Val Gly Glu Asp Asp Trp Ala Leu Asp Arg Met Lys Gln Leu
    200                 205                 210

Val His Ile Arg Asp Lys Phe Gly Thr Gln Val Met Ala Ile Gly Phe
215                 220                 225                 230

Glu Asp Glu Glu Lys Ser Arg Ala Leu Ala Lys Tyr Gln Phe Lys
                235                 240                 245

Phe Phe Tyr Ser Pro Ala Gly Ser His Tyr Asn Thr Trp Gln
            250                 255                 260

<210> SEQ ID NO 76
<211> LENGTH: 260
<212> TYPE: PRT
<213> ORGANISM: Lysinibacillus xylanilyticus

<400> SEQUENCE: 76

Thr Glu Ser Thr Thr Ser Ile Gln Ala Lys Leu Ala Asp Ile Lys Glu
1               5                   10                  15

Tyr Lys Tyr Tyr Leu Asp Gln Gly Asn Asp Lys Ile Gly Lys Glu Met
            20                  25                  30

Ala Asn Met Asp Leu Val Ile Val Glu Pro Ile Glu Met Gln Gln Lys
        35                  40                  45

Tyr Ile Asp His Ala Gln Lys Asn Gly Thr Leu Val Tyr Gly Tyr Ile
    50                  55                  60

Asn Ala Met Glu Ala Asp Lys Trp Asn Ser Ala Leu Tyr Ser Gln Leu
65              70                  75                  80

Asn Lys Ala Asp Phe Tyr Lys Asp Ala His Gly Glu Lys Met Tyr Phe
                85                  90                  95

Thr Glu Trp Asp Ser Tyr Leu Met Asp Met Thr Ser Gln His Tyr Gln
            100                 105                 110

Lys Leu Leu Leu Glu Glu Ile Gln Lys Gln Ile Val Gln Lys Gly Leu
        115                 120                 125

Asp Gly Val Phe Leu Asp Thr Val Gly Asn Ile Asn Ser Tyr Leu Pro
    130                 135                 140

Glu Lys Glu Gln Glu Ala Gln Asn Glu Ala Met Leu Ser Phe Ile Lys
145                 150                 155                 160

Lys Ile Lys Gln Gln Tyr Asn Gly Leu Ser Val Ala Gln Asn Trp Gly
                165                 170                 175

Phe Gln Thr Leu Ala Asp Tyr Thr Ala Pro Tyr Ile Asp Phe Ile Met
            180                 185                 190

Trp Glu Asn Phe Ser Tyr Asp Val Val Gly Glu Asp Asp Trp Ala Leu
        195                 200                 205

Asp Arg Met Lys Gln Leu Val His Ile Arg Asp Lys Phe Gly Thr Gln
    210                 215                 220

Val Met Ala Ile Gly Phe Glu Asp Glu Glu Lys Ser Arg Ala Leu Ala
225                 230                 235                 240

Glu Lys Tyr Gln Phe Lys Phe Phe Tyr Ser Pro Ala Gly Ser His Tyr
                245                 250                 255

Asn Thr Trp Gln

<210> SEQ ID NO 77
<211> LENGTH: 918
<212> TYPE: DNA
<213> ORGANISM: Tumebacillus ginsengisoli
<220> FEATURE:
<221> NAME/KEY: CDS
<222> LOCATION: (1)..(915)
<220> FEATURE:
<221> NAME/KEY: sig_peptide
<222> LOCATION: (1)..(90)
<220> FEATURE:
<221> NAME/KEY: mat_peptide
<222> LOCATION: (91)..(915)

<400> SEQUENCE: 77

```
atg aaa agc tcg atg ata aaa ctc gta aaa ctt gca gcg gtg aca gct      48
Met Lys Ser Ser Met Ile Lys Leu Val Lys Leu Ala Ala Val Thr Ala
-30             -25                 -20                 -15 gtc acc tgg gga att gga gca cag gtc acc gtc gcg tcg gcg caa gta      96
Val Thr Trp Gly Ile Gly Ala Gln Val Thr Val Ala Ser Ala Gln Val
        -10                 -5                  -1  1 aaa tgg cag gtc aac tat gcg ttg agc acg gag aaa gcg gtc aaa tca     144
Lys Trp Gln Val Asn Tyr Ala Leu Ser Thr Glu Lys Ala Val Lys Ser
        5                   10                  15 gta tcg cat aaa gca tcg tcg ctg agt gcc gtc aaa tcg ttc atg atc     192
Val Ser His Lys Ala Ser Ser Leu Ser Ala Val Lys Ser Phe Met Ile
    20                  25                  30 tac tat gga gat gcg tcg gac agc gcg atc aaa aag ctg agc cag tat     240
Tyr Tyr Gly Asp Ala Ser Asp Ser Ala Ile Lys Lys Leu Ser Gln Tyr
35                  40                  45                  50 caa ctg gtg atc atc gag ccg cgc aac tgg aat ggc acc gaa ttg gcg     288
Gln Leu Val Ile Ile Glu Pro Arg Asn Trp Asn Gly Thr Glu Leu Ala
                55                  60                  65 cag ttg aaa aaa agc ggg gtc aaa gtg ctc ggc tac ctg agc gtg ctg     336
Gln Leu Lys Lys Ser Gly Val Lys Val Leu Gly Tyr Leu Ser Val Leu
            70                  75                  80 gag cag aac agc aat tct tcg cta ctg ggt cag gtg caa aat gcg gac     384
Glu Gln Asn Ser Asn Ser Ser Leu Leu Gly Gln Val Gln Asn Ala Asp
        85                  90                  95 tac ctg ttg att aac ggc aaa cgt gat ccg cgt tcc gat tgg gat agc     432
Tyr Leu Leu Ile Asn Gly Lys Arg Asp Pro Arg Ser Asp Trp Asp Ser
    100                 105                 110 tgg agc atg aac atc aac agc ggt cat tat cgc gac ctg ttg ttt gct     480
Trp Ser Met Asn Ile Asn Ser Gly His Tyr Arg Asp Leu Leu Phe Ala
115                 120                 125                 130 gat tat cag aag gag atc gtg aac aaa ggg ctg gat ggc gtg ttt ttg     528
Asp Tyr Gln Lys Glu Ile Val Asn Lys Gly Leu Asp Gly Val Phe Leu
                135                 140                 145 gac acg atg ggc gat gcg gat gac ggc att tgg aac acg agc att tct     576
Asp Thr Met Gly Asp Ala Asp Asp Gly Ile Trp Asn Thr Ser Ile Ser
            150                 155                 160 gac agc cag cgc gat ggt gcg gtg aag ttc gtt gcc gac ctg cgc aac     624
Asp Ser Gln Arg Asp Gly Ala Val Lys Phe Val Ala Asp Leu Arg Asn
        165                 170                 175 aag tac ccg agc ctg tcg atc atg cag aac tgg ggc ctg caa cag ttg     672
Lys Tyr Pro Ser Leu Ser Ile Met Gln Asn Trp Gly Leu Gln Gln Leu
    180                 185                 190 aaa gac cgc acg gct ccg tac atc gac ggg atc ttg tgg gag gat ttc     720
Lys Asp Arg Thr Ala Pro Tyr Ile Asp Gly Ile Leu Trp Glu Asp Phe
195                 200                 205                 210
```

|  |  |  |  |  |  |  |  |  |  |  |  |  |  |  |  |
|---|---|---|---|---|---|---|---|---|---|---|---|---|---|---|---|
| acg | ccg | aag | acg | gtg | gtg | aaa | aac | gcg | tgg | agc | aag | agc | cgc | atg | cag |
| Thr | Pro | Lys | Thr | Val | Val | Lys | Asn | Ala | Trp | Ser | Lys | Ser | Arg | Met | Gln |
|  |  |  |  | 215 |  |  |  |  | 220 |  |  |  |  | 225 |  |

768

| gag | ttg | gac | aag | ctc | cac | gcg | gcg | aat | ggg | cta | agc | gtg | ttt | acg | tcg |
|---|---|---|---|---|---|---|---|---|---|---|---|---|---|---|---|
| Glu | Leu | Asp | Lys | Leu | His | Ala | Ala | Asn | Gly | Leu | Ser | Val | Phe | Thr | Ser |
|  |  | 230 |  |  |  |  | 235 |  |  |  |  | 240 |  |  |  |

816

| cat | gtc | ggc | ctg | agc | ggt | gcg | cag | aag | agc | aag | ttt | gat | tca | ttg | aat |
|---|---|---|---|---|---|---|---|---|---|---|---|---|---|---|---|
| His | Val | Gly | Leu | Ser | Gly | Ala | Gln | Lys | Ser | Lys | Phe | Asp | Ser | Leu | Asn |
|  |  | 245 |  |  |  |  | 250 |  |  |  |  | 255 |  |  |  |

864

| gta | gaa | cac | ggc | tat | gtc | ggg | caa | gtg | atc | aag | aag | agt | tat | gat | gtg |
|---|---|---|---|---|---|---|---|---|---|---|---|---|---|---|---|
| Val | Glu | His | Gly | Tyr | Val | Gly | Gln | Val | Ile | Lys | Lys | Ser | Tyr | Asp | Val |
|  | 260 |  |  |  | 265 |  |  |  |  | 270 |  |  |  |  |  |

912

| atc | taa |
|---|---|
| Ile |  |
| 275 |  |

918

<210> SEQ ID NO 78
<211> LENGTH: 305
<212> TYPE: PRT
<213> ORGANISM: Tumebacillus ginsengisoli

<400> SEQUENCE: 78

| Met | Lys | Ser | Ser | Met | Ile | Lys | Leu | Val | Lys | Leu | Ala | Ala | Val | Thr | Ala |
|---|---|---|---|---|---|---|---|---|---|---|---|---|---|---|---|
| -30 |  |  |  |  | -25 |  |  |  |  | -20 |  |  |  |  | -15 |

| Val | Thr | Trp | Gly | Ile | Gly | Ala | Gln | Val | Thr | Val | Ala | Ser | Ala | Gln | Val |
|---|---|---|---|---|---|---|---|---|---|---|---|---|---|---|---|
|  |  |  |  | -10 |  |  |  |  | -5 |  |  |  | -1 | 1 |  |

| Lys | Trp | Gln | Val | Asn | Tyr | Ala | Leu | Ser | Thr | Glu | Lys | Ala | Val | Lys | Ser |
|---|---|---|---|---|---|---|---|---|---|---|---|---|---|---|---|
|  |  |  | 5 |  |  |  |  | 10 |  |  |  |  | 15 |  |  |

| Val | Ser | His | Lys | Ala | Ser | Ser | Leu | Ser | Ala | Val | Lys | Ser | Phe | Met | Ile |
|---|---|---|---|---|---|---|---|---|---|---|---|---|---|---|---|
|  | 20 |  |  |  |  | 25 |  |  |  |  | 30 |  |  |  |  |

| Tyr | Tyr | Gly | Asp | Ala | Ser | Asp | Ser | Ala | Ile | Lys | Lys | Leu | Ser | Gln | Tyr |
|---|---|---|---|---|---|---|---|---|---|---|---|---|---|---|---|
| 35 |  |  |  |  | 40 |  |  |  |  | 45 |  |  |  |  | 50 |

| Gln | Leu | Val | Ile | Ile | Glu | Pro | Arg | Asn | Trp | Asn | Gly | Thr | Glu | Leu | Ala |
|---|---|---|---|---|---|---|---|---|---|---|---|---|---|---|---|
|  |  |  |  | 55 |  |  |  |  | 60 |  |  |  |  | 65 |  |

| Gln | Leu | Lys | Lys | Ser | Gly | Val | Lys | Val | Leu | Gly | Tyr | Leu | Ser | Val | Leu |
|---|---|---|---|---|---|---|---|---|---|---|---|---|---|---|---|
|  |  | 70 |  |  |  |  | 75 |  |  |  |  | 80 |  |  |  |

| Glu | Gln | Asn | Ser | Asn | Ser | Ser | Leu | Leu | Gly | Gln | Val | Gln | Asn | Ala | Asp |
|---|---|---|---|---|---|---|---|---|---|---|---|---|---|---|---|
|  |  |  | 85 |  |  |  |  | 90 |  |  |  |  | 95 |  |  |

| Tyr | Leu | Leu | Ile | Asn | Gly | Lys | Arg | Asp | Pro | Arg | Ser | Asp | Trp | Asp | Ser |
|---|---|---|---|---|---|---|---|---|---|---|---|---|---|---|---|
|  | 100 |  |  |  |  | 105 |  |  |  |  | 110 |  |  |  |  |

| Trp | Ser | Met | Asn | Ile | Asn | Ser | Gly | His | Tyr | Arg | Asp | Leu | Leu | Phe | Ala |
|---|---|---|---|---|---|---|---|---|---|---|---|---|---|---|---|
| 115 |  |  |  |  | 120 |  |  |  |  | 125 |  |  |  |  | 130 |

| Asp | Tyr | Gln | Lys | Glu | Ile | Val | Asn | Lys | Gly | Leu | Asp | Gly | Val | Phe | Leu |
|---|---|---|---|---|---|---|---|---|---|---|---|---|---|---|---|
|  |  |  |  | 135 |  |  |  |  | 140 |  |  |  |  | 145 |  |

| Asp | Thr | Met | Gly | Asp | Ala | Asp | Asp | Gly | Ile | Trp | Asn | Thr | Ser | Ile | Ser |
|---|---|---|---|---|---|---|---|---|---|---|---|---|---|---|---|
|  |  |  | 150 |  |  |  |  | 155 |  |  |  |  | 160 |  |  |

| Asp | Ser | Gln | Arg | Asp | Gly | Ala | Val | Lys | Phe | Val | Ala | Asp | Leu | Arg | Asn |
|---|---|---|---|---|---|---|---|---|---|---|---|---|---|---|---|
|  |  | 165 |  |  |  |  | 170 |  |  |  |  | 175 |  |  |  |

| Lys | Tyr | Pro | Ser | Leu | Ser | Ile | Met | Gln | Asn | Trp | Gly | Leu | Gln | Gln | Leu |
|---|---|---|---|---|---|---|---|---|---|---|---|---|---|---|---|
|  | 180 |  |  |  |  | 185 |  |  |  |  | 190 |  |  |  |  |

| Lys | Asp | Arg | Thr | Ala | Pro | Tyr | Ile | Asp | Gly | Ile | Leu | Trp | Glu | Asp | Phe |
|---|---|---|---|---|---|---|---|---|---|---|---|---|---|---|---|
| 195 |  |  |  |  | 200 |  |  |  |  | 205 |  |  |  |  | 210 |

| Thr | Pro | Lys | Thr | Val | Val | Lys | Asn | Ala | Trp | Ser | Lys | Ser | Arg | Met | Gln |
|---|---|---|---|---|---|---|---|---|---|---|---|---|---|---|---|
|  |  |  |  | 215 |  |  |  |  | 220 |  |  |  |  | 225 |  |

| Glu | Leu | Asp | Lys | Leu | His | Ala | Ala | Asn | Gly | Leu | Ser | Val | Phe | Thr | Ser |
|---|---|---|---|---|---|---|---|---|---|---|---|---|---|---|---|
|  |  | 230 |  |  |  |  | 235 |  |  |  |  | 240 |  |  |  |

His Val Gly Leu Ser Gly Ala Gln Lys Ser Lys Phe Asp Ser Leu Asn
            245                 250                 255

Val Glu His Gly Tyr Val Gly Gln Val Ile Lys Lys Ser Tyr Asp Val
    260                 265                 270

Ile
275

<210> SEQ ID NO 79
<211> LENGTH: 275
<212> TYPE: PRT
<213> ORGANISM: Tumebacillus ginsengisoli

<400> SEQUENCE: 79

Gln Val Lys Trp Gln Val Asn Tyr Ala Leu Ser Thr Glu Lys Ala Val
1               5                   10                  15

Lys Ser Val Ser His Lys Ala Ser Leu Ser Ala Val Lys Ser Phe
            20                  25                  30

Met Ile Tyr Tyr Gly Asp Ala Ser Asp Ser Ala Ile Lys Lys Leu Ser
        35                  40                  45

Gln Tyr Gln Leu Val Ile Ile Glu Pro Arg Asn Trp Asn Gly Thr Glu
    50                  55                  60

Leu Ala Gln Leu Lys Lys Ser Gly Val Lys Val Leu Gly Tyr Leu Ser
65                  70                  75                  80

Val Leu Glu Gln Asn Ser Asn Ser Ser Leu Leu Gly Gln Val Gln Asn
                85                  90                  95

Ala Asp Tyr Leu Leu Ile Asn Gly Lys Arg Asp Pro Arg Ser Asp Trp
            100                 105                 110

Asp Ser Trp Ser Met Asn Ile Asn Ser Gly His Tyr Arg Asp Leu Leu
        115                 120                 125

Phe Ala Asp Tyr Gln Lys Glu Ile Val Asn Lys Gly Leu Asp Gly Val
    130                 135                 140

Phe Leu Asp Thr Met Gly Asp Ala Asp Gly Ile Trp Asn Thr Ser
145                 150                 155                 160

Ile Ser Asp Ser Gln Arg Asp Gly Ala Val Lys Phe Val Ala Asp Leu
                165                 170                 175

Arg Asn Lys Tyr Pro Ser Leu Ser Ile Met Gln Asn Trp Gly Leu Gln
            180                 185                 190

Gln Leu Lys Asp Arg Thr Ala Pro Tyr Ile Asp Gly Ile Leu Trp Glu
        195                 200                 205

Asp Phe Thr Pro Lys Thr Val Val Lys Asn Ala Trp Ser Lys Ser Arg
    210                 215                 220

Met Gln Glu Leu Asp Lys Leu His Ala Ala Asn Gly Leu Ser Val Phe
225                 230                 235                 240

Thr Ser His Val Gly Leu Ser Gly Ala Gln Lys Ser Lys Phe Asp Ser
                245                 250                 255

Leu Asn Val Glu His Gly Tyr Val Gly Gln Val Ile Lys Lys Ser Tyr
            260                 265                 270

Asp Val Ile
275

<210> SEQ ID NO 80
<211> LENGTH: 891
<212> TYPE: DNA
<213> ORGANISM: Lysinibacillus boronitolerans
<220> FEATURE:
<221> NAME/KEY: CDS
<222> LOCATION: (1)..(888)

```
<220> FEATURE:
<221> NAME/KEY: sig_peptide
<222> LOCATION: (1)..(84)
<220> FEATURE:
<221> NAME/KEY: mat_peptide
<222> LOCATION: (85)..(888)

<400> SEQUENCE: 80 atg aaa aaa tta ttg ata ctc tta tta gcc cct cta atc gca ggt agt       48
Met Lys Lys Leu Leu Ile Leu Leu Leu Ala Pro Leu Ile Ala Gly Ser
            -25                 -20                 -15 atg tgg atg ctg ctt gct aaa aat cca gta tct tct tcc aca agt atc       96
Met Trp Met Leu Leu Ala Lys Asn Pro Val Ser Ser Ser Thr Ser Ile
        -10                  -5                  -1   1 caa gca aag ctt gct gat gtg aaa gat tac aca tac tac tta gat aaa      144
Gln Ala Lys Leu Ala Asp Val Lys Asp Tyr Thr Tyr Tyr Leu Asp Lys
  5                  10                  15                  20 ggc aac gat gcc att ggc aag agc atg acg aag tta gat tta gtg att      192
Gly Asn Asp Ala Ile Gly Lys Ser Met Thr Lys Leu Asp Leu Val Ile
                 25                  30                  35 gta gaa cct att gaa atg cag caa aag tat atc atc aat gct caa aaa      240
Val Glu Pro Ile Glu Met Gln Gln Lys Tyr Ile Ile Asn Ala Gln Lys
         40                  45                  50 agc gga act tta gtg tac ggc tat att aat gcg atg gaa gca gac aaa      288
Ser Gly Thr Leu Val Tyr Gly Tyr Ile Asn Ala Met Glu Ala Asp Lys
             55                  60                  65 tgg aat aca gca ctc tat cat caa ttg aag gaa gaa gat ttt tat cga      336
Trp Asn Thr Ala Leu Tyr His Gln Leu Lys Glu Glu Asp Phe Tyr Arg
 70                  75                  80 gac aaa cag ggg gaa aga atg tat ttt gcc aaa tgg gat tct ttt tta      384
Asp Lys Gln Gly Glu Arg Met Tyr Phe Ala Lys Trp Asp Ser Phe Leu
 85                  90                  95                 100 atg gat ttg act tct acg cac tat caa gac att ttg cta gca gaa ata      432
Met Asp Leu Thr Ser Thr His Tyr Gln Asp Ile Leu Leu Ala Glu Ile
                 105                 110                 115 cag cag caa att gtt gag aaa ggc tta gac ggt gtg ttt tta gat acg      480
Gln Gln Gln Ile Val Glu Lys Gly Leu Asp Gly Val Phe Leu Asp Thr
             120                 125                 130 gtt ggt aat atc aat tcc tat tta cct gaa gat gaa caa aag tgg caa      528
Val Gly Asn Ile Asn Ser Tyr Leu Pro Glu Asp Glu Gln Lys Trp Gln
         135                 140                 145 aat gaa gcc atc ttg tct ttt atc caa caa att aaa aaa cgt cat ccc      576
Asn Glu Ala Ile Leu Ser Phe Ile Gln Gln Ile Lys Lys Arg His Pro
 150                 155                 160 gat tta tct gtt gct caa aat tgg gga ttt caa aca ctt gct gat tat      624
Asp Leu Ser Val Ala Gln Asn Trp Gly Phe Gln Thr Leu Ala Asp Tyr
165                 170                 175                 180 aca gcg cca tat gtt gac ttt att atg tgg gag gat ttt tcg tat cct      672
Thr Ala Pro Tyr Val Asp Phe Ile Met Trp Glu Asp Phe Ser Tyr Pro
                 185                 190                 195 gtg gta gga aaa gat gaa tgg tca ctc gat atg atg caa cag ctt atc      720
Val Val Gly Lys Asp Glu Trp Ser Leu Asp Met Met Gln Gln Leu Ile
             200                 205                 210 cac ata cgc aat aaa ttt ggt aca caa gtg atg aca att ggt ttt gaa      768
His Ile Arg Asn Lys Phe Gly Thr Gln Val Met Thr Ile Gly Phe Glu
         215                 220                 225 gaa gaa tca aaa agc cgt gct tta gct gag aag cat cac ttc aaa ttc      816
Glu Glu Ser Lys Ser Arg Ala Leu Ala Glu Lys His His Phe Lys Phe
 230                 235                 240 ttt tat agt cct gct ggc tct tac tat aat agc tgg caa tca tcc tta      864
Phe Tyr Ser Pro Ala Gly Ser Tyr Tyr Asn Ser Trp Gln Ser Ser Leu
```

```
                245                 250                 255                 260
ctt ccc tct gac aaa caa ctg ttt tga                                                891
Leu Pro Ser Asp Lys Gln Leu Phe
                265

<210> SEQ ID NO 81
<211> LENGTH: 296
<212> TYPE: PRT
<213> ORGANISM: Lysinibacillus boronitolerans

<400> SEQUENCE: 81

Met Lys Lys Leu Leu Ile Leu Leu Ala Pro Leu Ile Ala Gly Ser
            -25                 -20                 -15

Met Trp Met Leu Leu Ala Lys Asn Pro Val Ser Ser Thr Ser Ile
            -10                  -5          -1   1

Gln Ala Lys Leu Ala Asp Val Lys Asp Tyr Thr Tyr Tyr Leu Asp Lys
 5                  10                  15                  20

Gly Asn Asp Ala Ile Gly Lys Ser Met Thr Lys Leu Asp Leu Val Ile
                25                  30                  35

Val Glu Pro Ile Glu Met Gln Gln Lys Tyr Ile Ile Asn Ala Gln Lys
            40                  45                  50

Ser Gly Thr Leu Val Tyr Gly Tyr Ile Asn Ala Met Glu Ala Asp Lys
        55                  60                  65

Trp Asn Thr Ala Leu Tyr His Gln Leu Lys Glu Glu Asp Phe Tyr Arg
    70                  75                  80

Asp Lys Gln Gly Glu Arg Met Tyr Phe Ala Lys Trp Asp Ser Phe Leu
85                  90                  95                  100

Met Asp Leu Thr Ser Thr His Tyr Gln Asp Ile Leu Leu Ala Glu Ile
                105                 110                 115

Gln Gln Gln Ile Val Glu Lys Gly Leu Asp Gly Val Phe Leu Asp Thr
            120                 125                 130

Val Gly Asn Ile Asn Ser Tyr Leu Pro Glu Asp Glu Gln Lys Trp Gln
        135                 140                 145

Asn Glu Ala Ile Leu Ser Phe Ile Gln Gln Ile Lys Lys Arg His Pro
    150                 155                 160

Asp Leu Ser Val Ala Gln Asn Trp Gly Phe Gln Thr Leu Ala Asp Tyr
165                 170                 175                 180

Thr Ala Pro Tyr Val Asp Phe Ile Met Trp Glu Asp Phe Ser Tyr Pro
                185                 190                 195

Val Val Gly Lys Asp Glu Trp Ser Leu Asp Met Met Gln Gln Leu Ile
            200                 205                 210

His Ile Arg Asn Lys Phe Gly Thr Gln Val Met Thr Ile Gly Phe Glu
        215                 220                 225

Glu Glu Ser Lys Ser Arg Ala Leu Ala Glu Lys His Phe Lys Phe
    230                 235                 240

Phe Tyr Ser Pro Ala Gly Ser Tyr Tyr Asn Ser Trp Gln Ser Ser Leu
245                 250                 255                 260

Leu Pro Ser Asp Lys Gln Leu Phe
                265

<210> SEQ ID NO 82
<211> LENGTH: 268
<212> TYPE: PRT
<213> ORGANISM: Lysinibacillus boronitolerans

<400> SEQUENCE: 82
```

```
Ser Thr Ser Ile Gln Ala Lys Leu Ala Asp Val Lys Asp Tyr Thr Tyr
1               5                   10                  15

Tyr Leu Asp Lys Gly Asn Asp Ala Ile Gly Lys Ser Met Thr Lys Leu
            20                  25                  30

Asp Leu Val Ile Val Glu Pro Ile Glu Met Gln Gln Lys Tyr Ile Ile
        35                  40                  45

Asn Ala Gln Lys Ser Gly Thr Leu Val Tyr Gly Tyr Ile Asn Ala Met
    50                  55                  60

Glu Ala Asp Lys Trp Asn Thr Ala Leu Tyr His Gln Leu Lys Glu Glu
65                  70                  75                  80

Asp Phe Tyr Arg Asp Lys Gln Gly Glu Arg Met Tyr Phe Ala Lys Trp
                85                  90                  95

Asp Ser Phe Leu Met Asp Leu Thr Ser Thr His Tyr Gln Asp Ile Leu
            100                 105                 110

Leu Ala Glu Ile Gln Gln Gln Ile Val Glu Lys Gly Leu Asp Gly Val
        115                 120                 125

Phe Leu Asp Thr Val Gly Asn Ile Asn Ser Tyr Leu Pro Glu Asp Glu
    130                 135                 140

Gln Lys Trp Gln Asn Glu Ala Ile Leu Ser Phe Ile Gln Gln Ile Lys
145                 150                 155                 160

Lys Arg His Pro Asp Leu Ser Val Ala Gln Asn Trp Gly Phe Gln Thr
                165                 170                 175

Leu Ala Asp Tyr Thr Ala Pro Tyr Val Asp Phe Ile Met Trp Glu Asp
            180                 185                 190

Phe Ser Tyr Pro Val Val Gly Lys Asp Glu Trp Ser Leu Asp Met Met
        195                 200                 205

Gln Gln Leu Ile His Ile Arg Asn Lys Phe Gly Thr Gln Val Met Thr
    210                 215                 220

Ile Gly Phe Glu Glu Ser Lys Ser Arg Ala Leu Ala Glu Lys His
225                 230                 235                 240

His Phe Lys Phe Phe Tyr Ser Pro Ala Gly Ser Tyr Tyr Asn Ser Trp
                245                 250                 255

Gln Ser Ser Leu Leu Pro Ser Asp Lys Gln Leu Phe
            260                 265

<210> SEQ ID NO 83
<211> LENGTH: 990
<212> TYPE: DNA
<213> ORGANISM: Microbulbifer hydrolyticus
<220> FEATURE:
<221> NAME/KEY: CDS
<222> LOCATION: (1)..(987)
<220> FEATURE:
<221> NAME/KEY: sig_peptide
<222> LOCATION: (1)..(48)
<220> FEATURE:
<221> NAME/KEY: mat_peptide
<222> LOCATION: (49)..(987)

<400> SEQUENCE: 83 atg aaa aaa ttt cta ctc ccc acc ttg ctt gcc gca gcg ctc acc gcc    48
Met Lys Lys Phe Leu Leu Pro Thr Leu Leu Ala Ala Ala Leu Thr Ala
    -15                 -10                 -5                  -1 tgc aat ctc gaa gat gtg ccc aac ttg tac ccg gaa cag ggc cac acc    96
Cys Asn Leu Glu Asp Val Pro Asn Leu Tyr Pro Glu Gln Gly His Thr
1               5                   10                  15 gac cac ccg cag gaa atg cgg gac ttt gtc acc ggc atc cga ggt tat   144
Asp His Pro Gln Glu Met Arg Asp Phe Val Thr Gly Ile Arg Gly Tyr
            20                  25                  30
```

```
gcc cgc ggg ctg aaa tct ggc ttc gtt gtt gtc ggc cac ggc gcc ctg      192
Ala Arg Gly Leu Lys Ser Gly Phe Val Val Val Gly His Gly Ala Leu
         35                  40                  45 ccg ctg gtg agc agc aat gaa cgc acc agc ggt gat cca gac agt gtg      240
Pro Leu Val Ser Ser Asn Glu Arg Thr Ser Gly Asp Pro Asp Ser Val
 50                  55                  60 tat atc ggc aat ctc gat gca ctc gcg cag gat tcg ctc ttt tac ggc      288
Tyr Ile Gly Asn Leu Asp Ala Leu Ala Gln Asp Ser Leu Phe Tyr Gly
 65                  70                  75                  80 cac gaa gga atc gat cag cca aca aca gac agc cgc cgc acg agc ttg      336
His Glu Gly Ile Asp Gln Pro Thr Thr Asp Ser Arg Arg Thr Ser Leu
                 85                  90                  95 cgc agc tac ctc gat atg gcc cga gac act ggc aac acg ata ttg          384
Arg Ser Tyr Leu Asp Met Ala Arg Asp Thr Gly Asn Thr Ile Leu
             100                 105                 110 atc aca gat ttt gcg gtt tca gag caa aag atc gac aac gcg tac caa      432
Ile Thr Asp Phe Ala Val Ser Glu Gln Lys Ile Asp Asn Ala Tyr Gln
             115                 120                 125 ctg aat gac gat gcc ggc tat ctt ggc ttc gtt gca gac cac act gag      480
Leu Asn Asp Asp Ala Gly Tyr Leu Gly Phe Val Ala Asp His Thr Glu
130                 135                 140 ctc gac aat att ccg atc tac ccc gcc gaa ccc ttc agc gta aat cga      528
Leu Asp Asn Ile Pro Ile Tyr Pro Ala Glu Pro Phe Ser Val Asn Arg
145                 150                 155                 160 cgc gat att ttt gac ctc gac gat gcc agc aat ttt ctg gtg ttg acg      576
Arg Asp Ile Phe Asp Leu Asp Asp Ala Ser Asn Phe Leu Val Leu Thr
                165                 170                 175 aat acg caa ctg tat tca aca cgc cag gat ctt gtc gat gac gtc gct      624
Asn Thr Gln Leu Tyr Ser Thr Arg Gln Asp Leu Val Asp Asp Val Ala
            180                 185                 190 gac acc gac tac gac ctg att gtt ttg gat ttc ttt ttc aac ggc gag      672
Asp Thr Asp Tyr Asp Leu Ile Val Leu Asp Phe Phe Phe Asn Gly Glu
            195                 200                 205 gaa ttc acc gct caa cag gtt cgc cag ttg caa cga aag cgc aat gga      720
Glu Phe Thr Ala Gln Gln Val Arg Gln Leu Gln Arg Lys Arg Asn Gly
210                 215                 220 aga acg cgg cag gtg ctc gcg acg gta aat att ggc cat gcg gaa agt      768
Arg Thr Arg Gln Val Leu Ala Thr Val Asn Ile Gly His Ala Glu Ser
225                 230                 235                 240 aac cgc tac tac tgg gaa aat cac tgg gtc tcc aac ccg cca agc tgg      816
Asn Arg Tyr Tyr Trp Glu Asn His Trp Val Ser Asn Pro Pro Ser Trp
                245                 250                 255 ttg cga gag gaa att tcc ggc agt aat ggt gac tac tat gtc aat tac      864
Leu Arg Glu Glu Ile Ser Gly Ser Asn Gly Asp Tyr Tyr Val Asn Tyr
                260                 265                 270 tgg aat ccc gct tgg cag gac atc atc tac ggg aaa aat ggc tcc tac      912
Trp Asn Pro Ala Trp Gln Asp Ile Ile Tyr Gly Lys Asn Gly Ser Tyr
            275                 280                 285 atc gaa aaa atc gcc aat gcc ggt ttc gac ggt gct tac ttg caa ggg      960
Ile Glu Lys Ile Ala Asn Ala Gly Phe Asp Gly Ala Tyr Leu Gln Gly
        290                 295                 300 cta gat gct tac gcg cat ttc cag aac tga                              990
Leu Asp Ala Tyr Ala His Phe Gln Asn
305                 310
```

<210> SEQ ID NO 84
<211> LENGTH: 329
<212> TYPE: PRT
<213> ORGANISM: Microbulbifer hydrolyticus

<400> SEQUENCE: 84

```
Met Lys Lys Phe Leu Leu Pro Thr Leu Leu Ala Ala Ala Leu Thr Ala
    -15                 -10                 -5                  -1
Cys Asn Leu Glu Asp Val Pro Asn Leu Tyr Pro Glu Gln Gly His Thr
 1               5                  10                  15
Asp His Pro Gln Glu Met Arg Asp Phe Val Thr Gly Ile Arg Gly Tyr
             20                  25                  30
Ala Arg Gly Leu Lys Ser Gly Phe Val Val Gly His Gly Ala Leu
         35                  40                  45
Pro Leu Val Ser Ser Asn Glu Arg Thr Ser Gly Asp Pro Asp Ser Val
 50                  55                  60
Tyr Ile Gly Asn Leu Asp Ala Leu Ala Gln Asp Ser Leu Phe Tyr Gly
 65                  70                  75                  80
His Glu Gly Ile Asp Gln Pro Thr Thr Asp Ser Arg Arg Thr Ser Leu
                 85                  90                  95
Arg Ser Tyr Leu Asp Met Ala Arg Asp Thr Gly Asn Thr Thr Ile Leu
            100                 105                 110
Ile Thr Asp Phe Ala Val Ser Glu Gln Lys Ile Asp Asn Ala Tyr Gln
            115                 120                 125
Leu Asn Asp Asp Ala Gly Tyr Leu Gly Phe Val Ala Asp His Thr Glu
130                 135                 140
Leu Asp Asn Ile Pro Ile Tyr Pro Ala Glu Pro Phe Ser Val Asn Arg
145                 150                 155                 160
Arg Asp Ile Phe Asp Leu Asp Asp Ala Ser Asn Phe Leu Val Leu Thr
                165                 170                 175
Asn Thr Gln Leu Tyr Ser Thr Arg Gln Asp Leu Val Asp Asp Val Ala
            180                 185                 190
Asp Thr Asp Tyr Asp Leu Ile Val Leu Asp Phe Phe Asn Gly Glu
            195                 200                 205
Glu Phe Thr Ala Gln Gln Val Arg Gln Leu Gln Arg Lys Arg Asn Gly
            210                 215                 220
Arg Thr Arg Gln Val Leu Ala Thr Val Asn Ile Gly His Ala Glu Ser
225                 230                 235                 240
Asn Arg Tyr Tyr Trp Glu Asn His Trp Val Ser Asn Pro Pro Ser Trp
                245                 250                 255
Leu Arg Glu Glu Ile Ser Gly Ser Asn Gly Asp Tyr Tyr Val Asn Tyr
            260                 265                 270
Trp Asn Pro Ala Trp Gln Asp Ile Ile Tyr Gly Lys Asn Gly Ser Tyr
            275                 280                 285
Ile Glu Lys Ile Ala Asn Ala Gly Phe Asp Gly Ala Tyr Leu Gln Gly
            290                 295                 300
Leu Asp Ala Tyr Ala His Phe Gln Asn
305                 310
```

<210> SEQ ID NO 85
<211> LENGTH: 313
<212> TYPE: PRT
<213> ORGANISM: Microbulbifer hydrolyticus

<400> SEQUENCE: 85

```
Cys Asn Leu Glu Asp Val Pro Asn Leu Tyr Pro Glu Gln Gly His Thr
 1               5                  10                  15
Asp His Pro Gln Glu Met Arg Asp Phe Val Thr Gly Ile Arg Gly Tyr
             20                  25                  30
```

-continued

```
Ala Arg Gly Leu Lys Ser Gly Phe Val Val Gly His Gly Ala Leu
         35                  40                  45

Pro Leu Val Ser Ser Asn Glu Arg Thr Ser Gly Asp Pro Asp Ser Val
 50                  55                  60

Tyr Ile Gly Asn Leu Asp Ala Leu Ala Gln Asp Ser Leu Phe Tyr Gly
 65                  70                  75                  80

His Glu Gly Ile Asp Gln Pro Thr Thr Asp Ser Arg Arg Thr Ser Leu
                 85                  90                  95

Arg Ser Tyr Leu Asp Met Ala Arg Asp Thr Gly Asn Thr Thr Ile Leu
            100                 105                 110

Ile Thr Asp Phe Ala Val Ser Glu Gln Lys Ile Asp Asn Ala Tyr Gln
        115                 120                 125

Leu Asn Asp Asp Ala Gly Tyr Leu Gly Phe Val Ala Asp His Thr Glu
130                 135                 140

Leu Asp Asn Ile Pro Ile Tyr Pro Ala Glu Pro Phe Ser Val Asn Arg
145                 150                 155                 160

Arg Asp Ile Phe Asp Leu Asp Ala Ser Asn Phe Leu Val Leu Thr
                165                 170                 175

Asn Thr Gln Leu Tyr Ser Thr Arg Gln Asp Leu Val Asp Asp Val Ala
            180                 185                 190

Asp Thr Asp Tyr Asp Leu Ile Val Leu Asp Phe Phe Asn Gly Glu
        195                 200                 205

Glu Phe Thr Ala Gln Gln Val Arg Gln Leu Gln Arg Lys Arg Asn Gly
210                 215                 220

Arg Thr Arg Gln Val Leu Ala Thr Val Asn Ile Gly His Ala Glu Ser
225                 230                 235                 240

Asn Arg Tyr Tyr Trp Glu Asn His Trp Val Ser Asn Pro Pro Ser Trp
                245                 250                 255

Leu Arg Glu Glu Ile Ser Gly Ser Asn Gly Asp Tyr Tyr Val Asn Tyr
            260                 265                 270

Trp Asn Pro Ala Trp Gln Asp Ile Ile Tyr Gly Lys Asn Gly Ser Tyr
        275                 280                 285

Ile Glu Lys Ile Ala Asn Ala Gly Phe Asp Gly Ala Tyr Leu Gln Gly
290                 295                 300

Leu Asp Ala Tyr Ala His Phe Gln Asn
305                 310

<210> SEQ ID NO 86
<211> LENGTH: 846
<212> TYPE: DNA
<213> ORGANISM: Carnobacterium inhibens subsp.
<220> FEATURE:
<221> NAME/KEY: CDS
<222> LOCATION: (1)..(843)
<220> FEATURE:
<221> NAME/KEY: sig_peptide
<222> LOCATION: (1)..(72)
<220> FEATURE:
<221> NAME/KEY: mat_peptide
<222> LOCATION: (73)..(843)

<400> SEQUENCE: 86 atg aaa act act gcg ata cgc ttt ttg ata gga gca atg gtt att tta        48
Met Lys Thr Thr Ala Ile Arg Phe Leu Ile Gly Ala Met Val Ile Leu
            -20                 -15                 -10 gga gta aca ggt tgt gca aac tta gaa gga aaa agc aac agt aaa ctc        96
Gly Val Thr Gly Cys Ala Asn Leu Glu Gly Lys Ser Asn Ser Lys Leu
        -5                  -1  1                   5
```

```
gaa aat aca ggt gag tat ggt gta ttt ttg agt tta gat gga agt gaa    144
Glu Asn Thr Gly Glu Tyr Gly Val Phe Leu Ser Leu Asp Gly Ser Glu
 10              15                  20 gca atc gaa gct agt gaa ggt tac gaa acg gtc att att gat gca caa    192
Ala Ile Glu Ala Ser Glu Gly Tyr Glu Thr Val Ile Ile Asp Ala Gln
 25              30                  35                  40 aat ctc tcc gaa gca gaa att act gag atg caa gat cga gga caa aaa    240
Asn Leu Ser Glu Ala Glu Ile Thr Glu Met Gln Asp Arg Gly Gln Lys
             45                  50                  55 gtt tat agt tat tta aat gta gga tca ttg gaa act tac agg cct tac    288
Val Tyr Ser Tyr Leu Asn Val Gly Ser Leu Glu Thr Tyr Arg Pro Tyr
             60                  65                  70 tat gaa gaa ttt cag tat ctt act ttg agg cct tat gaa aat tgg gaa    336
Tyr Glu Glu Phe Gln Tyr Leu Thr Leu Arg Pro Tyr Glu Asn Trp Glu
         75                  80                  85 gaa gaa tat tgg gtc gat gta acc aat gaa gac tgg caa aaa ttt agt    384
Glu Glu Tyr Trp Val Asp Val Thr Asn Glu Asp Trp Gln Lys Phe Ser
         90                  95                 100 gcc gtt act tta gct aac gaa cta ctt gat aag gga att gat ggc ttt    432
Ala Val Thr Leu Ala Asn Glu Leu Leu Asp Lys Gly Ile Asp Gly Phe
105                 110                 115                 120 tgg atc gat aat gta gat gta tac tgg caa ttt caa aca aaa gaa acg    480
Trp Ile Asp Asn Val Asp Val Tyr Trp Gln Phe Gln Thr Lys Glu Thr
                125                 130                 135 tat att gga gtg gaa aaa atc tta aag aca ctc atg agc tat ggc aaa    528
Tyr Ile Gly Val Glu Lys Ile Leu Lys Thr Leu Met Ser Tyr Gly Lys
            140                 145                 150 ccg gtc ctt att aat gga gga aat gaa ttt gtt agt gca tat tta cag    576
Pro Val Leu Ile Asn Gly Gly Asn Glu Phe Val Ser Ala Tyr Leu Gln
            155                 160                 165 caa aat cag caa cta gat gat att ttg act ggt gta aac caa gaa acc    624
Gln Asn Gln Gln Leu Asp Asp Ile Leu Thr Gly Val Asn Gln Glu Thr
        170                 175                 180 gtc ttt tca gct att gat ttt gag gaa gat aag ctg agt act caa aca    672
Val Phe Ser Ala Ile Asp Phe Glu Glu Asp Lys Leu Ser Thr Gln Thr
185                 190                 195                 200 aaa gaa aat caa acc tac tac tta aat tat tta gat aca gtt gat aaa    720
Lys Glu Asn Gln Thr Tyr Tyr Leu Asn Tyr Leu Asp Thr Val Asp Lys
                205                 210                 215 gct ggg aaa gag atc tat ttg ctt gaa tac tct aca aaa aaa gag ctg    768
Ala Gly Lys Glu Ile Tyr Leu Leu Glu Tyr Ser Thr Lys Lys Glu Leu
            220                 225                 230 gct aaa gat gtc cat gac tat gcg act aaa aga ggc tgg cag tat tat    816
Ala Lys Asp Val His Asp Tyr Ala Thr Lys Arg Gly Trp Gln Tyr Tyr
            235                 240                 245 ata tcc gat tca gtt gag ttg gat aat tga                            846
Ile Ser Asp Ser Val Glu Leu Asp Asn
        250                 255

<210> SEQ ID NO 87
<211> LENGTH: 281
<212> TYPE: PRT
<213> ORGANISM: Carnobacterium inhibens subsp.

<400> SEQUENCE: 87

Met Lys Thr Thr Ala Ile Arg Phe Leu Ile Gly Ala Met Val Ile Leu
            -20                 -15                 -10

Gly Val Thr Gly Cys Ala Asn Leu Glu Gly Lys Ser Asn Ser Lys Leu
         -5              -1   1               5

Glu Asn Thr Gly Glu Tyr Gly Val Phe Leu Ser Leu Asp Gly Ser Glu
```

```
            10                  15                  20
Ala Ile Glu Ala Ser Glu Gly Tyr Glu Thr Val Ile Asp Ala Gln
 25                  30                  35                  40

Asn Leu Ser Glu Ala Glu Ile Thr Glu Met Gln Asp Arg Gly Gln Lys
                 45                  50                  55

Val Tyr Ser Tyr Leu Asn Val Gly Ser Leu Glu Thr Tyr Arg Pro Tyr
                     60                  65                  70

Tyr Glu Glu Phe Gln Tyr Leu Thr Leu Arg Pro Tyr Glu Asn Trp Glu
                 75                  80                  85

Glu Glu Tyr Trp Val Asp Val Thr Asn Glu Asp Trp Gln Lys Phe Ser
         90                  95                 100

Ala Val Thr Leu Ala Asn Glu Leu Leu Asp Lys Gly Ile Asp Gly Phe
105                 110                 115                 120

Trp Ile Asp Asn Val Asp Val Tyr Trp Gln Phe Gln Thr Lys Glu Thr
                125                 130                 135

Tyr Ile Gly Val Glu Lys Ile Leu Lys Thr Leu Met Ser Tyr Gly Lys
                140                 145                 150

Pro Val Leu Ile Asn Gly Gly Asn Glu Phe Val Ser Ala Tyr Leu Gln
                155                 160                 165

Gln Asn Gln Gln Leu Asp Asp Ile Leu Thr Gly Val Asn Gln Glu Thr
170                 175                 180

Val Phe Ser Ala Ile Asp Phe Glu Glu Asp Lys Leu Ser Thr Gln Thr
185                 190                 195                 200

Lys Glu Asn Gln Thr Tyr Tyr Leu Asn Tyr Leu Asp Thr Val Asp Lys
                205                 210                 215

Ala Gly Lys Glu Ile Tyr Leu Leu Glu Tyr Ser Thr Lys Lys Glu Leu
                220                 225                 230

Ala Lys Asp Val His Asp Tyr Ala Thr Lys Arg Gly Trp Gln Tyr Tyr
                235                 240                 245

Ile Ser Asp Ser Val Glu Leu Asp Asn
                250                 255

<210> SEQ ID NO 88
<211> LENGTH: 257
<212> TYPE: PRT
<213> ORGANISM: Carnobacterium inhibens subsp.

<400> SEQUENCE: 88

Glu Gly Lys Ser Asn Ser Lys Leu Glu Asn Thr Gly Glu Tyr Gly Val
 1               5                  10                  15

Phe Leu Ser Leu Asp Gly Ser Glu Ala Ile Glu Ala Ser Glu Gly Tyr
                 20                  25                  30

Glu Thr Val Ile Ile Asp Ala Gln Asn Leu Ser Glu Ala Glu Ile Thr
             35                  40                  45

Glu Met Gln Asp Arg Gly Gln Lys Val Tyr Ser Tyr Leu Asn Val Gly
 50                  55                  60

Ser Leu Glu Thr Tyr Arg Pro Tyr Tyr Glu Glu Phe Gln Tyr Leu Thr
 65                  70                  75                  80

Leu Arg Pro Tyr Glu Asn Trp Glu Glu Glu Tyr Trp Val Asp Val Thr
                 85                  90                  95

Asn Glu Asp Trp Gln Lys Phe Ser Ala Val Thr Leu Ala Asn Glu Leu
                100                 105                 110

Leu Asp Lys Gly Ile Asp Gly Phe Trp Ile Asp Asn Val Asp Val Tyr
            115                 120                 125
```

```
Trp Gln Phe Gln Thr Lys Glu Thr Tyr Ile Gly Val Glu Lys Ile Leu
        130                 135                 140

Lys Thr Leu Met Ser Tyr Gly Lys Pro Val Leu Ile Asn Gly Gly Asn
145                 150                 155                 160

Glu Phe Val Ser Ala Tyr Leu Gln Gln Asn Gln Gln Leu Asp Asp Ile
                165                 170                 175

Leu Thr Gly Val Asn Gln Glu Thr Val Phe Ser Ala Ile Asp Phe Glu
            180                 185                 190

Glu Asp Lys Leu Ser Thr Gln Thr Lys Glu Asn Gln Thr Tyr Tyr Leu
        195                 200                 205

Asn Tyr Leu Asp Thr Val Asp Lys Ala Gly Lys Glu Ile Tyr Leu Leu
210                 215                 220

Glu Tyr Ser Thr Lys Lys Glu Leu Ala Lys Asp Val His Asp Tyr Ala
225                 230                 235                 240

Thr Lys Arg Gly Trp Gln Tyr Tyr Ile Ser Asp Ser Val Glu Leu Asp
                245                 250                 255

Asn
```

<210> SEQ ID NO 89
<211> LENGTH: 963
<212> TYPE: DNA
<213> ORGANISM: environmental bacterial community
<220> FEATURE:
<221> NAME/KEY: CDS
<222> LOCATION: (1)..(960)
<220> FEATURE:
<221> NAME/KEY: sig_peptide
<222> LOCATION: (1)..(72)
<220> FEATURE:
<221> NAME/KEY: mat_peptide
<222> LOCATION: (73)..(960)

<400> SEQUENCE: 89

```
atg aaa aag gtc att ttt ttg gtt att gga tta gca aca att tta gtt         48
Met Lys Lys Val Ile Phe Leu Val Ile Gly Leu Ala Thr Ile Leu Val
                -20                 -15                 -10 att acc tgt aac tca agt acg gca act caa gtt gtt tca aat caa aaa         96
Ile Thr Cys Asn Ser Ser Thr Ala Thr Gln Val Val Ser Asn Gln Lys
         -5                  -1  1                   5 gat act tca aaa aaa atg cag gat ttt gtt atc aat att tca aaa tat        144
Asp Thr Ser Lys Lys Met Gln Asp Phe Val Ile Asn Ile Ser Lys Tyr
         10                  15                  20 gct cga aaa ttt gat gcc gat ttt atc att att cct caa aat ggt gaa        192
Ala Arg Lys Phe Asp Ala Asp Phe Ile Ile Ile Pro Gln Asn Gly Glu
 25                  30                  35                  40 gaa tta gct ttc att gga gct aat ccg gac aaa aaa ctg aac acc act        240
Glu Leu Ala Phe Ile Gly Ala Asn Pro Asp Lys Lys Leu Asn Thr Thr
                 45                  50                  55 ttc ctt aat gca atc aac ggt ttt gga ata gaa gaa tta ttt tat aat        288
Phe Leu Asn Ala Ile Asn Gly Phe Gly Ile Glu Glu Leu Phe Tyr Asn
             60                  65                  70 gaa acc ttt aaa ccg aat gaa tac cgc att ggt ctt tta caa aaa atc        336
Glu Thr Phe Lys Pro Asn Glu Tyr Arg Ile Gly Leu Leu Gln Lys Ile
         75                  80                  85 aaa gac caa aag acc att ctg gtt tca gaa tat gtt aat gac aca aca        384
Lys Asp Gln Lys Thr Ile Leu Val Ser Glu Tyr Val Asn Asp Thr Thr
     90                  95                  100 att gta aat gat gct cac aac aaa aat tca aat gaa gga ttt atc agt        432
Ile Val Asn Asp Ala His Asn Lys Asn Ser Asn Glu Gly Phe Ile Ser
105                 110                 115                 120
```

```
ttc att cga aca aaa gac aac tac cac tac tct ata att ccg aag aaa    480
Phe Ile Arg Thr Lys Asp Asn Tyr His Tyr Ser Ile Ile Pro Lys Lys
            125                 130                 135 ata aac aac gaa aac agc gaa aac atc act tca ttg aaa gac gta aaa    528
Ile Asn Asn Glu Asn Ser Glu Asn Ile Thr Ser Leu Lys Asp Val Lys
            140                 145                 150 aac ttc ctt tat cta ata aac aac agc aat ttt tac agc aaa tcc ggt    576
Asn Phe Leu Tyr Leu Ile Asn Asn Ser Asn Phe Tyr Ser Lys Ser Gly
            155                 160                 165 ttt tta gaa gct att tcc aat acc aat tat gat tta att ttc atc gat    624
Phe Leu Glu Ala Ile Ser Asn Thr Asn Tyr Asp Leu Ile Phe Ile Asp
            170                 175                 180 ttg tat cac aat ggt gta ctt ttc aaa aaa gaa gaa ata gaa cga tta    672
Leu Tyr His Asn Gly Val Leu Phe Lys Lys Glu Glu Ile Glu Arg Leu
185                 190                 195                 200 aag cag aaa aaa aac gga gga aaa aga ctt gtc gtt tgt tat atg aac    720
Lys Gln Lys Lys Asn Gly Gly Lys Arg Leu Val Val Cys Tyr Met Asn
                205                 210                 215 att ggt gcc gcc gaa aaa tac aga aac tat tgg aaa aga gat tgg act    768
Ile Gly Ala Ala Glu Lys Tyr Arg Asn Tyr Trp Lys Arg Asp Trp Thr
            220                 225                 230 tta gga aat cca tcg tgg ttg aag aaa aaa tac gac ggc tat gat cag    816
Leu Gly Asn Pro Ser Trp Leu Lys Lys Lys Tyr Asp Gly Tyr Asp Gln
            235                 240                 245 gaa gtc tgg gta gaa ttt tgg aac aaa gat tgg caa aaa atc gtt tac    864
Glu Val Trp Val Glu Phe Trp Asn Lys Asp Trp Gln Lys Ile Val Tyr
250                 255                 260 gga aac gac caa tcc tat tta gca aaa ata ctg gaa gcc gga tat gat    912
Gly Asn Asp Gln Ser Tyr Leu Ala Lys Ile Leu Glu Ala Gly Tyr Asp
265                 270                 275                 280 ggt gca tat ctc gac aat gtt gaa gcc tat tac ttt tta tat aac gat    960
Gly Ala Tyr Leu Asp Asn Val Glu Ala Tyr Tyr Phe Leu Tyr Asn Asp
            285                 290                 295 taa                                                                963

<210> SEQ ID NO 90
<211> LENGTH: 320
<212> TYPE: PRT
<213> ORGANISM: environmental bacterial community

<400> SEQUENCE: 90

Met Lys Lys Val Ile Phe Leu Val Ile Gly Leu Ala Thr Ile Leu Val
                -20                 -15                 -10

Ile Thr Cys Asn Ser Ser Thr Ala Thr Gln Val Val Ser Asn Gln Lys
             -5                 -1   1                   5

Asp Thr Ser Lys Lys Met Gln Asp Phe Val Ile Asn Ile Ser Lys Tyr
     10                  15                  20

Ala Arg Lys Phe Asp Ala Asp Phe Ile Ile Pro Gln Asn Gly Glu
 25                  30                  35                  40

Glu Leu Ala Phe Ile Gly Ala Asn Pro Asp Lys Lys Leu Asn Thr Thr
                 45                  50                  55

Phe Leu Asn Ala Ile Asn Gly Phe Gly Ile Glu Glu Leu Phe Tyr Asn
             60                  65                  70

Glu Thr Phe Lys Pro Asn Glu Tyr Arg Ile Gly Leu Leu Gln Lys Ile
         75                  80                  85

Lys Asp Gln Lys Thr Ile Leu Val Ser Glu Tyr Val Asn Asp Thr Thr
 90                  95                 100

Ile Val Asn Asp Ala His Asn Lys Asn Ser Asn Glu Gly Phe Ile Ser
```

```
                105                 110                 115                 120
        Phe Ile Arg Thr Lys Asp Asn Tyr His Tyr Ser Ile Ile Pro Lys Lys
                        125                 130                 135

Ile Asn Asn Glu Asn Ser Glu Asn Ile Thr Ser Leu Lys Asp Val Lys
                        140                 145                 150

Asn Phe Leu Tyr Leu Ile Asn Asn Ser Asn Phe Tyr Ser Lys Ser Gly
                        155                 160                 165

Phe Leu Glu Ala Ile Ser Asn Thr Asn Tyr Asp Leu Ile Phe Ile Asp
                        170                 175                 180

Leu Tyr His Asn Gly Val Leu Phe Lys Lys Glu Ile Glu Arg Leu
        185                 190                 195                 200

Lys Gln Lys Lys Asn Gly Gly Lys Arg Leu Val Val Cys Tyr Met Asn
                        205                 210                 215

Ile Gly Ala Ala Glu Lys Tyr Arg Asn Tyr Trp Lys Arg Asp Trp Thr
                        220                 225                 230

Leu Gly Asn Pro Ser Trp Leu Lys Lys Tyr Asp Gly Tyr Asp Gln
                        235                 240                 245

Glu Val Trp Val Glu Phe Trp Asn Lys Asp Trp Gln Lys Ile Val Tyr
                        250                 255                 260

Gly Asn Asp Gln Ser Tyr Leu Ala Lys Ile Leu Glu Ala Gly Tyr Asp
        265                 270                 275                 280

Gly Ala Tyr Leu Asp Asn Val Glu Ala Tyr Tyr Phe Leu Tyr Asn Asp
                        285                 290                 295

<210> SEQ ID NO 91
<211> LENGTH: 296
<212> TYPE: PRT
<213> ORGANISM: environmental bacterial community

<400> SEQUENCE: 91

Thr Gln Val Val Ser Asn Gln Lys Asp Thr Ser Lys Lys Met Gln Asp
        1               5                   10                  15

Phe Val Ile Asn Ile Ser Lys Tyr Ala Arg Lys Phe Asp Ala Asp Phe
                        20                  25                  30

Ile Ile Ile Pro Gln Asn Gly Glu Glu Leu Ala Phe Ile Gly Ala Asn
                        35                  40                  45

Pro Asp Lys Lys Leu Asn Thr Thr Phe Leu Asn Ala Ile Asn Gly Phe
                        50                  55                  60

Gly Ile Glu Glu Leu Phe Tyr Asn Glu Thr Phe Lys Pro Asn Glu Tyr
        65                  70                  75                  80

Arg Ile Gly Leu Leu Gln Lys Ile Lys Asp Gln Lys Thr Ile Leu Val
                        85                  90                  95

Ser Glu Tyr Val Asn Asp Thr Thr Ile Val Asn Asp Ala His Asn Lys
                        100                 105                 110

Asn Ser Asn Glu Gly Phe Ile Ser Phe Ile Arg Thr Lys Asp Asn Tyr
                        115                 120                 125

His Tyr Ser Ile Ile Pro Lys Lys Ile Asn Asn Glu Asn Ser Glu Asn
                        130                 135                 140

Ile Thr Ser Leu Lys Asp Val Lys Asn Phe Leu Tyr Leu Ile Asn Asn
        145                 150                 155                 160

Ser Asn Phe Tyr Ser Lys Ser Gly Phe Leu Glu Ala Ile Ser Asn Thr
                        165                 170                 175

Asn Tyr Asp Leu Ile Phe Ile Asp Leu Tyr His Asn Gly Val Leu Phe
                        180                 185                 190
```

```
Lys Lys Glu Glu Ile Glu Arg Leu Lys Gln Lys Lys Asn Gly Gly Lys
                195                 200                 205

Arg Leu Val Val Cys Tyr Met Asn Ile Gly Ala Ala Glu Lys Tyr Arg
        210                 215                 220

Asn Tyr Trp Lys Arg Asp Trp Thr Leu Gly Asn Pro Ser Trp Leu Lys
225                 230                 235                 240

Lys Lys Tyr Asp Gly Tyr Asp Gln Glu Val Trp Val Glu Phe Trp Asn
                245                 250                 255

Lys Asp Trp Gln Lys Ile Val Tyr Gly Asn Asp Gln Ser Tyr Leu Ala
            260                 265                 270

Lys Ile Leu Glu Ala Gly Tyr Asp Gly Ala Tyr Leu Asp Asn Val Glu
        275                 280                 285

Ala Tyr Tyr Phe Leu Tyr Asn Asp
        290                 295

<210> SEQ ID NO 92
<211> LENGTH: 2772
<212> TYPE: DNA
<213> ORGANISM: Pseudomonas composti
<220> FEATURE:
<221> NAME/KEY: CDS
<222> LOCATION: (1)..(2769)
<220> FEATURE:
<221> NAME/KEY: sig_peptide
<222> LOCATION: (1)..(78)
<220> FEATURE:
<221> NAME/KEY: mat_peptide
<222> LOCATION: (79)..(2769)

<400> SEQUENCE: 92 atg cag gtg aag ttc tca acg gga att gcc aga ctt ttc ggt ctg gcc      48
Met Gln Val Lys Phe Ser Thr Gly Ile Ala Arg Leu Phe Gly Leu Ala
    -25                 -20                 -15 tta gca ttt ttc gct tct acg cca ttt gcc caa cct gcc agc gtg gcc      96
Leu Ala Phe Phe Ala Ser Thr Pro Phe Ala Gln Pro Ala Ser Val Ala
-10              -5                  -1  1                   5 ttc tgg tac gcc gat cag ttg ccc ctg cct gag ttg tcg cag ttc gag     144
Phe Trp Tyr Ala Asp Gln Leu Pro Leu Pro Glu Leu Ser Gln Phe Glu
                10                  15                  20 tgg gtg gtc gtc gag ccg gac cat gtc tcg cca ggc gat ctt gct tac     192
Trp Val Val Val Glu Pro Asp His Val Ser Pro Gly Asp Leu Ala Tyr
            25                  30                  35 ctc cag aag cag ggc agt gag gtc ttc gcc tac ctg tcc att ggc gaa     240
Leu Gln Lys Gln Gly Ser Glu Val Phe Ala Tyr Leu Ser Ile Gly Glu
        40                  45                  50 ttc gcc ggt gat gtt gcc cag gct ggt ttg agc gag gcc acc agc gtt     288
Phe Ala Gly Asp Val Ala Gln Ala Gly Leu Ser Glu Ala Thr Ser Val
55                  60                  65                  70 gtg cgc aac gat gcc tgg aac agc caa gtc atg aac ctg gcc tcg ccg     336
Val Arg Asn Asp Ala Trp Asn Ser Gln Val Met Asn Leu Ala Ser Pro
                75                  80                  85 gta tgg cgt gaa cat ctt ttc aag cgc acc agt acc ctg cgc cag cag     384
Val Trp Arg Glu His Leu Phe Lys Arg Thr Ser Thr Leu Arg Gln Gln
            90                  95                 100 ggg tac acg ggc ctt ttc ctc gac acg ctg gac agt ttc cag ctg caa     432
Gly Tyr Thr Gly Leu Phe Leu Asp Thr Leu Asp Ser Phe Gln Leu Gln
        105                 110                 115 gca cag gac ctt cag ggt agc cag cgt gag gcg ctc aag agc ctg ctg     480
Ala Gln Asp Leu Gln Gly Ser Gln Arg Glu Ala Leu Lys Ser Leu Leu
    120                 125                 130 agc gaa ctg cat cgg cgt gaa cca aca ctc aag ttg ttc ttc aac cgt     528
```

| | | |
|---|---|---|
| Ser Glu Leu His Arg Arg Glu Pro Thr Leu Lys Leu Phe Phe Asn Arg<br>135                    140                    145                    150 | | |
| ggt ttc gag gtg ctg ccg gaa ctg cca ggc gtt gcc tcc gcg gtc gcc<br>Gly Phe Glu Val Leu Pro Glu Leu Pro Gly Val Ala Ser Ala Val Ala<br>                      155                    160                    165 | | 576 |
| gtc gag tcc att tat gcg ggt tgg gac gcg ggc ggt ggt tac aag gag<br>Val Glu Ser Ile Tyr Ala Gly Trp Asp Ala Gly Gly Gly Tyr Lys Glu<br>            170                    175                    180 | | 624 |
| gtt tcg cag ggt gat cgt gac tgg ttg ttg ccg cgc ctc gat gcg gtg<br>Val Ser Gln Gly Asp Arg Asp Trp Leu Leu Pro Arg Leu Asp Ala Val<br>                185                    190                    195 | | 672 |
| cgc aaa cag ggt gtt ccg gtg gtg gcg atc gag tat ctg ccg ccc gag<br>Arg Lys Gln Gly Val Pro Val Val Ala Ile Glu Tyr Leu Pro Pro Glu<br>      200                    205                    210 | | 720 |
| cag cgc gaa cag gca cgc aag ctg gct acg cgc ctg acg cag gag ggc<br>Gln Arg Glu Gln Ala Arg Lys Leu Ala Thr Arg Leu Thr Gln Glu Gly<br>215                    220                    225                    230 | | 768 |
| ttc att ccc tat gta acg tcc ccg gcg ctg gat gcc atc ggc gtt ggc<br>Phe Ile Pro Tyr Val Thr Ser Pro Ala Leu Asp Ala Ile Gly Val Gly<br>                235                    240                    245 | | 816 |
| ggc gtg gaa gtc cag cct cgg cgt atc gcc ctg gtc tac gat gcg cgc<br>Gly Val Glu Val Gln Pro Arg Arg Ile Ala Leu Val Tyr Asp Ala Arg<br>      250                    255                    260 | | 864 |
| gaa ggt gag ctc gaa gat aac ccg ggg cac gtg cac ctg ggc ggt ttg<br>Glu Gly Glu Leu Glu Asp Asn Pro Gly His Val His Leu Gly Gly Leu<br>            265                    270                    275 | | 912 |
| ctc gag tat ctg ggc tac cgg gtc gac tat tgg ccg gcc gac acc acg<br>Leu Glu Tyr Leu Gly Tyr Arg Val Asp Tyr Trp Pro Ala Asp Thr Thr<br>280                    285                    290 | | 960 |
| ttg ccg cag cgt cct ctg aaa ggg ctc tac gcc ggt atc gtg gtg tgg<br>Leu Pro Gln Arg Pro Leu Lys Gly Leu Tyr Ala Gly Ile Val Val Trp<br>295                    300                    305                    310 | | 1008 |
| atg acc agc ggc tcg cca gtg gat cgc gat tac ttc gag aac tgg ttg<br>Met Thr Ser Gly Ser Pro Val Asp Arg Asp Tyr Phe Glu Asn Trp Leu<br>                315                    320                    325 | | 1056 |
| ggc cag cga ctc gat gag cag gta ccg ctc gcc ttt atg gct ggg atg<br>Gly Gln Arg Leu Asp Glu Gln Val Pro Leu Ala Phe Met Ala Gly Met<br>            330                    335                    340 | | 1104 |
| ccc acc gaa aac gac agc ctg ctg gac cgt ctg ggc att cgc acg cgt<br>Pro Thr Glu Asn Asp Ser Leu Leu Asp Arg Leu Gly Ile Arg Thr Arg<br>                345                    350                    355 | | 1152 |
| tcg cag ccg gtt ggc aag gat gct gtg ctg ctg tcc cat gac gct gcg<br>Ser Gln Pro Val Gly Lys Asp Ala Val Leu Leu Ser His Asp Ala Ala<br>      360                    365                    370 | | 1200 |
| ctg atc ggg ggc ttc gaa gcg ccg ctg cgc ttg cgc acg cgg gat gtc<br>Leu Ile Gly Gly Phe Glu Ala Pro Leu Arg Leu Arg Thr Arg Asp Val<br>375                    380                    385                    390 | | 1248 |
| ccg ccg ctg acc gtg acc gcc ccc gag cgt acc cag gcc gcg ctt tct<br>Pro Pro Leu Thr Val Thr Ala Pro Glu Arg Thr Gln Ala Ala Leu Ser<br>                395                    400                    405 | | 1296 |
| ctg cag agc gat gac cgg gtc tat gtg ccg gtg gcg acc ggg gac tgg<br>Leu Gln Ser Asp Asp Arg Val Tyr Val Pro Val Ala Thr Gly Asp Trp<br>            410                    415                    420 | | 1344 |
| ggc ggc tat gcg ttg gcg cct tat gtg ttc gaa gag ggg ctc gat cat<br>Gly Gly Tyr Ala Leu Ala Pro Tyr Val Phe Glu Glu Gly Leu Asp His<br>                425                    430                    435 | | 1392 |
| cgg cgc tgg gtg ctc gat ccc ttt gcc ttc att tcc cgt gcc ttc aag<br>Arg Arg Trp Val Leu Asp Pro Phe Ala Phe Ile Ser Arg Ala Phe Lys<br>440                    445                    450 | | 1440 |

```
                                                      -continued ctg ccg gcg ttg ccg cgt ccc gat acc acg acg gag aac ggc cgc cgc    1488
Leu Pro Ala Leu Pro Arg Pro Asp Thr Thr Thr Glu Asn Gly Arg Arg
455                 460                 465                 470 atc gcc acc gtg cat ctg gat ggc gat ggc ttc gtg tcc cgc gcc gaa    1536
Ile Ala Thr Val His Leu Asp Gly Asp Gly Phe Val Ser Arg Ala Glu
                475                 480                 485 gtc ccc ggc tca cct tac tcg ggt atc cag gta ctt gag gat ttc atc    1584
Val Pro Gly Ser Pro Tyr Ser Gly Ile Gln Val Leu Glu Asp Phe Ile
                490                 495                 500 aag cca tac cca ctg ctg acc tcg gtg tcg gtg atc gag ggc gaa gtc    1632
Lys Pro Tyr Pro Leu Leu Thr Ser Val Ser Val Ile Glu Gly Glu Val
            505                 510                 515 ggc cca cgc ggc atg tac ccg cat ctt tcg cgc gag ctg gaa ccc atc    1680
Gly Pro Arg Gly Met Tyr Pro His Leu Ser Arg Glu Leu Glu Pro Ile
            520                 525                 530 gcc cgc gag atc ttc gtc aac ccc aag gtc gag gtc gcc agt cat acc    1728
Ala Arg Glu Ile Phe Val Asn Pro Lys Val Glu Val Ala Ser His Thr
535                 540                 545                 550 ttc agt cac ccg ttc ttc tgg cag ccg gaa aag gct acg aaa cgg gag    1776
Phe Ser His Pro Phe Phe Trp Gln Pro Glu Lys Ala Thr Lys Arg Glu
                555                 560                 565 aac ttc gag gcg gag tac ggc tac atg atg gcc atc ccg ggg tac aag    1824
Asn Phe Glu Ala Glu Tyr Gly Tyr Met Met Ala Ile Pro Gly Tyr Lys
                570                 575                 580 acg ctg gac atg cag cgc gag gtc gtc ggc gcg cgt gac tat atc aat    1872
Thr Leu Asp Met Gln Arg Glu Val Val Gly Ala Arg Asp Tyr Ile Asn
            585                 590                 595 cag cgc ctg acc acc ccg aag aag ccg gtg aag atg atc ttc tgg tcc    1920
Gln Arg Leu Thr Thr Pro Lys Lys Pro Val Lys Met Ile Phe Trp Ser
600                 605                 610 ggc gat gcc atg ccc agc gcc gaa acc atc aag ctg gcc tat gac agc    1968
Gly Asp Ala Met Pro Ser Ala Glu Thr Ile Lys Leu Ala Tyr Asp Ser
615                 620                 625                 630 ggg ctg ccg aac gtc aac ggc ggc aac acc gta ctg acc aag gcc tat    2016
Gly Leu Pro Asn Val Asn Gly Gly Asn Thr Val Leu Thr Lys Ala Tyr
                635                 640                 645 ccc tcg ctg acc ggg ctc tat ccg ctg atc cga ccg acc act ggc ggg    2064
Pro Ser Leu Thr Gly Leu Tyr Pro Leu Ile Arg Pro Thr Thr Gly Gly
            650                 655                 660 ctg cac ttc tat gcc ccg gtg atc aac gag aac gtc tac acc aac ctg    2112
Leu His Phe Tyr Ala Pro Val Ile Asn Glu Asn Val Tyr Thr Asn Leu
            665                 670                 675 tgg acc ggg ccg tac tac ggc ttc cgt gac gtt cag gac acc ttt gca    2160
Trp Thr Gly Pro Tyr Tyr Gly Phe Arg Asp Val Gln Asp Thr Phe Ala
680                 685                 690 ctg act gac agt ccg cgc cgc ctg cgt ggc ttc cac ctc tat tac cac    2208
Leu Thr Asp Ser Pro Arg Arg Leu Arg Gly Phe His Leu Tyr Tyr His
695                 700                 705                 710 ttc tac tcg ggg acc aag cag gcc tcc atc cgg gcc atg cgc cag atc    2256
Phe Tyr Ser Gly Thr Lys Gln Ala Ser Ile Arg Ala Met Arg Gln Ile
                715                 720                 725 tat cag acc att ctc gat ggc cag ccg ctg tcg ttg tgg atg agc gat    2304
Tyr Gln Thr Ile Leu Asp Gly Gln Pro Leu Ser Leu Trp Met Ser Asp
            730                 735                 740 tac atc aaa cgg gtc gaa ggg ctg tac cgc gcg agc ctg gcc aga cgc    2352
Tyr Ile Lys Arg Val Glu Gly Leu Tyr Arg Ala Ser Leu Ala Arg Arg
            745                 750                 755 agc gac gga acc tgg cag gtc aag ggc ctg gtg ggc atg cgc acg ctg    2400
Ser Asp Gly Thr Trp Gln Val Lys Gly Leu Val Gly Met Arg Thr Leu
760                 765                 770
```

```
cgt ctc gat cct tct ctg ggc tgg cct gat ctg gct cgc tcc cag ggg   2448
Arg Leu Asp Pro Ser Leu Gly Trp Pro Asp Leu Ala Arg Ser Gln Gly
775             780                 785                 790 gtt gcc ggt gtg cgt gat cta gca cag ggg cgt tat gtc cac ctg acc   2496
Val Ala Gly Val Arg Asp Leu Ala Gln Gly Arg Tyr Val His Leu Thr
                795                 800                 805 ggc gcc gat gcg gtg ctg gcg ttg cgt gag act cgt gac ccg cgt cct   2544
Gly Ala Asp Ala Val Leu Ala Leu Arg Glu Thr Arg Asp Pro Arg Pro
        810                 815                 820 gcg ttg gaa gag gcc aat att cca ctg acc ggc tgg cgt tat ctg gat   2592
Ala Leu Glu Glu Ala Asn Ile Pro Leu Thr Gly Trp Arg Tyr Leu Asp
825                 830                 835 gac aag cgc gtg acg ttc tct ttc ctg ggg gag ttc ccg ctc agt ttc   2640
Asp Lys Arg Val Thr Phe Ser Phe Leu Gly Glu Phe Pro Leu Ser Phe
    840                 845                 850 agc gtg cgc tcg gcc gga gcg tgc cac gtg acg gcg ggg ggc ggc cgg   2688
Ser Val Arg Ser Ala Gly Ala Cys His Val Thr Ala Gly Gly Gly Arg
855                 860                 865                 870 ttc agc ggt acg cat gac aat ggc gta tgg cat ttt gaa ttg ccg atg   2736
Phe Ser Gly Thr His Asp Asn Gly Val Trp His Phe Glu Leu Pro Met
        875                 880                 885 aag cag gtg agc gat gca caa ctc gtc tgc aac taa                   2772
Lys Gln Val Ser Asp Ala Gln Leu Val Cys Asn
            890                 895
```

<210> SEQ ID NO 93
<211> LENGTH: 923
<212> TYPE: PRT
<213> ORGANISM: Pseudomonas composti

<400> SEQUENCE: 93

```
Met Gln Val Lys Phe Ser Thr Gly Ile Ala Arg Leu Phe Gly Leu Ala
    -25                 -20                 -15

Leu Ala Phe Phe Ala Ser Thr Pro Phe Ala Gln Pro Ala Ser Val Ala
-10                  -5             -1   1               5

Phe Trp Tyr Ala Asp Gln Leu Pro Leu Pro Glu Leu Ser Gln Phe Glu
                10                  15                  20

Trp Val Val Glu Pro Asp His Val Ser Pro Gly Asp Leu Ala Tyr
            25                  30                  35

Leu Gln Lys Gln Gly Ser Glu Val Phe Ala Tyr Leu Ser Ile Gly Glu
        40                  45                  50

Phe Ala Gly Asp Val Ala Gln Ala Gly Leu Ser Glu Ala Thr Ser Val
55                  60                  65                  70

Val Arg Asn Asp Ala Trp Asn Ser Gln Val Met Asn Leu Ala Ser Pro
                75                  80                  85

Val Trp Arg Glu His Leu Phe Lys Arg Thr Ser Thr Leu Arg Gln Gln
            90                  95                 100

Gly Tyr Thr Gly Leu Phe Leu Asp Thr Leu Asp Ser Phe Gln Leu Gln
        105                 110                 115

Ala Gln Asp Leu Gln Gly Ser Gln Arg Glu Ala Leu Lys Ser Leu Leu
    120                 125                 130

Ser Glu Leu His Arg Arg Glu Pro Thr Leu Lys Leu Phe Phe Asn Arg
135                 140                 145                 150

Gly Phe Glu Val Leu Pro Glu Leu Pro Gly Val Ala Ser Ala Val Ala
                155                 160                 165

Val Glu Ser Ile Tyr Ala Gly Trp Asp Ala Gly Gly Tyr Lys Glu
            170                 175                 180
```

```
Val Ser Gln Gly Asp Arg Asp Trp Leu Leu Pro Arg Leu Asp Ala Val
        185                 190                 195

Arg Lys Gln Gly Val Pro Val Ala Ile Glu Tyr Leu Pro Pro Glu
200                 205                 210

Gln Arg Glu Gln Ala Arg Lys Leu Ala Thr Arg Leu Thr Gln Glu Gly
215                 220                 225                 230

Phe Ile Pro Tyr Val Thr Ser Pro Ala Leu Asp Ala Ile Gly Val Gly
                235                 240                 245

Gly Val Glu Val Gln Pro Arg Arg Ile Ala Leu Val Tyr Asp Ala Arg
            250                 255                 260

Glu Gly Glu Leu Glu Asp Asn Pro Gly His Val His Leu Gly Gly Leu
                265                 270                 275

Leu Glu Tyr Leu Gly Tyr Arg Val Asp Tyr Trp Pro Ala Asp Thr Thr
        280                 285                 290

Leu Pro Gln Arg Pro Leu Lys Gly Leu Tyr Ala Gly Ile Val Val Trp
295                 300                 305                 310

Met Thr Ser Gly Ser Pro Val Asp Arg Asp Tyr Phe Glu Asn Trp Leu
                315                 320                 325

Gly Gln Arg Leu Asp Glu Gln Val Pro Leu Ala Phe Met Ala Gly Met
            330                 335                 340

Pro Thr Glu Asn Asp Ser Leu Leu Asp Arg Leu Gly Ile Arg Thr Arg
                345                 350                 355

Ser Gln Pro Val Gly Lys Asp Ala Val Leu Leu Ser His Asp Ala Ala
        360                 365                 370

Leu Ile Gly Gly Phe Glu Ala Pro Leu Arg Leu Arg Thr Arg Asp Val
375                 380                 385                 390

Pro Pro Leu Thr Val Thr Ala Pro Glu Arg Thr Gln Ala Ala Leu Ser
                395                 400                 405

Leu Gln Ser Asp Asp Arg Val Tyr Val Pro Val Ala Thr Gly Asp Trp
            410                 415                 420

Gly Gly Tyr Ala Leu Ala Pro Tyr Val Phe Glu Glu Gly Leu Asp His
        425                 430                 435

Arg Arg Trp Val Leu Asp Pro Phe Ala Phe Ile Ser Arg Ala Phe Lys
440                 445                 450

Leu Pro Ala Leu Pro Arg Pro Asp Thr Thr Thr Glu Asn Gly Arg Arg
455                 460                 465                 470

Ile Ala Thr Val His Leu Asp Gly Asp Gly Phe Val Ser Arg Ala Glu
                475                 480                 485

Val Pro Gly Ser Pro Tyr Ser Gly Ile Gln Val Leu Glu Asp Phe Ile
            490                 495                 500

Lys Pro Tyr Pro Leu Leu Thr Ser Val Ser Val Ile Glu Gly Glu Val
        505                 510                 515

Gly Pro Arg Gly Met Tyr Pro His Leu Ser Arg Glu Leu Glu Pro Ile
520                 525                 530

Ala Arg Glu Ile Phe Val Asn Pro Lys Val Glu Val Ala Ser His Thr
535                 540                 545                 550

Phe Ser His Pro Phe Phe Trp Gln Pro Glu Lys Ala Thr Lys Arg Glu
                555                 560                 565

Asn Phe Glu Ala Glu Tyr Gly Tyr Met Met Ala Ile Pro Gly Tyr Lys
            570                 575                 580

Thr Leu Asp Met Gln Arg Glu Val Val Gly Ala Arg Asp Tyr Ile Asn
585                 590                 595
```

```
Gln Arg Leu Thr Thr Pro Lys Lys Pro Val Lys Met Ile Phe Trp Ser
            600                 605                 610

Gly Asp Ala Met Pro Ser Ala Glu Thr Ile Lys Leu Ala Tyr Asp Ser
615                 620                 625                 630

Gly Leu Pro Asn Val Asn Gly Asn Thr Val Leu Thr Lys Ala Tyr
                635                 640                 645

Pro Ser Leu Thr Gly Leu Tyr Pro Leu Ile Arg Pro Thr Thr Gly Gly
            650                 655                 660

Leu His Phe Tyr Ala Pro Val Ile Asn Glu Asn Val Tyr Thr Asn Leu
            665                 670                 675

Trp Thr Gly Pro Tyr Tyr Gly Phe Arg Asp Val Gln Asp Thr Phe Ala
            680                 685                 690

Leu Thr Asp Ser Pro Arg Arg Leu Arg Gly Phe His Leu Tyr Tyr His
695                 700                 705                 710

Phe Tyr Ser Gly Thr Lys Gln Ala Ser Ile Arg Ala Met Arg Gln Ile
                715                 720                 725

Tyr Gln Thr Ile Leu Asp Gly Gln Pro Leu Ser Leu Trp Met Ser Asp
            730                 735                 740

Tyr Ile Lys Arg Val Glu Gly Leu Tyr Arg Ala Ser Leu Ala Arg Arg
            745                 750                 755

Ser Asp Gly Thr Trp Gln Val Lys Gly Leu Val Gly Met Arg Thr Leu
760                 765                 770

Arg Leu Asp Pro Ser Leu Gly Trp Pro Asp Leu Ala Arg Ser Gln Gly
775                 780                 785                 790

Val Ala Gly Val Arg Asp Leu Ala Gln Gly Arg Tyr Val His Leu Thr
                795                 800                 805

Gly Ala Asp Ala Val Leu Ala Leu Arg Glu Thr Arg Asp Pro Arg Pro
            810                 815                 820

Ala Leu Glu Glu Ala Asn Ile Pro Leu Thr Gly Trp Arg Tyr Leu Asp
            825                 830                 835

Asp Lys Arg Val Thr Phe Ser Phe Leu Gly Glu Phe Pro Leu Ser Phe
            840                 845                 850

Ser Val Arg Ser Ala Gly Ala Cys His Val Thr Ala Gly Gly Gly Arg
855                 860                 865                 870

Phe Ser Gly Thr His Asp Asn Gly Val Trp His Phe Glu Leu Pro Met
                875                 880                 885

Lys Gln Val Ser Asp Ala Gln Leu Val Cys Asn
                890                 895

<210> SEQ ID NO 94
<211> LENGTH: 897
<212> TYPE: PRT
<213> ORGANISM: Pseudomonas composti

<400> SEQUENCE: 94

Gln Pro Ala Ser Val Ala Phe Trp Tyr Ala Asp Gln Leu Pro Leu Pro
1               5                   10                  15

Glu Leu Ser Gln Phe Glu Trp Val Val Val Glu Pro Asp His Val Ser
            20                  25                  30

Pro Gly Asp Leu Ala Tyr Leu Gln Lys Gln Gly Ser Glu Val Phe Ala
        35                  40                  45

Tyr Leu Ser Ile Gly Glu Phe Ala Gly Asp Val Ala Gln Ala Gly Leu
    50                  55                  60

Ser Glu Ala Thr Ser Val Val Arg Asn Asp Ala Trp Asn Ser Gln Val
65                  70                  75                  80
```

```
Met Asn Leu Ala Ser Pro Val Trp Arg Glu His Leu Phe Lys Arg Thr
                85                  90                  95
Ser Thr Leu Arg Gln Gln Gly Tyr Thr Gly Leu Phe Leu Asp Thr Leu
            100                 105                 110
Asp Ser Phe Gln Leu Gln Ala Gln Asp Leu Gln Gly Ser Gln Arg Glu
        115                 120                 125
Ala Leu Lys Ser Leu Leu Ser Glu Leu His Arg Arg Glu Pro Thr Leu
    130                 135                 140
Lys Leu Phe Phe Asn Arg Gly Phe Glu Val Leu Pro Glu Leu Pro Gly
145                 150                 155                 160
Val Ala Ser Ala Val Ala Val Glu Ser Ile Tyr Ala Gly Trp Asp Ala
                165                 170                 175
Gly Gly Gly Tyr Lys Glu Val Ser Gln Gly Asp Arg Asp Trp Leu Leu
            180                 185                 190
Pro Arg Leu Asp Ala Val Arg Lys Gln Gly Val Pro Val Val Ala Ile
        195                 200                 205
Glu Tyr Leu Pro Pro Glu Gln Arg Glu Gln Ala Arg Lys Leu Ala Thr
    210                 215                 220
Arg Leu Thr Gln Glu Gly Phe Ile Pro Tyr Val Thr Ser Pro Ala Leu
225                 230                 235                 240
Asp Ala Ile Gly Val Gly Gly Val Glu Val Gln Pro Arg Arg Ile Ala
                245                 250                 255
Leu Val Tyr Asp Ala Arg Glu Gly Glu Leu Glu Asp Asn Pro Gly His
            260                 265                 270
Val His Leu Gly Gly Leu Leu Glu Tyr Leu Gly Tyr Arg Val Asp Tyr
        275                 280                 285
Trp Pro Ala Asp Thr Thr Leu Pro Gln Arg Pro Leu Lys Gly Leu Tyr
    290                 295                 300
Ala Gly Ile Val Val Trp Met Thr Ser Gly Ser Pro Val Asp Arg Asp
305                 310                 315                 320
Tyr Phe Glu Asn Trp Leu Gly Gln Arg Leu Asp Glu Gln Val Pro Leu
                325                 330                 335
Ala Phe Met Ala Gly Met Pro Thr Glu Asn Asp Ser Leu Leu Asp Arg
            340                 345                 350
Leu Gly Ile Arg Thr Arg Ser Gln Pro Val Gly Lys Asp Ala Val Leu
        355                 360                 365
Leu Ser His Asp Ala Ala Leu Ile Gly Gly Phe Glu Ala Pro Leu Arg
    370                 375                 380
Leu Arg Thr Arg Asp Val Pro Pro Leu Thr Val Thr Ala Pro Glu Arg
385                 390                 395                 400
Thr Gln Ala Ala Leu Ser Leu Gln Ser Asp Asp Arg Val Tyr Val Pro
                405                 410                 415
Val Ala Thr Gly Asp Trp Gly Gly Tyr Ala Leu Ala Pro Tyr Val Phe
            420                 425                 430
Glu Glu Gly Leu Asp His Arg Trp Val Leu Asp Pro Phe Ala Phe
        435                 440                 445
Ile Ser Arg Ala Phe Lys Leu Pro Ala Leu Pro Arg Pro Asp Thr Thr
    450                 455                 460
Thr Glu Asn Gly Arg Arg Ile Ala Thr Val His Leu Asp Gly Asp Gly
465                 470                 475                 480
Phe Val Ser Arg Ala Glu Val Pro Gly Ser Pro Tyr Ser Gly Ile Gln
                485                 490                 495
```

Val Leu Glu Asp Phe Ile Lys Pro Tyr Pro Leu Leu Thr Ser Val Ser
            500                 505                 510

Val Ile Glu Gly Glu Val Gly Pro Arg Gly Met Tyr Pro His Leu Ser
        515                 520                 525

Arg Glu Leu Glu Pro Ile Ala Arg Glu Ile Phe Val Asn Pro Lys Val
    530                 535                 540

Glu Val Ala Ser His Thr Phe Ser His Pro Phe Phe Trp Gln Pro Glu
545                 550                 555                 560

Lys Ala Thr Lys Arg Glu Asn Phe Glu Ala Tyr Gly Tyr Met Met
                565                 570                 575

Ala Ile Pro Gly Tyr Lys Thr Leu Asp Met Gln Arg Glu Val Val Gly
            580                 585                 590

Ala Arg Asp Tyr Ile Asn Gln Arg Leu Thr Thr Pro Lys Lys Pro Val
        595                 600                 605

Lys Met Ile Phe Trp Ser Gly Asp Ala Met Pro Ser Ala Glu Thr Ile
    610                 615                 620

Lys Leu Ala Tyr Asp Ser Gly Leu Pro Asn Val Asn Gly Gly Asn Thr
625                 630                 635                 640

Val Leu Thr Lys Ala Tyr Pro Ser Leu Thr Gly Leu Tyr Pro Leu Ile
            645                 650                 655

Arg Pro Thr Thr Gly Gly Leu His Phe Tyr Ala Pro Val Ile Asn Glu
        660                 665                 670

Asn Val Tyr Thr Asn Leu Trp Thr Gly Pro Tyr Tyr Gly Phe Arg Asp
    675                 680                 685

Val Gln Asp Thr Phe Ala Leu Thr Asp Ser Pro Arg Arg Leu Arg Gly
690                 695                 700

Phe His Leu Tyr Tyr His Phe Tyr Ser Gly Thr Lys Gln Ala Ser Ile
705                 710                 715                 720

Arg Ala Met Arg Gln Ile Tyr Gln Thr Ile Leu Asp Gly Gln Pro Leu
            725                 730                 735

Ser Leu Trp Met Ser Asp Tyr Ile Lys Arg Val Glu Gly Leu Tyr Arg
        740                 745                 750

Ala Ser Leu Ala Arg Arg Ser Asp Gly Thr Trp Gln Val Lys Gly Leu
    755                 760                 765

Val Gly Met Arg Thr Leu Arg Leu Asp Pro Ser Leu Gly Trp Pro Asp
770                 775                 780

Leu Ala Arg Ser Gln Gly Val Ala Gly Val Arg Asp Leu Ala Gln Gly
785                 790                 795                 800

Arg Tyr Val His Leu Thr Gly Ala Asp Ala Val Leu Ala Leu Arg Glu
            805                 810                 815

Thr Arg Asp Pro Arg Pro Ala Leu Glu Glu Ala Asn Ile Pro Leu Thr
        820                 825                 830

Gly Trp Arg Tyr Leu Asp Asp Lys Arg Val Thr Phe Ser Phe Leu Gly
    835                 840                 845

Glu Phe Pro Leu Ser Phe Ser Val Arg Ser Ala Gly Ala Cys His Val
850                 855                 860

Thr Ala Gly Gly Gly Arg Phe Ser Gly Thr His Asp Asn Gly Val Trp
865                 870                 875                 880

His Phe Glu Leu Pro Met Lys Gln Val Ser Asp Ala Gln Leu Val Cys
            885                 890                 895

Asn

<210> SEQ ID NO 95

```
<211> LENGTH: 271
<212> TYPE: PRT
<213> ORGANISM: Paraburkholderia phenazinium

<400> SEQUENCE: 95
```

| | | | | | | | | | | | | | | |
|---|---|---|---|---|---|---|---|---|---|---|---|---|---|---|
|Gln|Thr|Ala|Ala|Asp|Ala|Ala|Ser|Asn|Ala|Ser|Ala|Thr|Asn|Ala|
|1| | | |5| | | | |10| | | | |15|
|Ser|Ala|Gln|Pro|Ser|Val|Ala|Phe|Phe|Tyr|Gly|Gly|Gln|Val|Pro|Ala|
| | | |20| | | | |25| | | | |30| | |
|Ala|Ala|Leu|Ser|Glu|Phe|Asp|Ala|Val|Val|Glu|Pro|Asp|Ser|Gly|
| | |35| | | | |40| | | | |45| | |
|Phe|Asp|Pro|Glu|Ala|Gln|His|Gly|Gly|His|Thr|Ala|Trp|Phe|Ala|Tyr|
| |50| | | | |55| | | | |60| | | | |
|Val|Ser|Val|Gly|Glu|Val|Thr|Pro|Gln|Arg|Pro|Tyr|Tyr|Ala|Ala|Met|
|65| | | | |70| | | | |75| | | | |80|
|Pro|Lys|Glu|Trp|Leu|Val|Gly|His|Asn|Ala|Ala|Trp|Glu|Ser|Lys|Val|
| | | | |85| | | | |90| | | | |95| |
|Val|Asp|Gln|Asp|Ala|Pro|Gly|Trp|Pro|Ala|Phe|Tyr|Leu|Lys|Gln|Val|
| | | |100| | | | |105| | | | |110| | |
|Ile|Ala|Pro|Leu|Trp|Arg|Lys|Gly|Tyr|Arg|Gly|Phe|Phe|Leu|Asp|Thr|
| | |115| | | | |120| | | | |125| | | |
|Leu|Asp|Ser|Tyr|Gln|Leu|Ile|Ala|Lys|Thr|Asp|Ala|Asp|Arg|Gln|Arg|
|130| | | | |135| | | | |140| | | | | |
|Gln|Gln|Ala|Gly|Leu|Val|Ala|Val|Ile|Arg|Ala|Ile|Lys|Ala|Arg|Tyr|
|145| | | | |150| | | | |155| | | | |160|
|Pro|Arg|Ala|Met|Leu|Met|Phe|Asn|Arg|Gly|Phe|Glu|Ile|Leu|Pro|Gln|
| | | | |165| | | | |170| | | | |175| |
|Val|His|Glu|Leu|Val|Tyr|Ala|Val|Ala|Phe|Glu|Ser|Leu|Tyr|Ser|Gly|
| | | |180| | | | |185| | | | |190| | |
|Trp|Asp|Gln|Thr|Lys|Gln|Ser|Tyr|Thr|Gln|Val|Pro|Leu|Ala|Asp|Arg|
| | |195| | | | |200| | | | |205| | | |
|Asp|Trp|Leu|Leu|Gly|Gln|Ala|Arg|Ile|Ile|Arg|Glu|Gln|Tyr|Arg|Leu|
| |210| | | | |215| | | | |220| | | | |
|Pro|Val|Ile|Ser|Ile|Asp|Tyr|Cys|Ala|Pro|Gly|Asp|Glu|Gln|Cys|Ala|
|225| | | | |230| | | | |235| | | | |240|
|Arg|Asp|Thr|Val|Gln|Lys|Ile|Cys|Lys|Asp|Gly|Leu|Val|Pro|Tyr|Val|
| | | | |245| | | | |250| | | | |255| |
|Thr|Asp|Gly|Ala|Leu|Gln|Thr|Val|Gly|Val|Gly|Arg|Ala|Gly|Arg|
| | | |260| | | | |265| | | | |270| | |

```
<210> SEQ ID NO 96
<211> LENGTH: 266
<212> TYPE: PRT
<213> ORGANISM: Burkholderia sp-63093

<400> SEQUENCE: 96
```

| | | | | | | | | | | | | | | |
|---|---|---|---|---|---|---|---|---|---|---|---|---|---|---|
|Gln|Gly|Pro|Ala|Asp|Met|Pro|Ala|Gly|Pro|Ser|Val|Ala|Leu|Tyr|Tyr|
|1| | | |5| | | | |10| | | | |15| |
|Gly|Ala|Asn|Pro|Pro|Val|Glu|Glu|Leu|Ala|Thr|Phe|Asp|Val|Val|
| | | |20| | | | |25| | | | |30| | |
|Val|Asp|Pro|Asp|Ala|His|Phe|Asp|Pro|Arg|Ala|His|Ala|Lys|Ala|His|
| | | |35| | | | |40| | | | |45| | | |
|Pro|Val|Trp|Phe|Ala|Tyr|Val|Ser|Val|Gly|Glu|Val|Asn|Pro|His|Arg|
| |50| | | | |55| | | | |60| | | | |
|Ala|Tyr|Tyr|Ser|Ala|Met|Pro|Ser|Ala|Trp|Leu|Pro|Gly|Val|Asn|Asp|
|65| | | | |70| | | | |75| | | | |80|

```
Ala Trp Ala Ser His Val Ile Asp Gln Thr Ala Ala Glu Trp Pro Ala
                85                  90                  95

Phe Phe Val Asp Lys Val Ile Ala Pro Leu Trp Lys Lys Gly Tyr Arg
            100                 105                 110

Gly Phe Phe Leu Asp Thr Leu Asp Ser Tyr His Leu Ile Ala Lys Thr
        115                 120                 125

Asp Ala Ala Arg Ala Ala Gln Glu Ala Gly Leu Val Arg Val Ile Arg
    130                 135                 140

Ala Ile Lys Lys Arg Tyr Pro Lys Ala Lys Leu Ile Phe Asn Arg Gly
145                 150                 155                 160

Phe Glu Val Leu Pro Gln Ile His Asp Leu Ala Tyr Met Val Ala Phe
                165                 170                 175

Glu Ser Leu Tyr Arg Gly Trp Asp Ala Gly Lys Gln Arg Tyr Thr Glu
            180                 185                 190

Val Pro Gln Ala Asp Arg Asp Trp Leu Leu Met Gln Ala Ala Thr Ile
        195                 200                 205

Arg Asp Gln Tyr Lys Leu Pro Val Leu Ser Ile Asp Tyr Cys Pro Pro
    210                 215                 220

Ala Asp Asp Thr Cys Ala Ala Thr Ala Ala Arg Ile Thr Gln Ala
225                 230                 235                 240

Gly Phe Val Pro Tyr Val Thr Asp Gly Gly Leu Ala Thr Val Gly Val
                245                 250                 255

Gly Ala Ala Gly Thr Gly Asn Glu Arg Pro
            260                 265

<210> SEQ ID NO 97
<211> LENGTH: 8
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (2)..(2)
<223> OTHER INFORMATION: Xaa = any natural amino acid
<220> FEATURE:
<221> NAME/KEY: MISC_FEATURE
<222> LOCATION: (3)..(3)
<223> OTHER INFORMATION: Xaa = any natural amino acid
<220> FEATURE:
<221> NAME/KEY: MISC_FEATURE
<222> LOCATION: (5)..(5)
<223> OTHER INFORMATION: Xaa = any natural amino acid
<220> FEATURE:
<221> NAME/KEY: MISC_FEATURE
<222> LOCATION: (6)..(6)
<223> OTHER INFORMATION: Xaa = F(Phe) or Y(Tyr)
<220> FEATURE:
<221> NAME/KEY: MISC_FEATURE
<222> LOCATION: (7)..(7)
<223> OTHER INFORMATION: Xaa = L(Leu) or Y(Tyr) or F(Phe) or I (Ile)

<400> SEQUENCE: 97

Gly Xaa Xaa Gly Xaa Xaa Xaa Asp
1               5

<210> SEQ ID NO 98
<211> LENGTH: 5
<212> TYPE: PRT
<213> ORGANISM: Artificial
<220> FEATURE:
<223> OTHER INFORMATION: Motif
<220> FEATURE:
<221> NAME/KEY: MISC_FEATURE
```

```
<222> LOCATION: (1)..(1)
<223> OTHER INFORMATION: Xaa = I(Ile) or L (Leu) or F (Phe) or Q (Gln)
      or V (Val)
<220> FEATURE:
<221> NAME/KEY: MISC_FEATURE
<222> LOCATION: (3)..(3)
<223> OTHER INFORMATION: Xaa =R (Arg) or W (Trp)
<220> FEATURE:
<221> NAME/KEY: MISC_FEATURE
<222> LOCATION: (5)..(5)
<223> OTHER INFORMATION: Xaa =F (Phe) or L(Leu)

<400> SEQUENCE: 98

Xaa Asn Xaa Gly Xaa
1               5

<210> SEQ ID NO 99
<211> LENGTH: 6
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (6)..(6)
<223> OTHER INFORMATION: Xaa = Y (Tyr) or F (Phe)

<400> SEQUENCE: 99

Asp Thr Leu Asp Ser Xaa
1               5

<210> SEQ ID NO 100
<211> LENGTH: 13
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (2)..(2)
<223> OTHER INFORMATION: Xaa = V (Val) or L(Leu)
<220> FEATURE:
<221> NAME/KEY: MISC_FEATURE
<222> LOCATION: (11)..(11)
<223> OTHER INFORMATION: Xaa = Q (Gln) or T (Thr) or H (His)
<220> FEATURE:
<221> NAME/KEY: MISC_FEATURE
<222> LOCATION: (13)..(13)
<223> OTHER INFORMATION: Xaa = L(Leu) or M(Met) or Q (Gln)

<400> SEQUENCE: 100

Gly Xaa Phe Leu Asp Thr Leu Asp Ser Phe Xaa Leu Xaa
1               5                   10

<210> SEQ ID NO 101
<211> LENGTH: 7
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (3)..(3)
<223> OTHER INFORMATION: Xaa = V(Val) or I (Ile) or M (Met) or A (Ala)
<220> FEATURE:
<221> NAME/KEY: MISC_FEATURE
<222> LOCATION: (4)..(4)
<223> OTHER INFORMATION: Xaa = G(Gly) or D(Asp)
<220> FEATURE:
<221> NAME/KEY: MISC_FEATURE
<222> LOCATION: (5)..(5)
<223> OTHER INFORMATION: Xaa = D(Asp) or N(Asn) or W(Trp)
<220> FEATURE:
```

```
<221> NAME/KEY: MISC_FEATURE
<222> LOCATION: (6)..(6)
<223> OTHER INFORMATION: Xaa = V(Val) or I (Ile) or L(Leu)
<220> FEATURE:
<221> NAME/KEY: MISC_FEATURE
<222> LOCATION: (7)..(7)
<223> OTHER INFORMATION: Xaa = D (Asp) or E (Glu) or N (Asn)

<400> SEQUENCE: 101

Asp Thr Xaa Xaa Xaa Xaa Xaa
1               5

<210> SEQ ID NO 102
<211> LENGTH: 8
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (1)..(1)
<223> OTHER INFORMATION: Xaa = S(Ser) or E (Glu) or T (Trp) or C (Cys)
<220> FEATURE:
<221> NAME/KEY: MISC_FEATURE
<222> LOCATION: (4)..(4)
<223> OTHER INFORMATION: Xaa = E(Glu) or Q (Gln) or A (Ala)
<220> FEATURE:
<221> NAME/KEY: MISC_FEATURE
<222> LOCATION: (5)..(5)
<223> OTHER INFORMATION: Xaa = A(Ala) or L (Leu) or I (Ile)
<220> FEATURE:
<221> NAME/KEY: MISC_FEATURE
<222> LOCATION: (7)..(7)
<223> OTHER INFORMATION: Xaa = Any natural amino acid

<400> SEQUENCE: 102

Xaa Ile Gly Xaa Xaa Glu Xaa Tyr
1               5

<210> SEQ ID NO 103
<211> LENGTH: 6
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (1)..(1)
<223> OTHER INFORMATION: Xaa = Q(Gln) or L(Leu)
<220> FEATURE:
<221> NAME/KEY: MISC_FEATURE
<222> LOCATION: (3)..(3)
<223> OTHER INFORMATION: Xaa = A(Ala) or S(Ser)

<400> SEQUENCE: 103

Xaa Asn Xaa Pro Glu Leu
1               5

<210> SEQ ID NO 104
<211> LENGTH: 9
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (1)..(1)
<223> OTHER INFORMATION: Xaa = K (Lys) or L (Leu) or Y (Tyr) or M (Met)
      or Q (Gln)
<220> FEATURE:
<221> NAME/KEY: MISC_FEATURE
<222> LOCATION: (2)..(2)
<223> OTHER INFORMATION: Xaa = Any natural amino acid
```

```
<220> FEATURE:
<221> NAME/KEY: MISC_FEATURE
<222> LOCATION: (3)..(3)
<223> OTHER INFORMATION: Xaa = Any natural amino acid
<220> FEATURE:
<221> NAME/KEY: MISC_FEATURE
<222> LOCATION: (4)..(4)
<223> OTHER INFORMATION: Xaa = P(Phe) or V (Val)
<220> FEATURE:
<221> NAME/KEY: MISC_FEATURE
<222> LOCATION: (7)..(7)
<223> OTHER INFORMATION: Xaa = S(Ser) or A(Ala)

<400> SEQUENCE: 104

Xaa Xaa Xaa Xaa Gln Asn Xaa Pro Glu
1               5
```